(12) United States Patent
Pegg et al.

(10) Patent No.: US 10,696,666 B2
(45) Date of Patent: Jun. 30, 2020

(54) PHARMACEUTICAL COMPOUNDS

(71) Applicant: CELLCENTRIC LTD, Cambridge, Cambridgeshire (GB)

(72) Inventors: Neil Anthony Pegg, Cambridge (GB); Stuart Thomas Onions, Nottingham (GB); David Michel Adrien Taddei, Nottingham (GB); Jonathan Shannon, Nottingham (GB); Silvia Paoletta, Nottingham (GB); Richard James Brown, Nottingham (GB); Don Smyth, Nottingham (GB); Gareth Harbottle, Nottingham (GB)

(73) Assignee: CELLCENTRIC LIMITED, Cambridge (GB)

( * ) Notice: Subject to any disclaimer, the term of this patent is extended or adjusted under 35 U.S.C. 154(b) by 0 days.

(21) Appl. No.: 16/341,631

(22) PCT Filed: Oct. 18, 2017

(86) PCT No.: PCT/GB2017/053152
§ 371 (c)(1),
(2) Date: Apr. 12, 2019

(87) PCT Pub. No.: WO2018/073586
PCT Pub. Date: Apr. 26, 2018

(65) Prior Publication Data
US 2019/0375740 A1 Dec. 12, 2019

(30) Foreign Application Priority Data

Oct. 18, 2016 (GB) .................................. 1617630.7

(51) Int. Cl.
*C07D 471/04* (2006.01)
*C07D 417/14* (2006.01)
*C07D 413/14* (2006.01)
*A61K 45/06* (2006.01)

(52) U.S. Cl.
CPC ......... *C07D 413/14* (2013.01); *C07D 417/14* (2013.01); *C07D 471/04* (2013.01); *A61K 45/06* (2013.01)

(58) Field of Classification Search
CPC ... C07D 413/14; C07D 417/14; C07D 471/04
USPC ...................................................... 548/306.1
See application file for complete search history.

(56) References Cited

U.S. PATENT DOCUMENTS

| 6,498,165 | B1 * | 12/2002 | Armstrong | ........... C07D 401/14 514/256 |
|---|---|---|---|---|
| 2010/0179147 | A1 | 7/2010 | Chang et al. | |
| 2011/0190343 | A1 | 8/2011 | Gochin et al. | |
| 2014/0336190 | A1 | 11/2014 | Aktoudianakis et al. | |

| 2016/0184273 | A1 | 6/2016 | Liu et al. |
|---|---|---|---|

FOREIGN PATENT DOCUMENTS

| EP | 0694535 A1 | 1/1996 |
|---|---|---|
| EP | 2397471 A1 | 12/2011 |
| JP | 2014073982 A | 4/2014 |
| WO | 02/28839 A1 | 4/2002 |
| WO | 02/072549 A1 | 9/2002 |
| WO | 03/072099 A1 | 9/2003 |
| WO | 2004/063151 A2 | 7/2004 |
| WO | 2005/021510 A2 | 3/2005 |
| WO | 2005/118555 A1 | 12/2005 |
| WO | 2006/124780 A2 | 11/2006 |
| WO | 2006/136823 A1 | 12/2006 |
| WO | 2008/009348 A1 | 1/2008 |
| WO | 2008/070599 A1 | 6/2008 |
| WO | 2009/000413 A1 | 12/2008 |
| WO | 2009/023179 A2 | 2/2009 |
| WO | 2009/079011 A1 | 6/2009 |
| WO | 2010/068287 A2 | 6/2010 |
| WO | 2010/075282 A1 | 7/2010 |
| WO | 2011/045415 A2 | 4/2011 |
| WO | 2011/097607 A1 | 8/2011 |
| WO | 2011/143129 A1 | 11/2011 |
| WO | 2012/036168 A1 | 3/2012 |
| WO | 2012/107465 A1 | 8/2012 |

(Continued)

OTHER PUBLICATIONS

Jones et al., "The Epigenomics of Cancer", Cell, Feb. 23, 2007, vol. 128, pp. 683-692.
Zhong et al., "p300 Acetyltransferase Regulates Androgen Receptor Degradation and PTEN-Deficient Prostate Tumorigenesis", Cancer Research, Mar. 15, 2014, vol. 74, No. 6, pp. 1870-1880.
Cai et al., "Intratumoral De Novo Steroid Synthesis Activates Androgen Receptor in Castration-Resistant Prostate Cancer and Is Upregulated by Treatment with CYP17A1 Inhibitors", Cancer Research, Oct. 15, 2011, vol. 71, No. 20, pp. 6503-6513.
Ogiwara et al., "Targeting p300 Addiction in CBP-Deficient Cancers Causes Synthetic Lethality by Apoptotic Cell Death due to Abrogation of MYC Expression", Cancer Discovery, Apr. 2016, vol. 6, No. 4, 430-445.

(Continued)

*Primary Examiner* — Niloofar Rahmani
(74) *Attorney, Agent, or Firm* — MH2 Technology Law Group, LLP

(57) ABSTRACT

A compound which is an arylimidazolyl isoxazole of formula (I): (Formula (I)) or a pharmaceutically acceptable salt thereof. The compound has activity in modulating the activity of p300 and/or CBP and is used to treat cancer, particularly prostate cancer.

8 Claims, No Drawings

(56) References Cited

FOREIGN PATENT DOCUMENTS

| WO | 2012/116440 | A1 | 9/2012 |
|---|---|---|---|
| WO | 2012/133509 | A1 | 10/2012 |
| WO | 2013/130890 | A1 | 9/2013 |
| WO | 2013/186229 | A1 | 12/2013 |
| WO | 2014/012050 | A2 | 1/2014 |
| WO | 2014/054634 | A1 | 4/2014 |
| WO | 2014/078479 | A2 | 5/2014 |
| WO | 2014/157382 | A1 | 10/2014 |
| WO | 2014/182929 | A1 | 11/2014 |
| WO | 2015/023958 | A1 | 2/2015 |
| WO | 2015/086509 | A1 | 6/2015 |
| WO | 2016/016421 | A1 | 2/2016 |
| WO | 2016/086200 | A1 | 6/2016 |
| WO | 2016/200401 | A1 | 12/2016 |
| WO | 2017/024412 | A1 | 2/2017 |
| WO | 2017/059252 | A1 | 4/2017 |
| WO | 2017/100525 | A1 | 6/2017 |
| WO | 2017/106568 | A1 | 6/2017 |
| WO | 2017/223229 | A1 | 12/2017 |
| WO | 2017/223243 | A1 | 12/2017 |

OTHER PUBLICATIONS

Casey et al., "MYC regulates the antitumor immune response through CD47 and PD-L1", Science, Mar. 10, 2016, vol. 352, 15 pages.

Debes et al., "p300 in Prostate Cancer Proliferation and Progression", Cancer Research, Nov. 15, 2003, vol. 63, pp. 7638-7640.

Linja et al., "Expression of Androgen Receptor Coregulators in Prostate Cancer", Clinical Cancer Research, Feb. 1, 2004, vol. 10, 1032-1040.

Ghosh et al., "Regulatory T Cell Modulation by CBP/EP300 Bromodomain Inhibition", The Journal of Biological Chemistry, Jun. 17, 2016, vol. 291, No. 25, pp. 13014-13027.

Hay et al., "Discovery and Optimization of Small-Molecule Ligands for the CBP/p300 Bromodomains", J. Am. Chem. Soc., 2014, vol. 136, pp. 9308-9319 with Supporting Information (S1-S99).

* cited by examiner

PHARMACEUTICAL COMPOUNDS

CROSS-REFERENCE TO RELATED APPLICATIONS

This application is a U.S. National Stage application of PCT/GB2017/053152 filed 18 Oct. 2017, which claims priority to Great Britain Application No. 1617630.7 filed 18 Oct. 2016, the entire disclosures of which are hereby incorporated by reference in their entireties.

FIELD OF THE INVENTION

The present invention relates to a series of novel arylimidazolyl isoxazoles and to their use as modulators of p300 and/or CBP activity.

BACKGROUND TO THE INVENTION

Genetic and epigenetic modifications are critical to all stages of cancer disease progression and epigenetic silencing has been shown to be important in the misregulation of genes involved in all of the hallmarks of cancer (Jones, P. A. and Baylin, S. B. (2007) "The epigenomics of cancer", Cell, Vol. 128, pp. 683-692). The underlying epigenetic modifications that mediate regulation include DNA methylation and post translational histone modification. The latter includes methylation, acetylation, and ubiquitination. DNA-demethylating agents and histone deacetylase inhibitors have shown anti-tumour activity and a number of agents have been approved for use in the treatment of haematological malignancies. The enzymes mediating histone modification, including histone acetyltransferases (HATs) which acetylate histone and non-histone proteins, represent a wave of second generation targets for small molecule drug intervention.

Prostate cancer is one of the most common malignancies, and the second leading cause of cancer mortality among men. The treatment for clinically localised disease is typically surgery or radiation therapy. For patients who recur systemically after definitive treatment, or who present with loco-regional or metastatic disease, long term disease control is the primary objective. Typically, this entails a series of hormonal therapies that supress androgen receptor (AR) signalling, since prostate cancers are exquisitely dependent upon AR function for survival and progression. Although AR targeted therapies inhibit tumour growth, disease is rarely eliminated and resistance to therapy is acquired through restored AR function. Progression to this 'castration resistant' prostate cancer (CRPC) represents the lethal phenotype of the illness. It is estimated that between 50-60% of patients that develop metastatic disease have CRPC. Recently, several new therapeutic agents have been approved for the treatment of CRPC. These however, provide limited clinical efficacy and serve only to prolong progression. Novel and tolerable agents are therefore necessary to make further gains in the treatment of CRPC.

Multiple cellular mechanisms lead to the progression of CRPC. In all cases, acquisition of the CRPC phenotype is mediated via re-activation of the AR pathway. The acetyltransferase p300 directly regulates AR levels and AR signalling activity in prostate cancer cells (Zhong et al., 'p300 acetyltransferase regulates androgen-receptor degradation and PTEN-deficient prostate tumorigenesis,' Cancer Res., Vol. 74, pp. 1870-1880, 2014). Therapeutic modulation of p300 activity would therefore target all known adaptive mechanisms which lead to the development of CRPC. Approved therapies and those in clinical studies primarily target only one or other of theses cellular mechanisms. The modulation of p300 activity directly provides an opportunity to more broadly modulate AR activity in CRPC than current and other experimental therapeutic strategies. In addition, resistance mechanisms to recently approved agents have been shown to be AR-dependent (Cai, C. et al., (2011) 'Intratumoral de novo steroid synthesis activates androgen receptor in castration-resistant prostate cancer and is up-regulated by treatment with Cyp17A1 inhibitors,' Cancer Res., Vol. 71, pp. 6503-6513). Modulation of p300 should therefore inhibit resistance to current therapies and potentially provide improved and sustained efficacy and greater clinical utility.

In common with p300, the CREB (cyclic-AMP response element binding protein) binding protein (CBP) is an acetyltransferase that acts as a transcriptional co-activator in human cells. Both CBP and p300 possess a single bromodomain (BRD) and a lysine acetyltransferase (KAT) domain, which are involved in the post-translational modification and recruitment of histones and non-histone proteins. There is high sequence similarity between CBP and p300 in the conserved functional domains (see Duncan A. Hay et al, JACS 2014, 135, 9308-9319). Modulation of CBP activity therefore provides a promising route to the treatment of certain cancers. Accordingly, compounds that can modulate, e.g. inhibit, the activity of p300 and/or CBP are of interest in cancer therapy.

Tumours which harbour loss of function mutations in CBP become addicted to p300 and are uniquely sensitive to p300 inhibition (see Ogiwara et al. 2016 Cancer Discovery. 6; 430-445). Conversely tumours with mutations in p300 are uniquely sensitive to CBP inhibition. Genetic analysis reveals that up to 15% of both non-small cell and small cell lung tumours have these loss of function mutations. Similar mutations are also found in up to 25% of bladder cancers. Accordingly, compounds that can modulate, eg inhibit, the activity of p300 and/or CBP are of interest in cancer therapy for tumours with these molecular changes.

Furthermore, CBP/p300 regulates the expression of key tumour immune checkpoint proteins such as CTLA4/PD-L1 (see Casey et al., Science. 352; p 227-231, 2016) and plays an important role in the differentiation and function of T-regulatory cells which are involved in immune evasion by tumours. Accordingly, compounds that can modulate, eg inhibit, the activity of p300 and/or CBP are of interest for cancer therapy in combination with agents that target the onco-immune system.

SUMMARY OF THE INVENTION

It has now been found that a series of novel compounds have activity in modulating p300 and/or CBP activity. The compounds therefore have potential utility in treating cancer, particularly prostate cancer.

Accordingly, the present invention provides a compound which is an arylimidazolyl isoxazole of formula (I):

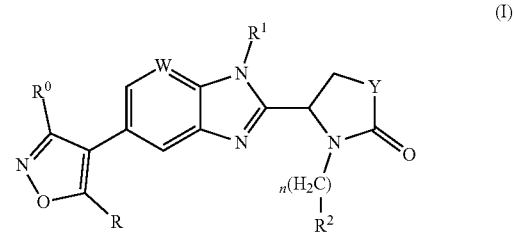

wherein:

$R^0$ and R, which are the same or different, are each H or $C_1$-$C_6$ alkyl which is unsubstituted or substituted by OH, —OC(O)R' or OR' wherein R' is unsubstituted $C_1$-$C_6$ alkyl;

W is N or CH;

$R^1$ is a group which is unsubstituted or substituted and is selected from C-linked 4- to 6-membered heterocyclyl; $C_3$-$C_6$ cycloalkyl; $C_1$-$C_6$ alkyl which is unsubstituted or substituted by $C_6$-$C_{10}$ aryl, 5- to 12-membered heteroaryl, $C_3$-$C_6$ cycloalkyl, OH, —OC(O)R' or OR' wherein R' is as defined above; and a spiro group of the following formula:

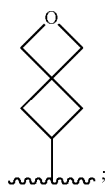

Y is —CH$_2$—, —CH$_2$CH$_2$— or —CH$_2$CH$_2$CH$_2$—;
n is 0 or 1;

$R^2$ is a group selected from $C_6$-$C_{10}$ aryl, 5- to 12-membered heteroaryl, $C_3$-$C_6$ cycloalkyl and $C_5$-$C_6$ cycloalkenyl, wherein the group is unsubstituted or substituted and wherein $C_6$-$C_{10}$ aryl is optionally fused to a 5- or 6-membered heterocyclic ring;

or a pharmaceutically acceptable salt thereof.

In another aspect the invention provides a pharmaceutical composition comprising an arylimidazolyl isoxazole of formula (I) as defined above or a pharmaceutically acceptable salt thereof and a pharmaceutically acceptable carrier. The pharmaceutical composition may further comprise one or more additional chemotherapeutic agents, for instance as mentioned below.

In a further aspect the invention provides an arylimidazolyl isoxazole of formula (I) as defined above, or a pharmaceutically acceptable salt thereof, for use as a modulator of p300 and/or CBP activity.

DETAILED DESCRIPTION OF THE INVENTION

The term "substituted" includes the implicit provision that substitution be in accordance with the permitted valence of the substituted atom and the substituent and that the substitution results in a stable compound (i.e. one that does not spontaneously undergo transformation such as a rearrangement cyclisation, or elimination). In certain embodiments, a single atom may be substituted with more than one substituent as long as such substitution is in accordance with the permitted valence of the atom. In certain embodiments, a group that is substituted may be substituted by one substituent group or it may be multiply substituted on multiple carbon atoms. When any group defined herein is substituted, it is typically substituted by $R^{10}$ as defined below. The group may, for instance, be mono-, di- or tri-substituted by a group $R^{10}$ as defined below.

In certain of the arylimidazolyl isoxazoles of formula (I), dependant on the nature of the substituent, there may be chiral carbon atoms and therefore the compounds may exist as stereoisomers. The invention extends to all optical isomers such as stereoisomeric forms of the compounds of formula (I), including enantiomers, diastereomers and mixtures thereof, such as racemates. The different stereoisomeric forms may be separated or resolved one from the other by conventional methods or any given isomer may be obtained by conventional stereoselective or sterospecific syntheses.

The compounds of the invention can exist in various tautomeric forms and it is to be understood that the invention encompasses all such tautomeric forms.

It is understood that certain compounds of the invention contain both acidic and basic groups and may therefore exist as zwitterions at certain pH values.

It is also to be understood that any atom present in a compound of the invention may be present in any available naturally-occurring isotopic form. For instance, a carbon atom may be $^{12}$C or $^{13}$C. A hydrogen atom may be $^{1}$H or $^{2}$H (deuterium).

As used herein, the terms "treat" and "treatment" refer to both therapeutic treatment and prophylactic or preventative measures, wherein the object is to prevent or slow down (lessen) an undesired physiological change or disorder, such as the development or spread of cancer. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "pharmaceutically acceptable" indicates that the substance or composition must be compatible chemically and/or toxicologically with the other ingredients comprising a formulation, and/or the patient being treated therewith.

A $C_{1-6}$ alkyl group or moiety is linear or branched. A $C_{1-6}$ alkyl group is typically a $C_{1-4}$ alkyl group, or a $C_{1-2}$ alkyl group. Examples of $C_{1-6}$ alkyl groups and moieties include methyl, ethyl, n-propyl, i-propyl, n-butyl, i-butyl, t-butyl, n-pentyl, i-pentyl (i.e. 3-methylbut-1-yl), t-pentyl (i.e. 2-methylbut-2-yl), neopentyl (i.e. 2,2-dimethylpropan-1-yl), n-hexyl, i-hexyl (i.e. 4-methylpentan-1-yl), t-hexyl (i.e. 3-methylpentan-3-yl) and neopentyl (i.e. 3,3-dimethylbutan-1-yl). Typically a $C_{1-6}$ alkyl group is methyl (Me). For the avoidance of doubt, where two alkyl moieties are present in a group, the alkyl moieties may be the same or different. A $C_{1-6}$ alkyl group is unsubstituted or substituted, typically by one or more groups $R^{10}$ as defined below. For example, a $C_{1-6}$ alkyl group is unsubstituted or substituted by 1, 2 or 3 groups $R^{10}$ as defined below.

A $C_{1-6}$ alkylene group or moiety is an unsubstituted or substituted, linear or branched, saturated divalent aliphatic hydrocarbon group or moiety containing 1 to 6 carbon atoms. Typically it is a $C_{1-3}$ alkylene group or moiety. Examples include methylene, ethylene, n-propylene and i-propylene groups and moieties. More typically it is methylene or ethylene. When the alkylene group is substituted it is typically substituted by a group $R^{10}$ as defined below.

A $C_{3-6}$ cycloalkyl group or moiety is a saturated monovalent hydrocarbon ring having 3 to 6 carbon atoms. It is thus a 3-, 4-, 5- or 6-membered carbocyclic ring containing only saturated bonds. Examples of a cycloalkyl group include cyclopropyl, cyclobutyl, cyclopentyl and cyclohexyl. In one embodiment a cycloalkyl group is cyclopropyl.

A 5- to 12-membered N-containing heteroaryl group or moiety is a monovalent 5- to 12-membered aromatic heterocyclic group which contains 1, 2, 3, or 4 nitrogen atoms, typically 1 or 2 N atoms, and 0, 1 or 2 other heteroatoms selected from O and S. It is linked via one of its ring N atoms or C atoms and is monocyclic or bicyclic. In one embodiment it is N-linked. In another embodiment it is C-linked. It may be, for example, a 5- to 7-membered N-containing monocyclic heteroaryl group, for instance a 5- or 6-membered N-containing heteroaryl group such as pyrrolyl, imidazolyl, pyridyl, pyrimidinyl, pyrazinyl, thiazolyl, isothiazolyl, oxazolyl or isoxazolyl.

Examples of a 5- to 12-membered, N-containing heteroaryl group include pyrrolyl, imidazolyl, pyridyl, pyrazinyl, pyrimidinyl, thiazolyl, isothiazolyl, oxazolyl, isoxazolyl, quinolyl, isoquinolyl, quinazolinyl, quinoxalinyl, indolyl, isoindolyl, indazolyl, pyrrolopyridinyl and pyrrolopyrimidinyl groups. When substituted, a 5- to 12-membered, N-containing heteroaryl group is typically substituted by one or more, e.g. 1, 2 or 3, groups selected from unsubstituted $C_{1-4}$ alkyl and a group $R^{10}$ as defined below In one embodiment a 5- to 12-membered, N-containing heteroaryl group is unsubstituted.

A 4- to 6-membered C-linked heterocyclic group is a saturated monovalent 4-, 5- or 6-membered heterocyclic ring containing at least one heteroatom selected from O, N and S. It is linked via one of its ring C atoms. Examples include oxetane, thietane, azetidine, pyrrolidine, piperidine, tetrahydropyran, tetrahydrothiopyran and tetrahydrofuran. A 4- to 6-membered C-linked, heterocyclic group is unsubstituted or substituted, typically by a group $R^{10}$ as defined below. It may be substituted on a ring carbon atom or on a ring N or S atom, as permitted by the valency of the atom.

A halogen or halo group is F, Cl, Br or I. Typically it is F, Cl or Br, more typically F.

A $C_{1-6}$ alkoxy group is linear or branched. It is typically a $C_{1-4}$ alkoxy group, for example a methoxy, ethoxy, propoxy, i-propoxy, n-propoxy, n-butoxy, sec-butoxy or tert-butoxy group. A $C_{1-6}$ alkoxy group is unsubstituted or substituted, typically by one or more groups $R^{10}$ as defined below.

When in formula (I) $R^1$ is substituted, the substituents are typically 1, 2 or 3 groups, more typically 1 or 2 groups, which are the same or different and are selected from —SO$_2$Me, —SO$_2$-cyclopropyl, oxo (═O), $C_1$-$C_6$ alkoxy, OH, hydroxy($C_1$-$C_6$)alkyl, halo, —NH$_2$, OH, CN, —OC(O)R″, —C(O)NHR″, —NHC(O)R″ and —COOR″, where R″ is H or $C_1$-$C_6$ alkyl optionally substituted by halo. In this context halo is typically F or Cl.

The 4- to 6-membered heterocyclyl is typically pyrrolidinyl, piperidinyl, tetrahydropyranyl or tetrahydrothiopyranyl. More typically it is pyrrolidin-3-yl, piperidin-4-yl, tetrahydropyran-4-yl or tetrahydrothiopyran-4-yl. Pyrrolidinyl and piperidinyl are typically substituted on the ring N atom by —SO$_2$Me or $C_1$-$C_6$ alkyl (e.g. methyl). Tetrahydropyranyl is typically substituted on a ring C atom by $C_1$-$C_6$ alkyl (e.g. methyl). Tetrahydrothiopyranyl is typically di-substituted on the ring S atom by oxo.

The $C_3$-$C_6$ cycloalkyl group is typically cyclobutyl, cyclopropyl or cyclohexyl. Cycloalkyl is typically substituted by 1 or 2 groups selected from halo, OH and $C_1$-$C_6$ alkoxy.

In the definition of $R^1$, $C_1$-$C_6$ alkyl substituted by 5- to 12-membered N-containing heteroaryl is typically $C_1$-$C_6$ alkyl, for instance methyl or ethyl, substituted by a 5- or 6-membered N-containing heteroaryl as defined above. Typical examples of $R^1$ in formula (I) as defined above include the following groupings:

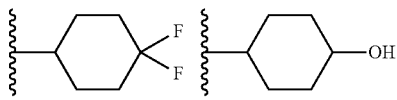

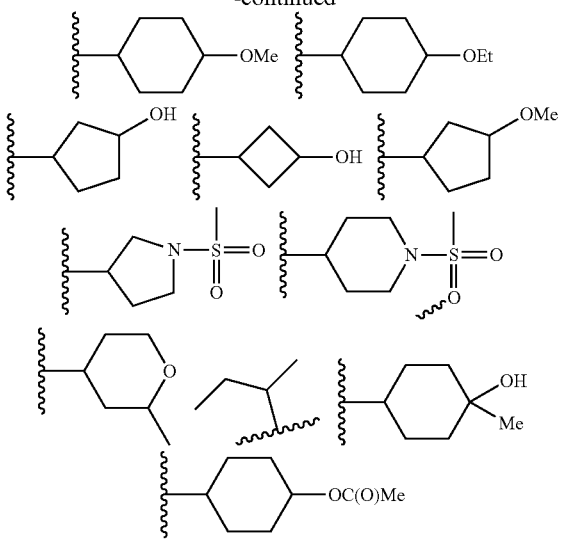

Each of $R^0$ and R in formula (I) is independently H or $C_{1-6}$ alkyl which is unsubstituted or substituted as defined above. Thus, for instance, $R^0$ is H and R is $C_{1-6}$ alkyl which is unsubstituted or substituted as defined above; R is H and $R^0$ is $C_{1-6}$ alkyl which is unsubstituted or substituted as defined above; each of $R^0$ and R is H; or each of $R^0$ and R is $C_{1-6}$ alkyl which is unsubstituted or substituted as defined above. In each of these variants $C_{1-6}$ alkyl is typically methyl or ethyl, preferably methyl.

The integer n in formula (I) as defined above is 0 or 1, typically 0.

Y is typically —CH$_2$— or —CH$_2$CH$_2$— such that the ring containing it is a 5- or 6-membered ring. When Y is —CH$_2$— the ring is pyrrolidin-2-one. When Y is —CH$_2$CH$_2$— the ring is piperidin-2-one. More typically Y is —CH$_2$CH$_2$— and the ring containing it is the 6-membered piperidin-2-one ring.

$R^2$ is typically aromatic. It is therefore typically a $C_6$-$C_{10}$ aryl or $C_5$-$C_6$ heteroaryl group wherein $C_6$-$C_{10}$ aryl is optionally fused to a 5- or 6-membered heterocyclic ring. The $C_6$-$C_{10}$ aryl group is typically phenyl or naphthyl. A $C_6$-$C_{10}$ aryl group fused to a 5- or 6-membered heterocyclic ring is typically a tetrahydrobenzofuranyl group.

When $R^2$ is a $C_6$-$C_{10}$ aryl group, for instance phenyl, it is typically mono-, di- or tri-substituted. The substituents are 1, 2 or 3 groups which are the same or different and are typically selected from $C_1$-$C_6$ alkyl, $C_1$-$C_6$ alkoxy, OH, cyano and halo, wherein the alkyl and alkoxy groups are each optionally substituted by halo. Halo in this context is typically F or Cl.

When the $C_6$-$C_{10}$ aryl group is phenyl, it is typically substituted by 1, 2 or 3 groups, more typically 1 or 2 groups. The 1 or 2 groups are typically positioned meta and/or para on the phenyl ring. The groups are typically selected from halo, OH, $C_1$-$C_6$ alkyl, $C_1$-$C_6$ alkoxy and CN.

$R^{10}$ is selected from unsubstituted $C_{1-6}$ alkyl, $C_{3-6}$ cycloalkyl, halo, OH, $C_{1-6}$ alkoxy, —C(O)R‴, —C(O)$_2$R‴, —C(O)NR‴$_2$, oxo (═O), dioxo, —CH$_2$OR‴, —S(O)$_m$R‴, —NR‴C(O)R‴, —S(O)$_m$NR‴$_2$, and CF$_3$, wherein m is 1 or 2 and each R‴ is independently selected from H and unsubstituted $C_{1-6}$ alkyl. Typically $R^{10}$ is selected from unsubstituted $C_{1-6}$ alkyl, halo, OH, $C_{1-6}$ alkoxy, —C(O)R‴, —C(O)NR‴$_2$, oxo (═O) and dioxo.

In one preferred embodiment, the arylimidazolyl isoxazole of the invention has the following formula (Ia):

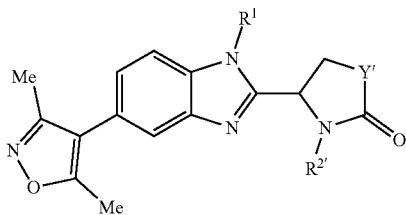 (Ia)

wherein
$R^1$ is as defined above for formula (I);
Y' is —$CH_2$— or —$CH_2CH_2$—; and
$R^{2'}$ is a group selected from $C_6$-$C_{10}$ aryl optionally fused to a 5- or 6-membered heterocyclic ring and $C_5$-$C_6$ heteroaryl, the group being unsubstituted or mono-, di- or tri-substituted.

Compounds of the invention may contain asymmetric or chiral centres and thus exist in different stereoisomeric forms. The structural formulae (I) and (Ia) above encompass all stereoisomeric forms of the compounds of the invention including disastereomers, enantiomers and racemic mixtures. Diastereomers and enantiomers may be obtained by stereoselective synthetic strategies, for instance via enantiomeric synthesis.

Stereoisomerism may occur in compounds of the present invention due to the presence of an asymmetric carbon atom in the piperidin-2-one or pyrrolidin-2-one ring. Thus, as depicted in the structural formula below:

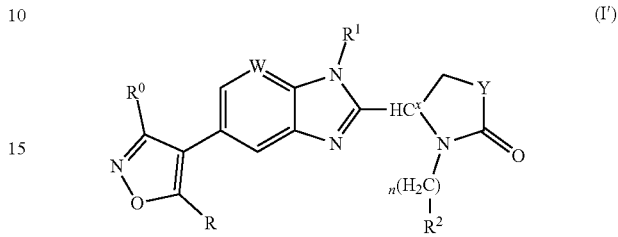 (I')

the carbon centre $C^x$ is chiral and each of R, $R^0$, W, $R^1$, Y, $R^2$ and n is as defined above for formula (I). The chirality at $C^x$ means that a compound of the invention can be racemic or optically pure. When optically pure it may be the R enantiomer or the S enantiomer, typically the S enantiomer.

Specific examples of compounds of the invention include those listed in the following table:

| No | Structure | Name |
|---|---|---|
| 1 | 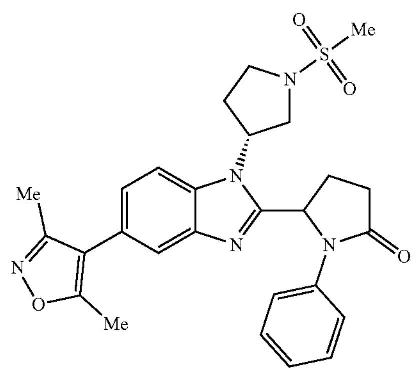 [SMILES: Cc1noc(C)c1-c1ccc2c(c1)nc(C1CCC(=O)N1c1ccccc1)n2[C@@H]1CCN(S(C)(=O)=O)C1] | 5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one |
| 2 | 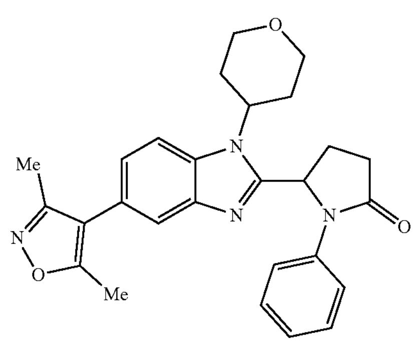 [SMILES: Cc1noc(C)c1-c1ccc2c(c1)nc(C1CCC(=O)N1c1ccccc1)n2C1CCOCC1] | 5-(5-(3,5-dimethylisoxazol-4-yl)-1-(tetrahydro-2H-pyran-4-yl)-1H-benzo[d]imidazol-2-yl)-1-phenylpyrrolidin-2-one |

-continued

| No | Structure | Name |
|---|---|---|
| 3 | 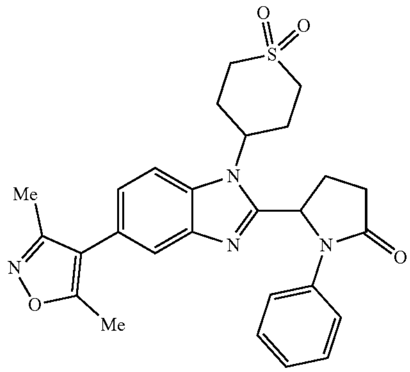 [SMILES: Cc1noc(C)c1-c1ccc2c(c1)nc(C1CCC(=O)N1c1ccccc1)n2C1CCS(=O)(=O)CC1] | 5-(5-(3,5-dimethylisoxazol-4-yl)-1-(1,1-dioxidotetrahydro-2H-thiopyran-4-yl)-1H-benzo[d]imidazol-2-yl)-1-phenylpyrrolidin-2-one |
| 4 | 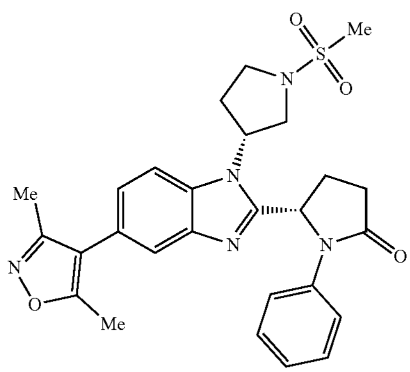 [SMILES: Cc1noc(C)c1-c1ccc2c(c1)nc([C@@H]1CCC(=O)N1c1ccccc1)n2[C@@H]1CCN(S(C)(=O)=O)C1] | (S)-5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one |
| 5 | 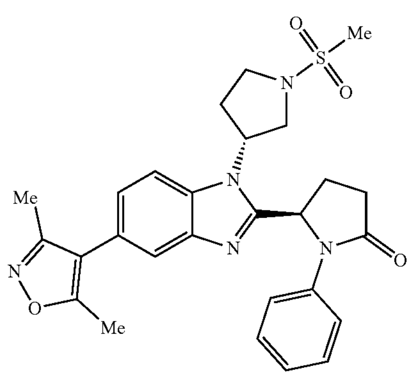 [SMILES: Cc1noc(C)c1-c1ccc2c(c1)nc([C@H]1CCC(=O)N1c1ccccc1)n2[C@@H]1CCN(S(C)(=O)=O)C1] | (R)-5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one |
| 6 | 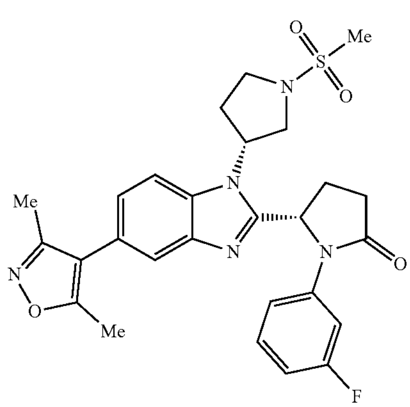 [SMILES: Cc1noc(C)c1-c1ccc2c(c1)nc([C@@H]1CCC(=O)N1c1cccc(F)c1)n2[C@@H]1CCN(S(C)(=O)=O)C1] | (S)-5-(5-(3,5-dimethylisoxazol-4-yl)-1-((R)-1-(methylsulfonyl)pyrrolidin-3-yl)-1H-benzo[d]imidazol-2-yl)-1-(3-fluorophenyl)pyrrolidin-2-one |

-continued

| No | Structure | Name |
|---|---|---|
| 7 | 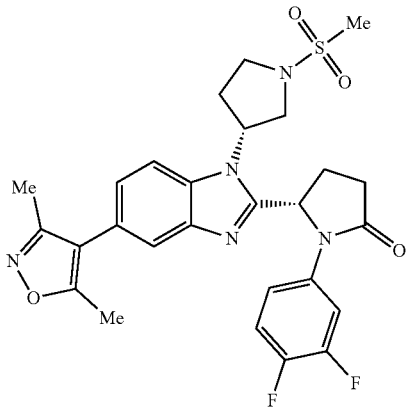 [SMILES: Cc1noc(C)c1-c1ccc2c(c1)nc([C@@H]1CCC(=O)N1c1ccc(F)c(F)c1)n2[C@@H]1CCN(S(C)(=O)=O)C1] | (S)-1-(3,4-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 8 | 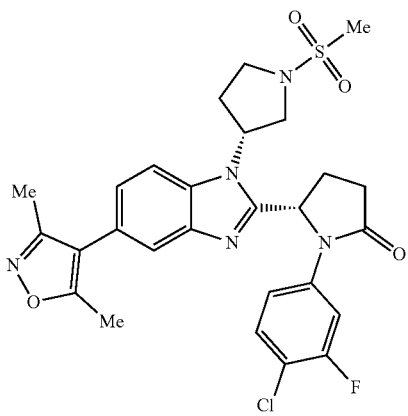 [SMILES: Cc1noc(C)c1-c1ccc2c(c1)nc([C@@H]1CCC(=O)N1c1ccc(Cl)c(F)c1)n2[C@@H]1CCN(S(C)(=O)=O)C1] | (S)-1-(4-chloro-3-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 9 | 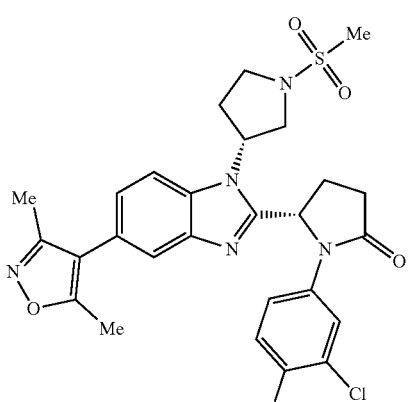 | (S)-1-(3-chloro-4-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |

-continued

| No | Structure | Name |
|---|---|---|
| 10 | 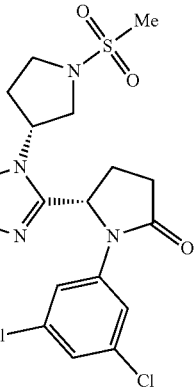 | (S)-1-(3,5-dichlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 11 | 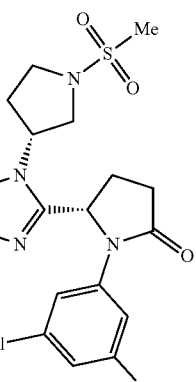 | (S)-1-(3-chloro-5-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 12 | 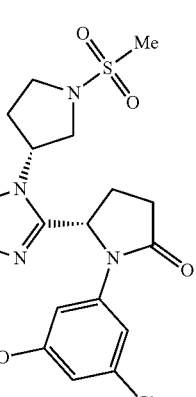 | (S)-1-(3-chloro-5-methoxyphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 13 | 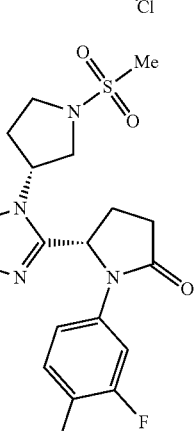 | (S)-5-(5-(3,5-dimethylisoxazol-4-yl)-1-((R)-1-(methylsulfonyl)pyrrolidin-3-yl)-1H-benzo[d]imidazol-2-yl)-1-(3-fluoro-4-methoxyphenyl)pyrrolidin-2-one |

-continued

| No | Structure | Name |
| --- | --- | --- |
| 14 | 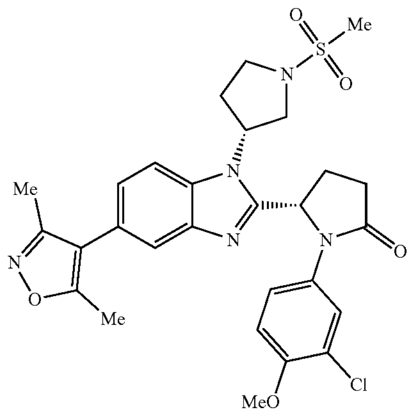 [SMILES: COc1ccc(N2C(=O)CC[C@H]2c2nc3cc(-c4c(C)noc4C)ccc3n2[C@@H]2CCN(S(C)(=O)=O)C2)cc1Cl] | (S)-1-(3-chloro-4-methoxyphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 15 | 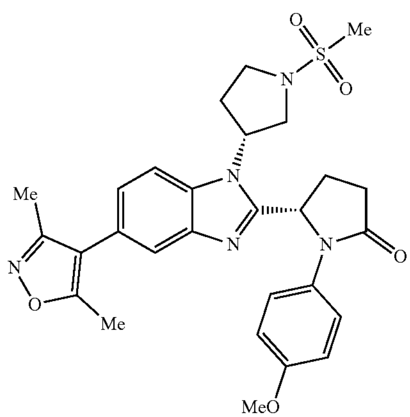 [SMILES: COc1ccc(N2C(=O)CC[C@H]2c2nc3cc(-c4c(C)noc4C)ccc3n2[C@@H]2CCN(S(C)(=O)=O)C2)cc1] | (S)-5-(5-(3,5-dimethylisoxazol-4-yl)-1-((R)-1-(methylsulfonyl)pyrrolidin-3-yl)-1H-benzo[d]imidazol-2-yl)-1-(4-methoxyphenyl)pyrrolidin-2-one |
| 16 | 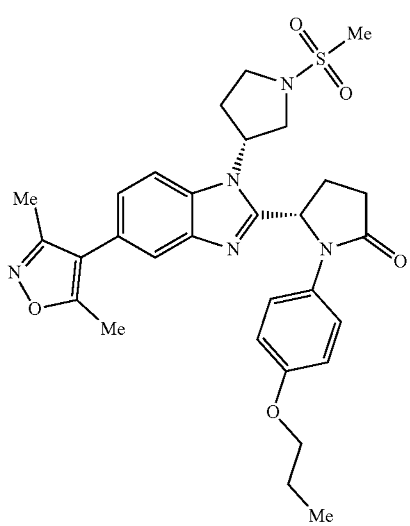 [SMILES: CCCOc1ccc(N2C(=O)CC[C@H]2c2nc3cc(-c4c(C)noc4C)ccc3n2[C@@H]2CCN(S(C)(=O)=O)C2)cc1] | (S)-5-(5-(3,5-dimethylisoxazol-4-yl)-1-((R)-1-(methylsulfonyl)pyrrolidin-3-yl)-1H-benzo[d]imidazol-2-yl)-1-(4-propoxyphenyl)pyrrolidin-2-one |

-continued

| No | Structure | Name |
|---|---|---|
| 17 | 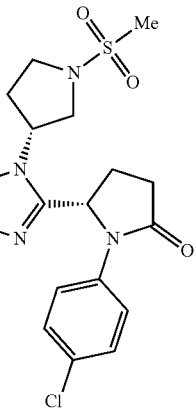 | (S)-1-(4-chlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 18 | 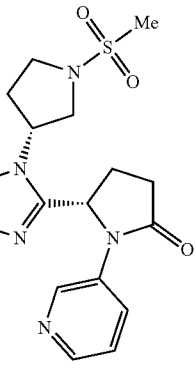 | (S)-5-(5-(3,5-dimethylisoxazol-4-yl)-1-((R)-1-(methylsulfonyl)pyrrolidin-3-yl)-1H-benzo[d]imidazol-2-yl)-1-(pyridin-3-yl)pyrrolidin-2-one |
| 19 | 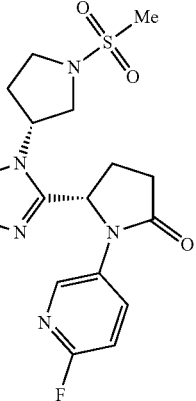 | (S)-5-(5-(3,5-dimethylisoxazol-4-yl)-1-((R)-1-(methylsulfonyl)pyrrolidin-3-yl)-1H-benzo[d]imidazol-2-yl)-1-(6-fluoropyridin-3-yl)pyrrolidin-2-one |
| 20 | 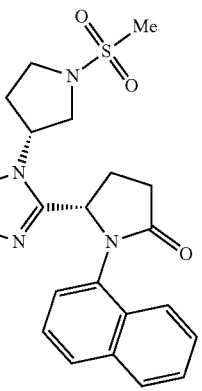 | (S)-5-(5-(3,5-dimethylisoxazol-4-yl)-1-((R)-1-(methylsulfonyl)pyrrolidin-3-yl)-1H-benzo[d]imidazol-2-yl)-1-(naphthalen-1-yl)pyrrolidin-2-one |

-continued

| No | Structure | Name |
|---|---|---|
| 22 | 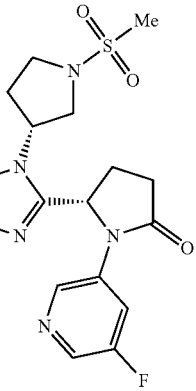 | (S)-5-(5-(3,5-dimethylisoxazol-4-yl)-1-((R)-1-(methylsulfonyl)pyrrolidin-3-yl)-1H-benzo[d]imidazol-2-yl)-1-(5-fluoropyridin-3-yl)pyrrolidine-2-one |
| 23 | 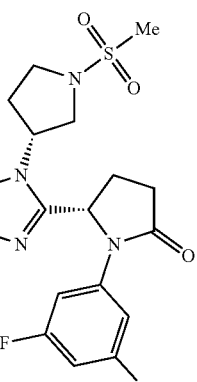 | (S)-1-(3,5-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 24 | 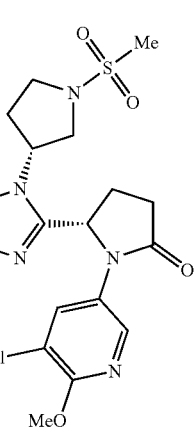 | (S)-1-(5-chloro-6-methoxypyridin-3-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 25 | 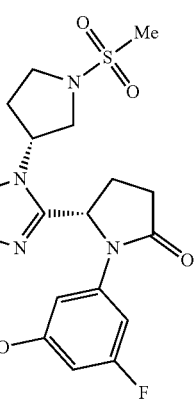 | (S)-5-(5-(3,5-dimethylisoxazol-4-yl)-1-((R)-1-(methylsulfonyl)pyrrolidin-3-yl)-1H-benzo[d]imidazol-2-yl)-1-(3-fluoro-5-methoxyphenyl)pyrrolidin-2-one |

-continued

| No | Structure | Name |
|----|-----------|------|
| 26 | 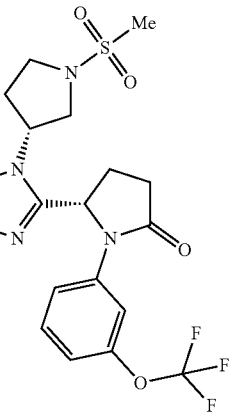 | (S)-5-(5-(3,5-dimethylisoxazol-4-yl)-1-((R)-1-(methylsulfonyl)pyrrolidin-3-yl)-1H-benzo[d]imidazol-2-yl)-1-(3-(trifluoromethoxy)phenyl)pyrrolidin-2-one |
| 27 | 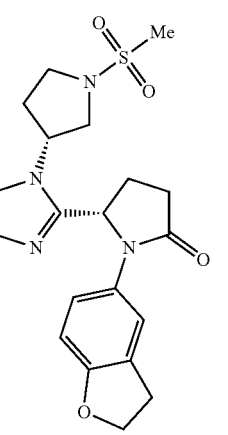 | (S)-1-(2,3-dihydrobenzofuran-5-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 28 | 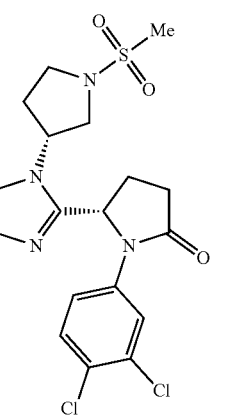 | (S)-1-(3,4-dichlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |

| No | Structure | Name |
|---|---|---|
| 29 | 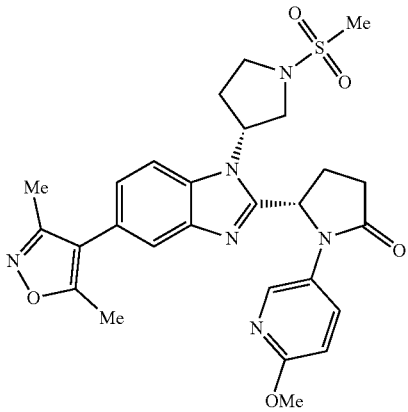 [SMILES: COc1ccc(N2C(=O)CC[C@H]2c2nc3cc(-c4c(C)noc4C)ccc3n2[C@@H]2CCN(S(C)(=O)=O)C2)cn1] | (S)-5-(5-(3,5-dimethylisoxazol-4-yl)-1-((R)-1-(methylsulfonyl)pyrrolidin-3-yl)-1H-benzo[d]imidazol-2-yl)-1-(6-methoxypyridin-3-yl)pyrrolidin-2-one |
| 30 | 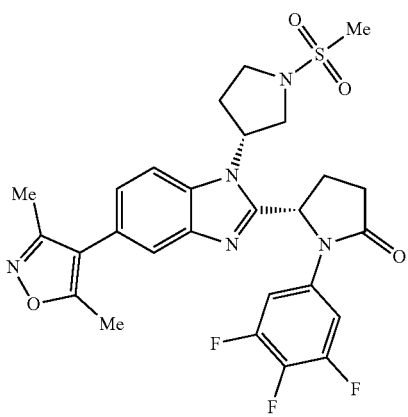 [SMILES: Cc1noc(C)c1-c1ccc2c(c1)nc([C@@H]1CCC(=O)N1c1cc(F)c(F)c(F)c1)n2[C@@H]1CCN(S(C)(=O)=O)C1] | (S)-5-(5-(3,5-dimethylisoxazol-4-yl)-1-((R)-1-(methylsulfonyl)pyrrolidin-3-yl)-1H-benzo[d]imidazol-2-yl)-1-(3,4,5-trifluorophenyl)pyrrolidin-2-one |
| 31 | 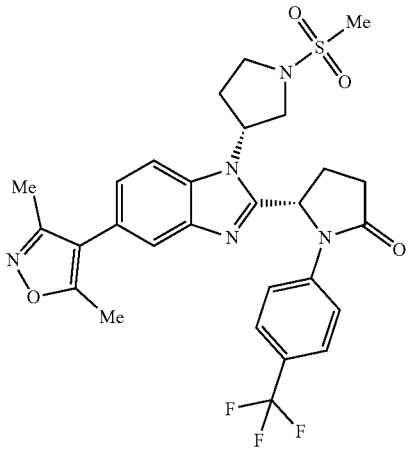 [SMILES: Cc1noc(C)c1-c1ccc2c(c1)nc([C@@H]1CCC(=O)N1c1ccc(C(F)(F)F)cc1)n2[C@@H]1CCN(S(C)(=O)=O)C1] | (S)-5-(5-(3,5-dimethylisoxazol-4-yl)-1-((R)-1-(methylsulfonyl)pyrrolidin-3-yl)-1H-benzo[d]imidazol-2-yl)-1-(4-(trifluoromethyl)phenyl)pyrrolidin-2-one |

-continued
| No | Structure | Name |
|---|---|---|
| 32 | 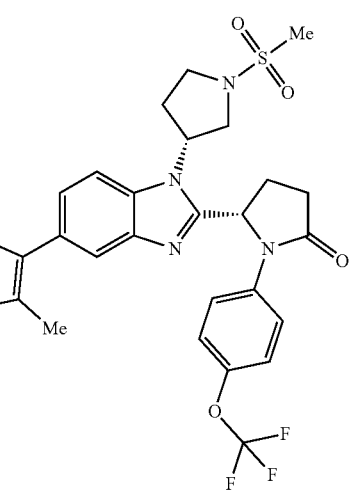 | (S)-5-(5-(3,5-dimethylisoxazol-4-yl)-1-((R)-1-(methylsulfonyl)pyrrolidin-3-yl)-1H-benzo[d]imidazol-2-yl)-1-(4-(trifluoromethoxy)phenyl)pyrrolidin-2-one |
| 33 | 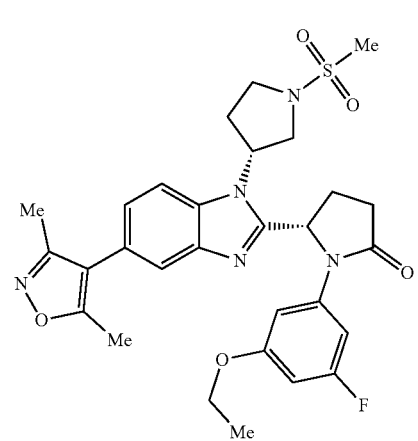 [SMILES: CCOc1cc(F)cc(N2C(=O)CC[C@H]2c2nc3cc(-c4c(C)noc4C)ccc3n2[C@@H]2CCN(S(C)(=O)=O)C2)c1] | (S)-5-(5-(3,5-dimethylisoxazol-4-yl)-1-((R)-1-(methylsulfonyl)pyrrolidin-3-yl)-1H-benzo[d]imidazol-2-yl)-1-(3-ethoxy-5-fluorophenyl)pyrrolidin-2-one |
| 34 | 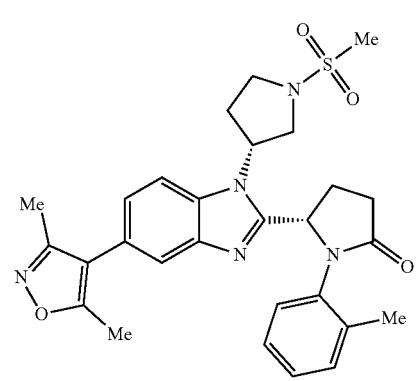 [SMILES: Cc1ccccc1N1C(=O)CC[C@H]1c1nc2cc(-c3c(C)noc3C)ccc2n1[C@@H]1CCN(S(C)(=O)=O)C1] | (S)-5-(5-(3,5-dimethylisoxazol-4-yl)-1-((R)-1-(methylsulfonyl)pyrrolidin-3-yl)-1H-benzo[d]imidazol-2-yl)-1-(o-tolyl)pyrrolidin-2-one |

-continued

| No | Structure | Name |
|---|---|---|
| 35 | 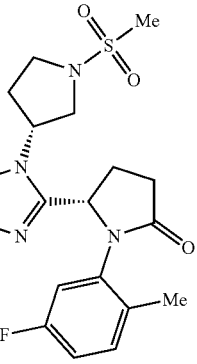 | (S)-5-(5-(3,5-dimethylisoxazol-4-yl)-1-((R)-1-(methylsulfonyl)pyrrolidin-3-yl)-1H-benzo[d]imidazol-2-yl)-1-(5-fluoro-2-methylphenyl)pyrrolidin-2-one |
| 36 | 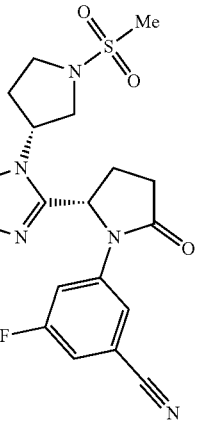 | 3-((S)-2-(5-(3,5-dimethylisoxazol-4-yl)-1-((R)-1-(methylsulfonyl)pyrrolidin-3-yl)-1H-benzo[d]imidazol-2-yl)-5-oxopyrrolidin-1-yl)-5-fluorobenzonitrile |
| 37 | 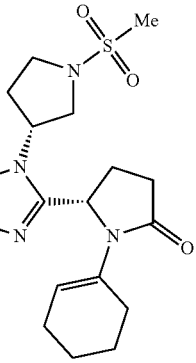 | (S)-1-(cyclohex-1-en-1-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 38 | 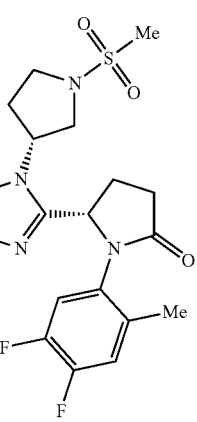 | (S)-1-(4,5-difluoro-2-methylphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |

-continued

| No | Structure | Name |
|----|-----------|------|
| 39 | 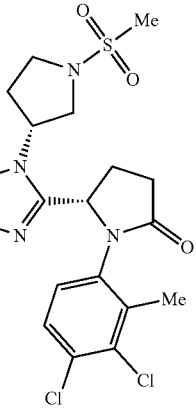 | (S)-1-(3,4-dichloro-2-methylphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 40 | 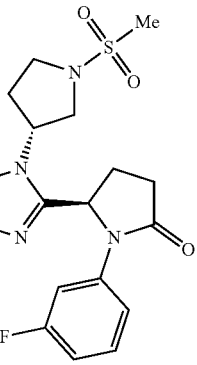 | (R)-5-(5-(3,5-dimethylisoxazol-4-yl)-1-((R)-1-(methylsulfonyl)pyrrolidin-3-yl)-1H-benzo[d]imidazol-2-yl)-1-(3-fluorophenyl)pyrrolidin-2-one |
| 41 | 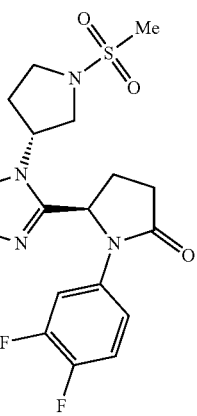 | (R)-1-(3,4-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 42 | 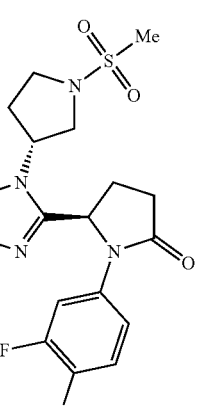 | (R)-1-(4-chloro-3-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |

-continued

| No | Structure | Name |
|---|---|---|
| 43 | 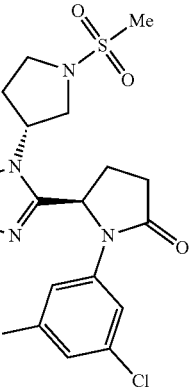 | (R)-1-(3,5-dichlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 44 | 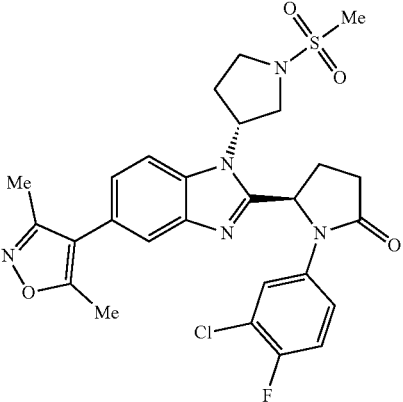 [SMILES: Cc1noc(C)c1-c1ccc2c(c1)nc([C@H]1CCC(=O)N1c1ccc(Cl)c(F)c1)n2[C@@H]1CCN(S(C)(=O)=O)C1] | (R)-1-(3-chloro-4-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |
| 45 | 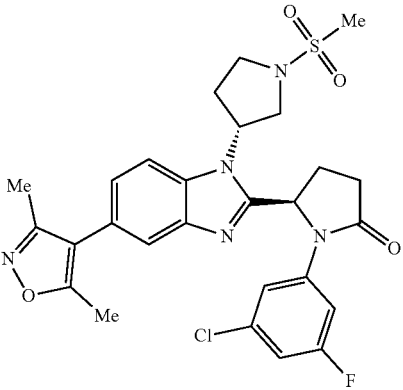 [SMILES: Cc1noc(C)c1-c1ccc2c(c1)nc([C@H]1CCC(=O)N1c1cc(F)cc(Cl)c1)n2[C@@H]1CCN(S(C)(=O)=O)C1] | (R)-1-(3-chloro-5-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one |

| No | Structure | Name |
| --- | --- | --- |
| 46 | 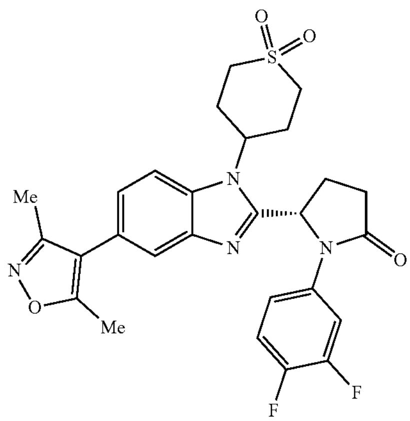 | (S)-1-(3,4-difluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one |
| 47 | 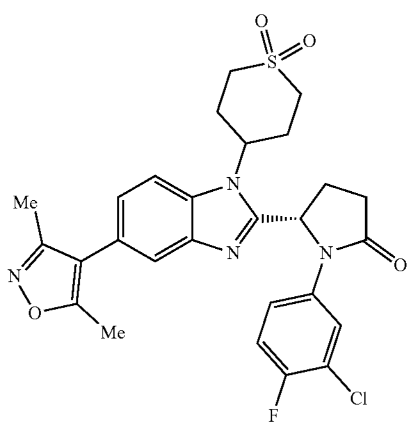 | (S)-1-(3-chloro-4-fluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one |
| 48 | 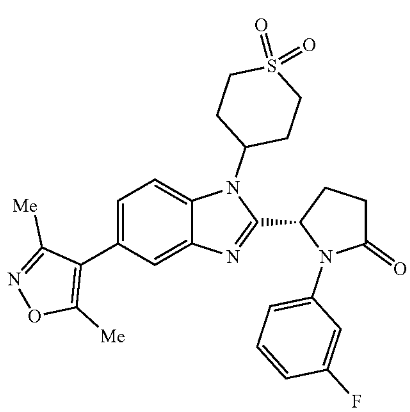 [SMILES: Cc1noc(C)c1-c1ccc2c(c1)nc([C@@H]1CCC(=O)N1c1cccc(F)c1)n2C1CCS(=O)(=O)CC1] | (S)-5-(5-(3,5-dimethylisoxazol-4-yl)-1-(1,1-dioxidotetrahydro-2H-thiopyran-4-yl)-1H-benzo[d]imidazol-2-yl)-1-(3-fluorophenyl)pyrrolidin-2-one |

-continued

| No | Structure | Name |
|----|-----------|------|
| 49 | 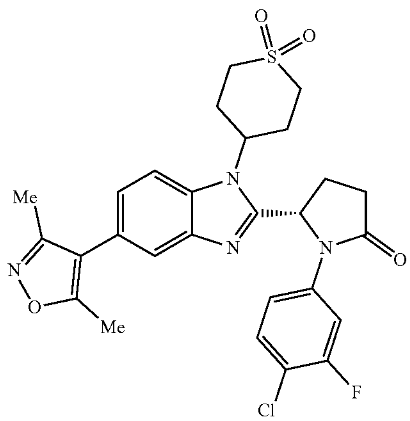 [SMILES: Cc1noc(C)c1-c1ccc2c(c1)nc([C@@H]1CCC(=O)N1c1ccc(Cl)c(F)c1)n2C1CCS(=O)(=O)CC1] | (S)-1-(4-chloro-3-fluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one |
| 50 | 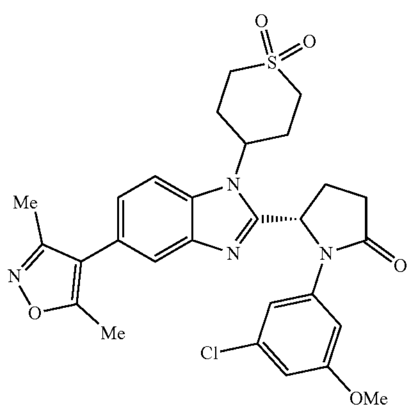 [SMILES: COc1cc(Cl)cc(N2C(=O)CC[C@H]2c2nc3cc(-c4c(C)noc4C)ccc3n2C2CCS(=O)(=O)CC2)c1] | (S)-1-(3-chloro-5-methoxyphenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one |
| 51 | 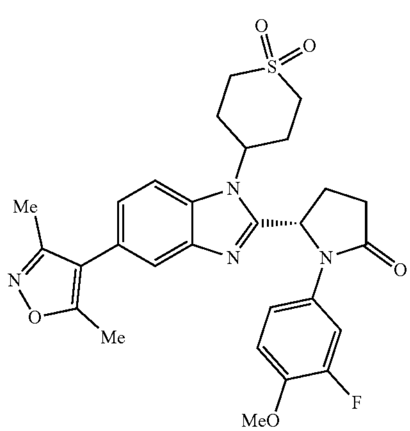 [SMILES: COc1ccc(N2C(=O)CC[C@H]2c2nc3cc(-c4c(C)noc4C)ccc3n2C2CCS(=O)(=O)CC2)cc1F] | (S)-5-(5-(3,5-dimethylisoxazol-4-yl)-1-(1,1-dioxidotetrahydro-2H-thiopyran-4-yl)-1H-benzo[d]imidazol-2-yl)-1-(3-fluoro-4-methoxyphenyl)pyrrolidin-2-one |

-continued

| No | Structure | Name |
|---|---|---|
| 52 | 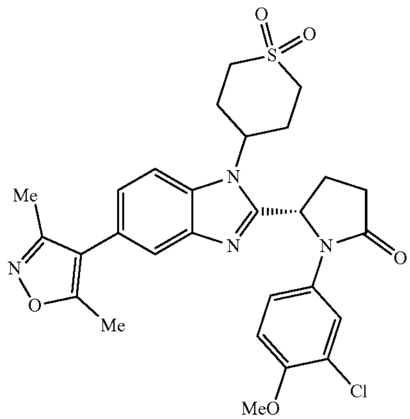 [SMILES: COc1ccc(N2C(=O)CC[C@H]2c2nc3cc(-c4c(C)noc4C)ccc3n2C2CCS(=O)(=O)CC2)cc1Cl] | (S)-1-(3-chloro-4-methoxyphenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one |
| 53 | 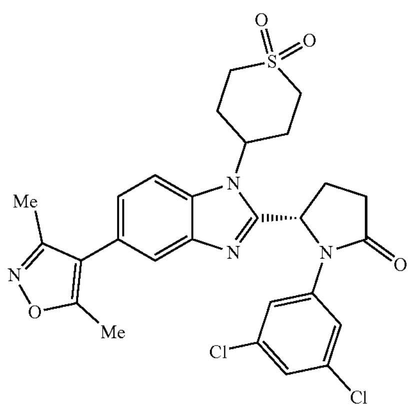 [SMILES: Cc1noc(C)c1-c1ccc2c(c1)nc([C@@H]1CCC(=O)N1c1cc(Cl)cc(Cl)c1)n2C1CCS(=O)(=O)CC1] | (S)-1-(3,5-dichlorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one |
| 54 | 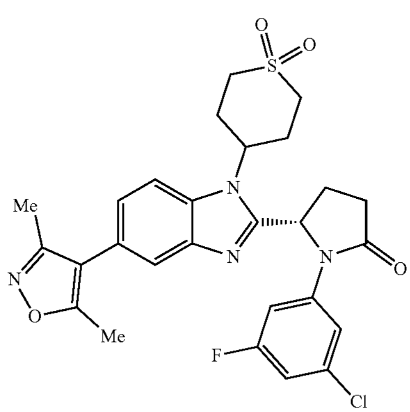 [SMILES: Cc1noc(C)c1-c1ccc2c(c1)nc([C@@H]1CCC(=O)N1c1cc(F)cc(Cl)c1)n2C1CCS(=O)(=O)CC1] | (S)-1-(3-chloro-5-fluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one |

| No | Structure | Name |
|---|---|---|
| 55 | 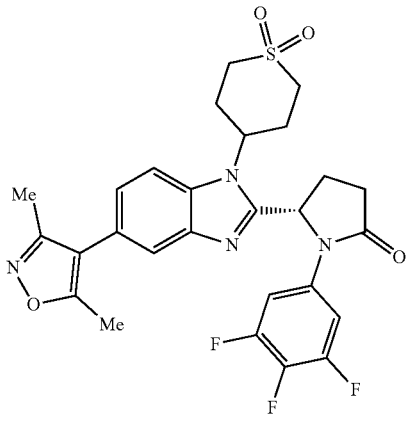 [SMILES: Cc1noc(C)c1-c1ccc2c(c1)nc([C@@H]1CCC(=O)N1c1cc(F)c(F)c(F)c1)n2C1CCS(=O)(=O)CC1] | (S)-5-(5-(3,5-dimethylisoxazol-4-yl)-1-(1,1-dioxidotetrahydro-2H-thiopyran-4-yl)-1H-benzo[d]imidazol-2-yl)-1-(3,4,5-trifluorophenyl)pyrrolidin-2-one |
| 56 | 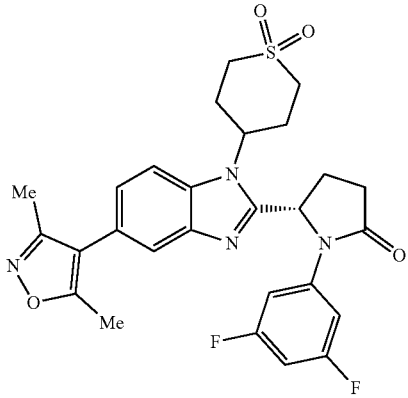 [SMILES: Cc1noc(C)c1-c1ccc2c(c1)nc([C@@H]1CCC(=O)N1c1cc(F)cc(F)c1)n2C1CCS(=O)(=O)CC1] | (S)-1-(3,5-difluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one |
| 57 | 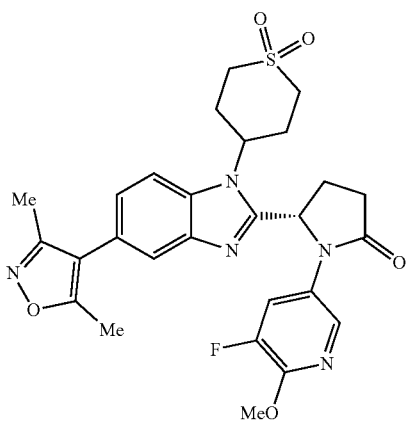 [SMILES: COc1ncc(N2C(=O)CC[C@H]2c2nc3cc(-c4c(C)noc4C)ccc3n2C2CCS(=O)(=O)CC2)cc1F] | (S)-5-(5-(3,5-dimethylisoxazol-4-yl)-1-(1,1-dioxidotetrahydro-2H-thiopyran-4-yl)-1H-benzo[d]imidazol-2-yl)-1-(5-fluoro-6-methoxypyridin-3-yl)pyrrolidin-2-one |

-continued

| No | Structure | Name |
|---|---|---|
| 58 | 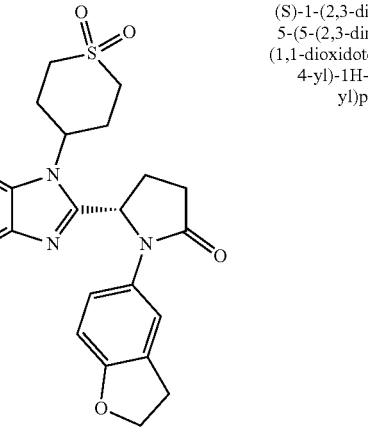 | (S)-1-(2,3-dihydrobenzofuran-5-yl)-5-(5-(2,3-dimethylisoxazol-4-yl)-1-(1,1-dioxidotetrahydro-2H-thiopyran-4-yl)-1H-benzo[d]imidazol-2-yl)pyrrolidin-2-one |
| 59 | 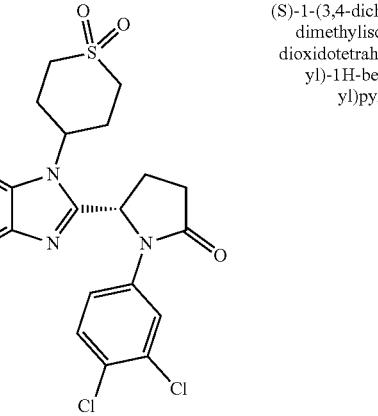 | (S)-1-(3,4-dichlorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one |
| E4 | 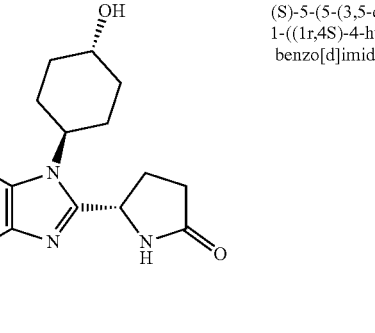 | (S)-5-(5-(3,5-dimethylisoxazol-4-yl)-1-((1r,4S)-4-hydroxycyclohexyl)-1H-benzo[d]imidazol-2-yl)pyrrolidin-2-one |
| 61 | 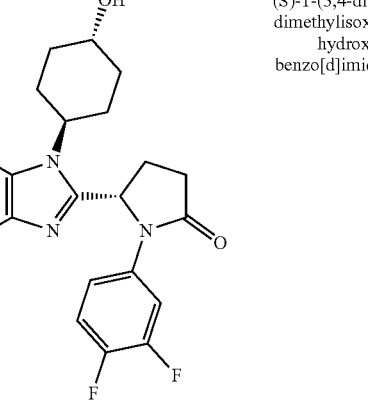 | (S)-1-(3,4-difluorophenyl)-5-(5-(3,5-dimethylisoxazol-4-yl)-1-((1r,4S)-4-hydroxycyclohexyl)-1H-benzo[d]imidazol-2-yl)pyrrolidin-2-one |

| No | Structure | Name |
|---|---|---|
| 62 | 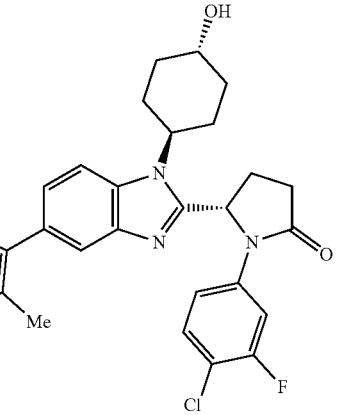 | (S)-1-(4-chloro-3-fluorophenyl)-5-(5-(3,5-dimethylisoxazol-4-yl)-1-((1r,4S)-4-hydroxycyclohexyl)-1H-benzo[d]imidazol-2-yl)pyrrolidin-2-one |
| 63 | 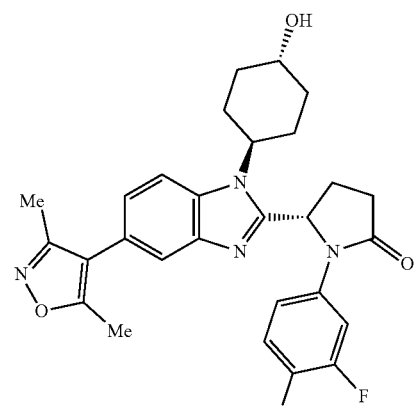 | (S)-5-(5-(3,5-dimethylisoxazol-4-yl)-1-((1r,4S)-4-hydroxycyclohexyl)-1H-benzo[d]imidazol-2-yl)-1-(3-fluoro-4-methoxyphenyl)pyrrolidin-2-one |
| 64 | 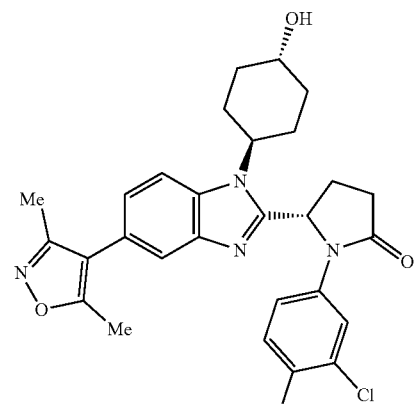 | (S)-1-(3-chloro-4-methoxyphenyl)-5-(5-(3,5-dimethylisoxazol-4-yl)-1-((1r,4S)-4-hydroxycyclohexyl)-1H-benzo[d]imidazol-2-yl)pyrrolidin-2-one |

| No | Structure | Name |
|---|---|---|
| 65 | 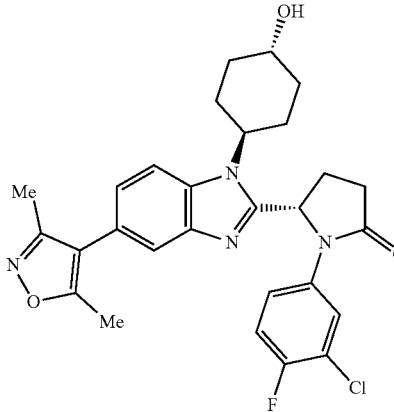 | (S)-1-(3-chloro-4-fluorophenyl)-5-(5-(3,5-dimethylisoxazol-4-yl)-1-((1r,4S)-4-hydroxycyclohexyl)-1H-benzo[d]imidazol-2-yl)pyrrolidin-2-one |
| 66 | 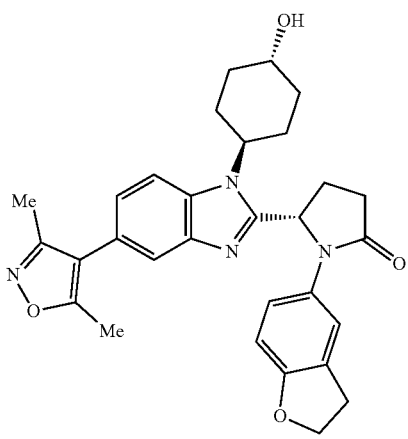 [SMILES: Cc1noc(C)c1-c1ccc2c(c1)nc([C@@H]1CCC(=O)N1c1ccc3c(c1)CCO3)n2[C@H]1CC[C@H](O)CC1] | (S)-1-(2,3-dihydrobenzofuran-5-yl)-5-(5-(3,5-dimethylisoxazol-4-yl)-1-((1r,4S)-4-hydroxycyclohexyl)-1H-benzo[d]imidazol-2-yl)pyrrolidin-2-one |
| 67 | 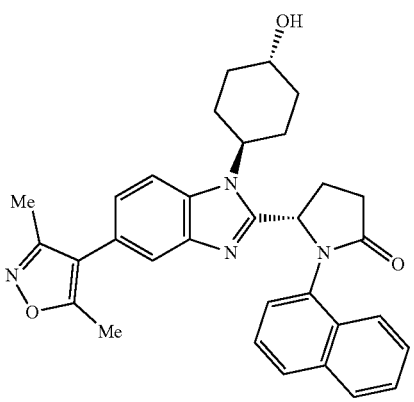 [SMILES: Cc1noc(C)c1-c1ccc2c(c1)nc([C@@H]1CCC(=O)N1c1cccc3ccccc13)n2[C@H]1CC[C@H](O)CC1] | (S)-5-(5-(3,5-dimethylisoxazol-4-yl)-1-((1r,4S)-4-hydroxycyclohexyl)-1H-benzo[d]imidazol-2-yl)-1-(naphthalen-1-yl)pyrrolidin-2-one |

-continued

| No | Structure | Name |
|---|---|---|
| 68 | 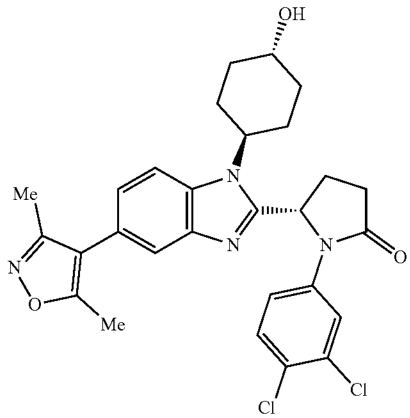 [SMILES: Cc1noc(C)c1-c1ccc2c(c1)nc([C@@H]1CCC(=O)N1c1ccc(Cl)c(Cl)c1)n2[C@H]1CC[C@H](O)CC1] | (S)-1-(3,4-dichlorophenyl)-5-(5-(3,5-dimethylisoxazol-4-yl)-1-(4-hydroxycyclohexyl)-1H-benzo[d]imidazol-2-yl)pyrrolidin-2-one |
| 69 | 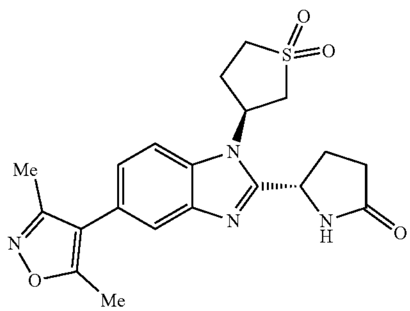 [SMILES: Cc1noc(C)c1-c1ccc2c(c1)nc([C@@H]1CCC(=O)N1)n2[C@H]1CCS(=O)(=O)C1] | (S)-5-(5-(3,5-dimethylisoxazol-4-yl)-1-((S)-1,1-dioxidotetrahydrothiophen-3-yl)-1H-benzo[d]imidazol-2-yl)pyrrolidin-2-one |
| 70 | 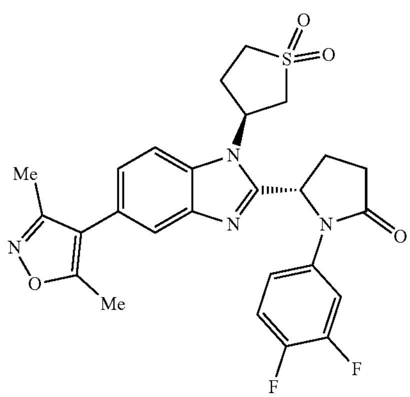 [SMILES: Cc1noc(C)c1-c1ccc2c(c1)nc([C@@H]1CCC(=O)N1c1ccc(F)c(F)c1)n2[C@H]1CCS(=O)(=O)C1] | (S)-1-(3,4-difluorophenyl)-5-(5-(3,5-dimethylisoxazol-4-yl)-1-((S)-1,1-dioxidotetrahydrothiophen-3-yl)-1H-benzo[d]imidazol-2-yl)pyrrolidin-2-one |
| 71 | 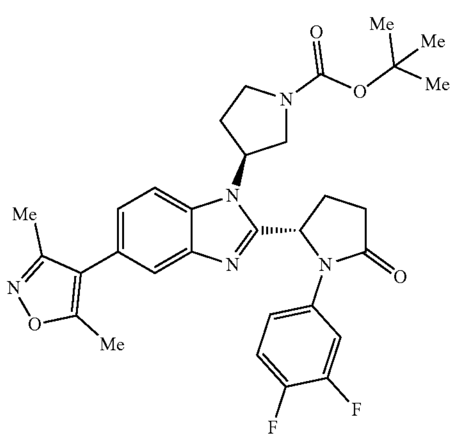 [SMILES: Cc1noc(C)c1-c1ccc2c(c1)nc([C@@H]1CCC(=O)N1c1ccc(F)c(F)c1)n2[C@H]1CCN(C(=O)OC(C)(C)C)C1] | Tert-butyl (S)-3-(2-((S)-1-(3,4-difluorophenyl)-5-oxopyrrolidin-2-yl)-5-(3,5-dimethylisoxazol-4-yl)-1H-benzo[d]imidazol-1-yl)pyrrolidine-1-carboxylate |

| No | Structure | Name |
|---|---|---|
| 72 | 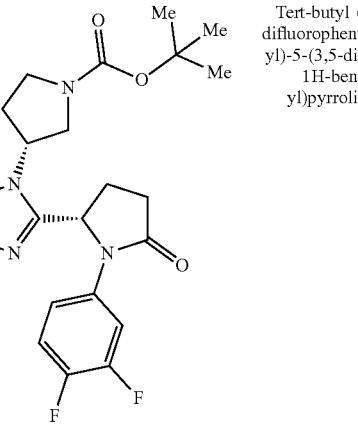 | Tert-butyl (R)-3-(2-((S)-1-(3,4-difluorophenyl)-5-oxopyrrolidin-2-yl)-5-(3,5-dimethylisoxazol-4-yl)-1H-benzo[d]imidazol-1-yl)pyrrolidine-1-carboxylate |
| 73 | 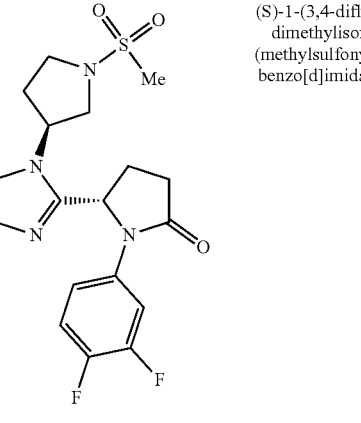 | (S)-1-(3,4-difluorophenyl)-5-(5-(3,5-dimethylisoxazol-4-yl)-1-((S)-1-(methylsulfonyl)pyrrolidin-3-yl)-1H-benzo[d]imidazol-2-yl)pyrrolidin-2-one |
| 74 | 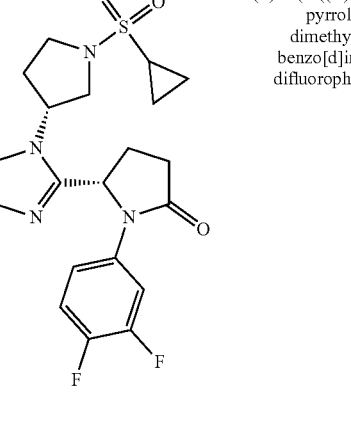 | (S)-5-(1-((R)-1-(cyclopropylsulfonyl)pyrrolidin-3-yl)-5-(3,5-dimethylisoxazol-4-yl)-1H-benzo[d]imidazol-2-yl)-1-(3,4-difluorophenyl)pyrrolidin-2-one |

-continued

| No | Structure | Name |
|---|---|---|
| 75 | 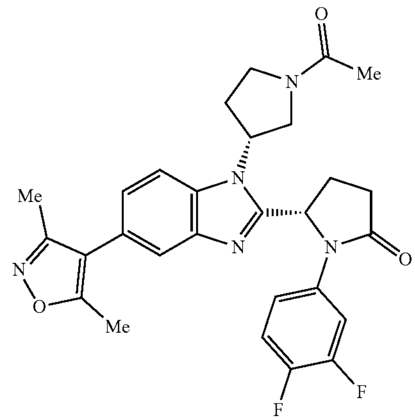 [SMILES: CC(=O)N1CC[C@@H](n2c([C@@H]3CCC(=O)N3c3ccc(F)c(F)c3)nc3cc(-c4c(C)noc4C)ccc32)C1] | (S)-5-(1-((R)-1-acetylpyrrolidin-3-yl)-5-(3,5-dimethylisoxazol-4-yl)-1H-benzo[d]imidazol-2-yl)-1-(3,4-difluorophenyl)pyrrolidin-2-one |
| 76 | 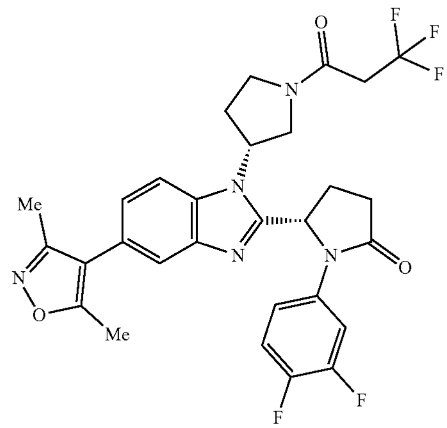 [SMILES: Cc1noc(C)c1-c1ccc2c(c1)nc([C@@H]1CCC(=O)N1c1ccc(F)c(F)c1)n2[C@@H]1CCN(C(=O)CC(F)(F)F)C1] | (S)-1-(3,4-difluorophenyl)-5-(5-(3,5-dimethylisoxazol-4-yl)-1-((R)-1-(3,3,3-trifluoropropanoyl)pyrrolidin-3-yl)-1H-benzo[d]imidazol-2-yl)pyrrolidin-2-one |
| 77 | 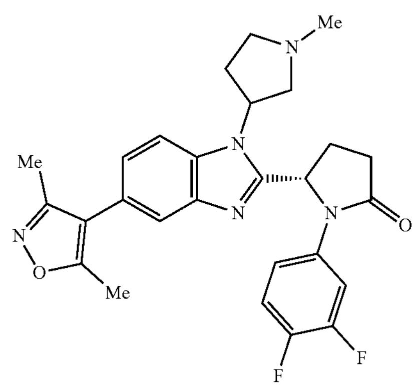 [SMILES: Cc1noc(C)c1-c1ccc2c(c1)nc([C@@H]1CCC(=O)N1c1ccc(F)c(F)c1)n2C1CCN(C)C1] | (5S)-1-(3,4-difluorophenyl)-5-(5-(3,5-dimethylisoxazol-4-yl)-1-(1-methylpyrrolidin-3-yl)-1H-benzo[d]imidazol-2-yl)pyrrolidin-2-one |
| 78 | 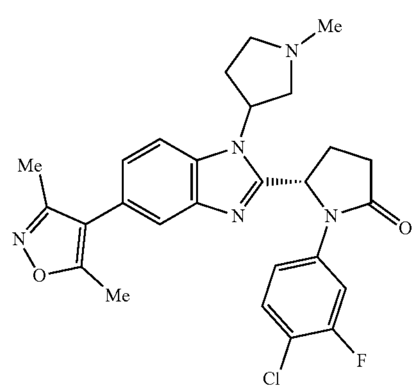 [SMILES: Cc1noc(C)c1-c1ccc2c(c1)nc([C@@H]1CCC(=O)N1c1ccc(Cl)c(F)c1)n2C1CCN(C)C1] | (5S)-1-(4-chloro-3-fluorophenyl)-5-(5-(3,5-dimethylisoxazol-4-yl)-1-(1-methylpyrrolidin-3-yl)-1H-benzo[d]imidazol-2-yl)pyrrolidin-2-one |

-continued
| No | Structure | Name |
| --- | --- | --- |
| 79 | 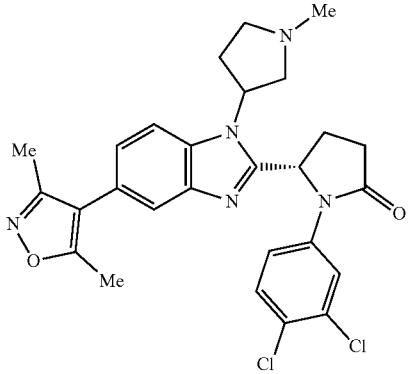 [SMILES: Cc1noc(C)c1-c1ccc2c(c1)nc([C@@H]1CCC(=O)N1c1ccc(Cl)c(Cl)c1)n2C1CCN(C)C1] | (5S)-1-(3,4-dichlorophenyl)-5-(5-(3,5-dimethylisoxazol-4-yl)-1-(1-methylpyrrolidin-3-yl)-1H-benzo[d]imidazol-2-yl)pyrrolidin-2-one |
| 81 | 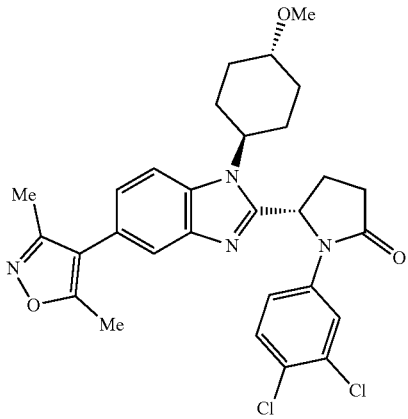 | (S)-1-(3,4-dichlorophenyl)-5-(5-(3,5-dimethylisoxazol-4-yl)-1-((1r,4S)-4-methoxycyclohexyl)-1H-benzo[d]imidazol-2-yl)pyrrolidin-2-one |
| 80 | 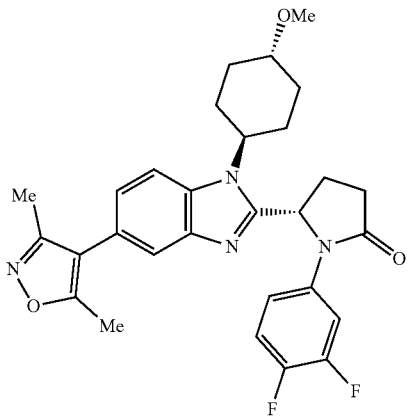 [SMILES: CO[C@H]1CC[C@H](n2c([C@@H]3CCC(=O)N3c3ccc(F)c(F)c3)nc3cc(-c4c(C)noc4C)ccc32)CC1] | (S)-1-(3,4-difluorophenyl)-5-(5-(3,5-dimethylisoxazol-4-yl)-1-((1r,4S)-4-methoxycyclohexyl)-1H-benzo[d]imidazol-2-yl)pyrrolidin-2-one |

-continued

| No | Structure | Name |
|---|---|---|
| 82 | 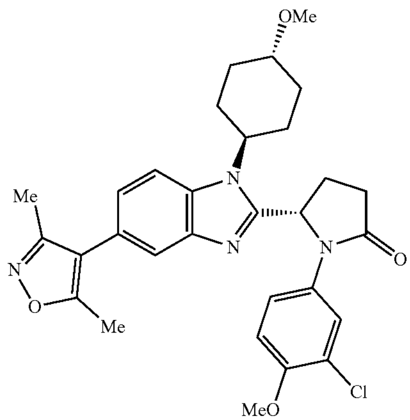 [SMILES: COc1ccc(N2C(=O)CC[C@H]2c2nc3cc(-c4c(C)noc4C)ccc3n2[C@H]2CC[C@H](OC)CC2)cc1Cl] | (S)-1-(3-chloro-4-methoxyphenyl)-5-(5-(3,5-dimethylisoxazol-4-yl)-1-((1r,4S)-4-methoxycyclohexyl)-1H-beno[d]imidazol-2-yl)pyrrolidin-2-one |
| 83 | 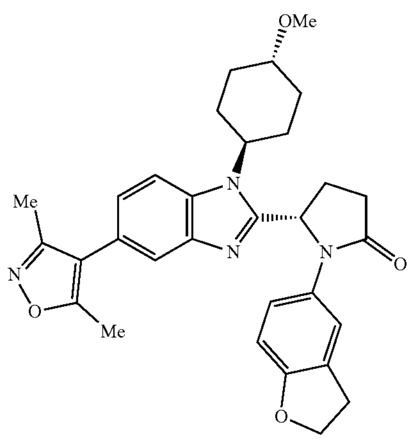 [SMILES: CO[C@H]1CC[C@H](n2c([C@@H]3CCC(=O)N3c3ccc4c(c3)CCO4)nc3cc(-c4c(C)noc4C)ccc32)CC1] | (S)-1-(2,3-dihydrobenzofuran-5-yl)-5-(5-(3,5-dimethylisoxazol-4-yl)-1-((1r,4S)-4-methoxycyclohexyl)-1H-benzo[d]imidazol-2-yl)pyrrolidin-2-one |
| 84 | 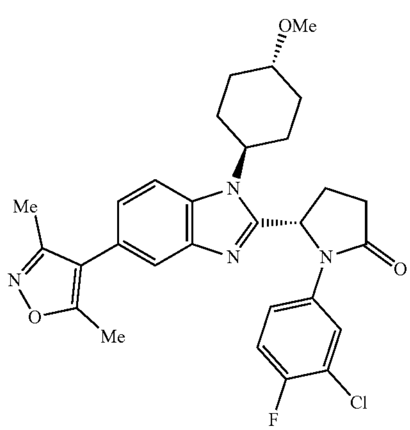 [SMILES: CO[C@H]1CC[C@H](n2c([C@@H]3CCC(=O)N3c3ccc(F)c(Cl)c3)nc3cc(-c4c(C)noc4C)ccc32)CC1] | (S)-1-(3-chloro-4-fluorophenyl)-5-(5-(3,5-dimethylisoxazol-4-yl)-1-((1r,4S)-4-methoxycyclohexyl)-1H-benzo[d]imidazol-2-yl)pyrrolidin-2-one |

-continued
| No | Structure | Name |
|---|---|---|
| 85 | 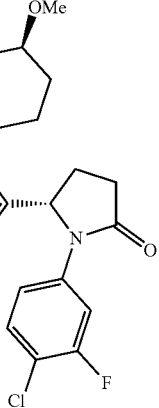 | (S)-1-(4-chloro-3-fluorophenyl)-5-(5-(3,5-dimethylisoxazol-4-yl)-1-((1r,4S)-4-methoxycyclohexyl)-1H-benzo[d]imidazol-2-yl)pyrrolidin-2-one |
| 86 | 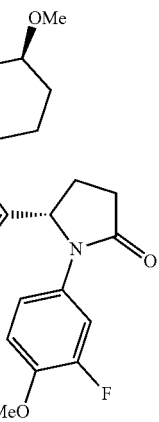 | (S)-5-(5-(3,5-dimethylisoxazol-4-yl)-1-((1r,4S)-4-methoxycyclohexyl)-1H-benzo[d]imidazol-2-yl)-1-(3-fluoro-4-methoxyphenyl)pyrrolidin-2-one |
| 87 | 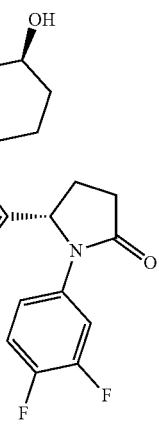 | (S)-1-(3,4-difluorophenyl)-5-(5-(3,5-dimethylisoxazol-4-yl)-1-((1s,4R)-4-hydroxycyclohexyl)-1H-benzo[d]imidazol-2-yl)pyrrolidin-2-one |

| No | Structure | Name |
|---|---|---|
| 88 | 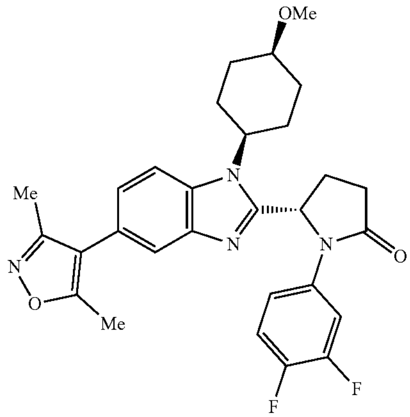 [SMILES: CO[C@H]1CC[C@@H](n2c([C@@H]3CCC(=O)N3c3ccc(F)c(F)c3)nc3cc(-c4c(C)noc4C)ccc32)CC1] | (S)-1-(3,4-difluorophenyl)-5-(5-(3,5-dimethylisoxazol-4-yl)-1-((1s,4R)-4-methoxycyclohexyl)-1H-benzo[d]imidazol-2-yl)pyrrolidin-2-one |
| 89 | 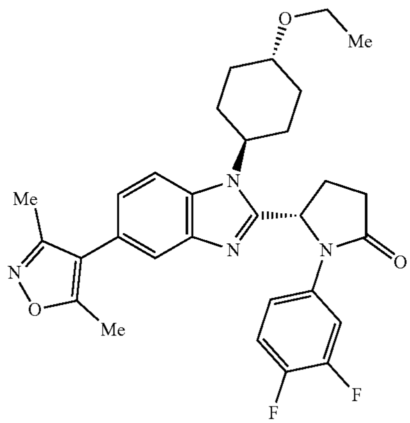 [SMILES: CCO[C@H]1CC[C@H](n2c([C@@H]3CCC(=O)N3c3ccc(F)c(F)c3)nc3cc(-c4c(C)noc4C)ccc32)CC1] | (S)-1-(3,4-difluorophenyl)-5-(5-(3,5-dimethylisoxazol-4-yl)-1-((1R,4s)-4-ethoxycyclohexyl)-1H-benzo[d]imidazol-2-yl)pyrrolidin-2-one |
| 90 | 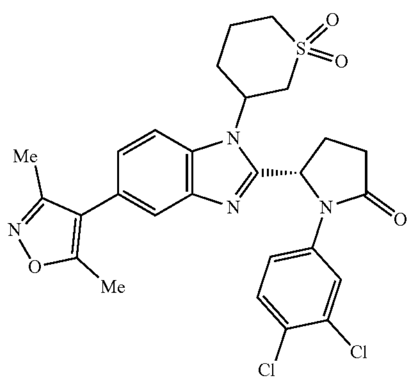 [SMILES: Cc1noc(C)c1-c1ccc2c(c1)nc([C@@H]1CCC(=O)N1c1ccc(Cl)c(Cl)c1)n2C1CCCS(=O)(=O)C1] | (5S)-1-(3,4-dichlorophenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one |
| 91 | 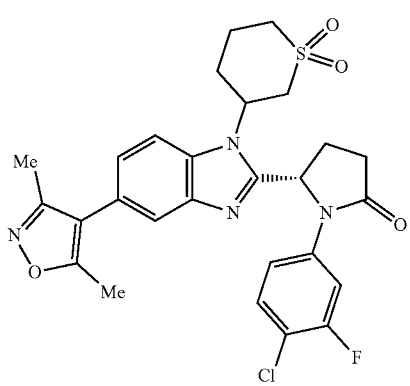 [SMILES: Cc1noc(C)c1-c1ccc2c(c1)nc([C@@H]1CCC(=O)N1c1ccc(Cl)c(F)c1)n2C1CCCS(=O)(=O)C1] | (5S)-1-(4-chloro-3-fluorophenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one |

-continued

| No | Structure | Name |
|----|-----------|------|
| 92 | 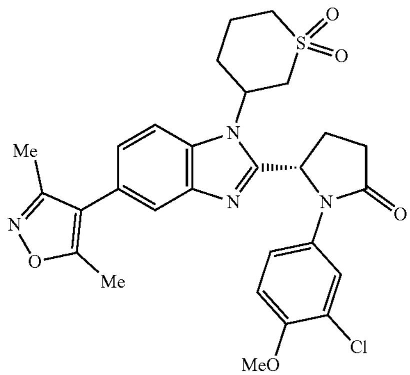 [SMILES: COc1ccc(N2C(=O)CC[C@H]2c2nc3cc(-c4c(C)noc4C)ccc3n2C2CCCS(=O)(=O)C2)cc1Cl] | (5S)-1-(3-chloro-4-methoxyphenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one |
| 93 | 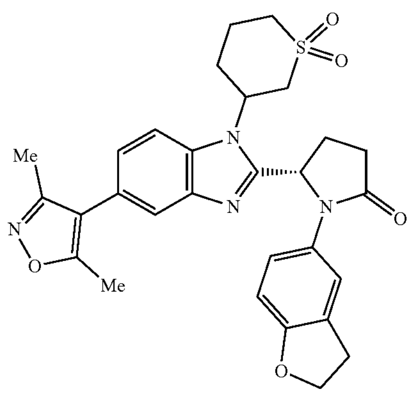 [SMILES: Cc1noc(C)c1-c1ccc2c(c1)nc([C@@H]1CCC(=O)N1c1ccc3c(c1)CCO3)n2C1CCCS(=O)(=O)C1] | (5S)-1-(2,3-dihydrobenzofuran-5-yl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one |
| 94 | 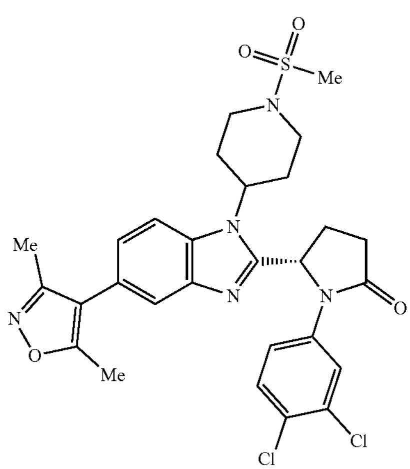 [SMILES: Cc1noc(C)c1-c1ccc2c(c1)nc([C@@H]1CCC(=O)N1c1ccc(Cl)c(Cl)c1)n2C1CCN(S(C)(=O)=O)CC1] | (S)-1-(3,4-dichlorophenyl)-5-(5-(3,5-dimethylisoxazol-4-yl)-1-(1-(methylsulfonyl)piperidin-4-yl)-1H-benzo[d]imidazol-2-yl)pyrrolidin-2-one |

-continued

| No | Structure | Name |
|---|---|---|
| 95 | 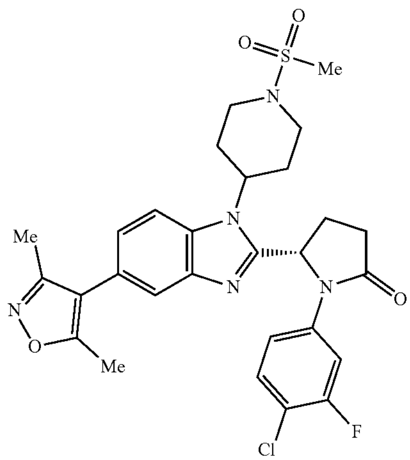 [SMILES: Cc1noc(C)c1-c1ccc2c(c1)nc([C@@H]1CCC(=O)N1c1ccc(Cl)c(F)c1)n2C1CCN(S(C)(=O)=O)CC1] | (S)-1-(4-chloro-3-fluorophenyl)-5-(5-(3,5-dimethylisoxazol-4-yl)-1-(1-(methylsulfonyl)piperidin-4-yl)-1H-benzo[d]imidazol-2-yl)pyrrolidin-2-one |
| 96 | 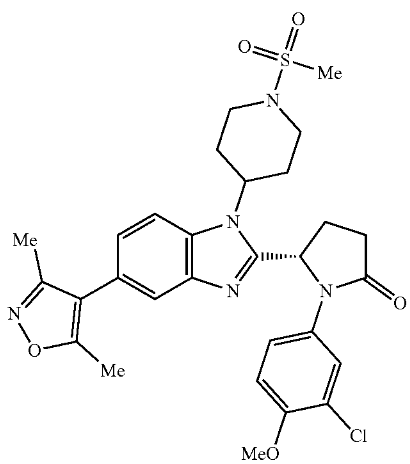 [SMILES: COc1ccc(N2C(=O)CC[C@H]2c2nc3cc(-c4c(C)noc4C)ccc3n2C2CCN(S(C)(=O)=O)CC2)cc1Cl] | (S)-1-(3-chloro-4-methoxyphenyl)-5-(5-(3,5-dimethylisoxazol-4-yl)-1-(1-(methylsulfonyl)piperidin-4-yl)-1H-benzo[d]imidazol-2-yl)pyrrolidin-2-one |
| 97 | 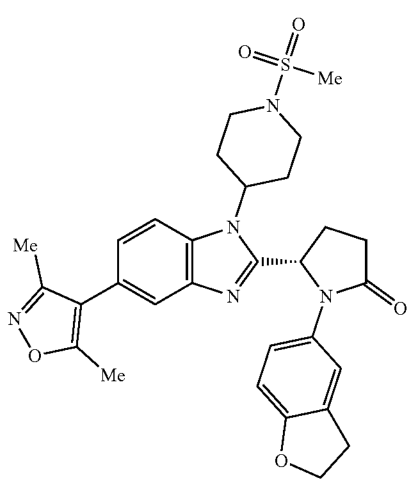 [SMILES: Cc1noc(C)c1-c1ccc2c(c1)nc([C@@H]1CCC(=O)N1c1ccc3c(c1)CCO3)n2C1CCN(S(C)(=O)=O)CC1] | (S)-1-(2,3-dihydrobenzofuran-5-yl)-5-(5-(3,5-dimethylisoxazol-4-yl)-1-(1-(methylsulfonyl)piperidin-4-yl)-1H-benzo[d]imidazol-2-yl)pyrrolidin-2-one |

| No | Structure | Name |
|---|---|---|
| 98 | 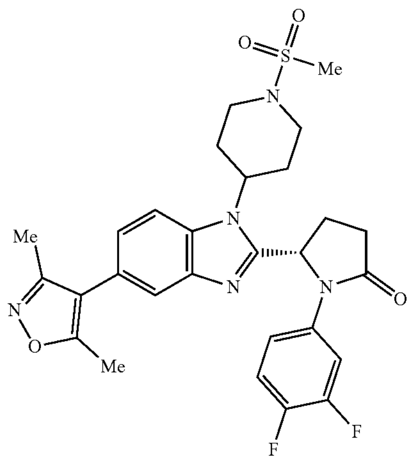 [SMILES: Cc1noc(C)c1-c1ccc2c(c1)nc([C@@H]1CCC(=O)N1c1ccc(F)c(F)c1)n2C1CCN(S(C)(=O)=O)CC1] | (S)-1-(3,4-difluorophenyl)-5-(5-(3,5-dimethylisoxazol-4-yl)-1-(1-(methylsulfonyl)piperidin-4-yl)-1H-benzo[d]imidazol-2-yl)pyrrolidin-2-one |
| 99 | 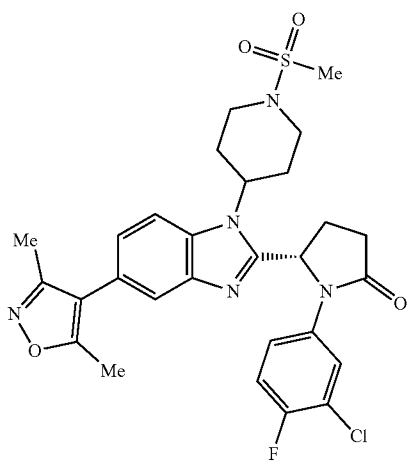 [SMILES: Cc1noc(C)c1-c1ccc2c(c1)nc([C@@H]1CCC(=O)N1c1ccc(F)c(Cl)c1)n2C1CCN(S(C)(=O)=O)CC1] | (S)-1-(3-chloro-4-fluorophenyl)-5-(5-(3,5-dimethylisoxazol-4-yl)-1-(1-(methylsulfonyl)piperidin-4-yl)-1H-benzo[d]imidazol-2-yl)pyrrolidin-2-one |
| 100 | 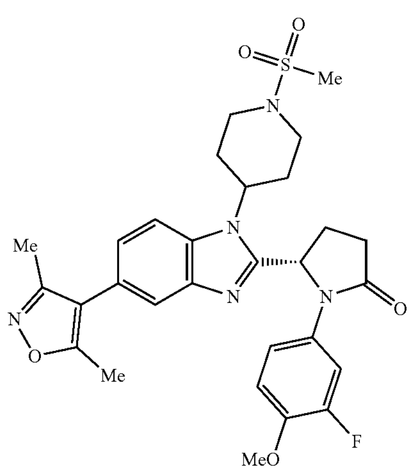 [SMILES: COc1ccc(N2C(=O)CC[C@H]2c2nc3cc(-c4c(C)noc4C)ccc3n2C2CCN(S(C)(=O)=O)CC2)cc1F] | (S)-5-(5-(3,5-dimethylisoxazol-4-yl)-1-(1-(methylsulfonyl)piperidin-4-yl)-1H-benzo[d]imidazol-2-yl)-1-(3-fluoro-4-methoxyphenyl)pyrrolidin-2-one |

-continued

| No | Structure | Name |
|---|---|---|
| 101 | 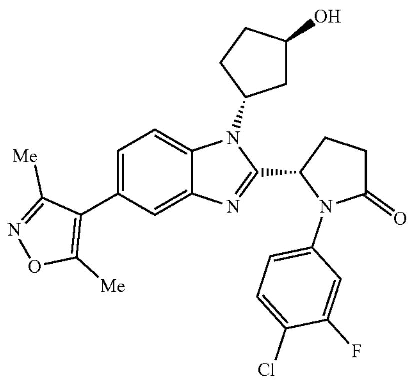 [SMILES: Cc1noc(C)c1-c1ccc2c(c1)nc([C@@H]1CCC(=O)N1c1ccc(Cl)c(F)c1)n2[C@@H]1CC[C@@H](O)C1] | (S)-1-(4-chloro-3-fluorophenyl)-5-(5-(3,5-dimethylisoxazol-4-yl)-1-((1R,3R)-3-hydroxycyclopentyl)-1H-benzo[d]imidazol-2-yl)pyrrolidin-2-one |
| 102 | 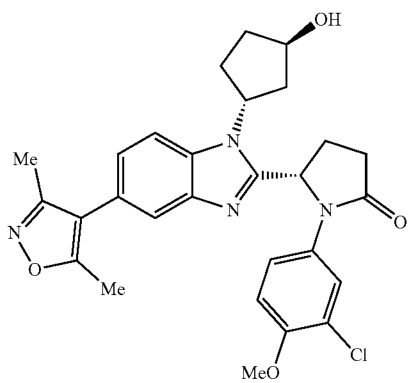 [SMILES: COc1ccc(N2C(=O)CC[C@H]2c2nc3cc(-c4c(C)noc4C)ccc3n2[C@@H]2CC[C@@H](O)C2)cc1Cl] | (S)-1-(3-chloro-4-methoxyphenyl)-5-(5-(3,5-dimethylisoxazol-4-yl)-1-((1R,3R)-3-hydroxycyclopentyl)-1H-benzo[d]imidazol-2-yl)pyrrolidin-2-one |
| 103 | 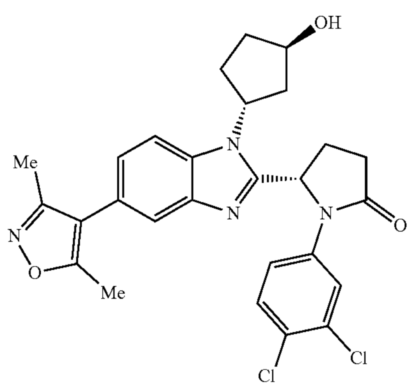 [SMILES: Cc1noc(C)c1-c1ccc2c(c1)nc([C@@H]1CCC(=O)N1c1ccc(Cl)c(Cl)c1)n2[C@@H]1CC[C@@H](O)C1] | (S)-1-(3,4-dichlorophenyl)-5-(5-(3,5-dimethylisoxazol-4-yl)-1-((1R,3R)-3-hydroxycyclopentyl)-1H-benzo[d]imidazol-2-yl)pyrrolidin-2-one |
| 104 | 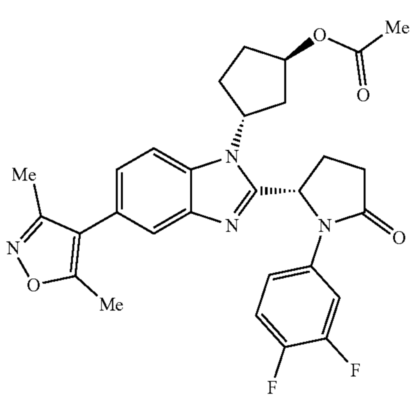 [SMILES: CC(=O)O[C@@H]1CC[C@@H](n2c([C@@H]3CCC(=O)N3c3ccc(F)c(F)c3)nc3cc(-c4c(C)noc4C)ccc32)C1] | (1R,3R)-3-(2-((S)-1-(3,4-difluorophenyl)-5-oxopyrrolidin-2-yl)-5-(3,5-dimethylisoxazol-4-yl)-1H-benzo[d]imidazol-1-yl)cyclopentyl acetate |

| No | Structure | Name |
|---|---|---|
| 105 | 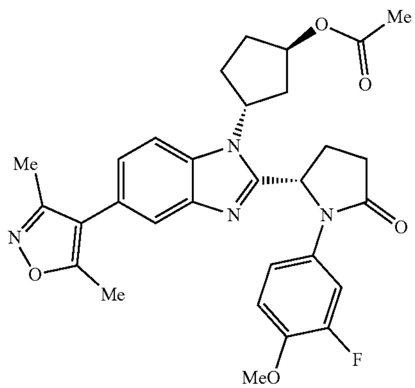 [SMILES: COc1ccc(N2C(=O)CC[C@H]2c2nc3cc(-c4c(C)noc4C)ccc3n2[C@@H]2CC[C@@H](OC(C)=O)C2)cc1F] | (1R,3R)-3-(2-((S)-1-(3-chloro-4-methoxyphenyl)-5-oxopyrrolidin-2-yl)-5-(3,5-dimethylisoxazol-4-yl)-1H-benzo[d]imidazol-1-yl)cyclopentyl acetate |
| 106 | 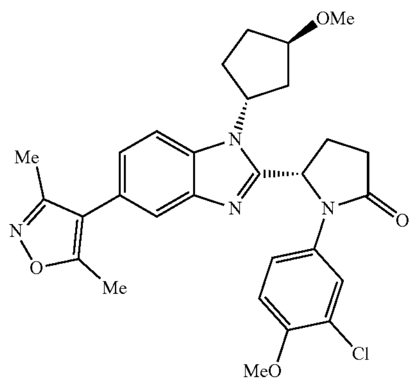 [SMILES: COc1ccc(N2C(=O)CC[C@H]2c2nc3cc(-c4c(C)noc4C)ccc3n2[C@@H]2CC[C@@H](OC)C2)cc1Cl] | (S)-1-(3-chloro-4-methoxyphenyl)-5-(5-(3,5-dimethylisoxazol-4-yl)-1-(trans-(1r,3r)-3-methoxycyclopentyl)-1H-benzo[d]imidazol-2-yl)pyrrolidin-2-one |
| 107 | 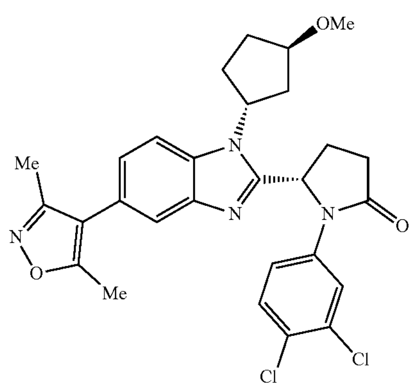 [SMILES: CO[C@@H]1CC[C@@H](n2c([C@@H]3CCC(=O)N3c3ccc(Cl)c(Cl)c3)nc3cc(-c4c(C)noc4C)ccc32)C1] | (S)-1-(3,4-dichlorophenyl)-5-(5-(3,5-dimethylisoxazol-4-yl)-1-(trans-(1r,3r)-3-methoxycyclopentyl)-1H-benzo[d]imidazol-2-yl)pyrrolidin-2-one |
| 108 | 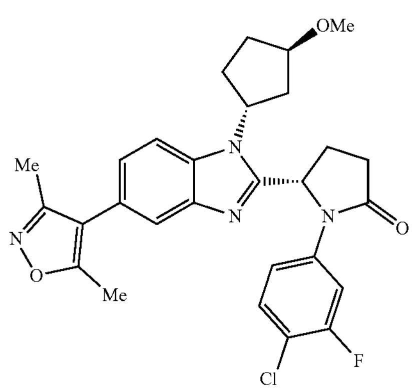 [SMILES: CO[C@@H]1CC[C@@H](n2c([C@@H]3CCC(=O)N3c3ccc(Cl)c(F)c3)nc3cc(-c4c(C)noc4C)ccc32)C1] | (S)-1-(4-chloro-3-fluorophenyl)-5-(5-(3,5-dimethylisoxazol-4-yl)-1-(trans-(1r,3r)-3-methoxycyclopentyl)-1H-benzo[d]imidazol-2-yl)pyrrolidin-2-one |

| No | Structure | Name |
|---|---|---|
| 109 | 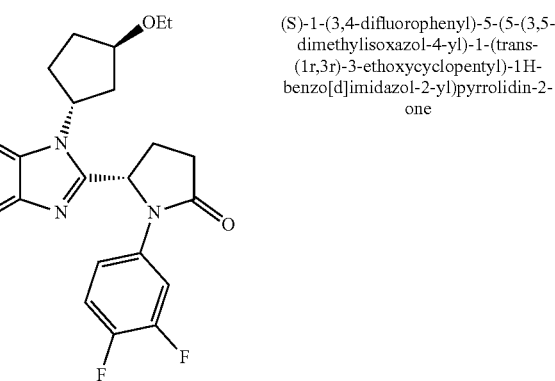 | (S)-1-(3,4-difluorophenyl)-5-(5-(3,5-dimethylisoxazol-4-yl)-1-(trans-(1r,3r)-3-ethoxycyclopentyl)-1H-benzo[d]imidazol-2-yl)pyrrolidin-2-one |
| 110 | 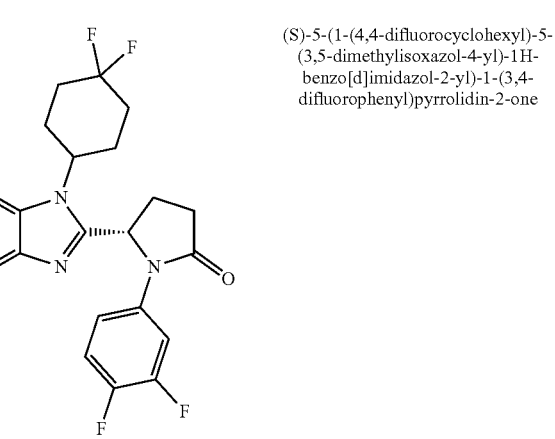 | (S)-5-(1-(4,4-difluorocyclohexyl)-5-(3,5-dimethylisoxazol-4-yl)-1H-benzo[d]imidazol-2-yl)-1-(3,4-difluorophenyl)pyrrolidin-2-one |
| 111 | 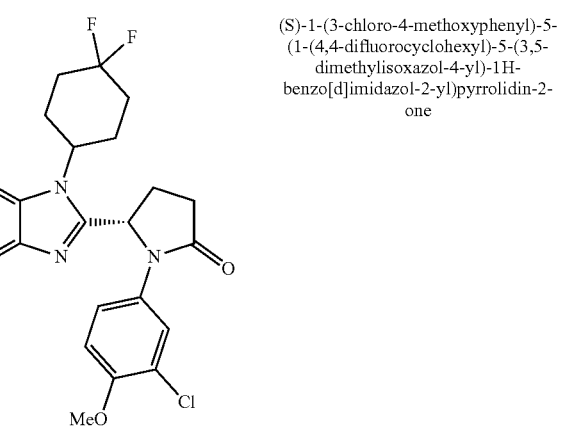 | (S)-1-(3-chloro-4-methoxyphenyl)-5-(1-(4,4-difluorocyclohexyl)-5-(3,5-dimethylisoxazol-4-yl)-1H-benzo[d]imidazol-2-yl)pyrrolidin-2-one |

| No | Structure | Name |
|---|---|---|
| 112 | 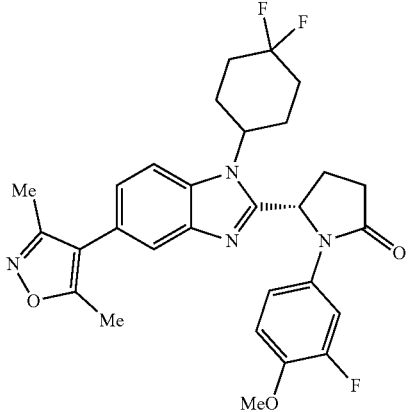 [SMILES: COc1ccc(N2C(=O)CC[C@H]2c2nc3cc(-c4c(C)noc4C)ccc3n2C2CCC(F)(F)CC2)cc1F] | (S)-1-(3-fluoro-4-methoxyphenyl)-5-(1-(4,4-difluorocyclohexyl)-5-(3,5-dimethylisoxazol-4-yl)-1H-benzo[d]imidazol-2-yl)pyrrolidin-2-one |
| 113 | 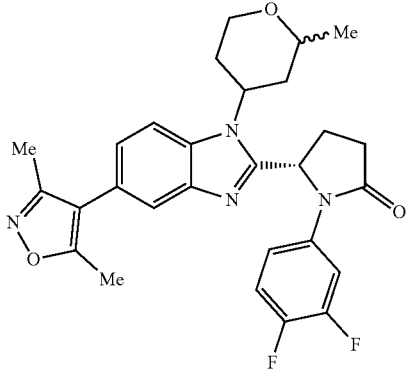 [SMILES: Cc1noc(C)c1-c1ccc2c(c1)nc([C@@H]1CCC(=O)N1c1ccc(F)c(F)c1)n2C1CCOC(C)C1] | (5S)-1-(3,4-difluorophenyl)-5-(5-(3,5-dimethylisoxazol-4-yl)-1-(2-methyltetrahydro-2H-pyran-4-yl)-1H-benzo[d]imidazol-2-yl)pyrrolidin-2-one |
| 114 | 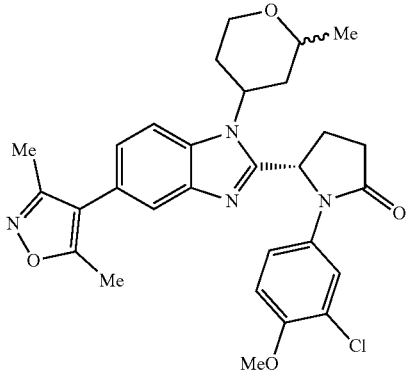 [SMILES: COc1ccc(N2C(=O)CC[C@H]2c2nc3cc(-c4c(C)noc4C)ccc3n2C2CCOC(C)C2)cc1Cl] | (5S)-1-(3-chloro-4-methoxyphenyl)-5-(5-(3,5-dimethylisoxazol-4-yl)-1-(2-methyltetrahydro-2H-pyran-4-yl)-1H-benzo[d]imidazol-2-yl)pyrrolidin-2-one |
| 115 | 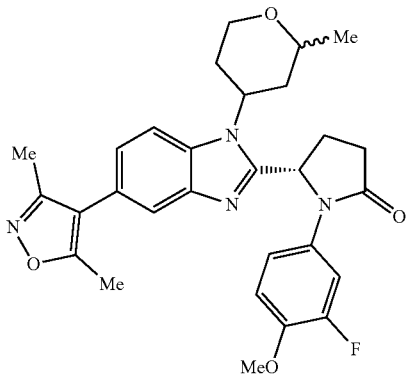 [SMILES: COc1ccc(N2C(=O)CC[C@H]2c2nc3cc(-c4c(C)noc4C)ccc3n2C2CCOC(C)C2)cc1F] | (5S)-5-(5-(3,5-dimethylisoxazol-4-yl)-1-(2-methyltetrahydro-2H-pyran-4-yl)-benzo[d]imidazol-2-yl)-1-(3-fluoro-4-methoxyphenyl)pyrrolidin-2-one |

| No | Structure | Name |
|---|---|---|
| 116 | 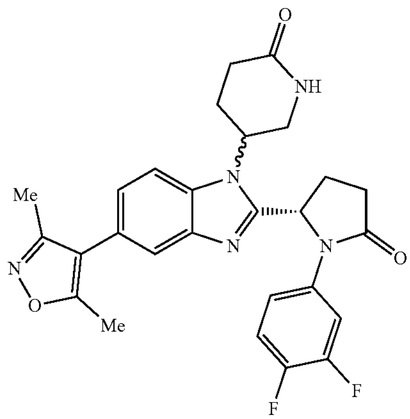 [SMILES: Cc1noc(C)c1-c1ccc2c(c1)nc([C@@H]1CCC(=O)N1c1ccc(F)c(F)c1)n2C1CCC(=O)NC1] | 5-(2-((S)-1-(3,4-difluorophenyl)-5-oxopyrrolidin-2-yl)-5-(3,5-dimethylisoxazol-4-yl)-1H-benzo[d]imidazol-1-yl)piperidin-2-one |
| 117 | 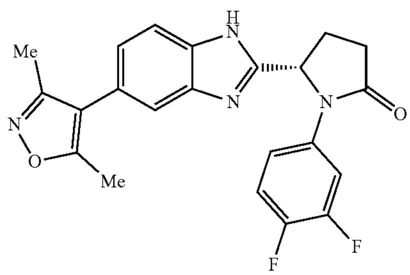 [SMILES: Cc1noc(C)c1-c1ccc2[nH]c([C@@H]3CCC(=O)N3c3ccc(F)c(F)c3)nc2c1] | (S)-1-(3,4-difluorophenyl)-5-(5-(3,5-dimethylisoxazol-4-yl)-1H-benzo[d]imidazol-2-yl)pyrrolidin-2-one |
| 118 | 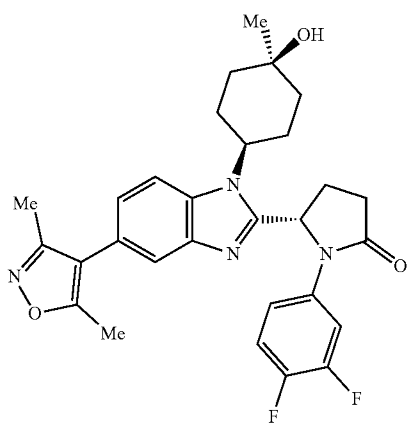 [SMILES: Cc1noc(C)c1-c1ccc2c(c1)nc([C@@H]1CCC(=O)N1c1ccc(F)c(F)c1)n2[C@H]1CC[C@@](C)(O)CC1] | (S)-1-(3,4-difluorophenyl)-5-(5-(3,5-dimethylisoxazol-4-yl)-1-((1s,4R)-4-hydroxy-4-methylcyclohexyl)-1H-benzo[d]imidazol-2-yl)pyrrolidin-2-one |
| 119 | 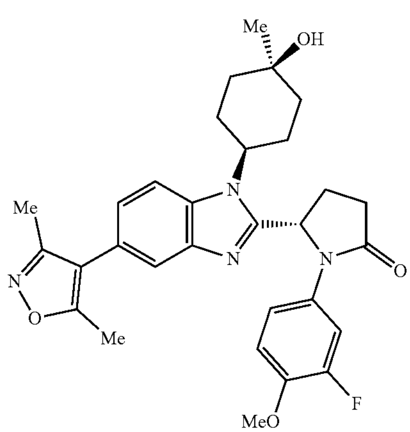 [SMILES: COc1ccc(N2C(=O)CC[C@H]2c2nc3cc(-c4c(C)noc4C)ccc3n2[C@H]2CC[C@@](C)(O)CC2)cc1F] | (S)-5-(5-(3,5-dimethylisoxazol-4-yl)-1-((1s,4R)-4-hydroxy-4-methylcyclohexyl)-1H-benzo[d]imidazol-2-yl)-1-(3-fluoro-4-methoxyphenyl)pyrrolidin-2-one |

| No | Structure | Name |
|---|---|---|
| 120 | 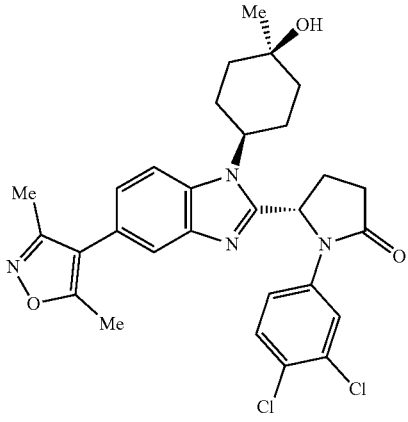 [SMILES: Cc1noc(C)c1-c1ccc2c(c1)nc([C@@H]1CCC(=O)N1c1ccc(Cl)c(Cl)c1)n2[C@H]1CC[C@@](C)(O)CC1] | (S)-1-(3,4-dichlorophenyl)-5-(5-(3,5-dimethylisoxazol-4-yl)-1-((1s,4R)-4-hydroxy-4-methylcyclohexyl)-1H-benzo[d]imidazol-2-yl)pyrrolidin-2-one |
| 121 | 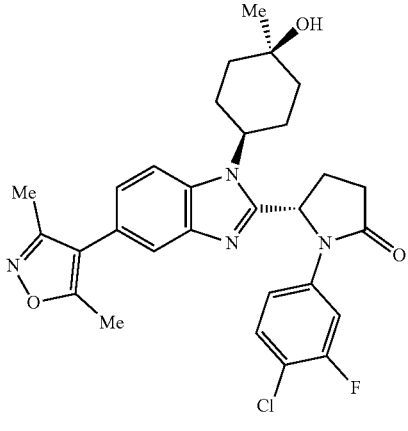 [SMILES: Cc1noc(C)c1-c1ccc2c(c1)nc([C@@H]1CCC(=O)N1c1ccc(Cl)c(F)c1)n2[C@H]1CC[C@@](C)(O)CC1] | (S)-1-(4-chloro-3-fluorophenyl)-5-(5-(3,5-dimethylisoxazol-4-yl)-1-((1s,4R)-4-hydroxy-4-methylcyclohexyl)-1H-benzo[d]imidazol-2-yl)pyrrolidin-2-one |
| 122 | 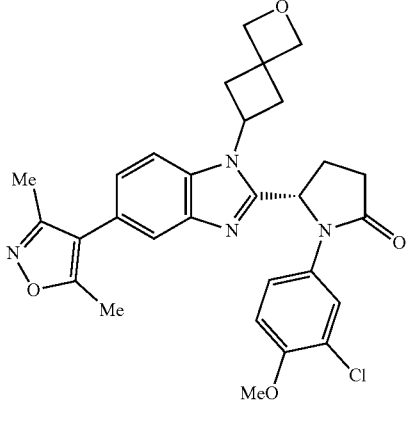 [SMILES: COc1ccc(N2C(=O)CC[C@H]2c2nc3cc(-c4c(C)noc4C)ccc3n2C2CC3(COC3)C2)cc1Cl] | (S)-1-(3-chloro-4-methoxyphenyl)-5-(5-(3,5-dimethylisoxazol-4-yl)-1-(2-oxaspiro[3.3]heptan-6-yl)-1H-benzo[d]imidazol-2-yl)pyrrolidin-2-one |

-continued

| No | Structure | Name |
| --- | --- | --- |
| 123 | 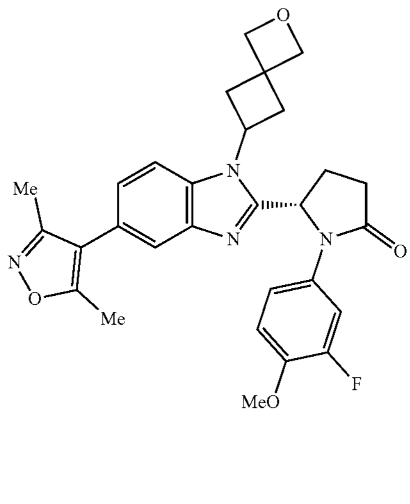 [SMILES: COc1ccc(N2C(=O)CC[C@H]2c2nc3cc(-c4c(C)noc4C)ccc3n2C2CC3(COC3)C2)cc1F] | (S)-5-(5-(3,5-dimethylisoxazol-4-yl)-1-(2-oxaspiro[3.3]heptan-6-yl)-1H-benzo[d]imidazol-2-yl)-1-(3-fluoro-4-methoxyphenyl)pyrrolidin-2-one |
| 124 | 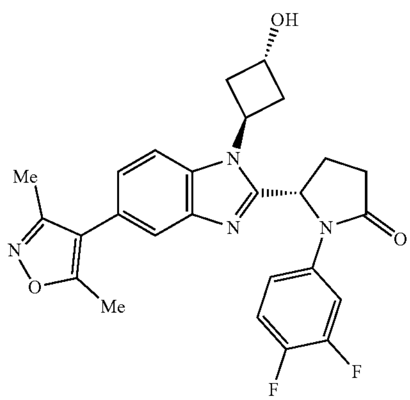 [SMILES: Cc1noc(C)c1-c1ccc2c(c1)nc([C@@H]1CCC(=O)N1c1ccc(F)c(F)c1)n2[C@H]1C[C@H](O)C1] | (S)-1-(3,4-difluorophenyl)-5-(5-(3,5-dimethylisoxazol-4-yl)-1-((1r,3S)-3-hydroxycyclobutyl)-1H-benzo[d]imidazol-2-yl)pyrrolidin-2-one |
| 125 | 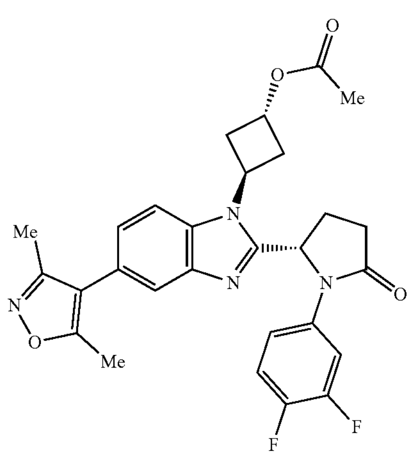 [SMILES: CC(=O)O[C@H]1C[C@H](n2c([C@@H]3CCC(=O)N3c3ccc(F)c(F)c3)nc3cc(-c4c(C)noc4C)ccc32)C1] | (1S,3r)-3-(2-((S)-1-(3,4-difluorophenyl)-5-oxopyrrolidin-2-yl)-5-(3,5-dimethylisoxazol-4-yl)-1H-benzo[d]imidazol-1-yl)cylcobutyl acetate |

-continued

| No | Structure | Name |
|---|---|---|
| 126 | 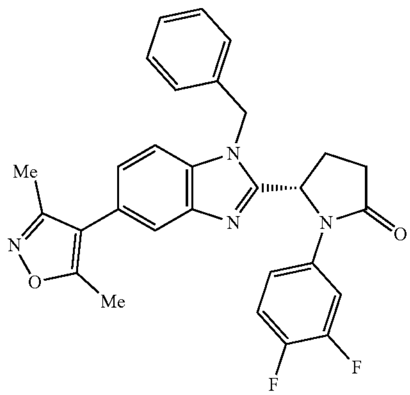 [SMILES: Cc1noc(C)c1-c1ccc2c(c1)nc([C@@H]1CCC(=O)N1c1ccc(F)c(F)c1)n2Cc1ccccc1] | (S)-5-(1-benzyl-5-(3,5-dimethylisoxazol-4-yl)-1H-benzo[d]imidazol-2-yl)-1-(3,4-difluorophenyl)pyrrolidin-2-one |
| 127 | 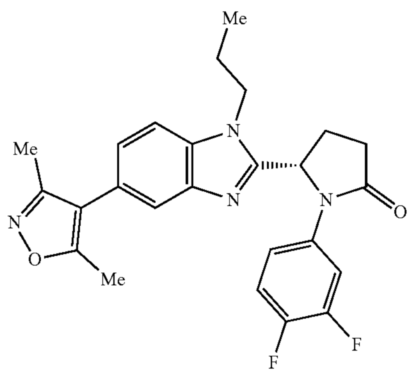 [SMILES: CCCn1c([C@@H]2CCC(=O)N2c2ccc(F)c(F)c2)nc2cc(-c3c(C)noc3C)ccc21] | (S)-1-(3,4-difluorophenyl)-5-(5-(3,5-dimethylisoxazol-4-yl)-1-propyl-1H-benzo[d]imidazol-2-yl)pyrrolidin-2-one |
| 128 | 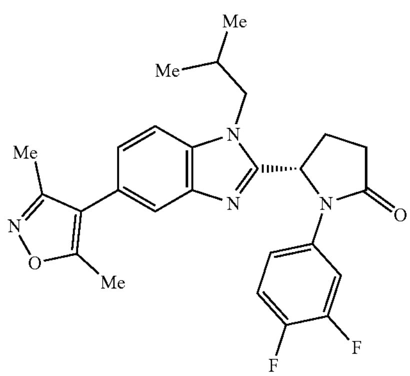 [SMILES: Cc1noc(C)c1-c1ccc2c(c1)nc([C@@H]1CCC(=O)N1c1ccc(F)c(F)c1)n2CC(C)C] | (S)-1-(3,4-difluorophenyl)-5-(5-(3,5-dimethylisoxazol-4-yl)-1-isobutyl-1H-benzo[d]imidazol-2-yl)pyrrolidin-2-one |
| 129 | 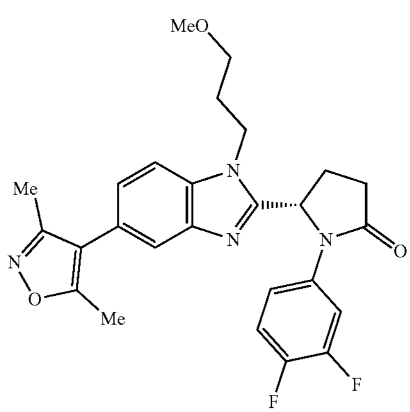 [SMILES: COCCCn1c([C@@H]2CCC(=O)N2c2ccc(F)c(F)c2)nc2cc(-c3c(C)noc3C)ccc21] | (S)-1-(3,4-difluorophenyl)-5-(5-(3,5-dimethylisoxazol-4-yl)-1-(3-methoxypropyl)-1H-benzo[d]imidazol-2-yl)pyrrolidin-2-one |

| No | Structure | Name |
|---|---|---|
| 130 | 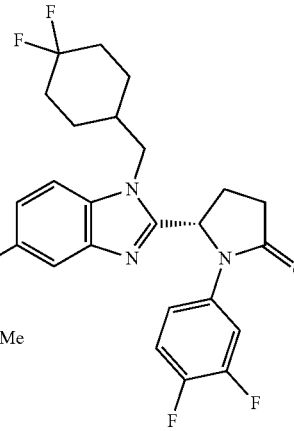 | (S)-5-(1-((4,4-difluorocyclohexyl)methyl)-5-(3,5-dimethylisoxazol-4-yl)-1H-benzo[d]imidazol-2-yl)-1-(3,4-difluorophenyl)pyrrolidin-2-one |
| 131 | 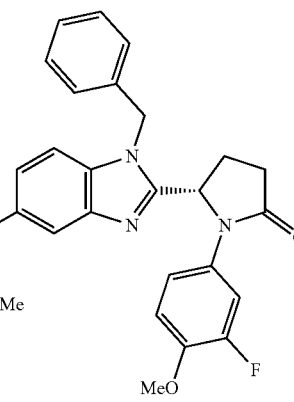 | (S)-5-(1-benzyl-5-(3,5-dimethylisoxazol-4-yl)-1H-benzo[d]imidazol-2-yl)-1-(3-fluoro-4-methoxyphenyl)pyrrolidin-2-one |
| 132 | 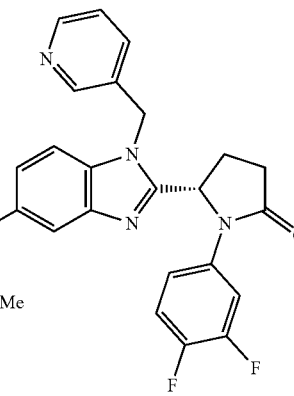 | (S)-1-(3,4-difluorophenyl)-5-(5-(3,5-dimethylisoxazol-4-yl)-1-(pyridin-3-ylmethyl)-1H-benzo[d]imidazol-2-yl)pyrrolidin-2-one |

| No | Structure | Name |
|---|---|---|
| 133 | 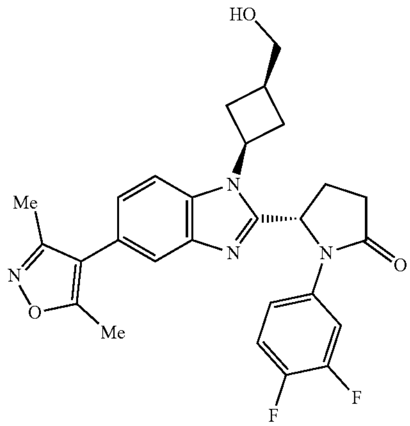 [SMILES: Cc1noc(C)c1-c1ccc2c(c1)nc([C@@H]1CCC(=O)N1c1ccc(F)c(F)c1)n2[C@H]1C[C@@H](CO)C1] | (S)-1-(3,4-difluorophenyl)-5-(5-(3,5-dimethylisoxazol-4-yl)-1-((1s,3R)-3-(hydroxymethyl)cyclobutyl)-1H-benzo[d]imidazol-2-yl)pyrrolidin-2-one |
| 134 | 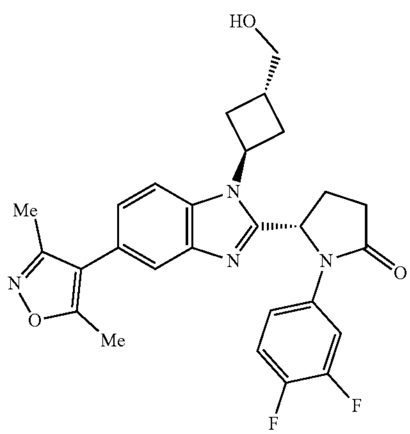 [SMILES: Cc1noc(C)c1-c1ccc2c(c1)nc([C@@H]1CCC(=O)N1c1ccc(F)c(F)c1)n2[C@H]1C[C@H](CO)C1] | (S)-1-(3,4-difluorophenyl)-5-(5-(3,5-dimethylisoxazol-4-yl)-1-((1r,3S)-3-(hydroxymethyl)cyclobutyl)-1H-benzo[d]imidazol-2-yl)pyrrolidin-2-one |
| 135 | 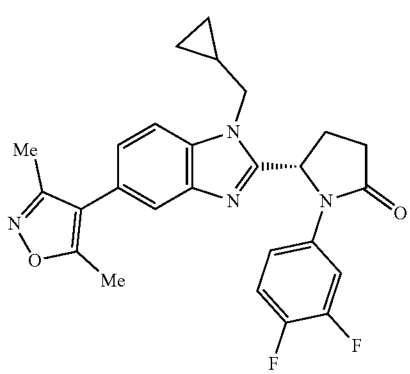 [SMILES: Cc1noc(C)c1-c1ccc2c(c1)nc([C@@H]1CCC(=O)N1c1ccc(F)c(F)c1)n2CC1CC1] | (S)-5-(1-(cyclopropylmethyl)-5-(3,5-dimethylisoxazol-4-yl)-1H-benzo[d]imidazol-2-yl)-1-(3,4-difluorophenyl)pyrrolidin-2-one |

| No | Structure | Name |
| --- | --- | --- |
| 136 | 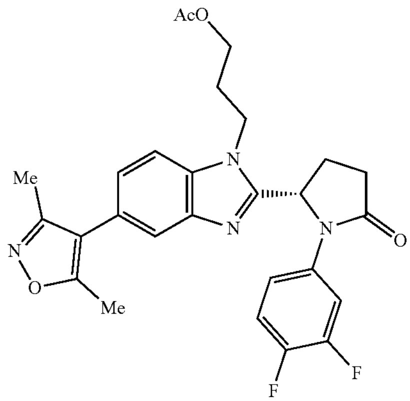 [SMILES: CC(=O)OCCCn1c([C@@H]2CCC(=O)N2c2ccc(F)c(F)c2)nc2cc(-c3c(C)noc3C)ccc21] | (S)-3-(2-(1-(3,4-difluorophenyl)-5-oxopyrrolidin-2-yl)-5-(3,5-dimethylisoxazol-4-yl)-1H-benzo[d]imidazol-1-yl)propyl acetate |
| 137 | 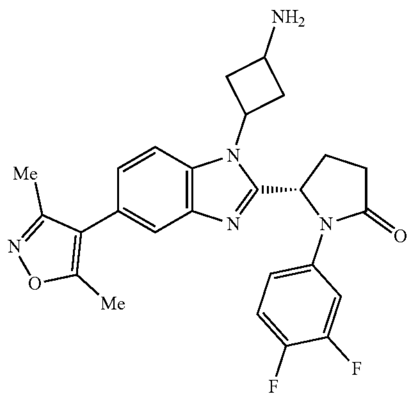 [SMILES: Cc1noc(C)c1-c1ccc2c(c1)nc([C@@H]1CCC(=O)N1c1ccc(F)c(F)c1)n2C1CC(N)C1] | (S)-5-(1-(3-aminocyclobutyl)-5-(3,5-dimethylisoxazol-4-yl)-1H-benzo[d]imidazol-2-yl)-1-(3,4-difluorophenyl)pyrrolidin-2-one |
| 138 | 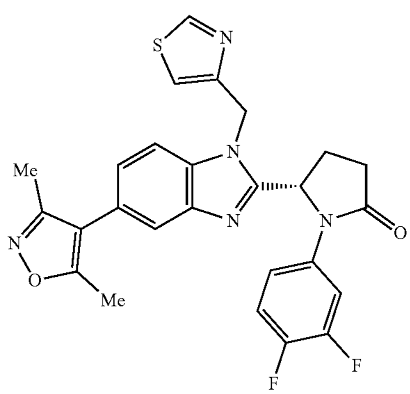 [SMILES: Cc1noc(C)c1-c1ccc2c(c1)nc([C@@H]1CCC(=O)N1c1ccc(F)c(F)c1)n2Cc1cscn1] | (S)-1-(3,4-difluorophenyl)-5-(5-(3,5-dimethylisoxazol-4-yl)-1-(thiazol-4-ylmethyl)-1H-benzo[d]imidazol-2-yl)pyrrolidin-2-one |
| 139 | 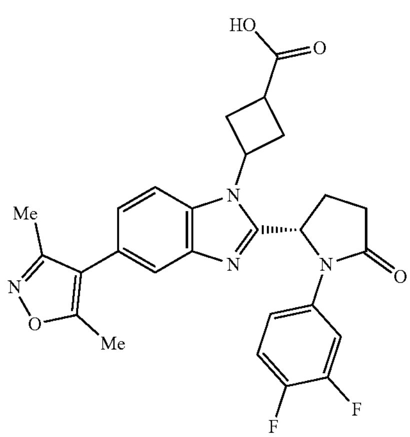 [SMILES: Cc1noc(C)c1-c1ccc2c(c1)nc([C@@H]1CCC(=O)N1c1ccc(F)c(F)c1)n2C1CC(C(=O)O)C1] | (S)-5-(1-(3-aminocyclobutyl)-5-(3,5-dimethylisoxazol-4-yl)-1H-benzo[d]imidazol-2-yl)-1-(3,4-difluorophenyl)pyrrolidin-2-one |

| No | Structure | Name |
|---|---|---|
| 140 | 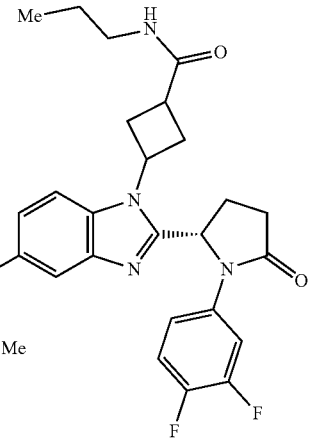 | (S)-3-(2-(1-(3,4-difluorophenyl)-5-oxopyrrolidin-2-yl)-5-(3,5-dimethylisoxazol-4-yl)-1H-benzo[d]imidazol-1-yl)-N-propylcyclobutanecarboxamide |
| 141 | 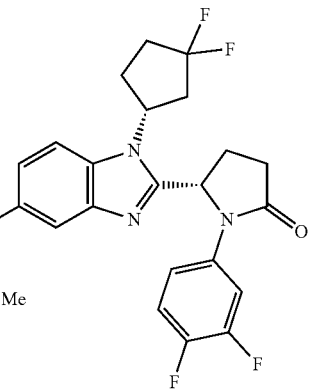 | (S)-5-(1-((R)-3,3-difluorocyclopentyl)-5-(3,5-dimethylisoxazol-4-yl)-1H-benzo[d]imidazol-2-yl)-1-(3,4-difluorophenyl)pyrrolidin-2-one |
| 142 | 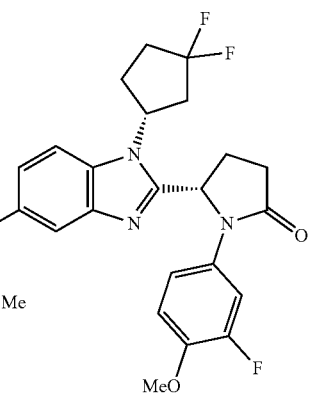 | (S)-5-(1-((R)-3,3-difluorocyclopentyl)-5-(3,5-dimethylisoxazol-4-yl)-1H-benzo[d]imidazol-2-yl)-1-(3-fluoro-4-methoxyphenyl)pyrrolidin-2-one |

| No | Structure | Name |
|---|---|---|
| 143 | 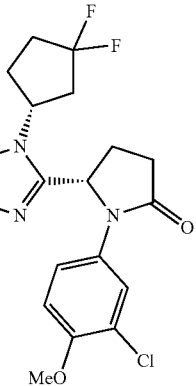 | (S)-5-(1-((R)-3,3-difluorocyclopentyl)-5-(3,5-dimethylisoxazol-4-yl)-1H-benzo[d]imidazol-2-yl)-1-(3-fluoro-4-methoxyphenyl)pyrrolidin-2-one |
| 144 | 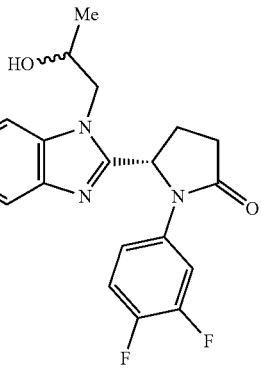 | (5S)-1-(3,4-difluorophenyl)-5-(5-(3,5-dimethylisoxazol-4-yl)-1-(2-hydroxypropyl)-1H-benzo[d]imidazol-2-yl)pyrrolidin-2-one (diastereomer 1) |
| 145 | 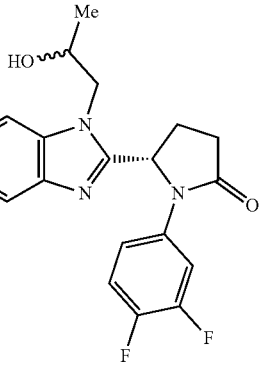 | (5S)-1-(3,4-difluorophenyl)-5-(5-(3,5-dimethylisoxazol-4-yl)-1-(2-hydroxypropyl)-1H-benzo[d]imidazol-2-yl)pyrrolidin-2-one (diastereomer 2) |
| 146 | 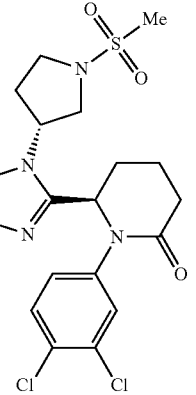 | (R)-1-(3,4-dichlorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one |

-continued

| No | Structure | Name |
|---|---|---|
| 147 | 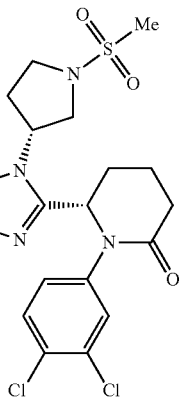 | (S)-1-(3,4-dichlorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one |
| 148 | 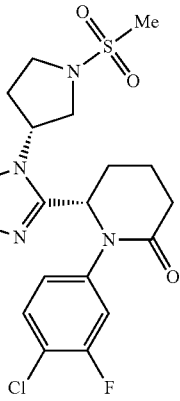 | (S)-1-(4-chloro-3-fluorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one |
| 149 | 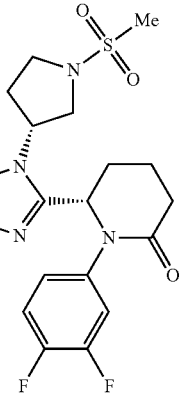 | (S)-1-(3,4-difluorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one |
| 150 | 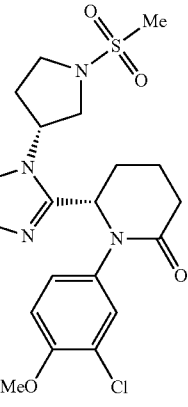 | (S)-1-(3-chloro-4-methoxyphenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one |

-continued
| No | Structure | Name |
| --- | --- | --- |
| 151 | 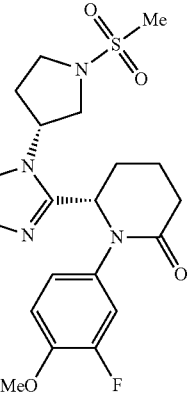 | (S)-1-(3-fluoro-4-methoxyphenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one |
| 152 | 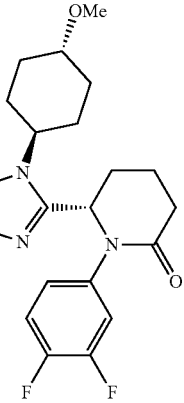 | (S)-6-(5-(3,5-dimethylisoxazol-4-yl)-1-((1r,4S)-4-methoxycyclohexyl)-1H-benzo[d]imidazol-2-yl)-1-(3,4-difluorophenyl)piperidin-2-one |
| 153 | 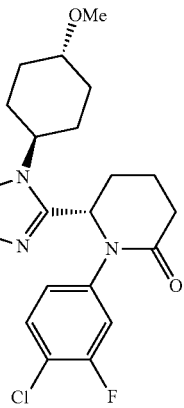 | (S)-1-(4-chloro-3-fluorophenyl)-6-(5-(3,5-dimethylisoxazol-4-yl)-1-((1r,4S)-4-methoxycyclohexyl)-1H-benzo[d]imidazol-2-yl)piperidin-2-one |

-continued

| No | Structure | Name |
|---|---|---|
| 154 | 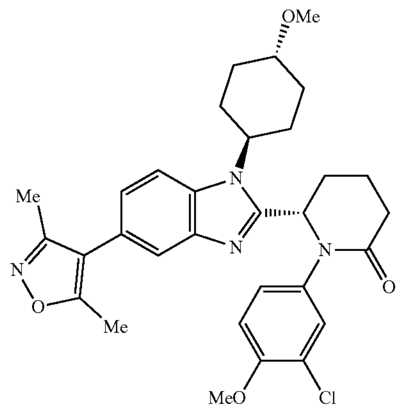 [SMILES: COc1ccc(N2C(=O)CCC[C@H]2c2nc3cc(-c4c(C)noc4C)ccc3n2[C@H]2CC[C@H](OC)CC2)cc1Cl] | (S)-1-(3-chloro-4-methoxyphenyl)-6-(5-(3,5-dimethylisoxazol-4-yl)-1-((1r,4S)-4-methoxycyclohexyl)-1H-benzo[d]imidazol-2-yl)piperidin-2-one |
| 155 | 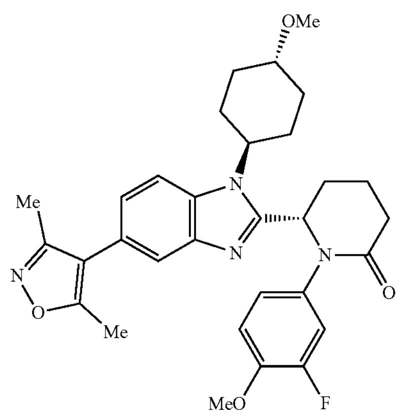 | (S)-6-(5-(3,5-dimethylisoxazol-4-yl)-1-((1r,4S)-4-methoxycyclohexyl)-1H-benzo[d]imidazol-2-yl)-1-(3-fluoro-4-methoxyphenyl)piperidin-2-one |
| 156 | 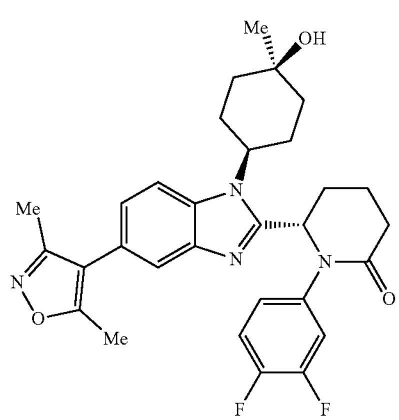 [SMILES: Cc1noc(C)c1-c1ccc2c(c1)nc([C@@H]1CCCC(=O)N1c1ccc(F)c(F)c1)n2[C@H]1CC[C@@](C)(O)CC1] | (S)-1-(3,4-difluorophenyl)-6-(5-(3,5-dimethylisoxazol-4-yl)-1-((1s,4R)-4-hydroxy-4-methylcyclohexyl)-1H-benzo[d]imidazol-2-yl)piperidin-2-one |

| No | Structure | Name |
|---|---|---|
| 157 | 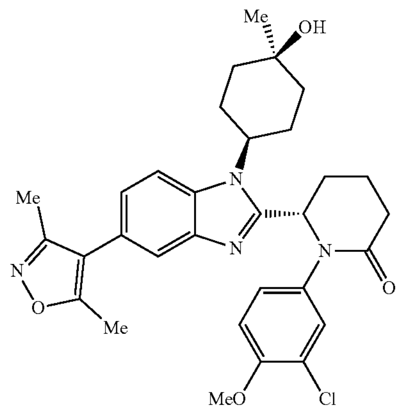 [SMILES: COc1ccc(N2C(=O)CCC[C@H]2c2nc3cc(-c4c(C)noc4C)ccc3n2[C@H]2CC[C@@](C)(O)CC2)cc1Cl] | (S)-1-(3-chloro-4-methoxyphenyl)-6-(5-(3,5-dimethylisoxazol-4-yl)-1-((1s,4R)-4-hydroxy-4-methylcyclohexyl)-1H-benzo[d]imidazol-2-yl)piperidin-2-one |
| 158 | 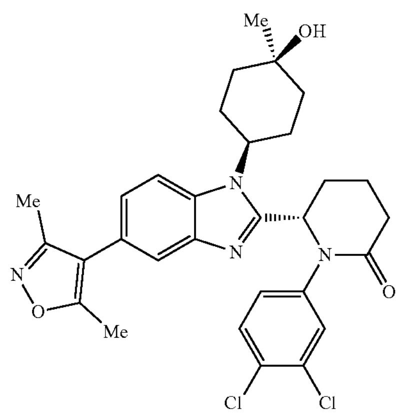 [SMILES: Cc1noc(C)c1-c1ccc2c(c1)nc([C@@H]1CCCC(=O)N1c1ccc(Cl)c(Cl)c1)n2[C@H]1CC[C@@](C)(O)CC1] | (S)-1-(3,4-dichlorophenyl)-6-(5-(3,5-dimethylisoxazol-4-yl)-1-((1s,4R)-4-hydroxy-4-methylcyclohexyl)-1H-benzo[d]imidazol-2-yl)piperidin-2-one |
| 159 | 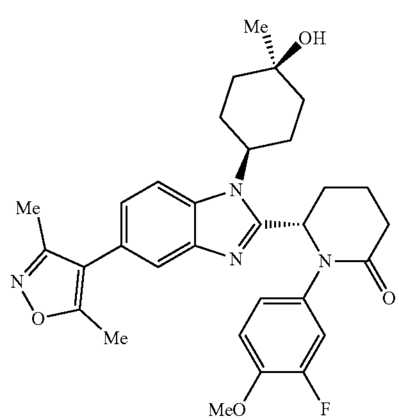 [SMILES: COc1ccc(N2C(=O)CCC[C@H]2c2nc3cc(-c4c(C)noc4C)ccc3n2[C@H]2CC[C@@](C)(O)CC2)cc1F] | (S)-6-(5-(3,5-dimethylisoxazol-4-yl)-1-((1s,4R)-4-hydroxy-4-methylcyclohexyl)-1H-benzo[d]imidazol-2-yl)-1-(3-fluoro-4-methoxyphenyl)piperidin-2-one |

-continued

| No | Structure | Name |
|---|---|---|
| 160 | 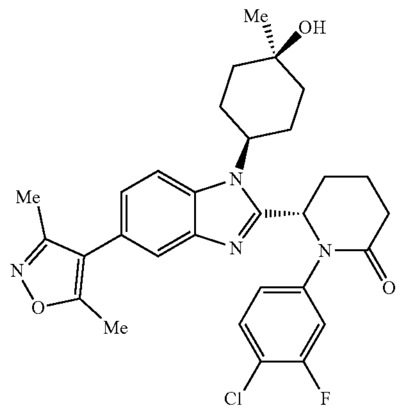 [SMILES: Cc1noc(C)c1-c1ccc2c(c1)nc([C@@H]1CCCC(=O)N1c1ccc(Cl)c(F)c1)n2[C@H]1CC[C@@](C)(O)CC1] | (S)-1-(4-chloro-3-fluorophenyl)-6-(5-(3,5-dimethylisoxazol-4-yl)-1-((1s,4R)-4-hydroxy-4-methylcyclohexyl)-1H-benzo[d]imidazol-2-yl)piperidin-2-one |
| 161 | 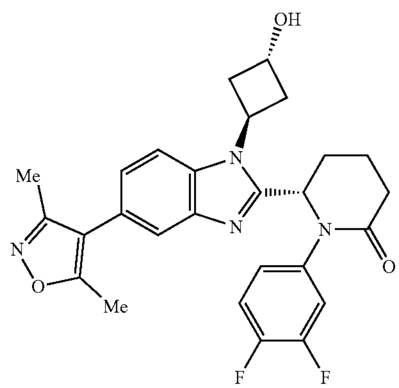 | (S)-1-(3,4-difluorophenyl)-6-(5-(3,5-dimethylisoxazol-4-yl)-1-((1r,3S)-3-hydroxycyclobutyl)-1H-benzo[d]imidazol-2-yl)piperidin-2-one |
| 162 | 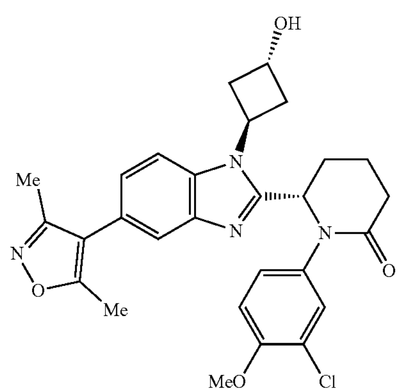 [SMILES: COc1ccc(N2C(=O)CCC[C@H]2c2nc3cc(-c4c(C)noc4C)ccc3n2[C@H]2C[C@H](O)C2)cc1Cl] | (S)-1-(3-chloro-4-methoxyphenyl)-6-(5-(3,5-dimethylisoxazol-4-yl)-1-((1r,3S)-3-hydroxycyclobutyl)-1H-benzo[d]imidazol-2-yl)piperidin-2-one |
| 163 | 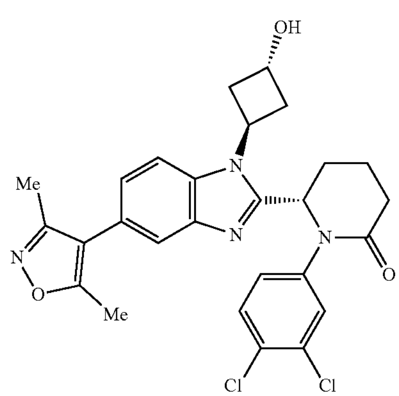 [SMILES: Cc1noc(C)c1-c1ccc2c(c1)nc([C@@H]1CCCC(=O)N1c1ccc(Cl)c(Cl)c1)n2[C@H]1C[C@H](O)C1] | (S)-1-(3,4-dichlorophenyl)-6-(5-(3,5-dimethylisoxazol-4-yl)-1-((1r,3S)-3-hydroxycyclobutyl)-1H-benzo[d]imidazol-2-yl)piperidin-2-one |

-continued

| No | Structure | Name |
|---|---|---|
| 164 | 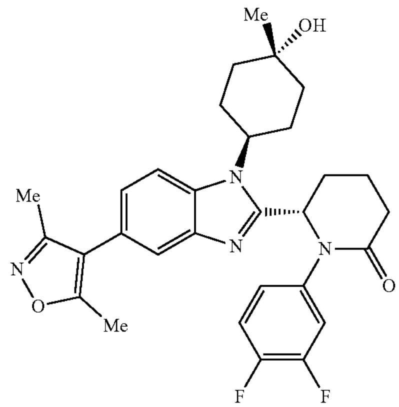 [SMILES: Cc1noc(C)c1-c1ccc2c(c1)nc([C@@H]1CCCC(=O)N1c1ccc(F)c(F)c1)n2[C@H]1CC[C@](C)(O)CC1] | (S)-1-(3,4-difluorophenyl)-6-(5-(3,5-dimethylisoxazol-4-yl)-1-((1r,4S)-4-hydroxy-4-methylcyclohexyl)-1H-benzo[d]imidazol-2-yl)piperidin-2-one |
| 165 | 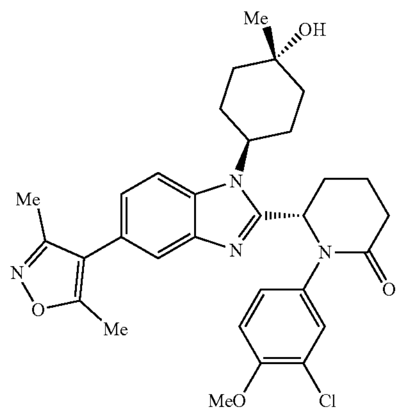 [SMILES: COc1ccc(N2C(=O)CCC[C@H]2c2nc3cc(-c4c(C)noc4C)ccc3n2[C@H]2CC[C@](C)(O)CC2)cc1Cl] | (S)-1-(3-chloro-4-methoxyphenyl)-6-(5-(3,5-dimethylisoxazol-4-yl)-1-((1r,4S)-4-hydroxy-4-methylcyclohexyl)-1H-benzo[d]imidazol-2-yl)piperidin-2-one |
| 166 | 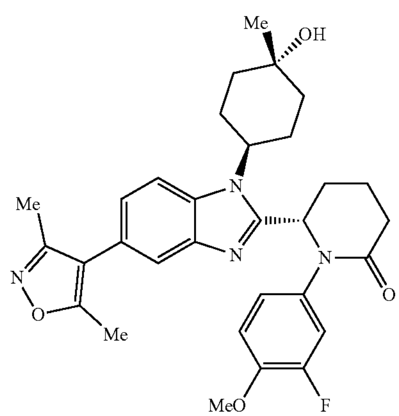 [SMILES: COc1ccc(N2C(=O)CCC[C@H]2c2nc3cc(-c4c(C)noc4C)ccc3n2[C@H]2CC[C@](C)(O)CC2)cc1F] | (S)-6-(5-(3,5-dimethylisoxazol-4-yl)-1-((1r,4S)-4-hydroxy-4-methylcyclohexyl)-1H-benzo[d]imidazol-2-yl)-1-(3-fluoro-4-methoxyphenyl)piperidin-2-one |
| 167 | 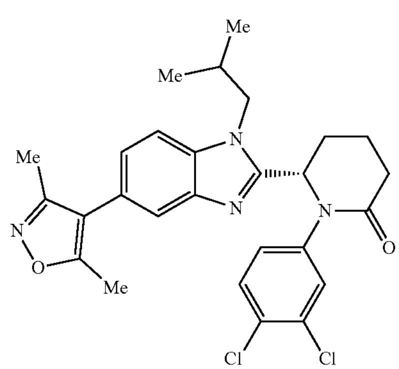 [SMILES: Cc1noc(C)c1-c1ccc2c(c1)nc([C@@H]1CCCC(=O)N1c1ccc(Cl)c(Cl)c1)n2CC(C)C] | (S)-1-(3,4-dichlorophenyl)-6-(5-(3,5-dimethylisoxazol-4-yl)-1-isobutyl-1H-benzo[d]imidazol-2-yl)piperidin-2-one |

| No | Structure | Name |
|---|---|---|
| 168 | 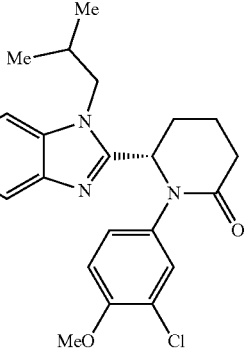 | (S)-1-(3-chloro-4-methoxyphenyl)-6-(5-(3,5-dimethylisoxazol-4-yl)-1-isobutyl-1H-benzo[d]imidazol-2-yl)piperidin-2-one |
| 169 | 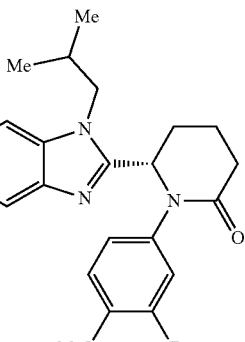 | (S)-6-(5-(3,5-dimethylisoxazol-4-yl)-1-isobutyl-1H-benzo[d]imidazol-2-yl)-1-(3-fluoro-4-methoxyphenyl)piperidin-2-one |
| 170 | 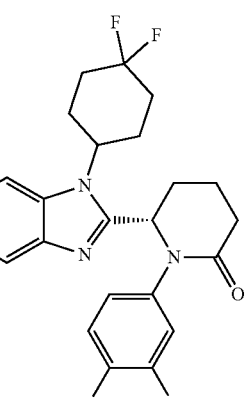 | (S)-6-(1-(4,4-difluorocyclohexyl)-5-(3,5-dimethylisoxazol-4-yl)-1H-benzo[d]imidazol-2-yl)-1-(3-fluoro-4-methoxyphenyl)piperidin-2-one |
| 171 | 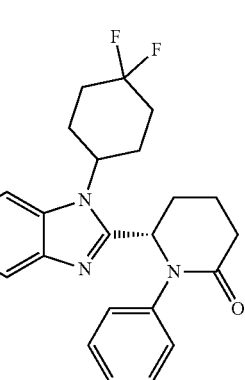 | (S)-6-(1-(4,4-difluorocyclohexyl)-5-(3,5-dimethylisoxazol-4-yl)-1H-benzo[d]imidazol-2-yl)-1-(3,4-difluorophenyl)piperidin-2-one |

-continued
| No | Structure | Name |
|---|---|---|
| 172 | 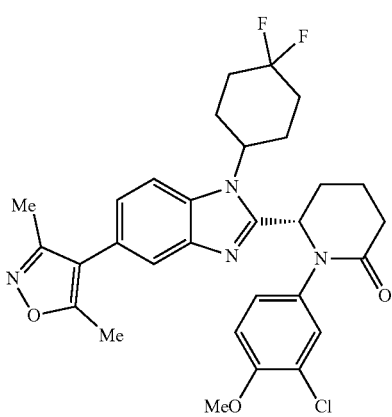 [SMILES: COc1ccc(N2C(=O)CCC[C@H]2c2nc3cc(-c4c(C)noc4C)ccc3n2C2CCC(F)(F)CC2)cc1Cl] | (S)-1-(3-chloro-4-methoxyphenyl)-6-(1-(4,4-difluorocyclohexyl)-5-(3,5-dimethylisoxazol-4-yl)-1H-benzo[d]imidazol-2-yl)piperidin-2-one |
| 173 | 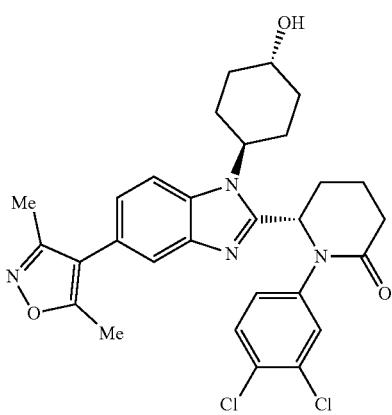 [SMILES: Cc1noc(C)c1-c1ccc2c(c1)nc([C@@H]1CCCC(=O)N1c1ccc(Cl)c(Cl)c1)n2[C@H]1CC[C@H](O)CC1] | (S)-1-(3,4-dichlorophenyl)-6-(5-(3,5-dimethylisoxazol-4-yl)-1-((1r,4S)-4-hydroxycyclohexyl)-1H-benzo[d]imidazol-2-yl)piperidin-2-one |
| 174 | 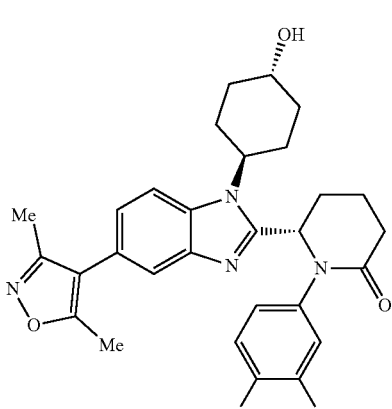 | (S)-1-(3,4-difluorophenyl)-6-(5-(3,5-dimethylisoxazol-4-yl)-1-((1r,4S)-4-hydroxycyclohexyl)-1H-benzo[d]imidazol-2-yl)piperidin-2-one |

-continued

| No | Structure | Name |
|---|---|---|
| 175 | 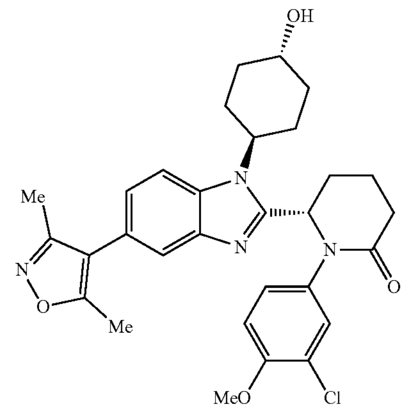 [SMILES: COc1ccc(N2C(=O)CCC[C@H]2c2nc3cc(-c4c(C)noc4C)ccc3n2[C@H]2CC[C@H](O)CC2)cc1Cl] | (S)-1-(3-chloro-4-methoxyphenyl)-6-(5-(3,5-dimethylisoxazol-4-yl)-1-((1r,4S)-4-hydroxycyclohexyl)-1H-benzo[d]imidazol-2-yl)piperidin-2-one |
| 176 | 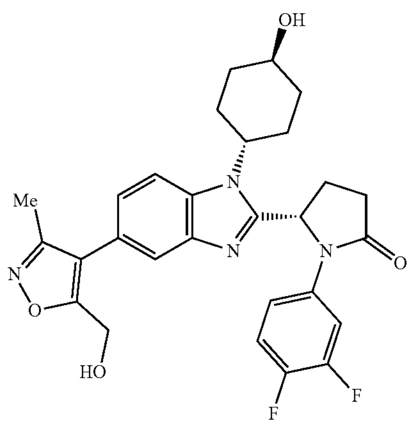 [SMILES: Cc1noc(CO)c1-c1ccc2c(c1)nc([C@@H]1CCC(=O)N1c1ccc(F)c(F)c1)n2[C@H]1CC[C@H](O)CC1] | (S)-1-(3,4-difluorophenyl)-5-(1-((1r,4S)-4-hydroxycyclohexyl)-5-(5-(hydroxymethyl)-3-methylisoxazol-4-yl)-1H-benzo[d]imidazol-2-yl)pyrrolidin-2-one |
| 177 | 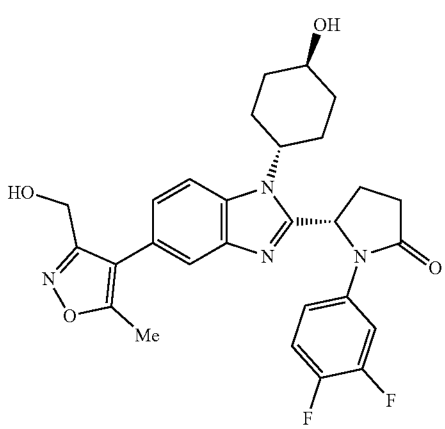 [SMILES: Cc1onc(CO)c1-c1ccc2c(c1)nc([C@@H]1CCC(=O)N1c1ccc(F)c(F)c1)n2[C@H]1CC[C@H](O)CC1] | (S)-1-(3,4-difluorophenyl)-5-(1-((1r,4S)-4-hydroxycyclohexyl)-5-(3-(hydroxymethyl)-5-methylisoxazol-4-yl)-1H-benzo[d]imidazol-2-yl)pyrrolidin-2-one |
| 178 | 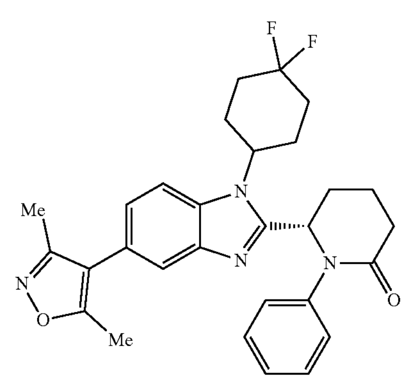 [SMILES: Cc1noc(C)c1-c1ccc2c(c1)nc([C@@H]1CCCC(=O)N1c1ccccc1)n2C1CCC(F)(F)CC1] | (S)-6-(1-(4,4-difluorocyclohexyl)-5-(3,5-dimethylisoxazol-4-yl)-1H-benzo[d]imidazol-2-yl)-1-phenylpiperidin-2-one |

| No | Structure | Name |
|---|---|---|
| 179 | 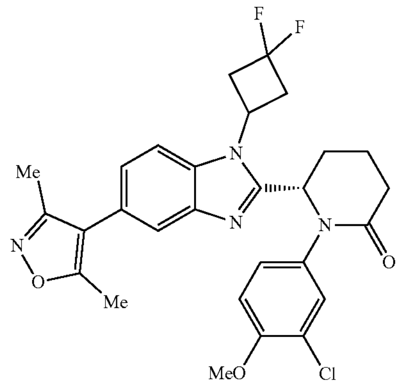 [SMILES: COc1ccc(N2C(=O)CCC[C@H]2c2nc3cc(-c4c(C)noc4C)ccc3n2C2CC(F)(F)C2)cc1Cl] | (S)-1-(3-chloro-4-methoxyphenyl)-6-(1-(3,3-difluorocyclobutyl)-5-(3,5-dimethylisoxazol-4-yl)-1H-benzo[d]imidazol-2-yl)piperidin-2-one |
| 180 | 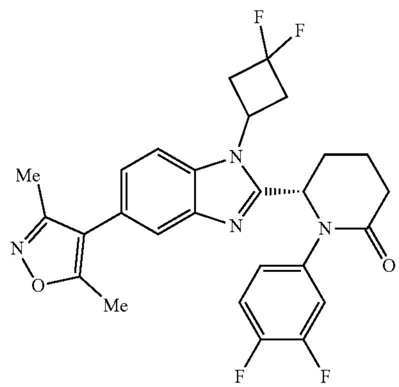 [SMILES: Cc1noc(C)c1-c1ccc2c(c1)nc([C@@H]1CCCC(=O)N1c1ccc(F)c(F)c1)n2C1CC(F)(F)C1] | (S)-6-(1-(3,3-difluorocyclobutyl)-5-(3,5-dimethylisoxazol-4-yl)-1H-benzo[d]imidazol-2-yl)-1-(3,4-difluorophenyl)piperidin-2-one |
| 181 | 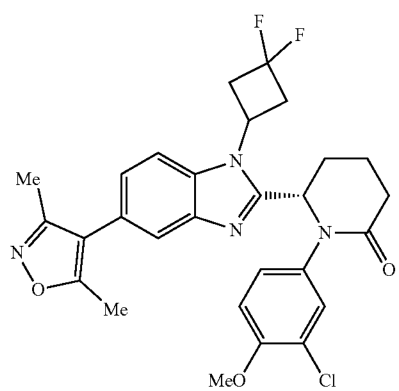 [SMILES: COc1ccc(N2C(=O)CCC[C@H]2c2nc3cc(-c4c(C)noc4C)ccc3n2C2CC(F)(F)C2)cc1Cl] | (S)-6-(1-(3,3-difluorocyclobutyl)-5-(3,5-dimethylisoxazol-4-yl)-1H-benzo[d]imidazol-2-yl)-1-(3-fluoro-4-methoxyphenyl)piperidin-2-one |
| 182 | 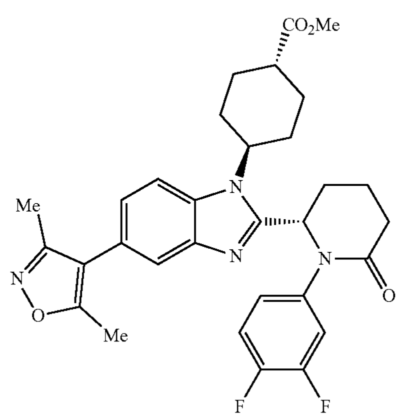 [SMILES: COC(=O)[C@H]1CC[C@H](n2c([C@@H]3CCCC(=O)N3c3ccc(F)c(F)c3)nc3cc(-c4c(C)noc4C)ccc32)CC1] | (1S,4r)-methyl 4-(2-((S)-1-(3,4-difluorophenyl)-6-oxopiperidin-2-yl)-5-(3,5-dimethylisoxazol-4-yl)-1H-benzo[d]imidazol-1-yl)cyclohexanecarboxylate |

-continued

| No | Structure | Name |
|---|---|---|
| 183 | 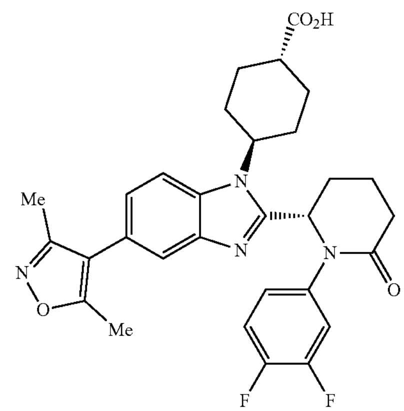 [SMILES: Cc1noc(C)c1-c1ccc2c(c1)nc([C@@H]1CCCC(=O)N1c1ccc(F)c(F)c1)n2[C@H]1CC[C@H](C(=O)O)CC1] | (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)cyclohexane carboxylic acid |
| 184 | 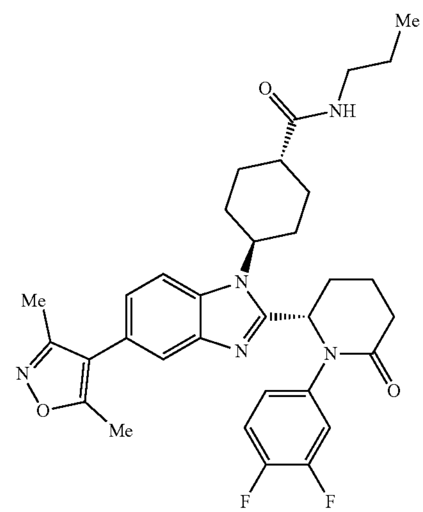 [SMILES: CCCNC(=O)[C@H]1CC[C@H](n2c([C@@H]3CCCC(=O)N3c3ccc(F)c(F)c3)nc3cc(-c4c(C)noc4C)ccc32)CC1] | (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)-N-propylcyclohexane carboxamide |
| 185 | 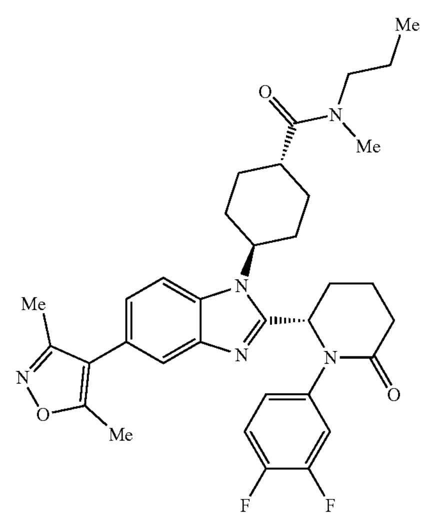 [SMILES: CCCN(C)C(=O)[C@H]1CC[C@H](n2c([C@@H]3CCCC(=O)N3c3ccc(F)c(F)c3)nc3cc(-c4c(C)noc4C)ccc32)CC1] | (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)-N-methyl-N-propylcyclohexanecarboxamide |

-continued

| No | Structure | Name |
|---|---|---|
| 186 | 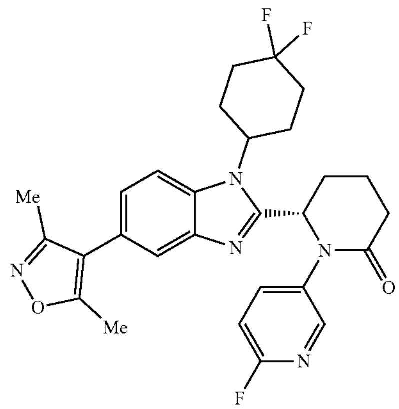 [SMILES: Cc1noc(C)c1-c1ccc2c(c1)nc([C@@H]1CCCC(=O)N1c1ccc(F)nc1)n2C1CCC(F)(F)CC1] | (S)-6-(1-(4,4-difluorocyclohexyl)-5-(3,5-dimethylisoxazol-4-yl)-1H-benzo[d]imidazol-2-yl)-1-(6-fluoropyridin-3-yl)piperidin-2-one |
| 187 | 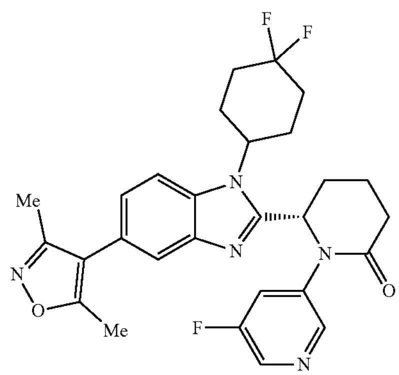 [SMILES: Cc1noc(C)c1-c1ccc2c(c1)nc([C@@H]1CCCC(=O)N1c1cncc(F)c1)n2C1CCC(F)(F)CC1] | (S)-6-(1-(4,4-difluorocyclohexyl)-5-(3,5-dimethylisoxazol-4-yl)-1H-benzo[d]imidazol-2-yl)-1-(5-fluoropyridin-3-yl)piperidin-2-one |
| 188 | 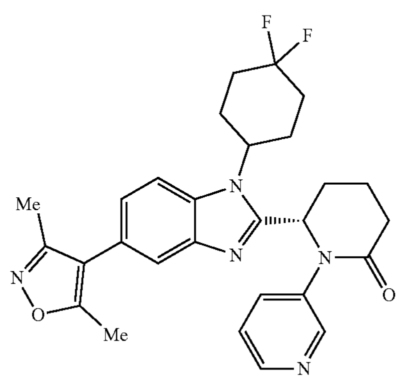 [SMILES: Cc1noc(C)c1-c1ccc2c(c1)nc([C@@H]1CCCC(=O)N1c1cccnc1)n2C1CCC(F)(F)CC1] | (S)-6-(1-(4,4-difluorocyclohexyl)-5-(3,5-dimethylisoxazol-4-yl)-1H-benzo[d]imidazol-2-yl)-1-(pyridin-3-yl)piperidin-2-one |
| 189 | 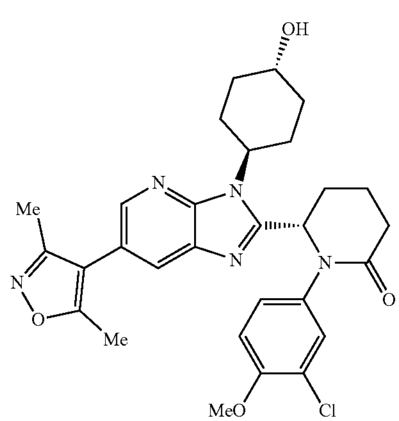 [SMILES: COc1ccc(N2C(=O)CCC[C@H]2c2nc3cc(-c4c(C)noc4C)cnc3n2[C@H]2CC[C@H](O)CC2)cc1Cl] | (S)-1-(3-chloro-4-methoxyphenyl)-6-(6-(3,4-dimethylisoxazol-4-yl)-3-((1r,4S)-4-hydroxycyclohexyl)-3H-imidazo[4,5-b]pyridin-2-yl)piperidin-2-one |

-continued

| No | Structure | Name |
|----|-----------|------|
| 190 | 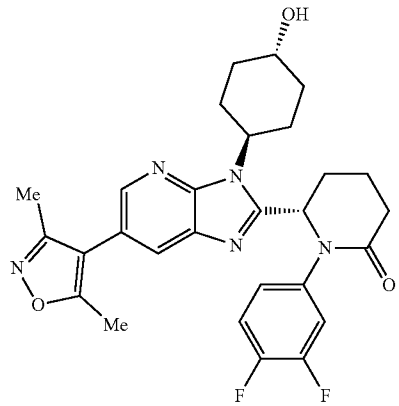 [SMILES: Cc1noc(C)c1-c1cnc2c(c1)nc([C@@H]1CCCC(=O)N1c1ccc(F)c(F)c1)n2[C@H]1CC[C@H](O)CC1] | (S)-1-(3,4-difluorophenyl)-6-(6-(3,5-dimethylisoxazol-4-yl)-3-((1r,4S)-4-hydroxycyclohexyl)-3H-imidazo[4,5-b]pyridin-2-yl)piperidin-2-one |
| 191 | 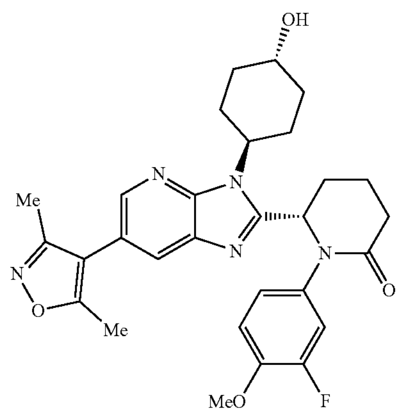 | (S)-6-(6-(3,5-dimethylisoxazol-4-yl)-3-((1r,4S)-4-hydroxycyclohexyl)-3H-imidazo[4,5-b]pyridin-2-yl)-1-(3-fluoro-4-methoxyphenyl)piperidin-2-one |
| 192 | 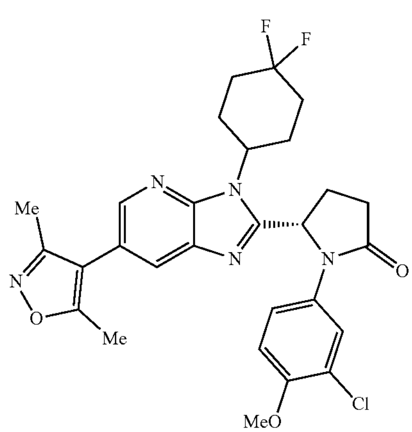 | (S)-1-(3-chloro-4-methoxyphenyl)-5-(3-(4,4-difluorocyclohexyl)-6-(3,5-dimethylisoxazol-4-yl)-3H-imidazo[4,5-b]pyridin-2-yl)pyrrolidin-2-one |

-continued

| No | Structure | Name |
|---|---|---|
| 193 | 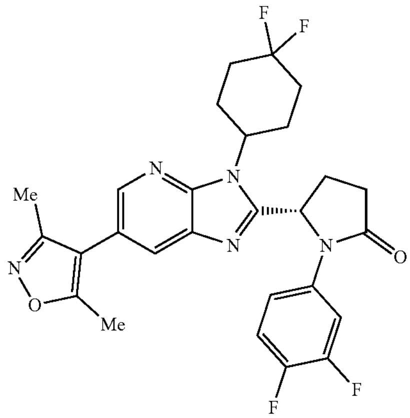 [SMILES: Cc1noc(C)c1-c1cnc2c(c1)nc([C@@H]1CCC(=O)N1c1ccc(F)c(F)c1)n2C1CCC(F)(F)CC1] | (S)-5-(3-(4,4-difluorocyclohexyl)-6-(3,5-dimethylisoxazol-4-yl)-3H-imidazo[4,5-b]pyridin-2-yl)-1-(3,4-difluorophenyl)pyrrolidin-2-one |
| 194 | 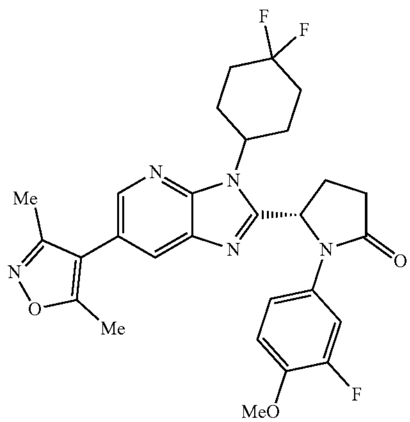 [SMILES: COc1ccc(N2C(=O)CC[C@H]2c2nc3cc(-c4c(C)noc4C)cnc3n2C2CCC(F)(F)CC2)cc1F] | (S)-5-(3-(4,4-difluorocyclohexyl)-6-(3,5-dimethylisoxazol-4-yl)-3H-imidazo[4,5-b]pyridin-2-yl)-1-(3-fluoro-4-methoxyphenyl)pyrrolidin-2-one |
| 195 | 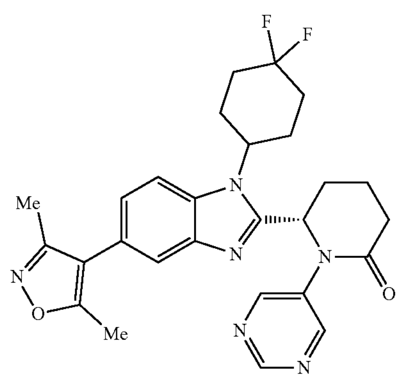 [SMILES: Cc1noc(C)c1-c1ccc2c(c1)nc([C@@H]1CCCC(=O)N1c1cncnc1)n2C1CCC(F)(F)CC1] | (S)-6-(1-(4,4-difluorocyclohexyl)-5-(3,5-dimethylisoxazol-4-yl)-1H-benzo[d]imidazol-2-yl)-1-(pyrimidin-5-yl)piperidin-2-one |
| 196 | 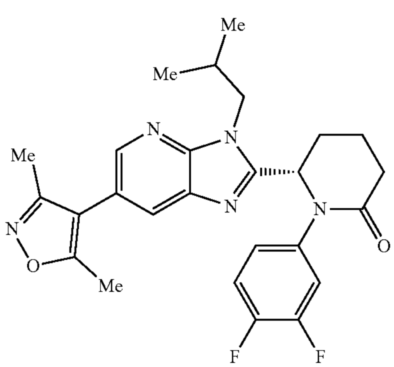 [SMILES: Cc1noc(C)c1-c1cnc2c(c1)nc([C@@H]1CCCC(=O)N1c1ccc(F)c(F)c1)n2CC(C)C] | (S)-1-(3,4-difluorophenyl)-6-(6-(3,5-dimethylisoxazol-4-yl)-3-isobutyl-3H-imidazo[4,5-b]pyridin-2-yl)piperidin-2-one |

-continued

| No | Structure | Name |
|---|---|---|
| 197 | 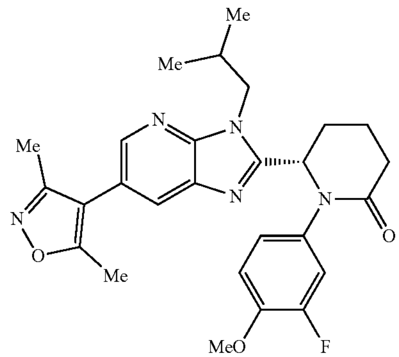 | (S)-6-(6-(3,5-dimethylisoxazol-4-yl)-3-isobutyl-3H-imidazo[4,5-b]pyridin-2-yl)-1-(3-fluoro-4-methoxyphenyl)piperidin-2-one |
| 198 | | (S)-1-benzyl-5-(5-(3,5-dimethylisoxazol-4-yl)-1-((1r,4S)-4-methoxycyclohexyl)-1H-benzo[d]imidazol-2-yl)pyrrolidin-2-one | and the pharmaceutically acceptable salts thereof.

A compound of the invention in which integer n=0 may be prepared by a process which comprises treating a compound of formula (II):

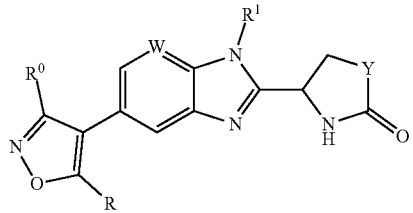

(II)

wherein each of R, $R^0$, $R^1$, W and Y is as defined above for formula (I), with a boronic acid of formula $R^2$—B(OH)$_2$ wherein $R^2$ is as defined above for formula (I), in the presence of Pd(PPh$_3$)$_4$ and Na$_2$CO$_3$ in aqueous ethanol. The aqueous ethanol is typically 20-60% EtOH/water.

A compound of the invention in which integer n=0 may also be prepared by a process which comprises treating a compound of formula (III):

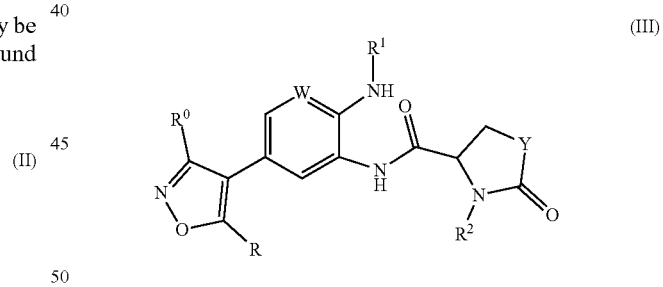

(III)

wherein each of R, $R^0$, $R^1$, $R^2$, W and Y is as defined above for formula (I), with acetic acid at 60-100° C. or HCl/1,4-dioxane 20-90%.

A compound of the invention in which integer n is 1 may be prepared by a process which comprises treating a compound of formula (II) as defined above with a compound of formula $R^2$—CH$_2$Br in which $R^2$ is as defined above for formula (I). Typically the reaction is conducted by adding sodium hexamethyldisilazane (NaHMDS) in THF to a solution of the compound of formula (II) in DMF, and then adding a solution of the compound of formula $R^2$—CH$_2$Br in DMF.

The schemes shown below illustrate synthetic strategies, including the above process steps, by which compounds of the invention may be produced.

123

Route A: Non-Convergent Approach to γ-Lactam Analogues

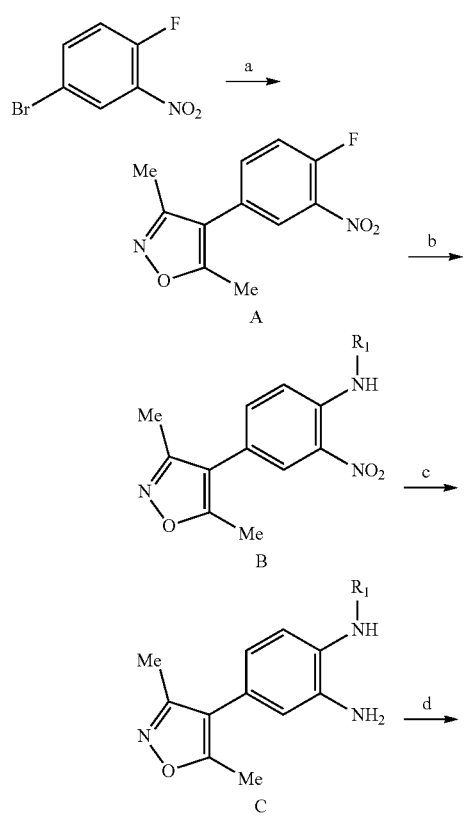

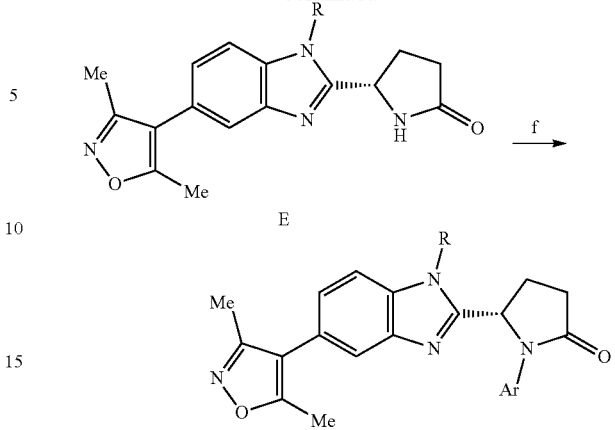

a. Dimethylisoxazoleboronic acid, Na$_2$CO$_3$, Pd(PPh$_3$)$_4$, EtOH/water—50-70%
b. R$_1$—NH$_2$, TEA, THF, rt or R$_1$—NH$_2$.HCl, TEA, DMF, 70-90° C.—60-90%
c. Na$_2$S$_2$O$_4$, THF/H$_2$O, NH$_4$OH or Fe, AcOH or Fe, NH$_4$Cl, EtOH/H$_2$O, 80° C.—30-80%
d. HATU, pyroglutamic acid, TEA, DCM or DMF—50-90% (either purified or used crude)
e. AcOH, 60-100° C.—20-60%
f. Arylboronic acid, Na$_2$CO$_3$, Pd(PPh$_3$)$_4$, EtOH/water—20-60%

Route B: Convergent Approach to γ-Lactam Analogues from N-Arylpyroglutamic Acid

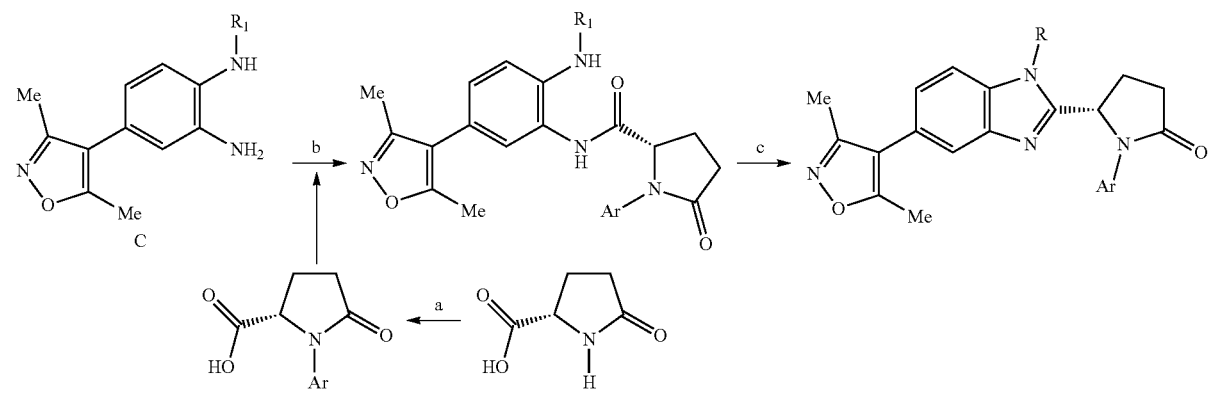

-continued

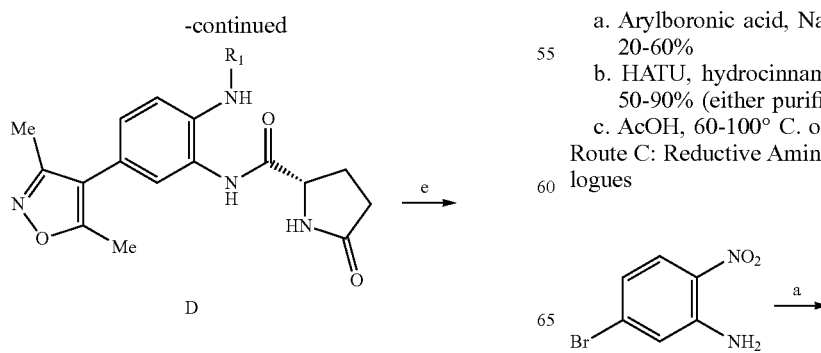

a. Arylboronic acid, Na$_2$CO$_3$, Pd(PPh$_3$)$_4$, EtOH/water—20-60%
b. HATU, hydrocinnamic acid, TEA, DCM or DMF—50-90% (either purified or used crude)
c. AcOH, 60-100° C. or HCl/1,4-dioxane—20-90%

Route C: Reductive Amination Approach to γ-Lactam Analogues

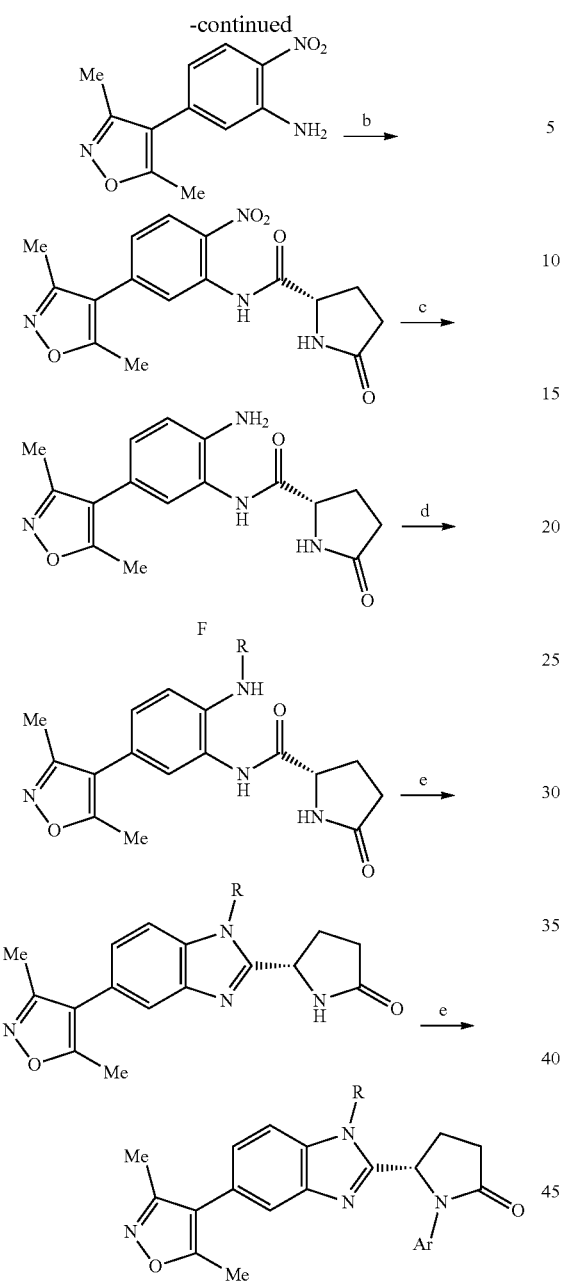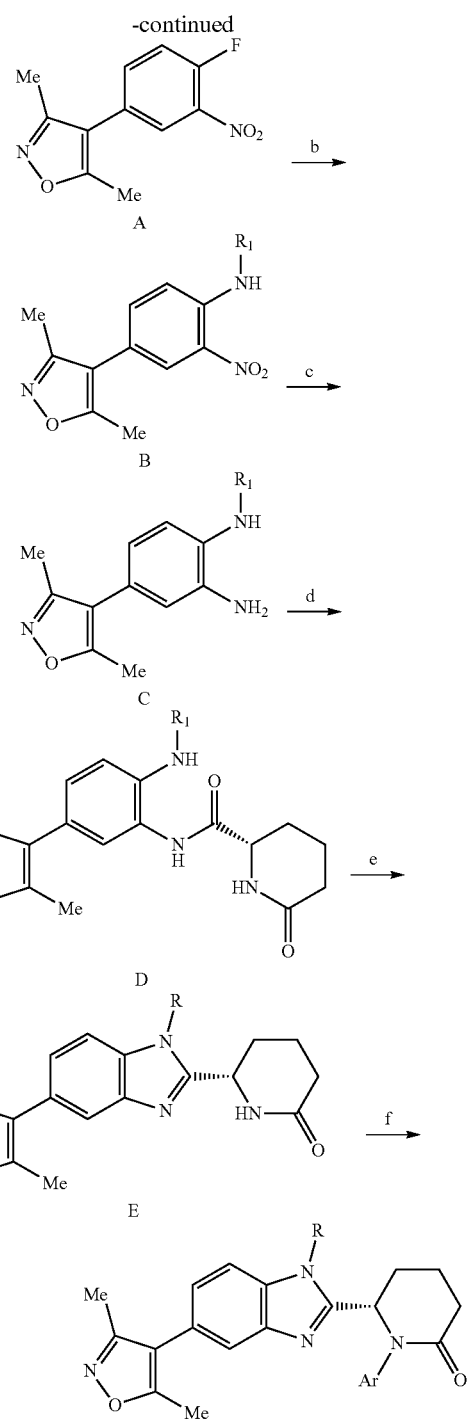

a. Dimethylisoxazoleboronic acid, Na₂CO₃, Pd(PPh₃)₄, EtOH/water
b. HATU, pyroglutamic acid, TEA, DCM or DMF
c. Pt, H₂, EtOH
d. Ketone or aldehyde, STAB, DCM
e. AcOH, 60-100° C.
f. Arylboronic acid, Na₂CO₃, Pd(PPh3)4, EtOH/water Route D: Non-Convergent Approach to Valerolactam Analogues

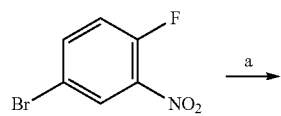

a. Dimethylisoxazoleboronic acid, Na₂CO₃, Pd(PPh₃)₄, EtOH/water—50-70%
b. R₁—NH₂, TEA, THF, rt or R₁—NH₂.HCl, TEA, DMF, 70-90° C.—60-90%
c. Na₂S₂O₄, THF/H₂O, NH₄OH or Fe, AcOH or Fe, NH₄Cl, EtOH/H₂O, 80° C.—30-80%
d. HATU, pyroglutamic acid, TEA, DCM or DMF—50-90% (either purified or used crude)
e. AcOH, 60-100° C.—20-60%
f. Arylboronic acid, Na₂CO₃, Pd(PPh₃)₄, EtOH/water or pyridine Route E: Non-Convergent Approach to Azabenzimidazole Analogues Route F. Convergent Approach to N-Alkyllactam Analogues

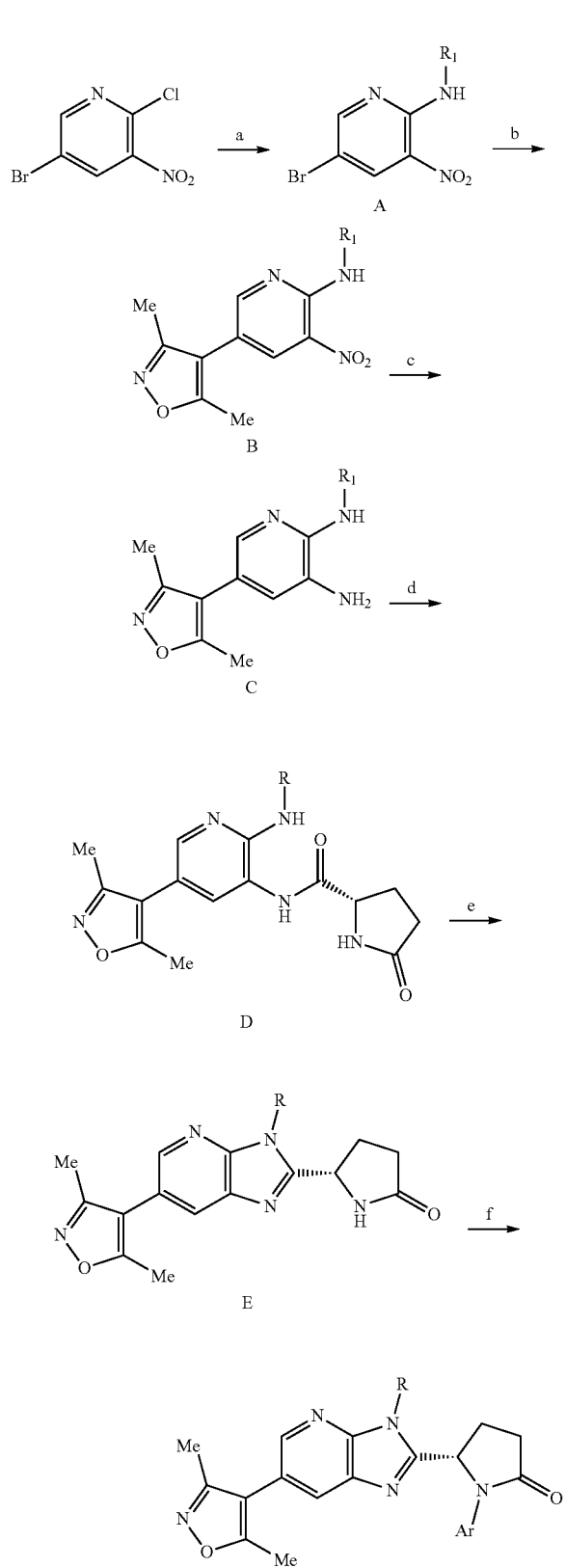

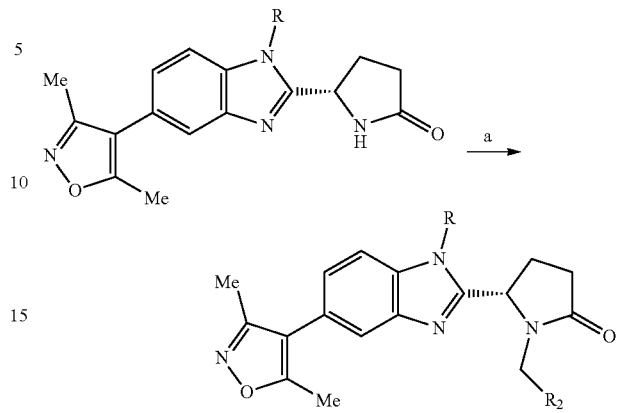

A key to the abbreviations used in all the above schemes is provided in the Examples section below.

An arylimidazolyl isoxazole of formula (I) may be converted into a pharmaceutically acceptable salt, and salts may be converted into the free compound, by conventional methods. Pharmaceutically acceptable salts include salts of inorganic acids such as hydrochloric acid, hydrobromic acid and sulfuric acid, and salts of organic acids such as acetic acid, oxalic acid, malic acid, methanesulfonic acid, trifluoroacetic acid, benzoic acid, citric acid and tartaric acid. In the case of compounds bearing a free carboxy substituent, the salts include both the above-mentioned acid addition salts and the salts of sodium, potassium, calcium and ammonium. The latter are prepared by treating the free benzarylimidazolyl isoxazole of formula (I), or an acid addition salt thereof, with the corresponding metal base or ammonia.

An arylimidazolyl isoxazole of formula (I) or a pharmaceutically acceptable salt thereof is hereafter referred to as a compound of the invention. Compounds of the invention have been found in biological tests to bind to the histone acetyltransferase (HAT), p300, and to CBP, as described in Example 199 below.

CREB binding protein (CBP) and its paralogue, p300, are two closely-related histone acetyl transferase co-factor proteins that are involved in a wide variety of cancer processes, including cell proliferation, apoptosis, cell cycle regulation and DNA damage response. CBP/p300 primarily functions as a transcription cofactor for a number of oncoproteins including Jun, Fos and E2F. In addition, it acts as a histone acetyltransferase and can also acetylate multiple non-histone proteins such as p53, p73, and Rb. CBP/p300 has been reported to act as a tumour suppressor or as an oncoprotein dependent upon the nature of the cancer. Multiple studies have shown that p300 expression correlates with disease progression and decreased survival.

CBP and p300 is up-regulated in human prostate cancer progression and has been shown to be an AR co-activator (Debes, J. D., et al., (2003) 'p[300] in prostate cancer proliferation and progression,' Cancer Res., Vol. 63, pp. 7638-7640; and Linja, M. J. et al., (2004) 'Expression of androgen receptor coregulators in prostate cancer,' Clin. Cancer Res., Vol. 10, pp. 1032-1040).

p300 has recently been shown to directly regulate AR protein degradation (Zhong et al., 2014). p300 mediated AR acetylation was shown to inhibit AR ubiquitination and subsequent AR proteasome degradation (Zhong et al., 2014, cited above). The direct inhibition of p300 activity would therefore promote AR degradation.

Given the high molecular heterogeneity of prostate cancer, the identification of appropriate biomarkers is critical to the effective positioning and evaluation of targeted small molecule therapies. It is proposed that markers of the development of the CRPC phenotype via AR resurgence are used for patient stratification for the evaluation of p300 modulators. These include PSA and circulating tumour cell (CTC) counts and the appearance of AR and AR splice variants in CTCs.

In terms of biomarkers to enable the monitoring of the modulation of p300 activity, direct readouts include; determination of the AR and AR splice variant levels; modulation of AR activity by assessing levels of AR responsive genes including TMPRSS2 and KLK3. Other surrogate markers of AR functional activity include p21, c-Myc and p53. Given that multiple therapeutic agents which modulate AR activity are approved for use in CRPC, biomarkers to assess effects of p300 targeting and subsequent AR modulation are already widely available and used in clinical settings.

Various types of cancer have been shown to express AR. In addition to prostate cancer, these include breast and bladder cancer. Modulation of p300 activity would be expected to have therapeutic utility in the treatment of such cancers and other indications in which AR is expressed. In addition, it is feasible that p300 regulates the levels of other nuclear hormone receptors, thereby further expanding the clinical utility of p300 targeted agents.

A recent publication (Ogiwara et al. (2016) Cancer Discovery. 6; 430-445) has shown that tumours which harbour loss of function mutations in CBP are uniquely sensitive to p300 inhibition. Conversely tumours with mutations of p300 are uniquely sensitive to CBP inhibition. In lung cancer, genetic analysis reveals that up to 15% of both non-small cell and small cell tumours have these loss of function mutations. Similar mutations are also found in up to 25% of bladder cancers, as well as in a number of haematological malignancies, including lymphoma and leukaemia. Modulation of p300 and/or CBP would be expected to have therapeutic utility in tumours which harbour these mutations Further recent publications (Casey et al. (2016) Science. 352; 227-231; Ghosh et al. (2016) JBC on line) has shown that CBP/p300 regulates the expression of key immune checkpoint proteins such as CTLA4/PDL1 as well as the differentiation and function of t-regulatory cells. Modulation of p300 and/or CBP would be expected to provide additional therapeutic utility when combined with agents that target the immune-oncology system.

A compound of the invention has activity as a modulator p300 and/or CBP activity. It may therefore be used to treat cancer, or another clinical condition in which AR is expressed, or in cancers in which there is activation of CBP and/or p300 function. The cancers that can be treated include those which express AR or are otherwise associated with AR, those that harbour loss of function mutations in CBP or p300 and those which have activated CBP and/or p300.

Cancers that may be treated include, but are not restricted to, prostate cancer, breast cancer, bladder cancer, lung cancer, lymphoma and leukaemia. The prostate cancer may be, for instance, castration-resistant prostate cancer (CRPC). The lung cancer may be, for instance, non-small cell lung cancer or small cell lung cancer. A human or animal patient suffering from cancer may thus be treated by a method comprising the administration thereto of a compound of the invention. The condition of the patient may thereby be improved or ameliorated.

A compound of the invention may thus be administered to a human or animal patient in conjunction with radiotherapy or another therapeutic agent for the treatment of cancer. The present invention therefore further provides a combination therapy wherein a compound of the invention, or a pharmaceutical composition comprising a compound of the invention, is administered concurrently or sequentially with radiotherapy; or is administered concurrently sequentially or as a combined preparation with another therapeutic agent or agents, for the treatment of cancer.

The or each other therapeutic agent will typically be an agent conventionally used for the type of cancer being treated. Classes of therapeutic agents with which a compound of the invention is typically combined for the treatment of prostate cancer include androgen receptor antagonists, for instance Enzalutamide, and inhibitors of CYP17A1 (17α-hydroxylase/C17,20 lyase), for instance Abiraterone; cyctotoxic chemotherapy, for instance Docetaxel; for the treatment of lung cancer include cytotoxic chemotherapies, for instance cisplatin, carboplatin, docetaxel; for the treatment of bladder cancer include cytotoxic chemotherapies, for instance gemcitabine, cisplatin or immune therapies, for instance, bacillus calmette-guérin (BCG). Other classes of agents with which a compound of the invention could be combined with include immune checkpoint inhibitors, for instance pembrolizumab, nivolumab, atezolizumab, ipilumumab; inhibitors of PARP (poly ADP ribose polymerase) such as Olaparib; and inhibitors of CDK4/6 (cyclin-dependant kinase 4 and 6).

The term "combination" as used herein refers to simultaneous, separate or sequential administration. Where the administration is sequential or separate, the delay in administering the second component should not be such as to lose the beneficial effect of the combination.

The present invention further provides a product comprising (a) a compound of the invention as defined above; and (b) one or more other therapeutic agent or agents;

for separate, simultaneous or sequential administration in the prophylactic or therapeutic treatment of cancer, for instance the specific types of cancer mentioned above. The other therapeutic agent may be, for instance, an androgen receptor antagonist, an inhibitor of CYP17A1, an inhibitor of PARP or an inhibitor of CDK4/6. More specifically, it may Enzalutamide, Abiraterone or Olaparib.

A compound of the invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A compound of the invention is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan monooleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents.

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables.

C) By inhalation, in the form of aerosols or solutions for nebulizers.

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols.

E) Topically, in the form of creams, ointments, jellies, collyriums, solutions or suspensions.

The invention will be further described in the Examples and Reference Examples which follow:

TABLE 1

| Abbreviations | |
|---|---|
| AcOH | glacial acetic acid |
| aq | aqueous |
| Ac | acetyl |
| Boc | tert-butoxycarbonyl |
| br | broad |
| CatCart ® | catalytic cartridge |
| CDI | 1,1-carbonyl-diimidazole |
| d | doublet |
| DCM | Dichloromethane |
| DIPEA | N,N-diisopropylethylamine |
| DMF | N,N-dimethylformamide |
| DMSO | dimethyl sulfoxide |
| (ES+) | electrospray ionization, positive mode |
| Et | Ethyl |
| EtOAc | ethyl acetate |
| FCS | foetal calf serum |
| HOBt | 1-hydroxybenzotriazole |
| hr | hour(s) |
| (M + H)+ | protonated molecular ion |
| Me | methyl |
| MeCN | acetonitrile |
| MeOH | methanol |
| MHz | megahertz |
| min | minute(s) |
| m/z: | mass-to-charge ratio |
| NMP | 1-methylpyrrolidin-2-one (N-methyl-2-pyrrolidone) |
| NMR | nuclear magnetic resonance (spectroscopy) |
| PdCl2dppf | (1,1'-Bis(diphenylphospino)ferrocene)palladium(II) dichloride |
| Ph | phenyl |
| PBS | phosphate buffered saline |
| PPh$_3$ | triphenylphosphine |
| q | quartet |
| RT | room temperature |
| RP HPLC | reverse phase high performance liquid chromatography |
| s | singlet |
| SCX | solid supported cation exchange (resin) |
| S$_N$Ar | nucleophilic aromatic substitution |
| t | triplet |
| TBAF | tetrabutylammonium fluoride |
| TEA | triethylamine |
| TFA | trifluoroacetic acid |
| THF | tetrahydrofuran |
| TIPS-Cl | chlorotriisopropylsilane |
| TMB | 3,3',5,5'-tetramethylbenzidine |
| XantPhos | 4,5-bis(diphenylphosphino)-9,9-dimethylxanthene |

General Procedures

All starting materials and solvents were either obtained from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 μM) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% NH$_3$ in MeOH.

Analytical Methods

Reverse Phase High Performance Liquid Chromatography:

Analytical HPLC was carried out using a Waters Xselect CSH C18, 2.5 μm, 4.6×30 mm column eluting with a gradient of 0.1% Formic Acid in MeCN in 0.1% aqueous Formic Acid; a Waters Xbridge BEH C18, 2.5 μm, 4.6×30 mm column eluting with a gradient of MeCN in aqueous 10 mM Ammonium Bicarbonate. UV spectra of the eluted peaks were measured using either a diode array or variable wavelength detector on an Agilent 1100 system.

Analytical LCMS was carried out using a Waters Xselect CSH C18, 2.5 μm, 4.6×30 mm column eluting with a gradient of 0.1% Formic Acid in MeCN in 0.1% aqueous Formic Acid (Method 1); a Waters Xbridge BEH C18, 2.5 μm, 4.6×30 mm column eluting with a gradient of MeCN in aqueous 10 mM Ammonium Bicarbonate (Method 2). UV and mass spectra of the eluted peaks were measured using a variable wavelength detector on either an Agilent 1200 with or an Agilent Infinity 1260 LCMS with 6120 single quadrupole mass spectrometer with positive and negative ion electrospray.

Preparative HPLC was carried out using a Waters Xselect CSH C18, 5 μm, 19×50 mm column using either a gradient of either 0.1% Formic Acid in MeCN in 0.1% aqueous Formic Acid or a gradient of MeCN in aqueous 10 mM Ammonium Bicarbonate; or a Waters Xbridge BEH C18, 5 μm, 19×50 mm column using a gradient MeCN in aqueous 10 mM Ammonium Bicarbonate. Fractions were collected following detection by UV at a single wavelength measured by a variable wavelength detector on a Gilson 215 preparative HPLC or Varian PrepStar preparative HPLC; by mass and UV at a single wavelength measured by a ZQ single quadrupole mass spectrometer, with positive and negative ion electrospray, and a dual wavelength detector on a Waters FractionLynx LCMS.

Chiral preparative HPLC was carried out using a Gilson Diacel Chiralpak IA or IB, 5 μm, 20×250 mm, 60 mn runs, 1.0 mL/mn, using the following solvent systems:

Method A—10% EtOH in 4:1 isohexane (0.1% DEA):DCM (Diacel Chiralpak IA)

Method B—10% EtOH in 4:1 isohexane (0.1% DEA):DCM (Diacel Chiralpak IA)

Method C—20% EtOH in 4:1 isohexane (0.2% DEA):DCM (Diacel Chiralpak IA)

Method D—35% EtOH in 4:1 isohexane (0.2% DEA):DCM (Diacel Chiralpak IC)

Method E—35% EtOH in 4:1 isohexane (0.2% DEA):DCM (Diacel Chiralpak IC)

Method F—20% EtOH in 4:1 isohexane (0.2% DEA): DCM (Diacel Chiralpak IA) 1H NMR Spectroscopy: 1H NMR spectra were acquired on a Bruker Advance III spectrometer at 400 MHz. Either the central peaks of chloroform-d, dimethylsulfoxide-d6 or an internal standard of tetramethylsilane were used as references.

$^1$H NMR Spectroscopy:

$^1$H NMR spectra were acquired on a Bruker Advance III spectrometer at 400 MHz using residual undeuterated solvent as reference

REFERENCE EXAMPLES

General Route A: Non-Convergent Approach to γ-Lactam Analogues 4-(4-fluoro-3-nitrophenyl)-3,5-dimethylisoxazole (Intermediate A)

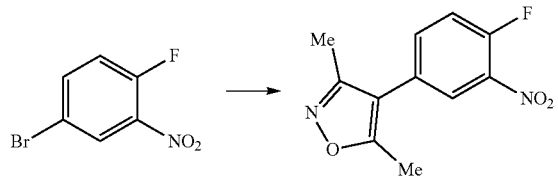 [SMILES: O=[N+]([O-])c1cc(Br)ccc1F ; Cc1noc(C)c1-c1ccc(F)c([N+](=O)[O-])c1]

PdCl₂(dppf) (60 g, 82 mmol) was added to a stirring mixture of potassium carbonate (407 g, 2947 mmol), (3,5-dimethylisoxazol-4-yl)boronic acid (180 g, 1277 mmol) and 4-bromo-1-fluoro-2-nitrobenzene (216 g, 982 mmol) in 4:1 Dioxane/water (3 L). The reaction mixture was stirred at 90° C. for 18 h. After cooling to RT the mixture was diluted with water (1 L) and extracted with ethyl acetate (1×2 L and 1×1 L). Combined organics were eluted through a Celite pad and evaporated under reduced pressure. DCM (1 L) was added to the crude product and the resultant solution was purified in three batches; each batch (400 mL) being loaded onto a 1 kg silica plug and eluting with DCM. Fractions from all three plugs were analysed by HPLC; product fractions were combined and concentrated in vacuo to afford 4-(4-fluoro-3-nitrophenyl)-3,5-dimethylisoxazole (177.6 g, 76%) as a light yellow solid; Rt 2.08 min (method 1), m/z 237 (M+H)+ (ES+).µ

(R)—N-(4-(3,5-dimethylisoxazol-4-yl)-2-nitrophenyl)-1-(methylsulfonyl)pyrrolidin-3-amine (B1)

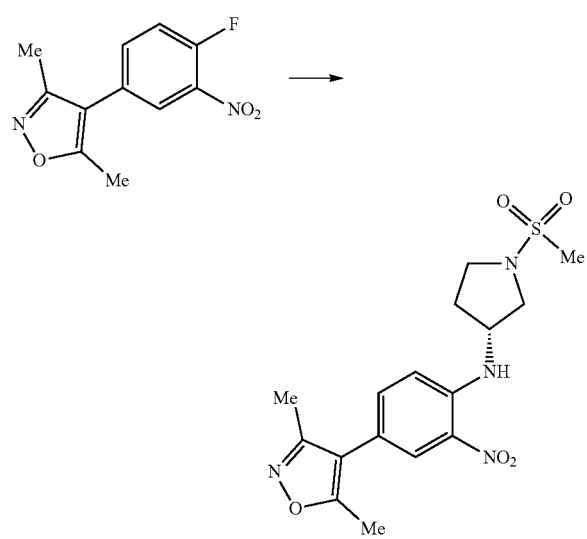

(R)-3-methyl-1-(methylsulfonyl)pyrrolidine hydrochloride (4.9 g, 24.54 mmol) and TEA (11.40 ml, 82 mmol) were dissolved in DMF (30 ml, 387 mmol), 4-(4-fluoro-3-nitrophenyl)-3,5-dimethylisoxazole (3.86 g, 16.36 mmol) added, and stirred at 45° C. for 30 h. The mixture was evaporated in vacuo, and the residue dissolved in EtOAc (200 mL), washed with water (2×100 mL) and brine (50 mL), dried (MgSO₄), filtered and evaporated in vacuo. The residual orange solid was purified by chromatography on silica gel (220 g column, 0-100% EtOAc in (50% DCM/isohexane) to give (R)—N-(4-(3,5-dimethylisoxazol-4-yl)-2-nitrophenyl)-1-(methylsulfonyl)pyrrolidin-3-amine (5.3 g, 85%); Rt 1.99 min (method 2); m/z 381 (M+H)+ (ES+).

(R)-4-(3,5-dimethylisoxazol-4-yl)-N1-(1-(methylsulfonyl)pyrrolidin-3-yl)benzene-1,2-diamine (Intermediate C1)

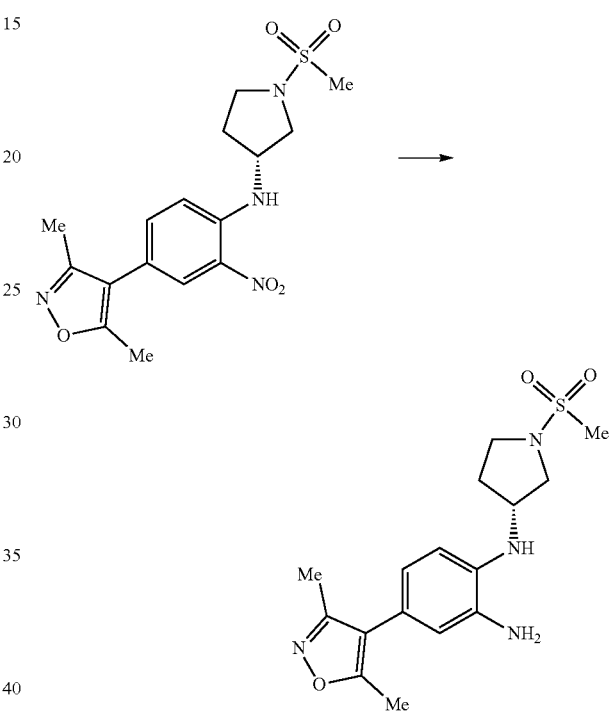

(R)—N-(4-(3,5-dimethylisoxazol-4-yl)-2-nitrophenyl)-1-(methylsulfonyl)pyrrolidin-3-amine (5.2 g, 13.67 mmol) was dissolved in THF/water (1:1, 400 mL) then aqueous concentrated ammonia (10.65 mL, 273 mmol) and sodium dithionite (23.80 g, 137 mmol) were added and the reaction stirred at RT for 1 h. The layers were separated and the aqueous extracts were extracted with EtOAc (20 mL). The combined organics washed with brine (20 mL), dried (MgSO₄), filtered and evaporated in vacuo to give (R)-4-(3,5-dimethylisoxazol-4-yl)-N1-(1-(methylsulfonyl)pyrrolidin-3-yl)benzene-1,2-diamine (3.89 g, 72%) as a pink foam; Rt 1.68 min (method 2); m/z 351 (M+H)+ (ES+).

N-(4-(3,5-dimethylisoxazol-4-yl)-2-nitrophenyl) tetrahydro-2H-pyran-4-amine (B2)

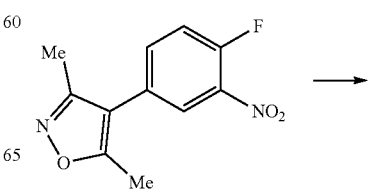

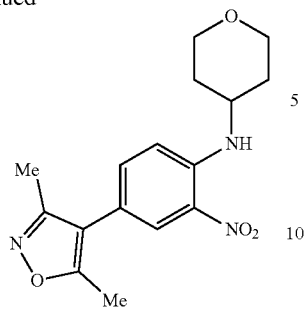

Tetrahydro-2H-pyran-4-amine (2.63 ml, 25.4 mmol) was dissolved in dry THF (10 ml, 122 mmol) and TEA (8.85 ml, 63.5 mmol) and cooled to 0° C. 4-(4-fluoro-3-nitrophenyl)-3,5-dimethylisoxazole Intermediate A (5 g, 21.17 mmol) was added and the reaction stirred at 60° C. for 16 hours. Further amine/base (½ molar equivalent) added and heated at 60° C. overnight. The reaction mixture was poured onto water (100 mL), The solid formed was filtered under vacuum, washed with water (50 mL), isohexane (100 mL) and dried in vacuo to give N-(4-(3,5-dimethylisoxazol-4-yl)-2-nitrophenyl)tetrahydro-2H-pyran-4-amine (6.5 g, 96%) as a bright orange solid; Rt 2.13 min (method 2); m/z 318 (M+H)+ (ES+).

4-(3,5-dimethylisoxazol-4-yl)-$N^1$-(tetrahydro-2H-pyran-4-yl)benzene-1,2-diamine (C2)

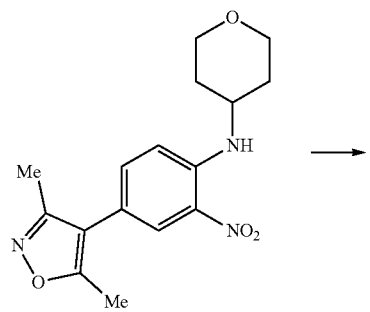

Sodium dithionite (75 g, 431 mmol) was added to a solution of N-(4-(3,5-dimethylisoxazol-4-yl)-2-nitrophenyl) tetrahydro-2H-pyran-4-amine (13.1 g, 40.9 mmol) and concentrated ammonia (32 ml, 822 mmol) in THF/water (1:1, 200 mL) and the reaction mixture stirred at RT for 2 hours. The reaction mixture was partitioned between EtOAc (200 mL) and brine (100 mL), the phases separated and the organics dried over MgSO₄, filtered and concentrated in vacuo to give a sticky pink foam. The foam was slurried in diethyl ether (150 mL) overnight then collected by filtration to yield 4-(3,5-dimethylisoxazol-4-yl)-$N^1$-(tetrahydro-2H-pyran-4-yl)benzene-1,2-diamine (8.57 g, 70%) as a pink solid; Rt 0.83 min (method 1); m/z 288 (M+H)+ (ES+).

N-(4-(3,5-dimethylisoxazol-4-yl)-2-nitrophenyl)tetrahydro-2H-pyran-4-amine (B3)

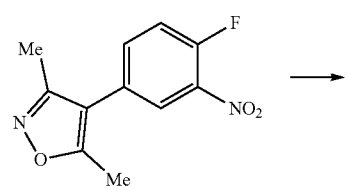

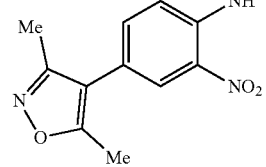

To a mixture of 4-(4-fluoro-3-nitrophenyl)-3,5-dimethylisoxazole (6.60 g, 27.9 mmol) and 4-aminotetrahydro-2H-thiopyran 1,1-dioxide (5 g, 33.5 mmol) in DMF (40 mL) was added TEA (8.56 ml, 61.4 mmol). The mixture was stirred at 60° C. for 18 h, then quenched in ice water (200 mL). The solid was collected by filtration and washed with water to afford 4-((4-(3,5-dimethylisoxazol-4-yl)-2-nitrophenyl)amino)tetrahydro-2H-thiopyran 1,1-dioxide (10.2 g, 92%) as a bright orange solid; Rt 1.91 min (method 1); m/z 366 (M+H)+ (ES+).

4-((2-amino-4-(3,5-dimethylisoxazol-4-yl)phenyl)amino)tetrahydro-2H-thiopyran 1,1-dioxide (C3)

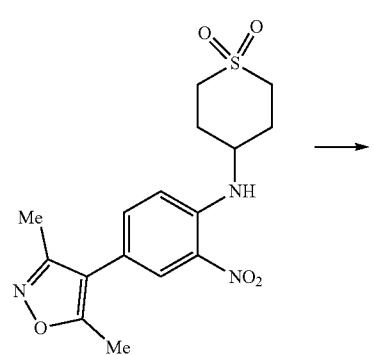

-continued

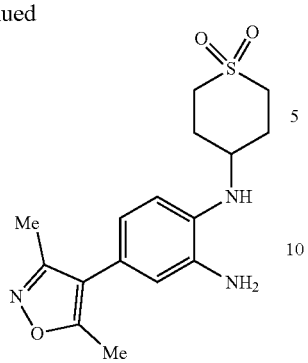

4-((4-(3,5-dimethylisoxazol-4-yl)-2-nitrophenyl)amino)tetrahydro-2H-thiopyran 1,1-dioxide (10.2 g, 27.9 mmol) was added to a solution of sodium dithionite (48.6 g, 279 mmol) and ammonium hydroxide (78 mL, 558 mmol) in THF (150 ml) and water (100 mL). The reaction mixture stirred at RT for 18 h, then concentrated in vacuo to remove organics. The remaining aqueous layer (containing solid present) was filtered under vacuum, washed with water (2×100 mL) and pulled to dryness. The solid was transferred to a flask and triturated with ether. Filtration and pulling to dryness afforded 4-((2-amino-4-(3,5-dimethylisoxazol-4-yl)phenyl)amino)tetrahydro-2H-thiopyran 1,1-dioxide (4.94 g, 48%) as a light beige solid; Rt 1.24 min (method 1); m/z 336 (M+H)+ (ES+).

(1r,4r)-4-((4-(3,5-dimethylisoxazol-4-yl)-2-nitrophenyl)amino)cyclohexan-1-ol (B4)

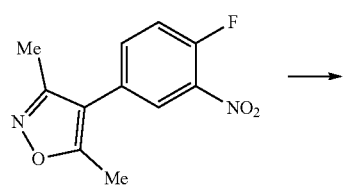

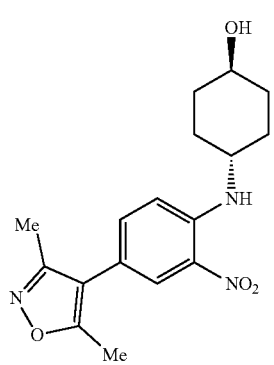

4-(4-fluoro-3-nitrophenyl)-3,5-dimethylisoxazole (32.6 g, 138 mmol), trans-4-aminocyclo hexanol (18.5 g, 160.6 mmol), and potassium carbonate (40 g, 289 mmol) were heated to reflux in acetonitrile (500 mL) for 3 h. The mixture was diluted dropwise with water (2 L) whilst stirring vigorously. The resulting precipitate was collected by filtration to yield (1r,4r)-4-((4-(3,5-dimethylisoxazol-4-yl)-2-nitrophenyl)amino)cyclohexanol (56.5 g, 99%) as a bright orange solid; Rt 2.00 min (method 1); m/z 332 (M+H)+ (ES+).

(1r,4r)-4-((2-amino-4-(3,5-dimethylisoxazol-4-yl)phenyl)amino)cyclohexan-1-ol (C4)

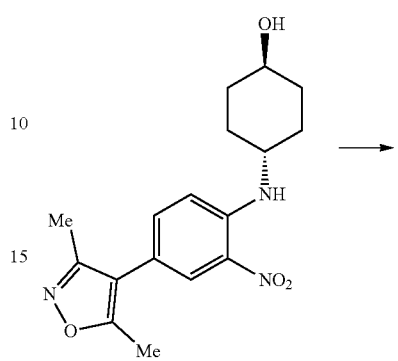

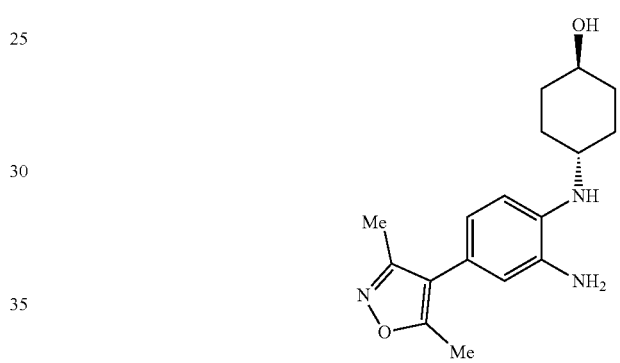

Sodium dithionite (300 g, 1465 mmol) was added slowly in three (ca. 100 g) portions to a mixture of (1r,4r)-4-((4-(3,5-dimethylisoxazol-4-yl)-2-nitrophenyl)amino)cyclohexanol (56 g, 135 mmol), concentrated ammonia (110 mL, 2825 mmol), THF/water (1:1, 1 L) then stirred at room temperature for a total of 40 minutes. The mixture was diltued with water (2 L) then the precipitate was collected by filtration to yield a pink solid. The solid was co-evaporated in acetonitrile (500 mL) to afford (1r,4r)-4-((2-amino-4-(3,5-dimethylisoxazol-4-yl)phenyl)amino)cyclohexan-1-ol (33 g, 80%) as a pink solid; Rt 1.05 min (method 1); m/z 302 (M+H)+ (ES+).

(S)-3-((4-(3,5-dimethylisoxazol-4-yl)-2-nitrophenyl)amino)tetrahydrothiophene 1,1-dioxide (B5)

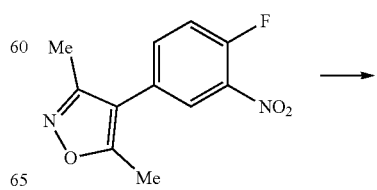

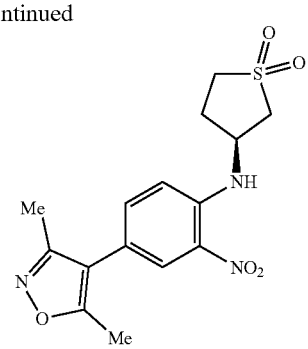

A mixture of 4-(4-fluoro-3-nitrophenyl)-3,5-dimethylisoxazole (2.92 g, 12.35 mmol) and (S)-3-aminotetrahydrothiophene 1,1-dioxide (1.67 g, 12.35 mmol) was stirred in dry THF (20 mL) and TEA (6.89 ml, 49.4 mmol) was added. The reaction was stirred at RT for 72 h, then poured into ice water (100 mL). A solid precipitated which was collected by filtration. The solid was washed with water to afford after filtration (S)-3-((4-(3,5-dimethylisoxazol-4-yl)-2-nitrophenyl)amino)tetrahydrothiophene 1,1-dioxide (B5) (4.47 g, 100%) as a bright orange solid; Rt 1.88 min (method 1); m/z 352 (M+H)+ (ES+).

(S)-3-((2-amino-4-(3,5-dimethylisoxazol-4-yl)phenyl)amino)tetrahydrothiophene 1,1-dioxide (C5)

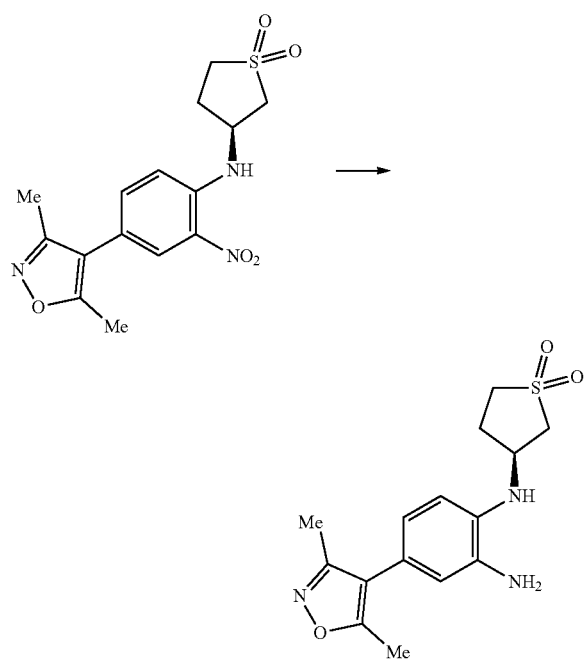

(S)-3-((4-(3,5-dimethylisoxazol-4-yl)-2-nitrophenyl)amino)tetrahydrothiophene 1,1-dioxide (3.42 g, 9.73 mmol) was dissolved in water (150 mL) and THF (150 mL). ammonium hydroxide solution (7.58 mL, 195 mmol) and sodium dithionite (16.95 g, 97 mmol) were added and the reaction stirred at RT for 2 h. EtOAc (200 mL) was added, the mixture transferred to a separating funnel and washed sequentially with 1M NaOH (2×200 mL) and brine (100 mL). The organic phase was dried (MgSO₄), filtered and concentrated in vacuo to give an off white solid, which was triturated with ether and collected by filtration to afford (S)-3-((2-amino-4-(3,5-dimethylisoxazol-4-yl)phenyl)amino)tetrahydrothiophene 1,1-dioxide (1.4 g, 42%) as a light pink fluffy solid; Rt 1.26 min (method 1); m/z 322 (M+H)+ (ES+).

tert-butyl (S)-3-((4-(3,5-dimethylisoxazol-4-yl)-2-nitrophenyl)amino)pyrrolidine-1-carboxylate (B6)

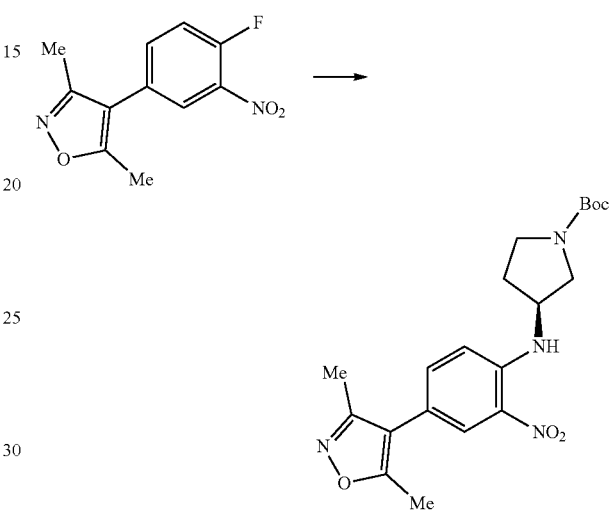

A mixture of 4-(4-fluoro-3-nitrophenyl)-3,5-dimethylisoxazole (6.34 g, 26.8 mmol) and (S)-tert-butyl 3-aminopyrrolidine-1-carboxylate (5 g, 26.8 mmol) was stirred in dry THF (100 mL) and TEA (11.23 mL, 81 mmol) was added. The reaction was stirred at 40° C. for 72 h then heated to 50° C. and stirred for 18 h. After cooling to RT, the reaction mixture was poured into ice water (300 mL). The mixture was extracted with ethyl acetate (2×500 mL). The combined organics were dried (MgSO₄) and concentrated in vacuo to afford (S)-tert-butyl 3-((4-(3,5-dimethylisoxazol-4-yl)-2-nitrophenyl)amino)pyrrolidine-1-carboxylate (11.57 g, 99%) as a thick orange oil; Rt 1.26 min (method 1); m/z 322 (M+H)+ (ES+).

tert-butyl (S)-3-((2-amino-4-(3,5-dimethylisoxazol-4-yl)phenyl)amino)pyrrolidine-1-carboxylate (C6)

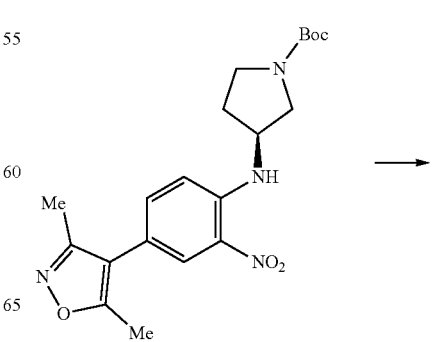

-continued

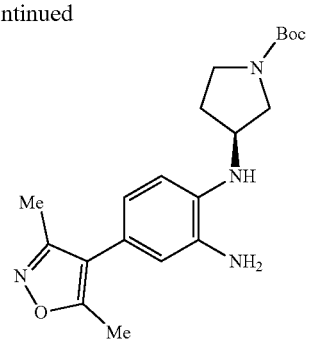

(S)-Tert-butyl 3-((4-(3,5-dimethylisoxazol-4-yl)-2-nitrophenyl)amino)pyrrolidine-1-carboxylate (10.8 g, 26.8 mmol) was dissolved in water (500 mL) and THF (500 mL). Concentrated ammonia (20.90 mL, 537 mmol) and sodium dithionite (46.7 g, 268 mmol) were added and the reaction stirred at RT for 18 h. EtOAc (500 mL) was added, the mixture transferred to a separating funnel and washed sequentially with 1M NaOH (400 mL) and brine (200 mL). The organic phase was dried (MgSO4), filtered and concentrated in vacuo to give an off white solid. The material was triturated with ether and collected by filtration. The filtrate was concentrated in vacuo to afford a light fluffy off white solid. After LCMS and NMR analysis the triturated material and the material obtained from the filtrate were combined to afford (S)-tert-butyl 3-((2-amino-4-(3,5-dimethylisoxazol-4-yl)phenyl)amino)pyrrolidine-1-carboxylate (7.64 g, 76%) as an off white fluffy solid; Rt 1.98 min (method 1); m/z 273 (M-Boc+H)+ (ES+).

tert-butyl (R)-3-((4-(3,5-dimethylisoxazol-4-yl)-2-nitrophenyl)amino)pyrrolidine-1-carboxylate (B6)

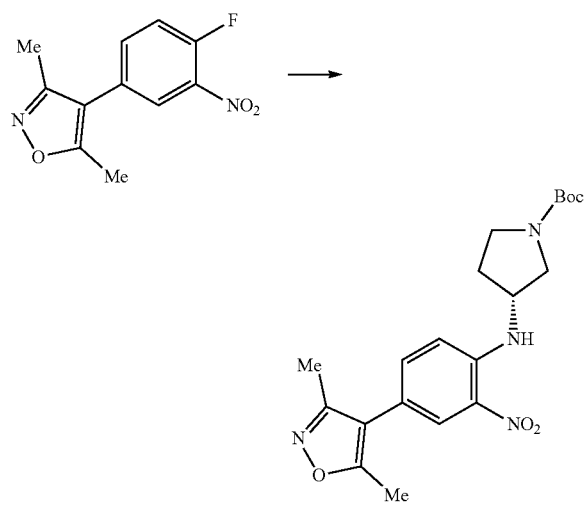

A mixture of 4-(4-fluoro-3-nitrophenyl)-3,5-dimethylisoxazole (10 g, 42.3 mmol) and (R)-tert-butyl 3-aminopyrrolidine-1-carboxylate (7.89 g, 42.3 mmol) was stirred in dry THF (100 mL) and TEA (17.70 mL, 127 mmol) was added. The reaction was stirred at RT for 18 h, then heated to 40° C. and stirred for 72 h, then heated to 50° C. and stirred for 18 h. After cooling to RT, the reaction mixture was poured into ice water (300 mL). The mixture was extracted with ethyl acetate (2×500 mL). The combined organics were dried (MgSO4) and concentrated in vacuo to afford (R)-tert-butyl 3-((4-(3,5-dimethylisoxazol-4-yl)-2-nitrophenyl)amino)pyrrolidine-1-carboxylate (17.85 g, 96%) as a thick orange oil; Rt 2.55 min (method 1); m/z 403 (M+H)+ (ES+).

tert-butyl (R)-3-((2-amino-4-(3,5-dimethylisoxazol-4-yl)phenyl)amino)pyrrolidine-1-carboxylate (C6)

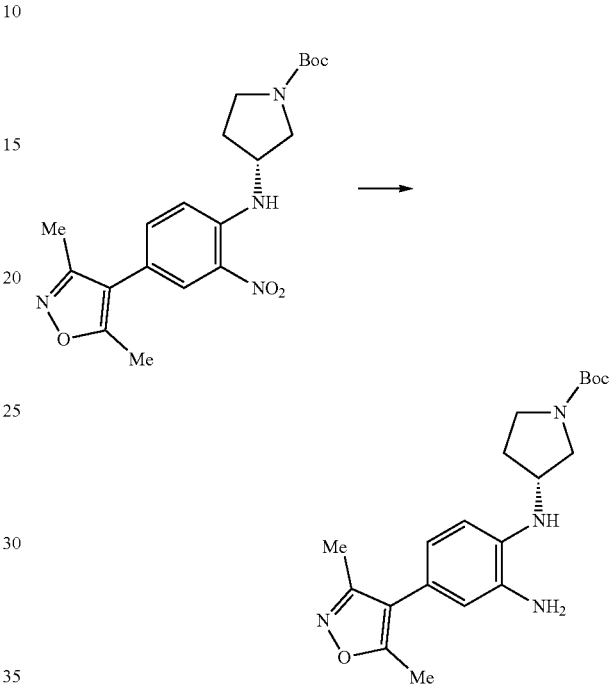

(R)-Tert-butyl 3-((4-(3,5-dimethylisoxazol-4-yl)-2-nitrophenyl)amino)pyrrolidine-1-carboxylate (17.04 g, 42.3 mmol) was dissolved in THF/water (1:1, 1 L). Ammonia (33.0 mL, 847 mmol) and sodium dithionite (73.7 g, 423 mmol) were added and the reaction stirred at RT for 18 h. EtOAc (500 mL) was added, the mixture transferred to a separating funnel and washed sequentially with 1M NaOH (400 mL) and brine (200 mL). The organic phase was dried (MgSO$_4$), filtered and concentrated in vacuo to give a light peach fluffy solid. The material was triturated with ether and collected by filtration. The filtrate was concentrated in vacuo to afford a light foam. The triturated material and the material obtained from the filtrate were combined to afford (R)-tert-butyl 3-((2-amino-4-(3,5-dimethylisoxazol-4-yl)phenyl)amino) pyrrolidine-1-carboxylate (13.58 g, 85%) as a light peach fluffy solid; Rt 1.98 min (method 1); m/z 273 (M-Boc+H)+ (ES+).

N-(4-(3,5-dimethylisoxazol-4-yl)-2-nitrophenyl)-1-methylpyrrolidin-3-amine (B7)

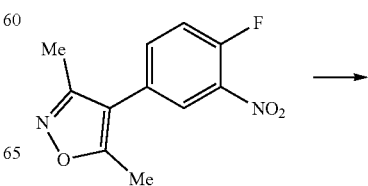

-continued

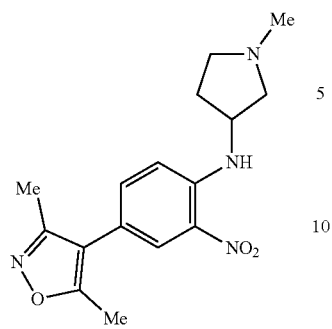

1-Methylpyrrolidin-3-amine (1.060 g, 10.58 mmol) was added to a suspension of 1-methylpyrrolidin-3-amine, bis-hydrochloride (2.75 g, 15.88 mmol) in DIPEA (8.32 mL, 47.6 mmol) and THF (30 mL, 366 mmol) and stirred and sonicated for 15 min. A solution of 4-(4-fluoro-3-nitrophenyl)-3,5-dimethylisoxazole (2.5 g, 10.58 mmol) in DMF (5 mL, 64.6 mmol) was added to the suspension and the reaction stirred at 50° C. for 20 h then for a further 20 h at 70° C. More 1-Methylpyrrolidin-3-amine (1.060 g, 10.58 mmol) was added and stirred for 5 h. Further DMF (10 mL, 129 mmol) was added and stirred for a further 20 h. The solvents were evaporated in vacuo and the residue partitioned between EtOAc (100 mL) and saturated aqueous sodium hydrogenocarbonate (100 mL) and the layers separated. The aqueous phase was extracted with further EtOAc (2×50 mL) and the combined organic extracts washed with water (50 mL) and brine (50 mL). The solution was dried (MgSO$_4$), filtered and evaporated in vacuo. The residual gum was purified by chromatography on the Companion (180 g column, 0-100% EtOAc in DCM, followed by 0-50% (DCM/MeOH/NH$_3$ (80:20:1) in DCM, loaded in DCM) to give N-(4-(3,5-dimethylisoxazol-4-yl)-2-nitrophenyl)-1-methylpyrrolidin-3-amine Intermediate B7 (2.5 g, 75%); Rt 1.10 min (method 1); m/z 317 (M+H)+ (ES+).

4-(3,5-dimethylisoxazol-4-yl)-N$^1$-(1-methylpyrrolidin-3-yl)benzene-1,2-diamine (C7)

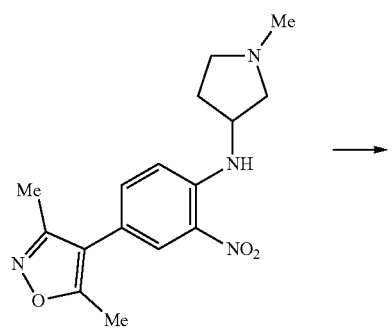

-continued

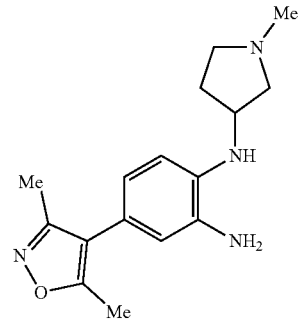

Intermediate B7 (2.5 g, 7.90 mmol) and concentrated ammonia (5 ml, 128 mmol) were dissolved in THF/water (1:1, 150 mL). Sodium dithionite (13.76 g, 79 mmol) was added and the reaction mixture stirred at RT for 3 h. The layers were separated, the aqueous extracted with EtOAc (100 mL), the combined organics washed with brine (50 mL), dried (MgSO4), filtered and evaporated in vacuo to give 4-(3,5-dimethylisoxazol-4-yl)-N$^1$-(1-methylpyrrolidin-3-yl)benzene-1,2-diamine Intermediate C7 (1.8 g, 77%) as a buff coloured solid; Rt 0.31 min (method 1); m/z 287 (M+H)+ (ES+).

4-(3,5-dimethylisoxazol-4-yl)-N-((1r,4r)-4-methoxycyclohexyl)-2-nitroaniline (B8)

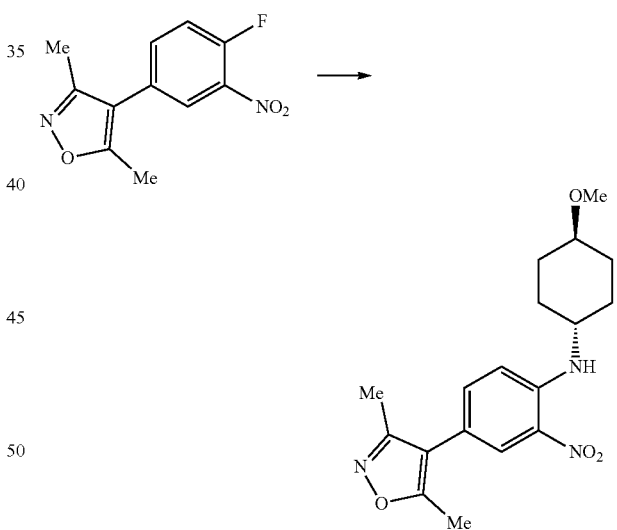

4-(4-fluoro-3-nitrophenyl)-3,5-dimethylisoxazole (0.609 g, 2.58 mmol) was dissolved in dry THF (20 ml) and TEA (1.079 ml, 7.74 mmol). (1r,4r)-4-methoxycyclohexanamine (0.4 g, 3.10 mmol) was added and the reaction warmed to 60° C. and left to stir at rt for 84 h. After cooling to rt the reaction mixture was poured into ice water (100 ml), then extracted with ethyl acetate (2×100 ml). Combined organics were concentrated in vacuo (azeotroping with acetonitrile) to afford the crude 4-(3,5-dimethylisoxazol-4-yl)-N-((1r,4r)-4-methoxycyclohexyl)-2-nitroaniline (1.1 g, 3.12 mmol, >100%), which was used without purification in the next step; Rt 2.40 min (method 1); m/z 346 (M+H)+ (ES+).

4-(3,5-dimethylisoxazol-4-yl)-$N^1$-((1r,4r)-4-methoxycyclohexyl)benzene-1,2-diamine (C8)

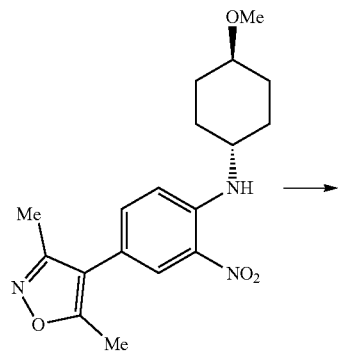

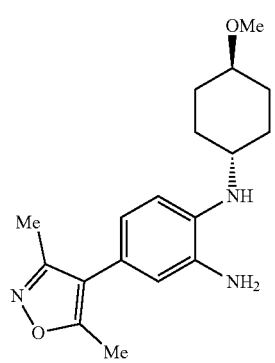

4-(3,5-Dimethylisoxazol-4-yl)-N-((1r,4r)-4-methoxycyclohexyl)-2-nitroaniline (0.89 g, 2.58 mmol) was dissolved in water (50 mL) and THF (50 mL). Concentrated ammonia (2.0 mL, 51.5 mmol) and sodium dithionite (4.49 g, 25.8 mmol) were added and the reaction stirred at RT for 2 h. EtOAc (250 mL) was added, the mixture transferred to a sep funnel and washed sequentially with 1M NaOH (150 mL) and brine (100 mL). The organic phase was passed through a phase sep cartridge and concentrated in vacuo to afford 4-(3,5-dimethylisoxazol-4-yl)-$N^1$-((1r,4r)-4-methoxycyclohexyl)benzene-1,2-diamine (680 mg, 81%) as an orange solid; Rt 1.24 min (method 1); m/z 316 (M+H)+ (ES+).

3-((4-(3,5-dimethylisoxazol-4-yl)-2-nitrophenyl)amino)tetrahydro-2H-thiopyran 1,1-dioxide (B9)

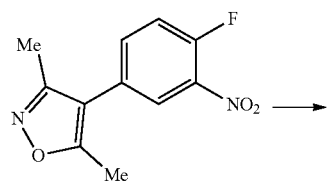

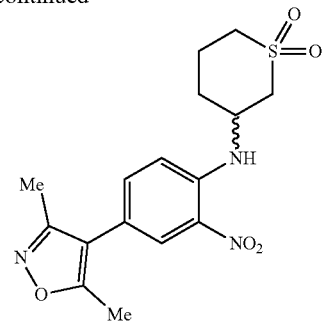

4-(4-Fluoro-3-nitrophenyl)-3,5-dimethylisoxazole (2 g, 8.47 mmol) was dissolved in dry THF (50 mL) and TEA (4.72 mL, 33.9 mmol). 3-Aminotetrahydro-2H-thiopyran 1,1-dioxide hydrochloride (1.89 g, 10.16 mmol) was added and the reaction warmed to 60° C. and left to stir at rt for 84 h. DMF (20 mL) was added and the reaction mixture heated at 70° C. for 18 h. After cooling to rt the reaction mixture was poured into ice water (200 mL), then extracted with ethyl acetate (2×200 mL). Combined organics were concentrated in vacuo (azeotroping with acetonitrile) to afford 3-((4-(3,5-dimethylisoxazol-4-yl)-2-nitrophenyl)amino)tetrahydro-2H-thiopyran 1,1-dioxide (3.6 g, 8.37 mmol, 99%) as an orange solid; Rt 1.93 min (method 1); m/z 366 (M+H)+ (ES+).

3-((2-Amino-4-(3,5-dimethylisoxazol-4-yl)phenyl)amino)tetrahydro-2H-thiopyran 1,1-dioxide (C9)

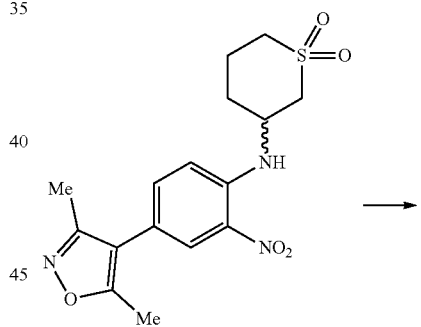

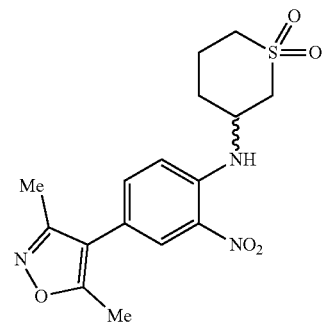

3-((4-(3,5-dimethylisoxazol-4-yl)-2-nitrophenyl)amino)tetrahydro-2H-thiopyran 1,1-dioxide (3.09 g, 8.46 mmol) was dissolved in THF/water (1:1, 400 ml). Concentrated ammonia (6.59 ml, 169 mmol) and sodium dithionite (14.72 g, 85 mmol) were added and the reaction stirred at RT for 2 h. EtOAc (500 mL) was added, the mixture transferred to a sep funnel and washed sequentially with 1M NaOH (400 mL) and brine (200 mL). The organic phase was passed through a PhaseSep© cartridge and concentrated in vacuo to afford 3-((2-amino-4-(3,5-dimethylisoxazol-4-yl)phenyl)amino)tetrahydro-2H-thiopyran 1,1-dioxide (1.80 g, 62%) as an off white foam; Rt 1.31 min (method 1); m/z 336 (M+H)+ (ES+).

N-(4-(3,5-dimethylisoxazol-4-yl)-2-nitrophenyl)-1-(methylsulfonyl)piperidin-4-amine (B10)

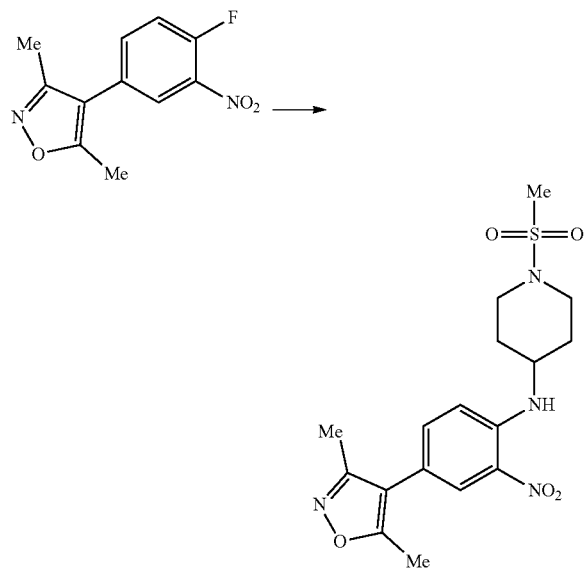

4-(4-fluoro-3-nitrophenyl)-3,5-dimethylisoxazole (2 g, 8.47 mmol) was dissolved in dry THF (50 ml) and TEA (4.72 ml, 33.9 mmol). 1-(methylsulfonyl)piperidin-4-amine hydrochloride (2.182 g, 10.16 mmol) was added and the reaction warmed to 60° C. and left to stir at rt for 84 h. DMF (20 ml) was added and the reaction mixture heated at 70° C. for 18 h. After cooling to rt the reaction mixture was poured into ice water (200 ml), then extracted with ethyl acetate (2×200 ml). Combined organics were concentrated in vacuo (azeotroping with acetonitrile) to afford N-(4-(3,5-dimethylisoxazol-4-yl)-2-nitrophenyl)-1-(methylsulfonyl)piperidin-4-amine (4.67 g, 11.72 mmol, 138% yield) as an orange solid, which was used without further purification in the next step; Rt 2.11 min (method 1); m/z 395 (M+H)+ (ES+).

4-(3,5-dimethylisoxazol-4-yl)-$N^1$-(1-(methylsulfonyl)piperidin-4-yl)benzene-1,2-diamine (C10)

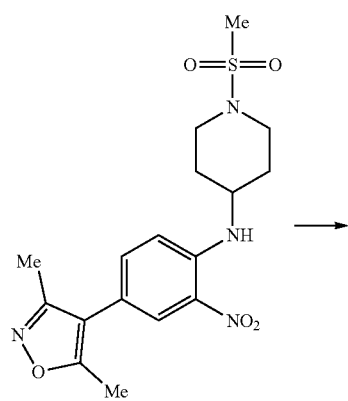

N-(4-(3,5-dimethylisoxazol-4-yl)-2-nitrophenyl)-1-(methylsulfonyl)piperidin-4-amine (3.34 g, 8.47 mmol) was dissolved in water (200 mL) and THF (200 mL). Concentrated ammonia (6.59 ml, 169 mmol) and sodium dithionite (14.74 g, 85 mmol) were added and the reaction stirred at RT for 2 h. EtOAc (500 ml) was added, the mixture transferred to a sep funnel and washed sequentially with 1M NaOH (400 ml) and brine (200 ml). The organic phase was passed through a phase sep cartridge and concentrated in vacuo to afford 4-(3,5-dimethylisoxazol-4-yl)-N1-(1-(methylsulfonyl)piperidin-4-yl)benzene-1,2-diamine (1.97 g, 4.97 mmol, 58.7% yield) as an off white foam; Rt 1.35 min (method 1); m/z 365 (M+H)+ (ES+).

(1R,3R)-3-((4-(3,5-dimethylisoxazol-4-yl)-2-nitrophenyl)amino)cyclopentan-1-ol (B11)

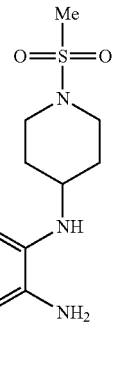

4-(4-fluoro-3-nitrophenyl)-3,5-dimethylisoxazole (1.14 g, 4.84 mmol), (1r,3r)-3-aminocyclopentanol hydrochloride (1.0 g, 7.27 mmol) and TEA (2.4 mL, 16.96 mmol) were heated to reflux in THF (17.47 mL, 213 mmol) for 18 h. The mixture was cooled to RT and concentrated in vacuo/preadsorbed onto silica. Purification by flash chromatography on the Companion (40 g column, 50-100% EtOAc/isohexane) afforded (1r,3r)-3-((4-(3,5-dimethylisoxazol-4-yl)-2-nitrophenyl)amino)cyclopentanol (0.66 g, 40%) as an orange solid; Rt 1.94 min (method 1); m/z 318 (M+H)+ (ES+).

151

(1R,3R)-3-((2-amino-4-(3,5-dimethylisoxazol-4-yl)phenyl)amino)cyclopentan-1-ol (C11)

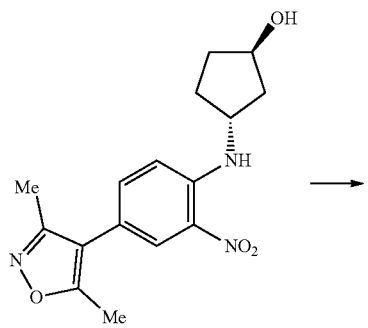

(1R,3R)-3-((4-(3,5-dimethylisoxazol-4-yl)-2-nitrophenyl)amino)cyclopentanol (0.66 g, 2.080 mmol) and concentrated ammonia (1.296 ml, 33.3 mmol) were dissolved in THF/water (40 mL). Sodium dithionite (3.62 g, 20.80 mmol) was added and the reaction mixture stirred at RT for 1.5 h. EtOAc (200 mL) was added, the mixture transferred to a separating funnel and washed sequentially with 1M NaOH (50 mL) and brine (100 mL). The organic phase was passed through a PhaseSep© cartridge and concentrated in vacuo to afford (1R,3R)-3-((2-amino-4-(3,5-dimethylisoxazol-4-yl)phenyl)amino)cyclopentanol (0.45 g, 1.535 mmol, 73.8% yield) as a purple solid; Rt 1.06 min (method 1); m/z 288 (M+H)+ (ES+).

N-(4,4-difluorocyclohexyl)-4-(3,5-dimethylisoxazol-4-yl)-2-nitroaniline (B12)

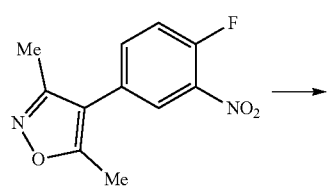

152

-continued

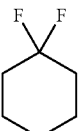

4-(4-fluoro-3-nitrophenyl)-3,5-dimethylisoxazole (4.0 g, 16.77 mmol), 4,4-difluorocyclohexanamine hydrochloride (3.0 g, 17.48 mmol) and potassium carbonate (7.0 g, 50.6 mmol) were heated to reflux in acetonitrile (60 mL) for 2 h. 4,4-Difluorocyclohexanamine hydrochloride (3.0 g, 17.48 mmol) and potassium carbonate (7.0 g, 50.6 mmol) were added and the mixture was heated for a further 4 h. The mixture was cooled then diluted with water (200 mL) and filtered to yield N-(4,4-difluorocyclohexyl)-4-(3,5-dimethylisoxazol-4-yl)-2-nitroaniline (5.85 g, 98%) as an orange crystalline solid; Rt 1.67 min (method 1); m/z 352 (M+H)+ (ES+).

N$^1$-(4,4-difluorocyclohexyl)-4-(3,5-dimethylisoxazol-4-yl)benzene-1,2-diamine (C12)

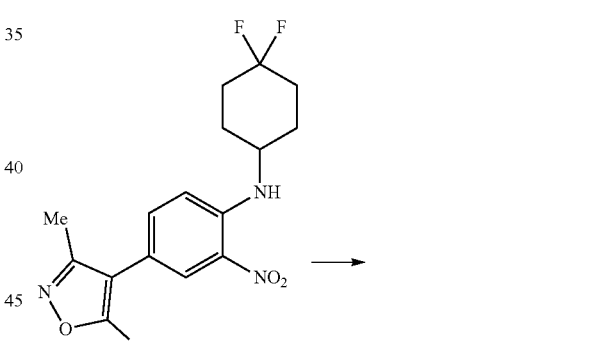

Sodium dithionite (38.5 g, 188 mmol) was added to a mixture of N-(4,4-difluorocyclohexyl)-4-(3,5-dimethylisoxazol-4-yl)-2-nitroaniline (5.85 g, 16.48 mmol), concentrated ammonia (15 ml, 385 mmol), THF/water (1:1, 120 ml) then stirred at room temperature for 2.5 h. The mixture was diluted with water (250 mL) then filtered to yield N$^1$-(4,4- difluorocyclohexyl)-4-(3,5-dimethylisoxazol-4-yl)benzene-1,2-diamine (4.1 g, 70% yield); Rt 1.27 min (method 1); m/z 322 (M+H)+ (ES+).

N-(4-(3,5-dimethylisoxazol-4-yl)-2-nitrophenyl)-2-methyltetrahydro-2H-pyran-4-amine (B13)

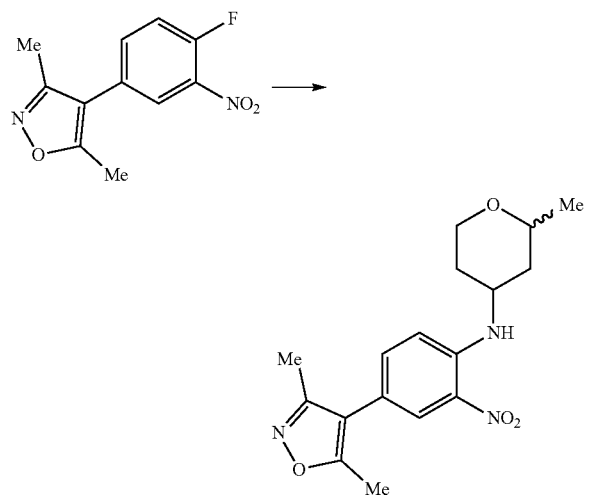

A solution of 2-methyltetrahydro-2H-pyran-4-amine (1.024 g, 8.89 mmol), DIPEA (2.59 ml, 14.82 mmol) and 4-(4-fluoro-3-nitrophenyl)-3,5-dimethylisoxazole (1.75 g, 7.41 mmol) in THF (40 mL) was heated at reflux for 24 h. The reaction mixture was concentrated in vacuo/pre-adsorbed onto silica. The crude product was purified by chromatography on silica gel (40 g column, 0-50% EtOAc/isohexane) to afford N-(4-(3,5-dimethylisoxazol-4-yl)-2-nitrophenyl)-2-methyltetrahydro-2H-pyran-4-amine (1.76 g, 71%) as a yellow solid; Rt 2.27 min (method 1); m/z 332 (M+H)+ (ES+). The product was analysed by LCMS (Agilent, X-Select, Waters X-Select C18, 2.5 µm, 4.6×30 mm, Acidic (0.1% Formic acid) 4 min method, 5-95% MeCN/water): 1576-41-P, m/z 332.2 (M+H)+ (ES+); at 2.27 min, 99% purity @ 254 nm. $^1$H NMR (d$_6$-DMSO) was consistent with product structure as a 9:1 mixture of diastereomers.

4-(3,5-dimethylisoxazol-4-yl)-N$^1$-(2-methyltetrahydro-2H-pyran-4-yl)benzene-1,2-diamine (C13)

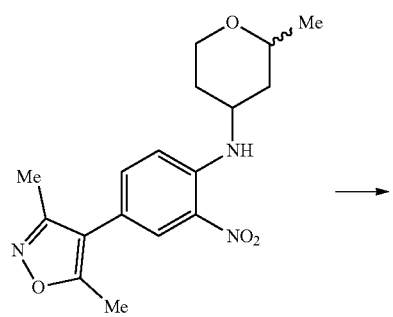

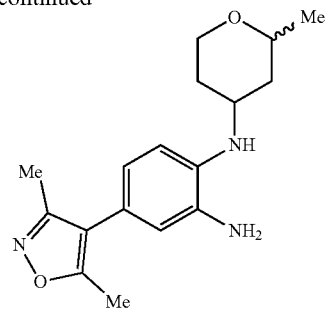

N-(4-(3,5-dimethylisoxazol-4-yl)-2-nitrophenyl)-2-methyltetrahydro-2H-pyran-4-amine (1.66 g, 5.01 mmol) was dissolved in THF (71.0 ml, 867 mmol), Water (68.2 ml, 3787 mmol), ammonia (3.90 ml, 100 mmol) and sodium dithionite (8.72 g, 50.1 mmol) added and the reaction stirred at RT for 2 h. The layers were separated and the aqueous was extracted with EtOAc (2×20 mL), the combined organics washed with brine (20 mL), dried (MgSO$_4$), filtered and evaporated in vacuo to give 4-(3,5-dimethylisoxazol-4-yl)-N$^1$-(2-methyltetrahydro-2H-pyran-4-yl)benzene-1,2-diamine (1.45 g, 85% yield) as a yellow oil; Rt 1.55 min (method 1); m/z 302 (M+H)+ (ES+); $^1$H NMR (d$_6$-DMSO) was consistent with product structure as a 9:1 mixture of diastereomers.

4-((4-(3,5-dimethylisoxazol-4-yl)-2-nitrophenyl)amino)piperidin-2-one (B14)

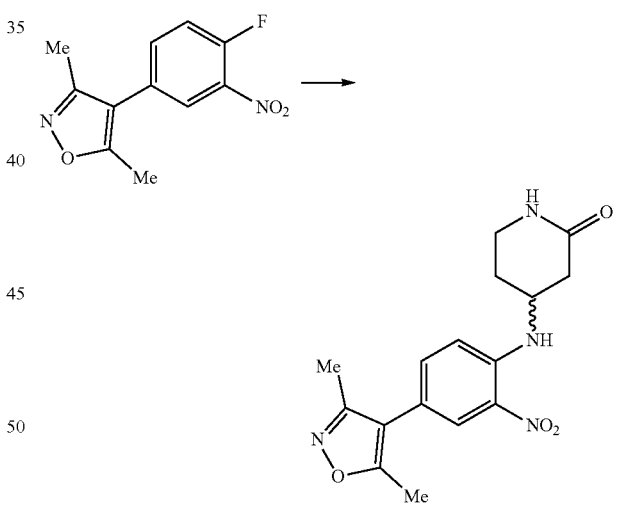

To a solution of 4-(4-fluoro-3-nitrophenyl)-3,5-dimethylisoxazole (1.3 g, 5.50 mmol) in tetrahydrofuran (26.6 mL) and DIPEA (1.923 ml, 11.01 mmol) was added 4-aminopiperidin-2-one (0.942 g, 8.26 mmol). The reaction stirred at 70° C. for 48 h. The reaction was cooled down to RT. The solvents were evaporated in vacuo and the orange residue was partitioned between EtOAc (100 mL), DCM (100 mL) and saturated aqueous NaHCO$_3$ (100 mL) and the layers separated. The aqueous phase was extracted with further DCM (2×100 mL) and the combined organic extracts washed with water (100 mL) and brine (100 mL). The solution was dried (MgSO$_4$), filtered and evaporated in vacuo. The residual orange solid was purified by chromatography on the Companion (24 g column, 0-100% EtOAc in DCM then 0-10% MeOH in DCM, loaded on silica) to give 4-((4-(3,5-dimethylisoxazol-4-yl)-2-nitrophenyl)amino)piperidin-2-one (1.0 g, 54%) as an orange foam; Rt 1.66 min (method 1); m/z 331 (M+H)+ (ES+).

4-((2-Amino-4-(3,5-dimethylisoxazol-4-yl)phenyl)amino)piperidin-2-one (C14)

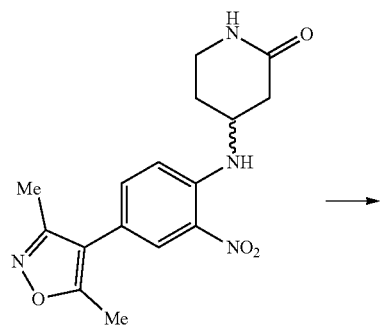

4-((4-(3,5-Dimethylisoxazol-4-yl)-2-nitrophenyl)amino)piperidin-2-one (1.0 g, 3.03 mmol) and concentrated ammonia (1.886 mL, 48.4 mmol) were dissolved in THF/water (1:1, 58 mL). Sodium dithionate (6.24 g, 30.3 mmol) was added and the reaction mixture stirred at RT. After 1 h of stirring, the layers were separated, the aqueous extracted with EtOAc (100 mL) and the combined organics washed with brine (50 mL), dried (MgSO4), filtered and evaporated in vacuo to give 4-((2-amino-4-(3,5-dimethylisoxazol-4-yl)phenyl)amino)piperidin-2-one (0.67 g, 71%) as a white solid; Rt 1.41 min (method 1); m/z 301 (M+H)+ (ES+).

(1s,4s)-4-((4-(3,5-dimethylisoxazol-4-yl)-2-nitrophenyl)amino)-1-methylcyclohexan-1-ol (B15)

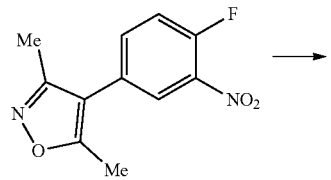

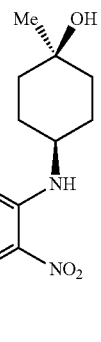

4-(4-Fluoro-3-nitrophenyl)-3,5-dimethylisoxazole (750 mg, 3.18 mmol), (1s,4s)-4-amino-1-methylcyclohexanol (500 mg, 3.87 mmol) and potassium carbonate (600 mg, 4.34 mmol) were heated to reflux in acetonitrile (10 mL) for 1 h. The mixture was diluted with water (50 mL) then the precipitate was collected by filtration. The crude product was purified by chromatography on the Companion (40 g column, 0-50% EtOAc/isohexane) to afford (is, 4s)-4-((4-(3,5-dimethylisoxazol-4-yl)-2-nitrophenyl)amino)-1-methylcyclohexanol (855 mg, 74%) as an orange solid; Rt 2.15 min (method 1); m/z 346 (M+H)+ (ES+).

(1s,4s)-4-((2-amino-4-(3,5-dimethylisoxazol-4-yl)phenyl)amino)-1-methylcyclohexan-1-ol (C15)

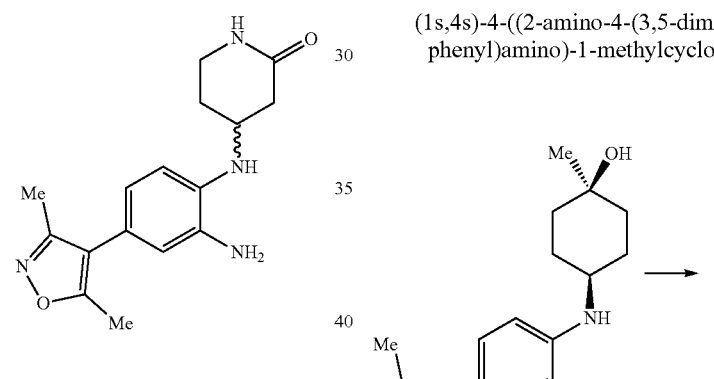

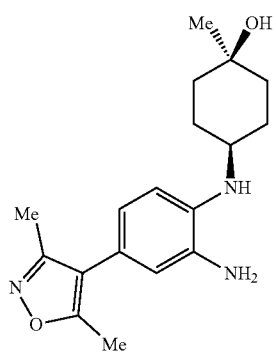

Sodium dithionite (5 g, 24.41 mmol) was added to a mixture of (is, 4s)-4-((4-(3,5-dimethylisoxazol-4-yl)-2-nitrophenyl)amino)-1-methylcyclohexanol (844 mg, 2.444 mmol), concentrated ammonia (2 ml, 51.4 mmol), THF/water (1:1 12 mL) then stirred at room temperature for 3 h. The mixture was diltued with brine (100 mL) then extracted with ethyl acetate (3×150 mL), then dichloromethane (2×50 mL). The combined organic phases were concentrated under reduced pressure. The residue was stirred in ethanol (15 mL) and water (35 mL) with sodium bicarbonate (205 mg, 2.444 mmol) for 15 minutes. The solid was collected by filtration to yield (1s,4s)-4-((2-amino-4-(3,5-dimethylisoxazol-4-yl)phenyl)amino)-1-methylcyclohexanol (574 mg, 73%) as a pink solid; Rt 1.28 min (method 1); m/z 316 (M+H)+ (ES+).

N-(4-(3,5-dimethylisoxazol-4-yl)-2-nitrophenyl)-2-oxaspiro[3.3]heptan-6-amine (B16)

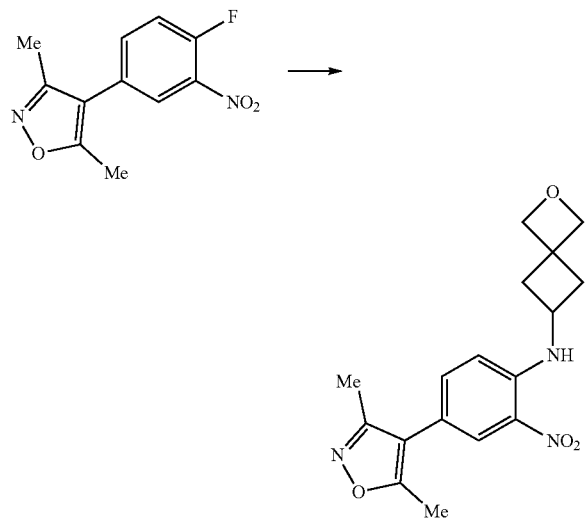

4-(4-fluoro-3-nitrophenyl)-3,5-dimethylisoxazole (1.435 g, 6.08 mmol) and 2-oxaspiro[3.3]heptan-6-amine hydrochloride (1 g, 6.68 mmol) was dissolved in dry dimethylformamide (20 mL). TEA (2.54 mL, 18.23 mmol) was added and the reaction warmed to 60° C. and left to stir at rt for 3 h. After cooling to RT, the reaction mixture was poured into ice water (100 mL), then extracted with ethyl acetate (2×100 mL). Combined organics were dried (MgSO₄) and concentrated in vacuo then azeotroping with acetonitrile to afford N-(4-(3,5-dimethylisoxazol-4-yl)-2-nitrophenyl)-2-oxaspiro[3.3]heptan-6-amine (2.58 g, >100% yield) as an orange solid, which was used without further purification at the next step; Rt 2.14 min (method 1); m/z 330 (M+H)+ (ES+).

4-(3,5-dimethylisoxazol-4-yl)-N¹-(2-oxaspiro[3.3]heptan-6-yl)benzene-1,2-diamine (C16)

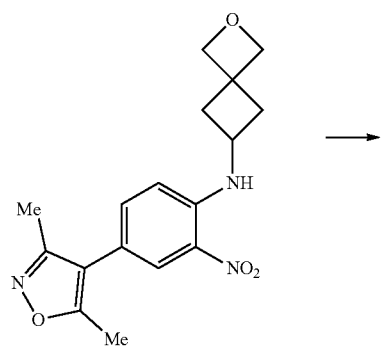

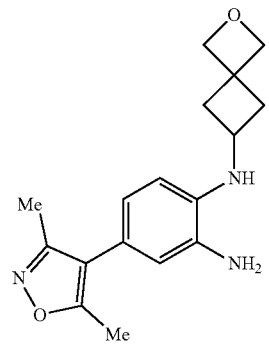

N-(4-(3,5-dimethylisoxazol-4-yl)-2-nitrophenyl)-2-oxaspiro[3.3]heptan-6-amine (2.00 g, 6.07 mmol) was dissolved in a mixture of THF/water (1:1, 300 mL). Sodium dithionite (10.57 g, 60.7 mmol) was added followed by concentrated ammonia (4.73 ml, 121 mmol) and the reaction mixture stirred at RT for 10 mins. EtOAc (200 mL) was added, the mixture transferred to a separating funnel and washed sequentially with 1M NaOH (100 mL) and brine (100 mL). The organic phase was passed through a PhaseSep© cartridge and concentrated in vacuo to afford 4-(3,5-dimethylisoxazol-4-yl)-N¹-(2-oxaspiro[3.3]heptan-6-yl)benzene-1,2-diamine (1.47 g, 4.76 mmol, 78% yield) as a light pink solid; Rt 1.35 min (method 1); m/z 300 (M+H)+ (ES+).

(1r,3r)-3-((4-(3,5-dimethylisoxazol-4-yl)-2-nitrophenyl)amino)cyclobutan-1-ol (B17)

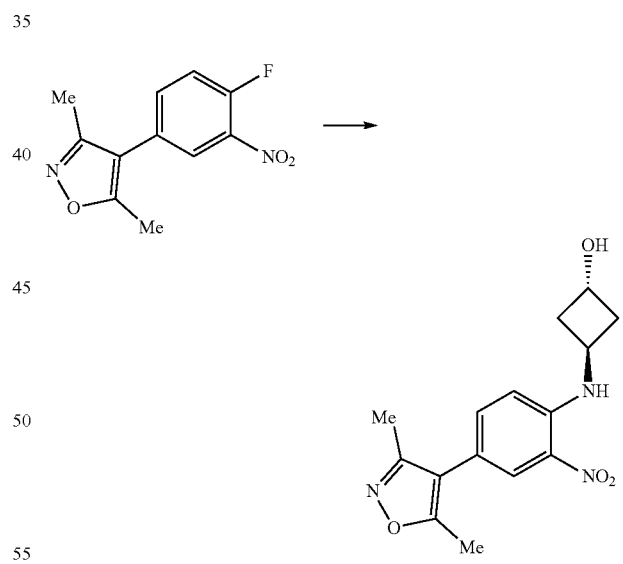

4-(4-fluoro-3-nitrophenyl)-3,5-dimethylisoxazole (8.69 g, 36.8 mmol) was dissolved in dry dimethylformamide (50 mL) and TEA (20.51 mL, 147 mmol). (1r,3r)-3-aminocyclobutanol hydrochloride (5 g, 40.5 mmol) was added and the reaction warmed to 60° C. and left to stir at RT for 18 h. After cooling to rt the reaction mixture was poured into ice water (300 mL) The precipitate was collected to afford (1r,3r)-3-((4-(3,5-dimethylisoxazol-4-yl)-2-nitrophenyl)amino)cyclobutanol (11.16 g, 98%) as an orange solid; Rt 1.89 min (method 1); m/z 304 (M+H)+ (ES+).

(1r,3r)-3-((2-amino-4-(3,5-dimethylisoxazol-4-yl)phenyl)amino)cyclobutan-1-ol (C17)

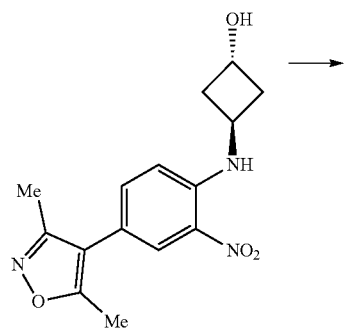

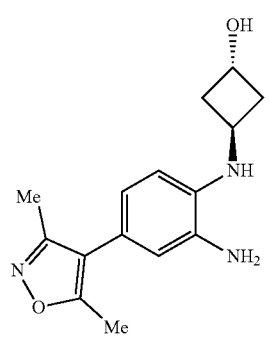

(1r,3r)-3-((4-(3,5-dimethylisoxazol-4-yl)-2-nitrophenyl)amino)cyclobutanol (11.16 g, 36.8 mmol) was dissolved in a mixture of THF/water (1:1, 800 mL). Sodium dithionate (64.1 g, 368 mmol) was added followed by concentrated ammonia, 28% soln (28.7 mL, 736 mmol) and the reaction mixture stirred at RT for 18 h. EtOAc (1 L) was added, followed by 1M NaOH (500 mL). After stirring for 5 mins, the layers were left to separated and the aqueous phase removed. The organic phase was stirred vigorously with brine (500 mL), left to separate, then collected and dried (MgSO$_4$). The solvent was removed in vacuo and the residue triturated with ether (200 mL) to afford (1r,3r)-3-((2-amino-4-(3,5-dimethylisoxazol-4-yl)phenyl)amino)cyclobutanol (7.07 g, 70%) as a beige solid; Rt 1.09 min (method 1); m/z 274 (M+H)+ (ES+).

(1r,4r)-4-((4-(3,5-dimethylisoxazol-4-yl)-2-nitrophenyl)amino)-1-methylcyclohexan-1-ol (B18)

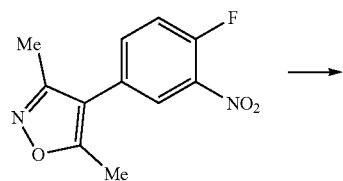

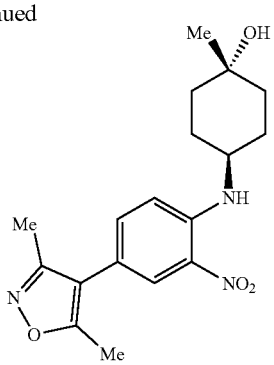

4-(4-Fluoro-3-nitrophenyl)-3,5-dimethylisoxazole (1.618 g, 6.85 mmol), (1r,4r)-4-amino-1-methylcyclohexanol (1.0 g, 7.74 mmol) and potassium carbonate (1.638 g, 11.85 mmol) were heated to reflux in acetonitrile (20.75 mL) for 1 h. The reaction was cooled down to RT and stirred overnight. The mixture was diluted with water (200 mL) then the orange precipitate was collected by filtration. The crude product (ca. 4 g as a wet solid) was purified by chromatography on the Companion (24 g column, 0-50% EtOAc/DCM) to afford (1r,4r)-4-((4-(3,5-dimethylisoxazol-4-yl)-2-nitrophenyl)amino)-1-methylcyclohexanol (2.0 g, 79%) as an orange solid; Rt 2.10 min (method 1); m/z 346 (M+H)+ (ES+).

(1r,4r)-4-((2-amino-4-(3,5-dimethylisoxazol-4-yl)phenyl)amino)-1-methylcyclohexan-1-ol (C18)

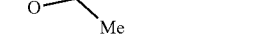

Sodium dithionite (11.10 g, 53.9 mmol) was added to a mixture of (1r,4r)-4-((4-(3,5-dimethylisoxazol-4-yl)-2-nitrophenyl)amino)-1-methylcyclohexanol (2.0 g, 5.39 mmol), concentrated ammonia (4.09 ml, 105 mmol), THF/water (1:1, 32.6 mL) then stirred at RT. The volume of solvent was doubled because of poor solubility. After 2 h, the layers were separated, the aqueous extracted with EtOAc (2×100 mL), the combined organics washed with water (50 mL) and brine (50 mL), dried (MgSO₄), filtered and evaporated in vacuo to give (1r,4r)-4-((2-amino-4-(3,5-dimethylisoxazol-4-yl)phenyl)amino)-1-methylcyclohexanol (1.45 g, 82%) as a pink purple solid; Rt 1.10 min (method 1); m/z 316 (M+H)+ (ES+).

1-((4-(3,5-dimethylisoxazol-4-yl)-2-nitrophenyl)amino)propan-2-ol (B19)

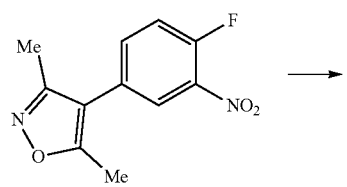

4-(4-Fluoro-3-nitrophenyl)-3,5-dimethylisoxazole (4 g, 16.93 mmol) was dissolved in dry THF (69.4 mL, 847 mmol) and TEA (7.08 mL, 50.8 mmol). 1-aminopropan-2-ol (1.438 mL, 18.63 mmol) was added and the reaction warmed to 60° C. and left to stir at RT for 18 h. After cooling to RT the reaction mixture was poured into ice water (300 mL) and extracted with EtOAc (2×75 mL). The organic extracts were combined and then dried over MgSO₄, filtered and concentrated in vacuo to afford a 1-((4-(3,5-dimethylisoxazol-4-yl)-2-nitrophenyl)amino)propan-2-ol (4.90 g, 98%) as a yellow solid; Rt 1.85 min (method 1); m/z 292 (M+H)+ (ES+).

1-((2-Amino-4-(3,5-dimethylisoxazol-4-yl)phenyl)amino)propan-2-ol (C19)

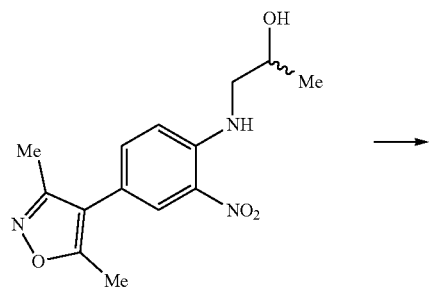

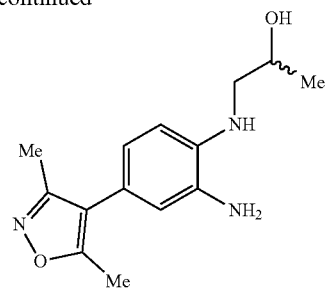

1-((4-(3,5-Dimethylisoxazol-4-yl)-2-nitrophenyl)amino)propan-2-ol (4.9 g, 16.82 mmol) was dissolved in a mixture of THF/water (1:1 132 mL). Sodium dithionite (34.5 g, 168 mmol) was added followed by concentrated ammonia (13.10 ml, 336 mmol) and the reaction mixture stirred at RT for 1 h. EtOAc (200 mL) was added, the mixture transferred to a sep funnel and washed sequentially with 1M NaOH (100 mL) and brine (100 mL). The organic phase was passed through a PhaseSep© cartridge and concentrated in vacuo to afford 1-((2-amino-4-(3,5-dimethylisoxazol-4-yl)phenyl)amino)propan-2-ol (3.7 g, 78%) as a red solid; Rt 2.10 min (method 1); m/z 262 (M+H)+ (ES+).

4-(3,5-dimethylisoxazol-4-yl)-N-isobutyl-2-nitroaniline (B20)

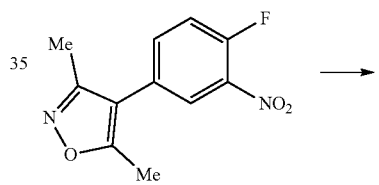

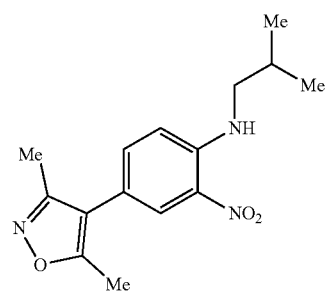

A mixture of 4-(4-fluoro-3-nitrophenyl)-3,5-dimethylisoxazole (10 g, 42.3 mmol) and 2-methylpropan-1-amine (21.04 mL, 212 mmol) was stirred in dry THF (100 mL) and the reaction was stirred at RT for 18 h then poured into ice water (300 mL). The mixture was extracted with ethyl acetate (2×500 mL). Combined organics were dried (MgSO₄) and concentrated in vacuo to afford 4-(3,5-dimethylisoxazol-4-yl)-N-isobutyl-2-nitroaniline (12.25 g, 100%) as an orange solid; Rt 2.64 min (method 1); m/z 290 (M+H)+ (ES+).

4-(3,5-dimethylisoxazol-4-yl)-N1-isobutylbenzene-1,2-diamine (C20)

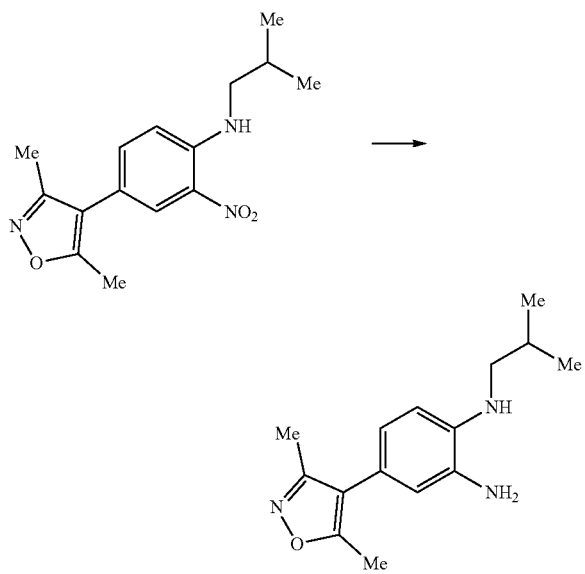

4-(3,5-Dimethylisoxazol-4-yl)-N-isobutyl-2-nitroaniline (12.25 g, 42.3 mmol) was dissolved in a mixture of THF/water (1:1, 800 mL). Sodium dithionite (73.7 g, 423 mmol) was added followed by concentrated ammonia (33.0 mL, 847 mmol) and the reaction mixture stirred at RT for 18 h. EtOAc (1 L) was added, followed by 1M NaOH (500 mL). After stirring for 5 mins, the layers were left to separate and the aqueous phase removed. The organic phase was stirred vigorously with brine (500 mL), left to separate, then collected and dried (MgSO$_4$). The solvent was removed in vacuo and the residue triturated with ether (200 mL) to afford 4-(3,5-dimethylisoxazol-4-yl)-N-isobutylbenzene-1,2-diamine as a beige solid; Rt 1.09 min (method 1); m/z 274 (M+H)+ (ES+).

N-(3,3-difluorocyclobutyl)-4-(3,5-dimethylisoxazol-4-yl)-2-nitroaniline (B21)

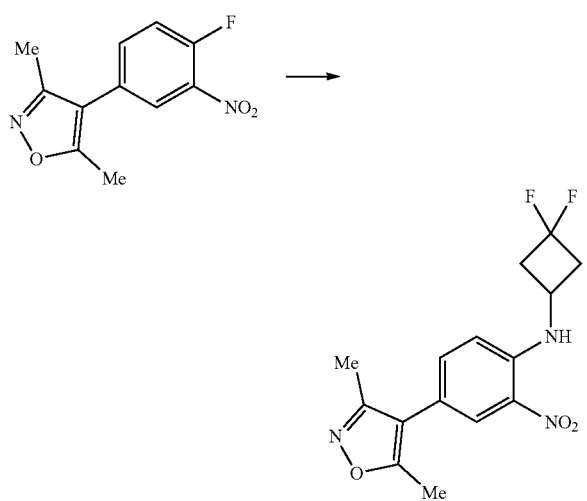

4-(4-fluoro-3-nitrophenyl)-3,5-dimethylisoxazole (1.870 g, 7.92 mmol) and 3,3-difluorocyclobutanamine hydrochloride (1.25 g, 8.71 mmol) was dissolved in dry dimethylformamide (20 ml). TEA (3.31 ml, 23.75 mmol) was added and the reaction warmed to 60° C. and left to stir at rt for 3 h. After cooling to rt the reaction mixture was poured into ice water (100 ml), then extracted with ethyl acetate (2×100 ml). Combined organics were dried (MgSO4) and concentrated in vacuo (azeotroping with acetonitrile) to afford N-(3,3-difluorocyclobutyl)-4-(3,5-dimethylisoxazol-4-yl)-2-nitroaniline (2.11 g, 5.94 mmol, 75% yield) as an orange solid; Rt 2.42 min (method 1); m/z 324 (M+H)+ (ES+).

N$^1$-(3,3-difluorocyclobutyl)-4-(3,5-dimethylisoxazol-4-yl)benzene-1,2-diamine (C21)

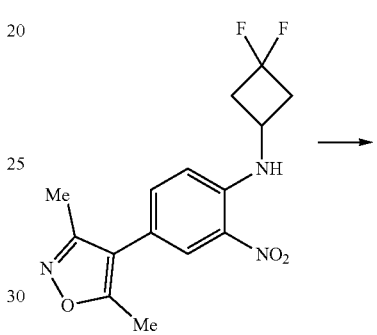

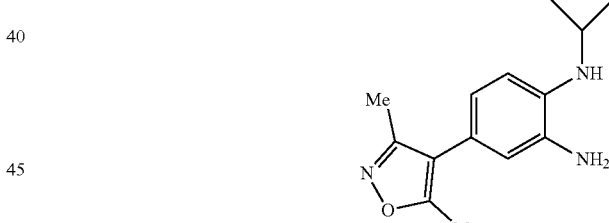

N-(3,3-difluorocyclobutyl)-4-(3,5-dimethylisoxazol-4-yl)-2-nitroaniline (2.10 g, 6.50 mmol) was dissolved in a mixture of THF/water (1,1, 200 mL). Sodium dithionate (11.31 g, 65.0 mmol) was added followed by concentrated ammonia (5.06 ml, 130 mmol) and the reaction mixture stirred at RT for 1 hr. EtOAc (200 mL) was added, followed by 1M NaOH (150 mL). The mixture was shaken vigorously and the aqueous phase discarded. The organic phase was washed with brine (100 mL), then collected and dried (MgSO$_4$). The solvent was removed in vacuo to afford N$^1$-(3,3-difluorocyclobutyl)-4-(3,5-dimethylisoxazol-4-yl)benzene-1,2-diamine (1.12 g, 58%) as an-off white solid; Rt 1.84 min (method 1); m/z 294 (M+H)+ (ES+).

Methyl (1r,4r)-4-((4-(3,5-dimethylisoxazol-4-yl)-2-nitrophenyl)amino)cyclohexane-1-carboxylate (B22)

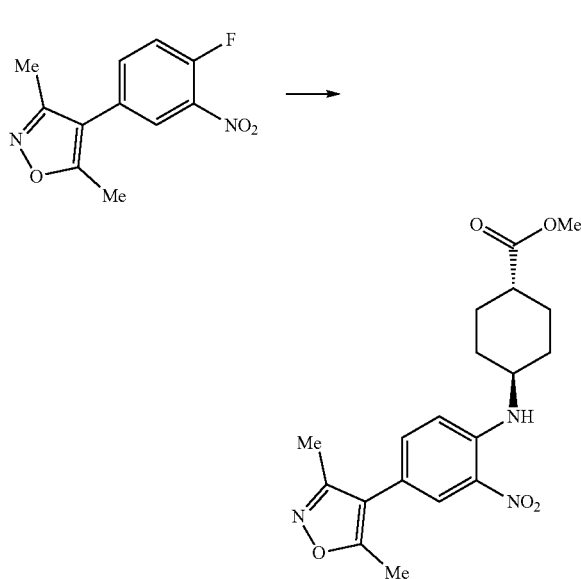

To a suspension of (1r,4r)-methyl 4-aminocyclohexanecarboxylate hydrochloride (3.4 g, 17.56 mmol) and DIPEA (7.67 mL, 43.9 mmol) in acetonitrile (68.8 mL) was added 4-(4-fluoro-3-nitrophenyl)-3,5-dimethylisoxazole (4.56 g, 19.31 mmol). The heterogeneous reaction was stirred at 75° C. for 39 h. The reaction was cooled down to RT and filtered. The filtrate was concentrated in vacuo to give a mixture of oil and orange solid (11 g). The solid was triturated twice with Et₂O (50 mL), then iso-hexanes (50 mL). The solid was dried in vacuo to give 7.5 g of solid which was dried loaded and purified by chromatography column (120 g, DCM/MeOH: 100/0 to 95/5) to give (1r,4r)-methyl 4-((4-(3,5-dimethylisoxazol-4-yl)-2-nitrophenyl)amino)cyclohexanecarboxylate (4.29 g, 63%) was isolated as an orange solid; Rt 2.49 min (method 1); m/z 374 (M+H)+ (ES+).

Methyl (1r,4r)-4-((2-amino-4-(3,5-dimethylisoxazol-4-yl)phenyl)amino)cyclohexane-1-carboxylate (C22)

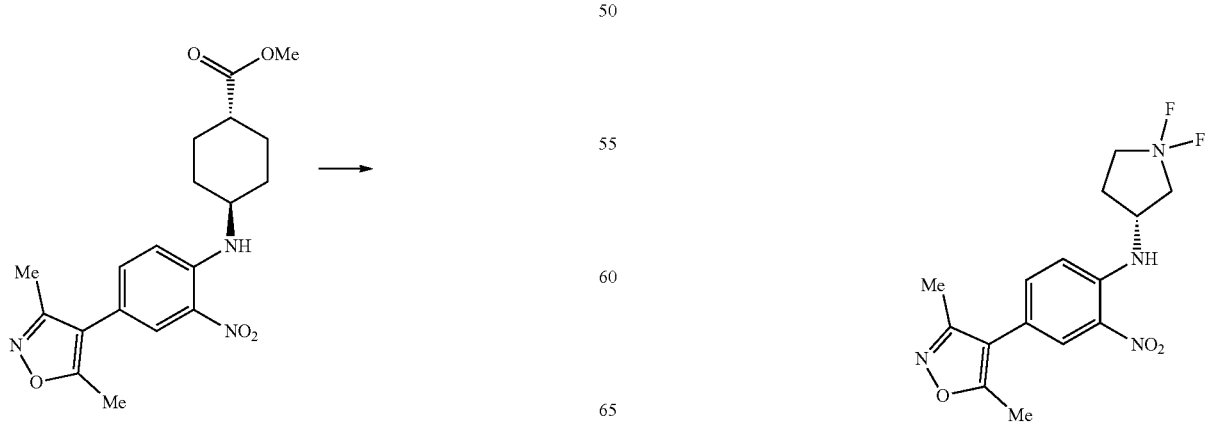

Sodium dithionite (23.68 g, 115 mmol) was added to a mixture of (1r,4r)-methyl 4-((4-(3,5-dimethylisoxazol-4-yl)-2-nitrophenyl)amino)cyclohexanecarboxylate (4.29 g, 11.49 mmol), concentrated ammonia (8.72 ml, 224 mmol), water (34.8 mL) and THF (43.3 mL) then stirred at room temperature for 15 h. The layers were separated, the aqueous extracted with EtOAc (2×100 mL), the combined organics washed with water (2×100 mL) and brine (100 mL), dried (MgSO₄), filtered and evaporated in vacuo to give (1r,4r)-methyl-4-((4-(3,5-dimethylisoxazol-4-yl)-2-nitrophenyl) amino) cyclohexanecarboxylate (3.52 g, 87%) as a crude pink red solid; Rt 1.49 min (method 1); m/z 344 (M+H)+ (ES+).

(R)—N¹-(3,3-difluorocyclopentyl)-4-(3,5-dimethylisoxazol-4-yl)benzene-1,2-diamine (B23)

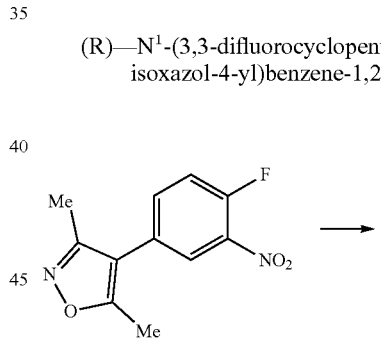

EXAMPLES

Example 1: 5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one N-(5-(3,5-dimethylisoxazol-4-yl)-2-(((R)-1-(methylsulfonyl)pyrrolidin-3-yl)amino)phenyl)-5-oxo-1-phenylpyrrolidine-2-carboxamide 5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one

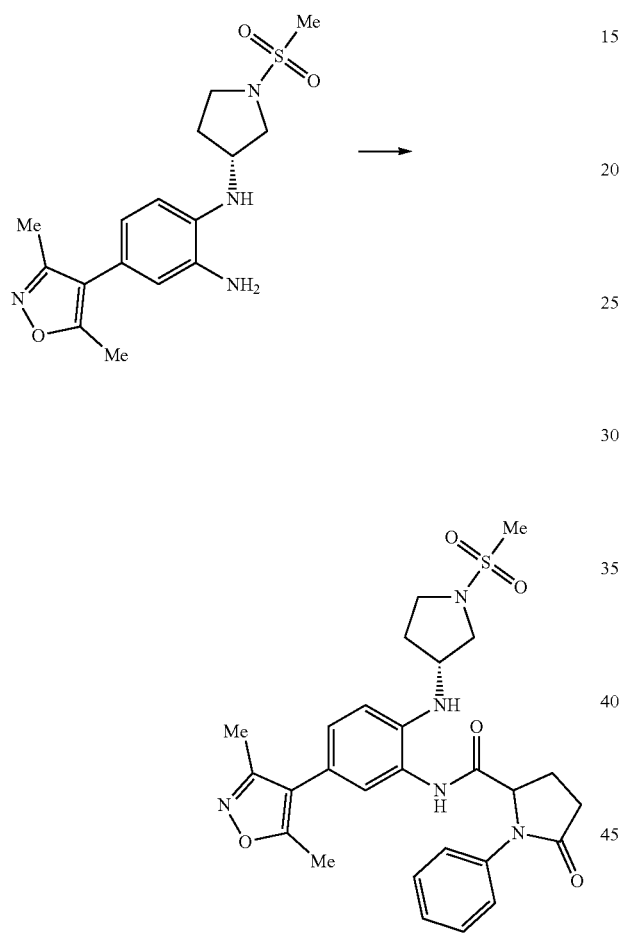

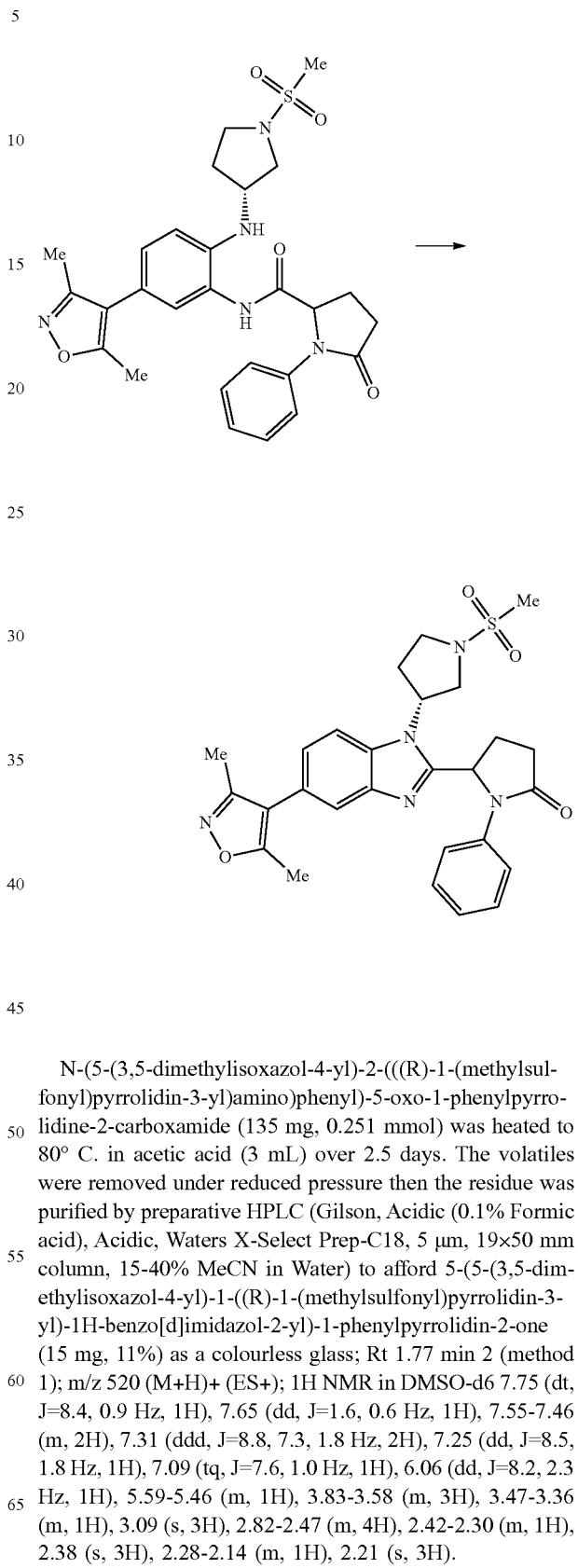

HATU (110 mg, 0.289 mmol) was added to a solution of Intermediate C1 (100 mg, 0.254 mmol), 5-oxo-1-phenylpyrrolidine-2-carboxylic acid (55 mg, 0.268 mmol) and N,N-diisopropylethylamine (55 µL, 0.315 mmol) in N,N-dimethylformamide (2 mL) then stirred at room temperature overnight. The mixture was diluted with water (20 mL) then extracted with ethyl acetate (2×20 mL). The combined organic phases were washed with 20% brine (2×20 mL), saturated brine (20 mL), then dried (MgSO₄), filtered and concentrated under reduced pressure. The crude product was purified by chromatography on the Companion (12 g column, 50-100% EtOAc/DCM) to afford N-(5-(3,5-dimethyl-isoxazol-4-yl)-2-(((R)-1-(methylsulfonyl)pyrrolidin-3-yl)amino)phenyl)-5-oxo-1-phenylpyrrolidine-2-carboxamide (87 mg, 63%) as a colourless foam; Rt 1.78 min (method 1); m/z 538 (M+H)+ (ES+).

N-(5-(3,5-dimethylisoxazol-4-yl)-2-(((R)-1-(methylsulfonyl)pyrrolidin-3-yl)amino)phenyl)-5-oxo-1-phenylpyrrolidine-2-carboxamide (135 mg, 0.251 mmol) was heated to 80° C. in acetic acid (3 mL) over 2.5 days. The volatiles were removed under reduced pressure then the residue was purified by preparative HPLC (Gilson, Acidic (0.1% Formic acid), Acidic, Waters X-Select Prep-C18, 5 µm, 19×50 mm column, 15-40% MeCN in Water) to afford 5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one (15 mg, 11%) as a colourless glass; Rt 1.77 min 2 (method 1); m/z 520 (M+H)+ (ES+); 1H NMR in DMSO-d6 7.75 (dt, J=8.4, 0.9 Hz, 1H), 7.65 (dd, J=1.6, 0.6 Hz, 1H), 7.55-7.46 (m, 2H), 7.31 (ddd, J=8.8, 7.3, 1.8 Hz, 2H), 7.25 (dd, J=8.5, 1.8 Hz, 1H), 7.09 (tq, J=7.6, 1.0 Hz, 1H), 6.06 (dd, J=8.2, 2.3 Hz, 1H), 5.59-5.46 (m, 1H), 3.83-3.58 (m, 3H), 3.47-3.36 (m, 1H), 3.09 (s, 3H), 2.82-2.47 (m, 4H), 2.42-2.30 (m, 1H), 2.38 (s, 3H), 2.28-2.14 (m, 1H), 2.21 (s, 3H).

Example 2: 5-(5-(3,5-dimethylisoxazol-4-yl)-1-(tetrahydro-2H-pyran-4-yl)-1H-benzo[d]imidazol-2-yl)-1-phenylpyrrolidin-2-one N-(5-(3,5-dimethylisoxazol-4-yl)-2-((tetrahydro-2H-pyran-4-yl)amino)phenyl)-5-oxo-1-phenyl pyrrolidine-2-carboxamide

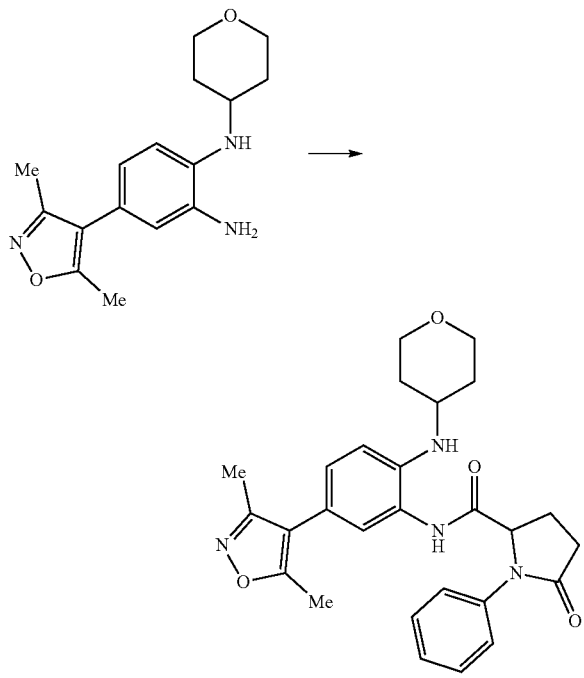

HATU (125 mg, 0.329 mmol) was added to a solution of Intermediate C2 (99 mg, 0.331 mmol), 5-oxo-1-phenylpyrrolidine-2-carboxylic acid (70 mg, 0.341 mmol) and N,N-diisopropylethylamine (70 µl, 0.401 mmol) in N,N-dimethylformamide (2 mL) then stirred at room temperature over a weekend. The mixture was added dropwise to a rapidly stirred flask of water (20 mL) then the precipitate was collected by filtration, washing with water (2×3 mL) to yield N-(5-(3,5-dimethylisoxazol-4-yl)-2-((tetrahydro-2H-pyran-4-yl)amino)phenyl)-5-oxo-1-phenylpyrrolidine-2-carboxamide (121 mg, 69%) as a red-orange gum; Rt 1.17 min 2 (method 1); m/z 475 (M+H)+ (ES+);

5-(5-(3,5-dimethylisoxazol-4-yl)-1-(tetrahydro-2H-pyran-4-yl)-1H-benzo[d]imidazol-2-yl)-1-phenylpyrrolidin-2-one

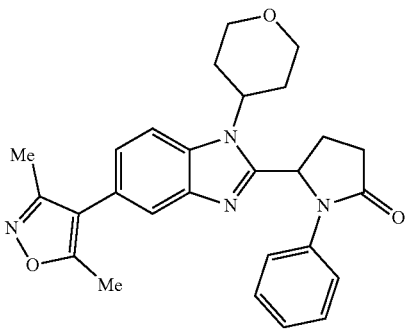

N-(5-(3,5-dimethylisoxazol-4-yl)-2-((tetrahydro-2H-pyran-4-yl)amino)phenyl)-5-oxo-1-phenyl pyrrolidine-2-carboxamide (121 mg, 0.227 mmol) was heated to 80° C. in pivalic acid (3 mL) for 2 h. 1,4-dioxane (3 mL) was added to improve solubility then the mixture was heated at 80° C. for a further 3 h. The temperature was increased to 100° C. and stirred for 18 h. The mixture was diluted with water (20 mL) then extracted with dichloromethane (3×10 mL). The combined organic phases were concentrated under reduced pressure then purified by chromatography on the Companion (RP Flash C18) (12 g column, 15-75% MeCN/Water 0.1% Formic Acid) to afford 5-(5-(3,5-dimethylisoxazol-4-yl)-1-(tetrahydro-2H-pyran-4-yl)-1H-benzo[d]imidazol-2-yl)-1-phenylpyrrolidin-2-one (18 mg, 16%) as an off-white solid; Rt 1.77 min (method 1); m/z 457 (M+H)+ (ES+); 1H NMR (d6-DMSO) δ: 7.74 (d, J=8.5 Hz, 1H), 7.61 (d, J=1.6 Hz, 1H), 7.51-7.45 (m, 2H), 7.29 (dd, J=8.6, 7.4 Hz, 2H), 7.17 (dd, J=8.5, 1.7 Hz, 1H), 7.11-7.04 (m, 1H), 6.10 (dd, J=8.3, 2.2 Hz, 1H), 4.87-4.74 (m, 1H), 4.04 (td, J=14.2, 12.9, 4.3 Hz, 2H), 3.57 (ddd, J=12.3, 9.6, 3.3 Hz, 2H), 2.85-2.72 (m, 1H), 2.65 (dq, J=12.0, 8.8 Hz, 1H), 2.59-2.51 (m, 1H), 2.43 (td, J=12.3, 4.6 Hz, 2H), 2.36 (s, 3H), 2.19 (s, 3H), 2.18-2.09 (m, 1H), 1.81 (d, J=12.6 Hz, 1H), 1.58 (d, J=12.5 Hz, 1H).

Example 3: 5-(5-(3,5-dimethylisoxazol-4-yl)-1-(1,1-dioxidotetrahydro-2H-thiopyran-4-yl)-1H-benzo[d]imidazol-2-yl)-1-phenylpyrrolidin-2-one N-(5-(3,5-dimethylisoxazol-4-yl)-2-((1,1-dioxidotetrahydro-2H-thiopyran-4-yl)amino)phenyl)-5-oxo-1-phenylpyrrolidine-2-carboxamide

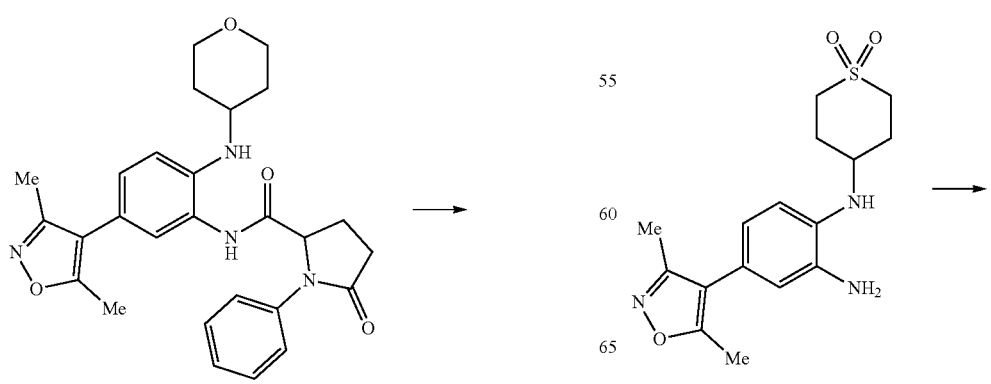

-continued

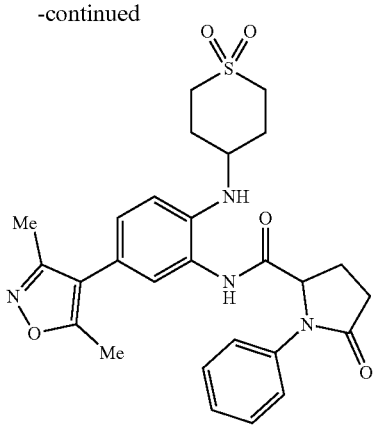

HATU (125 mg, 0.329 mmol) was added to a solution of Intermediate C3 (99 mg, 0.269 mmol), 5-oxo-1-phenylpyrrolidine-2-carboxylic acid (70 mg, 0.341 mmol) and N,N-diisopropylethylamine (70 µl, 0.401 mmol) in N,N-dimethylformamide (2 mL) then stirred at room temperature over a weekend. The mixture was added dropwise to a rapidly stirred flask of water (20 mL) then the precipitate was collected by filtration, washing with water (2×3 mL) to yield N-(5-(3,5-dimethylisoxazol-4-yl)-2-((1,1-dioxidotetrahydro-2H-thiopyran-4-yl)amino)phenyl)-5-oxo-1-phenylpyrrolidine-2-carboxamide (135 mg, 92%) as an off white solid; Rt 1.07 min (method 1), m/z 523 (M+H)+ (ES+).

5-(5-(3,5-dimethylisoxazol-4-yl)-1-(1,1-dioxidotetrahydro-2H-thiopyran-4-yl)-1H-benzo[d]imidazol-2-yl)-1-phenylpyrrolidin-2-one N-(5-(3,5-dimethylisoxazol-4-yl)-2-((1,1-dioxidotetrahydro-2H-thiopyran-4-yl)amino)phenyl)-5-oxo-1-phenylpyrrolidine-2-carboxamide (135 mg, 0.248 mmol) was heated to 80° C. in pivalic acid (3 mL). for 2 h. 1,4-dioxane (3 mL) was added to improve solubility then the mixture was heated at 80° C. for a further 3 h. The temperature was increased to 100° C. and stirred for 18 h, further heated for 3 h at 160° C. using microwave heating and then for a further 4 h at 180° C. using microwave heating. The solvents were removed under reduced pressure then the crude product was purified by chromatography on the Companion (RP Flash C18) (12 g column, 15-75% MeCN/Water 0.1% Formic Acid) to afford 5-(5-(3,5-dimethylisoxazol-4-yl)-1-(1,1-dioxidotetrahydro-2H-thiopyran-4-yl)-1H-benzo[d]imidazol-2-yl)-1-phenylpyrrolidin-2-one (37 mg, 28%) as a pale cream solid; Rt 1.69 min (method 1), m/z 505 (M+H)+ (ES+); 1H NMR (d6-DMSO) δ: 7.65 (d, J=1.6 Hz, 1H), 7.61 (d, J=8.5 Hz, 1H), 7.53-7.45 (m, 2H), 7.34-7.25 (m, 3H), 7.10 (dt, 1H), 5.97 (d, J=7.1 Hz, 1H), 5.12-4.95 (m, 1H), 3.63-3.51 (m, 2H), 3.31-3.21 (m, 2H), 2.96-2.53 (m, 5H), 2.38 (s, 3H), 2.29-2.14 (m, 2H), 2.21 (s, 3H), 1.97 (br d, J=13.5 Hz, 1H).

Example 4: (S)-5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one (S)—N-(5-(3,5-dimethylisoxazol-4-yl)-2-(((R)-1-(methylsulfonyl)pyrrolidin-3-yl)amino)phenyl)-5-oxopyrrolidine-2-carboxamide (Intermediate D1)

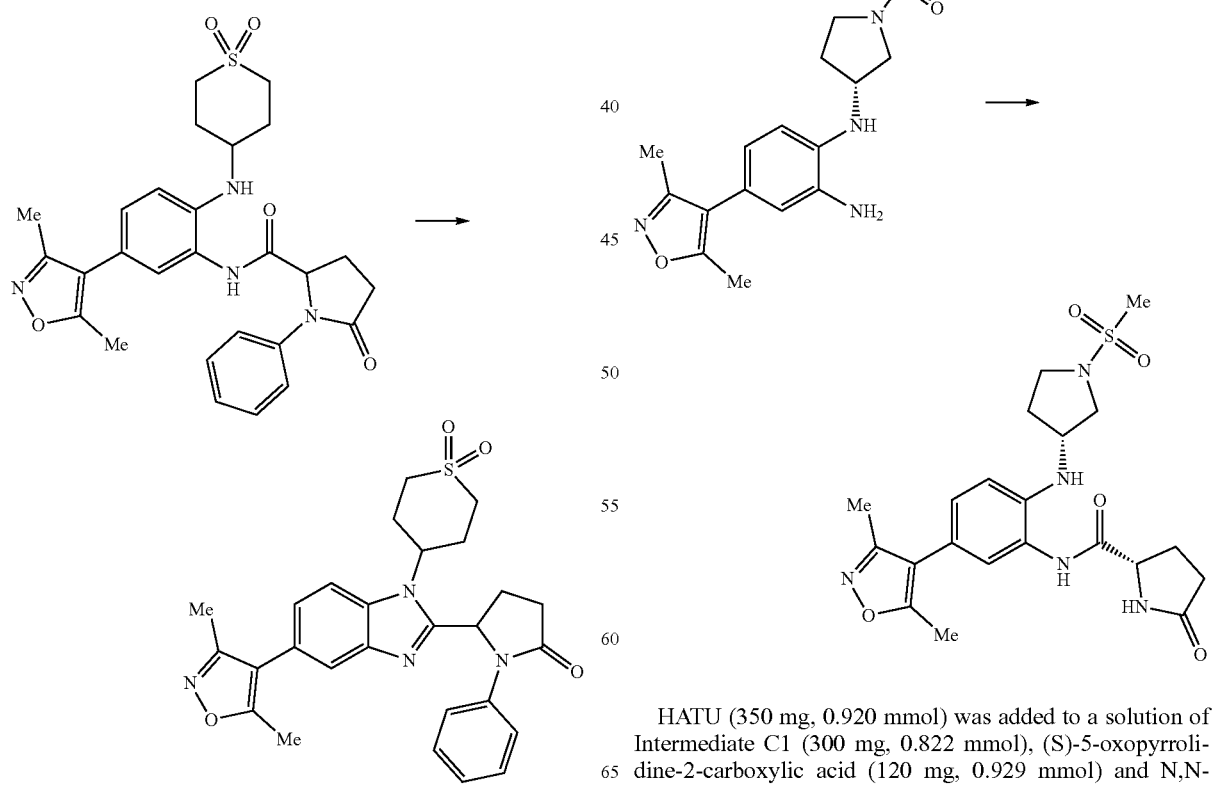

HATU (350 mg, 0.920 mmol) was added to a solution of Intermediate C1 (300 mg, 0.822 mmol), (S)-5-oxopyrrolidine-2-carboxylic acid (120 mg, 0.929 mmol) and N,N-diisopropylethylamine (175 µl, 1.002 mmol) in N,N-dimethylformamide (5 mL) then stirred at room temperature for 2 h. The mixture was diluted with water (40 mL) then extracted with ethyl acetate (3×20 mL). The combined organic phases were washed with 20% brine (2×20 mL), saturated brine (20 mL), then dried (MgSO$_4$), filtered and concentrated under reduced pressure to yield (S)—N-(5-(3, 5-dimethylisoxazol-4-yl)-2-(((R)-1-(methylsulfonyl)pyrrolidin-3-yl)amino)phenyl)-5-oxo pyrrolidine-2-carboxamide (293 mg, 66%) as a red-brown gum; Rt 1.45 min (method 1), m/z 462 (M+H)+ (ES+).

(S)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (Intermediate E1)

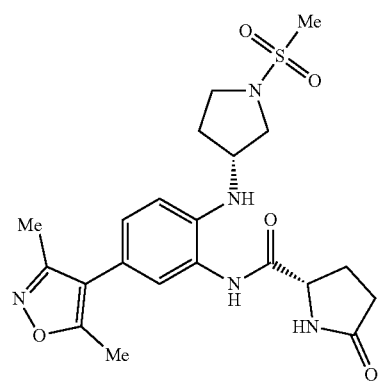

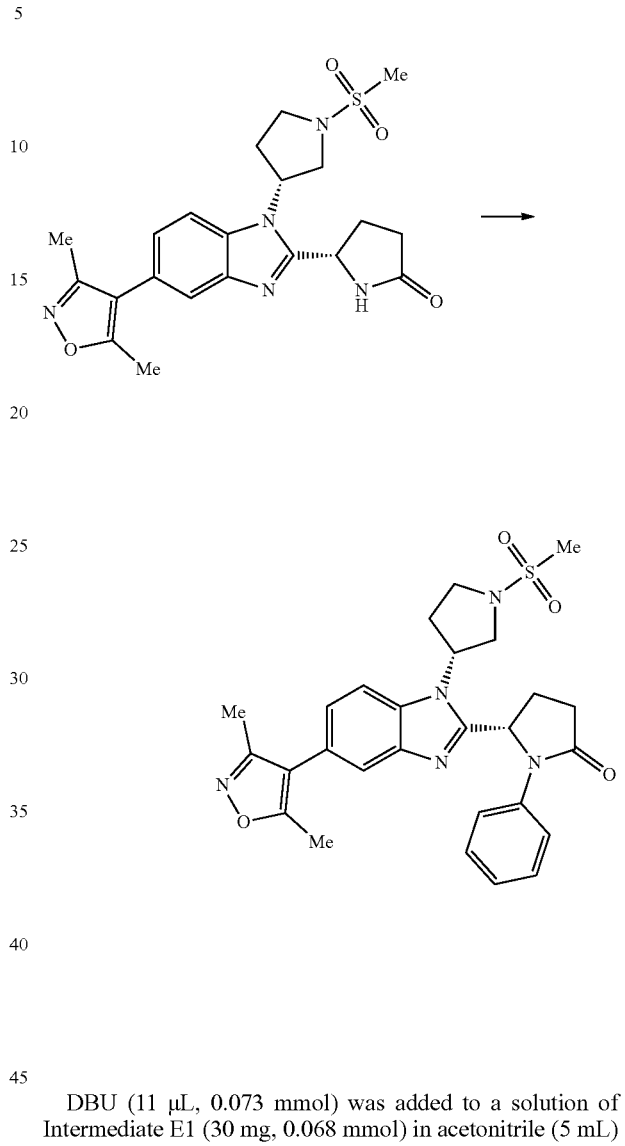

Intermediate D1 (293 mg, 0.546 mmol) was heated to 80° C. in acetic acid (5 mL) for 6 h. The mixture was concentrated under reduced pressure then diluted with water (40 mL) and extracted with ethyl acetate (3×20 mL). The combined organic phases were washed with 20% brine (2×20 mL), saturated brine (20 mL), then dried (MgSO$_4$), filtered and concentrated under reduced pressure. The crude product was purified by chromatography on the Companion (12 g column, 15-75% MeAc/DCM) to afford (S)-5-(5-(3, 5-dimethylisoxazol-4-yl)-1-((R)-1-(methylsulfonyl)pyrrolidin-3-yl)-1H-benzo[d]imidazol-2-yl)pyrrolidin-2-one (99 mg, 41%) as a tan solid; Rt 0.84 min (method 1), m/z 444 (M+H)+ (ES+).

(S)-5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one DBU (11 μL, 0.073 mmol) was added to a solution of Intermediate E1 (30 mg, 0.068 mmol) in acetonitrile (5 mL) then stirred for 5 minutes. CuTMEDA (5 mg, 10.77 μmol) was added and the suspension was stirred for a further 2 minutes before adding phenylboronic acid (10 mg, 0.082 mmol) and stirring for 18 h. The mixture was concentrated under reduced pressure then purified by chromatography on the Companion (12 g column, 15-75% acetone/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one (12 mg, 33%) as a pale yellow solid; Rt 1.75 min (method 1), m/z 520 (M+H)+ (ES+); 1H NMR (d6-DMSO) δ: 7.79-7.70 (m, 1H), 7.70-7.60 (m, 1H), 7.50 (dd, J=8.7, 1.2 Hz, 2H), 7.31 (dd, J=8.6, 7.4 Hz, 2H), 7.25 (dd, J=8.4, 1.7 Hz, 1H), 7.13-7.05 (m, 1H), 6.06 (dd, J=8.2, 2.3 Hz, 1H), 5.59-5.44 (m, 1H), 3.83-3.55 (m, 3H), 3.43-3.36 (m, 1H), 3.09 (s, 3H), 2.83-2.54 (m, 3H), 2.49-2.43 (m, 1H), 2.41-2.30 (m, 1H), 2.38 (s, 3H), 2.26-2.16 (m, 1H), 2.21 (s, 3H). Chiral HPLC (Diacel Chiralpak IA, 5 um, 4.6×250 mm, 30 min method, 1.0 mL/min, isocratic 30% EtOH in isohexane (0.2% TFA): RT=9.36 min, 96%, 92% de @ 254 nm.

Example 5: (R)-5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one (R)—N-(5-(3,5-dimethylisoxazol-4-yl)-2-(((R)-1-(methylsulfonyl)pyrrolidin-3-yl)amino)phenyl)-5-oxopyrrolidine-2-carboxamide (R)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (Intermediate E23)

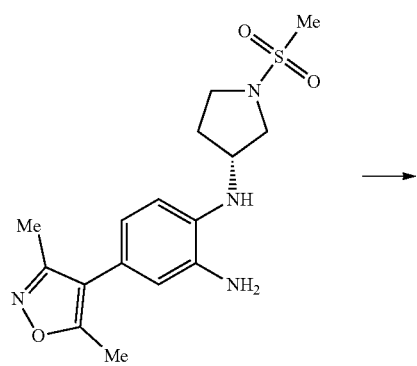

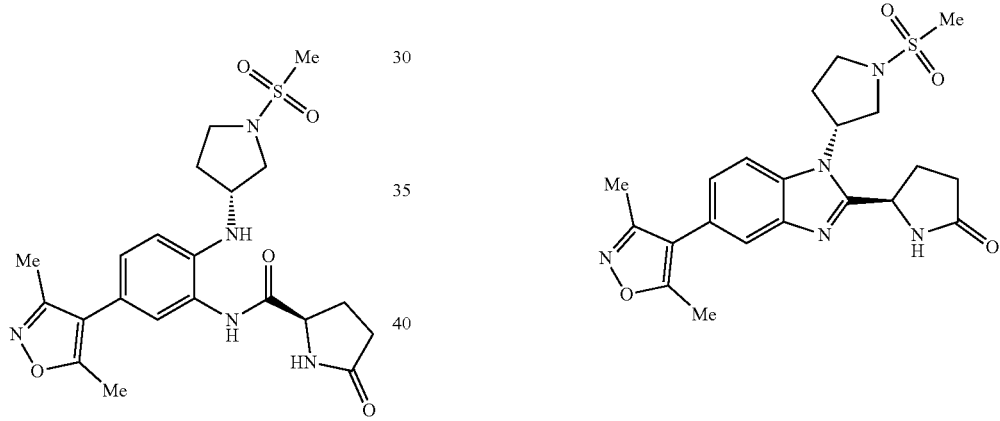

HATU (225 mg, 0.592 mmol) was added to a solution of Intermediate C1 (200 mg, 0.548 mmol), (R)-5-oxopyrrolidine-2-carboxylic acid (75 mg, 0.581 mmol) and N,N-diisopropylethylamine (110 µl, 0.630 mmol) in N,N-dimethylformamide (3 mL) then stirred at room temperature for 18 h. The mixture was diluted with water (15 mL) then extracted with ethyl acetate (3×15 mL). The combined organic phases were washed with 20% brine (2×20 mL), saturated brine (20 mL), then dried (MgSO₄), filtered and concentrated under reduced pressure to yield (R)—N-(5-(3,5-dimethylisoxazol-4-yl)-2-(((R)-1-(methylsulfonyl)pyrrolidin-3-yl)amino)phenyl)-5-oxopyrrolidine-2-carboxamide (253 mg, 0.548 mmol, 100% yield) as a red-brown gum; Rt 1.45 min (method 1), m/z 462 (M+H)+ (ES+).

(R)—N-(5-(3,5-dimethylisoxazol-4-yl)-2-(((R)-1-(methylsulfonyl)pyrrolidin-3-yl)amino)phenyl)-5-oxopyrrolidine-2-carboxamide (253 mg, 0.548 mmol) was heated to 80° C. in acetic acid (3 mL) for 5 h. The solvent was removed under reduced pressure then diluted with water (40 mL) and extracted with ethyl acetate (3×20 mL). The combined organic phases were washed with 20% brine (2×20 mL), saturated brine (20 mL), then dried (MgSO₄), filtered and concentrated under reduced pressure. The crude product was purified by flash chromatography on the Companion (12 g column, 15-75% MeAc/DCM) to afford (R)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (71 mg, 0.158 mmol, 28.9% yield) as an off white solid. Rt 1.33 min (method 1), m/z 444 (M+H)+ (ES+).

(R)-5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one Example 6: (S)-5-(5-(3,5-dimethylisoxazol-4-yl)-1-((R)-1-(methylsulfonyl)pyrrolidin-3-yl)-1H-benzo[d]imidazol-2-yl)-1-(3-fluorophenyl)pyrrolidin-2-one

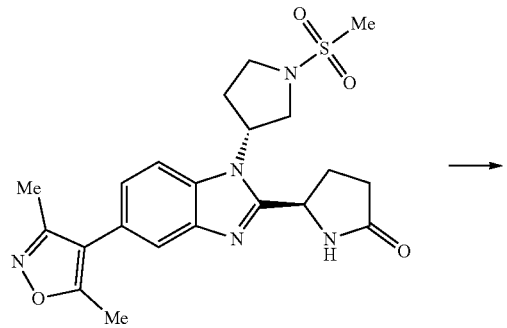

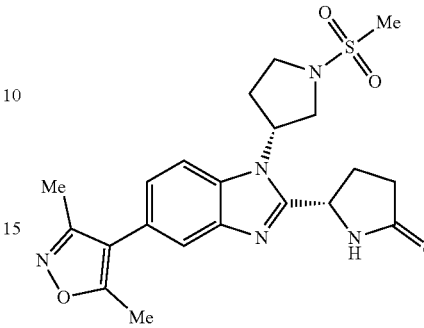

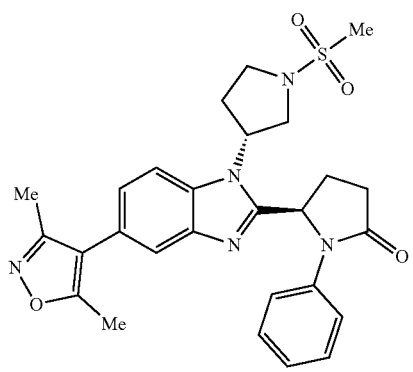

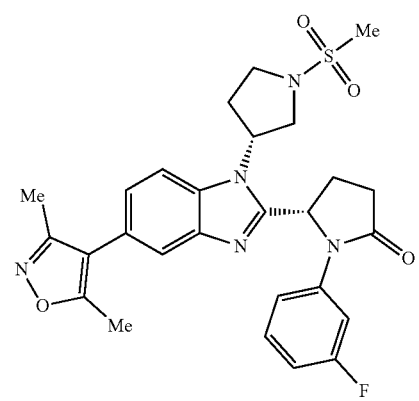

DBU (25 μL, 0.166 mmol) was added to a solution of (R)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (70 mg, 0.156 mmol) in acetonitrile (5 mL) then stirred for 5 minutes. CuTMEDA (10 mg, 0.022 mmol) was added and the suspension was stirred for a further 2 minutes before adding phenylboronic acid (20 mg, 0.164 mmol) and stirring for 18 h. The mixture was concentrated under reduced pressure then purified by chromatography on the Companion (4 g column, 0-50% MeAc/DCM) to afford (R)-5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one (18 mg, 22%) as an off white solid; Rt 1.78 min (method 1), m/z 520 (M+H)+ (ES+); 1H NMR (d6-DMSO) δ: 7.78-7.72 (m, 1H), 7.69-7.62 (m, 1H), 7.56-7.45 (m, 2H), 7.30 (dd, J=8.6, 7.3 Hz, 2H), 7.25 (dd, J=8.4, 1.7 Hz, 1H), 7.13-7.05 (m, 1H), 6.11-5.99 (m, 1H), 5.60-5.44 (m, 1H), 3.72 (ddd, J=11.1, 8.6, 2.9 Hz, 2H), 3.63 (dd, J=10.5, 6.8 Hz, 1H), 3.47-3.36 (m, 1H), 3.10 (s, 3H), 2.79-2.59 (m, 2H), 2.59-2.40 (m, 3H), 2.38 (s, 3H), 2.21 (s, 3H), 2.20-2.10 (m, 1H). Chiral HPLC (Diacel Chiralpak IA, 5 μm, 4.6×250 mm, 30 min method, 1.0 mL/min, isocratic 30% EtOH in isohexane (0.2% TFA): RT=10.49 min, 99.8%, 99.6% de @ 254 nm.

A solution of DBU (25 μL, 0.166 mmol) and Intermediate E1 (70 mg, 0.156 mmol) in acetonitrile (4 mL) was added to a vial charged with CuTMEDA (10 mg, 0.022 mmol) and (3-fluorophenyl)boronic acid (25 mg, 0.179 mmol) before stirring for 18 h at 40° C. The mixture was concentrated under reduced pressure then purified by chromatography on the Companion (4 g column, 0-50% MeAc/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(3-fluorophenyl) pyrrolidin-2-one (30 mg, 34% yield) as an off white solid; Rt 1.85 min (method 1), m/z 538 (M+H)+ (ES+); 1H NMR (d6-DMSO) δ: 7.77 (d, J=8.4 Hz, 1H), 7.65 (d, J=1.6 Hz, 1H), 7.61 (dt, J=11.9, 2.3 Hz, 1H), 7.34 (td, J=8.3, 6.9 Hz, 1H), 7.26 (dd, J=8.5, 1.7 Hz, 1H), 7.22 (ddd, J=8.4, 2.1, 0.9 Hz, 1H), 6.93 (tdd, J=8.4, 2.5, 0.9 Hz, 1H), 6.12 (dd, J=8.1, 1.9 Hz, 1H), 5.62-5.46 (m, 1H), 3.95-3.61 (m, 3H), 3.47-3.36 (m, 1H), 3.10 (s, 3H), 2.81-2.52 (m, 5H), 2.37 (s, 3H), 2.21 (s, 3H), 2.19-2.13 (m, 1H). Chiral HPLC (Diacel Chiralpak IA, 5 μm, 4.6×250 mm, 30 min method, 1.0 mL/min, isocratic 30% EtOH in isohexane (0.2% TFA): RT=8.38 min, 93%, 86% de @ 254 nm.

Example 7: (S)-1-(3,4-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(3,4-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one Example 8: (S)-1-(4-chloro-3-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(4-chloro-3-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one

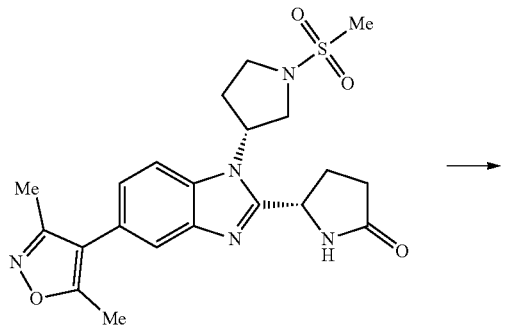

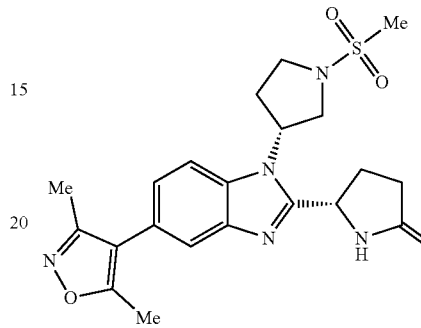

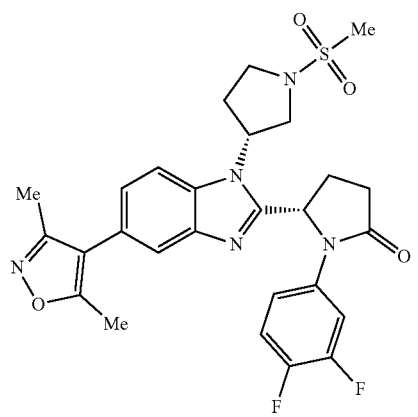

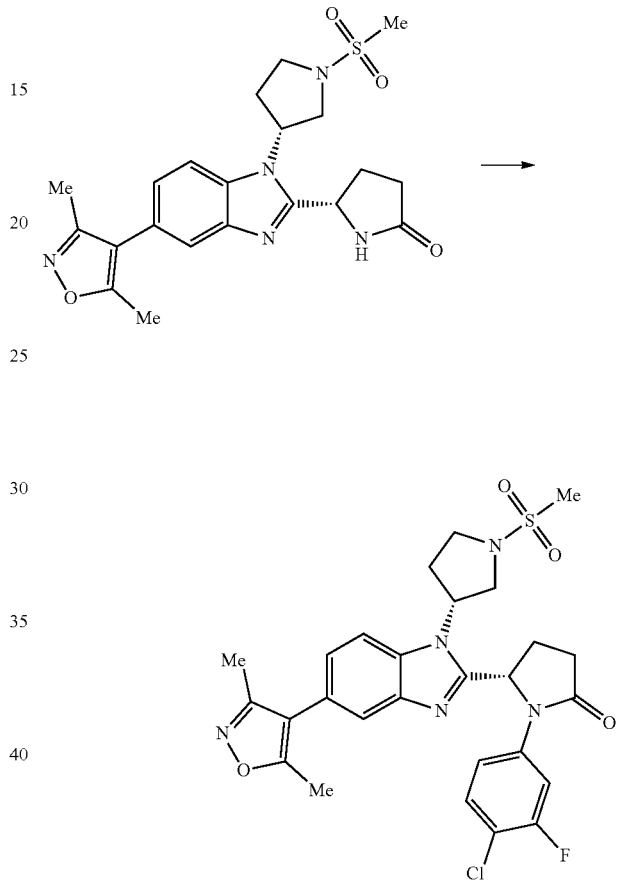

A solution of DBU (25 µl, 0.166 mmol) and Intermediate E1 (70 mg, 0.156 mmol) in acetonitrile (4 mL) was added to a vial charged with CuTMEDA (10 mg, 0.022 mmol) and (3,4-difluorophenyl)boronic acid (25 mg, 0.158 mmol) before stirring for 18 h at 40° C. The mixture was concentrated under reduced pressure then purified by chromatography on the Companion (4 g column, 0-50% MeAc/DCM) to afford (S)-1-(3,4-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (43 mg, 0.074 mmol, 47.1% yield) as an off-white solid; Rt 1.92 min (method 1), m/z 556 (M+H)+ (ES+); 1H NMR (d6-DMSO) δ: 7.83 (ddd, J=13.3, 7.4, 2.7 Hz, 1H), 7.77 (d, J=8.4 Hz, 1H), 7.65 (d, J=1.6 Hz, 1H), 7.39 (dt, J=10.6, 9.2 Hz, 1H), 7.26 (dd, J=8.4, 1.7 Hz, 1H), 7.24-7.16 (m, 1H), 6.16-6.02 (m, 1H), 5.58-5.44 (m, 1H), 3.88-3.61 (m, 3H), 3.45-3.35 (m, 1H), 3.10 (s, 3H), 2.78-2.52 (m, 5H), 2.38 (s, 3H), 2.21 (s, 3H), 2.20-2.13 (m, 1H). Chiral HPLC (Diacel Chiralpak IA, 5 µm, 4.6×250 mm, 30 min method, 1.0 mL/min, isocratic 30% EtOH in isohexane (0.2% TFA): RT=6.78 min, 93%, 86% de @ 254 nm.

DBU (25 µL, 0.166 mmol) was added to a solution of Intermediate E1 (70 mg, 0.156 mmol) in acetonitrile (5 mL) then stirred for 5 minutes. CuTMEDA (10 mg, 0.022 mmol) was added and the suspension was stirred for a further 2 minutes before adding (4-chloro-3-fluorophenyl)boronic acid (30 mg, 0.172 mmol) and stirring for 18 h at 40° C. The mixture was concentrated under reduced pressure then purified by chromatography on the Companion (4 g column, 0-50% MeAc/DCM) to afford (S)-1-(4-chloro-3-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (39 mg, 41%) as an off-white solid; Rt 2.05 min (method 1), m/z 572 (M+H)+ (ES+); 1H NMR (d6-DMSO) δ: 7.85 (dd, J=12.1, 2.5 Hz, 1H), 7.81-7.74 (m, 1H), 7.64 (dd, J=1.6, 0.6 Hz, 1H), 7.52 (t, J=8.8 Hz, 1H), 7.30-7.23 (m, 2H), 6.18-6.08 (m, 1H), 5.58-5.46 (m, 1H), 3.87-3.63 (m, 3H), 3.46-3.36 (m, 1H), 3.10 (s, 3H), 2.77-2.52 (m, 5H), 2.37 (s, 3H), 2.20 (s, 3H), 2.19-2.12 (m, 1H). Chiral HPLC (Diacel Chiralpak IA, 5 mm, 4.6×250 mm, 30 min method, 1.0 ml/min, isocratic 30% EtOH in isohexane (0.2% TFA): RT=7.75 min, 86%, 73% de @ 254 nm.

Example 9: (S)-1-(3-chloro-4-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(3-chloro-4-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one

Example 10: (S)-1-(3,5-dichlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(3,5-dichlorophenyl)-5-(5-(3,5-dimethylisoxazol-4-yl)-1-((R)-1-(methylsulfonyl) pyrrolidin-3-yl)-1H-benzo[d]imidazol-2-yl)pyrrolidin-2-one

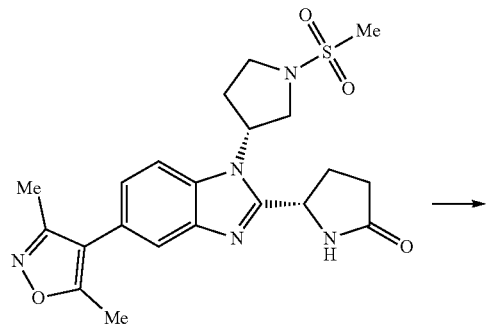

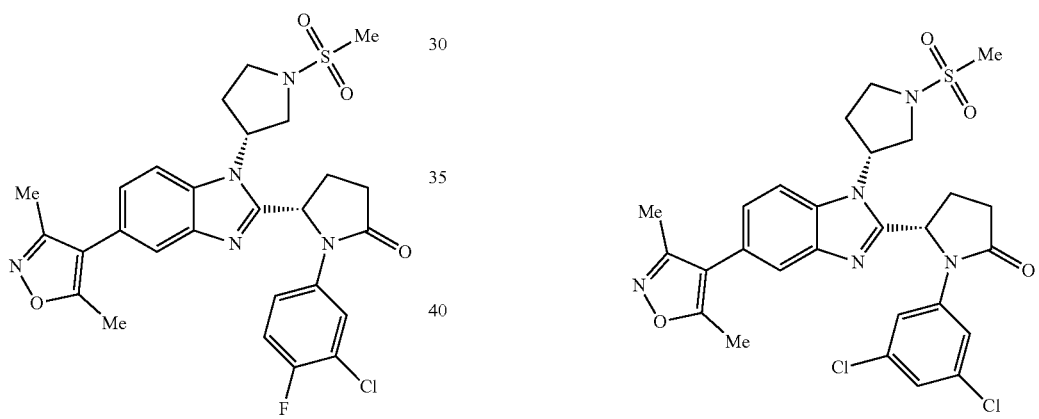

DBU (25 µl, 0.166 mmol) was added to a solution of Intermediate E1 (70 mg, 0.156 mmol) in acetonitrile (5 mL) then stirred for 5 minutes. CuTMEDA (10 mg, 0.022 mmol) was added and the suspension was stirred for a further 2 minutes before adding (3-chloro-4-fluorophenyl)boronic acid (30 mg, 0.172 mmol) and stirring for 18 h at 40° C. The mixture was concentrated under reduced pressure then purified by chromatography on the Companion (4 g column, 0-50% MeAc/DCM) to afford (S)-1-(3-chloro-4-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (44 mg, 0.073 mmol, 46.8% yield) as an off white solid; Rt 2.07 min (method 1), m/z 572 (M+H)+ (ES+); 1H NMR (d6-DMSO) δ: 7.95 (dd, J=6.9, 2.3 Hz, 1H), 7.77 (d, J=8.5 Hz, 1H), 7.66 (d, J=1.5 Hz, 1H), 7.44-7.33 (m, 2H), 7.26 (dd, J=8.5, 1.7 Hz, 1H), 6.17-6.06 (m, 1H), 5.56-5.49 (m, 1H), 3.86-3.62 (m, 3H), 3.44-3.36 (m, 1H), 3.10 (s, 3H), 2.79-2.52 (m, 5H), 2.38 (s, 3H), 2.21 (s, 3H), 2.20-2.12 (m, 1H). Chiral HPLC (Diacel Chiralpak IA, 5 µm, 4.6×250 mm, 30 min method, 1.0 mL/min, isocratic 30% EtOH in isohexane (0.2% TFA): RT=6.89 min, 93%, 86% de @ 254 nm.

DBU (25 µL, 0.166 mmol) was added to a solution of Intermediate E1 (70 mg, 0.156 mmol) in acetonitrile (5 mL) then stirred for 5 minutes. CuTMEDA (10 mg, 0.022 mmol) was added and the suspension was stirred for a further 2 minutes before adding (3,5-dichlorophenyl)boronic acid (35 mg, 0.183 mmol) and stirring for 18 h at 40° C. The mixture was concentrated under reduced pressure then purified by chromatography on the Companion (4 g column, 0-50% MeAc/DCM) to afford (S)-1-(3,5-dichlorophenyl)-5-(5-(3,5-dimethylisoxazol-4-yl)-1-((R)-1-(methylsulfonyl)pyrrolidin-3-yl)-1H-benzo[d]imidazol-2-yl) pyrrolidin-2-one (40 mg, 0.065 mmol, 41.3% yield) as an off-white solid; Rt 2.18 min (method 1), m/z 588 (M+H)+ (ES+); 1H NMR (d6-DMSO) δ: 7.83-7.75 (m, 1H), 7.69 (d, J=1.9 Hz, 2H), 7.66 (dd, J=1.6, 0.5 Hz, 1H), 7.34 (t, J=1.8 Hz, 1H), 7.27 (dd, J=8.5, 1.7 Hz, 1H), 6.29-6.17 (m, 1H), 5.60-5.49 (m, 1H), 3.88-3.65 (m, 3H), 3.40 (q, J=9.4, 9.0 Hz, 1H), 3.10 (s, 3H), 2.82-2.53 (m, 5H), 2.38 (s, 3H), 2.21 (s, 3H), 2.17 (d, J=9.9 Hz, 1H). Chiral HPLC (Lab 1 Bay 4, Diacel Chiralpak IA, 5 µm, 4.6×250 mm, 30 min method, 1.0 mL/min, isocratic 30% EtOH in isohexane (0.2% TFA): RT=7.02 min, 90%, 80% de @ 254 nm.

Example 11: (S)-1-(3-chloro-5-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(3-chloro-5-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one

Example 12: (S)-1-(3-chloro-5-methoxyphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(3-chloro-5-methoxyphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one

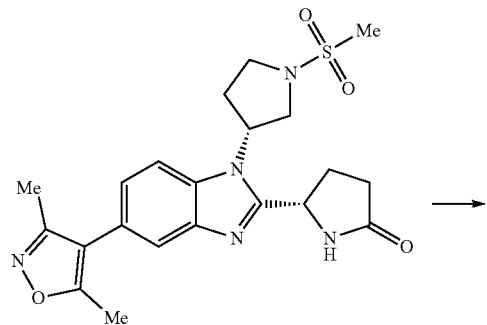

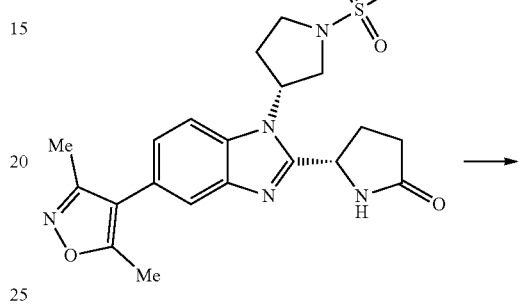

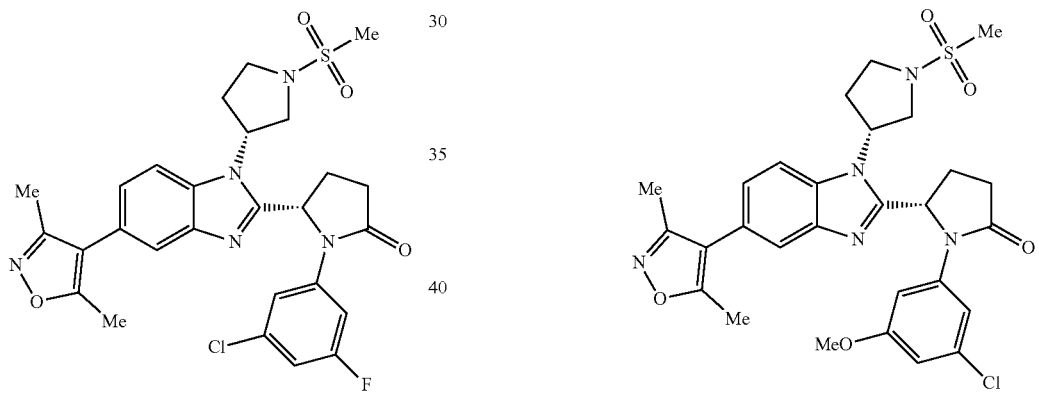

A solution of DBU (25 μl, 0.166 mmol) and Intermediate E1 (70 mg, 0.156 mmol) in acetonitrile (4 mL) was added to a vial charged with CuTMEDA (10 mg, 0.022 mmol) and (3-chloro-5-fluorophenyl)boronic acid (30 mg, 0.172 mmol) before stirring for 18 h at 40° C. The mixture was concentrated under reduced pressure then purified by chromatography on the Companion (4 g column, 0-50% MeAc/DCM) to afford (S)-1-(3-chloro-5-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (40 mg, 42%) as an off-white solid; Rt 2.08 min (method 1), m/z 572 (M+H)+ (ES+); 1H NMR (d6-DMSO) δ: 7.79 (d, J=8.5 Hz, 1H), 7.66 (dd, J=1.7, 0.6 Hz, 1H), 7.57 (dt, J=2.4, 1.2 Hz, 1H), 7.49 (dt, J=11.4, 2.2 Hz, 1H), 7.27 (dd, J=8.4, 1.7 Hz, 1H), 7.18 (dt, J=8.5, 2.1 Hz, 1H), 6.23-6.15 (m, 1H), 5.59-5.47 (m, 1H), 3.88-3.66 (m, 3H), 3.40 (q, J=9.0 Hz, 1H), 3.10 (s, 3H), 2.79-2.52 (m, 5H), 2.38 (s, 3H), 2.21 (s, 3H), 2.19-2.12 (m, 1H). Chiral HPLC (Diacel Chiralpak IA, 5 μm, 4.6×250 mm, 30 min method, 1.0 mL/min, isocratic 30% EtOH in isohexane (0.2% TFA): RT=7.10 min, 89%, 78% de @ 254 nm.

DBU (25 μl, 0.166 mmol) was added to a solution of Intermediate E1 (70 mg, 0.156 mmol) in acetonitrile (5 mL) then stirred for 5 minutes. CuTMEDA (10 mg, 0.022 mmol) was added and the suspension was stirred for a further 2 minutes before adding (3-chloro-5-methoxyphenyl)boronic acid (33 mg, 0.177 mmol) and stirring for 2 h at 40° C. The mixture was concentrated under reduced pressure then purified by chromatography on the Companion (4 g column, 0-50% MeAc/DCM) to afford (S)-1-(3-chloro-5-methoxyphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (39 mg, 40%) as an off white solid; Rt 2.02 min (method 1), m/z 584 (M+H)+ (ES+); 1H NMR (d6-DMSO) δ: 7.77 (dd, J=8.5, 0.6 Hz, 1H), 7.65 (dd, J=1.7, 0.6 Hz, 1H), 7.33 (t, J=1.9 Hz, 1H), 7.26 (dd, J=8.4, 1.7 Hz, 1H), 7.06 (t, J=2.1 Hz, 1H), 6.78 (t, J=2.0 Hz, 1H), 6.19-6.08 (m, 1H), 5.61-5.51 (m, 1H), 3.86-3.64 (m, 3H), 3.69 (s, 3H), 3.40 (td, J=9.6, 7.3 Hz, 1H), 3.09 (s, 3H), 2.82-2.52 (m, 5H), 2.38 (s, 3H), 2.21 (s, 3H), 2.19-2.11 (m, 1H). Chiral HPLC (Diacel Chiralpak IA, 5 μm, 4.6×250 mm, 30 min method, 1.0 mL/min, isocratic 30% EtOH in isohexane (0.2% TFA): RT=8.44 min, 94%, 88% de @ 254 nm.

Example 13: (S)-5-(5-(3,5-dimethylisoxazol-4-yl)-1-((R)-1-(methylsulfonyl)pyrrolidin-3-yl)-1H-benzo[d]imidazol-2-yl)-1-(3-fluoro-4-methoxyphenyl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(3-fluoro-4-methoxyphenyl)pyrrolidin-2-one Example 14: (S)-1-(3-chloro-4-methoxyphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(3-chloro-4-methoxyphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one

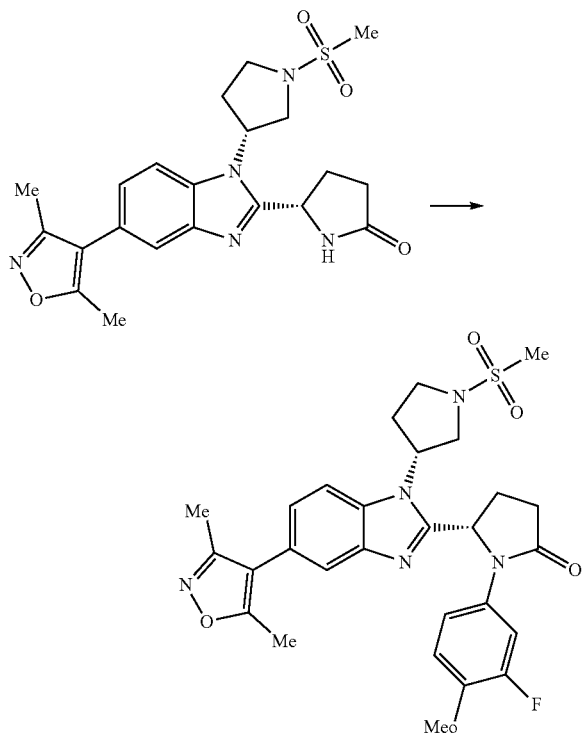

DBU (25 µL, 0.166 mmol) was added to a solution of Intermediate E1 (70 mg, 0.156 mmol) in acetonitrile (5 mL) then stirred for 5 minutes. CuTMEDA (10 mg, 0.022 mmol) was added and the suspension was stirred for a further 2 minutes before adding (3-fluoro-4-methoxyphenyl)boronic acid (30 mg, 0.177 mmol) and stirring for 2 h at 40° C. The mixture was concentrated under reduced pressure then purified by chromatography on the Companion (4 g column, 0-50% MeAc/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(3-fluoro-4-methoxy phenyl)pyrrolidin-2-one (52 mg, 56%) as an off white solid; Rt 1.83 min (method 1), m/z 568 (M+H)+ (ES+); 1H NMR (d6-DMSO) δ: 7.76 (dd, J=8.5, 0.7 Hz, 1H), 7.65 (dd, J=1.7, 0.6 Hz, 1H), 7.64-7.55 (m, 1H), 7.25 (dd, J=8.4, 1.7 Hz, 1H), 7.14-7.03 (m, 2H), 6.02 (dd, J=8.2, 2.3 Hz, 1H), 5.56-5.46 (m, 1H), 3.86-3.62 (m, 3H), 3.76 (s, 3H), 3.44-3.33 (m, 1H), 3.09 (s, 3H), 2.79-2.53 (m, 4H), 2.45-2.38 (m, 1H), 2.38 (s, 3H), 2.21 (s, 3H), 2.20-2.12 (m, 1H). Chiral HPLC (Diacel Chiralpak IA, 5 am, 4.6×250 mm, 30 min method, 1.0 mL/min, isocratic 30% EtOH in isohexane (0.2% TFA): RT=9.72 min, 94%, 88% de @ 254 nm.

DBU (25 µl, 0.166 mmol) was added to a solution of Intermediate E1 (70 mg, 0.156 mmol) in acetonitrile (5 mL) then stirred for 5 minutes. CuTMEDA (10 mg, 0.022 mmol) was added and the suspension was stirred for a further 2 minutes before adding (3-chloro-4-methoxyphenyl)boronic acid (33 mg, 0.177 mmol) and stirring for 2 h at 40° C. The mixture was concentrated under reduced pressure then purified by chromatography on the Companion (4 g column, 0-50% MeAc/CH2Cl2) to afford (S)-1-(3-chloro-4-methoxyphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (42 mg, 44%) as an off white solid; Rt 1.91 min (method 1), m/z 584 (M+H)+ (ES+); 1H NMR (d6-DMSO) δ: 7.77 (d, J=2.6 Hz, 1H), 7.76-7.73 (m, 1H), 7.66 (dd, J=1.7, 0.6 Hz, 1H), 7.30 (dd, J=9.0, 2.6 Hz, 1H), 7.25 (dd, J=8.4, 1.7 Hz, 1H), 7.08 (d, J=9.1 Hz, 1H), 6.05 (dd, J=8.2, 2.4 Hz, 1H), 5.57-5.47 (m, 1H), 3.84-3.60 (m, 3H), 3.78 (s 3H), 3.38 (td, J=9.6, 7.2 Hz, 1H), 3.09 (s, 3H), 2.80-2.52 (m, 4H), 2.42-2.32 (m, 1H), 2.38 (s, 3H), 2.24-2.16 (m, 1H), 2.21 (s, 3H). Chiral HPLC (Diacel Chiralpak IA, 5 cm, 4.6×250 mm, 30 min method, 1.0 mL/min, isocratic 30% EtOH in isohexane (0.2% TFA): RT=9.55 min, 94%, 88% de @ 254 nm.

Example 15: (S)-5-(5-(3,5-dimethylisoxazol-4-yl)-1-((R)-1-(methylsulfonyl)pyrrolidin-3-yl)-1H-benzo[d]imidazol-2-yl)-1-(4-methoxyphenyl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(4-methoxyphenyl)pyrrolidin-2-one

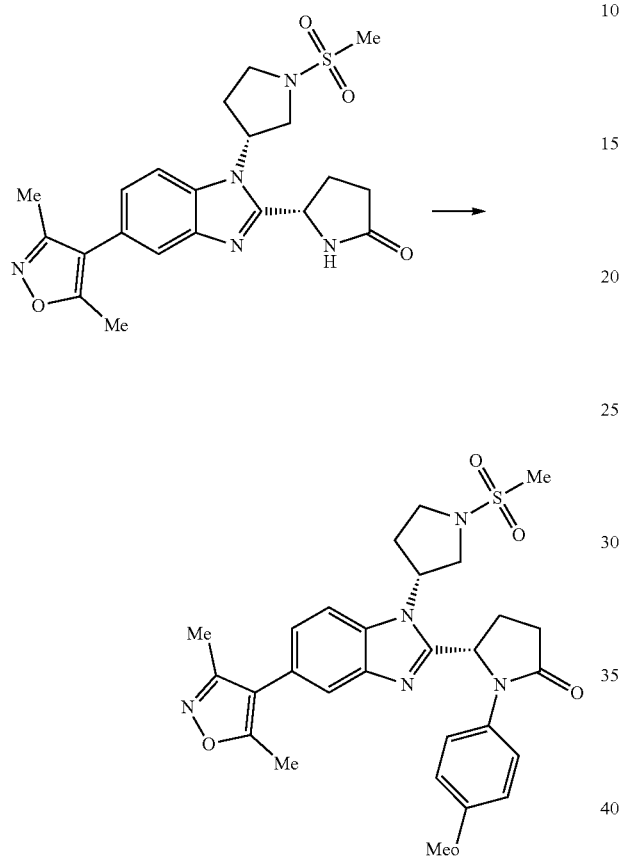

A solution of DBU (25 μL, 0.166 mmol) and Intermediate E1 (70 mg, 0.156 mmol) in acetonitrile (4 mL) was added to a vial charged with CuTMEDA (10 mg, 0.022 mmol) and (4-methoxyphenyl)boronic acid (28 mg, 0.184 mmol) before stirring for 18 h at 40° C. The mixture was concentrated under reduced pressure then purified by chromatography on the Companion (4 g column, 0-50% MeAc/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(4-methoxyphenyl) pyrrolidin-2-one (54 mg, 60%) as an off white solid; Rt 1.75 min (method 1), m/z 550 (M+H)+ (ES+); 1H NMR (d6-DMSO) δ: 7.73 (d, J=8.5 Hz, 1H), 7.66 (d, J=1.6 Hz, 1H), 7.41-7.33 (m, 2H), 7.24 (dd, J=8.4, 1.7 Hz, 1H), 6.91-6.81 (m, 2H), 5.97 (dd, J=8.2, 2.7 Hz, 1H), 5.52-4.42 (m, 1H), 3.82-3.49 (m, 3H), 3.68 (s, 3H), 3.39-3.28 (m, 1H), 3.08 (s, 3H), 2.82-2.52 (m, 3H), 2.50-2.40 (m, 1H), 2.38 (s, 3H), 2.27-2.17 (m, 2H), 2.22 (s, 3H). Chiral HPLC (Diacel Chiralpak IA, 5 μm, 4.6×250 mm, 30 min method, 1.0 mL/min, isocratic 30% EtOH in isohexane (0.2% TFA): RT=10.41 min, 95.7%, 91.4% de @ 254 nm.

Example 16 (S)-5-(5-(3,5-dimethylisoxazol-4-yl)-1-((R)-1-(methylsulfonyl)pyrrolidin-3-yl)-1H-benzo[d]imidazol-2-yl)-1-(4-propoxyphenyl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(4-propoxyphenyl)pyrrolidin-2-one

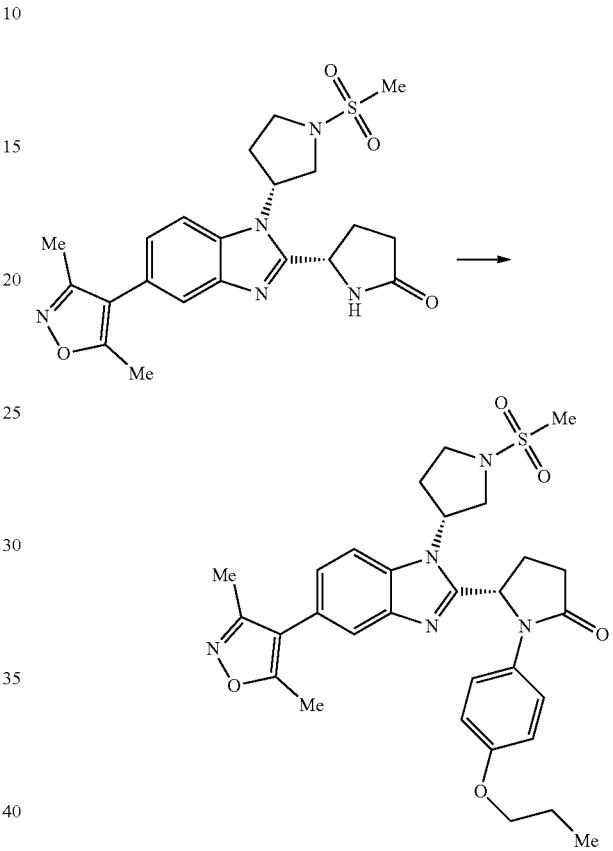

A solution of DBU (25 μL, 0.166 mmol) and Intermediate E1 (70 mg, 0.156 mmol) in acetonitrile (4 mL) was added to a vial charged with CuTMEDA (10 mg, 0.022 mmol) and (4-propoxyphenyl)boronic acid (32 mg, 0.178 mmol) before stirring for 18 h at 40° C. The mixture was concentrated under reduced pressure then purified by chromatography on the Companion (4 g column, 0-50% MeAc/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(4-propoxyphenyl) pyrrolidin-2-one (56 mg, 59%) as an off white solid; Rt 2.00 min (method 1), m/z 578 (M+H)+ (ES+); 1H NMR (d6-DMSO) δ: 7.73 (d, J=8.5 Hz, 1H), 7.66 (d, J=1.6 Hz, 1H), 7.39-7.31 (m, 2H), 7.24 (dd, J=8.5, 1.7 Hz, 1H), 6.90-6.82 (m, 2H), 5.96 (dd, J=8.2, 2.7 Hz, 1H), 5.52-5.42 (m, 1H), 3.84 (t, J=6.6 Hz, 2H), 3.75 (dd, J=10.6, 8.9 Hz, 1H), 3.68 (td, J=9.5, 8.5, 2.5 Hz, 1H), 3.60 (dd, J=10.6, 6.8 Hz, 1H), 3.40-3.29 (m, 1H), 3.08 (s, 3H), 2.83-2.52 (m, 3H), 2.47-2.40 (m, 1H), 2.38 (s, 3H), 2.28-2.16 (m, 2H), 2.22 (s, 3H), 1.71-1.62 (m, 2H), 0.92 (t, J=7.4 Hz, 3H). Chiral HPLC (Diacel Chiralpak IA, 5 μm, 4.6×250 mm, 30 min method, 1.0 mL/min, isocratic 30% EtOH in isohexane (0.2% TFA): RT=8.07 min, 94.9%, 89.8% de @ 254 nm.

Example 17: (S)-1-(4-chlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(4-chlorophenyl)-5-(5-(3,5-dimethylisoxazol-4-yl)-1-((R)-1-(methylsulfonyl) pyrrolidin-3-yl)-1H-benzo[d]imidazol-2-yl)pyrrolidin-2-one

Example 18: (S)-5-(5-(3,5-dimethylisoxazol-4-yl)-1-((R)-1-(methylsulfonyl)pyrrolidin-3-yl)-1H-benzo[d]imidazol-2-yl)-1-(pyridin-3-yl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(pyridin-3-yl)pyrrolidin-2-one

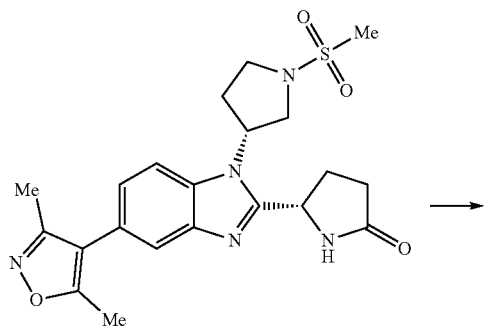

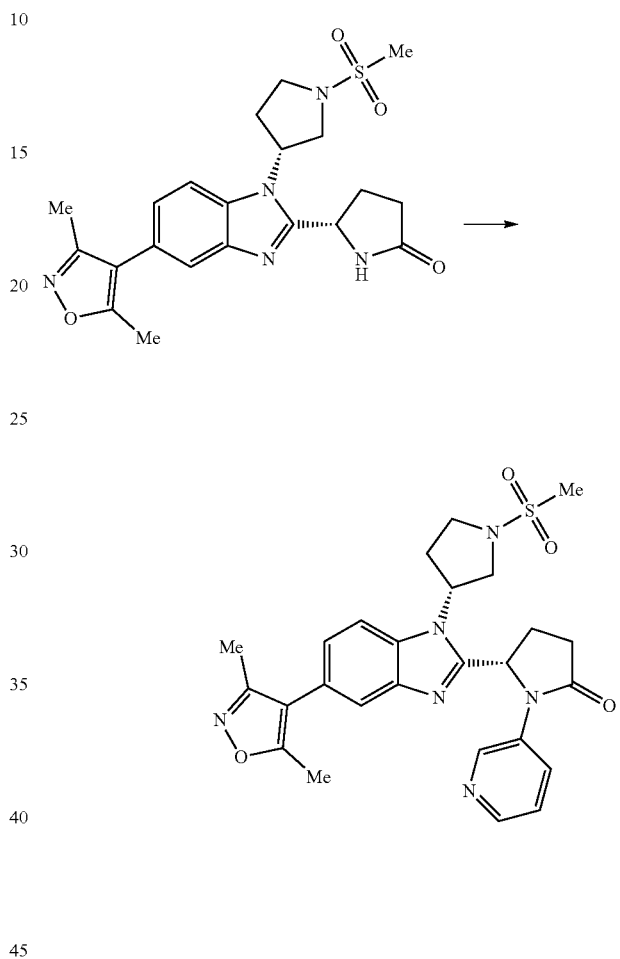

A solution of DBU (25 μl, 0.166 mmol) and Intermediate E1 (70 mg, 0.156 mmol) in acetonitrile (4 mL) was added to a vial charged with CuTMEDA (10 mg, 0.022 mmol) and (4-chlorophenyl)boronic acid (28 mg, 0.179 mmol) before stirring for 18 h at 40° C. The mixture was concentrated under reduced pressure then purified by chromatography on the Companion (4 g column, 0-50% MeAc/CH2Cl2) to afford (S)-1-(4-chlorophenyl)-5-(5-(3,5-dimethylisoxazol-4-yl)-1-((R)-1-(methylsulfonyl)pyrrolidin-3-yl)-1H-benzo[d]imidazol-2-yl) pyrrolidin-2-one (43 mg, 47%) as an off white solid; Rt 1.96 min (method 1), m/z 554 (M+H)+ (ES+); 1H NMR (d6-DMSO) δ: 7.81-7.72 (m, 1H), 7.64 (dd, J=1.7, 0.6 Hz, 1H), 7.61-7.51 (m, 2H), 7.42-7.31 (m, 2H), 7.25 (dd, J=8.5, 1.7 Hz, 1H), 6.08 (dd, J=8.1, 2.3 Hz, 1H), 5.57-5.47 (m, 1H), 3.79 (t, J=9.8 Hz, 1H), 3.72 (td, J=9.3, 8.1, 2.8 Hz, 1H), 3.66 (dd, J=10.6, 6.7 Hz, 1H), 3.44-3.35 (m, 1H), 3.10 (s, 3H), 2.78-2.52 (m, 4H), 2.49-2.43 (m, 1H), 2.37 (s, 3H), 2.21 (s, 3H), 2.20-2.14 (m, 1H). Chiral HPLC (Diacel Chiralpak IA, 5 μm, 4.6×250 mm, 30 min method, 1.0 mL/min, isocratic 30% EtOH in isohexane (0.2% TFA): 148476, RT=9.53 min, 94.8%, 89.6% de @ 254 nm.

A solution of DBU (20 μl, 0.133 mmol) and Intermediate E1 (50 mg, 0.113 mmol) in acetonitrile (4 mL) was added to a vial charged with CuTMEDA (10 mg, 0.022 mmol) and pyridin-3-ylboronic acid (15.24 mg, 0.124 mmol) before stirring for 18 h at 40° C. The mixture was concentrated under reduced pressure then purified by chromatography on the Companion (12 g column, 0-80% MeAc/CH2Cl2) to afford (S)-5-(5-(3,5-dimethylisoxazol-4-yl)-1-((R)-1-(methylsulfonyl)pyrrolidin-3-yl)-1H-benzo[d]imidazol-2-yl)-1-(pyridin-3-yl)pyrrolidin-2-one (23 mg, 39%) as an off white solid; Rt 1.40 min (method 1), m/z 521 (M+H)+ (ES+); 1H NMR (d6-DMSO) δ: 8.69 (1H, d, J=2.6 Hz), 8.28 (1H, dd, J=4.7, 1.4 Hz), 7.98 (1H, ddd, J=8.4, 2.6, 1.4 Hz), 7.76 (1H, d, J=8.4 Hz), 7.64 (1H, d, J=1.8 Hz), 7.36 (1H, ddd, J=8.4, 4.7, 0.7 Hz), 7.25 (1H, dd, J=8.5, 1.7 Hz), 6.13 (1H, d, J=6.4 Hz), 5.58-5.41 (1H, m), 3.86-3.75 (1H, m), 3.75-3.59 (2H, m), 3.45-3.35 (1H, m), 3.09 (3H, s), 2.76-2.61 (2H, m), 2.61-2.51 (2H, m), 2.36 (3H, s), 2.23 (1H, d, J=8.2 Hz), 2.20 (3H, s), 1.14 (1H, s). Chiral HPLC (Diacel Chiralpak IA, 5 μm, 4.6×250 mm, 30 min method, 1.0 mL/min, isocratic 30% EtOH in isohexane (0.2% TFA): RT=11.85 min, >99% de @ 254 nm.

Example 19: (S)-5-(5-(3,5-dimethylisoxazol-4-yl)-1-((R)-1-(methylsulfonyl)pyrrolidin-3-yl)-1H-benzo[d]imidazol-2-yl)-1-(6-fluoropyridin-3-yl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(6-fluoropyridin-3-yl)pyrrolidin-2-one Example 20: (S)-5-(5-(3,5-dimethylisoxazol-4-yl)-1-((R)-1-(methylsulfonyl)pyrrolidin-3-yl)-1H-benzo[d]imidazol-2-yl)-1-(naphthalen-1-yl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(naphthalen-1-yl)pyrrolidin-2-one

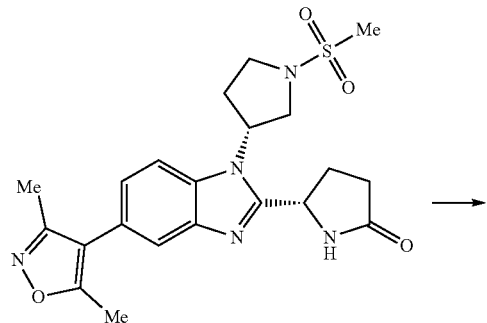

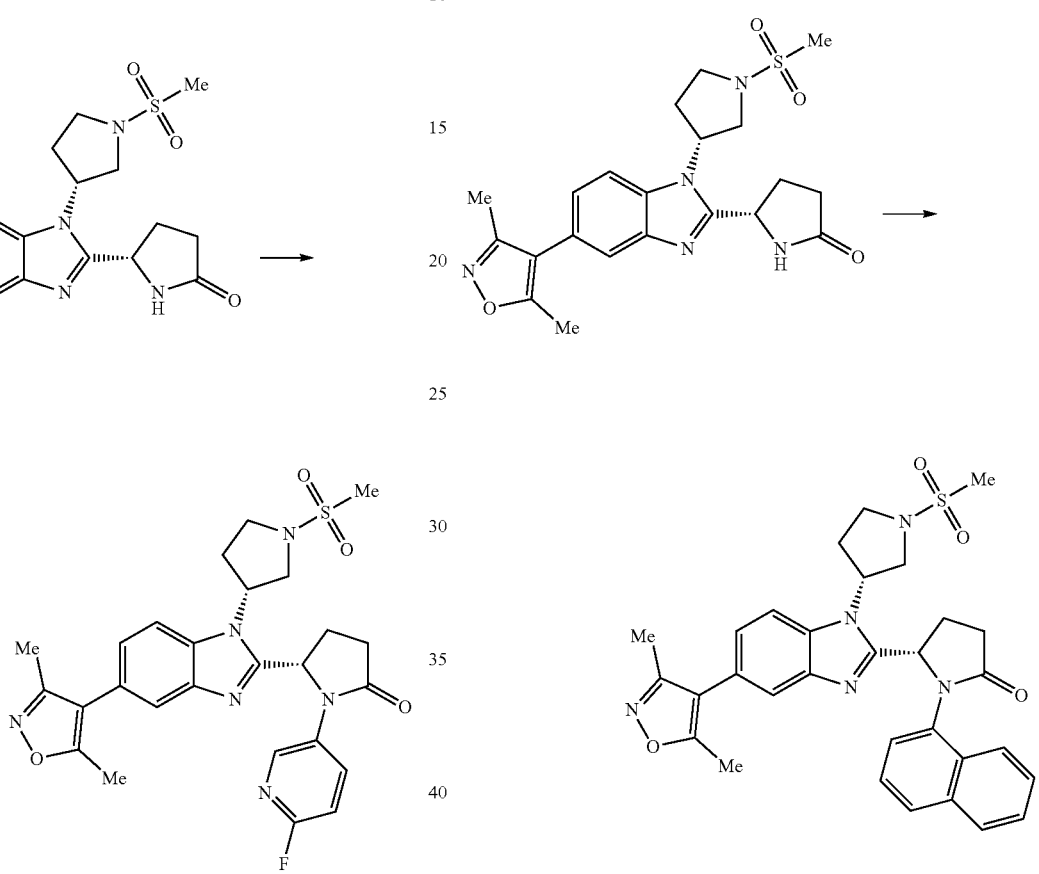

A solution of DBU (20 µl, 0.133 mmol) and Intermediate E1 (50 mg, 0.113 mmol) in acetonitrile (4 mL) was added to a vial charged with CuTMEDA (10 mg, 0.022 mmol) and (6-fluoropyridin-3-yl)boronic acid (17.47 mg, 0.124 mmol) before stirring for 18 h at 40° C. The mixture was concentrated under reduced pressure then purified by chromatography on the Companion (12 g column, 0-50% MeAc/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(6-fluoropyridin-3-yl)pyrrolidin-2-one (18 mg, 0.033 mmol, 29.3% yield) as an off white solid; Rt 1.70 min (method 1), m/z 539 (M+H)+ (ES+); 1H NMR (d6-DMSO) δ: 8.33 (1H, dd, J=3.0, 1.3 Hz), 8.18 (1H, ddd, J=8.9, 7.2, 2.8 Hz), 7.76 (1H, d, J=8.4 Hz), 7.64 (1H, d, J=1.6 Hz), 7.25 (1H, dd, J=8.4, 1.7 Hz), 7.18 (1H, dd, J=9.0, 3.3 Hz), 6.15-6.04 (1H, m), 5.51-5.39 (1H, m), 3.85-3.76 (1H, m), 3.76-3.61 (2H, m), 3.42-3.34 (1H, m), 3.08 (3H, s), 2.79-2.62 (2H, m), 2.51 (3H, s), 2.37 (3H, s), 2.26-2.21 (1H, m), 2.20 (3H, s); Chiral HPLC (Diacel Chiralpak IA, 5 µm, 4.6×250 mm, 30 min method, 1.0 mL/min, isocratic 30% EtOH in isohexane (0.2% TFA): RT=9.00 min, >99% de @ 254 nm.

A solution of DBU (20 µl, 0.133 mmol) and Intermediate E1 (50 mg, 0.113 mmol) in acetonitrile (4 mL) was added to a vial charged with CuTMEDA (10 mg, 0.022 mmol) and naphthalen-1-ylboronic acid (21.33 mg, 0.124 mmol) before stirring for 18 h at 40° C. The mixture was concentrated under reduced pressure then purified by chromatography on the Companion (12 g column, 0-50% MeAc/CH2Cl2) to afford (S)-5-(5-(3,5-dimethylisoxazol-4-yl)-1-((R)-1-(methylsulfonyl)pyrrolidin-3-yl)-1H-benzo[d]imidazol-2-yl)-1-(naphthalen-1-yl)pyrrolidin-2-one (7 mg, 11%) as an off white solid; Rt 1.86 min (method 1), m/z 570 (M+H)+ (ES+); 1H NMR (d6-DMSO) δ: 7.96 (2H, br. s), 7.90 (1H, d, J=8.4 Hz), 7.74 (1H, s), 7.64-7.35 (5H, m), 7.18 (1H, d, J=8.4 Hz), 5.99-5.82 (1H, m), 4.93 (1H, br. s), 3.68-3.56 (1H, m), 3.45-3.36 (2H, m), 3.05-2.81 (6H, m), 2.78-2.63 (2H, m), 2.56-2.51 (2H, m), 2.40 (3H, s), 2.23 (3H, s); Chiral HPLC (Diacel Chiralpak IA, 5 µm, 4.6×250 mm, 30 min method, 1.0 mL/min, isocratic 30% EtOH in isohexane (0.2% TFA): RT=9.23 min, 97% de @ 254 nm.

Example 22: (S)-5-(5-(3,5-dimethylisoxazol-4-yl)-1-((R)-1-(methylsulfonyl)pyrrolidin-3-yl)-1H-benzo[d]imidazol-2-yl)-1-(5-fluoropyridin-3-yl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(5-fluoropyridin-3-yl)pyrrolidin-2-one

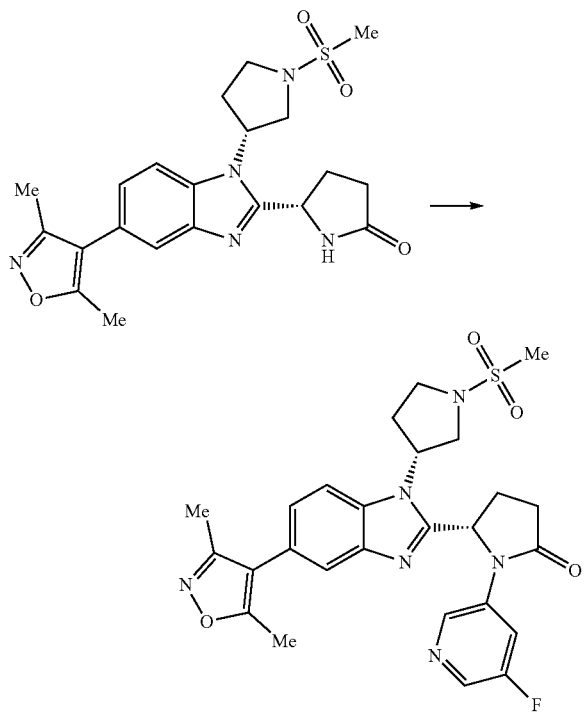

A solution of DBU (20 µl, 0.133 mmol) and Intermediate E1 (50 mg, 0.113 mmol) in acetonitrile (4 mL) was added to a vial charged with CuTMEDA (10 mg, 0.022 mmol) and (5-fluoropyridin-3-yl)boronic acid (17.47 mg, 0.124 mmol) before stirring for 18 h at 40° C. The mixture was concentrated under reduced pressure then purified by chromatography on the Companion (12 g column, 0-50% MeAc/DCM) to afford a solid. The solid was dissolved in EtOAc (~3 mL) and then Hexane (20 mL) was added. The resultant solid precipitate was collected by filtration, washing with Hexane (5 mL), and dried in vacuo to afford (S)-5-(5-(3,5-dimethylisoxazol-4-yl)-1-((R)-1-(methylsulfonyl)pyrrolidin-3-yl)-1H-benzo[d]imidazol-2-yl)-1-(5-fluoropyridin-3-yl)pyrrolidin-2-one (12 mg, 20%) as an off white solid; Rt 1.68 min (method 1), m/z 539 (M+H)+ (ES+); 1H NMR (d6-DMSO) δ: 8.51 (1H, s), 8.32 (1H, d, J=2.6 Hz), 8.14 (1H, dt, J=11.4, 2.3 Hz), 7.78 (1H, d, J=8.5 Hz), 7.64 (1H, d, J=1.6 Hz), 7.26 (1H, dd, J=8.5, 1.7 Hz), 6.24-6.17 (1H, m), 5.55-5.43 (1H, m), 3.88-3.78 (1H, m), 3.77-3.64 (2H, m), 3.39 (1H, q, J=8.7 Hz), 3.09 (3H, s), 2.76-2.65 (2H, m), 2.65-2.53 (3H, m), 2.36 (3H, s), 2.26-2.20 (1H, m), 2.19 (3H, s). Chiral HPLC (Lab 1 Bay 4, Diacel Chiralpak IA, 5 µm, 4.6×250 mm, 30 min method, 1.0 mL/min, isocratic 30% EtOH in isohexane (0.2% TFA): RT=9.22 min, >99% de @ 254 nm.

Example 23 (S)-1-(3,5-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(3,5-difluorophenyl)-5-(5-(3,5-dimethylisoxazol-4-yl)-1-((R)-1-(methylsulfonyl) pyrrolidin-3-yl)-1H-benzo[d]imidazol-2-yl)pyrrolidin-2-one

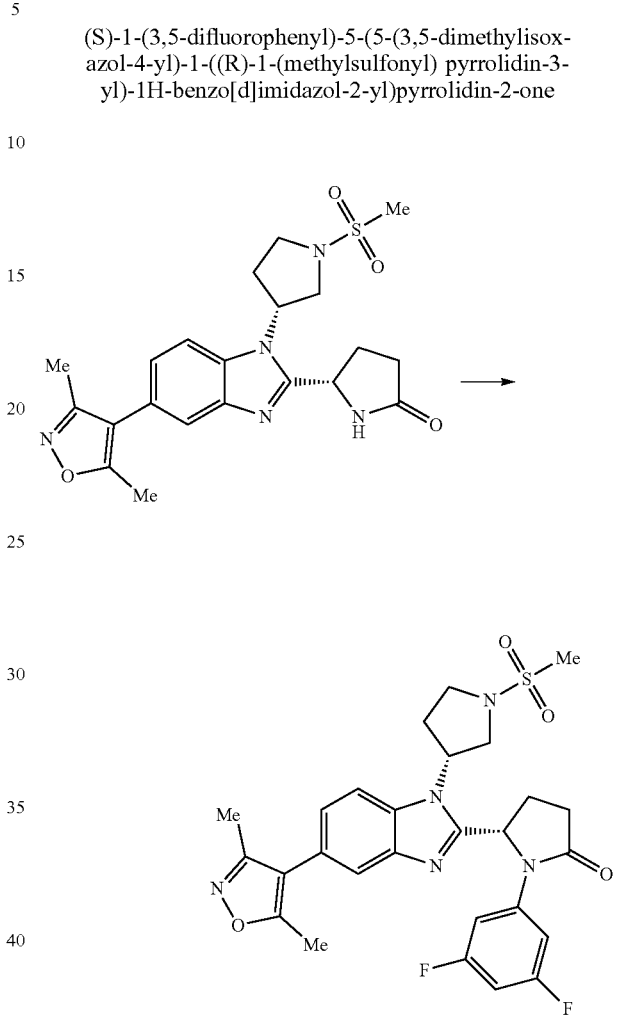

A solution of DBU (20 µl, 0.133 mmol) and Intermediate E1 (50 mg, 0.113 mmol) in acetonitrile (4 mL) was added to a vial charged with CuTMEDA (10 mg, 0.022 mmol) and (3,5-difluorophenyl)boronic acid (19.58 mg, 0.124 mmol) before stirring for 18 h at 40° C. The mixture was concentrated under reduced pressure then purified by chromatography on the Companion (12 g column, 0-50% MeAc/DCM) to afford a solid. The solid was dissolved in EtOAc (~3 mL) and then Hexane (20 mL) was added. The resultant solid precipitate was collected by filtration, washing with Hexane (5 ml), and dried in vacuo to afford (S)-1-(3,5-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (18 mg, 28%) as an off white solid; Rt 1.92 min (method 1), m/z 556 (M+H)+ (ES+); 1H NMR (d6-DMSO) δ: 7.78 (d, J=8.5 Hz, 1H), 7.66 (d, J=1.7 Hz, 1H), 7.41-7.32 (m, 2H), 7.27 (dd, J=8.4, 1.7 Hz, 1H), 7.05-6.93 (m, 1H), 6.16 (d, J=7.4 Hz, 1H), 5.60-5.45 (m, 1H), 3.83 (t, J=9.8 Hz, 1H), 3.79-3.64 (m, 2H), 3.40 (q, J=9.0 Hz, 1H), 3.10 (s, 3H), 2.78-2.53 (m, 5H), 2.38 (s, 3H), 2.21 (s, 3H), 2.16 (d, J=10.1 Hz, 1H); Chiral HPLC (Diacel Chiralpak IA, 5 µm, 4.6×250 mm, 30 min method, 1.0 mL/min, isocratic 30% EtOH in isohexane (0.2% TFA): RT=10.83 min, >99% de @254 nm.

Example 24 (S)-1-(5-chloro-6-methoxypyridin-3-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(5-chloro-6-methoxypyridin-3-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one Example 25 (S)-5-(5-(3,5-dimethylisoxazol-4-yl)-1-((R)-1-(methylsulfonyl)pyrrolidin-3-yl)-1H-benzo[d]imidazol-2-yl)-1-(3-fluoro-5-methoxyphenyl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(3-fluoro-5-methoxyphenyl)pyrrolidin-2-one

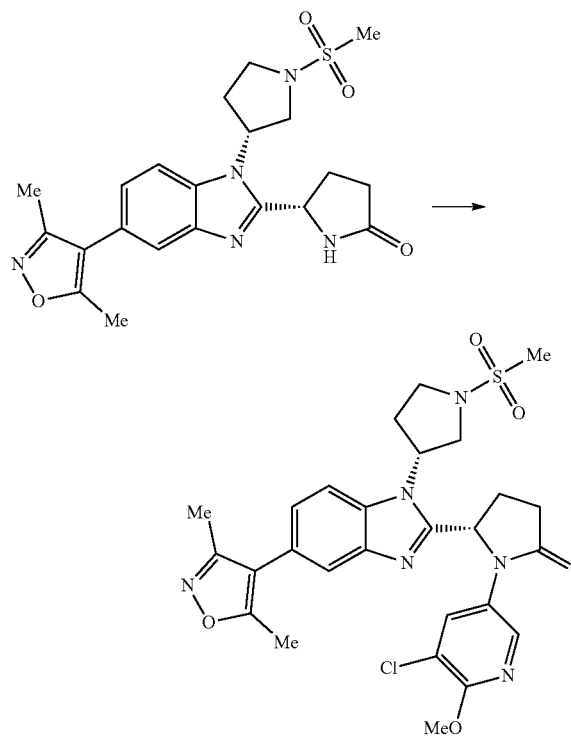

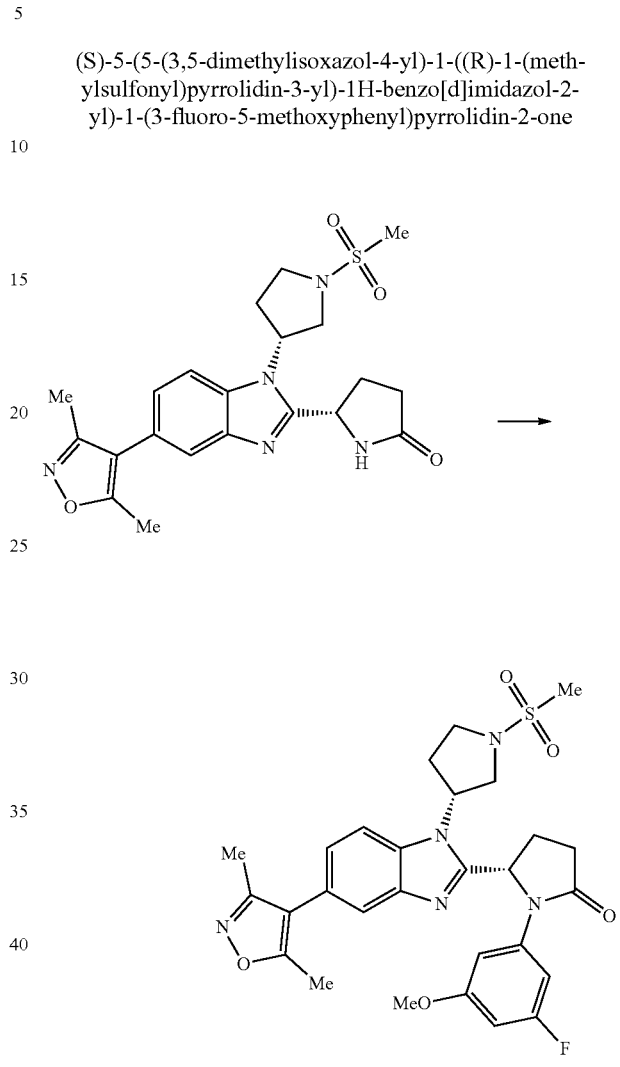

A solution of DBU (20 µl, 0.133 mmol) and Intermediate E1 (50 mg, 0.113 mmol) in acetonitrile (4 mL) was added to a vial charged with CuTMEDA (10 mg, 0.022 mmol) and (5-chloro-6-methoxypyridin-3-yl)boronic acid (23.24 mg, 0.124 mmol) before stirring for 18 h at 40° C. The mixture was concentrated under reduced pressure then purified by chromatography on the Companion (12 g column, 0-50% MeAc/CH2Cl2) to afford a solid. The solid was dissolved in EtOAc (~3 ml) and then Hexane (20 ml) was added. The resultant solid precipitate was collected by filtration, washing with Hexane (5 ml), and dried in vacuo to afford (S)-1-(5-chloro-6-methoxypyridin-3-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (15 mg, 22%) as a yellow solid; Rt 1.91 min (method 1), m/z 585 (M+H)+ (ES+); 1H NMR (d6-DMSO) δ: 8.31 (1H, d, J=2.4 Hz), 8.11 (1H, d, J=2.4 Hz), 7.76 (1H, d, J=8.4 Hz), 7.67 (1H, d, J=1.6 Hz), 7.26 (1H, dd, J=8.4, 1.7 Hz), 6.13-6.03 (1H, m), 5.53-5.39 (1H, m), 3.86 (3H, s), 3.85-3.78 (1H, m), 3.77-3.61 (2H, m), 3.44-3.36 (1H, m), 3.09 (3H, s), 2.78-2.61 (2H, m), 2.59-2.53 (1H, m), 2.48-2.42 (2H, m), 2.38 (3H, s), 2.27-2.23 (1H, m), 2.21 (3H, s); Chiral HPLC (Diacel Chiralpak IA, 5 µm, 4.6×250 mm, 30 min method, 1.0 mL/min, isocratic 30% EtOH in isohexane (0.2% TFA): RT=8.32 min, >99% de @ 254 nm.

A solution of DBU (20 µl, 0.133 mmol) and Intermediate E1 (50 mg, 0.113 mmol) in acetonitrile (4 mL) was added to a vial charged with CuTMEDA (10 mg, 0.022 mmol) and (3-fluoro-5-methoxyphenyl)boronic acid (21.07 mg, 0.124 mmol) before stirring for 18 h at 40° C. The mixture was concentrated under reduced pressure then purified by chromatography on the Companion (12 g column, 0-50% MeAc/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(3-fluoro-5-methoxyphenyl)pyrrolidin-2-one (19 mg, 29%) as an off white solid; Rt 1.91 min (method 1), m/z 568 (M+H)+ (ES+); 1H NMR (d6-DMSO) δ: 7.77 (d, J=8.5 Hz, 1H), 7.66 (d, J=1.6 Hz, 1H), 7.26 (dd, J=8.5, 1.7 Hz, 1H), 7.12 (dt, J=11.5, 2.1 Hz, 1H), 6.95-6.89 (m, 1H), 6.60 (dt, J=10.8, 2.3 Hz, 1H), 6.12 (d, J=8.3 Hz, 1H), 5.63-5.49 (m, 1H), 3.87-3.69 (m, 3H), 3.68 (s, 3H), 3.44-3.35 (m, 1H), 3.10 (s, 3H), 2.81-2.65 (m, 1H), 2.66-2.52 (m, 4H), 2.38 (s, 3H), 2.21 (s, 3H), 2.16 (d, J=9.9 Hz, 1H); Chiral HPLC (Diacel Chiralpak IA, 5 µm, 4.6×250 mm, 30 min method, 1.0 mL/min, isocratic 30% EtOH in isohexane (0.2% TFA): RT=8.56 min, >99% de @ 254 nm.

197

Example 26: (S)-5-(5-(3,5-dimethylisoxazol-4-yl)-1-((R)-1-(methylsulfonyl)pyrrolidin-3-yl)-1H-benzo[d]imidazol-2-yl)-1-(3-(trifluoromethoxy)phenyl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(3-(trifluoromethoxy)phenyl)pyrrolidin-2-one

198

Example 27: (S)-1-(2,3-dihydrobenzofuran-5-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(2,3-dihydrobenzofuran-5-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one

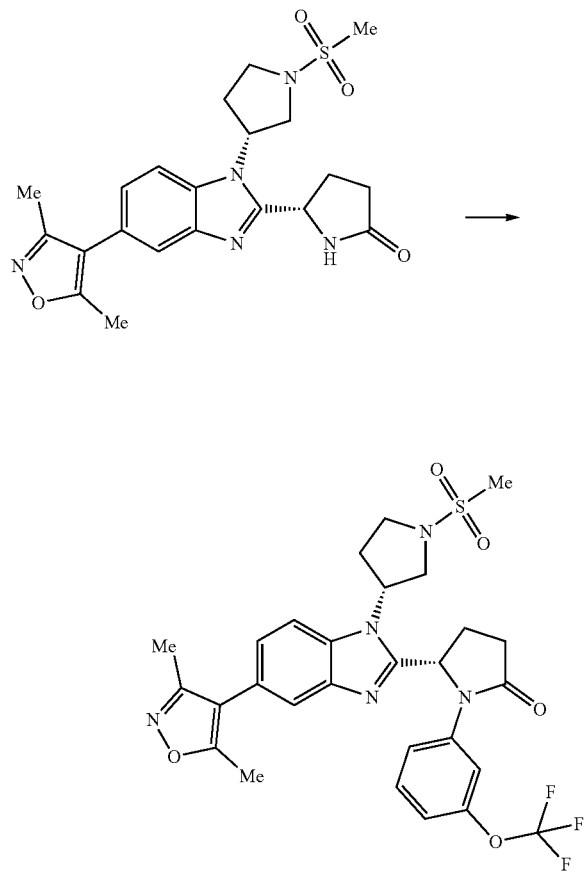

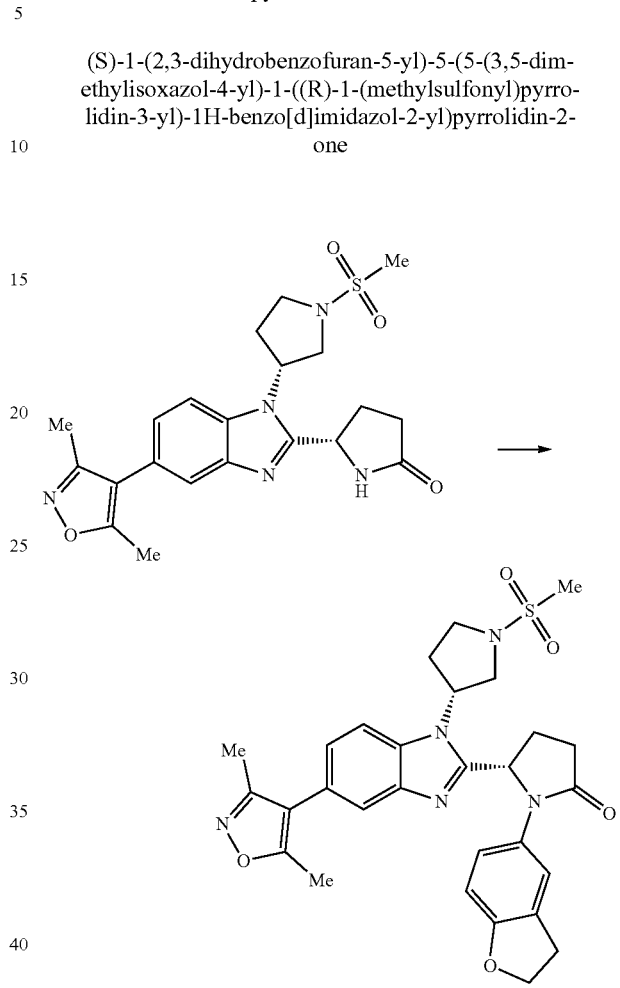

A solution of DBU (20 μl, 0.133 mmol) and Intermediate E1 (50 mg, 0.113 mmol) in acetonitrile (4 mL) was added to a vial charged with CuTMEDA (10 mg, 0.022 mmol) and 3-(trifluoromethoxy)phenyl)boronic acid (25.5 mg, 0.124 mmol) before stirring for 18 h at 40° C. The mixture was concentrated under reduced pressure then purified by chromatography on the Companion (12 g column, 0-50% MeAc/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(3-(trifluoro methoxy)phenyl)pyrrolidin-2-one (20 mg, 29%) as an off white solid; Rt 2.09 min (method 1), m/z 604 (M+H)+ (ES+); 1H NMR (d6-DMSO) δ: 7.90-7.85 (m, 1H), 7.77 (d, J=8.4 Hz, 1H), 7.65 (d, J=1.6 Hz, 1H), 7.43 (t, J=8.3 Hz, 1H), 7.32-7.22 (m, 2H), 7.13-7.06 (m, 1H), 6.13 (d, J=7.5 Hz, 1H), 5.59-5.48 (m, 1H), 3.85-3.77 (m, 1H), 3.77-3.61 (m, 2H), 3.44-3.35 (m, 2H), 3.09 (s, 3H), 2.79-2.63 (m, 2H), 2.63-2.52 (m, 2H), 2.37 (s, 3H), 2.20 (s, 3H), 2.20-2.16 (m, 1H); Chiral HPLC (Diacel Chiralpak IA, 5 μm, 4.6×250 mm, 30 min method, 1.0 mL/min, isocratic 30% EtOH in isohexane (0.2% TFA): RT=6.30 min, >99% de @254 nm.

A solution of DBU (20 μl, 0.133 mmol) and Intermediate E1 (50 mg, 0.113 mmol) in acetonitrile (4 mL) was added to a vial charged with CuTMEDA (10 mg, 0.022 mmol) and (2,3-dihydrobenzofuran-5-yl)boronic acid (20.33 mg, 0.124 mmol) before stirring for 18 h at 40° C. The mixture was concentrated under reduced pressure then purified by chromatography on the Companion (12 g column, 0-50% MeAc/DCM) to afford (S)-1-(2,3-dihydrobenzofuran-5-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (24 mg, 37%) as an off white solid; Rt 1.72 min (method 1), m/z 562 (M+H)+ (ES+); 1H NMR (d6-DMSO) δ: 7.72 (d, J=8.5 Hz, 1H), 7.68 (d, J=1.6 Hz, 1H), 7.38 (dd, J=2.3, 1.2 Hz, 1H), 7.24 (dd, J=8.5, 1.6 Hz, 1H), 7.05 (dd, J=8.5, 2.3 Hz, 1H), 6.67 (d, J=8.6 Hz, 1H), 5.93 (dd, J=8.3, 2.8 Hz, 1H), 5.52-5.40 (m, 1H), 4.47 (t, J=8.7 Hz, 2H), 3.80-3.71 (m, 1H), 3.71-3.64 (m, 1H), 3.63-3.55 (m, 1H), 3.33-3.29 (m, 1H), 3.14-3.09 (m, 2H), 3.08 (s, 3H), 2.84-2.70 (m, 1H), 2.68-2.57 (m, 1H), 2.49-2.41 (m, 2H), 2.39 (s, 3H), 2.26 (s, 1H), 2.22 (s, 3H), 2.21-2.09 (m, 1H); Chiral HPLC (Diacel Chiralpak IA, 5 μm, 4.6×250 mm, 30 min method, 1.0 mL/min, isocratic 30% EtOH in isohexane (0.2% TFA): RT=11.67 min, >99% de @ 254 nm.

Example 28: (S)-1-(3,4-dichlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(3,4-dichlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one Example 29: (S)-5-(5-(3,5-dimethylisoxazol-4-yl)-1-((R)-1-(methylsulfonyl)pyrrolidin-3-yl)-1H-benzo[d]imidazol-2-yl)-1-(6-methoxypyridin-3-yl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(6-methoxypyridin-3-yl)pyrrolidin-2-one

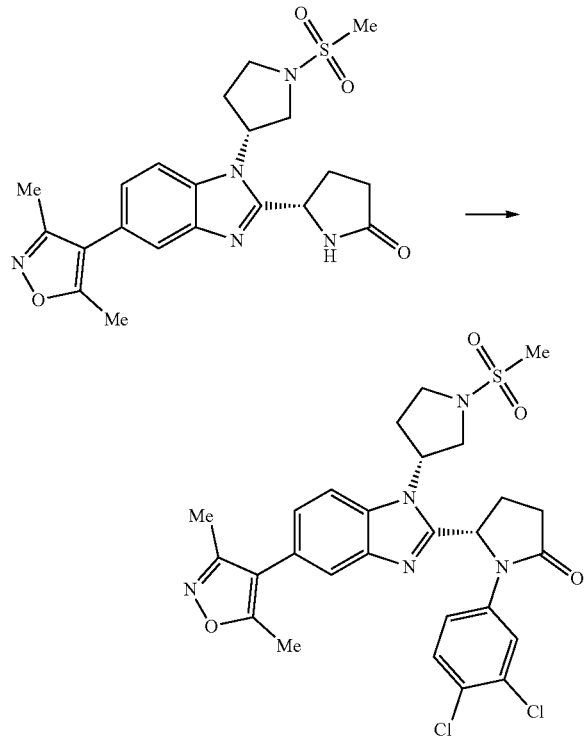

A solution of DBU (20 μl, 0.133 mmol) and Intermediate E1 (60 mg, 0.129 mmol) in acetonitrile (4 mL) was added to a vial charged with CuTMEDA (10 mg, 0.022 mmol) and (3,4-dichlorophenyl)boronic acid (25 mg, 0.131 mmol) before stirring for 18 h at 40° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford (S)-1-(3,4-dichlorophenyl)-5-(5-(3,5-dimethylisoxazol-4-yl)-1-((R)-1-(methyl sulfonyl)pyrrolidin-3-yl)-1H-benzo[d]imidazol-2-yl)pyrrolidin-2-one (48 mg, 62%) as a pale yellow glass; Rt 2.13 min (method 1), m/z 588 (M+H)+ (ES+); 1H NMR (d6-DMSO) δ: 8.03 (d, J=2.6 Hz, 1H), 7.80-7.74 (m, 1H), 7.68-7.62 (m, 1H), 7.57 (d, J=8.9 Hz, 1H), 7.43 (dd, J=8.9, 2.6 Hz, 1H), 7.26 (dd, J=8.4, 1.7 Hz, 1H), 6.19-6.12 (m, 1H), 5.61-5.47 (m, 1H), 3.87-3.64 (m, 3H), 3.45-3.35 (m, 1H), 3.10 (s, 3H), 2.78-2.53 (m, 5H), 2.37 (s, 3H), 2.21 (s, 3H), 2.19-2.12 (m, 1H); Chiral HPLC (Diacel Chiralpak IA, 5 um, 4.6×250 mm, 30 min method, 1.0 ml/min, isocratic 30% EtOH in isohexane (0.2% TFA), RT=8.80 min, >99%, >98% de @ 254 nm.

A solution of DBU (20 μL, 0.133 mmol) and Intermediate E1 (60 mg, 0.129 mmol) in acetonitrile (4 mL) was added to a vial charged with CuTMEDA (10 mg, 0.022 mmol) and (6-methoxypyridin-3-yl)boronic acid (25 mg, 0.163 mmol) before stirring for 18 h at 40° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(6-methoxypyridin-3-yl)pyrrolidin-2-one (38 mg, 52%) as a pale yellow glass; Rt 1.69 min (method 1), m/z 551 (M+H)+ (ES+); 1H NMR (d6-DMSO) δ: 8.19-8.13 (m, 1H), 7.92 (dd, J=8.9, 2.8 Hz, 1H), 7.75 (d, J=8.4 Hz, 1H), 7.67 (d, J=1.5 Hz, 1H), 7.26 (dd, J=8.5, 1.7 Hz, 1H), 6.81 (dd, J=8.9, 0.6 Hz, 1H), 6.05-5.95 (m, 1H), 5.52-5.39 (m, 1H), 3.84-3.78 (m, 1H), 3.77 (s, 3H), 3.74-3.59 (m, 2H), 3.40-3.35 (m, 1H), 3.09 (s, 3H), 2.77-2.61 (m, 2H), 2.58-2.52 (m, 1H), 2.49-2.43 (m, 1H), 2.38 (s, 3H), 2.37-2.29 (m, 1H), 2.26-2.22 (m, 1H), 2.22 (s, 3H); Chiral HPLC (Diacel Chiralpak IA, 5 μm, 4.6×250 mm, 30 min method, 1.0 mL/min, isocratic 30% EtOH in isohexane (0.2% TFA): RT=11.55 min, >99%, >98% de @ 254 nm.

Example 30: (S)-5-(5-(3,5-dimethylisoxazol-4-yl)-1-((R)-1-(methylsulfonyl)pyrrolidin-3-yl)-1H-benzo[d]imidazol-2-yl)-1-(3,4,5-trifluorophenyl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(3,4,5-trifluorophenyl)pyrrolidin-2-one

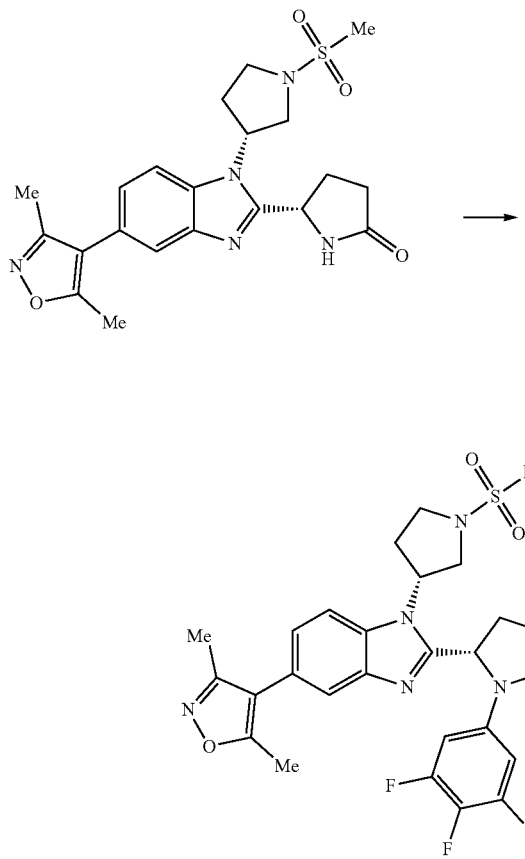

A solution of DBU (20 μl, 0.133 mmol), Intermediate E1 (60 mg, 0.129 mmol) in acetonitrile (4 mL) was added to a vial charged with CuTMEDA (10 mg, 0.022 mmol) and (3,4,5-trifluorophenyl)boronic acid (25 mg, 0.142 mmol) before stirring for 18 h at 40° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(3,4,5-trifluorophenyl)pyrrolidin-2-one (47 mg, 61%) as a pale yellow glass; Rt 2.05 min (method 1), m/z 574 (M+H)+ (ES+); 1H NMR (d6-DMSO) δ: 7.82-7.74 (m, 1H), 7.67-7.63 (m, 1H), 7.59 (dd, J=10.5, 6.4 Hz, 2H), 7.27 (dd, J=8.5, 1.7 Hz, 1H), 6.13 (d, J=7.3 Hz, 1H), 5.55-5.43 (m, 1H), 3.83 (s, 1H), 3.79-3.64 (m, 2H), 3.45-3.35 (m, 1H), 3.10 (s, 3H), 2.77-2.53 (m, 5H), 2.37 (s, 3H), 2.21 (s, 3H), 2.19-2.12 (m, 1H). Chiral HPLC (Diacel Chiralpak IA, 5 μm, 4.6×250 mm, 30 min method, 1.0 mL/min, isocratic 30% EtOH in isohexane (0.2% TFA): 148497, RT=6.32 min, 98.5%, 97% de @ 254 nm.

Example 31: (S)-5-(5-(3,5-dimethylisoxazol-4-yl)-1-((R)-1-(methylsulfonyl)pyrrolidin-3-yl)-1H-benzo[d]imidazol-2-yl)-1-(4-(trifluoromethyl)phenyl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(4-(trifluoromethyl)phenyl)pyrrolidin-2-one

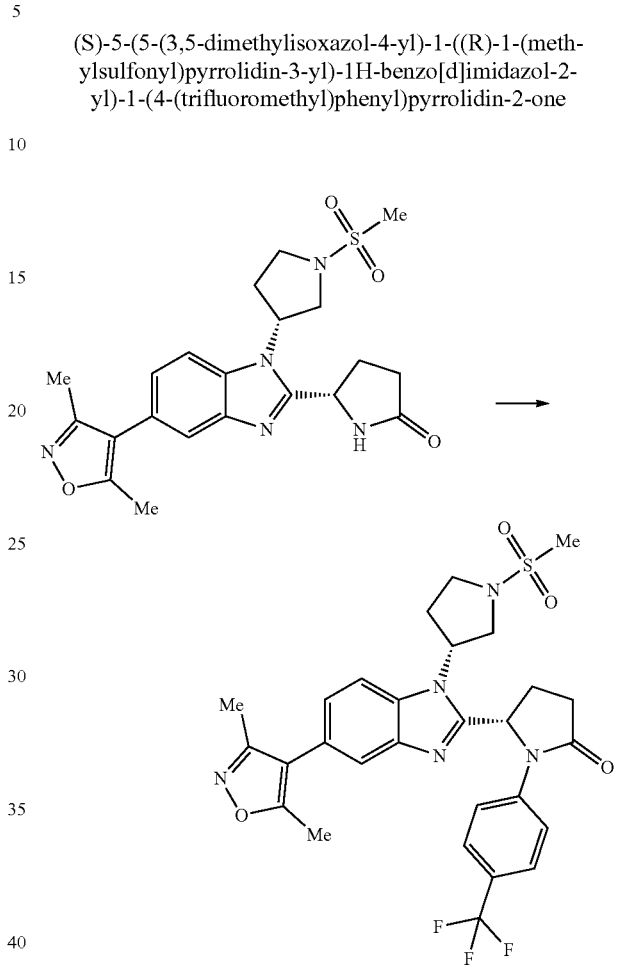

A solution of DBU (20 μL, 0.133 mmol) and Intermediate E1 (60 mg, 0.129 mmol) in acetonitrile (4 mL) was added to a vial charged with CuTMEDA (10 mg, 0.022 mmol) and (4-(trifluoromethyl)phenyl)boronic acid (28 mg, 0.147 mmol) before stirring for 18 h at 40° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(4-(trifluoromethyl)phenyl)pyrrolidin-2-one (42 mg, 54%) as a pale yellow glass; Rt 2.09 min (method 1), m/z 588 (M+H)+ (ES+); 1H NMR (d6-DMSO) δ: 7.83-7.73 (m, 3H), 7.73-7.65 (m, 2H), 7.63 (d, J=1.6 Hz, 1H), 7.26 (dd, J=8.4, 1.7 Hz, 1H), 6.21-6.12 (m, 1H), 5.63-5.48 (m, 1H), 3.88-3.78 (m, 1H), 3.78-3.64 (m, 2H), 3.46-3.36 (m, 1H), 3.10 (s, 3H), 2.79-2.54 (m, 5H), 2.37 (s, 3H), 2.25-2.14 (m, 1H), 2.20 (s, 3H); Chiral HPLC (Diacel Chiralpak IA, 5 μm, 4.6×250 mm, 30 min method, 1.0 mL/min, isocratic 30% EtOH in isohexane (0.2% TFA): RT=7.19 min, >99%, >98% de @ 254 nm.

Example 32: (S)-5-(5-(3,5-dimethylisoxazol-4-yl)-1-((R)-1-(methylsulfonyl)pyrrolidin-3-yl)-1H-benzo[d]imidazol-2-yl)-1-(4-(trifluoromethyl)phenyl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(4-(trifluoromethyl)phenyl)pyrrolidin-2-one

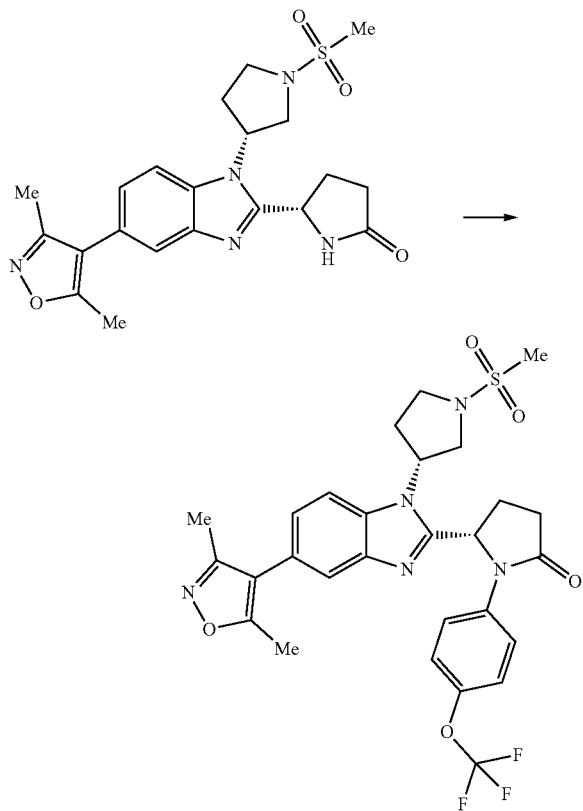

A solution of DBU (20 μL, 0.133 mmol) and Intermediate E1 (60 mg, 0.129 mmol) in acetonitrile (4 mL) was added to a vial charged with CuTMEDA (10 mg, 0.022 mmol) and (4-(trifluoromethoxy)phenyl)boronic acid (30 mg, 0.146 mmol) before stirring for 18 h at 40° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(4-(trifluoromethoxy)phenyl)pyrrolidin-2-one (40 mg, 50%) as a pale yellow glass; Rt 2.14 min (method 1), m/z 604 (M+H)+ (ES+); 1H NMR (d6-DMSO) δ: 7.77 (d, J=8.5 Hz, 1H), 7.69-7.59 (m, 3H), 7.39-7.29 (m, 2H), 7.26 (dd, J=8.4, 1.7 Hz, 1H), 6.13-6.02 (m, 1H), 5.57-5.44 (m, 1H), 3.87-3.76 (m, 1H), 3.76-3.63 (m, 2H), 3.44-3.35 (m, 1H), 3.10 (s, 3H), 2.80-2.53 (m, 4H), 2.49-2.40 (m, 1H), 2.38 (s, 3H), 2.27-2.15 (m, 1H), 2.21 (s, 3H); Chiral HPLC (Diacel Chiralpak IA, 5 μm, 4.6×250 mm, 30 min method, 1.0 mL/min, isocratic 30% EtOH in isohexane (0.2% TFA): RT=6.26 min, >99%, >98% de @ 254 nm.

Example 33: (S)-5-(5-(3,5-dimethylisoxazol-4-yl)-1-((R)-1-(methylsulfonyl)pyrrolidin-3-yl)-1H-benzo[d]imidazol-2-yl)-1-(3-ethoxy-5-fluorophenyl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(3-ethoxy-5-fluorophenyl)pyrrolidin-2-one

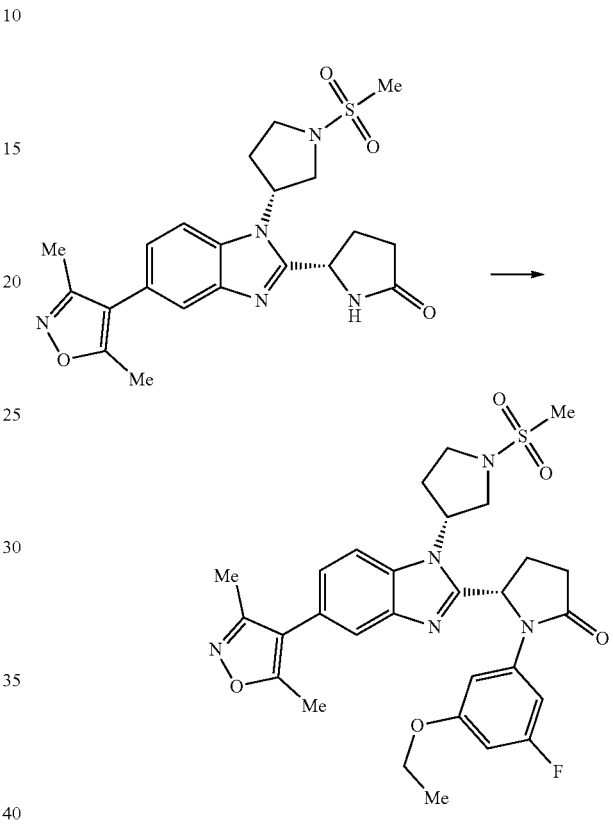

A solution of DBU (20 μL, 0.133 mmol) and Intermediate E1 (60 mg, 0.129 mmol) in acetonitrile (4 mL) was added to a vial charged with CuTMEDA (10 mg, 0.022 mmol) and (3-ethoxy-5-fluorophenyl)boronic acid (25 mg, 0.136 mmol) before stirring for 18 h at 40° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(3-ethoxy-5-fluorophenyl)pyrrolidin-2-one (39 mg, 51%) as a pale yellow glass; Rt 2.02 min (method 1), m/z 582 (M+H)+ (ES+); 1H NMR (d6-DMSO) δ: 7.77 (d, J=8.5 Hz, 1H), 7.66 (d, J=1.6 Hz, 1H), 7.26 (dd, J=8.5, 1.7 Hz, 1H), 7.08 (dt, J=11.4, 2.1 Hz, 1H), 6.94 (t, J=1.8 Hz, 1H), 6.57 (dt, J=10.9, 2.3 Hz, 1H), 6.17-6.07 (m, 1H), 5.61-5.49 (m, 1H), 3.94 (dq, J=6.9, 2.2 Hz, 2H), 3.80 (t, J=9.8 Hz, 1H), 3.77-3.70 (m, 1H), 3.67 (dd, J=10.6, 6.9 Hz, 1H), 3.43-3.35 (m, 1H), 3.10 (s, 3H), 2.81-2.45 (m, 5H), 2.38 (s, 3H), 2.21 (s, 3H), 2.19-2.13 (m, 1H), 1.25 (t, J=7.0 Hz, 3H); Chiral HPLC (Diacel Chiralpak IA, 5 μm, 4.6×250 mm, 30 min method, 1.0 mL/min, isocratic 30% EtOH in isohexane (0.2% TFA): RT=8.70 min, >99%, >98% de @ 254 nm.

Example 34: (S)-5-(5-(3,5-dimethylisoxazol-4-yl)-1-((R)-1-(methylsulfonyl)pyrrolidin-3-yl)-1H-benzo[d]imidazol-2-yl)-1-(o-tolyl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(o-tolyl)pyrrolidin-2-one Example 35: (S)-5-(5-(3,5-dimethylisoxazol-4-yl)-1-((R)-1-(methylsulfonyl)pyrrolidin-3-yl)-1H-benzo[d]imidazol-2-yl)-1-(5-fluoro-2-methylphenyl)pyrrolidin-2-one (S)-5-(5-(3,5-dimethylisoxazol-4-yl)-1-((R)-1-(methylsulfonyl)pyrrolidin-3-yl)-1H-benzo[d]imidazol-2-yl)-1-(5-fluoro-2-methylphenyl)pyrrolidin-2-one

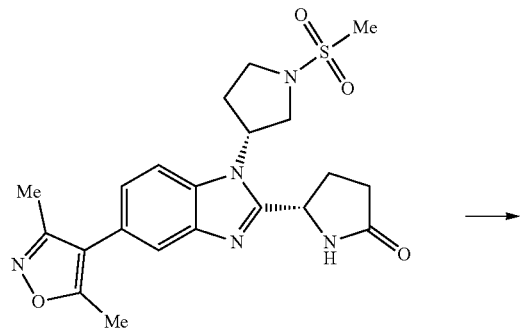

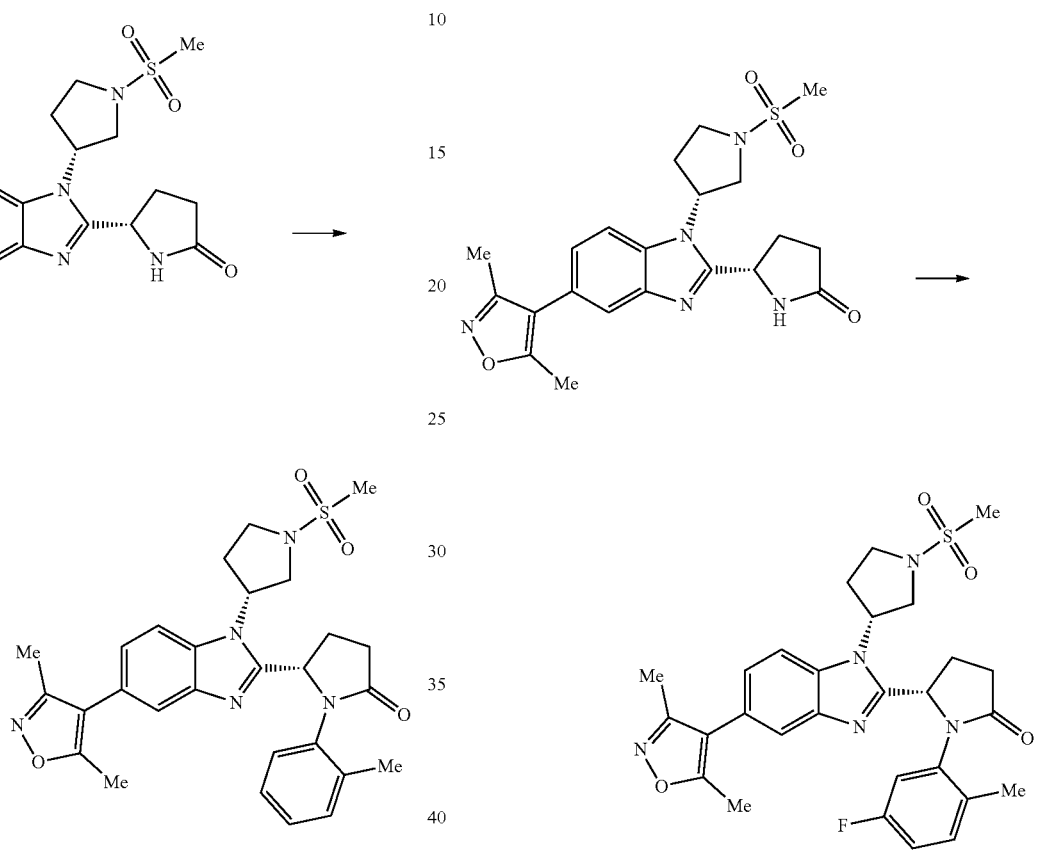

A solution of DBU (20 µl, 0.133 mmol) and Intermediate E1 (60 mg, 0.129 mmol) in acetonitrile (4 mL) was added to a vial charged with CuTMEDA (10 mg, 0.022 mmol) and o-tolylboronic acid (20 mg, 0.147 mmol) before stirring for 18 h at 40° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(o-tolyl)pyrrolidin-2-one (22 mg, 30%) as a pale yellow glass; Rt 1.78 min (method 1), m/z 534 (M+H)+ (ES+); 1H NMR (d6-DMSO) δ: 7.73 (d, J=1.6 Hz, 1H), 7.66 (d, J=8.5 Hz, 1H), 7.30-7.06 (m, 5H), 5.84-5.69 (m, 1H), 5.21-5.06 (m, 1H), 3.75-3.66 (m, 1H), 3.58-3.44 (m, 2H), 3.19-3.09 (m, 1H), 3.03 (s, 3H), 2.94-2.82 (m, 1H), 2.78-2.65 (m, 1H), 2.64-2.52 (m, 3H), 2.42 (s, 3H), 2.25 (s, 3H), 2.17-2.00 (m, 1H), 2.05 (s, 3H); Chiral HPLC (Diacel Chiralpak IA, 5 µm, 4.6×250 mm, 30 min method, 1.0 mL/min, isocratic 30% EtOH in isohexane (0.2% TFA): RT=6.68 min, >96.8%, >93.6% de @ 254 nm.

A solution of DBU (20 µL, 0.133 mmol) and Intermediate E1 (60 mg, 0.129 mmol) in acetonitrile (4 mL) was added to a vial charged with CuTMEDA (10 mg, 0.022 mmol) and (5-fluoro-2-methylphenyl)boronic acid (22 mg, 0.143 mmol) before stirring for 18 h at 40° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford (S)-5-(5-(3,5-dimethylisoxazol-4-yl)-1-((R)-1-(methylsulfonyl)pyrrolidin-3-yl)-1H-benzo[d]imidazol-2-yl)-1-(5-fluoro-2-methylphenyl)pyrrolidin-2-one (16 mg, 21%) as a pale yellow glass; Rt 1.84 min (method 1), m/z 552 (M+H)+ (ES+); 1H NMR (d6-DMSO) δ: 7.72 (d, J=1.6 Hz, 1H), 7.69 (d, J=8.4 Hz, 1H), 7.31-7.21 (m, 2H), 7.21-7.12 (m, 1H), 7.06 (td, J=8.5, 2.8 Hz, 1H), 5.84-5.75 (m, 1H), 5.34-5.21 (m, 1H), 3.73 (dd, J=10.6, 8.8 Hz, 1H), 3.60 (td, J=9.2, 2.6 Hz, 1H), 3.53 (dd, J=10.6, 6.8 Hz, 1H), 3.28-3.17 (m, 1H), 3.05 (s, 3H), 2.90-2.65 (m, 2H), 2.61-2.52 (m, 1H), 2.49-2.45 (m, 1H), 2.41 (s, 3H), 2.27-2.15 (m, 1H), 2.24 (s, 3H), 2.07 (s, 3H). Chiral HPLC (Lab 1 Bay 4, Diacel Chiralpak IA, 5 µm, 4.6×250 mm, 30 min method, 1.0 mL/min, isocratic 30% EtOH in isohexane (0.2% TFA): RT=6.53 min, >99%, >98% de @ 254 nm.

Example 36: 3-((S)-2-(5-(3,5-dimethylisoxazol-4-yl)-1-((R)-1-(methylsulfonyl)pyrrolidin-3-yl)-1H-benzo[d]imidazol-2-yl)-5-oxopyrrolidin-1-yl)-5-fluorobenzonitrile 3-((S)-2-(5-(3,5-dimethylisoxazol-4-yl)-1-((R)-1-(methylsulfonyl)pyrrolidin-3-yl)-1H-benzo[d]imidazol-2-yl)-5-oxopyrrolidin-1-yl)-5-fluorobenzonitrile

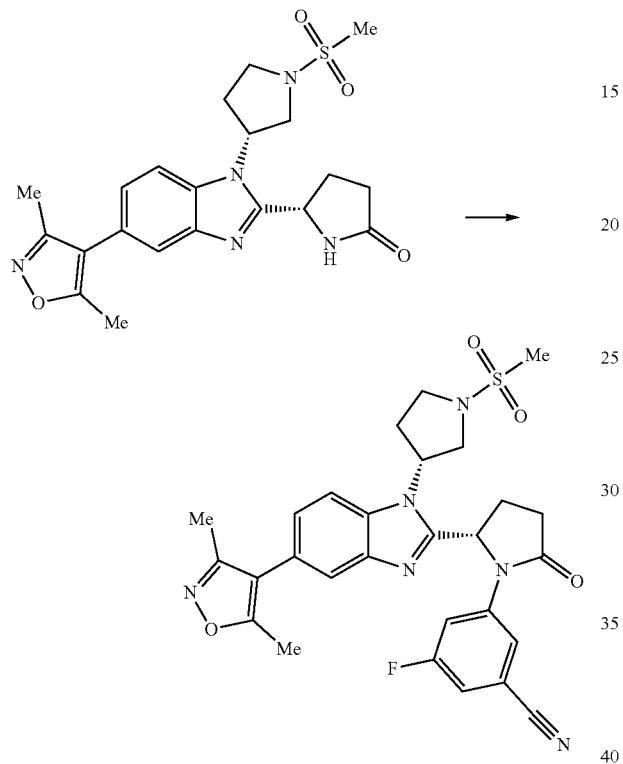

A solution of DBU (20 µL, 0.133 mmol) and Intermediate E1 (60 mg, 0.129 mmol) in acetonitrile (4 mL) was added to a vial charged with CuTMEDA (10 mg, 0.022 mmol) and (3-cyano-5-fluorophenyl)boronic acid (25 mg, 0.152 mmol) before stirring for 18 h at 40° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford 3-((S)-2-(5-(3,5-dimethylisoxazol-4-yl)-1-((R)-1-(methylsulfonyl) pyrrolidin-3-yl)-1H-benzo[d]imidazol-2-yl)-5-oxopyrrolidin-1-yl)-5-fluorobenzonitrile (35 mg, 47%) as a pale yellow glass; Rt 1.92 min (method 1), m/z 563 (M+H)+ (ES+); 1H NMR (d6-DMSO) δ: 7.94-7.86 (m, 2H), 7.78 (d, J=8.5 Hz, 1H), 7.64 (d, J=1.6 Hz, 1H), 7.60 (ddd, 1H), 7.27 (dd, J=8.5, 1.7 Hz, 1H), 6.22 (d, J=7.1 Hz, 1H), 5.56-5.43 (m, 1H), 3.89-3.80 (m, 1H), 3.80-3.73 (m, 1H), 3.69 (dd, J=10.6, 6.8 Hz, 1H), 3.46-3.36 (m, 1H), 3.10 (s, 3H), 2.78-2.53 (m, 5H), 2.37 (s, 3H), 2.28-2.12 (m, 1H), 2.20 (s, 3H). Chiral HPLC (Diacel Chiralpak IA, 5 µm, 4.6×250 mm, 30 min method, 1.0 mL/min, isocratic 30% EtOH in isohexane (0.2% TFA): RT=8.95 min, >99%, >98% de @ 254 nm.

Example 37: (S)-1-(cyclohex-1-en-1-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one 3-((S)-2-(5-(3,5-dimethylisoxazol-4-yl)-1-((R)-1-(methylsulfonyl)pyrrolidin-3-yl)-1H-benzo[d]imidazol-2-yl)-5-oxopyrrolidin-1-yl)-5-fluorobenzonitrile

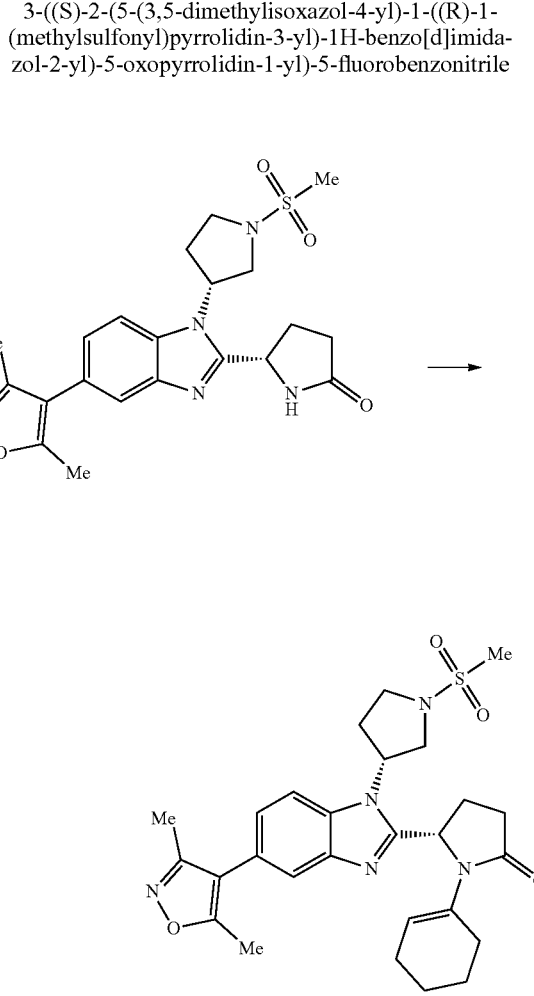

A solution of DBU (50 µl, 0.332 mmol) and Intermediate E1 (150 mg, 0.321 mmol) in acetonitrile (4 mL) was added to a vial charged with CuTMEDA (10 mg, 0.022 mmol) and cyclohex-1-en-1-ylboronic acid (50 mg, 0.397 mmol) before stirring for 18 h at 70° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford (S)-1-(cyclohex-1-en-1-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (58 mg, 0.105 mmol, 32.7% yield) as a pale yellow glass; Rt 1.78 min (method 1), m/z 524 (M+H)+ (ES+); 1H NMR (d6-DMSO) δ: 7.78 (d, J=8.5 Hz, 1H), 7.71 (d, J=1.6 Hz, 1H), 7.27 (dd, J=8.4, 1.6 Hz, 1H), 5.58 (dd, J=8.2, 2.6 Hz, 1H), 5.55-5.44 (m, 1H), 5.43-5.36 (m, 1H), 3.82-3.62 (m, 3H), 3.44-3.34 (m, 2H), 2.70-2.52 (m, 2H), 2.50-2.42 (m, 3H), 2.41 (s, 3H), 2.40-2.03 (m, 5H), 2.25 (s, 3H), 1.98-1.89 (m, 2H), 1.56-1.35 (m, 4H). Contains 1.9% w/w isohexane; Chiral HPLC (Diacel Chiralpak IA, 5 µm, 4.6×250 mm, 30 min method, 1.0 mL/min, isocratic 30% EtOH in isohexane (0.2% TFA): RT=7.95 min, 97.5%, 95% de @ 254 nm.

Example 38: (S)-1-(4,5-difluoro-2-methylphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one 3-((S)-2-(5-(3,5-dimethylisoxazol-4-yl)-1-((R)-1-(methylsulfonyl)pyrrolidin-3-yl)-1H-benzo[d]imidazol-2-yl)-5-oxopyrrolidin-1-yl)-5-fluorobenzonitrile

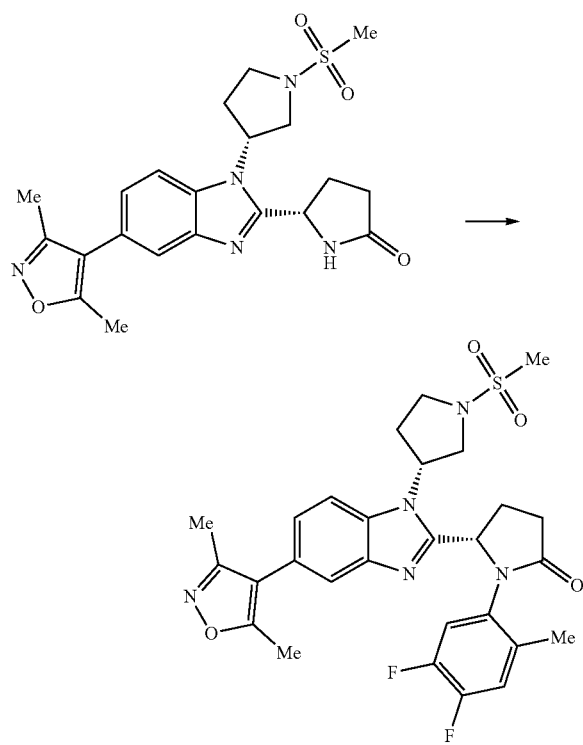

A solution of DBU (20 µL, 0.133 mmol) and Intermediate E1 (60 mg, 0.129 mmol) in acetonitrile (4 mL) was added to a vial charged with CuTMEDA (10 mg, 0.022 mmol) and (4,5-difluoro-2-methylphenyl)boronic acid (25 mg, 0.145 mmol) before stirring for 18 h at 70° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford a pale brown gum. The gum was purified by chromatography on the Companion (RP Flash C18) (12 g column, 15-75% MeCN/Water 0.1% Formic Acid) to afford (S)-1-(4,5-difluoro-2-methylphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (22 mg, 28%) as a pale yellow glass; Rt 1.99 min (method 1), m/z 570 (M+H)+ (ES+); 1H NMR (d6-DMSO) δ: 7.75-7.67 (m, 2H), 7.47 (dd, J=11.5, 7.9 Hz, 1H), 7.34 (dd, J=11.7, 8.9 Hz, 1H), 7.26 (dd, J=8.4, 1.7 Hz, 1H), 5.77 (dd, J=7.9, 3.5 Hz, 1H), 5.37-5.26 (m, 1H), 3.79-3.69 (m, 1H), 3.68-3.59 (m, 1H), 3.55 (dd, J=10.6, 6.7 Hz, 1H), 3.33-3.21 (m, 2H), 3.06 (s, 3H), 2.86-2.64 (m, 2H), 2.59-2.53 (m, 1H), 2.46-2.42 (m, 1H), 2.41 (s, 3H), 2.35-2.24 (m, 1H), 2.24 (s, 3H), 2.11 (s, 3H).

The product was analysed by Chiral HPLC (Lab 1 Bay 4, Diacel Chiralpak IA, 5 um, 4.6×250 mm, 30 min method, 1.0 ml/min, isocratic 30% EtOH in isohexane (0.2% TFA): 1561183, RT=6.17 min, >99%, >98% de @ 254 nm.

Example 39: (S)-1-(3,4-dichloro-2-methylphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (S)-1-(3,4-dichloro-2-methylphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one

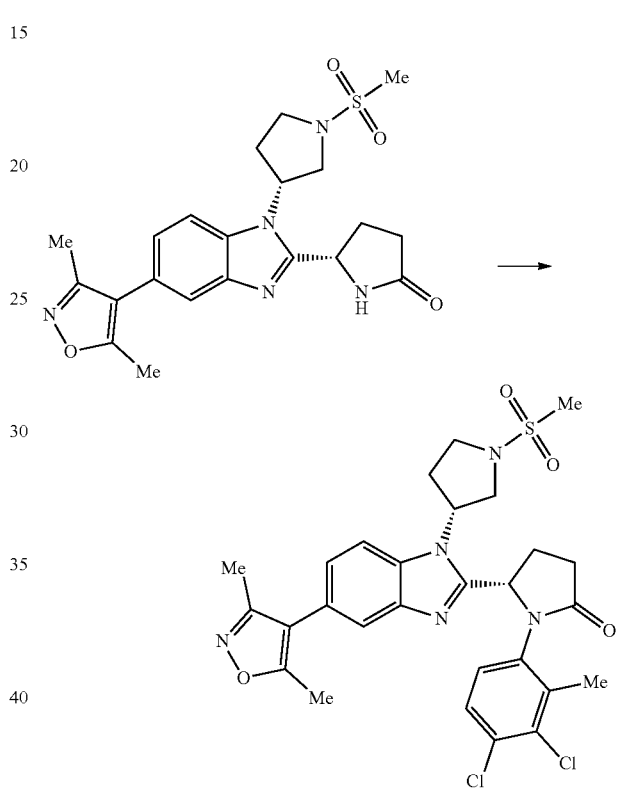

A solution of DBU (21 µL, 0.139 mmol) and Intermediate E1 (60 mg, 0.129 mmol) in acetonitrile (4 mL) was added to a vial charged with CuTMEDA (10 mg, 0.022 mmol) and (3,4-dichloro-2-methylphenyl)boronic acid (30 mg, 0.146 mmol) before stirring for 18 h at 70° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford a pale brown gum. The gum was purified by chromatography on the Companion (RP Flash C18) (12 g column, 15-75% MeCN/Water 0.1% Formic Acid) to afford (S)-1-(3,4-dichloro-2-methylphenyl)-5-(5-(3,5-dimethylisoxazol-4-yl)-1-((R)-1-(methylsulfonyl) pyrrolidin-3-yl)-1H-benzo[d]imidazol-2-yl)pyrrolidin-2-one (14 mg, 17%) as a pale yellow glass; Rt 2.10 min (method 1), m/z 602 (M+H)+ (ES+); 1H NMR (d6-DMSO) δ: 7.77-7.60 (m, 2H), 7.58-7.45 (m, 1H), 7.47-7.01 (m, 2H), 6.06-5.54 (m, 1H), 5.40-5.20 (m, 1H), 3.81-3.68 (m, 1H), 3.67-3.58 (m, 1H), 3.58-3.47 (m, 1H), 3.32-3.20 (m, 2H), 3.06 (s, 3H), 2.89-2.69 (m, 2H), 2.65-2.54 (m, 1H), 2.47-2.37 (m, 1H), 2.41 (s, 3H), 2.35-2.12 (m, 4H), 2.24 (s, 3H).

211

Example 40: (R)-5-(5-(3,5-dimethylisoxazol-4-yl)-1-((R)-1-(methylsulfonyl)pyrrolidin-3-yl)-1H-benzo[d]imidazol-2-yl)-1-(3-fluorophenyl)pyrrolidin-2-one (R)-5-(5-(3,5-dimethylisoxazol-4-yl)-1-((R)-1-(methylsulfonyl)pyrrolidin-3-yl)-1H-benzo[d]imidazol-2-yl)-1-(3-fluorophenyl)pyrrolidin-2-one

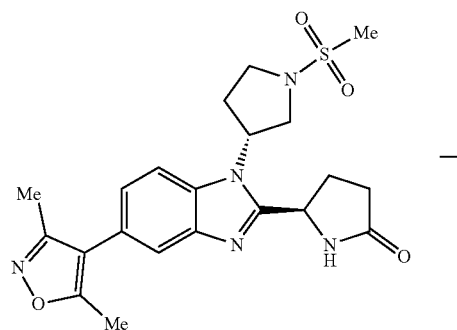

212

Example 41: (R)-1-(3,4-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (R)-1-(3,4-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one

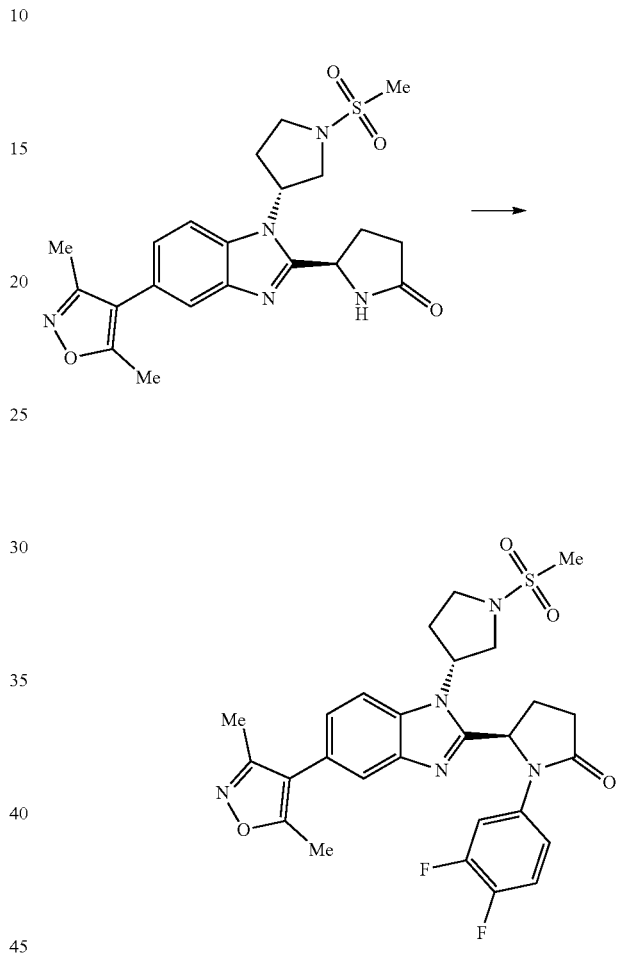

A solution of DBU (25 μl, 0.166 mmol) and Intermediate E23 (70 mg, 0.158 mmol) in acetonitrile (4 mL) was added to a vial charged with CuTMEDA (10 mg, 0.022 mmol) and (3-fluorophenyl)boronic acid (25 mg, 0.179 mmol) before stirring for 18 h at 40° C. The mixture was concentrated under reduced pressure then purified by chromatography on the Companion (12 g column, 0-50% MeAc/DCM) to afford (R)-5-(5-(3,5-dimethylisoxazol-4-yl)-1-((R)-1-(methylsulfonyl)pyrrolidin-3-yl)-1H-benzo[d]imidazol-2-yl)-1-(3-fluorophenyl) pyrrolidin-2-one (41 mg, 48%) as an off white solid; Rt 1.85 min (method 1), m/z 538 (M+H)+ (ES+); 1H NMR (d6-DMSO) δ: 7.76 (1H, d, J=8.5 Hz), 7.69-7.57 (2H, m), 7.39-7.18 (3H, m), 6.92 (1H, tdd, J=8.4, 2.6, 0.9 Hz), 6.10 (1H, d, J=6.9 Hz), 5.59-5.42 (1H, m), 3.85 (1H, dd, J=10.5, 8.9 Hz), 3.78-3.62 (2H, m), 3.49-3.37 (1H, m), 3.11 (3H, s), 2.79-2.60 (2H, m), 2.60-2.52 (2H, m), 2.49-2.43 (1H, m), 2.37 (3H, s), 2.20 (3H, s), 2.17-2.08 (1H, m); Chiral HPLC (Diacel Chiralpak IA, 5 μm, 4.6×250 mm, 30 min method, 1.0 mL/min, isocratic 30% EtOH in isohexane (0.2% TFA): RT=10.83 min, >99% de @ 254 nm.

A solution of DBU (25 μl, 0.166 mmol) and Intermediate E23 (70 mg, 0.158 mmol) in acetonitrile (4 mL) was added to a vial charged with CuTMEDA (10 mg, 0.022 mmol) and boronic acid (3,4-difluorophenyl)boronic acid (27.4 mg, 0.174 mmol) before stirring for 18 h at 40° C. The mixture was concentrated under reduced pressure then purified by chromatography on the Companion (12 g column, 0-50% MeAc/DCM) to afford (R)-1-(3,4-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (31 mg, 35%) as an off white solid; Rt 1.91 min (method 1), m/z 556 (M+H)+ (ES+); 1H NMR (d6-DMSO) δ: 7.85 (1H, ddd, J=13.3, 7.4, 2.7 Hz), 7.76 (1H, d, J=8.4 Hz), 7.64 (1H, d, J=1.6 Hz), 7.41-7.31 (1H, m), 7.28-7.19 (2H, m), 6.11-6.04 (1H, m), 5.54-5.40 (1H, m), 3.83 (1H, dd, J=10.5, 8.8 Hz), 3.77-3.64 (2H, m), 3.48-3.36 (1H, m), 3.10 (3H, s), 2.75-2.60 (2H, m), 2.60-2.51 (3H, m), 2.37 (3H, s), 2.20 (3H, s), 2.14-2.09 (1H, m); Chiral HPLC (Diacel Chiralpak IA, 5 μm, 4.6×250 mm, 30 min method, 1.0 mL/min, isocratic 30% EtOH in isohexane (0.2% TFA): RT=9.57 min, >99% de @254 nm.

213

Example 42: (R)-1-(4-chloro-3-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (R)-1-(4-chloro-3-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one

214

Example 43: (R)-1-(3,5-dichlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (R)-1-(3,5-dichlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one

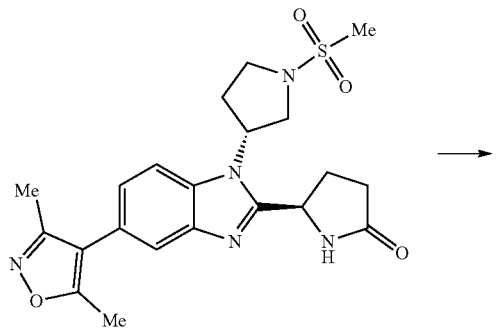

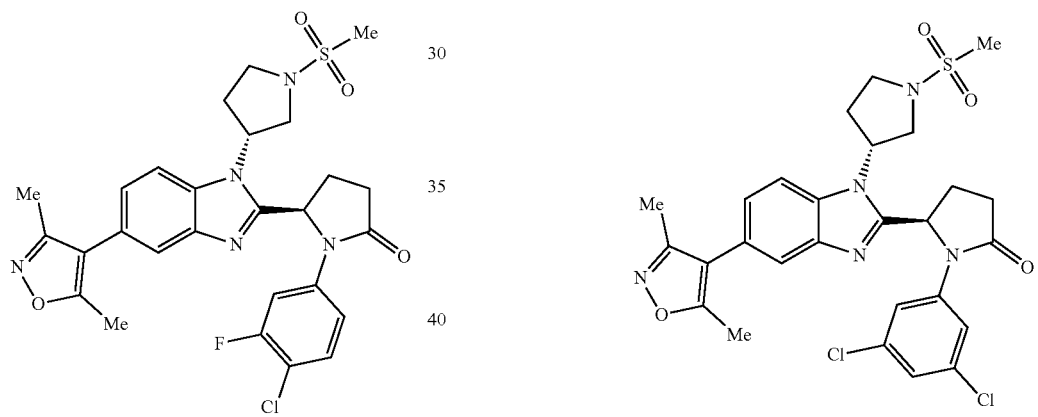

A solution of DBU (25 µl, 0.166 mmol) and Intermediate E23 (70 mg, 0.158 mmol) in acetonitrile (4 mL) was added to a vial charged with CuTMEDA (10 mg, 0.022 mmol) and (4-chloro-3-fluorophenyl)boronic acid (30.3 mg, 0.174 mmol) before stirring for 18 h at 40° C. The mixture was concentrated under reduced pressure then purified by chromatography on the Companion (12 g column, 0-50% MeAc/DCM) to afford (R)-1-(4-chloro-3-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (30 mg, 33%) as an off white solid; Rt 2.03 min (method 1), m/z 572 (M+H)+ (ES+); 1H NMR (d6-DMSO) δ: 7.86 (1H, dd, J=12.2, 2.5 Hz), 7.77 (1H, d, J=8.5 Hz), 7.63 (1H, d, J=1.5 Hz), 7.50 (1H, t, J=8.8 Hz), 7.30 (1H, ddd, J=9.0, 2.6, 1.0 Hz), 7.26 (1H, dd, J=8.5, 1.7 Hz), 6.11 (1H, d, J=6.7 Hz), 5.55-5.41 (1H, m), 3.89 (1H, dd, J=10.5, 8.8 Hz), 3.73 (2H, dd, J=10.4, 7.1 Hz), 3.49-3.35 (1H, m), 3.11 (3H, s), 2.76-2.61 (2H, m), 2.61-2.51 (3H, m), 2.36 (3H, s), 2.20 (3H, s), 2.14-2.08 (1H, m); Chiral HPLC (Diacel Chiralpak IA, 5 µm, 4.6×250 mm, 30 min method, 1.0 mL/min, isocratic 30% EtOH in isohexane (0.2% TFA): RT=11.66 min, >99% de @ 254 nm.

C: (3-chloro-5-fluorophenyl)boronic acid (30.3 mg, 0.174 mmol)

A solution of DBU (25 µl, 0.166 mmol) and Intermediate E23 (70 mg, 0.158 mmol) in acetonitrile (4 mL) was added to a vial charged with CuTMEDA (10 mg, 0.022 mmol) and (3,5-dichlorophenyl)boronic acid (33.1 mg, 0.174 mmol) before stirring for 18 h at 40° C. The mixture was concentrated under reduced pressure then purified by chromatography on the Companion (12 g column, 0-40% MeAc/DCM) to afford (R)-1-(3,5-dichlorophenyl)-5-(5-(3,5-dimethylisoxazol-4-yl)-1-((R)-1-(methylsulfonyl)pyrrolidin-3-yl)-1H-benzo[d]imidazol-2-yl) pyrrolidin-2-one (40 mg, 43%) as an off white solid; Rt 2.15 min (method 1), m/z 588 (M+H)+ (ES+); 1H NMR (d6-DMSO) δ: 7.77 (1H, d, J=8.5 Hz), 7.70 (2H, d, J=1.8 Hz), 7.65 (1H, d, J=1.7 Hz), 7.34 (1H, t, J=1.8 Hz), 7.26 (1H, dd, J=8.4, 1.7 Hz), 6.21 (1H, d, J=7.0 Hz), 5.55-5.43 (1H, m), 3.92-3.84 (1H, m), 3.78-3.66 (2H, m), 3.49-3.39 (1H, m), 3.12 (3H, s), 2.75-2.62 (2H, m), 2.61-2.52 (3H, m), 2.37 (3H, s), 2.20 (3H, s), 2.11 (1H, s); Chiral HPLC (Diacel Chiralpak IA, 5 µm, 4.6×250 mm, 30 min method, 1.0 mL/min, isocratic 30% EtOH in isohexane (0.2% TFA): RT=9.00 min, >99% de @ 254 nm.

Example 44: (R)-1-(3-chloro-4-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (R)-1-(3-chloro-4-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one

Example 45: (R)-1-(3-chloro-5-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (R)-1-(3-chloro-5-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one

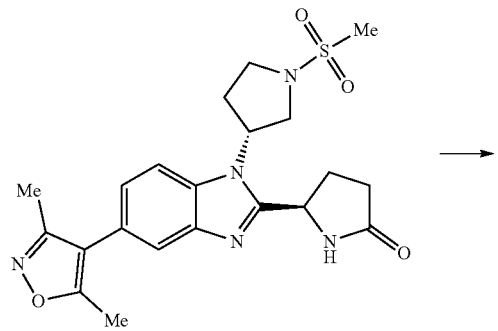

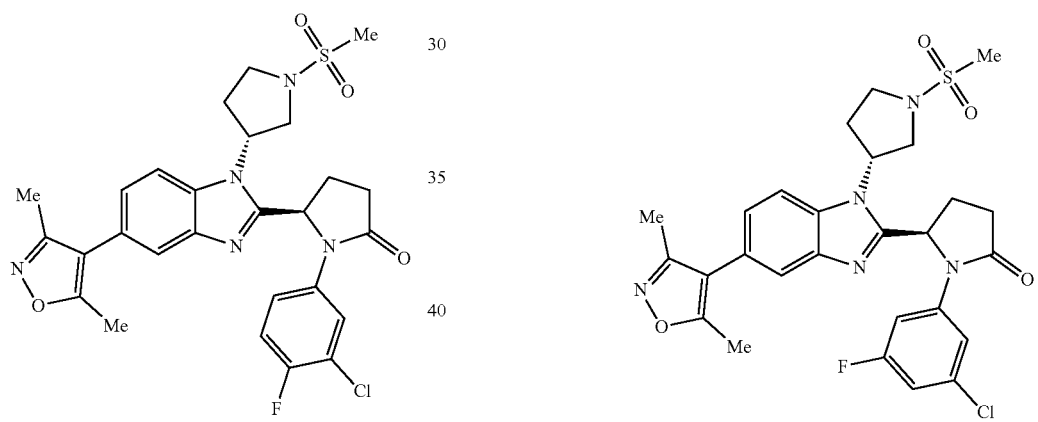

A solution of DBU (25 µl, 0.166 mmol) and Intermediate E23 (70 mg, 0.158 mmol) in acetonitrile (4 mL) was added to a vial charged with CuTMEDA (10 mg, 0.022 mmol) and (3-chloro-4-fluorophenyl)boronic acid (30.3 mg, 0.174 mmol) before stirring for 18 h at 40° C. The mixture was concentrated under reduced pressure then purified by chromatography on the Companion (12 g column, 0-40% MeAc/DCM) to afford (R)-1-(3-chloro-4-fluorophenyl)-5-(5-(3,5-dimethylisoxazol-4-yl)-1-((R)-1-(methylsulfonyl)pyrrolidin-3-yl)-1H-benzo[i]imidazol-2-yl)pyrrolidin-2-one (27 mg, 30%) as an off white solid; Rt 1.97 min (method 1), m/z 572 (M+H)+ (ES+); 1H NMR (d6-DMSO) δ: 8.02-7.96 (1H, m), 7.76 (1H, d, J=8.4 Hz), 7.65 (1H, d, J=1.6 Hz), 7.42-7.31 (2H, m), 7.25 (1H, dd, J=8.5, 1.7 Hz), 6.13-6.07 (1H, m), 5.53-5.42 (1H, m), 3.82 (1H, dd, J=10.5, 8.8 Hz), 3.77-3.64 (2H, m), 3.48-3.36 (1H, m), 3.10 (3H, s), 2.77-2.60 (2H, m), 2.61-2.51 (3H, m), 2.37 (3H, s), 2.20 (3H, s), 2.15-2.10 (1H, m); Chiral HPLC (Diacel Chiralpak IA, 5 µm, 4.6×250 mm, 30 min method, 1.0 mL/min, isocratic 30% EtOH in isohexane (0.2% TFA): RT=10.55 min, >99% de @ 254 nm.

A solution of DBU (25 µl, 0.166 mmol) and Intermediate E23 (70 mg, 0.158 mmol) in acetonitrile (4 mL) was added to a vial charged with CuTMEDA (10 mg, 0.022 mmol) and (3,5-dichlorophenyl)boronic acid (33.1 mg, 0.174 mmol) before stirring for 18 h at 40° C. The mixture was concentrated under reduced pressure then purified by chromatography on the Companion (12 g column, 0-40% MeAc/DCM) to afford (R)-1-(3-chloro-5-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one (31 mg, 34%) as an off white solid; Rt 2.05 min (method 1), m/z 572 (M+H)+ (ES+); 1H NMR (d6-DMSO) δ: 7.78 (1H, d, J=8.4 Hz), 7.68-7.59 (2H, m), 7.46 (1H, dt, J=11.4, 2.1 Hz), 7.26 (1H, dd, J=8.5, 1.7 Hz), 7.16 (1H, dt, J=8.5, 2.1 Hz), 6.16 (1H, d, J=6.9 Hz), 5.54-5.41 (1H, m) 3.90 (1H, dd, J=10.4, 8.8 Hz), 3.78-3.67 (2H, m), 3.50-3.38 (1H, m), 3.12 (3H, s), 2.78-2.61 (2H, m), 2.61-2.51 (3H, m), 2.37 (3H, s), 2.20 (3H, s), 2.15-2.09 (1H, m); Chiral PLC (Diacel Chiralpak IA, 5 µm, 4.6×250 mm, 30 min method, 1.0 mL/min, isocratic 30% EtOH in isohexane (0.2% TFA): RT=8.76 min, >99% de @ 254 nm.

Example 46: (S)-1-(3,4-difluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (S)—N-(5-(3,5-dimethylisoxazol-4-yl)-2-((1,1-dioxidotetrahydro-2H-thiopyran-4-yl)amino)phenyl)-5-oxo-1-phenylpyrrolidine-2-carboxamide (Intermediate D3)

(S)-5-(5-(3,5-dimethylisoxazol-4-yl)-1-(1,1-dioxidotetrahydro-2H-thiopyran-4-yl)-1H-benzo[d]imidazol-2-yl)-1-phenylpyrrolidin-2-one (Intermediate E3)

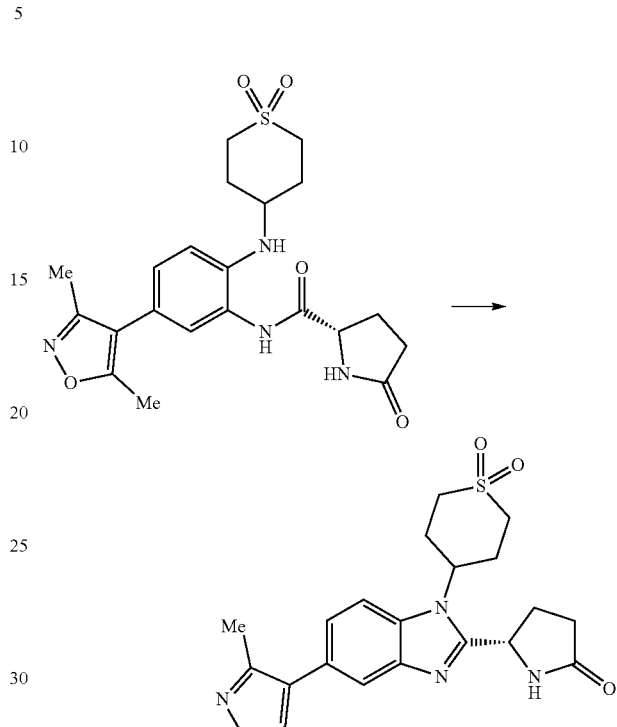

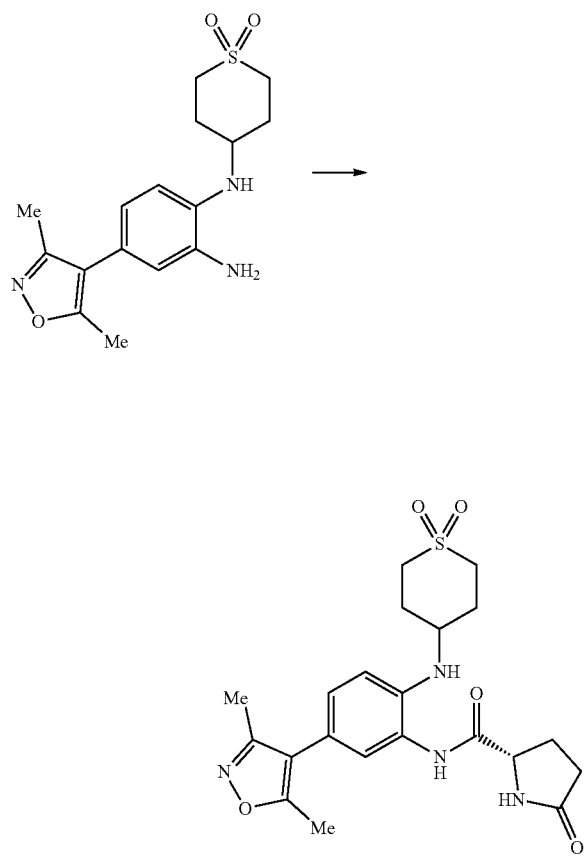

Intermediate D3 (438 mg, 0.961 mmol) was heated to 80° C. in acetic acid (10 mL) for 4 h. The volatiles were removed under reduced pressure then the residue was diluted with saturated sodium hydrogen carbonate solution (25 mL) and extracted with dichloromethane (3×20 mL). The combined organic phases were dried (Na2SO4) then filtered and concentrated under reduced pressure. The crude product was purified by chromatography on the Companion (24 g column, 50-100% MeAc/CH2Cl2) to afford (S)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one Intermediate E3 (139 mg, 33%) as a colourless glass; Rt 1.32 min (method 1), m/z 429 (M+H)+ (ES+).

(S)-1-(3,4-difluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one

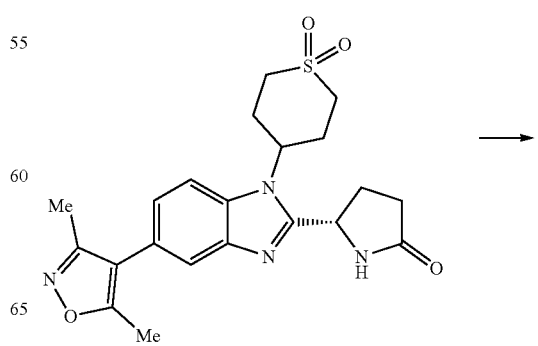

HATU (550 mg, 1.446 mmol) was added to a solution of Intermediate C3 (194 mg, 0.526 mmol), (S)-5-oxopyrrolidine-2-carboxylic acid (200 mg, 1.549 mmol) and N,N-diisopropylethylamine (0.27 mL, 1.546 mmol) in N,N-dimethylformamide (5 mL) then stirred at room temperature for 18 h. The mixture was diluted with 30% brine (100 mL) then extracted with ethyl acetate (3×75 mL). The combined organic phases were dried (MgSO4), filtered and concentrated under reduced pressure to yield a red-brown oil. The oil was dissolved in acetone (25 mL) then diluted with diethyl ether (75 mL). The resulting precipitate was collected by filtration to yield (S)—N-(5-(3,5-dimethylisoxazol-4-yl)-2-((1,1-dioxidotetrahydro-2H-thiopyran-4-yl)amino)phenyl)-5-oxopyrrolidine-2-carboxamide Intermediate D3 (438 mg, 68%) as a pale brown solid; Rt 1.36 min (method 1), m/z 447 (M+H)+ (ES+).

-continued

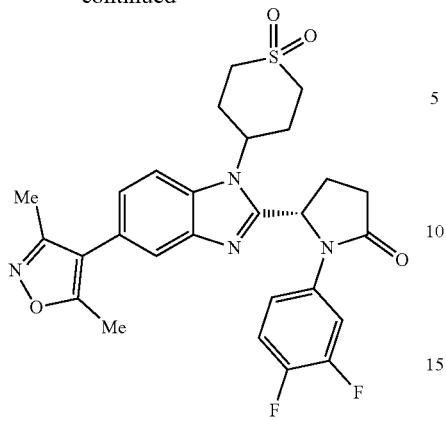

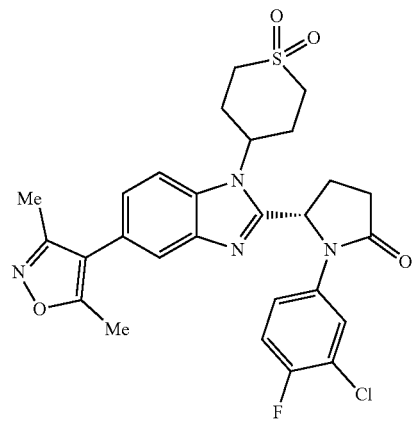

A solution of DBU (22 μL, 0.146 mmol) and Intermediate E3 (60 mg, 0.139 mmol) in acetonitrile (4 mL) was added to a vial charged with CuTMEDA (10 mg, 0.022 mmol) and (3,4-difluorophenyl)boronic acid (25 mg, 0.158 mmol) before stirring for 18 h at 40° C. The mixture was concentrated under reduced pressure then purified by chromatography on the Companion (4 g column, 0-50% MeAc/DCM) to afford (S)-1-(3,4-difluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (31 mg, 39%) as an off white solid; Rt 1.88 min (method 1), m/z 541 (M+H)+ (ES+); 1H NMR (d6-DMSO) δ: 7.85 (ddd, J=13.3, 7.4, 2.7 Hz, 1H), 7.69-7.59 (m, 2H), 7.37 (dt, J=10.7, 9.2 Hz, 1H), 7.29 (dd, J=8.5, 1.7 Hz, 1H), 7.19 (d, J=9.0 Hz, 1H), 5.99 (d, J=7.3 Hz, 1H), 5.02 (t, J=12.3 Hz, 1H), 3.58 (q, J=12.7 Hz, 2H), 3.32-3.23 (m, 2H), 2.90 (q, J=13.1 Hz, 2H), 2.78-2.51 (m, 3H), 2.38 (s, 3H), 2.35-2.22 (m, 2H), 2.21 (s, 3H), 2.19-2.10 (m, 1H); Chiral HPLC (Diacel Chiralpak IA, 5 μm, 4.6×250 mm, 30 min method, 1.0 mL/min, isocratic 30% EtOH in isohexane (0.2% TFA): 148480, RT=8.82 min, 96.9%, 93.8% de @ 254 nm.

A solution of DBU (22 μL, 0.146 mmol) and Intermediate E3 (60 mg, 0.139 mmol) in acetonitrile (4 mL) was added to a vial charged with CuTMEDA (10 mg, 0.022 mmol) and (3-chloro-4-fluorophenyl)boronic acid (25 mg, 0.143 mmol) before stirring for 18 h at 40° C. The mixture was concentrated under reduced pressure then purified by chromatography on the Companion (4 g column, 0-50% MeAc/DCM) to afford (S)-1-(3-chloro-4-fluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (34 mg, 42%) as an off white solid; Rt 1.94 min (method 1), m/z 557 (M+H)+ (ES+); 1H NMR (d6-DMSO) δ: 7.98 (dt, J=6.9, 1.4 Hz, 1H), 7.70-7.58 (m, 2H), 7.39-7.33 (m, 2H), 7.29 (dd, J=8.5, 1.7 Hz, 1H), 6.01 (d, J=7.1 Hz, 1H), 5.11-4.95 (m, 1H), 3.68-3.48 (m, 2H), 3.32-3.23 (m, 2H), 2.90 (q, J=13.0 Hz, 2H), 2.80-2.52 (m, 3H), 2.38 (s, 3H), 2.32-2.11 (m, 3H), 2.21 (s, 3H); Chiral HPLC (Diacel Chiralpak IA, 5 μm, 4.6×250 mm, 30 min method, 1.0 mL/min, isocratic 30% EtOH in isohexane (0.2% TFA): RT=8.90 min, 96.1%, 92.2% de @ 254 nm.

Example 47: (S)-1-(3-chloro-4-fluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (S)-1-(3-chloro-4-fluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one Example 48: (S)-5-(5-(3,5-dimethylisoxazol-4-yl)-1-(1,1-dioxidotetrahydro-2H-thiopyran-4-yl)-1H-benzo[d]imidazol-2-yl)-1-(3-fluorophenyl)pyrrolidin-2-one (S)-5-(5-(3,5-dimethylisoxazol-4-yl)-1-(1,1-dioxidotetrahydro-2H-thiopyran-4-yl)-1H-benzo[d]imidazol-2-yl)-1-(3-fluorophenyl)pyrrolidin-2-one

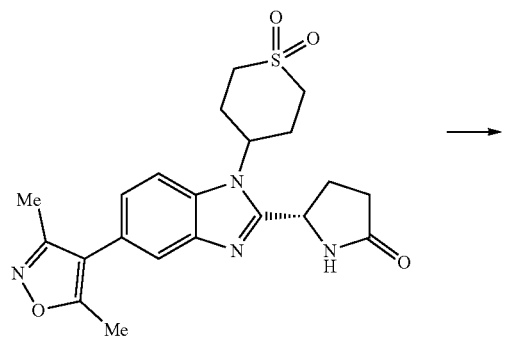

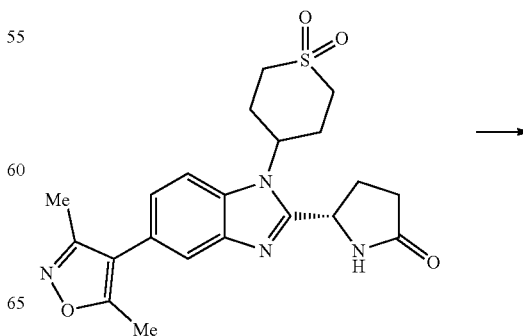

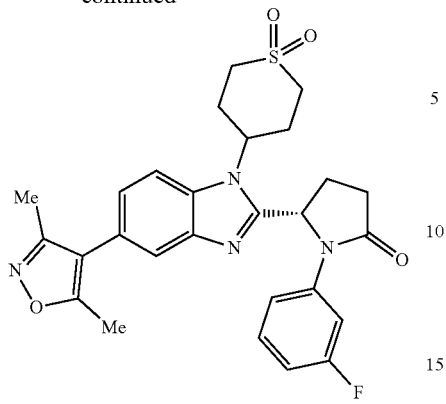

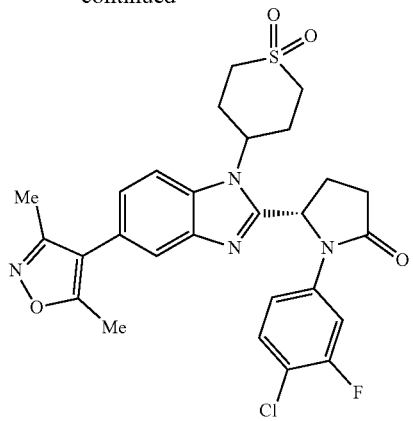

A solution of DBU (22 µL, 0.146 mmol) and Intermediate E3 (60 mg, 0.139 mmol) in acetonitrile (4 mL) was added to a vial charged with CuTMEDA (10 mg, 0.022 mmol) and (3-fluorophenyl)boronic acid (20 mg, 0.143 mmol) before stirring for 18 h at 40° C. The mixture was concentrated under reduced pressure then purified by chromatography on the Companion (4 g column, 0-50% MeAc/DCM) to afford a colourless gum. The gum was dissolved in methyl ethyl ketone (0.5 mL) then diluted with diethyl ether (2 mL). The supernatant was removed then the solid was dried overnight in a desiccator at 50° C. to give (S)-5-(5-(3,5-dimethylisoxazol-4-yl)-1-(1,1-dioxidotetrahydro-2H-thiopyran-4-yl)-1H-benzo[d]imidazol-2-yl)-1-(3-fluorophenyl)pyrrolidin-2-one (23 mg, 30%) as white solid; Rt 1.80 min (method 1), m/z 523 (M+H)+ (ES+); 1H NMR (d6-DMSO) δ: 7.70-7.56 (m, 3H), 7.39-7.24 (m, 2H), 7.24-7.14 (m, 1H), 6.93 (tdd, J=8.4, 2.5, 0.9 Hz, 1H), 6.01 (d, J=7.4 Hz, 1H), 5.12-4.98 (m, 1H), 3.58 (t, J=13.6 Hz, 2H), 3.33-3.25 (m, 2H), 2.91 (q, J=12.9 Hz, 2H), 2.80-2.62 (m, 2H), 2.60-2.52 (m, 1H), 2.38 (s, 3H), 2.34-2.10 (m, 3H), 2.21 (s, 3H); Chiral HPLC (Diacel Chiralpak IA, m, 4.6×250 mm, 30 min method, 1.0 mL/min, isocratic 30% EtOH in isohexane (0.2% TFA): 148483, RT=11.76 min, >99%, >98% de @ 254 nm.

A solution of DBU (22 µL, 0.146 mmol) and Intermediate E3 (60 mg, 0.139 mmol) in acetonitrile (4 mL) was added to a vial charged with CuTMEDA (10 mg, 0.022 mmol) and (4-chloro-3-fluorophenyl)boronic acid (25 mg, 0.143 mmol) before stirring for 18 h at 40° C. The mixture was concentrated under reduced pressure then purified by chromatography on the Companion (4 g column, 0-50% MeAc/CH2Cl2) to afford a gum. The gum was triturated in diethyl ether to yield (S)-1-(4-chloro-3-fluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (41 mg, 50%) as an off white solid; Rt 2.00 min (method 1), m/z 557 (M+H)+ (ES+); 1H NMR (d6-DMSO) δ: 7.87 (dd, J=12.1, 2.5 Hz, 1H), 7.71-7.57 (m, 2H), 7.51 (t, J=8.8 Hz, 1H), 7.30 (dd, J=8.5, 1.6 Hz, 1H), 7.25 (ddd, J=8.9, 2.6, 1.0 Hz, 1H), 6.03 (d, J=7.2 Hz, 1H), 5.13-4.93 (m, 1H), 3.58 (dd, J=16.1, 7.0 Hz, 2H), 3.33-3.23 (m, 2H), 2.92 (q, J=12.9 Hz, 2H), 2.79-2.62 (m, 2H), 2.62-2.52 (m, 1H), 2.40-2.26 (m, 2H), 2.37 (s, 3H), 2.20 (s, 3H), 2.18-2.10 (m, 1H); Chiral HPLC (Diacel Chiralpak IA, 5 µm, 4.6×250 mm, 30 min method, 1.0 mL/min, isocratic 30% EtOH in isohexane (0.2% TFA): RT=10.81 min, 98.3%, 96.6% de @ 254 nm.

Example 49: (S)-1-(4-chloro-3-fluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (S)-1-(4-chloro-3-fluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one Example 50: (S)-1-(3-chloro-5-methoxyphenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (S)-1-(3-chloro-5-methoxyphenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one

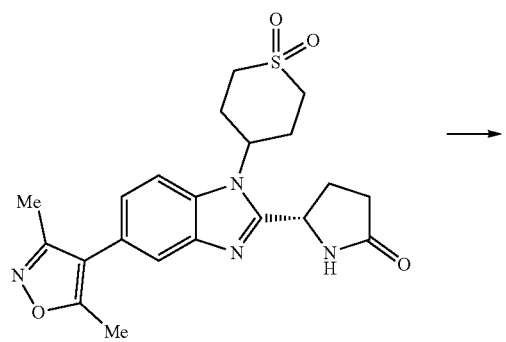

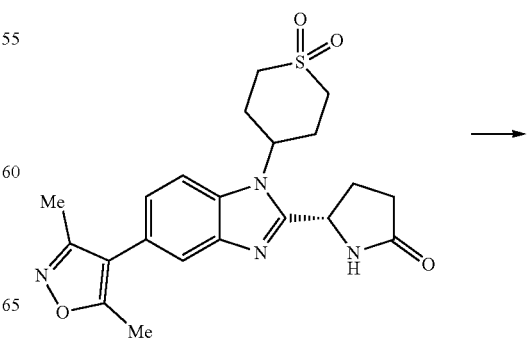

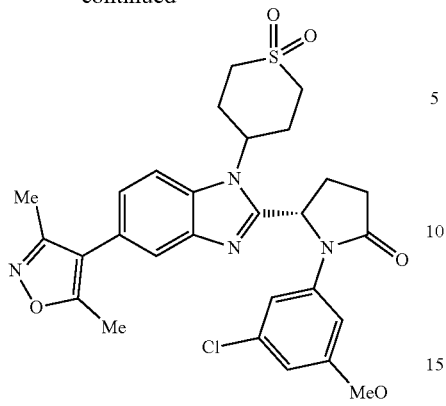

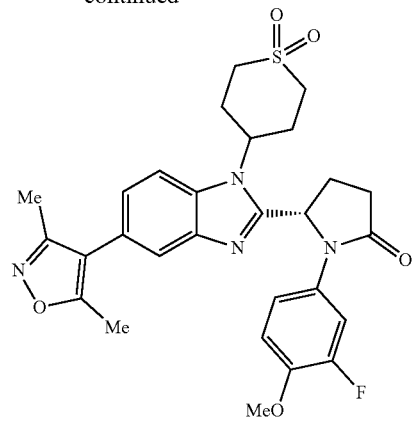

A solution of DBU (22 µL, 0.146 mmol) and Intermediate E3 (60 mg, 0.139 mmol) in acetonitrile (4 mL) was added to a vial charged with CuTMEDA (10 mg, 0.022 mmol) and (3-chloro-5-methoxyphenyl)boronic acid (28 mg, 0.150 mmol) before stirring for 18 h at 40° C. The mixture was concentrated under reduced pressure then purified by chromatography on the Companion (4 g column, 0-50% MeAc/DCM) to afford a colourless gum. The gum was dissolved in methyl ethyl ketone (0.5 mL) then diluted with diethyl ether. The supernatant was removed then the solid was dried overnight in a desiccator at 50° C. to yield (S)-1-(3-chloro-5-methoxyphenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (47 mg, 57%) as a white solid; Rt 1.94 min (method 1), m/z 569 (M+H)+ (ES+); 1H NMR (d6-DMSO) δ: 7.66 (d, J=1.6 Hz, 1H), 7.63 (d, J=8.6 Hz, 1H), 7.33 (t, J=1.9 Hz, 1H), 7.30 (dd, J=8.5, 1.7 Hz, 1H), 7.06 (t, J=2.1 Hz, 1H), 6.79 (t, J=2.0 Hz, 1H), 6.05 (d, J=7.5 Hz, 1H), 5.16-4.99 (m, 1H), 3.69 (s, 3H), 3.64-3.51 (m, 2H), 3.33-3.26 (m, 2H), 3.02-2.83 (m, 2H), 2.83-2.52 (m, 3H), 2.38 (s, 3H), 2.35-2.23 (m, 1H), 2.21 (s, 3H), 2.19-2.08 (m, 2H; Chiral HPLC (Diacel Chiralpak IA, 5 µm, 4.6×250 mm, 30 min method, 1.0 mL/min, isocratic 30% EtOH in isohexane (0.2% TFA): 148485, RT=10.72 min, >99%, >98% de @ 254 nm.

Example 51: (S)-5-(5-(3,5-dimethylisoxazol-4-yl)-1-(1,1-dioxidotetrahydro-2H-thiopyran-4-yl)-1H-benzo[d]imidazol-2-yl)-1-(3-fluoro-4-methoxyphenyl)pyrrolidin-2-one (S)-5-(5-(3,5-dimethylisoxazol-4-yl)-1-(1,1-dioxidotetrahydro-2H-thiopyran-4-yl)-1H-benzo[d]imidazol-2-yl)-1-(3-fluoro-4-methoxyphenyl)pyrrolidin-2-one A solution of DBU (22 µL, 0.146 mmol) and Intermediate E3 (60 mg, 0.139 mmol) in acetonitrile (4 mL) was added to a vial charged with CuTMEDA (10 mg, 0.022 mmol) and (3-fluoro-4-methoxyphenyl)boronic acid (25 mg, 0.147 mmol) before stirring for 18 h at 40° C. The mixture was concentrated under reduced pressure then purified by chromatography on the Companion (4 g column, 0-50% MeAc/DCM) to afford a gum. The gum was dissolved in methyl ethyl ketone (0.5 mL) then diluted with diethyl ether (2 mL). The supernatent was removed then the solid was dried overnight in a desiccator at 50° C. (S)-5-(5-(3,5-dimethylisoxazol-4-yl)-1-(1,1-dioxidotetrahydro-2H-thiopyran-4-yl)-1H-benzo[d]imidazol-2-yl)-1-(3-fluoro-4-methoxyphenyl)pyrrolidin-2-one (28 mg, 35%) as an off white solid; Rt 1.76 min (method 1), m/z 553 (M+H)+ (ES+); 1H NMR (d6-DMSO) δ: 7.70-7.56 (m, 3H), 7.29 (dd, J=8.4, 1.6 Hz, 1H), 7.15-7.02 (m, 2H), 5.93 (d, J=7.7 Hz, 1H), 5.11-4.93 (m, 1H), 3.75 (s, 3H), 3.65-3.48 (m, 2H), 3.32-3.23 (m, 2H), 2.88 (d, J=13.4 Hz, 2H), 2.81-2.53 (m, 3H), 2.38 (s, 3H), 2.35-1.98 (m, 6H), 2.21 (s, 3H); Chiral HPLC (Diacel Chiralpak IA, 5 µm, 4.6×250 mm, 30 min method, 1.0 mL/min, isocratic 30% EtOH in isohexane (0.2% TFA): 148486, RT=12.91 min, >99%, >98% de @ 254 nm.

Example 52: (S)-1-(3-chloro-4-methoxyphenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (S)-1-(3-chloro-4-methoxyphenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one

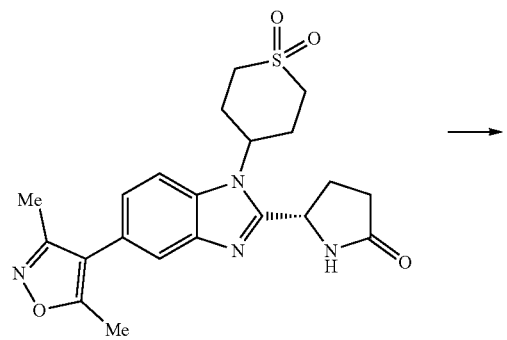

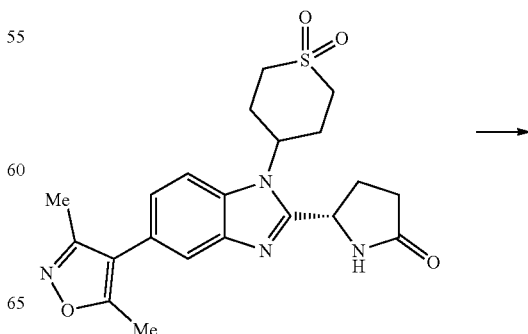

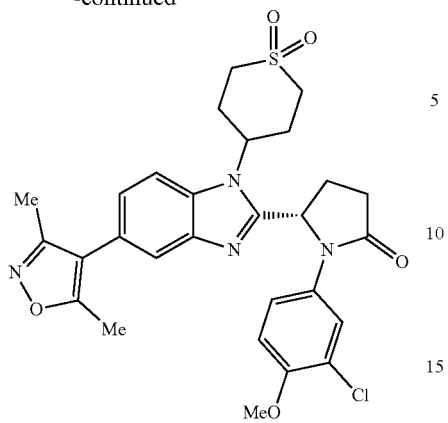

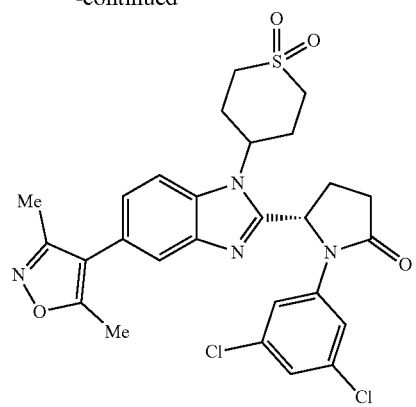

A solution of DBU (22 µL, 0.146 mmol) and Intermediate E3 (60 mg, 0.139 mmol) in acetonitrile (4 mL) was added to a vial charged with CuTMEDA (10 mg, 0.022 mmol) and (3-chloro-4-methoxyphenyl)boronic acid (28 mg, 0.150 mmol) before stirring for 18 h at 40° C. The mixture was concentrated under reduced pressure then purified by chromatography on the Companion (4 g column, 0-50% MeAc/DCM) to afford a gum. The gum was dissolved in methyl ethyl ketone (0.5 mL) then diluted with diethyl ether (3 mL). The supernatant was removed and the solid was dried at 50° C. in a desiccator overnight to yield (S)-1-(3-chloro-4-methoxyphenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (39 mg, 48%) as an off white solid; Rt 1.83 min (method 1), m/z 569 (M+H)+ (ES+); 1H NMR (d6-DMSO) δ: 7.80 (d, J=2.6 Hz, 1H), 7.66 (d, J=1.6 Hz, 1H), 7.61 (d, J=8.5 Hz, 1H), 7.27 (td, J=8.7, 2.1 Hz, 2H), 7.07 (d, J=9.1 Hz, 1H), 5.96 (d, J=7.8 Hz, 1H), 5.11-4.98 (m, 1H), 3.77 (s, 3H), 3.64-3.49 (m, 2H), 3.33-3.23 (m, 2H), 2.95-2.52 (m, 5H), 2.38 (s, 3H), 2.34-2.14 (m, 2H), 2.20 (s, 3H), 2.05-1.92 (m, 1H); Chiral HPLC (Diacel Chiralpak IA, 5 µm, 4.6×250 mm, 30 min method, 1.0 mL/min, isocratic 30% EtOH in isohexane (0.2% TFA): RT=12.12 min, >99%, >98% de @ 254 nm.

Example 53: (S)-1-(3,5-dichlorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (S)-1-(3,5-dichlorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one A solution of DBU (22 µL, 0.146 mmol) and Intermediate E3 (60 mg, 0.139 mmol) in acetonitrile (4 mL) was added to a vial charged with CuTMEDA (10 mg, 0.022 mmol) and (3,5-dichlorophenyl)boronic acid (28 mg, 0.147 mmol) before stirring for 18 h at 40° C. The mixture was concentrated under reduced pressure then purified by chromatography on the Companion (4 g column, 0-50% MeAc/DCM) then triturated in diethyl ether to afford (S)-1-(3,5-dichlorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (49 mg, 60%) as an off white solid; Rt 2.12 min (method 1), m/z 573 (M+H)+ (ES+); 1H NMR (d6-DMSO) δ: 7.70 (d, J=1.9 Hz, 2H), 7.67-7.61 (m, 2H), 7.34 (t, J=1.8 Hz, 1H), 7.31 (dd, J=8.4, 1.7 Hz, 1H), 6.13 (d, J=7.6 Hz, 1H), 5.14-4.98 (m, 1H), 3.69-3.50 (m, 2H), 3.33-3.25 (m, 2H), 3.04-2.84 (m, 2H), 2.83-2.53 (m, 3H), 2.38 (s, 3H), 2.35-2.22 (m, 2H), 2.21 (s, 3H), 2.18-2.11 (m, 1H); Chiral HPLC (Diacel Chiralpak IA, 5 µm, 4.6×250 mm, 30 min method, 1.0 mL/min, isocratic 30% EtOH in isohexane (0.2% TFA): RT=10.02 min, >99%, >98% de @ 254 nm.

Example 54: (S)-1-(3-chloro-5-fluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (S)-1-(3-chloro-5-fluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one

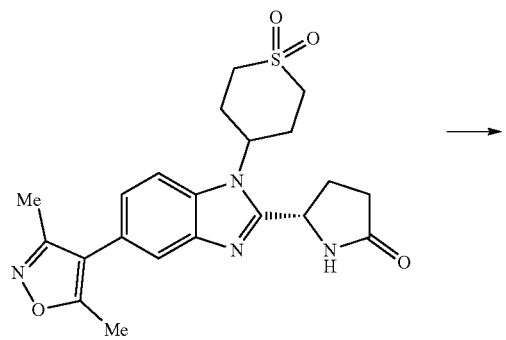

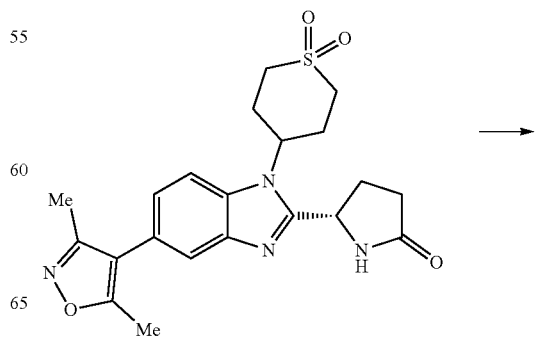

227

-continued

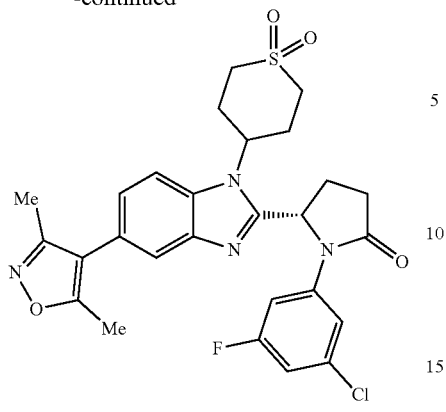

A solution of DBU (22 μL, 0.146 mmol) and Intermediate E3 (60 mg, 0.139 mmol) in acetonitrile (4 mL) was added to a vial charged with CuTMEDA (10 mg, 0.022 mmol) and (3-chloro-5-fluorophenyl)boronic acid (25 mg, 0.143 mmol) before stirring for 18 h at 40° C. The mixture was concentrated under reduced pressure then purified by chromatography on the Companion (4 g column, 0-50% MeAc/DCM) to afford a gum which was triturated in diethyl ether to yield (S)-1-(3-chloro-5-fluorophenyl)-5-(5-(3,5-dimethylisoxazol-4-yl)-1-(1,1-dioxido tetrahydro-2H-thiopyran-4-yl)-1H-benzo[d]imidazol-2-yl)pyrrolidin-2-one (28 mg, 34%) as an off white solid; Rt 2.02 min (method 1), m/z 557 (M+H)+ (ES+); 1H NMR (d6-DMSO) δ: 7.67-7.62 (m, 2H), 7.62-7.57 (m, 1H), 7.47 (dt, J=11.4, 2.1 Hz, 1H), 7.31 (dd, J=8.5, 1.6 Hz, 1H), 7.17 (dt, J=8.5, 2.1 Hz, 1H), 6.09 (d, J=7.4 Hz, 1H), 5.12-4.96 (m, 1H), 3.71-3.48 (m, 2H), 3.29 (d, J=4.0 Hz, 2H), 3.05-2.84 (m, 2H), 2.83-2.53 (m, 3H), 2.38 (s, 3H), 2.36-2.23 (m, 2H), 2.21 (s, 3H), 2.18-2.10 (m, 1H); Chiral HPLC (Diacel Chiralpak IA, 5 μm, 4.6×250 mm, 30 min method, 1.0 mL/min, isocratic 30% EtOH in isohexane (0.2% TFA): RT=10.55 min, >99%, >98% de @ 254 nm.

Example 55: (S)-5-(5-(3,5-dimethylisoxazol-4-yl)-1-(1,1-dioxidotetrahydro-2H-thiopyran-4-yl)-1H-benzo[d]imidazol-2-yl)-1-(3,4,5-trifluorophenyl) pyrrolidin-2-one (S)-5-(5-(3,5-dimethylisoxazol-4-yl)-1-(1,1-dioxidotetrahydro-2H-thiopyran-4-yl)-1H-benzo[d]imidazol-2-yl)-1-(3,4,5-trifluorophenyl)pyrrolidin-2-one

228

-continued

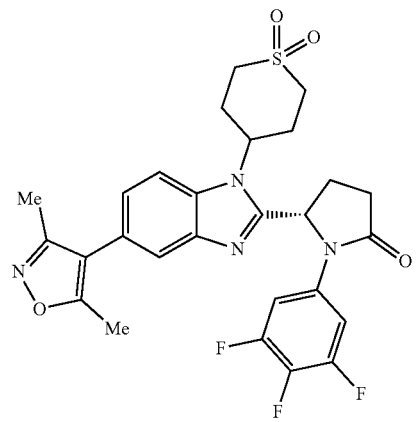

A solution of DBU (22 μl, 0.146 mmol) and Intermediate E3 (60 mg, 0.139 mmol) in acetonitrile (4 mL) was added to a vial charged with CuTMEDA (10 mg, 0.022 mmol) and (3,4,5-trifluorophenyl)boronic acid (25 mg, 0.142 mmol) before stirring for 18 h at 40° C. The mixture was concentrated under reduced pressure then purified by chromatography on the Companion (4 g column, 0-50% MeAc/DCM) to afford (S)-5-(5-(3,5-dimethylisoxazol-4-yl)-1-(1,1-dioxidotetrahydro-2H-thiopyran-4-yl)-1H-benzo[d]imidazol-2-yl)-1-(3,4,5-trifluorophenyl) pyrrolidin-2-one (49 mg, 61%) as an off white solid; Rt 2.00 min (method 1), m/z 559 (M+H)+ (ES+); 1H NMR (d6-DMSO) δ: 7.69-7.52 (m, 4H), 7.30 (dd, J=8.5, 1.6 Hz, 1H), 6.03 (d, J=6.9 Hz, 1H), 5.06-4.88 (m, 1H), 3.64 (td, J=13.6, 3.5 Hz, 1H), 3.55 (td, J=13.7, 3.5 Hz, 1H), 3.33-3.24 (m, 2H), 2.92 (q, J=13.1 Hz, 2H), 2.77-2.63 (m, 2H), 2.63-2.53 (m, 1H), 2.41-2.27 (m, 2H), 2.38 (s, 3H), 2.21 (s, 3H), 2.17-2.10 (m, 1H); Chiral HPLC (Diacel Chiralpak IA, 5 mm, 4.6×250 mm, 30 min method, 1.0 mL/min, isocratic 30% EtOH in isohexane (0.2% TFA): RT=9.04 min, >99%, >98% de @ 254 nm.

Example 56: (S)-1-(3,5-difluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (S)-1-(3,5-difluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one

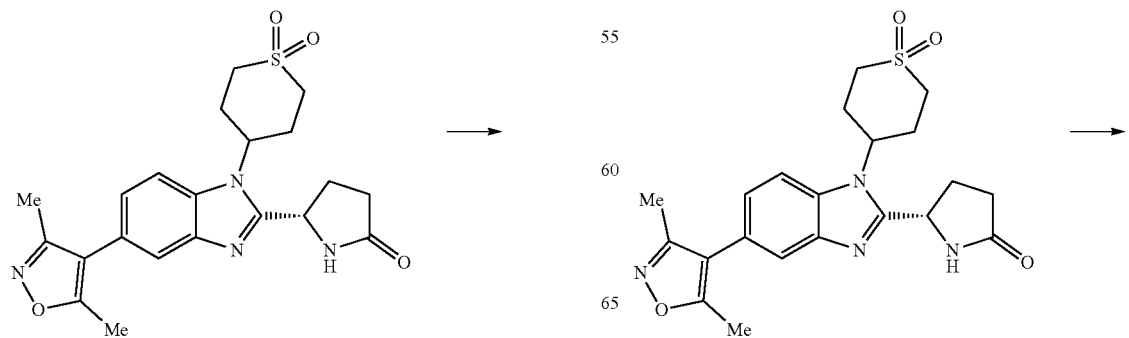

229

-continued

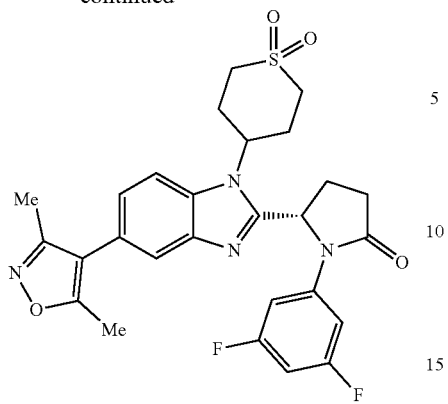

A solution of DBU (22 μL, 0.146 mmol) and Intermediate E3 (60 mg, 0.139 mmol) in acetonitrile (4 mL) was added to a vial charged with CuTMEDA (10 mg, 0.022 mmol) and (3,5-difluorophenyl)boronic acid (23 mg, 0.146 mmol) before stirring for 18 h at 40° C. The mixture was concentrated under reduced pressure then purified by chromatography on the Companion (4 g column, 0-50% MeAc/DCM) to afford (S)-1-(3,5-difluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (36 mg, 43%) as an off white solid; Rt 1.92 min (method 1), m/z 541 (M+H)+ (ES+); 1H NMR (d6-DMSO) δ: 7.69-7.60 (m, 2H), 7.41-7.33 (m, 2H), 7.30 (dd, J=8.6, 1.6 Hz, 1H), 6.98 (tt, J=9.2, 2.3 Hz, 1H), 6.05 (d, J=7.3 Hz, 1H), 5.02 (t, J=12.4 Hz, 1H), 3.70-3.48 (m, 2H), 3.33-3.24 (m, 2H), 3.04-2.85 (m, 2H), 2.80-2.53 (m, 3H), 2.38 (s, 3H), 2.36-2.28 (m, 2H), 2.21 (s, 3H), 2.13 (q, J=7.9, 7.3 Hz, 1H); Chiral HPLC (Diacel Chiralpak IA, m, 4.6×250 mm, 30 min method, 1.0 mL/min, isocratic 30% EtOH in isohexane (0.2% TFA): RT=11.07 min, >99%, >98% de @ 254 nm.

Example 57: (S)-5-(5-(3,5-dimethylisoxazol-4-yl)-1-(1,1-dioxidotetrahydro-2H-thiopyran-4-yl)-1H-benzo[d]imidazol-2-yl)-1-(5-fluoro-6-methoxypyridin-3-yl)pyrrolidin-2-one (S)-5-(5-(3,5-dimethylisoxazol-4-yl)-1-(1,1-dioxidotetrahydro-2H-thiopyran-4-yl)-1H-benzo[d]imidazol-2-yl)-1-(5-fluoro-6-methoxypyridin-3-yl)pyrrolidin-2-one

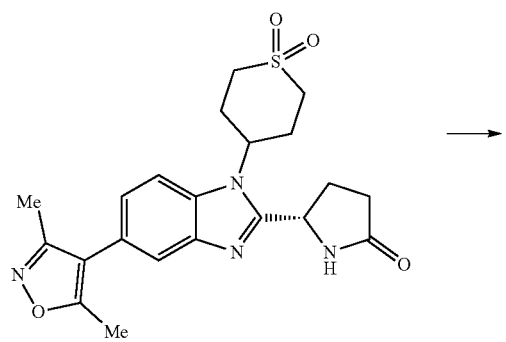

230

-continued

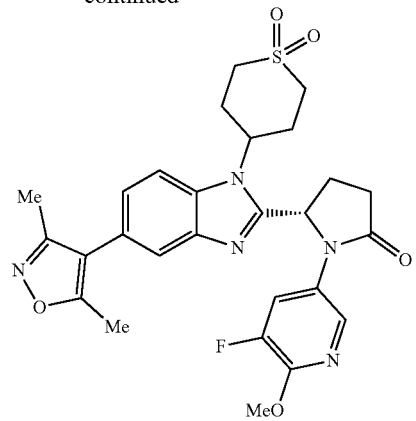

A solution of DBU (22 μL, 0.146 mmol) and Intermediate E3 (60 mg, 0.139 mmol) in acetonitrile (4 mL) was added to a vial charged with CuTMEDA (10 mg, 0.022 mmol) and (5-fluoro-6-methoxypyridin-3-yl)boronic acid (25 mg, 0.146 mmol) before stirring for 18 h at 40° C. The mixture was concentrated under reduced pressure then purified by chromatography on the Companion (4 g column, 0-50% MeAc/DCM) then triturated in diethyl ether to afford (S)-5-(5-(3,5-dimethylisoxazol-4-yl)-1-(1,1-dioxidotetrahydro-2H-thiopyran-4-yl)-1H-benzo[d]imidazol-2-yl)-1-(5-fluoro-6-methoxypyridin-3-yl)pyrrolidin-2-one (20 mg, 26%) as an off white solid; Rt 1.78 min (method 1), m/z 554 (M+H)+ (ES+); 1H NMR (d6-DMSO) δ: 8.13 (dd, J=12.2, 2.3 Hz, 1H), 7.97 (d, J=2.2 Hz, 1H), 7.71-7.58 (m, 2H), 7.30 (dd, J=8.4, 1.7 Hz, 1H), 5.96 (d, J=7.2 Hz, 1H), 5.04-4.88 (m, 1H), 3.86 (s, 3H), 3.70-3.57 (m, 1H), 3.57-3.46 (m, 1H), 3.33-3.24 (m, 2H), 3.00-2.79 (m, 2H), 2.79-2.63 (m, 2H), 2.60-2.52 (m, 1H), 2.38 (s, 3H), 2.36-2.25 (m, 1H), 2.25-2.15 (m, 2H), 2.21 (s, 3H); Chiral HPLC (Diacel Chiralpak IA, 5 μm, 4.6×250 mm, 30 min method, 1.0 mL/min, isocratic 30% EtOH in isohexane (0.2% TFA): RT=12.97 min, >99%, >98% de @ 254 nm.

Example 58: (S)-1-(2,3-dihydrobenzofuran-5-yl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (S)-1-(2,3-dihydrobenzofuran-5-yl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one

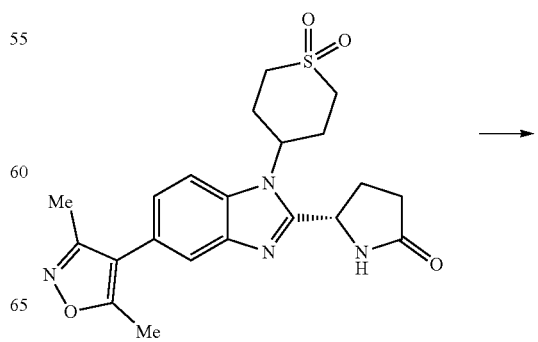

231
-continued

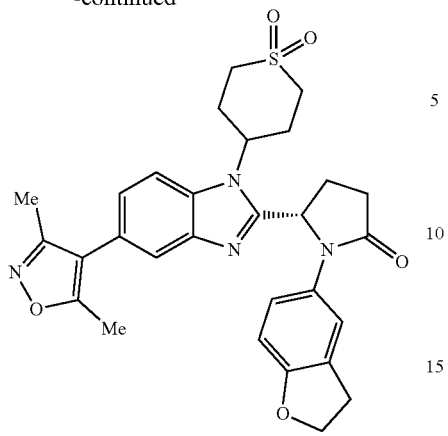

A solution of DBU (22 µL, 0.146 mmol) and Intermediate E3 (60 mg, 0.139 mmol) in acetonitrile (4 mL) was added to a vial charged with CuTMEDA (10 mg, 0.022 mmol) and (2,3-dihydrobenzofuran-5-yl)boronic acid (25 mg, 0.152 mmol) before stirring for 18 h at 70° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford (S)-1-(2,3-dihydrobenzofuran-5-yl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (35 mg, 44%) as a pale yellow glass; Rt 1.68 min (method 1), m/z 547 (M+H)+ (ES+); 1H NMR (d6-DMSO) δ: 7.68 (d, J=1.6 Hz, 1H), 7.58 (d, J=8.5 Hz, 1H), 7.40 (d, J=2.2 Hz, 1H), 7.27 (dd, J=8.5, 1.7 Hz, 1H), 7.01 (dd, J=8.6, 2.3 Hz, 1H), 6.66 (d, J=8.5 Hz, 1H), 5.84 (d, J=7.8 Hz, 1H), 5.04-4.91 (m, 1H), 4.47 (t, J=8.7 Hz, 2H), 3.61-3.42 (m, 2H), 3.31-3.20 (m, 2H), 3.10 (t, J=8.7 Hz, 2H), 2.93-2.72 (m, 3H), 2.71-2.58 (m, 1H), 2.44-2.33 (m, 1H), 2.39 (s, 3H), 2.32-2.10 (m, 2H), 2.22 (s, 3H), 1.75-1.61 (m, 1H); Chiral HPLC (Diacel Chiralpak IA, 5 µm, 4.6×250 mm, 30 min method, 1.0 mL/min, isocratic 30% EtOH in isohexane (0.2% TFA): RT=16.8 min, 97.4%, 94.8% de @ 254 nm.

Example 59: (S)-1-(3,4-dichlorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (S)-1-(3,4-dichlorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one 232
-continued

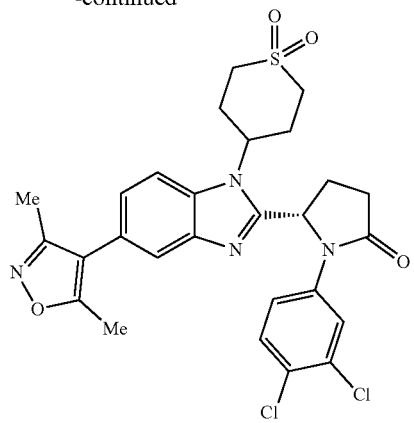

A solution of DBU (22 µL, 0.146 mmol) and Intermediate E3 (60 mg, 0.139 mmol) in acetonitrile (4 mL) was added to a vial charged with CuTMEDA (10 mg, 0.022 mmol) and (3,4-dichlorophenyl)boronic acid (28 mg, 0.147 mmol) before stirring for 18 h at 70° C. The mixture was diluted with water then extracted with dichloromethane (3×8 mL). The organic phases were combined then filtered and concentrated under reduced pressure. The crude product was purified by chromatography on the Companion (4 g column, 2-5% MeOH/DCM) to afford (S)-1-(3,4-dichlorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one (41 mg, 49%) as a pale yellow glass; Rt 2.08 min (method 1), m/z 573 (M+H)+ (ES+); 1H NMR (d6-DMSO) δ: 8.07 (d, J=2.5 Hz, 1H), 7.68-7.60 (m, 2H), 7.56 (d, J=8.9 Hz, 1H), 7.39 (dd, J=8.9, 2.6 Hz, 1H), 7.30 (dd, J=8.5, 1.6 Hz, 1H), 6.06 (d, J=7.2 Hz, 1H), 5.14-4.97 (m, 1H), 3.66-3.51 (m, 2H), 3.33-3.23 (m, 2H), 3.00-2.84 (m, 2H), 2.80-2.52 (m, 3H), 2.37 (s, 3H), 2.35-2.25 (m, 2H), 2.21 (s, 3H), 2.18-2.10 (m, 1H); Chiral HPLC (Diacel Chiralpak IA, 5 µm, 4.6×250 mm, 30 min method, 1.0 mL/min, isocratic 30% EtOH in isohexane (0.2% TFA): RT=10.91 min, 83.6%, 67.2% de @ 254 nm.

Example 61: (S)-1-(3,4-difluorophenyl)-5-(5-(3,5-dimethylisoxazol-4-yl)-1-((1r,4S)-4-hydroxycyclohexyl)-1H-benzo[d]imidazol-2-yl)pyrrolidin-2-one (S)—N-(5-(3,5-dimethylisoxazol-4-yl)-2-(((1r,4S)-4-hydroxycyclohexyl)amino)phenyl)-5-oxopyrrolidine-2-carboxamide (Intermediate D4)

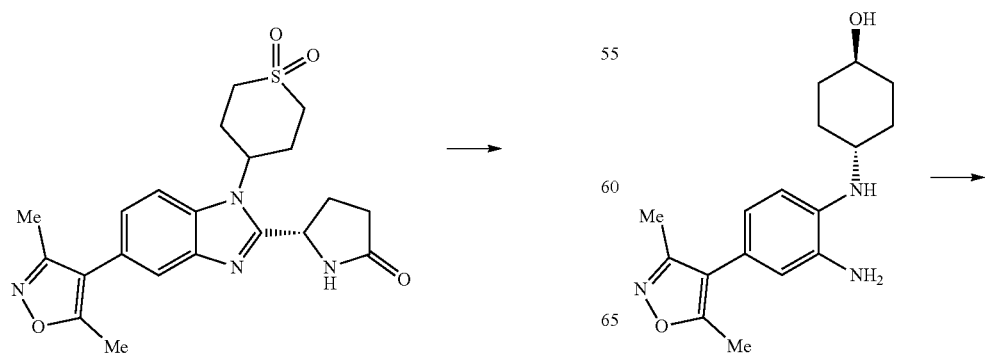

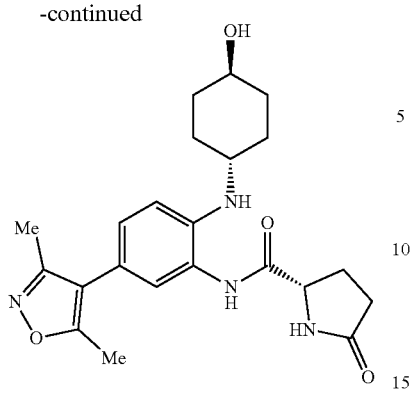

HATU (1.5 g, 3.94 mmol) was added to a stirred solution of TEA (0.6 ml, 4.30 mmol), (S)-5-oxopyrrolidine-2-carboxylic acid (0.5 g, 3.87 mmol) and (1r,4r)-4-((2-amino-4-(3,5-dimethylisoxazol-4-yl)phenyl)amino)cyclohexanol (1.15 g, 3.78 mmol) in N,N-dimethylformamide (10 mL) then the mixture was stirred at room temperature for 18 h. The solvents were removed under reduced pressure (co-evaporating with xylenes) then adsorbed onto loose silica gel. The silicate was purified by flash chromatography on the Companion (80 g column, 0-10% MeOH/DCM) to afford (S)—N-(5-(3,5-dimethylisoxazol-4-yl)-2-(((1r,4S)-4-hydroxycyclohexyl)amino)phenyl)-5-oxopyrrolidine-2-carboxamide Intermediate D4 (1.5 g, 89%) as a pale pink solid; Rt 1.31 min (method 1), m/z 413 (M+H)+ (ES+).

(S)-5-(5-(3,5-dimethylisoxazol-4-yl)-1-((1r,4S)-4-hydroxycyclohexyl)-1H-benzo[d]imidazol-2-yl)pyrrolidin-2-one (Intermediate E4)

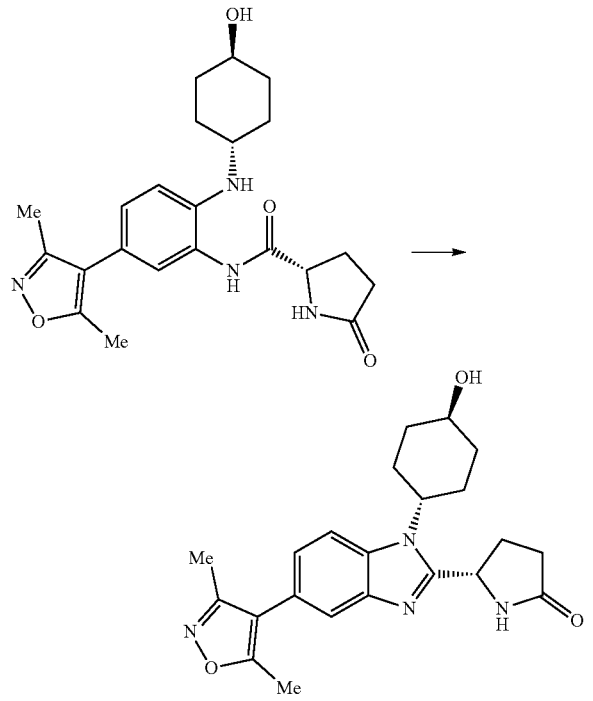

Intermediate D4 (500 mg, 1.115 mmol) was heated to 80° C. in acetic acid (10 mL) for 4 h. The mixture was concentrated under reduced pressure then redissolved in methanol (20 mL). Solid potassium carbonate (2 g) was added and the mixture was stirred for 1 h before concentrating onto loose silica gel. The crude product was purified by chromatography on the Companion (40 g column, 5-15% MeOH/DCM) to afford a colourless gum. The gum was stirred overnight in diethyl ether (25 mL) then collected by filtration to yield (S)-5-(5-(3,5-dimethylisoxazol-4-yl)-1-((1r,4S)-4-hydroxycyclohexyl)-1H-benzo[d]imidazol-2-yl)pyrrolidin-2-one (Intermediate E4) (232 mg, 52%) as a white solid; Rt 1.13 min (method 1), m/z 395 (M+H)+ (ES+).

(S)-1-(3,4-difluorophenyl)-5-(5-(3,5-dimethylisoxazol-4-yl)-1-((1r,4S)-4-hydroxycyclohexyl)-1H-benzo[d]imidazol-2-yl)pyrrolidin-2-one

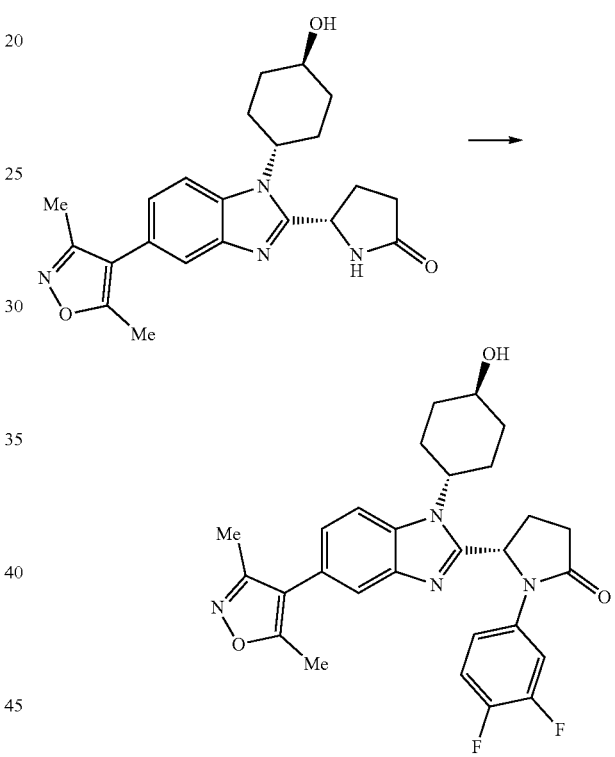

A solution of DBU (22 μL, 0.146 mmol) and Intermediate E4 (55 mg, 0.137 mmol) in acetonitrile (4 mL) was added to a vial charged with CuTMEDA (10 mg, 0.022 mmol) and (3,4-difluorophenyl)boronic acid (25 mg, 0.158 mmol) before stirring for 2 h at 70° C. The mixture was diluted with water (8 mL) then extracted with dichloromethane (3×8 mL). The organic phases were combined then filtered and concentrated under reduced pressure. The crude product was purified by chromatography on the Companion (4 g column, 2-5% MeOH/DCM) to afford a pale brown gum. The gum was purified by chromatography on the Companion (12 g column, 0-10% MeOH/DCM) to afford (S)-1-(3,4-difluorophenyl)-5-(5-(3,5-dimethylisoxazol-4-yl)-1-((1r,4S)-4-hydroxycyclohexyl)-1H-benzo[d]imidazol-2-yl)pyrrolidin-2-one (40 mg, 56%) as an off white solid; Rt 1.78 min; m/z 507 (M+H)+ (ES+); 1H NMR (d$_6$-DMSO) δ: 7.89-7.76 (m, 2H), 7.59 (d, J=1.6 Hz, 1H), 7.44-7.33 (m, 1H), 7.22-7.11 (m, 2H), 6.17-6.05 (m, 1H), 4.75 (d, J=4.2 Hz, 1H), 4.57-4.43 (m, 1H), 3.82-3.66 (m, 1H), 2.81-2.52 (m, 3H), 2.43-2.26

(m, 2H), 2.37 (s, 3H), 2.20 (s, 3H), 2.14-2.05 (m, 1H), 2.04-1.93 (m, 2H), 1.87-1.79 (m, 1H), 1.78-1.68 (m, 1H), 1.61-1.39 (m, 2H).

Example 62: (S)-1-(4-chloro-3-fluorophenyl)-5-(5-(3,5-dimethylisoxazol-4-yl)-1-((1r,4S)-4-hydroxycyclohexyl)-1H-benzo[d]imidazol-2-yl)pyrrolidin-2-one (S)-1-(4-chloro-3-fluorophenyl)-5-(5-(3,5-dimethylisoxazol-4-yl)-1-((1r,4S)-4-hydroxycyclohexyl)-1H-benzo[d]imidazol-2-yl)pyrrolidin-2-one

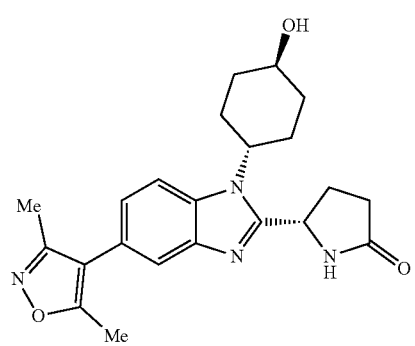

Example 63: (S)-5-(5-(3,5-dimethylisoxazol-4-yl)-1-((1r,4S)-4-hydroxycyclohexyl)-1H-benzo[d]imidazol-2-yl)-1-(3-fluoro-4-methoxyphenyl)pyrrolidin-2-one (S)-5-(5-(3,5-dimethylisoxazol-4-yl)-1-((1r,4S)-4-hydroxycyclohexyl)-1H-benzo[d]imidazol-2-yl)-1-(3-fluoro-4-methoxyphenyl)pyrrolidin-2-one

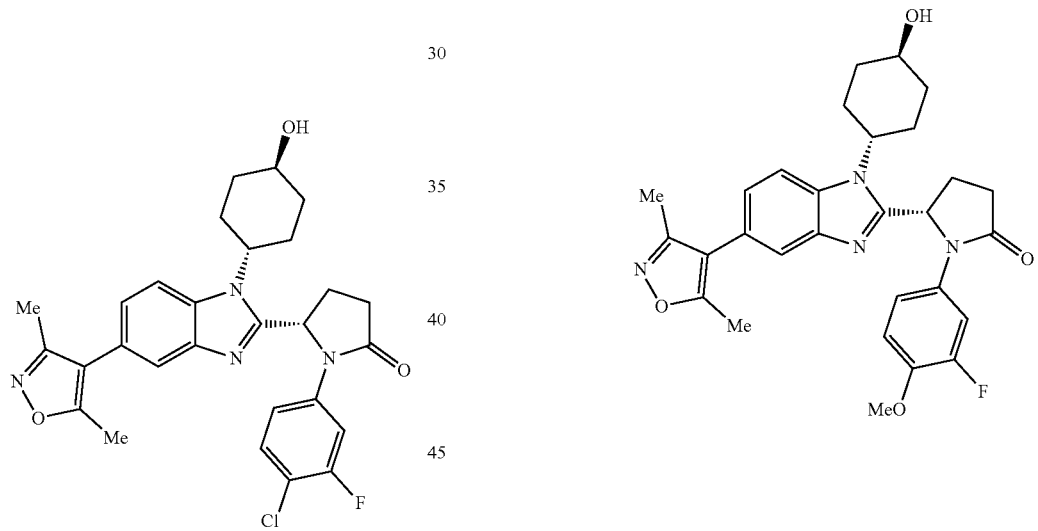

CuTMEDA (8.83 mg, 0.019 mmol) was added to a solution of DBU (20.06 μL, 0.133 mmol), Intermediate E4 (50 mg, 0.127 mmol) and (4-chloro-3-fluorophenyl)boronic acid (24.31 mg, 0.139 mmol) in acetonitrile (4 ml) with stirring for 108 h at 40° C. The mixture was concentrated under reduced pressure then purified by chromatography on the Companion (12 g column, 0-10% MeOH in DCM, gradient elution) to afford (S)-1-(4-chloro-3-fluorophenyl)-5-(5-(3,5-dimethylisoxazol-4-yl)-1-(4-hydroxycyclohexyl)-1H-benzo[d]imidazol-2-yl)pyrrolidin-2-one (15 mg, 22%) as an off white solid; Rt 1.56 min; m/z 523 (M+H)+ (ES+); 1H NMR (d$_6$-DMSO) δ: 7.87-7.79 (m, 2H), 7.58 (d, J=1.6 Hz, 1H), 7.52 (t, J=8.8 Hz, 1H), 7.23 (ddd, J=8.9, 2.6, 1.0 Hz, 1H), 7.16 (dd, J=8.5, 1.7 Hz, 1H), 6.22-6.08 (m, 1H), 4.76 (d, J=4.2 Hz, 1H), 4.59-4.45 (m, 1H), 3.81-3.67 (m, 1H), 2.80-2.53 (m, 3H), 2.41-2.29 (m, 2H), 2.36 (s, 3H), 2.20 (s, 3H), 2.11-1.95 (m, 3H), 1.89-1.78 (m, 2H), 1.63-1.39 (m, 2H).

CuTMEDA (8.83 mg, 0.019 mmol) was added to a solution of DBU (20.06 μl, 0.133 mmol), Intermediate E4 (50 mg, 0.127 mmol) and (3-fluoro-4-methoxyphenyl)boronic acid (23.70 mg, 0.139 mmol) in acetonitrile (4 mL) with stirring for 108 h at 40° C. The mixture was concentrated under reduced pressure then purified by chromatography on the Companion (12 g column, 0-10% MeOH in DCM, gradient elution) to afford (S)-5-(5-(3,5-dimethylisoxazol-4-yl)-1-(4-hydroxycyclohexyl)-1H-benzo[d]imidazol-2-yl)-1-(3-fluoro-4-methoxyphenyl)pyrrolidin-2-one (9 mg, 13%) as an off white solid; Rt 1.69 min; m/z 519 (M+H)+ (ES+); 1H NMR (d$_6$-DMSO) δ: 7.81 (d, J=8.5 Hz, 1H), 7.59 (td, J=7.2, 6.5, 1.9 Hz, 2H), 7.14 (dd, J=8.5, 1.7 Hz, 1H), 7.12-7.03 (m, 2H), 6.04 (dd, J=8.4, 2.2 Hz, 1H), 4.75 (d, J=4.1 Hz, 1H), 4.56-4.43 (m, 1H), 3.82-3.65 (m, 1H), 3.75 (s, 3H), 2.82-2.52 (m, 3H), 2.37 (s, 3H), 2.35-2.25 (m, 2H), 2.20 (s, 3H), 2.15-2.06 (m, 1H), 2.03-1.91 (m, 2H), 1.84-1.75 (m, 1H), 1.65-1.39 (m, 3H).

Example 64: (S)-1-(3-chloro-4-methoxyphenyl)-5-(5-(3,5-dimethylisoxazol-4-yl)-1-((1r,4S)-4-hydroxycyclohexyl)-1H-benzo[d]imidazol-2-yl)pyrrolidin-2-one (S)-1-(3-chloro-4-methoxyphenyl)-5-(5-(3,5-dimethylisoxazol-4-yl)-1-((1r,4S)-4-hydroxycyclohexyl)-1H-benzo[d]imidazol-2-yl)pyrrolidin-2-one

Example 65: (S)-1-(3-chloro-4-fluorophenyl)-5-(5-(3,5-dimethylisoxazol-4-yl)-1-((1r,4S)-4-hydroxycyclohexyl)-1H-benzo[d]imidazol-2-yl)pyrrolidin-2-one (S)-1-(3-chloro-4-fluorophenyl)-5-(5-(3,5-dimethylisoxazol-4-yl)-1-((1r,4S)-4-hydroxycyclohexyl)-1H-benzo[d]imidazol-2-yl)pyrrolidin-2-one]

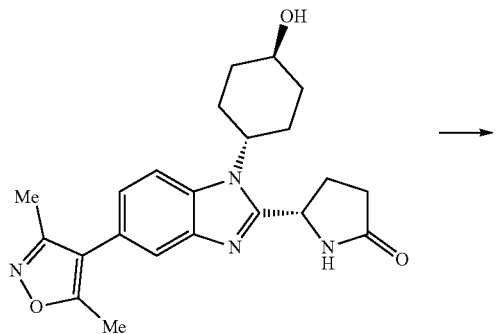

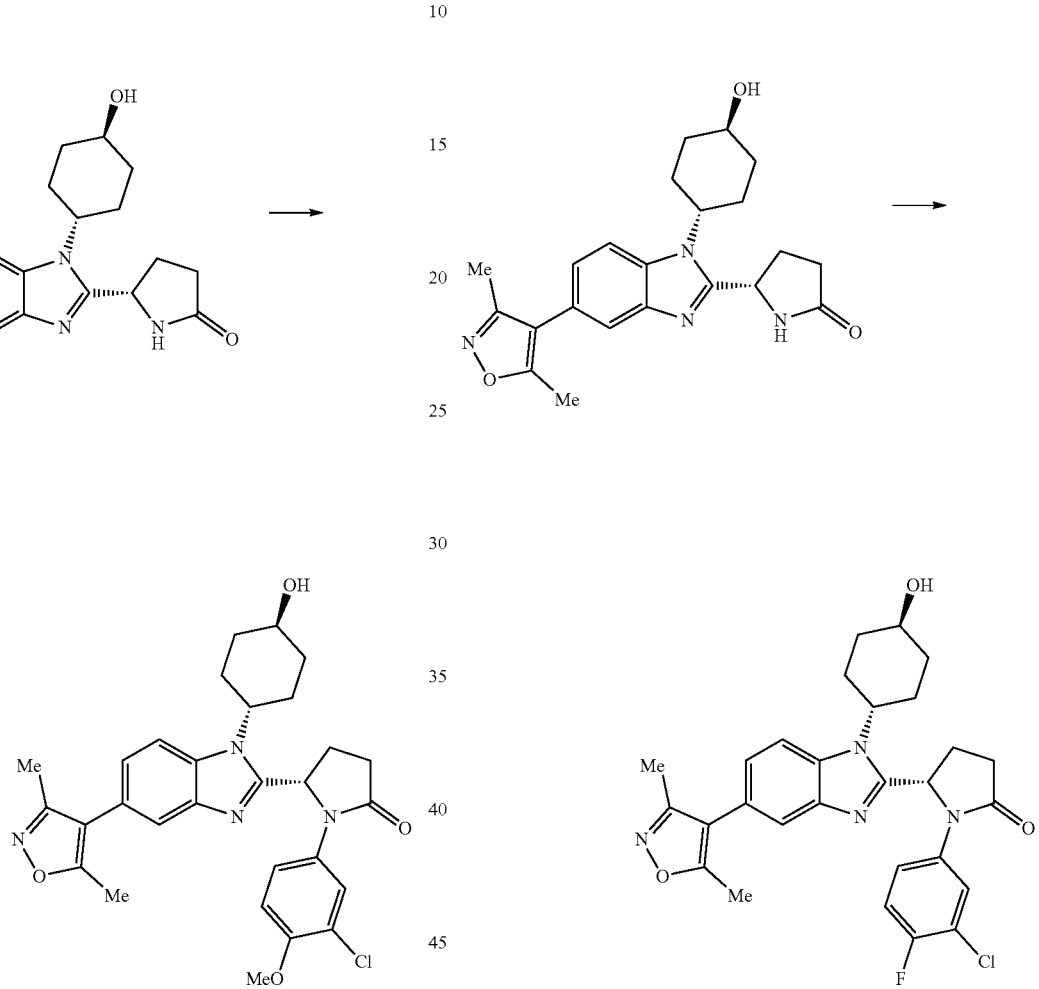

CuTMEDA (8.83 mg, 0.019 mmol) was added to a solution of DBU (20.06 µL, 0.133 mmol), Intermediate E4 and (3-chloro-4-methoxyphenyl)boronic acid (26.0 mg, 0.139 mmol) in acetonitrile (4 mL) with stirring for 108 h at 40° C. The mixture was concentrated under reduced pressure then purified by chromatography on the Companion (12 g column, 0-10% MeOH in DCM, gradient elution) to afford (S)-1-(3-chloro-4-methoxyphenyl)-5-(5-(3,5-dimethylisoxazol-4-yl)-1-(4-hydroxycyclohexyl)-1H-benzo[d]imidazol-2-yl)pyrrolidin-2-one (15 mg, 22%) as an off white solid; Rt 1.76 min; m/z 535 (M+H)+ (ES+); 1H NMR ($d_6$-DMSO) δ: 7.80 (d, J=8.5 Hz, 1H), 7.75 (d, J=2.6 Hz, 1H), 7.59 (d, J=1.7 Hz, 1H), 7.27 (dd, J=9.0, 2.6 Hz, 1H), 7.13 (dd, J=8.5, 1.7 Hz, 1H), 7.07 (d, J=9.0 Hz, 1H), 6.11-6.03 (m, 1H), 4.74 (d, J=4.2 Hz, 1H), 4.50 (s, 1H), 3.76 (s, 3H), 3.71 (s, 2H), 2.83-2.69 (m, 1H), 2.67-2.53 (m, 1H), 2.37 (s, 3H), 2.28 (d, J=12.3 Hz, 1H), 2.20 (s, 3H), 2.15-2.05 (m, 1H), 1.96 (t, J=13.6 Hz, 3H), 1.77 (m, 1H), 1.52 (m, 3H).

CuTMEDA (8.83 mg, 0.019 mmol) was added to a solution of DBU (20.06 µL, 0.133 mmol), Intermediate E4 (50 mg, 0.127 mmol) and (3-chloro-4-fluorophenyl)boronic acid (24.31 mg, 0.139 mmol) in acetonitrile (4 mL) with stirring for 108 h at 40° C. The mixture was concentrated under reduced pressure then purified by chromatography on the Companion (12 g column, 0-10% MeOH in DCM, gradient elution) to afford (S)-1-(3-chloro-4-fluorophenyl)-5-(5-(3,5-dimethylisoxazol-4-yl)-1-(4-hydroxycyclohexyl)-1H-benzo[d]imidazol-2-yl)pyrrolidin-2-one (16 mg, 24%) as an off white solid; Rt 1.90 min; m/z 523 (M+H)+ (ES+); 1H NMR ($d_6$-DMSO) δ: 7.92 (dt, J=6.8, 1.4 Hz, 1H), 7.82 (d, J=8.5 Hz, 1H), 7.58 (d, J=1.6 Hz, 1H), 7.40-7.33 (m, 2H), 7.14 (dd, J=8.4, 1.7 Hz, 1H), 6.17-6.10 (m, 1H), 4.75 (d, J=4.2 Hz, 1H), 4.50 (s, 1H), 3.72 (m, 1H), 2.75 (dt, J=15.4, 9.1 Hz, 1H), 2.66-2.54 (m, 1H), 2.36-2.31 (m, 6H), 2.19 (s, 3H), 2.14-2.03 (m, 1H), 1.97 (s, 2H), 1.82 (s, 1H), 1.71 (s, 1H), 1.50 (dd, J=29.4, 13.8 Hz, 2H).

239

Example 66: (S)-1-(2,3-dihydrobenzofuran-5-yl)-5-(5-(3,5-dimethylisoxazol-4-yl)-1-((1r,4S)-4-hydroxycyclohexyl)-1H-benzo[d]imidazol-2-yl)pyrrolidin-2-one (S)-1-(2,3-dihydrobenzofuran-5-yl)-5-(5-(3,5-dimethylisoxazol-4-yl)-1-((1r,4S)-4-hydroxycyclohexyl)-1H-benzo[d]imidazol-2-yl)pyrrolidin-2-one

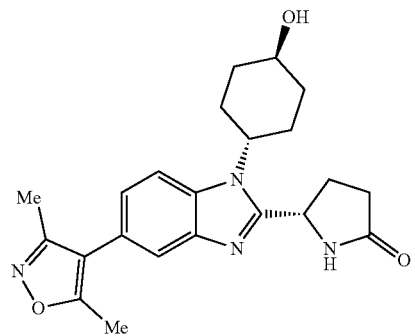

240

Example 67: (S)-5-(5-(3,5-dimethylisoxazol-4-yl)-1-((1r,4S)-4-hydroxycyclohexyl)-1H-benzo[d]imidazol-2-yl)-1-(naphthalen-1-yl)pyrrolidin-2-one (S)-5-(5-(3,5-dimethylisoxazol-4-yl)-1-((1r,4S)-4-hydroxycyclohexyl)-1H-benzo[d]imidazol-2-yl)-1-(naphthalen-1-yl)pyrrolidin-2-one

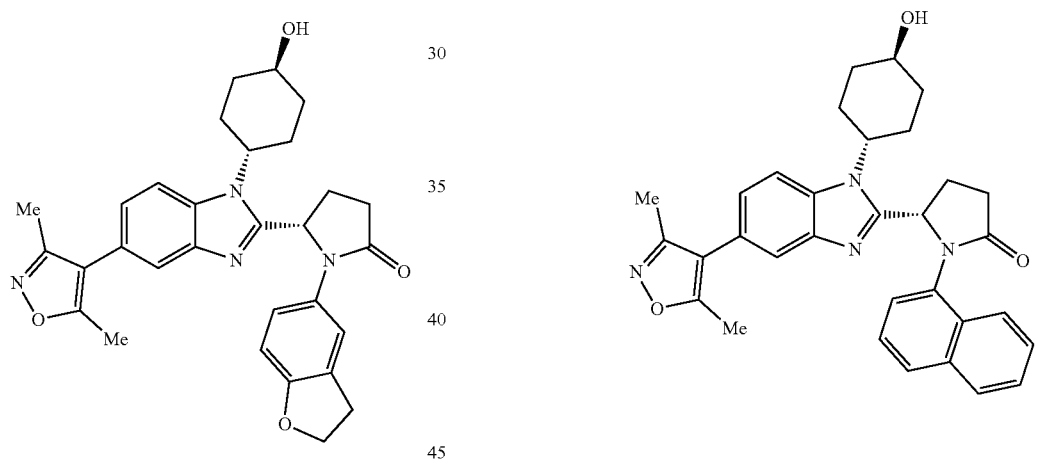

CuTMEDA (8.83 mg, 0.019 mmol) was added to a solution of DBU (20.06 μL, 0.133 mmol), (S)-5-(5-(3,5-dimethylisoxazol-4-yl)-1-(4-hydroxycyclohexyl)-1H-benzo[d]imidazol-2-yl) pyrrolidin-2-one (50 mg, 0.127 mmol) and (2,3-dihydrobenzofuran-5-yl)boronic acid (22.86 mg, 0.139 mmol) in acetonitrile (4 mL) with stirring for 108 h at 40° C. The mixture was concentrated under reduced pressure then purified by chromatography on the Companion (12 g column, 0-10% MeOH in DCM, gradient elution) to afford (S)-1-(2,3-dihydrobenzofuran-5-yl)-5-(5-(3,5-dimethylisoxazol-4-yl)-1-(4-hydroxycyclohexyl)-1H-benzo[d]imidazol-2-yl)pyrrolidin-2-one (13 mg, 19%) as an off white solid; Rt 1.59 min; m/z 513 (M+H)+ (ES+); 1H NMR ($d_6$-DMSO) δ: 7.77 (d, J=8.5 Hz, 1H), 7.60 (d, J=1.6 Hz, 1H), 7.38 (dd, J=2.2, 1.2 Hz, 1H), 7.12 (dd, J=8.4, 1.7 Hz, 1H), 7.01 (dd, J=8.6, 2.3 Hz, 1H), 6.65 (d, J=8.5 Hz, 1H), 5.94 (dd, J=8.3, 2.7 Hz, 1H), 4.72 (d, J=4.2 Hz, 1H), 4.45 (m, 4H), 3.67 (m, 1H), 3.43-3.28 (m, 1H), 3.20-3.05 (m, 2H), 2.78 (dt, J=16.0, 9.0 Hz, 1H), 2.66-2.51 (m, 1H), 2.38 (s, 3H), 2.31-2.15 (m, 5H), 2.01-1.91 (m, 1H), 1.88 (m, 1H), 1.75 (m, 1H), 1.48-1.30 (m, 3H).

CuTMEDA (8.83 mg, 0.019 mmol) was added to a solution of DBU (20.06 μl, 0.133 mmol), Intermediate E4 (50 mg, 0.127 mmol) and naphthalen-1-ylboronic acid (23.98 mg, 0.139 mmol) in acetonitrile (4 ml) with stirring for 108 h at 40° C. The mixture was concentrated under reduced pressure then purified by chromatography on the Companion (12 g column, 0-10% MeOH in DCM, gradient elution) to afford (S)-5-(5-(3,5-dimethylisoxazol-4-yl)-1-(4-hydroxycyclohexyl)-1H-benzo[d]imidazol-2-yl)-1-(naphthalen-1-yl)pyrrolidin-2-one (4 mg, 6%) as an off white solid; Rt 1.75 min; m/z 521 (M+H)+ (ES+); 1H NMR ($d_6$-DMSO) δ: 7.96 (s, 1H), 7.88 (d, J=8.4 Hz, 1H), 7.68 (s, 1H), 7.60 (d, J=8.6 Hz, 1H), 7.40 (bs, 6H), 7.07 (d, J=8.4 Hz, 1H), 5.89 (s, 1H), 4.54 (s, 1H), 3.81 (bs, 1H), 3.38 (bm, 2H), 2.96 (bs, 1H), 2.84 (bs, 1H), 2.73 (bm, 4H), 2.40 (s, 3H), 2.22 (s, 3H), 1.99 (bm, 1H), 1.75 (m, 2H), 1.63 (m, 1H)—Broad spectrum, rotamers.

Example 68: (S)-1-(3,4-dichlorophenyl)-5-(5-(3,5-dimethylisoxazol-4-yl)-1-(4-hydroxycyclohexyl)-1H-benzo[d]imidazol-2-yl)pyrrolidin-2-one (S)-1-(3-chloro-4-fluorophenyl)-5-(5-(3,5-dimethyl-isoxazol-4-yl)-1-((1r,4S)-4-hydroxycyclohexyl)-1H-benzo[d]imidazol-2-yl)pyrrolidin-2-one

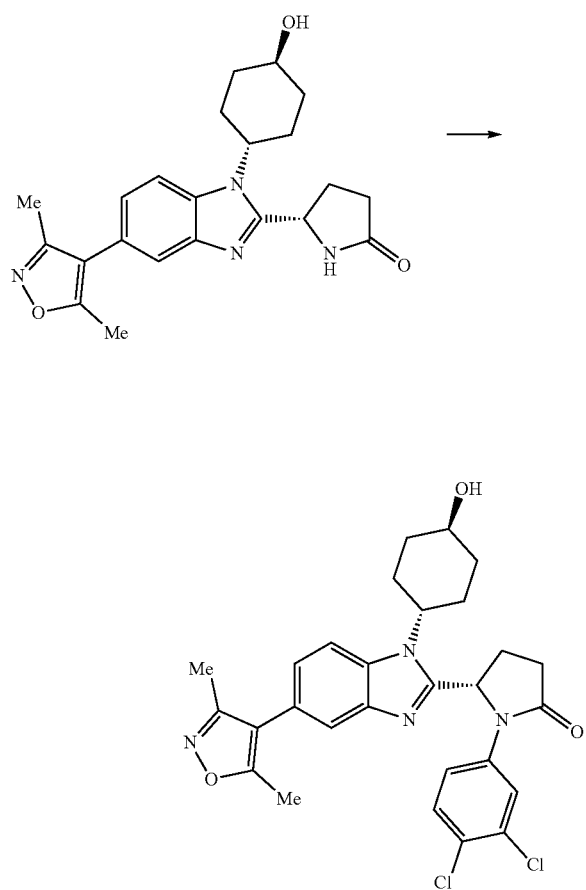

CuTMEDA (8.83 mg, 0.019 mmol) was added to a solution of DBU (20.06 µl, 0.133 mmol), Intermediate E4 (50 mg, 0.127 mmol) and (3,4-dichlorophenyl)boronic acid (26.6 mg, 0.139 mmol) in acetonitrile (4 ml) with stirring for 18 h at 40° C. The mixture was concentrated under reduced pressure then purified by chromatography on the Companion (12 g column, 0-10% MeOH in DCM, gradient elution) to afford (S)-1-(3,4-dichlorophenyl)-5-(5-(3,5-dimethylisoxazol-4-yl)-1-(4-hydroxycyclohexyl)-1H-benzo[d]imidazol-2-yl)pyrrolidin-2-one (25 mg, 36%) as an off white solid; Rt 2.03 min; m/z 539 (M+H)+ (ES+); 1H NMR ($d_6$-DMSO) δ: 7.99 (d, J=2.5 Hz, 1H), 7.84 (d, J=8.4 Hz, 1H), 7.63-7.50 (m, 2H), 7.42 (dd, J=8.9, 2.5 Hz, 1H), 7.16 (dd, J=8.5, 1.7 Hz, 1H), 6.24-6.13 (m, 1H), 4.76 (d, J=4.3 Hz, 1H), 4.60-4.46 (m, 1H), 3.84-3.63 (m, 1H), 2.82-2.53 (m, 3H), 2.42-2.28 (m, 2H), 2.37 (s, 3H), 2.20 (s, 3H), 2.13-1.93 (m, 3H), 1.89-1.74 (m, 2H), 1.65-1.39 (m, 2H); Chiral HPLC (Diacel Chiralpak IA, 5 µm, 4.6×250 mm, 30 min method, 1.0 mL/min, isocratic 30% EtOH in isohexane (0.2% TFA): 156120, RT=5.88 min, 98%, 96% ee @ 254 nm

Example 69: (S)-5-(5-(3,5-dimethylisoxazol-4-yl)-1-((S)-1,1-dioxidotetrahydrothiophen-3-yl)-1H-benzo[d]imidazol-2-yl)pyrrolidin-2-one (S)—N-(5-(3,5-dimethylisoxazol-4-yl)-2-(((S)-1,1-dioxidotetrahydrothiophen-3-1)amino)phenyl)-5-oxopyrrolidine-2-carboxamide (Intermediate D5)

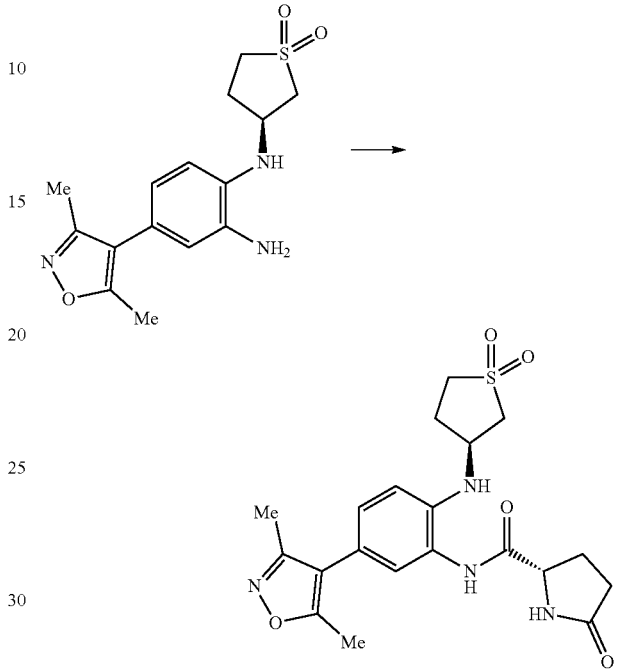

A solution of Intermediate C5 (500 mg, 1.556 mmol), 2-(3H-[1,2,3]triazolo[4,5-b]pyridin-3-yl)-1,1,3,3-tetramethylisouronium hexafluorophosphate(V) (651 mg, 1.711 mmol), (S)-5-oxopyrrolidine-2-carboxylic acid (221 mg, 1.711 mmol) and triethylamine (651 µL, 4.67 mmol) in DMF (5 mL) was stirred at room temperature for 18 h. The mixture was partitioned between DCM (20 mL) and saturated sodium bicarbonate (10 mL). The organic phase was collected and washed sequentially with saturated sodium bicarbonate (10 mL) and water (2×10 mL), then the layers separated through a PhaseSep© cartridge. The organic phase was evaporated in vacuo and to the crude Intermediate D5 (quantitative yield assumed) was used without further purification; Rt 1.38 min; m/z 433 (M+H)+ (ES+).

(S)-5-(5-(3,5-dimethylisoxazol-4-yl)-1-((S)-1,1-dioxidotetrahydrothiophen-3-yl)-1H-benzo[d]imidazol-2-yl)pyrrolidin-2-one (Intermediate E5)

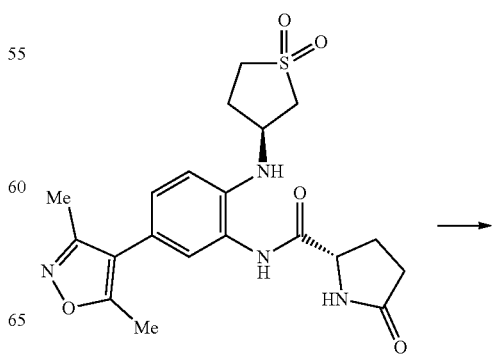

243

-continued

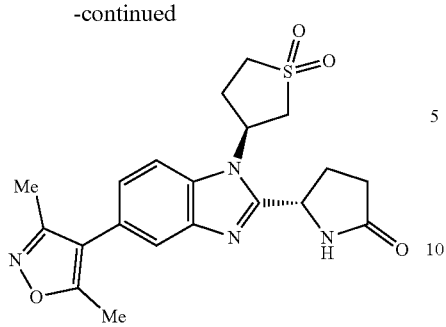

A solution of Intermediate D5 (336 mg, 0.777 mmol) in acetic acid (1 ml) was heated to 80° C. for 18 h. The solvent was removed in vacuo and the residue was purified by chromatography (12 g silica, 0-10% methanol in DCM, gradient elution) to afford (S)-5-(5-(3,5-dimethylisoxazol-4-yl)-1-((S)-1,1-dioxidotetrahydrothiophen-3-yl)-1H-benzo[d]imidazol-2-yl)pyrrolidin-2-one Intermediate E5 (80 mg, 24%) as a glassy white solid;

Example 70: (S)-1-(3,4-difluorophenyl)-5-(5-(3,5-dimethylisoxazol-4-yl)-1-((S)-1,1-dioxidotetrahydrothiophen-3-yl)-1H-benzo[d]imidazol-2-yl)pyrrolidin-2-one (S)-1-(3,4-difluorophenyl)-5-(5-(3,5-dimethylisoxazol-4-yl)-1-((S)-1,1-dioxidotetrahydrothiophen-3-yl)-1H-benzo[d]imidazol-2-yl)pyrrolidin-2-one

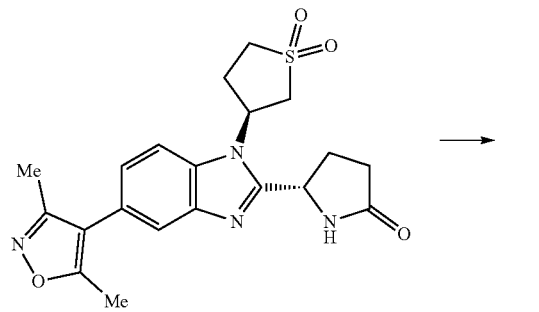

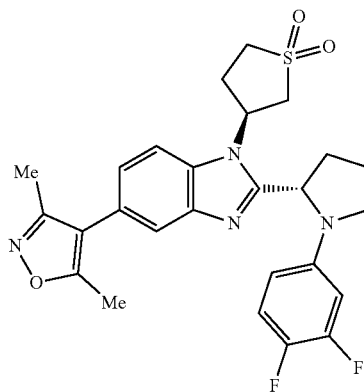

CuTMEDA (13.11 mg, 0.028 mmol) was added to a solution of DBU (29.8 µL, 0.198 mmol), Intermediate E5 (78 mg, 0.188 mmol) and (3,4-difluorophenyl)boronic acid (32.7 mg, 0.207 mmol) in acetonitrile (4 mL) with stirring for 18 h at 40° C. The mixture was concentrated under reduced pressure then purified by flash chromatography on the Companion (12 g column, 0-10% MeOH in DCM, gradient elution) to afford (S)-1-(3,4-difluorophenyl)-5-(5-(3,5-dimethylisoxazol-4-yl)-1-((S)-1,1-dioxidotetrahydrothiophen-3-yl)-1H-benzo[d]imidazol-2-yl)pyrrolidin-2-one (12 mg, 12%) as an off white solid; Rt 1.96 min; m/z 527 (M+H)+ (ES+);

Example 71: Tert-butyl (S)-3-(2-((S)-1-(3,4-difluorophenyl)-5-oxopyrrolidin-2-yl)-5-(3,5-dimethylisoxazol-4-yl)-1H-benzo[d]imidazol-1-yl)pyrrolidine-1-carboxylate Tert-butyl (S)-3-((2-((S)-1-(3,4-difluorophenyl)-5-oxopyrrolidine-2-carboxamido)-4-(3,5-dimethylisoxazol-4-yl)phenyl)amino)pyrrolidine-1-carboxylate (Intermediate D6)

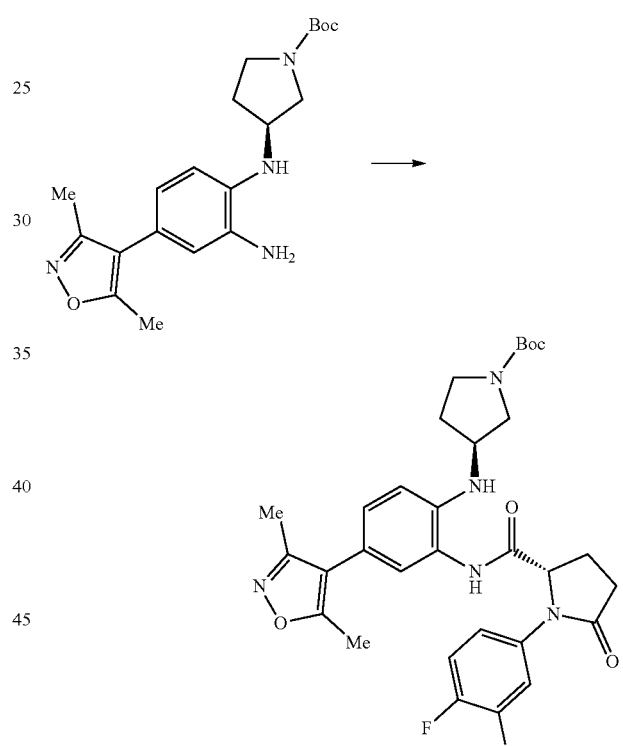

A solution of Intermediate C6 (600 mg, 1.611 mmol), 2-(3H-[1,2,3]triazolo[4,5-b]pyridin-3-yl)-1,1,3,3-tetramethylisouronium hexafluorophosphate(V) (674 mg, 1.772 mmol), (S)-5-oxopyrrolidine-2-carboxylic acid (229 mg, 1.772 mmol) and triethylamine (674 µL, 4.83 mmol) in DMF (5 mL) was stirred at room temperature for 18 h. The mixture was partitioned between DCM (20 mL) and saturated sodium bicarbonate (10 mL). The organic phase was collected and washed sequentially with saturated sodium bicarbonate (10 mL) and water (2×10 mL), then the layers separated through a PhaseSep© cartridge. The organic phase was evaporated in vacuo and to the loose residue was added DCM (2 mL). 1 mL of the solution was removed via pipette and used (after removing the solvent) in 1493-51. The remaining solution was concentrated in vacuo into the crude Intermediate D6 (quantitative yield assumed), which was used without further purification; Rt 1.93 min; m/z 384 (M+H)+ (ES+).

(S)-tert-butyl 3-(5-(3,5-dimethylisoxazol-4-yl)-2-((S)-5-oxopyrrolidin-2-yl)-1H-benzo[d]imidazol-1-yl)pyrrolidine-1-carboxylate (Intermediate E6)

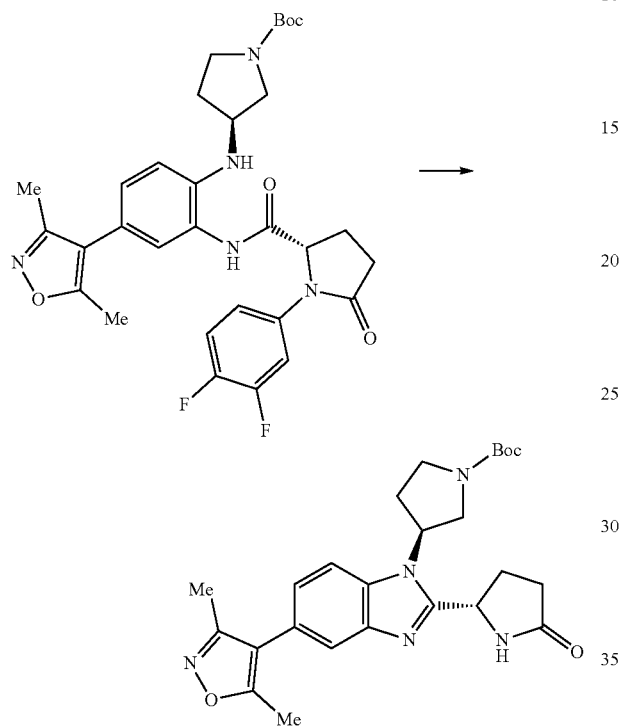

A solution of Intermediate D6 (389 mg, 0.804 mmol) in acetic acid (1 mlL) was heated to 80° C. for 18 h. The solvent was removed in vacuo and the residue was purified by chromatography (12 g silica, 0-10% methanol in DCM, gradient elution) to afford (S)-tert-butyl 3-(5-(3,5-dimethylisoxazol-4-yl)-2-((S)-5-oxopyrrolidin-2-yl)-1H-benzo[d]imidazol-1-yl) pyrrolidine-1-carboxylate Intermediate E6 (54 mg, 14%) as a glass which scratched to a white solid; Rt 1.77 min; m/z 466 (M+H)+ (ES.

Tert-butyl (S)-3-(2-((S)-1-(3,4-difluorophenyl)-5-oxopyrrolidin-2-yl)-5-(3,5-dimethylisoxazol-4-yl)-1H-benzo[d]imidazol-1-yl)pyrrolidine-1-carboxylate

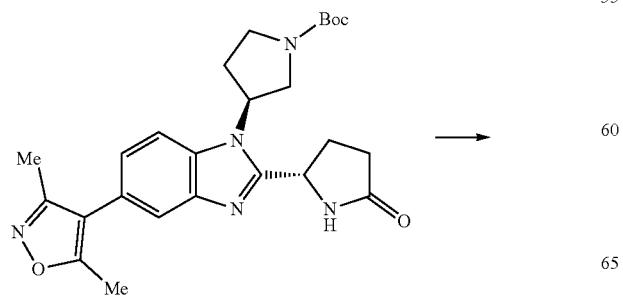

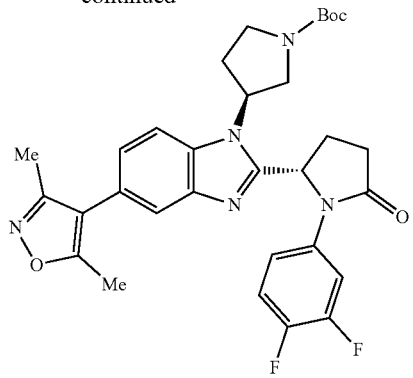

CuTMEDA (7.78 mg, 0.017 mmol) was added to a solution of DBU (17.68 µL, 0.117 mmol), Intermediate E6 (52 mg, 0.112 mmol) and (3,4-difluorophenyl)boronic acid (19.40 mg, 0.123 mmol) in acetonitrile (4 ml) with stirring for 18 h at 40° C. The mixture was concentrated under reduced pressure then purified by flash chromatography on the Companion (12 g column, 0-10% MeOH in DCM, gradient elution) to afford (S)-tert-butyl 3-(2-((S)-1-(3,4-difluorophenyl)-5-oxopyrrolidin-2-yl)-5-(3,5-dimethylisoxazol-4-yl)-1H-benzo[d]imidazol-1-yl)pyrrolidine-1-carboxylate (28 mg, 43%) as an off white solid; Rt 2.36 min; m/z 578 (M+H)+ (ES+); 7.82 (s, 1H), 7.71-7.60 (m, 2H), 7.43-7.31 (m, 1H), 7.27-7.15 (m, 2H), 6.08 (s, 1H), 5.40 (m, 1H), 3.87 (m, 1H), 3.75-3.65 (m, 2H), 3.39 (m, 1H), 2.67-2.53 (m, 2H), 2.36 (s, 3H), 2.33 (m, 1H), 2.19 (s, 3H), 2.13 (m, 1H), 1.45 (d, J=9.6 Hz, 9H). 2H's short Example 72: Tert-butyl (R)-3-(2-((S)-1-(3,4-difluorophenyl)-5-oxopyrrolidin-2-yl)-5-(3,5-dimethylisoxazol-4-yl)-1H-benzo[d]imidazol-1-yl)pyrrolidine-1-carboxylate (R)-tert-butyl 3-((4-(3,5-dimethylisoxazol-4-yl)-2-nitrophenyl)amino)pyrrolidine-1-carboxylate

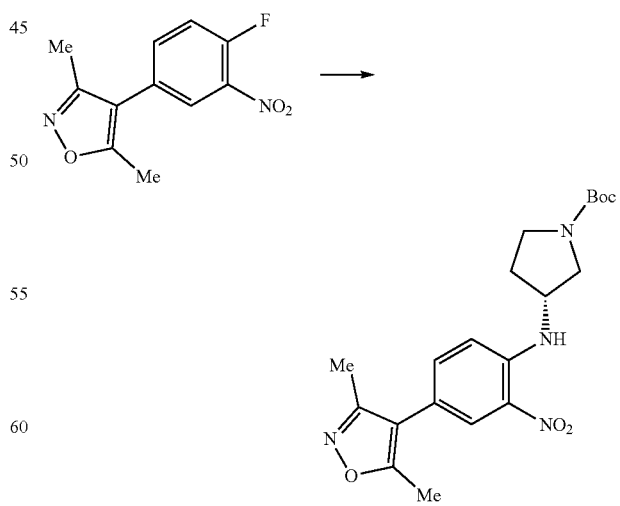

A mixture of Intermediate A (10 g, 42.3 mmol) and (R)-tert-butyl 3-aminopyrrolidine-1-carboxylate (7.89 g, 42.3 mmol) was stirred in dry THF (100 mL) and TEA (17.70 mL, 127 mmol) was added. The reaction was stirred at rt for 18 h, then heated to 40° C. and stirred for 72 h, then heated to 50° C. and stirred for 18 h. After cooling to RT, the reaction mixture was poured into ice water (300 mL). The mixture was extracted with ethyl acetate (2×500 mL). The combined organic extracts were dried (MgSO$_4$) and concentrated in vacuo to afford (R)-tert-butyl-3-((4-(3,5-dimethylisoxazol-4-yl)-2-nitrophenyl)amino)pyrrolidine-1-carboxylate (17.85 g, 96%) as a thick orange oil; Rt 2.48 min; m/z 403 (M+H)+ (ES+).

(R)-tert-butyl 3-((2-amino-4-(3,5-dimethylisoxazol-4-yl)phenyl)amino)pyrrolidine-1-carboxylate

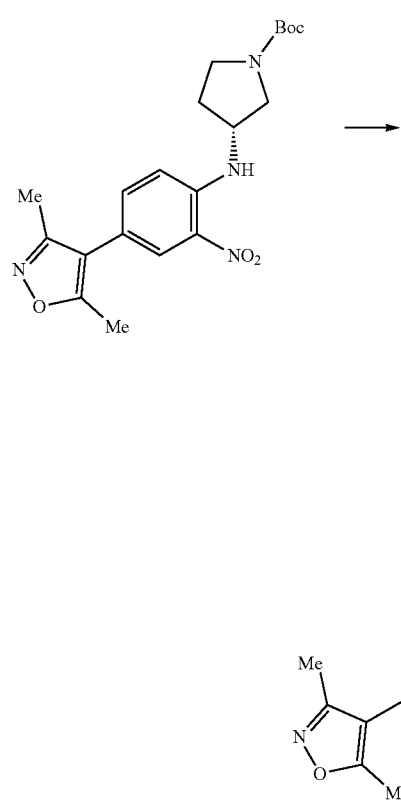

(R)-tert-butyl 3-((4-(3,5-dimethylisoxazol-4-yl)-2-nitrophenyl)amino)pyrrolidine-1-carboxylate (17.04 g, 42.3 mmol) was dissolved in THF/water (1:1, 1,000 mL). Concentrated ammonia (33.0 mL, 847 mmol) and sodium dithionite (73.7 g, 423 mmol) were added and the reaction stirred at RT for 18 h. EtOAc (500 mL) was added, the mixture transferred to a separating funnel and washed sequentially with 1M NaOH (400 mL) and brine (200 mL). The organic phase was dried (MgSO$_4$), filtered and concentrated in vacuo to give a light fluffy solid. The material was triturated with diethyl ether and collected by filtration. The filtrate was concentrated in vacuo to afford a light fluffy peach solid. After LCMS and NMR analysis the triturated material and the material obtained from the filtrate were combined to afford (R)-tert-butyl 3-((2-amino-4-(3,5-dimethylisoxazol-4-yl)phenyl)amino)pyrrolidine-1-carboxylate (13.58 g, 85%) as a light peach fluffy solid; Rt 2.24 min; m/z 372 (M+H)+ (ES+).

(S)—N-(5-(3,5-dimethylisoxazol-4-yl)-2-((4-hydroxycyclohexyl)amino)phenyl)-5-oxopyrrolidine-2-carboxamide

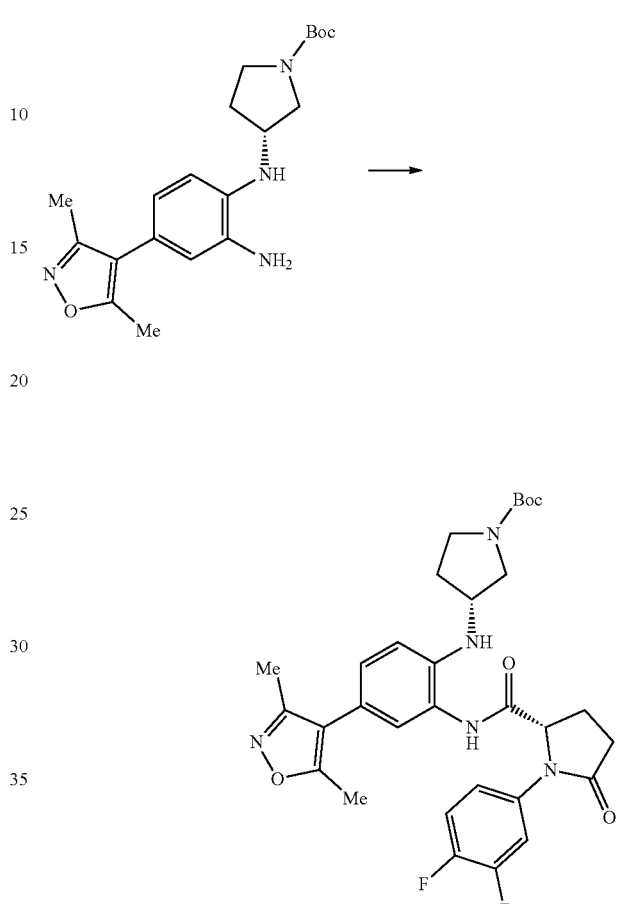

A solution of (R)-tert-butyl 3-((2-amino-4-(3,5-dimethylisoxazol-4-yl)phenyl)amino)pyrrolidine-1-carboxylate (600 mg, 1.611 mmol), 2-(3H-[1,2,3]triazolo[4,5-b]pyridin-3-yl)-1,1,3,3-tetramethylisouronium hexafluorophosphate(V) (674 mg, 1.772 mmol), (S)-5-oxopyrrolidine-2-carboxylic acid (229 mg, 1.772 mmol) and triethylamine (674 µL, 4.83 mmol) in DMF (5 mL) was stirred at room temperature for 18 h. The mixture was partitioned between DCM (20 mL) and saturated sodium bicarbonate (10 mL). The organic phase was collected and washed sequentially with saturated sodium bicarbonate (10 mL) and water (2×10 mL), then the layers separated through a PhaseSep© cartridge. The organic phase was evaporated in vacuo to afford the crude (S)—N-(5-(3,5-dimethylisoxazol-4-yl)-2-((4-hydroxycyclohexyl)amino)phenyl)-5-oxopyrrolidine-2-carboxamide (quantitative yield assumed), which was used without further purification; Rt 1.94 min; m/z 384 (M+H)+ (ES+).

249

(R)-tert-butyl 3-(5-(3,5-dimethylisoxazol-4-yl)-2-((S)-5-oxopyrrolidin-2-yl)-1H-benzo[d]imidazol-1-yl)pyrrolidine-1-carboxylate

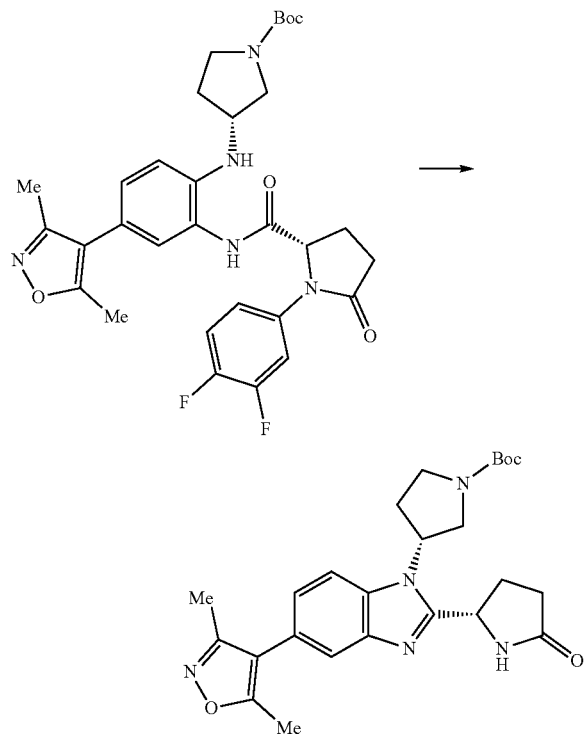

A solution of (S)—N-(5-(3,5-dimethylisoxazol-4-yl)-2-((4-hydroxycyclohexyl)amino)phenyl)-5-oxopyrrolidine-2-carboxamide (342 mg, 0.829 mmol) in acetic acid was heated to 80° C. for 3 h. The solvent was removed in vacuo and the residue was purified by chromatography (12 g silica, 0-10% methanol in DCM, gradient elution) to afford (R)-tert-butyl 3-(5-(3,5-dimethylisoxazol-4-yl)-2-((S)-5-oxopyrrolidin-2-yl)-1H-benzo[d]imidazol-1-yl)pyrrolidine-1-carboxylate (54 mg, 14%) as a glass which scratched to a white solid; Rt 1.77 min; m/z 466 (M+H)+ (ES+).

Tert-butyl (R)-3-(2-((S)-1-(3,4-difluorophenyl)-5-oxopyrrolidin-2-yl)-5-(3,5-dimethylisoxazol-4-yl)-1H-benzo[i]imidazol-1-yl)pyrrolidine-1-carboxylate

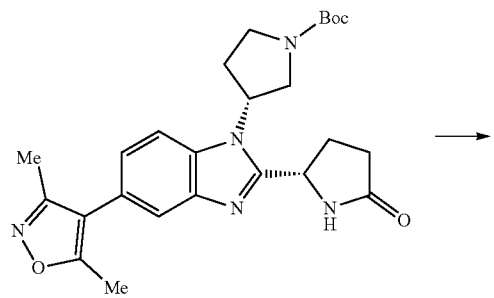

250

-continued

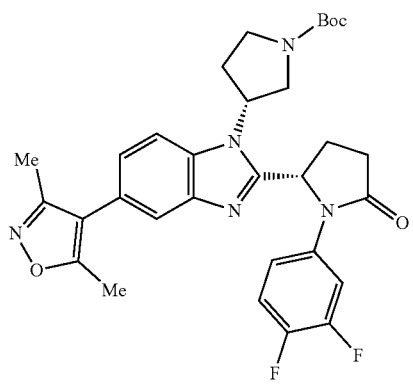

CuTMEDA (7.78 mg, 0.017 mmol) was added to a solution of DBU (17.68 μL, 0.117 mmol), (R)-tert-butyl 3-(5-(3,5-dimethylisoxazol-4-yl)-2-((S)-5-oxopyrrolidin-2-yl)-1H-benzo[d]imidazol-1-yl)pyrrolidine-1-carboxylate (52 mg, 0.112 mmol) and (3,4-difluorophenyl)boronic acid (19.40 mg, 0.123 mmol) in acetonitrile (4 mL) with stirring for 18 h at 40° C. The mixture was concentrated under reduced pressure then purified by chromatography on the Companion (12 g column, 0-10% MeOH in DCM, gradient elution) to afford (R)-tert-butyl 3-(2-((S)-1-(3,4-difluorophenyl)-5-oxopyrrolidin-2-yl)-5-(3,5-dimethylisoxazol-4-yl)-1H-benzo[d]imidazol-1-yl)pyrrolidine-1-carboxylate (28 mg, 43% yield) as an off white solid; Rt 2.38 min; m/z 578 (M+H)+ (ES+); 7.82 (ddd, J=13.1, 7.3, 2.7 Hz, 1H), 7.71-7.60 (m, 2H), 7.38 (dt, J=10.6, 9.2 Hz, 1H), 7.19 (dd, J=8.4, 1.8 Hz, 1H), 6.07 (d, J=8.1 Hz, 1H), 5.46-5.37 (m, 1H), 3.72 (m, 3H), 3.42 (m, 1H), 2.79-2.53 (m, 2H), 2.36 (s, 3H), 2.32 (m, 1H), 2.19 (s, 3H), 2.15 (d, J=10.5 Hz, 1H), 1.44 (d, J=13.6 Hz, 9H).

Example 73: (S)-1-(3,4-difluorophenyl)-5-(5-(3,5-dimethylisoxazol-4-yl)-1-((S)-1-(methylsulfonyl)pyrrolidin-3-yl)-1H-benzo[d]imidazol-2-yl)pyrrolidin-2-one (S)-1-(3,4-difluorophenyl)-5-(5-(3,5-dimethylisoxazol-4-yl)-1-((S)-pyrrolidin-3-yl)-1H-benzo[d]imidazol-2-yl)pyrrolidin-2-one

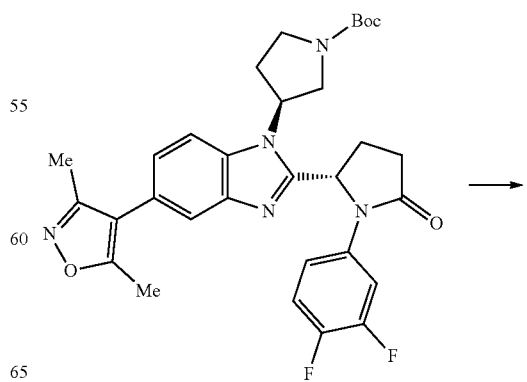

-continued

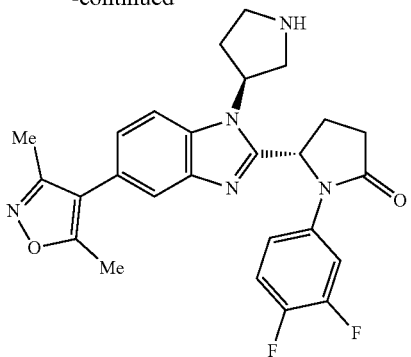

To a solution of (S)-tert-butyl 3-(2-((S)-1-(3,4-difluorophenyl)-5-oxopyrrolidin-2-yl)-5-(3,5-dimethylisoxazol-4-yl)-1H-benzo[d]imidazol-1-yl)pyrrolidine-1-carboxylate (26 mg, 0.045 mmol) in DCM (5 ml) and TFA (1 ml) was stirred at rt for 1 h. The solvents were removed in vacuo to afford (S)-1-(3,4-difluorophenyl)-5-(5-(3,5-dimethylisoxazol-4-yl)-1-((S)-pyrrolidin-3-yl)-1H-benzo[d]imidazol-2-yl)pyrrolidin-2-one (22 mg, 0.046 mmol, 102% yield) as a smear on the inside of the scintillation vial; Rt 1.31 min; m/z 478 (M+H)+ (ES+);

(S)-1-(3,4-difluorophenyl)-5-(5-(3,5-dimethylisoxazol-4-yl)-1-((S)-1-(methylsulfonyl)pyrrolidin-3-yl)-1H-benzo[d]imidazol-2-yl)pyrrolidin-2-one To a solution of (S)-1-(3,4-difluorophenyl)-5-(5-(3,5-dimethylisoxazol-4-yl)-1-((S)-pyrrolidin-3-yl)-1H-benzo[d]imidazol-2-yl)pyrrolidin-2-one (21 mg, 0.044 mmol) and methanesulfonyl chloride (3.74 µL, 0.048 mmol) in DCM (2 mL) was added DIPEA (15.36 µL, 0.088 mmol). The reaction mixture was stirred at RT for 18 h, then DIPEA (38.4 µL, 0.220 mmol) and methanesulfonyl chloride (6.81 µL, 0.088 mmol) were added. After stirring for 1 h, the reaction was diluted with DCM (10 mL) and washed with 0.2M aqueous hydrochloric acid (5 mL). The organic phase was collected via PhaseSep© cartridge and concentrated in vacuo. The residue was purified by chromatography (4 g silica, 0-10% methanol in DCM, gradient elution). Product fractions were concentrated in vacuo and the residue triturated with ether to afford (S)-1-(3,4-difluorophenyl)-5-(5-(3,5-dimethylisoxazol-4-yl)-1-((S)-1-(methylsulfonyl) pyrrolidin-3-yl)-1H-benzo[d]imidazol-2-yl)pyrrolidin-2-one (13 mg, 53%) as a white solid; Rt 1.96 min; m/z 556 (M+H)+ (ES+); 1H NMR (400 MHz, DMSO-d6) δ 7.90-7.73 (m, 2H), 7.64 (d, J=1.6 Hz, 1H), 7.44-7.30 (m, 1H), 7.24 (ddd, J=11.3, 8.1, 1.5 Hz, 2H), 6.11-6.04 (m, 1H), 5.47 (p, J=8.6 Hz, 1H), 3.83 (dd, J=10.5, 8.8 Hz, 1H), 3.70 (dd, J=10.4, 7.0 Hz, 2H), 3.47-3.28 (m, 2H), 3.10 (d, J=6.1 Hz, 3H), 2.75-2.51 (m, 2H), 2.46 (m, 2H), 2.37 (s, 3H), 2.20 (s, 3H), 2.11 (m, 1H).

Example 74: (S)-5-(1-((R)-1-(cyclopropylsulfonyl)pyrrolidin-3-yl)-5-(3,5-dimethylisoxazol-4-yl)-1H-benzo[d]imidazol-2-yl)-1-(3,4-difluorophenyl) pyrrolidin-2-one (S)-1-(3,4-difluorophenyl)-5-(5-(3,5-dimethylisoxazol-4-yl)-1-((R)-pyrrolidin-3-yl)-1H-benzo[d]imidazol-2-yl)pyrrolidin-2-one

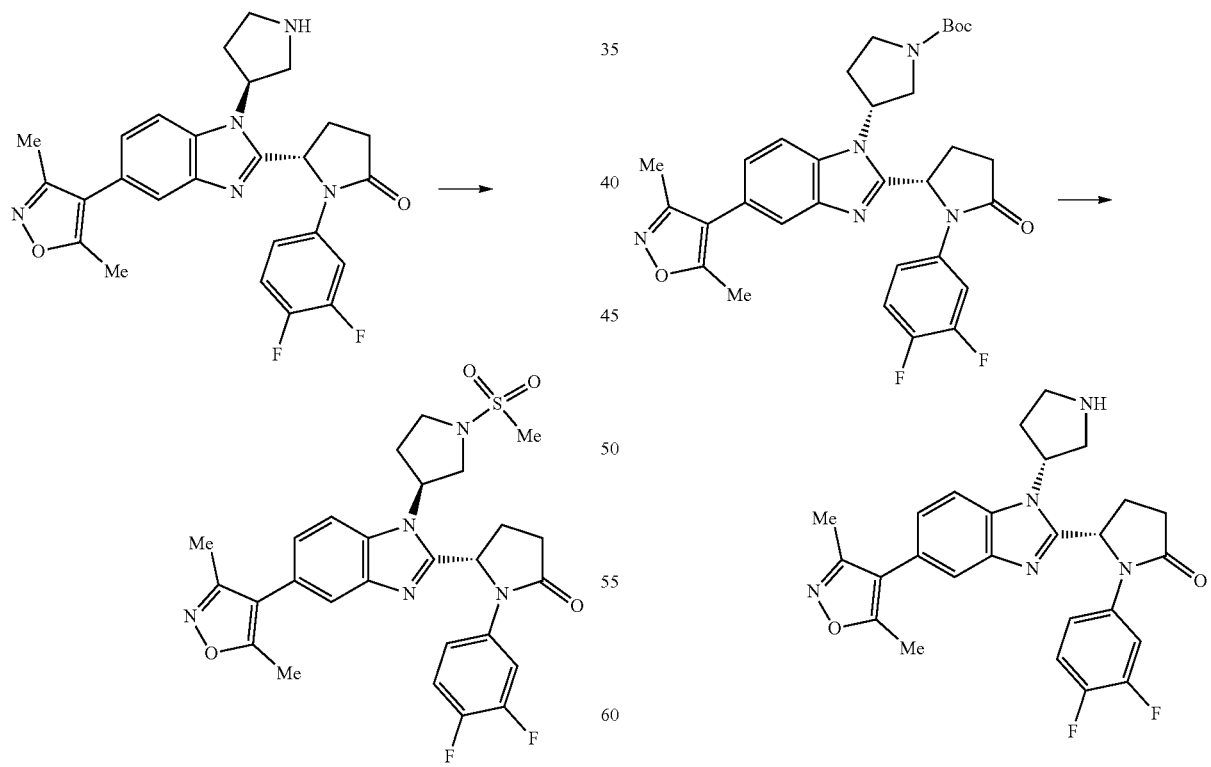

To a solution of (R)-tert-butyl 3-(2-((S)-1-(3,4-difluorophenyl)-5-oxopyrrolidin-2-yl)-5-(3,5-dimethylisoxazol-4-yl)-1H-benzo[d]imidazol-1-yl)pyrrolidine-1-carboxylate (29 mg, 0.050 mmol) in DCM (5 mL) and TFA (1 mL) was stirred at RT for 1 h. The solvents were removed in vacuo to afford (S)-1-(3,4-difluorophenyl)-5-(5-(3,5-dimethylisoxazol-4-yl)-1-((R)-pyrrolidin-3-yl)-1H-benzo[d]imidazol-2-yl)pyrrolidin-2-one (24 mg, 100% yield) as a smear on the inside of the scintillation vial; Rt 1.35 min; m/z 478 (M+H)+ (ES+).

(S)-5-(1-((R)-1-(cyclopropylsulfonyl) pyrrolidin-3-yl)-5-(3,5-dimethylisoxazol-4-yl)-1H-benzo[d]imidazol-2-yl)-1-(3,4-difluorophenyl) pyrrolidin-2-one

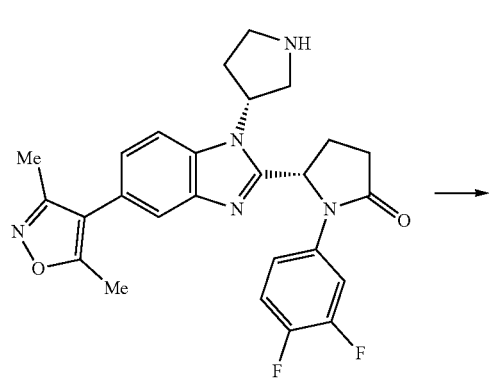

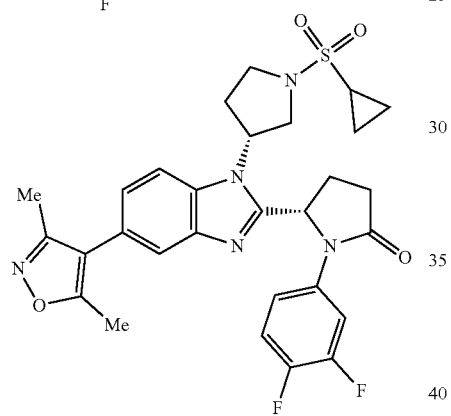

To a solution of (S)-1-(3,4-difluorophenyl)-5-(5-(3,5-dimethylisoxazol-4-yl)-1-((R)-pyrrolidin-3-yl)-1H-benzo[d]imidazol-2-yl)pyrrolidin-2-one (24 mg, 0.050 mmol) and cyclopropanesulfonyl chloride (5.63 µl, 0.055 mmol) in DCM (2 mL) was added DIPEA (17.56 µl, 0.101 mmol). The reaction mixture was stirred at RT for 18 h. The reaction mixture was stirred at RT for 18 h, then DIPEA (43.9 µl, 0.251 mmol) and cyclopropanesulfonyl chloride (10.24 µl, 0.101 mmol) were added. After stirring for 1 h, the reaction was diluted with DCM (10 mL) and washed with 0.2M aqHCl (5 mL). The organic phase was collected via phase sep cartridge and concentrated in vacuo. The residue was purified by chromatography (4 g silica, 0-10% methanol in DCM, gradient elution). Product fractions were concentrated in vacuo and the residue triturated with ether to afford (S)-5-(1-((R)-1-(cyclopropylsulfonyl)pyrrolidin-3-yl)-5-(3,5-dimethylisoxazol-4-yl)-1H-benzo[d]imidazol-2-yl)-1-(3,4-difluorophenyl)pyrrolidin-2-one (8 mg, 27%) as a white solid; Rt 2.10 min; m/z 582 (M+H)+ (ES+); 1H NMR (400 MHz, DMSO-d6) δ 7.82 (ddd, J=13.2, 7.4, 2.7 Hz, 1H), 7.75 (d, J=8.4 Hz, 1H), 7.65 (d, J=1.6 Hz, 1H), 7.44-7.30 (m, 1H), 7.30-7.17 (m, 2H), 6.07 (dd, J=10.5, 8.1 Hz, 1H), 5.52 (t, J=8.0 Hz, 1H), 3.93-3.65 (m, 3H), 3.46 (q, J=8.8 Hz, 1H), 2.96-2.83 (m, 1H), 2.77-2.44 (m, 4H), 2.37 (s, 3H), 2.20 (m, 4H), 2.20-2.06 (m, 1H), 1.09 (s, 1H), 1.10-0.97 (m, 3H).

Example 75: (S)-5-(1-((R)-1-acetylpyrrolidin-3-yl)-5-(3,5-dimethylisoxazol-4-yl)-1H-benzo[d]imidazol-2-yl)-1-(3,4-difluorophenyl)pyrrolidin-2-one (S)-5-(1-((R)-1-acetylpyrrolidin-3-yl)-5-(3,5-dimethylisoxazol-4-yl)-1H-benzo[d]imidazol-2-yl)-1-(3,4-difluorophenyl)pyrrolidin-2-one

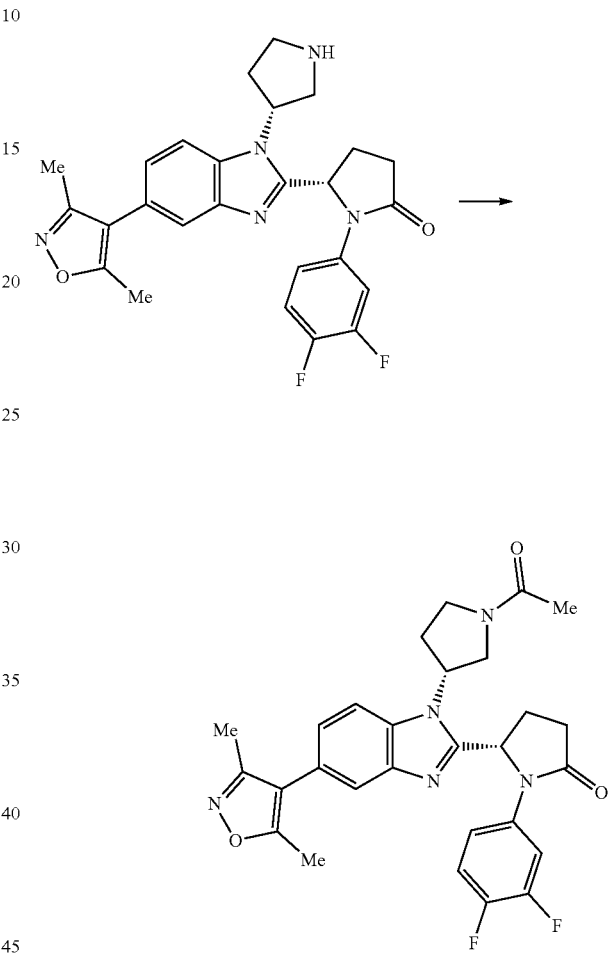

Acetyl chloride (8.11 µL, 0.114 mmol) was added to a solution of (S)-1-(3,4-difluorophenyl)-5-(5-(3,5-dimethylisoxazol-4-yl)-1-((R)-pyrrolidin-3-yl)-1H-benzo[d]imidazol-2-yl)pyrrolidin-2-one (66 mg, 0.104 mmol) and DIPEA (0.036 ml, 0.207 mmol) in DCM (3 ml). The reaction was stirred for 16 hours, water (3 ml) was added and the phases separated. The organic layer was dried (MgSO4), filtered and concentrated in vacuo. The crude product was purified by chromatography on the Companion (40 g column, 0-10% MeOH/DCM) and further purified by preparative HPLC (Waters, Acidic (0.1% Formic acid) Waters X-Select Prep-C18, 5 µm, 19×50 mm column, 15-35% MeCN in Water) to afford (S)-5-(1-((R)-1-acetylpyrrolidin-3-yl)-5-(3,5-dimethylisoxazol-4-yl)-1H-benzo[d]imidazol-2-yl)-1-(3,4-difluorophenyl)pyrrolidin-2-one (10 mg, 18%) as a light white solid; Rt 1.80 min (method 1), m/z 520 (M+H)+ (ES+); 1H NMR (d6-DMSO) δ: 7.73-7.55 (m, 3H), 7.36-7.14 (m, 3H), 6.02-5.94 (m, 1H), 5.48-5.38 (m, 1H), 3.90 (m, 3H), 3.56 (m, 1H), 2.86-2.63 (m, 2H), 2.61-2.50 (m, 1H), 2.37 (s, 3H), 2.23-2.17 (1H, m) 2.19 (s, 3H), 2.04 (s, 3H).

Example 76: (S)-1-(3,4-difluorophenyl)-5-(5-(3,5-dimethylisoxazol-4-yl)-1-((R)-1-(3,3,3-trifluoropropanoyl)pyrrolidin-3-yl)-1H-benzo[d]imidazol-2-yl)pyrrolidin-2-one (S)-1-(3,4-difluorophenyl)-5-(5-(3,5-dimethylisoxazol-4-yl)-1-((R)-1-(3,3,3-trifluoropropanoyl)pyrrolidin-3-yl)-1H-benzo[d]imidazol-2-yl)pyrrolidin-2-one

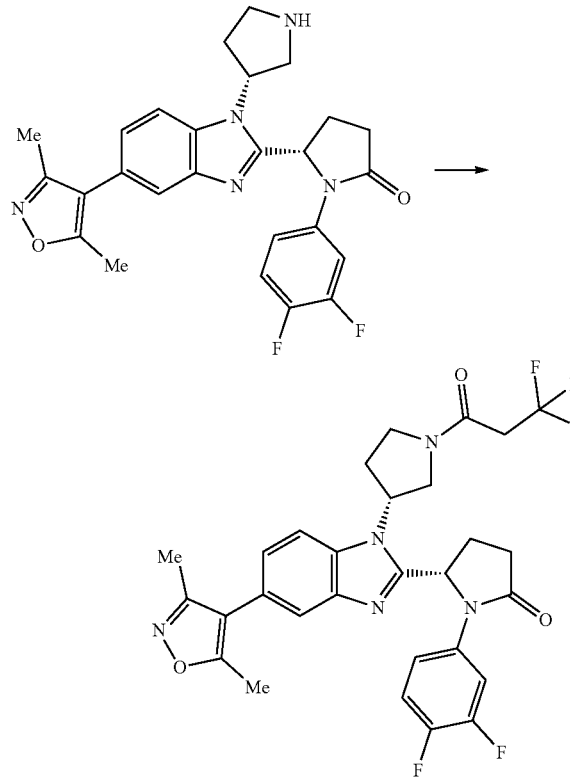

Example 77: (5S)-1-(3,4-difluorophenyl)-5-(5-(3,5-dimethylisoxazol-4-yl)-1-(1-methylpyrrolidin-3-yl)-1H-benzo[d]imidazol-2-yl)pyrrolidin-2-one (2S)—N-(5-(3,5-dimethylisoxazol-4-yl)-2-((1-methylpyrrolidin-3-yl)amino)phenyl)-5-oxo pyrrolidine-2-carboxamide

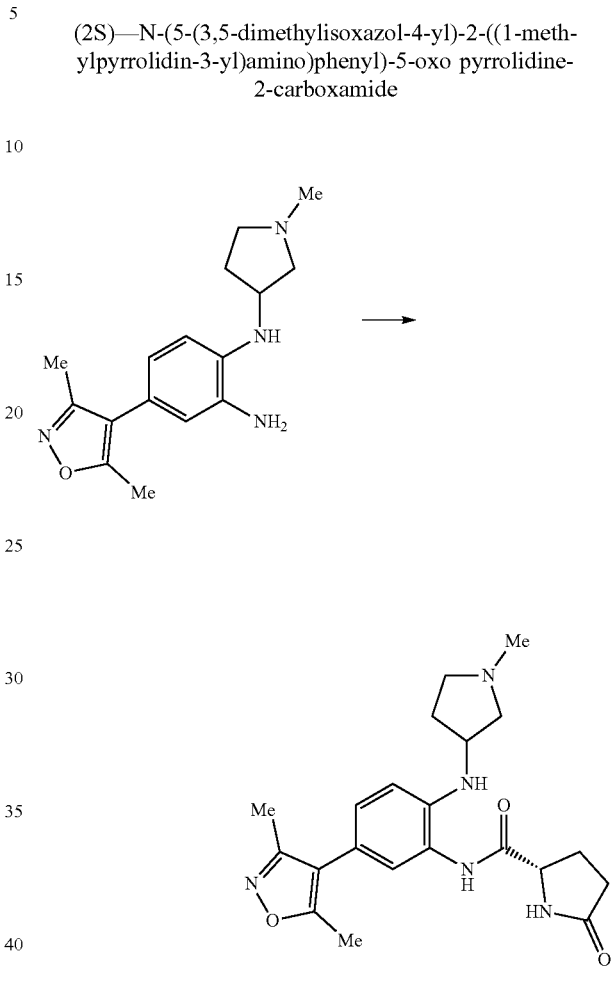

DIPEA (0.057 mL, 0.328 mmol) was added to a solution of 3,3,3-trifluoropropanoic acid (0.016 ml, 0.180 mmol), HATU (81 mg, 0.213 mmol) and (S)-1-(3,4-difluorophenyl)-5-(5-(3,5-dimethylisoxazol-4-yl)-1-((R)-pyrrolidin-3-yl)-1H-benzo[d]imidazol-2-yl)pyrrolidin-2-one (89 mg, 0.164 mmol) in DMF (2 ml, 25.8 mmol) stirred at RT for 3 h. The reaction mixture was diluted with EtOAc (10 ml) and washed with water (5 ml). The organic layer was separated and then dried over MgSO$_4$, filtered and concentrated in vacuo. The crude product was purified by flash chromatography on the Companion (40 g column, 0-10% MeOH/DCM) and further purified by preparative HPLC (Varian, Acidic (0.1% Formic acid), Acidic, Waters X-Select Prep-C18, 5 μm, 19×50 mm column, 5-50% MeCN in Water) to afford (S)-1-(3,4-difluorophenyl)-5-(5-(3,5-dimethylisoxazol-4-yl)-1-((R)-1-(3,3,3-trifluoropropanoyl)pyrrolidin-3-yl)-1H-benzo[d]imidazol-2-yl)pyrrolidin-2-one (5 mg, 5%) as white solid; Rt 2.09 min (method 1), m/z 588 (M+H)+ (ES+); 1H NMR (d6-DMSO) δ: 7.75-7.55 (m, 3H), 7.35-7.15 (m, 3H), 5.98 (d, J=7.8 Hz, 1H), 5.45 (m, 1H), 3.96 (m, 3H), 3.54 (m, 3H), 2.85-2.5 (m, 6H), 2.36 (s, 3H), 2.19 (s, 3H).

HATU (1.111 g, 2.92 mmol) was added to a solution of 4-(3,5-dimethylisoxazol-4-yl)-N1-(1-methylpyrrolidin-3-yl)benzene-1,2-diamine (0.82 g, 2.86 mmol), (S)-5-oxopyrrolidine-2-carboxylic acid (0.373 g, 2.89 mmol) and DIPEA (0.545 ml, 3.12 mmol) in N,N-dimethylformamide (5 mL) then stirred at room temperature for 18 h. The mixture was diluted with 30% brine solution (100 mL) then extracted with ethyl acetate (3×75 mL). The aqueous layer was concentrated in vacuo to give a yellow solid. The solid was sonicated in DCM (100 mL)/MeOH (100 mL). The suspension was filtered and the liquor was concentrated in vacuo to give a yellow sticky oil (2.7 g), which was supported on silica. The crude was purified by chromatography column (12 g, DCM/10% NH3/MeOH in DCM: 100/0 to 0/100 to give (2S)—N-(5-(3,5-dimethylisoxazol-4-yl)-2-((1-methylpyrrolidin-3-yl)amino)phenyl)-5-oxo pyrrolidine-2-carboxamide (0.68 g, 59%) was isolated as a sticky gum; Rt 0.81 min (method 1), m/z 398 (M+H)+ (ES+).

(5S)-5-(5-(3,5-dimethylisoxazol-4-yl)-1-(1-methyl-pyrrolidin-3-yl)-1H-benzo[d]imidazol-2-yl)pyrrolidin-2-one

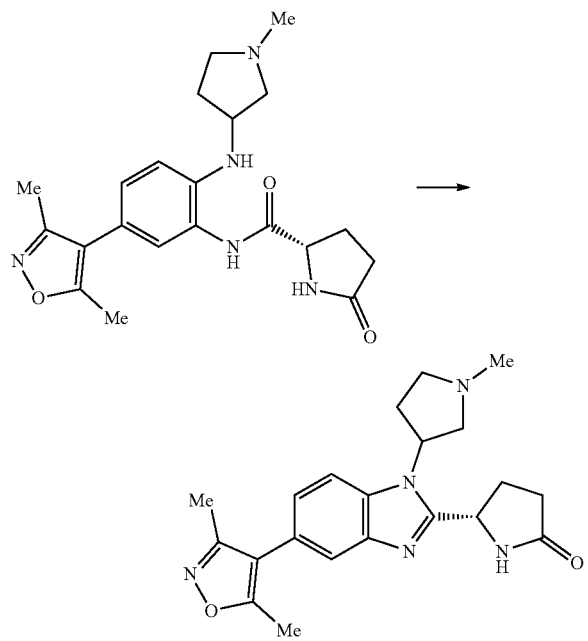

(2S)—N-(5-(3,5-dimethylisoxazol-4-yl)-2-((1-methyl-pyrrolidin-3-yl)amino)phenyl)-5-oxopyrrolidine-2-carboxamide (0.68 g, 1.711 mmol) was dissolved in acetic acid (6.86 mL, 120 mmol) and stirred at 70° C. for 15 h. The reaction was cooled down to RT. and concentrated in vacuo to give a brown oil. The oil was dissolved in DCM (20 mL) and washed with aqueous sodium bicarbonate solution (20 mL). The aqueous layer was extracted with DCM (20 mL). The organic extracts were combined and concentrated in vacuo to give a brown oil (0.73 g), which was purified by flash chromatography (4 g, 0-10% MeOH in DCM) to give (5S)-5-(5-(3,5-dimethylisoxazol-4-yl)-1-(1-methylpyrrolidin-3-yl)-1H-benzo[d]imidazol-2-yl)pyrrolidin-2-one (0.38 g, 53%) as a beige foam; Rt 0.83 min (method 1), m/z 380 (M+H)+ (ES+).

(5S)-1-(3,4-difluorophenyl)-5-(5-(3,5-dimethylisoxazol-4-yl)-1-(1-methylpyrrolidin-3-yl)-1H-benzo[d]imidazol-2-yl)pyrrolidin-2-one -continued

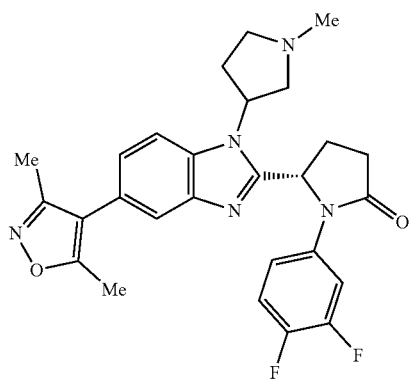

CuTMEDA (9.18 mg, 0.020 mmol) was added to a solution of DBU (0.021 mL, 0.138 mmol), (5S)-5-(5-(3,5-dimethylisoxazol-4-yl)-1-(1-methylpyrrolidin-3-yl)-1H-benzo[d]imidazol-2-yl) pyrrolidin-2-one Intermediate E7 (50 mg, 0.132 mmol) and (3,4-difluorophenyl)boronic acid (22.89 mg, 0.145 mmol) in acetonitrile (3.99 mL, 76 mmol) with stirring for 15 h at 40° C. The reaction mixture was cooled down to RT, then concentrated under reduced pressure and purified by flash chromatography on the Companion (12 g column, 0-10% MeOH in DCM, gradient elution) to afford (5S)-1-(3,4-difluorophenyl)-5-(5-(3,5-dimethyl-isoxazol-4-yl)-1-(1-methylpyrrolidin-3-yl)-1H-benzo[d]imidazol-2-yl)pyrrolidin-2-one (20.8 mg, 31%) as an off white foam; Rt 1.25 min (method 1), m/z 492 (M+H)+ (ES+); 1H NMR (d6-DMSO) δ: 8.13 (d, 1H), 7.86-7.72 (m, 1H), 7.59 (s, 1H), 7.44-7.31 (m, 1H), 7.25-7.16 (m, 2H), 6.16-6.07 (m, 1H), 5.43-5.30 (m, 1H), 3.21-3.05 (m, 2H), 2.81-2.53 (m, 4H), 2.47-2.26 (s+m, 8H), 2.20 (s, 3H), 2.17-2.01 (m, 2H).

Example 78: (5S)-1-(4-chloro-3-fluorophenyl)-5-(5-(3,5-dimethylisoxazol-4-yl)-1-(1-methylpyrrolidin-3-yl)-1H-benzo[d]imidazol-2-yl)pyrrolidin-2-one

(5S)-1-(4-chloro-3-fluorophenyl)-5-(5-(3,5-dimethylisoxazol-4-yl)-1-(1-methylpyrrolidin-3-yl)-1H-benzo[d]imidazol-2-yl)pyrrolidin-2-one

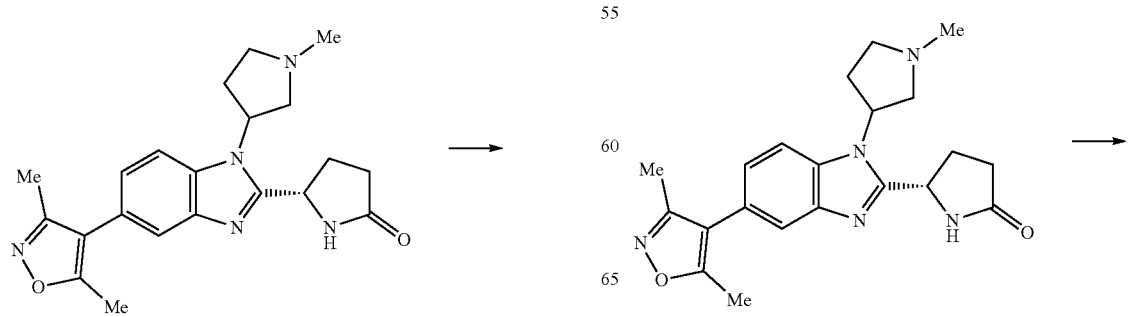

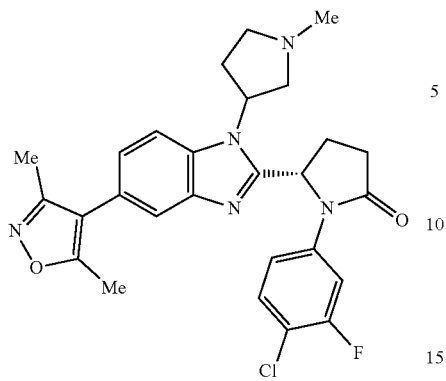

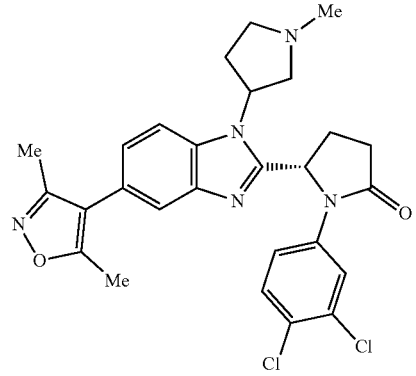

CuTMEDA (9.18 mg, 0.020 mmol) was added to a solution of DBU (0.021 mL, 0.138 mmol), (5S)-5-(5-(3,5-dimethylisoxazol-4-yl)-1-(1-methylpyrrolidin-3-yl)-1H-benzo[d]imidazol-2-yl)pyrrolidin-2-one (50 mg, 0.132 mmol) and (4-chloro-3-fluorophenyl)boronic acid (25.3 mg, 0.145 mmol) in acetonitrile (3.99 mL, 76 mmol) with stirring for 15 h at 40° C. The reaction mixture was cooled down to RT and concentrated under reduced pressure then purified by chromatography on the Companion (12 g column, 0-10% MeOH in DCM, gradient elution) to afford (5S)-1-(4-chloro-3-fluorophenyl)-5-(5-(3,5-dimethylisoxazol-4-yl)-1-(1-methylpyrrolidin-3-yl)-1H-benzo[d]imidazol-2-yl)pyrrolidin-2-one (33.8 mg, 49%) as an off white foam; Rt 1.36 min (method 1), m/z 508 (M+H)+ (ES+); 1H NMR (d6-DMSO) δ: 8.13 (dd, J=25.6, 8.5 Hz, 1H), 7.81 (ddd, J=12.4, 10.1, 2.5 Hz, 1H), 7.61-7.56 (m, 1H), 7.56-7.46 (m, 1H), 7.32-7.25 (m, 1H), 7.21 (dd, J=8.4, 1.7 Hz, 1H), 6.19-6.11 (m, 1H), 5.43-5.33 (m, 1H), 3.24-3.06 (m, 2H), 2.80-2.52 (m, 4H), 2.45-2.28 (m, 7H), 2.19 (s, 3H), 2.16-2.01 (m, 2H).

Example 79: (5S)-1-(3,4-dichlorophenyl)-5-(5-(3,5-dimethylisoxazol-4-yl)-1-(1-methylpyrrolidin-3-yl)-1H-benzo[d]imidazol-2-yl)pyrrolidin-2-one (5S)-1-(3,4-dichlorophenyl)-5-(5-(3,5-dimethylisoxazol-4-yl)-1-(1-methylpyrrolidin-3-yl)-1H-benzo[d]imidazol-2-yl)pyrrolidin-2-one CuTMEDA (9.18 mg, 0.020 mmol) was added to a solution of DBU (0.021 mL, 0.138 mmol), (5S)-5-(5-(3,5-dimethylisoxazol-4-yl)-1-(1-methylpyrrolidin-3-yl)-1H-benzo[d]imidazol-2-yl)pyrrolidin-2-one (50 mg, 0.132 mmol) and (3,4-dichlorophenyl)boronic acid (27.7 mg, 0.145 mmol) in acetonitrile (3.99 mL, 76 mmol) with stirring for 15 h at 40° C. The reaction mixture was cooled down to RT, concentrated under reduced pressure then purified by flash chromatography on the Companion (12 g column, 0-10% MeOH in DCM, gradient elution) to afford (5S)-1-(3,4-dichlorophenyl)-5-(5-(3,5-dimethylisoxazol-4-yl)-1-(1-methylpyrrolidin-3-yl)-1H-benzo[d]imidazol-2-yl)pyrrolidin-2-one (31 mg, 43%) as a yellowish solid; Rt 1.42 min (method 1), m/z 524 (M+H)+ (ES+); 1H NMR (d6-DMSO) δ: 8.13 (dd, J=16.9, 8.4 Hz, 1H), 8.00 (dd, J=2.6 Hz, 1H), 7.60-7.53 (d+dd, 2H), 7.43 (ddd, J=18.4, 8.9, 2.6 Hz, 1H), 7.21 (dd, J=8.5, 1.7 Hz, 1H), 6.21-6.16 (m, 1H), 5.43-5.36 (m, 1H), 3.24-3.07 (m, 2H), 2.79-2.52 (m, 4H), 2.45-2.27 (m, 8H), 2.20 (s, 3H), 2.17-2.01 (m, 2H).

Example 80: (S)-1-(3,4-difluorophenyl)-5-(5-(3,5-dimethylisoxazol-4-yl)-1-(((1r,4S)-4-methoxycyclohexyl)-1H-benzo[d]imidazol-2-yl)pyrrolidin-2-one (S)—N-(5-(3,5-dimethylisoxazol-4-yl)-2-(((1r,4S)-4-methoxycyclohexyl)amino)phenyl)-5-oxopyrrolidine-2-carboxamide (Intermediate D8)

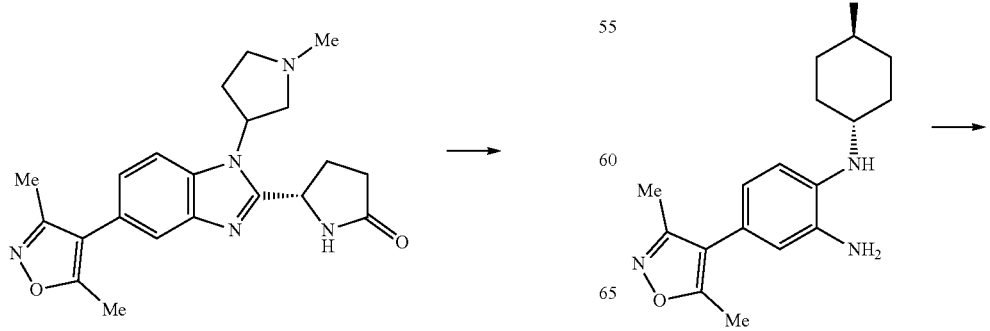

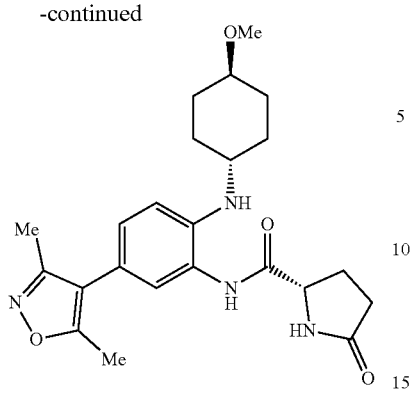

A solution of Intermediate C8 (680 mg, 2.156 mmol), 2-(3H-[1,2,3]triazolo[4,5-b]pyridin-3-yl)-1,1,3,3-tetramethyl isouronium hexafluorophosphate(V) (902 mg, 2.372 mmol), (S)-5-oxopyrrolidine-2-carboxylic acid (306 mg, 2.372 mmol) and triethylamine (901 μL, 6.47 mmol) in DMF (20 mL) was stirred at room temperature for 3 h. The mixture was partitioned between ethyl acetate (200 mL) and water (100 mL), then the layers separated. The organic phase was washed with water (100 mL), passed through a PhaseSep© cartridge and evaporated in vacuo to afford (S)—N-(5-(3,5-dimethylisoxazol-4-yl)-2-(((1r,4S)-4-methoxycyclohexyl)amino)phenyl)-5-oxo pyrrolidine-2-carboxamide Intermediate D8 (0.96 g, quantitative yield) as a crude residue, which was used without further purification; Rt 1.65 min (method 1), m/z 427 (M+H)+ (ES+).

(S)-5-(5-(3,5-dimethylisoxazol-4-yl)-1-((1r,4S)-4-methoxycyclohexyl)-1H-benzo[d]imidazol-2-yl)pyrrolidin-2-one (Intermediate E8)

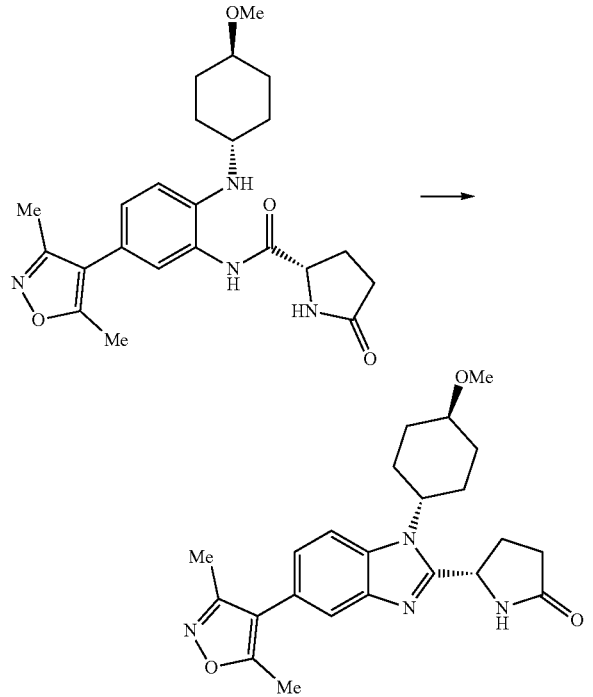

A solution of Intermediate D8 (0.92 g, 2.157 mmol) in acetic acid (1 mL) was heated to 80° C. for 18 h. The solvent was removed in vacuo and the residue was purified by chromatography (12 g silica, 0-10% methanol in DCM, gradient elution) to afford (S)-5-(5-(3,5-dimethylisoxazol-4-yl)-1-((1r,4S)-4-methoxycyclohexyl)-1H-benzo[d]imidazol-2-yl) pyrrolidin-2-one Intermediate E8 (480 mg, 52%) as a glass which scratched to an orange solid; Rt 1.41 min (method 1), m/z 409 (M+H)+ (ES+).

(S)-1-(3,4-difluorophenyl)-5-(5-(3,5-dimethylisoxazol-4-yl)-1-((1r,4S)-4-methoxycyclohexyl)-1H-benzo[d]imidazol-2-yl)pyrrolidin-2-one

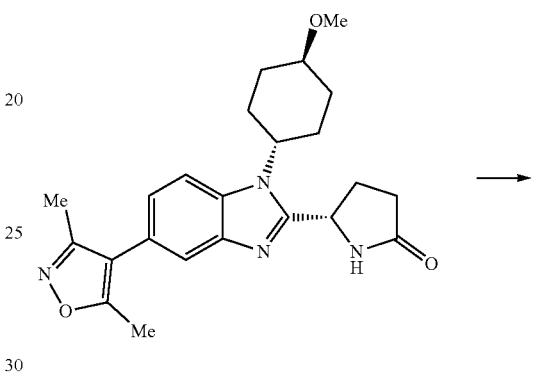

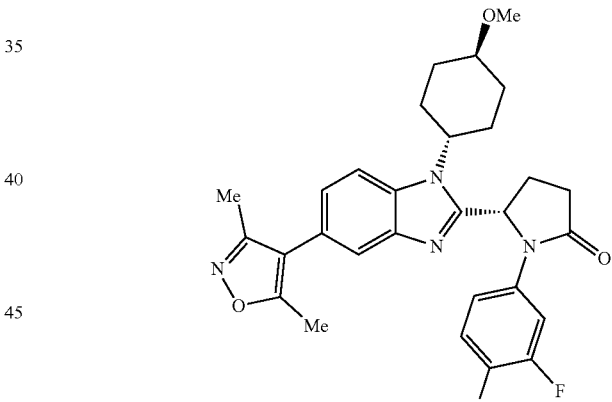

CuTMEDA (8.53 mg, 0.018 mmol)) was added to a solution of DBU (19.37 μL, 0.129 mmol), Intermediate E8 (50 mg, 0.122 mmol) and (3,4-difluorophenyl)boronic acid (21.26 mg, 0.135 mmol) in acetonitrile (4 ml) with stirring for 18 h at 40° C. The mixture was concentrated under reduced pressure. The residue was taken up in the minimum of DCM, passed through a syringe filter and the solution purified by chromatography on the Companion (4 g column, 0-10% MeOH in DCM, gradient elution) to afford (S)-1-(3,4-difluorophenyl)-5-(5-(3,5-dimethylisoxazol-4-yl)-1-((1r,4S)-4-methoxycyclohexyl)-1H-benzo[d]imidazol-2-yl)pyrrolidin-2-one (33 mg, 51%) as an off white solid; Rt 2.16 min (method 1), m/z 521 (M+H)+ (ES+); 1H NMR (d6-DMSO) δ: 7.77 (d, J=8.7 Hz, 1H), 7.67 (m, 1H), 7.54 (s, 1H), 7.29 (d, J=9.7 Hz, 1H), 7.15 (m, 2H), 5.98 (s, 1H), 4.51 (s, 1H), 3.45 (s, 1H), 2.92 (s, 4H), 2.37 (s, 5H), 2.20 (s, 7H), 1.79 (s, 2H), 1.48 (m, 3H).

Example 81: (S)-1-(3,4-dichlorophenyl)-5-(5-(3,5-dimethylisoxazol-4-yl)-1-((1r,4S)-4-methoxycyclohexyl)-1H-benzo[d]imidazol-2-yl)pyrrolidin-2-one (S)-1-(3,4-dichlorophenyl)-5-(5-(3,5-dimethylisoxazol-4-yl)-1-((1r,4S)-4-methoxycyclohexyl)-1H-benzo[d]imidazol-2-yl)pyrrolidin-2-one

Example 82: (S)-1-(3-chloro-4-methoxyphenyl)-5-(5-(3,5-dimethylisoxazol-4-yl)-1-((1r,4S)-4-methoxycyclohexyl)-1H-benzo[d]imidazol-2-yl)pyrrolidin-2-one (S)-1-(3-chloro-4-methoxyphenyl)-5-(5-(3,5-dimethylisoxazol-4-yl)-1-((1r,4S)-4-methoxycyclohexyl)-1H-benzo[d]imidazol-2-yl)pyrrolidin-2-one

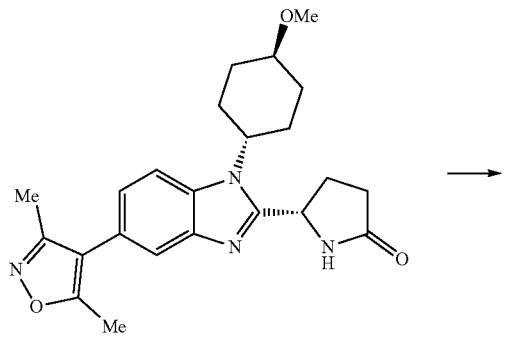

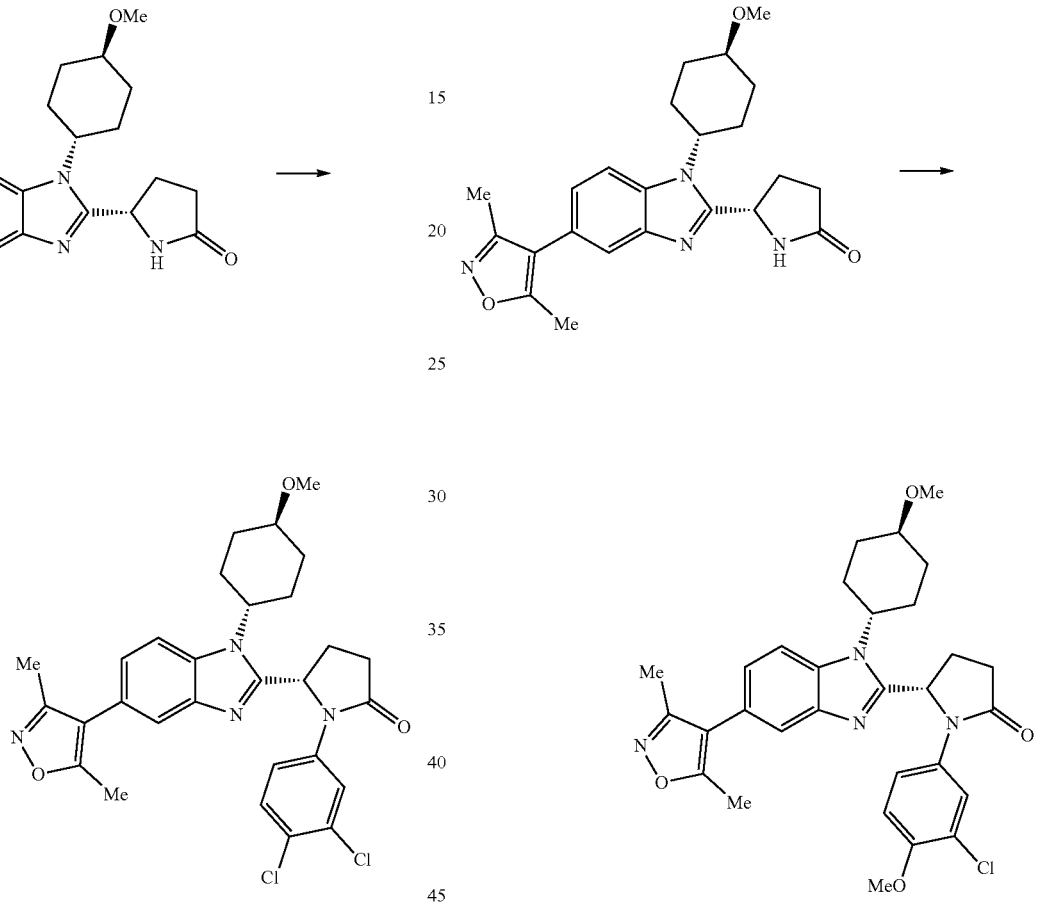

CuTMEDA (8.53 mg, 0.018 mmol) was added to a solution of DBU (19.37 μl, 0.129 mmol), Intermediate E8 (50 mg, 0.122 mmol) and (3,4-dichlorophenyl)boronic acid (25.7 mg, 0.135 mmol) in acetonitrile (4 ml) with stirring for 18 h at 40° C. The mixture was concentrated under reduced pressure. The residue was taken up in the minimum of DCM, passed through a syringe filter and the solution purified by chromatography on the Companion (12 g column, 0-10% MeOH in DCM, gradient elution) to afford (S)-1-(3,4-dichlorophenyl)-5-(5-(3,5-dimethylisoxazol-4-yl)-1-((1r,4S)-4-methoxycyclohexyl)-1H-benzo[d]imidazol-2-yl)pyrrolidin-2-one (35 mg, 51%) as an off white solid; Rt 2.39 min (method 1), m/z 553 (M+H)+ (ES+); 1H NMR (d6-DMSO) δ: 7.99 (d, J=2.5 Hz, 1H), 7.85 (d, J=8.5 Hz, 1H), 7.61-7.53 (m, 2H), 7.41 (dd, J=8.9, 2.5 Hz, 1H), 7.15 (dd, J=8.5, 1.7 Hz, 1H), 6.20-6.13 (m, 1H), 4.58 (t, J=12.7 Hz, 1H), 3.44 (m, 1H), 3.31 (s, 4H), 2.75 (dt, J=15.4, 9.0 Hz, 1H), 2.66-2.51 (m, 1H), 2.36 (m, 5H), 2.19 (m, 4H), 2.07 (t, J=10.5 Hz, 1H), 1.94-1.81 (m, 3H), 1.45 (dt, J=37.1, 12.1 Hz, 2H).

CuTMEDA (8.53 mg, 0.018 mmol) was added to a solution of DBU (19.37 μl, 0.129 mmol), Intermediate E8 (50 mg, 0.122 mmol) and (3-chloro-4-methoxyphenyl)boronic acid (25.10 mg, 0.135 mmol) in acetonitrile (4 ml) with stirring for 18 h at 40° C. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (S)-1-(3-chloro-4-methoxyphenyl)-5-(5-(3,5-dimethylisoxazol-4-yl)-1-((1r,4S)-4-methoxycyclohexyl)-1H-benzo[d]imidazol-2-yl)pyrrolidin-2-one (49 mg, 0.088 mmol, 72.2% yield) as an off white solid; Rt 2.11 min (method 1), m/z 549 (M+H)+ (ES+); 1H NMR (d6-DMSO) δ: 7.82 (d, J=8.5 Hz, 1H), 7.75 (d, J=2.6 Hz, 1H), 7.60 (d, J=1.6 Hz, 1H), 7.27 (dd, J=9.0, 2.6 Hz, 1H), 7.18-7.03 (m, 2H), 6.06 (dd, J=8.2, 2.3 Hz, 1H), 4.55 (t, J=11.9 Hz, 1H), 3.76 (s, 3H), 3.44 (m, 1H), 3.30 (s, 3H), 2.77 (dt, J=16.0, 9.1 Hz, 1H), 2.67-2.52 (m, 1H), 2.45 (m, 1H), 2.37 (s, 3H), 2.29 (m, 2H), 2.20 (s, 3H), 2.12 (m, 3H), 1.85 (d, J=12.3 Hz, 1H), 1.62 (d, J=12.1 Hz, 1H), 1.44 (dd, J=21.1, 11.4 Hz, 2H).

Example 83: (S)-1-(2,3-dihydrobenzofuran-5-yl)-5-(5-(3,5-dimethylisoxazol-4-yl)-1-((1r,4S)-4-methoxycyclohexyl)-1H-benzo[d]imidazol-2-yl)pyrrolidin-2-one (S)-1-(2,3-dihydrobenzofuran-5-yl)-5-(5-(3,5-dimethylisoxazol-4-yl)-1-((1r,4S)-4-methoxycyclohexyl)-1H-benzo[d]imidazol-2-yl)pyrrolidin-2-one

Example 84: (S)-1-(3-chloro-4-fluorophenyl)-5-(5-(3,5-dimethylisoxazol-4-yl)-1-((1r,4S)-4-methoxycyclohexyl)-1H-benzo[d]imidazol-2-yl)pyrrolidin-2-one (S)-1-(3-chloro-4-fluorophenyl)-5-(5-(3,5-dimethylisoxazol-4-yl)-1-((1r,4S)-4-methoxycyclohexyl)-1H-benzo[d]imidazol-2-yl)pyrrolidin-2-one

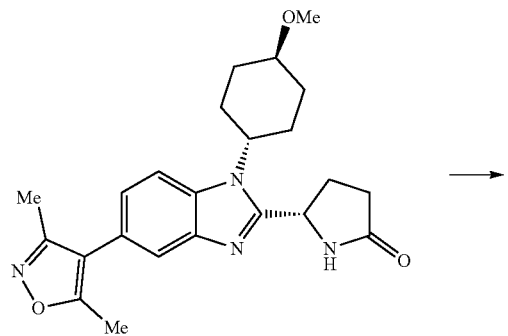

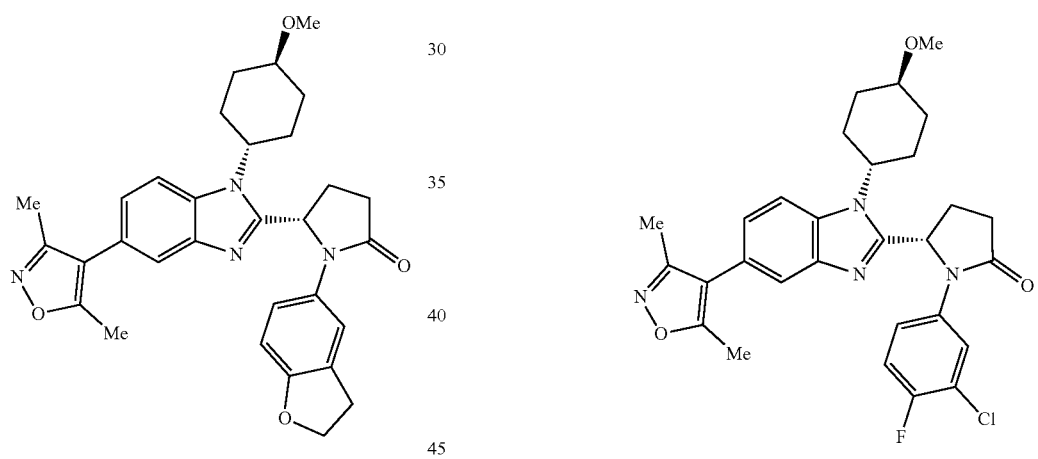

CuTMEDA (8.53 mg, 0.018 mmol) was added to a solution of DBU (19.37 µl, 0.129 mmol), Intermediate E8 (50 mg, 0.122 mmol) and (2,3-dihydrobenzofuran-5-yl)boronic acid (22.08 mg, 0.135 mmol) in acetonitrile (4 ml) with stirring for 18 h at 40° C. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (S)-1-(2,3-dihydrobenzofuran-5-yl)-5-(5-(3,5-dimethylisoxazol-4-yl)-1-((1r,4S)-4-methoxycyclohexyl)-1H-benzo[d]imidazol-2-yl)pyrrolidin-2-one (46 mg, 71%) as an off white solid; Rt 1.88 min (method 1), m/z 527 (M+H)+ (ES+); 1H NMR (d6-DMSO) δ: 7.79 (d, J=8.5 Hz, 1H), 7.61 (d, J=1.8 Hz, 1H), 7.38 (d, J=2.2 Hz, 1H), 7.13 (dd, J=8.5, 1.7 Hz, 1H), 7.01 (dd, J=8.5, 2.4 Hz, 1H), 6.65 (d, J=8.5 Hz, 1H), 5.97-5.89 (m, 1H), 4.45 (m, 2H), 3.29 (d, J=8.7 Hz, 1H), 3.29 (s, 3H), 3.20-3.04 (m, 2H), 2.77 (dd, J=16.3, 8.9 Hz, 1H), 2.60 (m, 1H), 2.38 (s, 3H), 2.28 (m, 1H), 2.21 (s, 3H), 2.16 (m, 1H), 2.12 (m, 4H), 1.81 (d, J=12.4 Hz, 1H), 1.38 (m, 4H).

CuTMEDA (8.53 mg, 0.018 mmol) was added to a solution of DBU (19.37 µl, 0.129 mmol), Intermediate E8 (50 mg, 0.122 mmol) and (3-chloro-4-fluorophenyl)boronic acid (23.48 mg, 0.135 mmol) in acetonitrile (4 ml) with stirring for 18 h at 40° C. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (S)-1-(3-chloro-4-fluorophenyl)-5-(5-(3,5-dimethylisoxazol-4-yl)-1-((1r,4S)-4-methoxycyclohexyl)-1H-benzo[d]imidazol-2-yl)pyrrolidin-2-one (34 mg, 51%) as an off white solid; Rt 2.24 min (method 1), m/z 537 (M+H)+ (ES+); 1H NMR (d6-DMSO) δ: 7.91 (dt, J=6.8, 1.2 Hz, 1H), 7.84 (d, J=8.5 Hz, 1H), 7.59 (d, J=1.6 Hz, 1H), 7.40-7.33 (m, 2H), 7.15 (dd, J=8.5, 1.7 Hz, 1H), 6.13 (d, J=7.1 Hz, 1H), 4.56 (t, J=12.2 Hz, 1H), 3.41 (m, 1H), 3.31 (s, 3H), 2.76 (dt, J=15.7, 9.0 Hz, 1H), 2.67-2.51 (m, 1H), 2.36-2.29 (m, 5H), 2.20-2.16 (m, 6H), 2.09 (t, J=10.8 Hz, 1H), 1.88 (d, J=12.7 Hz, 1H), 1.75 (d, J=12.2 Hz, 1H), 1.45 (dq, J=24.3, 10.9 Hz, 2H).

Example 85: (S)-1-(4-chloro-3-fluorophenyl)-5-(5-(3,5-dimethylisoxazol-4-yl)-1-((1r,4S)-4-methoxycyclohexyl)-1H-benzo[d]imidazol-2-yl)pyrrolidin-2-one (S)-1-(4-chloro-3-fluorophenyl)-5-(5-(3,5-dimethylisoxazol-4-yl)-1-((1r,4S)-4-methoxycyclohexyl)-1H-benzo[d]imidazol-2-yl)pyrrolidin-2-one

Example 86: (S)-5-(5-(3,5-dimethylisoxazol-4-yl)-1-((1r,4S)-4-methoxycyclohexyl)-1H-benzo[d]imidazol-2-yl)-1-(3-fluoro-4-methoxyphenyl)pyrrolidin-2-one (S)-5-(5-(3,5-dimethylisoxazol-4-yl)-1-((1r,4S)-4-methoxycyclohexyl)-1H-benzo[d]imidazol-2-yl)-1-(3-fluoro-4-methoxyphenyl)pyrrolidin-2-one

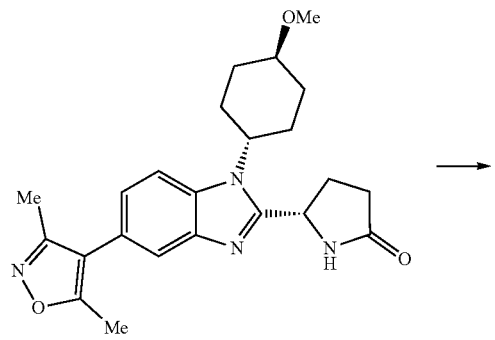

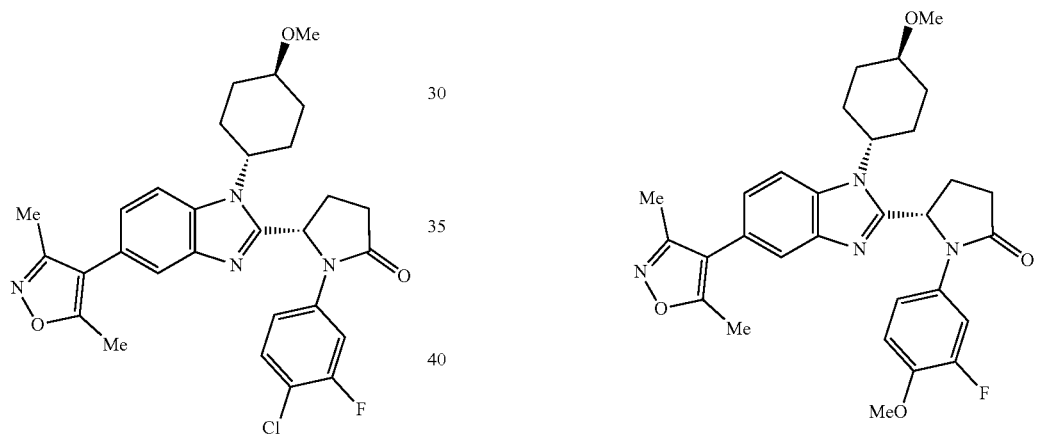

CuTMEDA (8.53 mg, 0.018 mmol) was added to a solution of DBU (19.37 µl, 0.129 mmol), Intermediate E8 (50 mg, 0.122 mmol) and (4-chloro-3-fluorophenyl)boronic acid (23.48 mg, 0.135 mmol) in acetonitrile (4 ml) with stirring for 18 h at 40° C. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (S)-1-(4-chloro-3-fluorophenyl)-5-(5-(3,5-dimethylisoxazol-4-yl)-1-((1r,4S)-4-methoxycyclohexyl)-1H-benzo[d]imidazol-2-yl)pyrrolidin-2-one (36 mg, 54%) as an off white solid; Rt 2.28 min (method 1), m/z 537 (M+H)+ (ES+); 1H NMR (d6-DMSO) δ: 7.89-7.79 (m, 2H), 7.58 (d, J=1.6 Hz, 1H), 7.52 (t, J=8.8 Hz, 1H), 7.22 (ddd, J=9.0, 2.5, 1.0 Hz, 1H), 7.15 (dd, J=8.5, 1.7 Hz, 1H), 6.14 (d, J=7.1 Hz, 1H), 4.62-4.51 (m, 1H), 3.52-3.42 (m, 1H), 3.31 (s, 3H), 2.80-2.50 (m, 3H), 2.36 (m, 5H), 2.19 (m, 5H), 2.06 (t, J=10.4 Hz, 1H), 1.89 (s, 2H), 1.46 (dq, J=35.4, 11.8 Hz, 2H).

CuTMEDA (8.53 mg, 0.018 mmol) was added to a solution of DBU (19.37 µl, 0.129 mmol), Intermediate E8 (50 mg, 0.122 mmol) and (3-fluoro-4-methoxyphenyl)boronic acid (22.88 mg, 0.135 mmol) in acetonitrile (4 mL) with stirring for 18 h at 40° C. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (S)-5-(5-(3,5-dimethylisoxazol-4-yl)-1-((1r,4S)-4-methoxycyclohexyl)-1H-benzo[d]imidazol-2-yl)-1-(3-fluoro-4-methoxyphenyl)pyrrolidin-2-one (16 mg, 24%) as an off white solid; Rt 2.01 min (method 1), m/z 533 (M+H)+ (ES+); 1H NMR (d6-DMSO) δ: 7.82 (d, J=8.5 Hz, 1H), 7.64-7.55 (m, 2H), 7.18-7.02 (m, 3H), 6.04 (d, J=7.2 Hz, 1H), 4.54 (s, 1H), 3.74 (s, 3H), 3.50-3.35 (m, 1H), 3.30 (s, 3H), 2.74 (dd, J=15.9, 9.3 Hz, 1H), 2.67-2.52 (m, 1H), 2.37 (s, 3H), 2.34-2.23 (m, 1H), 2.20 (m, 4H), 2.14-2.08 (m, 4H), 1.87 (s, 1H), 1.64 (d, J=11.5 Hz, 1H), 1.43 (t, J=13.3 Hz, 2H).

Example 87: (S)-1-(3,4-difluorophenyl)-5-(5-(3,5-dimethylisoxazol-4-yl)-1-((1s,4R)-4-hydroxycyclohexyl)-1H-benzo[d]imidazol-2-yl)pyrrolidin-2-one (1R,4s)-4-(2-((S)-1-(3,4-difluorophenyl)-5-oxopyrrolidin-2-yl)-5-(3,5-dimethylisoxazol-4-yl)-1H-benzo[d]imidazol-1-yl)cyclohexyl acetate

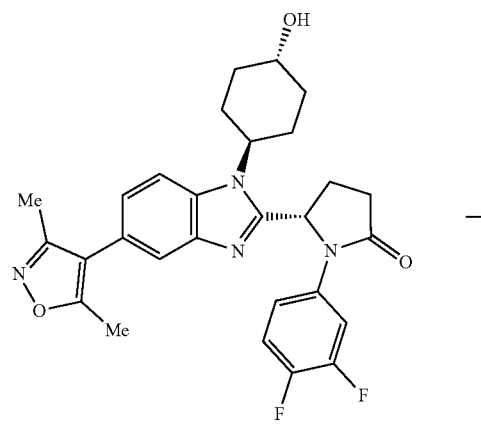

(S)-1-(3,4-difluorophenyl)-5-(5-(3,5-dimethylisoxazol-4-yl)-1-((1s,4R)-4-hydroxycyclohexyl)-1H-benzo[d]imidazol-2-yl)pyrrolidin-2-one DIAD (110 µL, 0.566 mmol) was added to a solution of (S)-1-(3,4-difluorophenyl)-5-(5-(3,5-dimethylisoxazol-4-yl)-1-((1r,4S)-4-hydroxycyclohexyl)-1H-benzo[d]imidazol-2-yl)pyrrolidin-2-one (150 mg, 0.290 mmol), acetic acid (50 µL, 0.873 mmol) and triphenylphosphine (200 mg, 0.763 mmol) in tetrahydrofuran (2 mL) then stirred at room temperature for 1 h. DIAD (110 µL, 0.566 mmol) was added and the mixture was stirred for a further 18 h. The mixture was concentrated onto loose silica gel then the silicate was purified by chromatography on the Companion (12 g column, 5-25% THF/CH2Cl2) to afford (1R,4s)-4-(2-((S)-1-(3,4-difluorophenyl)-5-oxopyrrolidin-2-yl)-5-(3,5-dimethylisoxazol-4-yl)-1H-benzo[d]imidazol-1-yl)cyclohexyl acetate (109 mg, 66%) as a white solid; Rt 2.20 min (method 1), m/z 549 (M+H)+ (ES+);

Potassium carbonate (50 mg, 0.362 mmol) was added to a solution of (1R,4s)-4-(2-((S)-1-(3,4-difluorophenyl)-5-oxopyrrolidin-2-yl)-5-(3,5-dimethylisoxazol-4-yl)-1H-benzo[d]imidazol-1-yl)cyclohexyl acetate (108 mg, 0.191 mmol) in methanol (3 mL) and tetrahydrofuran (3 mL) then stirred at room temperature for 1 h. Methanol (8 mL) was added followed by 1.0 M aqueous hydrogen chloride (1.0 ml, 1.000 mmol). The solution was loaded onto SCX (1 g) the washed with methanol (3×10 mL). The product was eluted with 0.7 M ammonia in methanol (3×5 ml) to yield (S)-1-(3,4-difluorophenyl)-5-(5-(3,5-dimethylisoxazol-4-yl)-1-((1s,4R)-4-hydroxycyclohexyl)-1H-benzo[d]imidazol-2-yl)pyrrolidin-2-one (97 mg, 0.182 mmol, 95% yield) as a white solid; Rt 1.81 min (method 1), m/z 507 (M+H)+ (ES+); 1H NMR (d6-DMSO) δ: 7.83 (ddd, J=13.3, 7.4, 2.6 Hz, 1H), 7.74 (d, J=8.5 Hz, 1H), 7.61 (d, J=1.6 Hz, 1H), 7.39 (dd, J=10.7, 9.2 Hz, 1H), 7.23 (dd, J=8.5, 1.7 Hz, 1H), 7.20-7.13 (m, 1H), 6.10 (dd, J=8.1, 1.9 Hz, 1H), 4.73 (d, J=2.9 Hz, 1H), 4.64-4.49 (m, 1H), 4.05-3.91 (m, 1H), 2.81-2.52 (m, 5H), 2.38 (s, 3H), 2.21 (s, 3H), 2.14-2.04 (m, 1H), 1.93-1.81 (m, 2H), 1.79-1.50 (m, 4H).

Example 88: (S)-1-(3,4-difluorophenyl)-5-(5-(3,5-dimethylisoxazol-4-yl)-1-((1s,4R)-4-methoxycyclohexyl)-1H-benzo[d]imidazol-2-yl)pyrrolidin-2-one (S)-1-(3,4-difluorophenyl)-5-(5-(3,5-dimethylisoxazol-4-yl)-1-((1s,4R)-4-methoxycyclohexyl)-1H-benzo[d]imidazol-2-yl)pyrrolidin-2-one

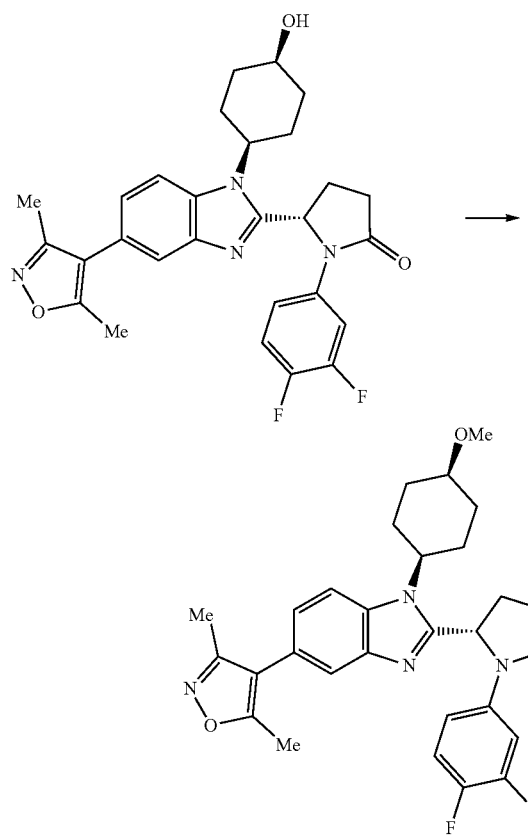

Sodium hydride, 60% dispersion in mineral oil (5 mg, 0.125 mmol) was added to a solution of (S)-1-(3,4-difluorophenyl)-5-(5-(3,5-dimethylisoxazol-4-yl)-1-((1s,4R)-4-hydroxycyclohexyl)-1H-benzo[d]imidazol-2-yl)pyrrolidin-2-one (51 mg, 0.096 mmol) in N,N-dimethylformamide (2 mL) then stirred for 2 minutes at room temperature. Iodomethane (7 µL, 0.112 mmol) was added then the mixture was stirred at room temperature overnight. Ammonium chloride (15 mg, 0.280 mmol) was added then the mixture was purified by chromatography on the Companion (RP Flash C18) (12 g column, 15-75% MeCN/Water 0.1% Formic Acid) then by chromatography on the Companion (4 g column, 5-15% THF/DCM) then triturated in diethyl ether to afford (S)-1-(3,4-difluorophenyl)-5-(5-(3,5-dimethylisoxazol-4-yl)-1-((1s,4R)-4-methoxycyclohexyl)-1H-benzo[d]imidazol-2-yl)pyrrolidin-2-one (6 mg, 11%) as a white solid; Rt 2.22 min (method 1), m/z 521 (M+H)+ (ES+); 1H NMR (d6-DMSO) δ: 7.83 (ddd, J=13.3, 7.4, 2.6 Hz, 1H), 7.61 (d, J=1.6 Hz, 1H), 7.59 (d, J=8.6 Hz, 1H), 7.39 (dd, J=10.6, 9.2 Hz, 1H), 7.24 (dd, J=8.4, 1.7 Hz, 1H), 7.20-7.14 (m, 1H), 6.10 (d, J=7.6 Hz, 1H), 4.68-4.52 (m, 1H), 3.60-3.52 (m, 1H), 3.36 (s, 3H), 2.82-2.52 (m, 4H), 2.49-2.40 (m, 1H), 2.38 (s, 3H), 2.21 (s, 3H), 2.16-2.03 (m, 3H), 1.75-1.52 (m, 4H).

Example 89: (S)-1-(3,4-difluorophenyl)-5-(5-(3,5-dimethylisoxazol-4-yl)-1-((1R,4s)-4-ethoxycyclohexyl)-1H-benzo[d]imidazol-2-yl)pyrrolidin-2-one (S)-1-(3,4-difluorophenyl)-5-(5-(3,5-dimethylisoxazol-4-yl)-1-((1s,4R)-4-ethoxycyclohexyl)-1H-benzo[d]imidazol-2-yl)pyrrolidin-2-one

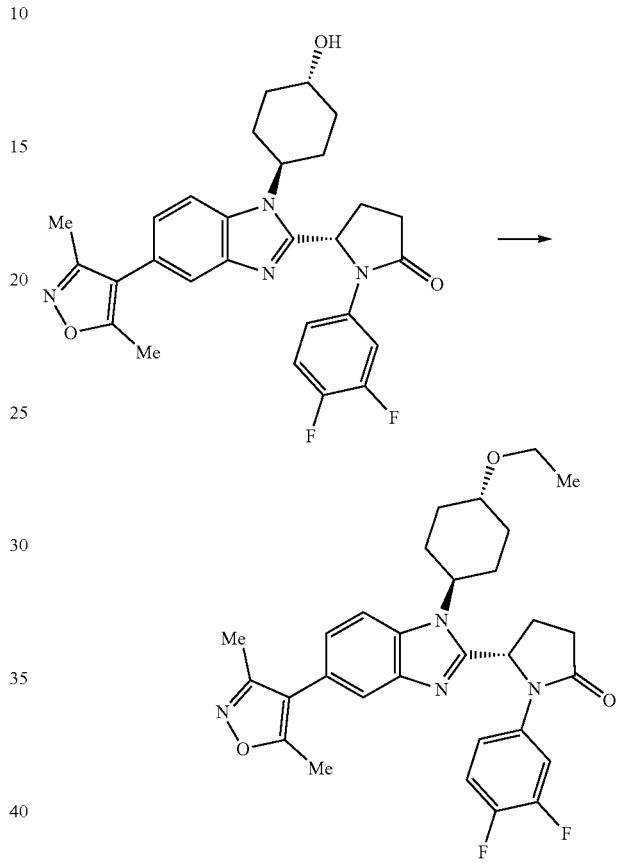

NaHMDS (148 µL, 0.148 mmol) was added to a suspension of (S)-1-(3,4-difluorophenyl)-5-(5-(3,5-dimethylisoxazol-4-yl)-1-((1r,4S)-4-hydroxycyclohexyl)-1H-benzo[d]imidazol-2-yl)pyrrolidin-2-one (75 mg, 0.148 mmol) in dry THF (849 µL, 10.36 mmol) at 0° C. The suspension was stirred for 5 mn. DMF (894 µl, 11.55 mmol) was added to dissolve the solid. Then ethyl iodide (14.36 µL, 0.178 mmol) was added dropwise. After 4.5 h of stirring, the reaction was diluted into DCM (5 mL) and was with saturated aqueous ammonium chloride (10 mL). The layers were separated and the organic layer was washed with water (5 mL). The organic was combined and concentrated in vacuo to give a brown oil, which was purified by chromatography column (4 g, DCM/MeOH: 100/0 to 90/10) then (4 g, DCM/MeOH: 100/0 to 90/10) to give (S)-1-(3,4-difluorophenyl)-5-(5-(3,5-dimethylisoxazol-4-yl)-1-((1r,4S)-4-ethoxycyclohexyl)-1H-benzo[d]imidazol-2-yl)pyrrolidin-2-one (10.6 mg, 13%) as a white solid; Rt 2.25 min (method 1), m/z 535 (M+H)+ (ES+); 1H NMR (d6-DMSO) δ: 7.88-7.77 (m, 2H), 7.59 (d, J=1.7 Hz, 1H), 7.44-7.32 (m, 1H), 7.19-7.11 (m, 2H), 6.10 (dd, J=7.6, 1.6 Hz, 1H), 4.59-4.47 (m, 1H), 3.61-3.47 (m+q, 3H), 2.81-2.50 (m, 3H), 2.41-2.26 (m+s, 5H), 2.19 (s, 3H), 2.16-2.03 (m, 3H), 1.91-1.83 (m, 1H), 1.81-1.73 (m, 1H), 1.54-1.39 (m, 2H), 1.14 (t, J=7.0 Hz, 3H).

Example 90: (5S)-1-(3,4-dichlorophenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one (2S)—N-(5-(3,5-dimethylisoxazol-4-yl)-2-((1,1-dioxidotetrahydro-2H-thiopyran-3-yl)amino)phenyl)-5-oxopyrrolidine-2-carboxamide (Intermediate D9)

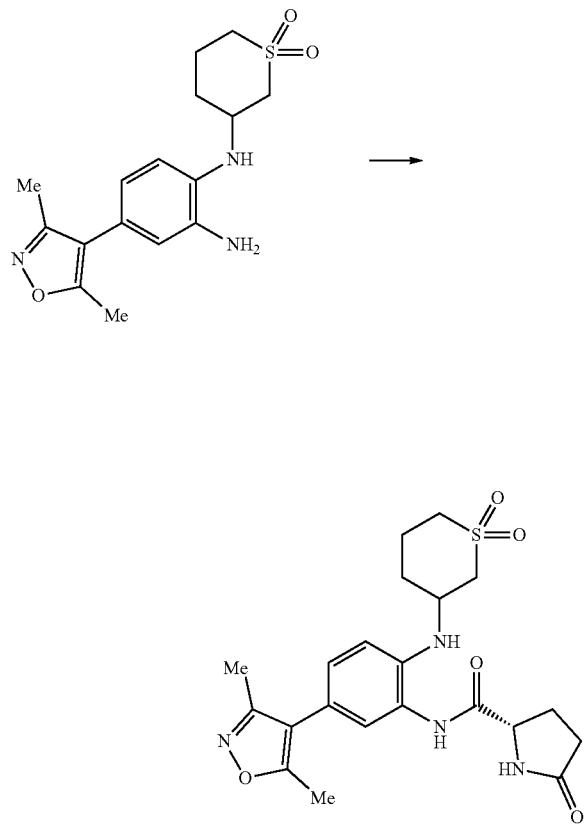

A solution of Intermediate C9 (1.8 g, 5.37 mmol), 2-(3H-[1,2,3]triazolo[4,5-b]pyridin-3-yl)-1,1,3,3-tetramethylisouronium hexafluorophosphate(V) (2.245 g, 5.90 mmol), (S)-5-oxopyrrolidine-2-carboxylic acid (0.762 g, 5.90 mmol) and triethylamine (2.24 mL, 16.10 mmol) in DMF (20 mL) was stirred at room temperature for 3 h. The mixture was partitioned between ethyl acetate (200 mL) and water (100 mL), then the layers separated. The organic phase was washed with water (100 mL), passed through a PhaseSep© and evaporated in vacuo to afford (2S)—N-(5-(3,5-dimethylisoxazol-4-yl)-2-((1,1-dioxidotetrahydro-2H-thiopyran-3-yl)amino)phenyl)-5-oxopyrrolidine-2-carboxamide Intermediate D9 (1.05 g, 35%) as a crude residue; Rt 1.42 min (method 1), m/z 447 (M+H)+ (ES+).

(5S)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one (Intermediate E9)

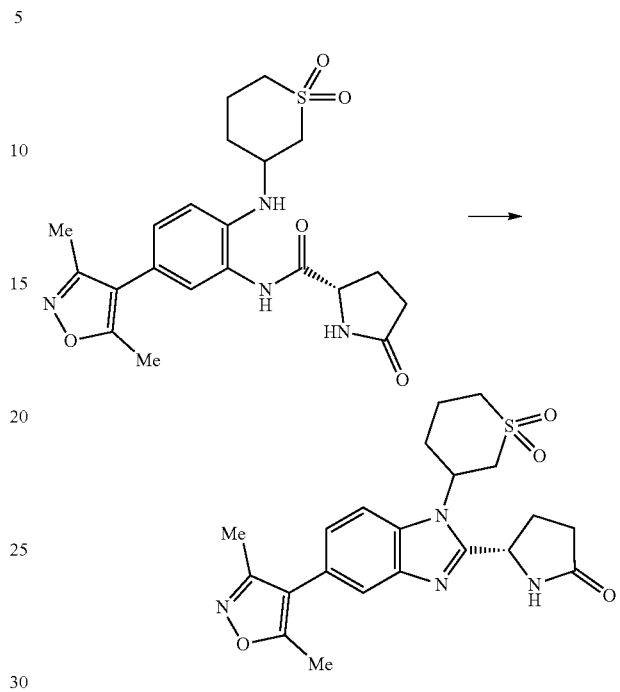

A solution of (2S)—N-(5-(3,5-dimethylisoxazol-4-yl)-2-((1,1-dioxidotetrahydro-2H-thiopyran-3-yl)amino)phenyl)-5-oxopyrrolidine-2-carboxamide (1.05 g, 2.352 mmol) in acetic acid (5 mL) was heated to 80° C. for 48 h then left to cool to RT. The reaction was cooled down to RT and concentrated in vacuo to give a brown oil, which was dissolved in MeOH then loaded onto a SCX column. The column was washed with MeOH and then the product was eluted with 7 M ammonia in MeOH (30 ml). The resultant mixture was concentrated in vacuo then sonicated with diethyl ether (15 mL) and concentrated again to afford a brown solid (520 mg). Purification by flash chromatography (4 g, DCM/AcOEt: 100/0 to 60/40 then DCM/10% MeOH in DCM: 60/40 to 0/100) to afford (5S)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one (0.295 g, 27%) as an off white solid; Rt 1.33 min (method 1), m/z 429 (M+H)+ (ES+).

(5S)-1-(3,4-dichlorophenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one

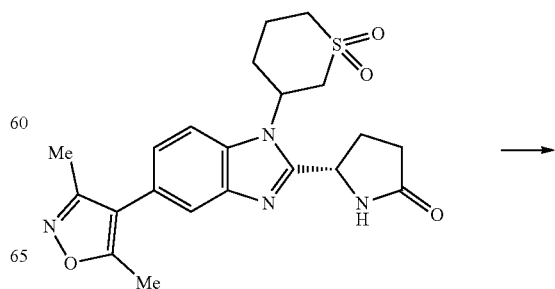

275
-continued

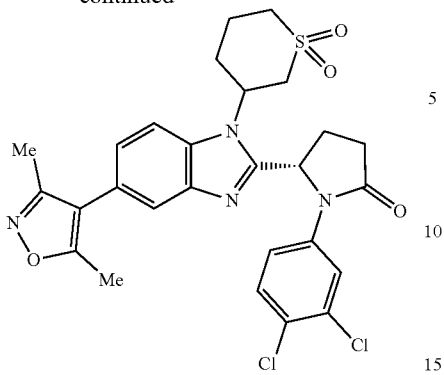

CuTMEDA (8.13 mg, 0.018 mmol) was added to a solution of DBU (0.018 mL, 0.123 mmol), (5S)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one (50 mg, 0.117 mmol) and (3,4-dichlorophenyl)boronic acid (24.49 mg, 0.128 mmol) in acetonitrile (3.535 mL, 67.7 mmol) with stirring for 15 h at 40° C. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (5S)-1-(3,4-dichlorophenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one (30.6 mg, 43%) as a yellow solid; Rt 2.10 min (method 1), m/z 573 (M+H)+ (ES+); 1H NMR (d6-DMSO) δ: 8.17-8.12 (m, 1H), 8.12-8.04 (m, 1H), 7.62 (dd, J=9.2, 1.6 Hz, 1H), 7.54 (dd, J=8.9, 6.1 Hz, 1H), 7.46 (d, J=9.3 Hz, 0.5H), 7.33 (dd, 0.5H), 7.21 (ddd, J=8.4, 6.5, 1.7 Hz, 1H), 6.39-6.24 (m, 0.5H), 6.02-5.90 (m, 0.5H), 4.99-4.89 (m, 0.5H), 4.88-4.75 (m, 0.5H), 4.23-4.08 (m, 1H), 3.81-3.61 (m, 1H), 3.61-3.49 (m, 1H), 3.27-3.14 (m, 1H), 2.80-2.55 (m, 2H), 2.54-2.42 (m, 3H), 2.36 (d, J=3.7 Hz, 3H), 2.27-2.06 (m+d, 5H), 2.07-1.92 (m, 1H).

Example 91: (5S)-1-(4-chloro-3-fluorophenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one (5S)-1-(4-chloro-3-fluorophenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one 276
-continued

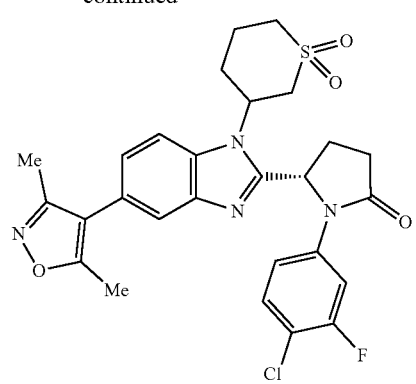

CuTMEDA (8.13 mg, 0.018 mmol) was added to a solution of DBU (0.018 mL, 0.123 mmol), Intermediate E9 (50 mg, 0.117 mmol) and (4-chloro-3-fluorophenyl)boronic acid (22.38 mg, 0.128 mmol) in acetonitrile (3.535 mL, 67.7 mmol) with stirring for 15 h at 40° C. After 15 h of stirring, the mixture was concentrated under reduced pressure. The residue was taken up in the minimum of DCM, passed through a syringe filter and the solution then purified by chromatography on the Companion (12 g column, 0-10% MeOH in DCM, gradient elution) to afford (5S)-1-(4-chloro-3-fluorophenyl)-5-(5-(3,5-dimethylisoxazol-4-yl)-1-(1,1-dioxidotetra hydro-2H-thiopyran-3-yl)-1H-benzo[d]imidazol-2-yl)pyrrolidin-2-one (34 mg, 50%) as a yellow solid; Rt 2.03 min (method 1), m/z 557 (M+H)+ (ES+); 1H NMR (d6-DMSO) δ: 8.19-8.08 (m, 1H), 7.87 (ddd, J=12.9, 10.5, 2.5 Hz, 1H), 7.61 (dd, J=9.8, 1.7 Hz, 1H), 7.53-7.43 (m, 1H), 7.38-7.24 (m, 1H), 7.24-7.18 (m, 1H), 6.33-6.26 (m, 0.5H), 5.99-5.86 (m, 0.5H), 4.99-4.87 (m, 0.5H), 4.86-4.75 (m, 0.5H), 4.21-4.07 (m, 1H), 3.86-3.63 (m, 1H), 3.61-3.48 (m, 1H), 3.26-3.15 (m, 1H), 2.77-2.65 (m, 1H), 2.65-2.54 (m, 1H), 2.50 (m, J=1.8 Hz, 2H), 2.36 (d, J=4.1 Hz, 3H), 2.27-2.01 (m+d, 6H), 1.99 (m, 1H).

Example 92: (5S)-1-(3-chloro-4-methoxyphenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one (5S)-1-(3-chloro-4-methoxyphenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one

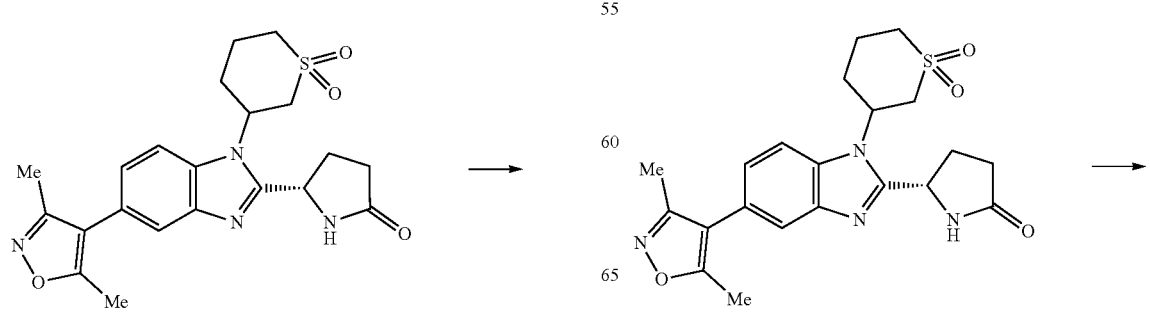

277
-continued

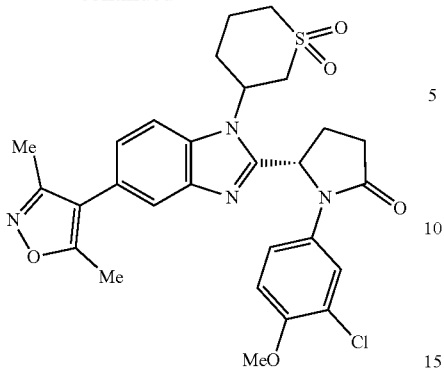

CuTMEDA (8.13 mg, 0.018 mmol) was added to a solution of DBU (0.018 mL, 0.123 mmol), (5S)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one (50 mg, 0.117 mmol) and (3-chloro-4-methoxyphenyl)boronic acid (23.93 mg, 0.128 mmol) in acetonitrile (3.53 mL, 67.7 mmol) with stirring for 15 h at 40° C. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (5S)-1-(3-chloro-4-methoxyphenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one (27 mg, 39%) as a yellow solid; Rt 1.84 min (method 1), m/z 569 (M+H)+ (ES+); 1H NMR (d6-DMSO) δ: 8.16-8.03 (m, 1H), 7.80 (dd, J=39.1, 2.6 Hz, 1H), 7.64 (dd, J=9.8, 1.6 Hz, 1H), 7.33 (d, 0.5H), 7.25-7.15 (m, 1.5H), 7.06 (dd, J=9.1, 1.7 Hz, 1H), 6.19-6.12 (m, 0.5H), 5.94-5.87 (m, 0.5H), 4.96-4.79 (m, 1H), 4.17-4.07 (m, 1H), 3.77 (s, 3H), 3.68-3.43 (m, 2H), 3.24-3.13 (m, 1H), 2.80-2.52 (m, 2H), 2.51-2.38 (m, 2H), 2.37 (d, J=3.8 Hz, 3H), 2.35-2.24 (m, 1H), 2.20 (d, 3H), 2.20-2.00 (m, 2H), 1.97-1.70 (m, 1H).

Example 93: (5S)-1-(2,3-dihydrobenzofuran-5-yl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one (5S)-1-(2,3-dihydrobenzofuran-5-yl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one

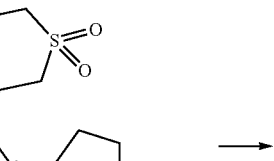

278
-continued

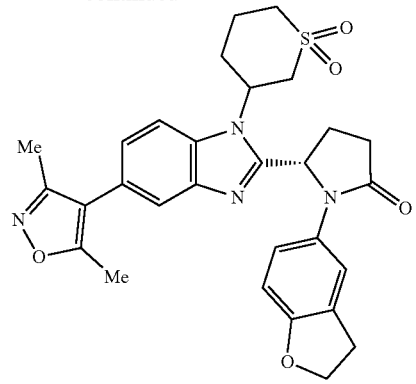

CuTMEDA (8.13 mg, 0.018 mmol) was added to a solution of DBU (0.018 mL, 0.123 mmol), Intermediate E9 (50 mg, 0.117 mmol) and (2,3-dihydrobenzofuran-5-yl)boronic acid (21.05 mg, 0.128 mmol) in acetonitrile (3.53 mL, 67.7 mmol) with stirring for 15 h at 40° C. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (5S)-1-(2,3-dihydrobenzofuran-5-yl)-5-(5-(3,5-dimethylisoxazol-4-yl)-1-(1,1-dioxido tetrahydro-2H-thiopyran-3-yl)-1H-benzo[d]imidazol-2-yl)pyrrolidin-2-one (28 mg, 42%) as a yellow solid; Rt 1.72 min (method 1), m/z 547 (M+H)+ (ES+); 1H NMR (d6-DMSO) δ: 8.13-8.02 (m, 1H), 7.65 (dd, J=8.2, 1.7 Hz, 1H), 7.38 (dd, J=44.0, 2.2 Hz, 1H), 7.21-7.16 (m, 1H), 7.06 (dd, J=8.6, 2.3 Hz, 0.5H), 6.86 (d, J=8.7 Hz, 0.5H), 6.63 (dd, J=14.3, 8.5 Hz, 1H), 5.94 (dd, J=8.2, 2.4 Hz, 0.5H), 5.87-5.79 (m, 0.5H), 4.90-4.72 (m, 1H), 4.49-4.42 (m, 2H), 4.11-3.97 (m, 1H), 3.65-3.45 (m, 1H), 3.23-3.05 (m, 3H), 2.86-2.54 (m, 2H), 2.50 (p, J=1.8 Hz, 2H), 2.39 (m+d, J=4.1 Hz, 4H), 2.34-2.25 (m, 1H), 2.21 (d, J=3.8 Hz, 3H), 2.11 (d, J=18.1 Hz, 1H), 1.99 (m, 1H).

Example 94: (S)-1-(3,4-dichlorophenyl)-5-(5-(3,5-dimethylisoxazol-4-yl)-1-(1-(methylsulfonyl)piperidin-4-yl)-1H-benzo[d]imidazol-2-yl)pyrrolidin-2-one (S)—N-(5-(3,5-dimethylisoxazol-4-yl)-2-((1-(methylsulfonyl)piperidin-4-yl)amino)phenyl)-5-oxopyrrolidine-2-carboxamide (Intermediate D10)

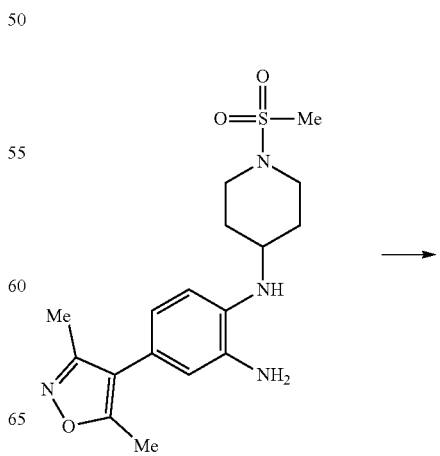

-continued

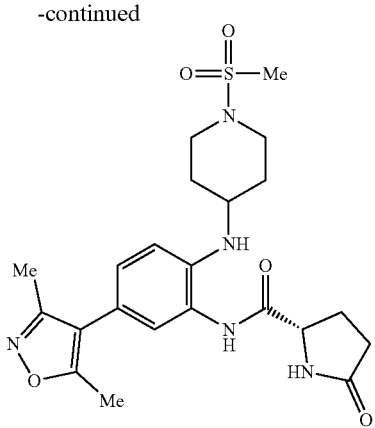

A solution of Intermediate C10 (1.97 g, 5.41 mmol), 2-(3H-[1,2,3]triazolo[4,5-b]pyridin-3-yl)-1,1,3,3-tetramethylisouronium hexafluorophosphate(V) (2.26 g, 5.95 mmol), (S)-5-oxopyrrolidine-2-carboxylic acid (0.768 g, 5.95 mmol) and TEA (2.26 mL, 16.22 mmol) in DMF (20 mL) was stirred at room temperature for 3 h. The mixture was partitioned between ethyl acetate (200 mL) and water (100 mL), then the layers separated. The organic phase was washed with water (100 mL), passed through a PhaseSep© cartridge and evaporated in vacuo to afford (S)—N-(5-(3,5-dimethylisoxazol-4-yl)-2-((1-(methylsulfonyl)piperidin-4-yl)amino)phenyl)-5-oxopyrrolidine-2-carboxamide Intermediate D10 (1.92 g, 68%), which was used without further purification; Rt 1.55 min (method 1), m/z 476 (M+H)+ (ES+).

(S)-5-(5-(3,5-dimethylisoxazol-4-yl)-1-(1-(methylsulfonyl)piperidin-4-yl)-1H-benzo[d]imidazol-2-yl)pyrrolidin-2-one (Intermediate E10)

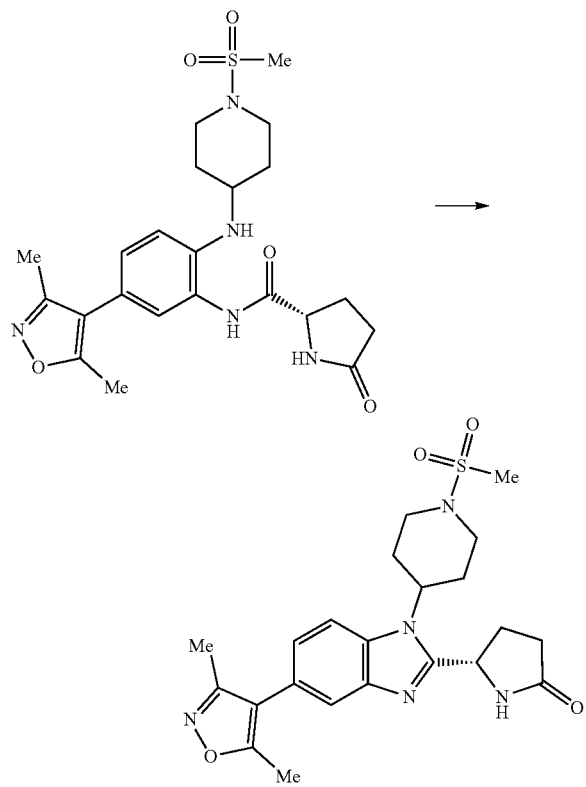

A solution of Intermediate D10 (1.92 g, 4.04 mmol) in acetic acid (5 mL) was heated to 80° C. for 48 h then left to cool to rt. The reaction mixture was passed on to FL for workup and purification. The reaction mixture was concentrated in vacuo to give a beige solid. MeOH (5 mL) was added followed by DCM (5 mL). The beige suspension was filtered through a PhaseSep© cartridge. The solid was washed with MeOH (4 mL) followed with diethyl ether (10 mL). The solid was dissolved in DCM (100 mL) washed with saturated aqueous sodium bicarbonate solution (2×50 mL). The organic was was washed with water (100 mL), dried (MgSO4), filtered and concentrated in vacuo to give (S)-5-(5-(3,5-dimethylisoxazol-4-yl)-1-(1-(methylsulfonyl)piperidin-4-yl)-1H-benzo[d]imidazol-2-yl)pyrrolidin-2-one Intermediate E10 (0.798 g, 41%) as a white solid; Rt 1.34 min (method 1), m/z 458 (M+H)+ (ES+).

(S)-1-(3,4-dichlorophenyl)-5-(5-(3,5-dimethylisoxazol-4-yl)-1-(1-(methylsulfonyl)piperidin-4-yl)-1H-benzo[d]imidazol-2-yl)pyrrolidin-2-one

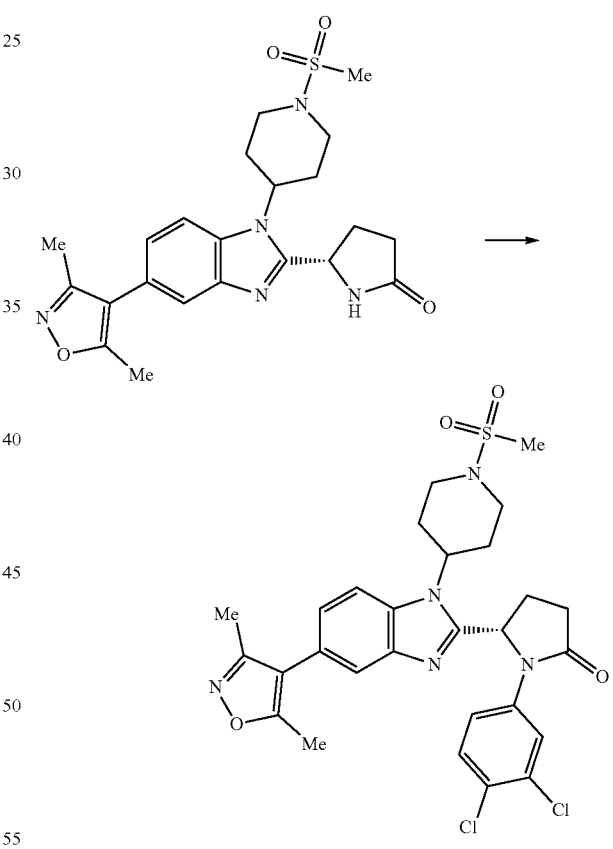

CuTMEDA (7.61 mg, 0.016 mmol) was added to a solution of DBU (0.017 ml, 0.115 mmol), Intermediate E10 (0.050 g, 0.109 mmol) and (3,4-dichlorophenyl)boronic acid (0.023 g, 0.120 mmol) in acetonitrile (3.31 ml, 63.4 mmol) with stirring for 15 h at 40° C. The reaction mixture is a grey suspension. DCM (1.5 mL) was added to the reaction mixture. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (S)-1-(3,4- dichlorophenyl)-5-(5-(3,5-dimethylisoxazol-4-yl)-1-(1-(methylsulfonyl)piperidin-4-yl)-1H-benzo[d]imidazol-2-yl)pyrrolidin-2-one (33 mg, 48%) as a yellow solid; Rt 2.19 min (method 1), m/z 602 (M+H)+ (ES+); 1H NMR (d6-DMSO) δ: 8.03 (d, J=2.5 Hz, 1H), 7.75 (d, J=8.5 Hz, 1H), 7.61 (d, J=1.6 Hz, 1H), 7.57 (d, J=8.9 Hz, 1H), 7.40 (dd, J=8.9, 2.6 Hz, 1H), 7.19 (dd, J=8.5, 1.7 Hz, 1H), 6.17 (d, 1H), 4.82-4.69 (m, 1H), 3.87-3.79 (m, 2H), 3.13-2.99 (m+s, 5H), 2.81-2.51 (m, 4H), 2.36 (s, 3H), 2.19 (s, 3H), 2.15-2.07 (m, 2H), 2.06-1.96 (m, 2H).

Example 95: (S)-1-(4-chloro-3-fluorophenyl)-5-(5-(3,5-dimethylisoxazol-4-yl)-1-(1-(methylsulfonyl)piperidin-4-yl)-1H-benzo[d]imidazol-2-yl)pyrrolidin-2-one (S)-1-(4-chloro-3-fluorophenyl)-5-(5-(3,5-dimethylisoxazol-4-yl)-1-(1-(methylsulfonyl)piperidin-4-yl)-1H-benzo[d]imidazol-2-yl)pyrrolidin-2-one

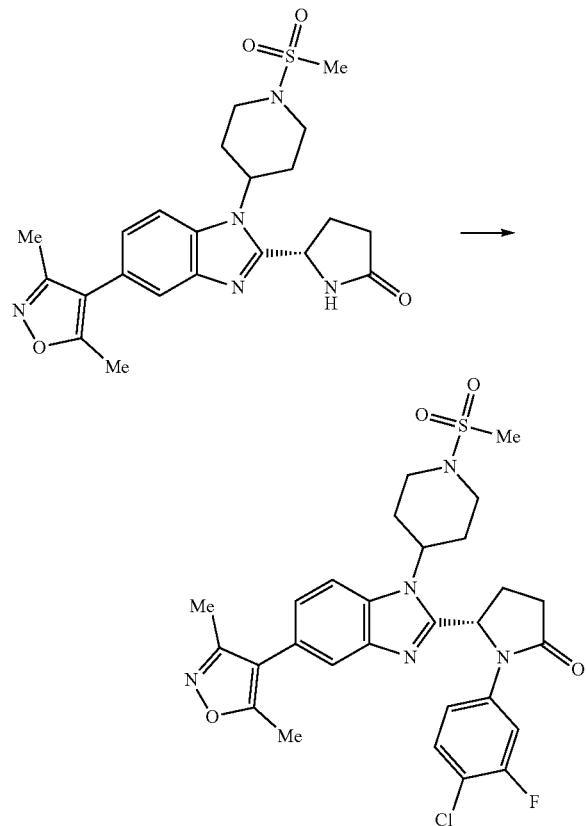

CuTMEDA (7.61 mg, 0.016 mmol) was added to a solution of DBU (17.30 μL, 0.115 mmol), Intermediate E10 (50 mg, 0.109 mmol) and (4-chloro-3-fluorophenyl)boronic acid (20.96 mg, 0.120 mmol) in acetonitrile (3310 μL, 63.4 mmol) and DCM (1.5 mL) with stirring for 15 h at 40° C. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (S)-1-(4-chloro-3-fluorophenyl)-5-(5-(3,5-dimethylisoxazol-4-yl)-1-(1-(methylsulfonly) piperidin-4-yl)-1H-benzo[d]imidazol-2-yl)pyrrolidin-2-one (36 mg, 55%) as a white solid; Rt 2.08 min (method 1), m/z 587 (M+H)+ (ES+); 1H NMR (d6-DMSO) δ: 7.85 (dd, J=12.1, 2.5 Hz, 1H), 7.75 (d, J=8.5 Hz, 1H), 7.60 (d, J=1.6 Hz, 1H), 7.51 (t, J=8.8 Hz, 1H), 7.24 (dd, J=9.0, 2.5, 1.1 Hz, 1H), 7.19 (dd, J=8.5, 1.7 Hz, 1H), 6.14 (d, J=7.9 Hz, 1H), 4.77-4.72 (m, 1H), 3.83 (d, J=12.1 Hz, 2H), 3.13-2.98 (m+s, 5H), 2.79-2.59 (m, 2H), 2.58-2.43 (m, 2H), 2.36 (s, 3H), 2.19 (s, 3H), 2.15-2.00 (m, 3H).

Example 96: (S)-1-(3-chloro-4-methoxyphenyl)-5-(5-(3,5-dimethylisoxazol-4-yl)-1-(1-(methylsulfonyl)piperidin-4-yl)-1H-benzo[d]imidazol-2-yl)pyrrolidin-2-one (S)-1-(3-chloro-4-methoxyphenyl)-5-(5-(3,5-dimethylisoxazol-4-yl)-1-(1-(methylsulfonyl)piperidin-4-yl)-1H-benzo[d]imidazol-2-yl)pyrrolidin-2-one

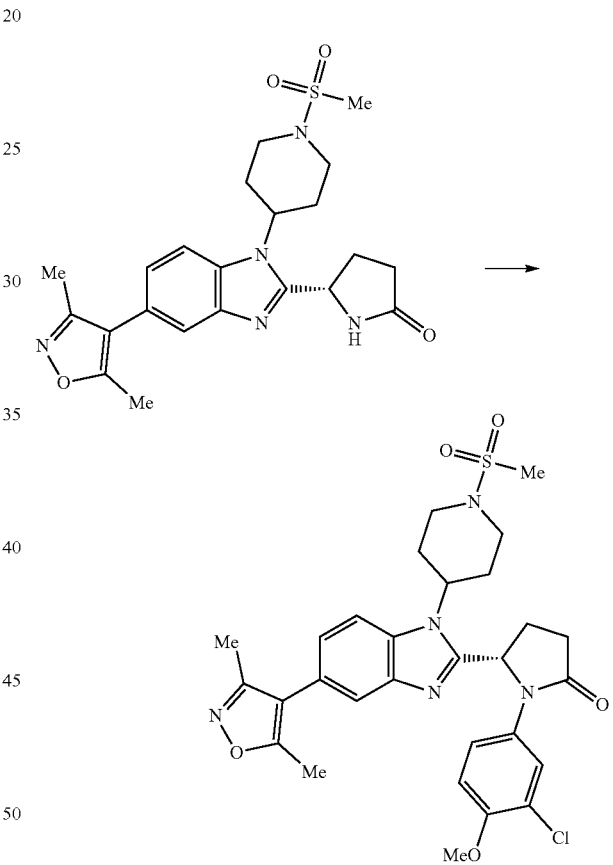

CuTMEDA (7.61 mg, 0.016 mmol) was added to a solution of DBU (17.30 μL, 0.115 mmol), Intermediate E10 (50 mg, 0.109 mmol) and (3-chloro-4-methoxyphenyl)boronic acid (22.41 mg, 0.120 mmol) in acetonitrile (3310 μL, 63.4 mmol) and DCM (1.5 mL) with stirring for 15 h at 40° C. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (S)-1-(3-chloro-4-methoxyphenyl)-5-(5-(3,5-dimethylisoxazol-4-yl)-1-(1-(methyl sulfonyl) piperidin-4-yl)-1H-benzo[d]imidazol-2-yl)pyrrolidin-2-one (33.8 mg, 51%) as a white solid; Rt 1.90 min (method 1), m/z 598 (M+H)+ (ES+); 1H NMR (d6-

DMSO) δ: 7.79 (d, J=2.6 Hz, 1H), 7.73 (d, J=8.5 Hz, 1H), 7.63 (d, J=1.6 Hz, 1H), 7.28 (dd, J=9.0, 2.6 Hz, 1H), 7.19 (dd, J=8.5, 1.7 Hz, 1H), 7.08 (d, J=9.1 Hz, 1H), 6.07 (dd, J=8.1, 2.2 Hz, 1H), 4.82-4.70 (m, 1H), 3.81 (m, 2H), 3.77 (s, 3H), 3.10-2.96 (m+s, 5H), 2.77 (dt, 1H), 2.69-2.53 (m, 2H), 2.50-2.39 (m, 2H), 2.37 (s, 3H), 2.24-2.11 (m+s, 4H), 2.03-1.95 (m, 1H), 1.80-1.70 (m, 1H).

Example 97: (S)-1-(2,3-dihydrobenzofuran-5-yl)-5-(5-(3,5-dimethylisoxazol-4-yl)-1-(1-(methylsulfonyl)piperidin-4-yl)-1H-benzo[d]imidazol-2-yl)pyrrolidin-2-one (S)-1-(2,3-dihydrobenzofuran-5-yl)-5-(5-(3,5-dimethylisoxazol-4-yl)-1-(1-(methylsulfonyl)piperidin-4-yl)-1H-benzo[d]imidazol-2-yl)pyrrolidin-2-one

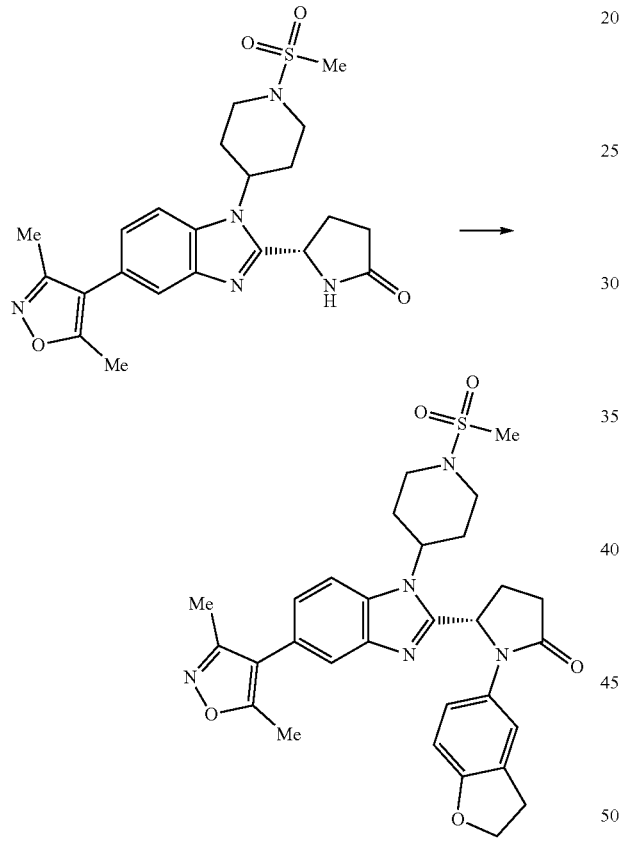

CuTMEDA (7.61 mg, 0.016 mmol) was added to a solution of DBU (17.30 μL, 0.115 mmol), Intermediate E10 (50 mg, 0.109 mmol) and (2,3-dihydrobenzofuran-5-yl)boronic acid (19.71 mg, 0.120 mmol) in acetonitrile (3310 μL, 63.4 mmol) and DCM (1.5 mL) with stirring for 15 h at 40° C. The mixture was concentrated under reduced pressure. The residue was taken up in the minimum of DCM, passed through a syringe filter and the solution then purified by flash chromatography on the Companion (12 g column, 0-10% MeOH in DCM, gradient elution) to afford (S)-1-(2,3-dihydrobenzofuran-5-yl)-5-(5-(3,5-dimethylisoxazol-4-yl)-1-(1-(methylsulfonyl)piperidin-4-yl)-1H-benzo[d]imidazol-2-yl)pyrrolidin-2-one (32 mg, 50%) as a white solid; Rt 1.75 min (method 1), m/z 576 (M+H)+ (ES+); 1H NMR (d6-DMSO) δ: 7.70 (d, J=8.5 Hz, 1H), 7.65 (d, J=1.6 Hz, 1H), 7.39-7.36 (m, 1H), 7.18 (dd, J=8.4, 1.7 Hz, 1H), 7.05 (dd, J=8.5, 2.4 Hz, 1H), 6.68 (d, J=8.5 Hz, 1H), 5.94 (dd, J=8.2, 2.7 Hz, 1H), 4.73-4.63 (m, 1H), 4.47 (t, J=8.7 Hz, 2H), 3.77 (t, J=14.9 Hz, 2H), 3.10 (t, J=8.7 Hz, 2H), 3.02 (s, 3H), 3.00-2.90 (m, 2H), 2.78 (dt, 1H), 2.70-2.56 (m, 1H), 2.46-2.31 (m+s, 5H), 2.26-2.16 (m+s, 4H), 1.99-1.90 (m, 1H), 1.52-1.44 (m, 1H).

Example 98: (S)-1-(3,4-difluorophenyl)-5-(5-(3,5-dimethylisoxazol-4-yl)-1-(1-(methylsulfonyl)piperidin-4-yl)-1H-benzo[d]imidazol-2-yl)pyrrolidin-2-one (S)-1-(3,4-difluorophenyl)-5-(5-(3,5-dimethylisoxazol-4-yl)-1-(1-(methylsulfonyl)piperidin-4-yl)-1H-benzo[d]imidazol-2-yl)pyrrolidin-2-one

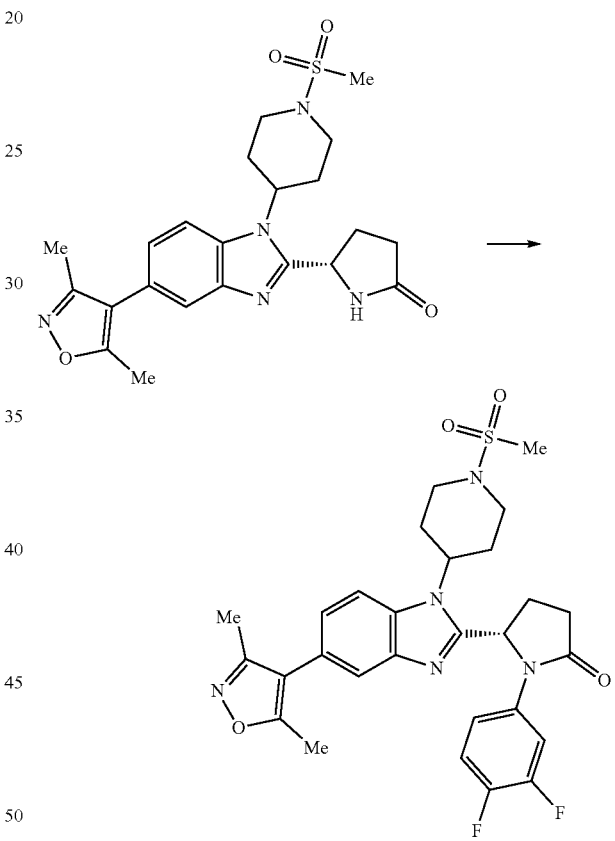

CuTMEDA (7.61 mg, 0.016 mmol) was added to a solution of DBU (17.30 μl, 0.115 mmol), Intermediate E10 (50 mg, 0.109 mmol) and (3,4-difluorophenyl)boronic acid (18.98 mg, 0.120 mmol) in acetonitrile (3310 μL, 63.4 mmol) and DCM (1.5 mL) with stirring for 15 h at 40° C. The mixture was concentrated under reduced pressure. The residue was taken up in the minimum of DCM, passed through a syringe filter and the solution then purified by chromatography on the Companion (4 g column, 0-10% MeOH in DCM, gradient elution) to afford (S)-1-(3,4-difluorophenyl)-5-(5-(3,5-dimethylisoxazol-4-yl)-1-(1-(methylsulfonyl) piperidin-4-yl)-1H-benzo[d]imidazol-2-yl)pyrrolidin-2-one (41.9 mg, 66%) as a beige solid; Rt 2.00 min (method 1), m/z 570 (M+H)+ (ES+); 1H NMR (d6-DMSO) δ: 7.83 (ddd, J=13.3, 7.4, 2.7 Hz, 1H), 7.74 (d, J=8.5

Hz, 1H), 7.61 (d, J=1.6 Hz, 1H), 7.38 (dt, J=10.6, 9.2 Hz, 1H), 7.22-7.14 (m, 2H), 6.10 (dd, J=8.2, 1.9 Hz, 1H), 4.80-4.65 (m, 1H), 3.82 (d, J=11.7 Hz, 2H), 3.11-2.93 (m+s, 5H), 2.78-2.59 (m, 2H), 2.58-2.43 (m, 3H), 2.36 (s, 3H), 2.19 (s, 3H), 2.14-2.06 (m, 1H), 2.05-1.90 (m, 2H).

Example 99: (S)-1-(3-chloro-4-fluorophenyl)-5-(5-(3,5-dimethylisoxazol-4-yl)-1-(1-(methylsulfonyl)piperidin-4-yl)-1H-benzo[d]imidazol-2-yl)pyrrolidin-2-one (S)-1-(3-chloro-4-fluorophenyl)-5-(5-(3,5-dimethylisoxazol-4-yl)-1-(1-(methylsulfonyl)piperidin-4-yl)-1H-benzo[d]imidazol-2-yl)pyrrolidin-2-one 3.82 (d, J=11.8 Hz, 2H), 3.11-2.96 (m+s, 5H), 2.81-2.59 (m, 2H), 2.58-2.41 (m, 3H), 2.36 (s, 3H), 2.19 (s, 3H), 2.16-2.07 (m, 1H), 2.06-1.97 (m, 1H), 1.95-1.85 (m, 1H).

Example 100: (S)-5-(5-(3,5-dimethylisoxazol-4-yl)-1-(1-(methylsulfonyl)piperidin-4-yl)-1H-benzo[d]imidazol-2-yl)-1-(3-fluoro-4-methoxyphenyl)pyrrolidin-2-one (S)-5-(5-(3,5-dimethylisoxazol-4-yl)-1-(1-(methylsulfonyl)piperidin-4-yl)-1H-benzo[d]imidazol-2-yl)-1-(3-fluoro-4-methoxyphenyl)pyrrolidin-2-one

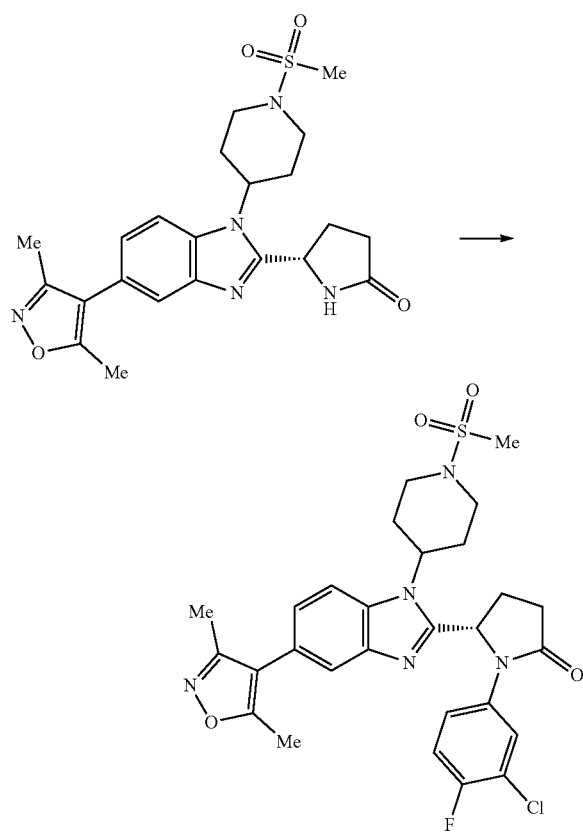

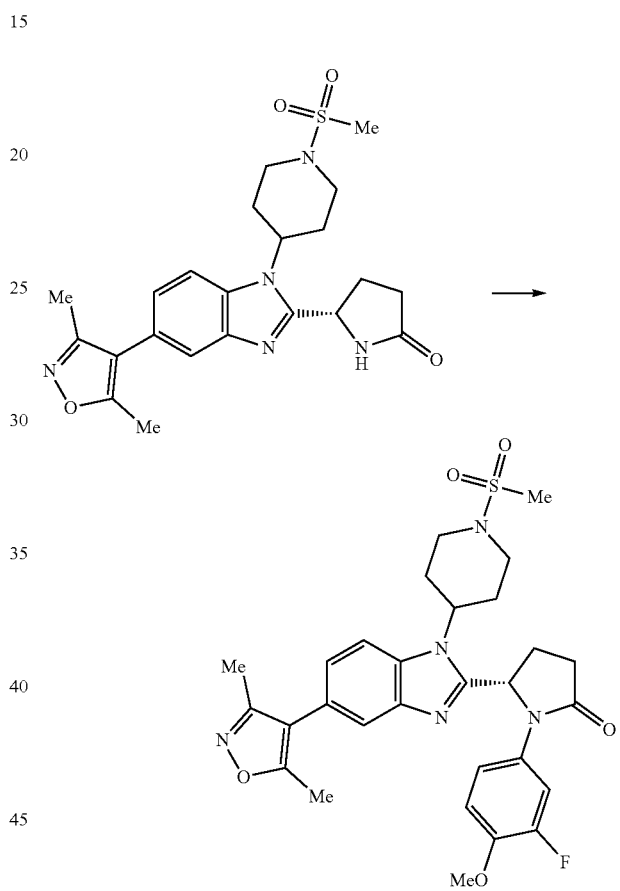

CuTMEDA (7.61 mg, 0.016 mmol) was added to a solution of DBU (17.30 µl, 0.115 mmol), Intermediate E10 (50 mg, 0.109 mmol) and (3-chloro-4-fluorophenyl)boronic acid (20.96 mg, 0.120 mmol) in acetonitrile (3310 µL, 63.4 mmol) and DCM (1.5 mL) with stirring for 15 h at 40° C. The mixture was concentrated under reduced pressure. The residue was taken up in the minimum of DCM, passed through a syringe filter and the solution then purified by chromatography on the Companion (4 g column, 0-10% MeOH in DCM, gradient elution) to afford (S)-1-(3-chloro-4-fluorophenyl)-5-(5-(3,5-dimethylisoxazol-4-yl)-1-(1-(methylsulfonyl) piperidin-4-yl)-1H-benzo[d]imidazol-2-yl)pyrrolidin-2-one (35.5 mg, 54%) as a beige solid; Rt 2.03 min (method 1), m/z 586 (M+H)+ (ES+); 1H NMR (d6-DMSO) δ: 7.99-7.90 (m, 1H), 7.74 (d, J=8.4 Hz, 1H), 7.62 (d, J=1.6 Hz, 1H), 7.42-7.32 (m, 2H), 7.19 (dd, J=8.5, 1.7 Hz, 1H), 6.12 (dd, J=8.1, 1.9 Hz, 1H), 4.81-4.68 (m, 1H), CuTMEDA (7.61 mg, 0.016 mmol) was added to a solution of DBU (17.30 µl, 0.115 mmol Intermediate E10 (50 mg, 0.109 mmol) and (3-fluoro-4-methoxyphenyl)boronic acid (20.43 mg, 0.120 mmol) in acetonitrile (3310 µL, 63.4 mmol) and DCM (1.5 mL) with stirring for 15 h at 40° C. The mixture was concentrated under reduced pressure. The residue was taken up in the minimum of DCM, passed through a syringe filter and the solution then purified by chromatography on the Companion (4 g column, 0-10% MeOH in DCM, gradient elution) to afford (S)-5-(5-(3,5-dimethylisoxazol-4-yl)-1-(1-(methylsulfonyl)piperidin-4-yl)-1H-benzo[d]imidazol-2-yl)-1-(3-fluoro-4-methoxyphenyl)pyrrolidin-2-one (36.4 mg, 55%) as a beige solid; Rt 1.85 min (method 1), m/z 582 (M+H)+ (ES+); 1H NMR (d6-DMSO) δ: 7.73 (d, J=8.5 Hz, 1H), 7.64-7.57 (m, 2H), 7.18 (dd, J=8.5, 1.7 Hz, 1H), 7.12-7.04 (m, 2H), 6.03 (dd, J=8.3, 2.1 Hz, 1H), 4.79-4.67 (m, 1H), 3.86-3.76 (m, 2H), 3.75 (s, 3H), 3.09-2.97 (m+s, 5H), 2.81-2.69 (m, 1H), 2.69-2.56 (m, 1H), 2.57-2.40 (m, 3H), 2.36 (s, 3H), 2.20 (s, 3H), 2.16-2.08 (m, 1H), 2.00-1.97 (m, 1H), 1.84-1.74 (m, 1H).

Example 101: (S)-1-(4-chloro-3-fluorophenyl)-5-(5-(3,5-dimethylisoxazol-4-yl)-1-((1R,3R)-3-hydroxycyclopentyl)-1H-benzo[d]imidazol-2-yl)pyrrolidin-2-one (S)—N-(5-(3,5-dimethylisoxazol-4-yl)-2-(((1R,3R)-3-hydroxycyclopentyl)amino)phenyl)-5-oxopyrrolidine-2-carboxamide (Intermediate D11)

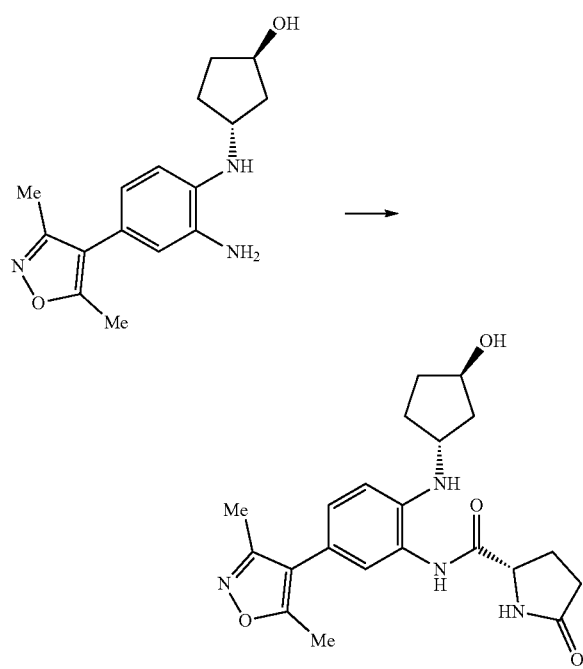

A solution of Intermediate C11 (450 mg, 1.566 mmol), (S)-5-oxopyrrolidine-2-carboxylic acid (222 mg, 1.723 mmol), HATU (655 mg, 1.723 mmol), (S)-5-oxopyrrolidine-2-carboxylic acid (222 mg, 1.723 mmol) and TEA (655 µL, 4.70 mmol) in DMF (121 µl, 1.566 mmol) was stirred at room temperature for 15 h. The mixture was partitioned between ethyl acetate (200 mL) and water (100 mL), then the layers separated. The organic phase was washed with brine (100 ml), concentrated in vacuo to give a crude purple mixture. The crude product was purified by chromatography on the Companion (12 g column, 0-10% MeOH/DCM) to afford (S)—N-(5-(3,5-dimethylisoxazol-4-yl)-2-(((1R,3R)-3-hydroxycyclo pentyl)amino)phenyl)-5-oxopyrrolidine-2-carboxamide Intermediate D11 (57 mg, 9%) as a white sticky solid; Rt 1.31 min (method 1), m/z 399 (M+H)+ (ES+); More product was obtained from the aqueous layer by concentration in vacuo. The resulting solid was washed with DCM (2×50 mL) and MeOH (50 mL). The organics were combined and concentrated in vacuo. The yellow residue was loaded on SCX resin (capture and release) to give 659 mg of a yellow green sticky solid, which was purified by flash chromatography (12 g, Companion, DCM/10% MeOH in DCM from 100/0 to 0/100) to give the major crop of (S)—N-(5-(3,5-dimethylisoxazol-4-yl)-2-(((1R,3R)-3-hydroxycyclopentyl)amino)phenyl)-5-oxopyrrolidine-2-carboxamide Intermediate D11 (334 mg, 0.830 mmol, 53.0% yield) was isolated as a white colorless glass; Rt 1.31 min (method 1), m/z 399 (M+H)+ (ES+).

(S)-5-(5-(3,5-dimethylisoxazol-4-yl)-1-((1R,3R)-3-hydroxycyclopentyl)-1H-benzo[d]imidazol-2-yl)pyrrolidin-2-one (Intermediate E11)

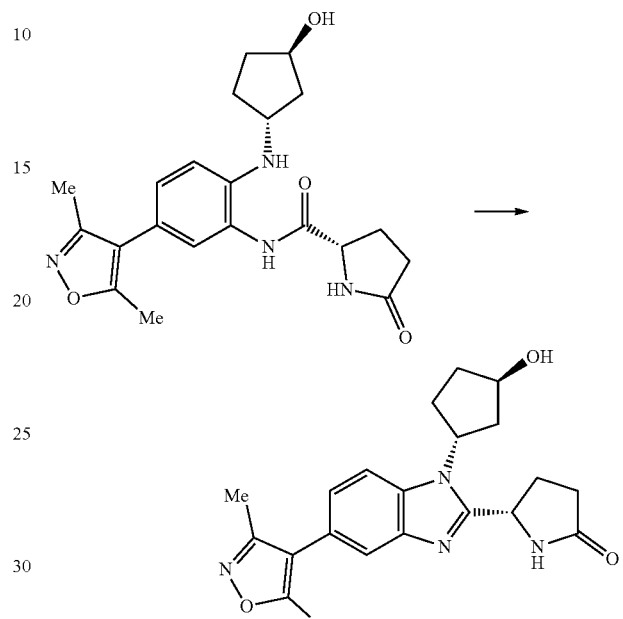

(S)—N-(5-(3,5-dimethylisoxazol-4-yl)-2-(((1R,3R)-3-hydroxycyclopentyl)amino)phenyl)-5-oxopyrrolidine-2-carboxamide Intermediate D11 (391 mg, 0.981 mmol) was dissolved in acetic acid (3932 µL, 68.7 mmol) and stirred at 80° C. for 15 h. The mixture was concentrated under reduced pressure then redissolved in methanol (20 mL). Solid potassium carbonate (1.5 g) was added and the mixture was stirred for 1 h. Filtering the suspension was difficult so it was concentrated in vacuo/pre-adsorbed on silica gel. The crude product was purified by chromatography on the Companion (4 g column, 5-15% MeOH/DCM) to give (S)-5-(5-(3,5-dimethylisoxazol-4-yl)-1-((1R,3R)-3-hydroxycyclopentyl)-1H-benzo[d]imidazol-2-yl)pyrrolidin-2-one (140 mg, 36%) was isolated as a white solid; Rt 1.13 min (method 1), m/z 381 (M+H)+ (ES+).

(S)-5-(5-(3,5-dimethylisoxazol-4-yl)-1-(1-(methylsulfonyl)piperidin-4-yl)-1H-benzo[d]imidazol-2-yl)-1-(3-fluoro-4-methoxyphenyl)pyrrolidin-2-one

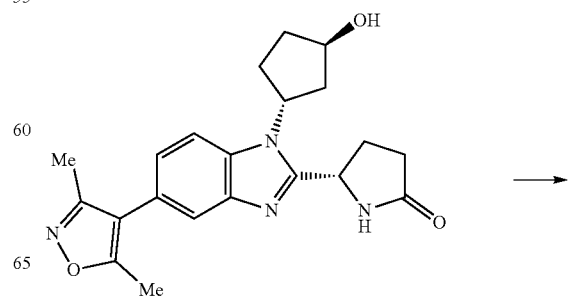

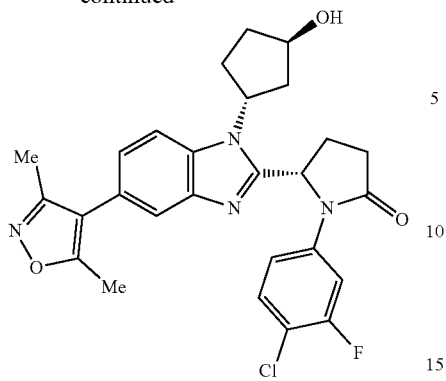

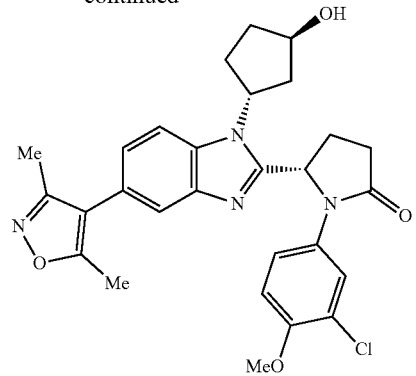

CuTMEDA (8.39 mg, 0.018 mmol) was added to a solution of DBU (19.14 μL, 0.127 mmol), Intermediate E11 (46 mg, 0.121 mmol) and (4-chloro-3-fluorophenyl)boronic acid (23.19 mg, 0.133 mmol) in acetonitrile (4 mL) with stirring for 18 hrs at 40° C. The mixture was concentrated under reduced pressure. The residue was taken up in the minimum of DCM, passed through a syringe filter and the solution then purified by chromatography on the Companion (12 g column, 0-5% MeOH in DCM, gradient elution) to afford (S)-1-(4-chloro-3-fluorophenyl)-5-(5-(3,5-dimethylisoxazol-4-yl)-1-((1R,3R)-3-hydroxycyclopentyl)-1H-benzo[d]imidazol-2-yl)pyrrolidin-2-one (46 mg, 42%) as an off-white solid; Rt 1.97 min (method 1), m/z 508 (M+H)+ (ES+); 1H NMR (d6-DMSO) δ: 7.81 (td, J=12.1, 2.5 Hz, 1H), 7.62-7.55 (m, 2H), 7.51 (td, J=8.7, 2.2 Hz, 1H), 7.35-7.23 (m, 1H), 7.17 (dt, J=8.5, 2.1 Hz, 1H), 6.14 (dd, J=37.6, 7.5 Hz, 1H), 5.34-5.25 (m, 1H), 4.89 (dd, J=3.6, 1.5 Hz, 1H), 4.50 (s, 1H), 2.69 (m, 1H), 2.56 (m, 1H), 2.36 (d, J=1.1 Hz, 3H), 2.31-2.27 (m, 4H), 2.19 (d, J=1.0 Hz, 3H), 2.15-2.04 (m, 3H), 1.76 (d, J=9.5 Hz, 1H).

Example 102: (S)-1-(3-chloro-4-methoxyphenyl)-5-(5-(3,5-dimethylisoxazol-4-yl)-1-((1R,3R)-3-hydroxycyclopentyl)-1H-benzo[d]imidazol-2-yl)pyrrolidin-2-one (S)-1-(3-chloro-4-methoxyphenyl)-5-(5-(3,5-dimethylisoxazol-4-yl)-1-((1R,3R)-3-hydroxycyclopentyl)-1H-benzo[d]imidazol-2-yl)pyrrolidin-2-one CuTMEDA (8.39 mg, 0.018 mmol) was added to a solution of DBU (19.14 μl, 0.127 mmol), Intermediate E11 (46 mg, 0.121 mmol) and (3-chloro-4-methoxyphenyl)boronic acid (24.79 mg, 0.133 mmol) in acetonitrile (4 ml) with stirring for 18 h at 40° C. The mixture was concentrated under reduced pressure. The residue was taken up in the minimum of DCM, passed through a syringe filter and the solution then purified by chromatography on the Companion (12 g column, 0-5% MeOH in DCM, gradient elution) to afford (S)-1-(3-chloro-4-methoxyphenyl)-5-(5-(3,5-dimethylisoxazol-4-yl)-1-((1R,3R)-3-hydroxycyclopentyl)-1H-benzo[d]imidazol-2-yl)pyrrolidin-2-one (26 mg, 41%) as an light yellow solid; Rt 1.77 min (method 1), m/z 521 (M+H)+ (ES+); 1H NMR (d6-DMSO) δ: 7.74 (dd, J=20.7, 2.6 Hz, 1H), 7.65-7.52 (m, 2H), 7.32 (ddd, J=11.8, 9.0, 2.6 Hz, 1H), 7.16 (ddd, J=8.5, 3.0, 1.6 Hz, 1H), 7.07 (dd, J=9.1, 2.8 Hz, 1H), 6.04 (dd, J=7.4, 7.7 Hz, 1H), 5.29 (m, 1H), 4.88 (t, J=3.2 Hz, 1H), 4.48 (s, 1H), 3.76 (d, J=0.7 Hz, 3H), 2.76-2.55 (m, 1H), 2.37 (d, J=0.9 Hz, 3H), 2.30-2.25 (m, 5H), 2.20 (d, J=0.9 Hz, 3H), 2.12-2.05 (m, 2H), 1.97 (dd, J=14.6, 7.2 Hz, 1H), 1.74 (d, J=6.2 Hz, 1H).

Example 103: (S)-1-(3,4-dichlorophenyl)-5-(5-(3,5-dimethylisoxazol-4-yl)-1-((1R,3R)-3-hydroxycyclopentyl)-1H-benzo[d]imidazol-2-yl)pyrrolidin-2-one (S)-1-(3,4-dichlorophenyl)-5-(5-(3,5-dimethylisoxazol-4-yl)-1-((1R,3R)-3-hydroxycyclopentyl)-1H-benzo[d]imidazol-2-yl)pyrrolidin-2-one

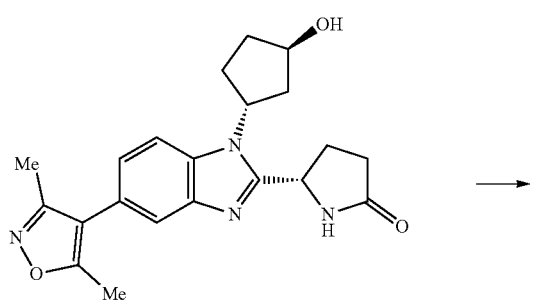

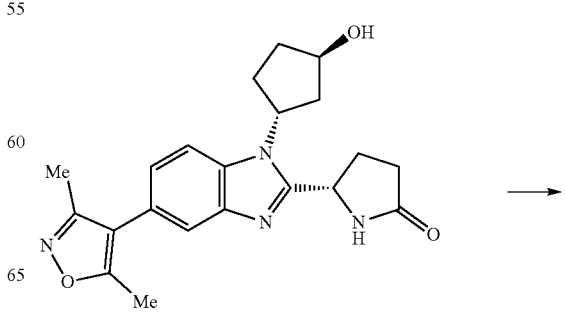

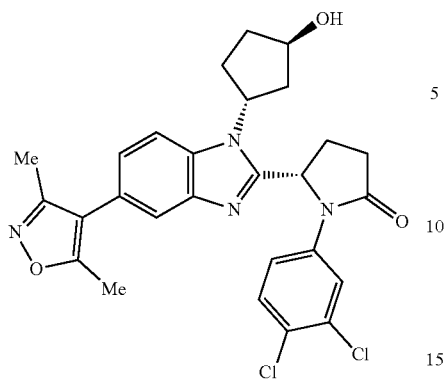

CuTMEDA (7.61 mg, 0.016 mmol) was added to a solution of DBU (17.30 µL, 0.115 mmol), Intermediate E11 (50 mg, 0.109 mmol) and (3,4-difluorophenyl)boronic acid (18.98 mg, 0.120 mmol) in acetonitrile (3310 µl, 63.4 mmol) and DCM (1.5 mL) with stirring for 15 h at 40° C. The mixture was concentrated under reduced pressure. The residue was taken up in the minimum of DCM, passed through a syringe filter and the solution then purified by chromatography on the Companion (4 g column, 0-10% MeOH in DCM, gradient elution) to afford (S)-1-(3,4-dichlorophenyl)-5-(5-(3,5-dimethylisoxazol-4-yl)-1-((1R,3R)-3-hydroxycyclo pentyl)-1H-benzo[d]imidazol-2-yl)pyrrolidin-2-one (69.3 mg, 38%) as a beige solid; Rt 2.04 min (method 1), m/z 525 (M+H)+ (ES+); 1H NMR (d6-DMSO) δ: 7.97 (dd, J=19.0, 2.5 Hz, 1H), 7.65-7.53 (m, 3H), 7.46 (ddd, J=14.9, 9.0, 2.6 Hz, 1H), 7.17 (ddd, J=8.3, 2.8, 1.6 Hz, 1H), 6.17 (dd, J=38.2, 7.2 Hz, 1H), 5.31 (h, J=8.7 Hz, 1H), 4.90 (dd, J=3.4, 1.0 Hz, 1H), 4.56-4.45 (m, 1H), 2.78-2.61 (m, 2H), 2.61-2.46 (m, 1H), 2.43-2.21 (m+s, 5H), 2.19 (d, J=1.0 Hz, 3H), 2.17-1.95 (m, 2H), 1.81-1.70 (m, 1H).

Example 104: (1R,3R)-3-(2-((S)-1-(3,4-difluorophenyl)-5-oxopyrrolidin-2-yl)-5-(3,5-dimethylisoxazol-4-yl)-1H-benzo[d]imidazol-1-yl)cyclopentyl acetate (1R,3R)-3-(5-(3,5-dimethylisoxazol-4-yl)-2-((S)-5-oxopyrrolidin-2-yl)-1H-benzo[d]imidazol-1-yl)cyclopentyl acetate

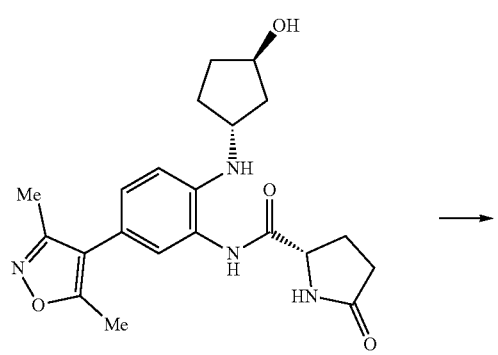

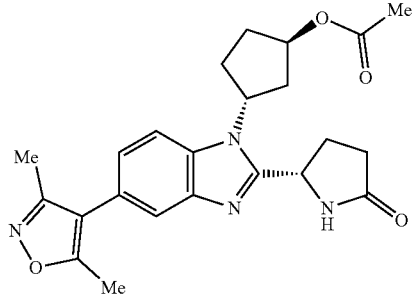

Intermediate D11 (1.35 g, 3.39 mmol) was dissolved in acetic acid (5 mL) and stirred at 80° C. for 18 hrs. The reaction mixture was cooled to RT and the solvent was removed in vacuo. The residue was purified by chromatography (24 g silica, 0-10% methanol in DCM, gradient elution). Fractions containing (1R,3R)-3-(5-(3,5-dimethylisoxazol-4-yl)-2-((S)-5-oxopyrrolidin-2-yl)-1H-benzo[d]imidazol-1-yl)cyclopentyl acetate were combined and concentrated in vacuo to afford (1R,3R)-3-(5-(3,5-dimethylisoxazol-4-yl)-2-((S)-5-oxopyrrolidin-2-yl)-1H-benzo[d]imidazol-1-yl)cyclopentyl acetate (354 mg, 26%) as a white solid; Rt 1.37 mn (method 1), m/z 423 (M+H)+ (ES+).

(1R,3R)-3-(2-((S)-1-(3,4-difluorophenyl)-5-oxopyrrolidin-2-yl)-5-(3,5-dimethylisoxazol-4-yl)-1H-benzo[d]imidazol-1-yl)cyclopentyl acetate

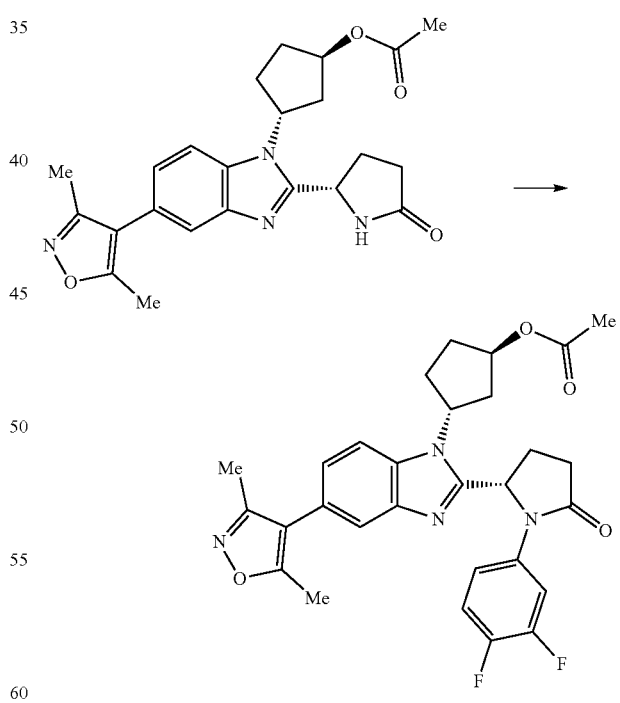

CuTMEDA (8.24 mg, 0.018 mmol) was added to a solution of DBU (0.019 mL, 0.124 mmol), (1R,3R)-3-(5-(3,5-dimethylisoxazol-4-yl)-2-((S)-5-oxopyrrolidin-2-yl)-1H-benzo[d]imidazol-1-yl)cyclopentyl acetate (50 mg, 0.118 mmol) and (3,4-difluorophenyl)boronic acid (20.56 mg, 0.130 mmol) in acetonitrile (3.585 mL, 68.6 mmol) with stirring for 15 h at 40° C. The reaction mixture was cooled down to RT, and the mixture filtered and then purified by flash chromatography on the Companion (4 g column, 0-10% MeOH in DCM, gradient elution) to afford (1R,3R)-3-(2-((S)-1-(3,4-difluorophenyl)-5-oxopyrrolidin-2-yl)-5-(3,5-dimethylisoxazol-4-yl)-1H-benzo[d]imidazol-1-yl)cyclopentyl acetate (40 mg, 60%) as a colorless glass; Rt 2.12 min (method 1), m/z 535 (M+H)+ (ES+); 1H NMR (d6-DMSO) δ: 7.86-7.76 (m, 1H), 7.68 (dd, J=8.5, 4.1 Hz, 1H), 7.62 (t, J=2.0 Hz, 1H), 7.44-7.32 (m, 1H), 7.29-7.13 (m, 2H), 6.17-6.07 (m, 1H), 5.46-5.35 (m, 1H), 5.31-5.15 (m, 1H), 2.78-2.44 (m, 5H), 2.37 (d, 3H), 2.30-2.20 (m, 2H), 2.20 (d, J=1.5 Hz, 3H), 2.18-2.05 (m+d, 5H), 1.92-1.80 (m, 1H).

Example 105: (1R,3R)-3-(2-((S)-1-(3-chloro-4-methoxyphenyl)-5-oxopyrrolidin-2-yl)-5-(3,5-dimethylisoxazol-4-yl)-1H-benzo[d]imidazol-1-yl)cyclopentyl acetate (1R,3R)-3-(2-((S)-1-(3-chloro-4-methoxyphenyl)-5-oxopyrrolidin-2-yl)-5-(3,5-dimethylisoxazol-4-yl)-1H-benzo[d]imidazol-1-yl)cyclopentyl acetate

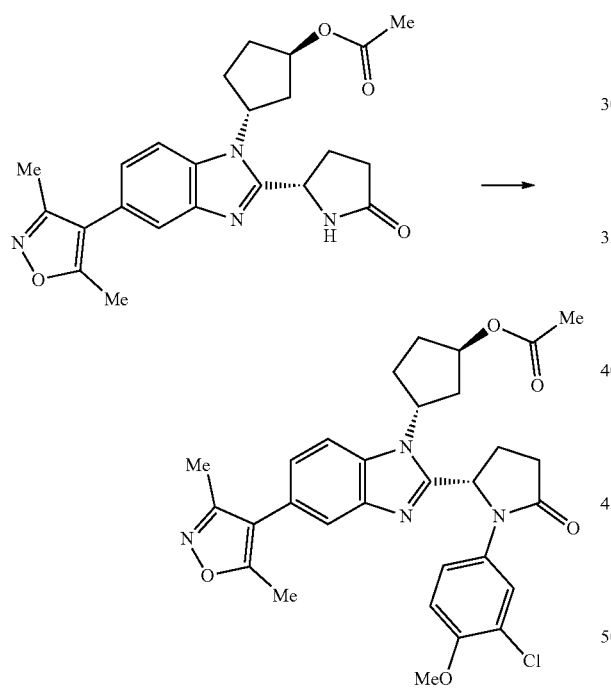

CuTMEDA (8.24 mg, 0.018 mmol) was added to a solution of DBU (0.019 mL, 0.124 mmol), (1R,3R)-3-(5-(3,5-dimethylisoxazol-4-yl)-2-((S)-5-oxopyrrolidin-2-yl)-1H-benzo[d]imidazol-1-yl)cyclopentyl acetate (50 mg, 0.118 mmol) and (3-chloro-4-methoxyphenyl)boronic acid (24.27 mg, 0.130 mmol) in acetonitrile (3.58 mL, 68.6 mmol) with stirring for 15 h at 40° C. The reaction mixture was cooled down to RT, and the mixture was filtered and then purified by chromatography on the Companion (12 g column, 0-10% MeOH in DCM, gradient elution) to afford (1R,3R)-3-(2-((S)-1-(3-chloro-4-methoxyphenyl)-5-oxopyrrolidin-2-yl)-5-(3,5-dimethylisoxazol-4-yl)-1H-benzo[d]imidazol-1-yl)cyclopentyl acetate (19.1 mg, 27% yield) as a beige solid; Rt 2.06 min (method 1), m/z 563 (M+H)+ (ES+); 1H NMR (d6-DMSO) δ: 7.74 (dd, J=22.2, 2.6 Hz, 1H), 7.66 (dd, J=8.5, 3.6 Hz, 1H), 7.63 (dd, J=3.2, 1.6 Hz, 1H), 7.29 (ddd, J=26.2, 9.0, 2.6 Hz, 1H), 7.20-7.15 (m, 1H), 7.06 (dd, J=9.1, 4.7 Hz, 1H), 6.08 (dd, 1H), 5.42-5.34 (m, 1H), 5.24 (h, J=9.3 Hz, 1H), 3.76 (d, 3H), 2.80-2.57 (m, 2H), 2.56-2.41 (m, 3H), 2.37 (d, J=1.9 Hz, 3H), 2.26-2.09 (m+d, 6H), 2.08 (s, 3H), 2.04-1.94 (m, 1H), 1.89-1.75 (m, 1H).

Example 106: (S)-1-(3-chloro-4-methoxyphenyl)-5-(5-(3,5-dimethylisoxazol-4-yl)-1-(trans-(1r,3r)-3-methoxycyclopentyl)-1H-benzo[d]imidazol-2-yl)pyrrolidin-2-one 4-(3,5-dimethylisoxazol-4-yl)-N-(trans-(1r,3r)-3-methoxycyclopentyl)-2-nitroaniline

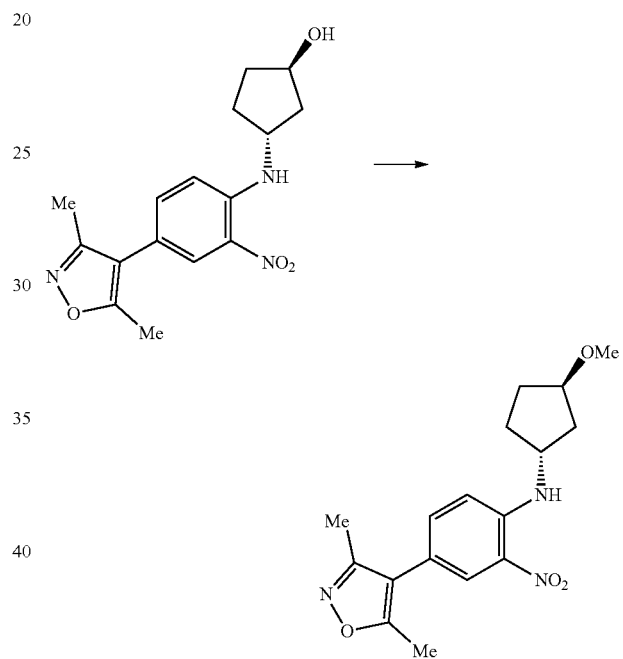

Trans-(1r,3r)-3-((4-(3,5-dimethylisoxazol-4-yl)-2-nitrophenyl)amino)cypenpentanol (815 mg, 2.57 mmol) is dissolved in THF (1.62E+04 μL, 198 mmol). This solution is cooled to 0° C., then 18-CROWN-6 (45.8 mg, 0.173 mmol) in dry THF (0.1 mL) was added followed with NaH (60% in oil) (113 mg, 2.83 mmol). After 15 mn of stirring, METHYL IODIDE (177 μL, 2.83 mmol) is added. The reaction was allowed to warm up to RT overnight. After 15 h, NaH (40 mg) was added at 0° C. then the reaction was stirred for 1 h before methyl iodide (18 μL) was added. 18-CROWN-6 (75 mg) was added. After 20 mn, more methyl iodide (18 μL) was added. The reaction was stirred overnight and then saturated aqueous ammonium chloride (10 mL) was added, followed by DCM (2×5 mL) in a separating funnel and the organic layer was dried (MgSO4), filtered, evaporated, and concentrated to give an orange sticky gum, which was purified by flash chromatography (24 g, DCM/MeOH: 100/0 to 90/10) to give 4-(3,5-dimethylisoxazol-4-yl)-N-(trans-(1r, 3r)-3-methoxycyclopentyl)-2-nitroaniline (481 mg, 55%) as a red orange glass; Rt 2.36 min (method 1), m/z 332 (M+H)+ (ES+).

295

(S)—N-(5-(3,5-dimethylisoxazol-4-yl)-2-((trans-(1r,3r)-3-methoxycyclopentyl) amino)phenyl)-5-oxopyrrolidine-2-carboxamide

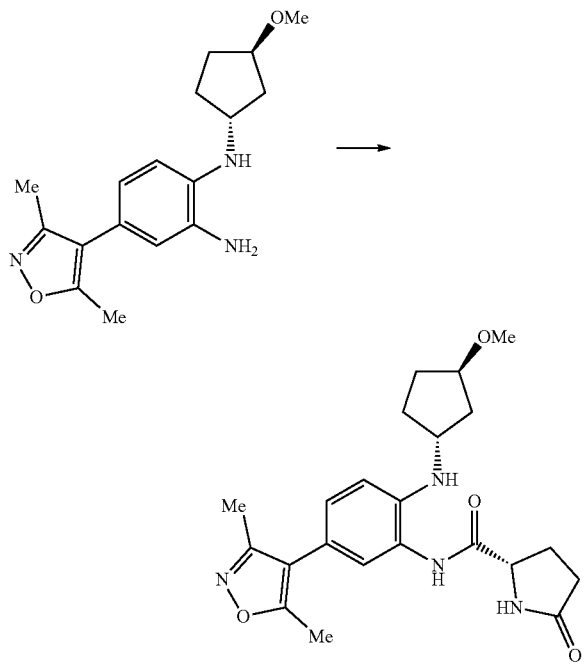

HATU (550 mg, 1.445 mmol) was added to a solution of 4-(3,5-dimethylisoxazol-4-yl)-N$^1$-(trans-(1r,3r)-3-methoxycyclopentyl)benzene-1,2-diamine (363 mg, 1.108 mmol), (S)-5-oxopyrrolidine-2-carboxylic acid (171 mg, 1.325 mmol) and DIPEA (0.316 mL, 1.806 mmol) in DMF (3.357 mL, 43.4 mmol) then stirred at room temperature for 18 h. The mixture was partitioned between ethyl acetate (100 mL) and water (100 mL), then the layers separated. The organic phase was washed with brine (100 ml), concentrated in vacuo to give a crude pink oil (693 mg). The crude product was purified by chromatography on the Companion (12 g column, 0-10% MeOH/DCM) to afford (S)—N-(5-(3,5-dimethylisoxazol-4-yl)-2-((trans-(1r,3r)-3-methoxycyclopentyl)amino)phenyl)-5-oxopyrrolidine-2-carboxamide (0.42 g, 82%) as a colourless foam; Rt 1.58 min (method 1), m/z 413 (M+H)+ (ES+).

(S)—N-(5-(3,5-dimethylisoxazol-4-yl)-2-((trans-(1r,3r)-3-methoxycyclopentyl) amino)phenyl)-5-oxopyrrolidine-2-carboxamide

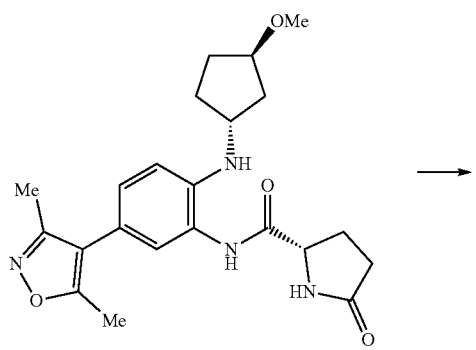

296

-continued

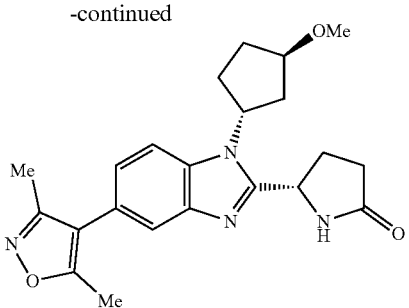

(S)—N-(5-(3,5-dimethylisoxazol-4-yl)-2-((trans-(1r,3r)-3-methoxycyclopentyl)amino)phenyl)-5-oxopyrrolidine-2-carboxamide (0.42 g, 0.988 mmol) was dissolved in acetic acid (3.96 ml, 69.1 mmol) and stirred at 70° C. for 15 h. The mixture was concentrated in vacuo. The crude brown oil was purified by flash chromatography (4 g, DCM/MeOH: 100/0 to 90/10) to give (S)-5-(5-(3,5-dimethylisoxazol-4-yl)-1-(trans-(1r,3r)-3-methoxycyclopentyl)-1H-benzo[d]imidazol-2-yl)pyrrolidin-2-one (202 mg, 48%) was isolated as a pink foam; Rt 1.38 min (method 1), m/z 395 (M+H)+ (ES+).

(S)-1-(3-chloro-4-methoxyphenyl)-5-(5-(3,5-dimethylisoxazol-4-yl)-1-(trans-(1r,3r)-3-methoxycyclopentyl)-1H-benzo[d]imidazol-2-yl)pyrrolidin-2-one

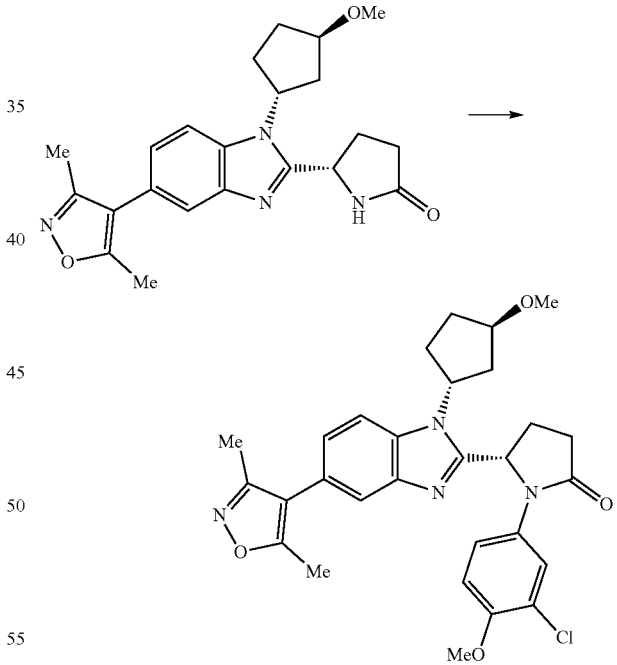

CuTMEDA (8.83 mg, 0.019 mmol) was added to a solution of DBU (20.06 µl, 0.133 mmol), (S)-5-(5-(3,5-dimethylisoxazol-4-yl)-1-(trans-(1r,3r)-3-methoxycyclopentyl)-1H-benzo[d]imidazol-2-yl)pyrrolidin-2-one (50 mg, 0.127 mmol) and (3-chloro-4-methoxyphenyl)boronic acid (26.0 mg, 0.139 mmol) in acetonitrile (3840 µL, 73.5 mmol) with stirring for 22 h at 40° C. The mixture was concentrated under reduced pressure. The residue was taken up in the minimum of DCM, passed through a syringe filter and the solution then purified by chromatography on the Companion (4 g column, 0-10% MeOH in DCM, gradient elution) to afford (S)-1-(3-chloro-4-methoxyphenyl)-5-(5-(3,5-dimethylisoxazol-4-yl)-1-(trans-(1r,3r)-3-methoxycyclopentyl)-1H-benzo[d]imidazol-2-yl)pyrrolidin-2-one (41 mg, 57%) as a greenish solid; Rt 2.10 min (method 1), m/z 535 (M+H)+ (ES+); 1H NMR (d6-DMSO) δ: 7.74 (dd, J=25.9, 2.6 Hz, 1H), 7.65-7.57 (m, 2H), 7.31 (ddd, J=15.8, 8.9, 2.6 Hz, 1H), 7.16 (ddd, J=8.4, 2.8, 1.7 Hz, 1H), 7.07 (dd, J=9.1, 3.3 Hz, 1H), 6.07 (ddd, 1H), 5.24-5.11 (m, 1H), 4.19-4.08 (m, 1H), 3.76 (d, J=1.5 Hz, 3H), 3.27 (s, 3H), 2.78-2.56 (m, 2H), 2.37 (d, J=1.6 Hz, 3H), 2.36-2.25 (m, 2H), 2.20 (d, J=1.6 Hz, 3H), 2.18-2.03 (m, 5H), 1.90-1.78 (m, 1H).

Example 107: (S)-1-(3,4-dichlorophenyl)-5-(5-(3,5-dimethylisoxazol-4-yl)-1-(trans-(1r,3r)-3-methoxycyclopentyl)-1H-benzo[d]imidazol-2-yl)pyrrolidin-2-one (S)-1-(3,4-dichlorophenyl)-5-(5-(3,5-dimethylisoxazol-4-yl)-1-(trans-(1r,3r)-3-methoxycyclopentyl)-1H-benzo[d]imidazol-2-yl)pyrrolidin-2-one

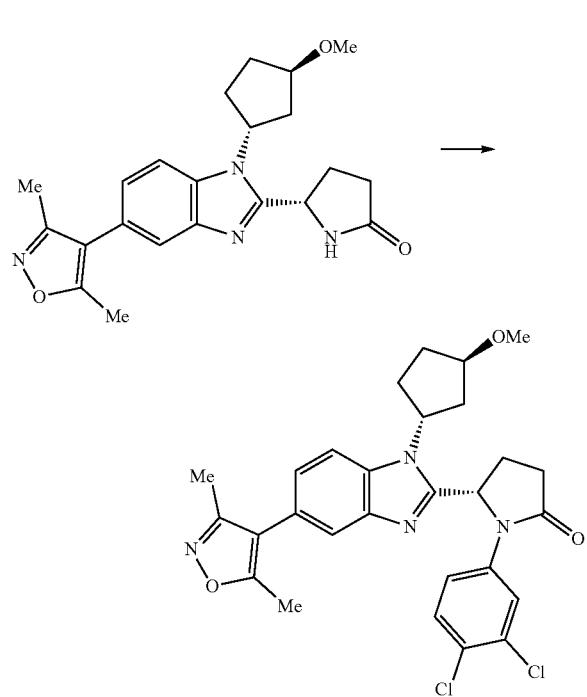

CuTMEDA (8.83 mg, 0.019 mmol) was added to a solution of DBU (20.06 µL, 0.133 mmol), (S)-5-(5-(3,5-dimethylisoxazol-4-yl)-1-(trans-(1r,3r)-3-methoxycyclopentyl)-1H-benzo[d]imidazol-2-yl)pyrrolidin-2-one (50 mg, 0.127 mmol) and (3,4-dichlorophenyl)boronic acid (26.6 mg, 0.139 mmol) in acetonitrile (3840 µL, 73.5 mmol) with stirring for 22 h at 40° C. The mixture was concentrated under reduced pressure. The residue was taken up in the minimum of DCM, passed through a syringe filter and the solution then purified by chromatography on the Companion (4 g column, 0-10% MeOH in DCM, gradient elution) to afford (S)-1-(3,4-dichlorophenyl)-5-(5-(3,5-dimethylisoxazol-4-yl)-1-(trans-(1r,3r)-3-methoxy cyclopentyl)-1H-benzo[d]imidazol-2-yl)pyrrolidin-2-one (44 mg, 62%) as a beige foam; Rt 2.37 min (method 1), m/z 539 (M+H)+ (ES+); 1H NMR (d6-DMSO) δ: 7.98 (dd, J=16.4, 2.6 Hz, 1H), 7.67-7.59 (m, 2H), 7.56 (dd, J=8.9, 3.5 Hz, 1H), 7.45 (ddd, J=11.7, 8.9, 2.6 Hz, 1H), 7.22-7.14 (m, 1H), 6.19 (dd, J=25.2, 7.6 Hz, 1H), 5.25-5.16 (m, 1H), 4.24-4.07 (m, 1H), 3.29 (d, 3H), 2.79-2.59 (m, 2H), 2.58-2.45 (m, 1H), 2.44-2.28 (m+d, 6H), 2.27-2.11 (m+d, 5H), 2.10-2.00 (m, 1H), 1.94-1.79 (m, 1H).

Example 108: (S)-1-(4-chloro-3-fluorophenyl)-5-(5-(3,5-dimethylisoxazol-4-yl)-1-(trans-(1r,3r)-3-methoxycyclopentyl)-1H-benzo[d]imidazol-2-yl) pyrrolidin-2-one (S)-1-(4-chloro-3-fluorophenyl)-5-(5-(3,5-dimethylisoxazol-4-yl)-1-(trans-(r,3r)-3-methoxycyclopentyl)-1H-benzo[d]imidazol-2-yl)pyrrolidin-2-one

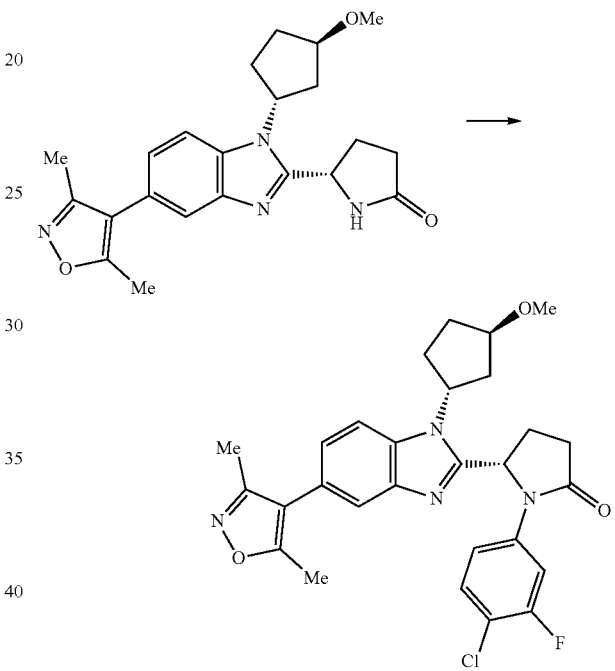

CuTMEDA (8.83 mg, 0.019 mmol) was added to a solution of DBU (20.06 µL, 0.133 mmol), (S)-5-(5-(3,5-dimethylisoxazol-4-yl)-1-(trans-(1r,3r)-3-methoxycyclopentyl)-1H-benzo[d]imidazol-2-yl)pyrrolidin-2-one (50 mg, 0.127 mmol) and (4-chloro-3-fluorophenyl)boronic acid (24.31 mg, 0.139 mmol) in acetonitrile (3840 µL, 73.5 mmol) with stirring for 15 h at 40° C. The mixture was concentrated under reduced pressure. The residue was taken up in the minimum of DCM, passed through a syringe filter and the solution then purified by flash chromatography on the Companion (4 g column, 0-10% MeOH in DCM, gradient elution) to afford (S)-1-(4-chloro-3-fluorophenyl)-5-(5-(3,5-dimethylisoxazol-4-yl)-1-(trans-(1r,3r)-3-methoxycyclopentyl)-1H-benzo[d]imidazol-2-yl)pyrrolidin-2-one (47.8 mg, 68%) as a beige solid; Rt 2.25 min (method 1), m/z 523 (M+H)+ (ES+); 1H NMR (d6-DMSO) δ: 7.81 (ddd, J=12.1, 7.6, 2.5 Hz, 1H), 7.63 (dd, J=8.5, 4.0 Hz, 1H), 7.60 (t, J=2.0 Hz, 1H), 7.51 (td, J=8.8, 3.4 Hz, 1H), 7.33-7.24 (m, 1H), 7.18 (dt, J=8.4, 2.0 Hz, 1H), 6.17 (dd, J=26.0, 7.8 Hz, 1H), 5.25-5.14 (m, 1H), 4.21-4.10 (m, 1H), 3.29 (d, 3H), 2.78-2.59 (m, 2H), 2.59-2.50 (m, 1H), 2.47-2.25 (m+d, 6H), 2.26-2.11 (m+d, 5H), 2.11-2.01 (m, 1H), 1.92-1.80 (m, 1H).

Example 110: (S)-5-(1-(4,4-difluorocyclohexyl)-5-(3,5-dimethylisoxazol-4-yl)-1H-benzo[d]imidazol-2-yl)-1-(3,4-difluorophenyl)pyrrolidin-2-one (S)—N-(2-((4,4-difluorocyclohexyl)amino)-5-(3,5-dimethylisoxazol-4-yl)phenyl)-5-oxo pyrrolidine-2-carboxamide (Intermediate D12)

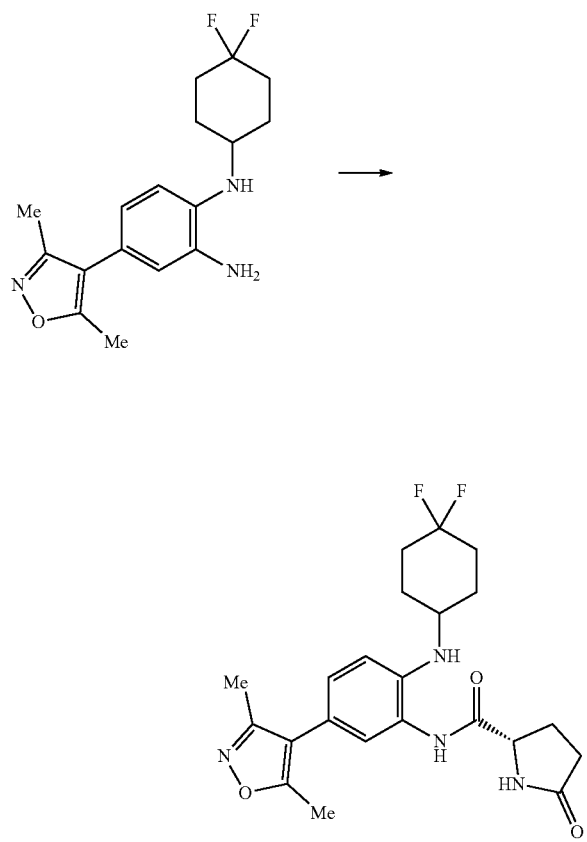

HATU (600 mg, 1.578 mmol) was added to a stirred solution of TEA (0.25 ml, 1.794 mmol), (S)-5-oxopyrrolidine-2-carboxylic acid (250 mg, 1.936 mmol) and Intermediate C12 (500 mg, 1.400 mmol) in N,N-dimethylformamide (5 mL) then the mixture was stirred at room temperature for 18 h. The mixture was diluted with water (40 mL) then extracted with ethyl acetate (2×40 mL). The combined organic phases were washed with 20% brine (2×40 mL) then saturated brine (40 mL). The organic phase was dried (MgSO$_4$), filtered and concentrated under reduced pressure. The crude product was purified by chromatography on the Companion (40 g column, 0-50% THF/DCM) then triturated in diethyl ether to afford (S)—N-(2-((4,4-difluorocyclohexyl)amino)-5-(3,5-dimethylisoxazol-4-yl)phenyl)-5-oxopyrrolidine-2-carboxamide (605 mg, 99%) as a white solid; Rt 1.86 min (method 1), m/z 433 (M+H)+ (ES+).

(S)-5-(1-(4,4-difluorocyclohexyl)-5-(3,5-dimethylisoxazol-4-yl)-1H-benzo[d]imidazol-2-yl)pyrrolidin-2-one (Intermediate E12)

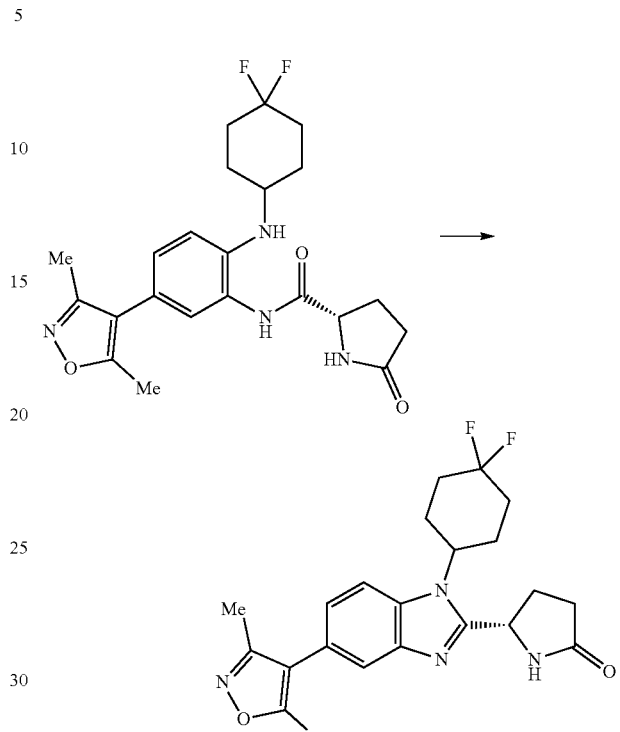

Intermediate D12 (605 mg, 1.385 mmol) was heated to 80° C. in acetic acid (15 mL) for 2 h. The bulk of the solvents were removed under reduced pressure then the residue (ca. 1 mL) was added slowly to a stirred solution of 1 M aqueous sodium carbonate (50 mL). The resulting solid was collected by filtration then was purified by chromatography on the Companion (40 g column, 15-75% THF/DCM) then triturated in diethyl ether to afford (S)-5-(1-(4,4-difluorocyclohexyl)-5-(3,5-dimethylisoxazol-4-yl)-1H-benzo[d]imidazol-2-yl)pyrrolidin-2-one Intermediate E12 (420 mg, 72%) as a white solid; Rt 1.70 min (method 1), m/z 415 (M+H)+ (ES+).

4-(2-(1-(3-fluoro-4-(trifluoromethoxy)phenyl)propan-2-yl)-1-(3-(methylsulfonyl)propyl)-1H-benzo[d]imidazol-5-yl)-3,5-dimethylisoxazole

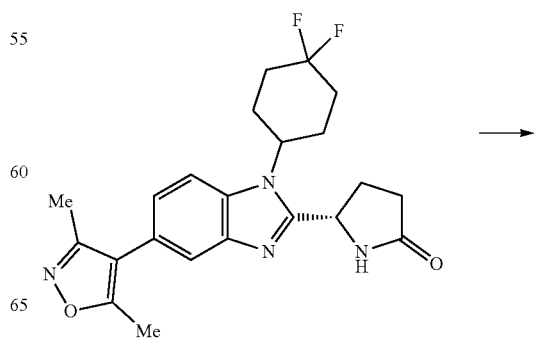

301

-continued

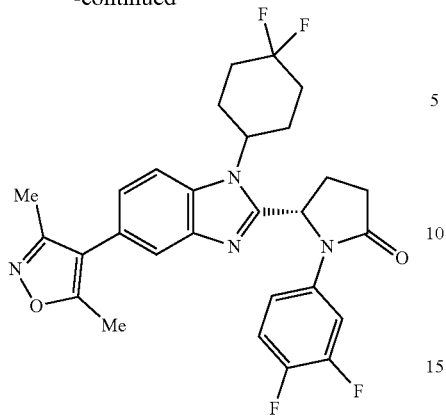

CuTMEDA (55 mg, 0.118 mmol) was added to a stirred solution of Intermediate E12 (100 mg, 0.239 mmol) in pyridine (3 mL) then the mixture was stirred for 15 min at 40° C. (3,4-difluorophenyl)boronic acid (100 mg, 0.633 mmol) was added then the mixture was heated to 40° C. for 2 h. The mixture was diluted with ethyl acetate (25 mL) then washed with water (3×25 mL) and saturated brine (25 mL). The organic phase was dried (MgSO$_4$), filtered and concentrated under reduced pressure. The crude product was purified by flash chromatography on the Companion (12 g column, 0-25% THF) then triturated in diethyl ether to (S)-5-(1-(4,4-difluorocyclohexyl)-5-(3,5-dimethylisoxazol-4-yl)-1H-benzo[d]imidazol-2-yl)-1-(3,4-difluorophenyl) pyrrolidin-2-one (106 mg, 83%) as a white solid; Rt 2.32 min; m/z 527 (M+H)+ (ES+); 1H NMR (d6-DMSO) δ: 7.84 (1H, ddd, J=13.2, 7.4, 2.7 Hz), 7.62 (1H, d, J=1.6 Hz), 7.59 (1H, d, J=8.5 Hz), 7.38 (1H, dt, J=10.5, 9.2 Hz), 7.22 (1H, dd, J=8.5, 1.7 Hz), 7.20-7.12 (1H, m), 6.06 (1H, d, J=8.1 Hz), 4.81 (1H, s), 2.80-2.58 (2H, m), 2.60-2.52 (1H, m), 2.43 (2H, s), 2.36 (3H, s), 2.30-2.21 (4H, m), 2.19 (3H, s), 2.17-2.08 (1H, m), 2.07-1.98 (1H, m), 1.98-1.89 (1H, m); Chiral HPLC (Diacel Chiralpak IA, 5 μm, 4.6×250 mm, 30 min method, 1.0 mL/min, isocratic 30% EtOH in isohexane (0.2% TFA): RT=4.13 min (5.65 min minor), ~90% ee @ 254 nm.

Example 111: (S)-1-(3-chloro-4-methoxyphenyl)-5-(1-(4,4-difluorocyclohexyl)-5-(3,5-dimethylisoxazol-4-yl)-1H-benzo[d]imidazol-2-yl)pyrrolidin-2-one (S)-1-(3-chloro-4-methoxyphenyl)-5-(1-(4,4-difluorocyclohexyl)-5-(3,5-dimethylisoxazol-4-yl)-1H-benzo[d]imidazol-2-yl)pyrrolidin-2-one

302

-continued

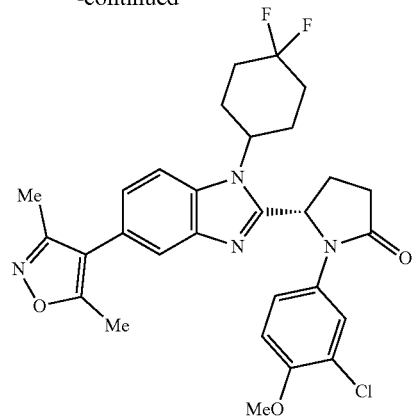

DBU (0.027 ml, 0.181 mmol) was added to a solution of Intermediate E12 (50 mg, 0.121 mmol) in MeCN (2 ml, 38.3 mmol), and stirred for 10 min. CuTMEDA (11.21 mg, 0.024 mmol) was added, sonicated and stirred for a 10 min, (3-chloro-4-methoxyphenyl)boronic acid (33.7 mg, 0.181 mmol) added and the reaction stirred at RT for 18 hr. The mixture was concentrated under reduced pressure then the crude product was purified by chromatography on silica gel (12 g column, 0-10% MeOH/DCM) to afford (S)-1-(3-chloro-4-methoxyphenyl)-5-(1-(4,4-difluorocyclohexyl)-5-(3,5-dimethylisoxazol-4-yl)-1H-benzo[d]imidazol-2-yl)pyrrolidin-2-one (36 mg, 53%) as a tan solid; Rt 2.26 min; m/z 555 (M+H)+ (ES+); 1H NMR (d6-DMSO) δ: 7.78 (1H, d, J=2.6 Hz), 7.63 (1H, d, J=1.6 Hz), 7.57 (1H, d, J=8.5 Hz), 7.26 (1H, dd, J=9.0, 2.7 Hz), 7.21 (1H, dd, J=8.5, 1.7 Hz), 7.07 (1H, d, J=9.1 Hz), 6.08-5.98 (2H, m), 4.89-4.77 (1H, m), 3.76 (3H, s), 2.84-2.70 (1H, m), 2.70-2.58 (1H, m), 2.48-2.39 (2H, m), 2.37 (3H, s), 2.29-2.21 (4H, m), 2.20 (3H, s), 2.18-2.12 (1H, m), 2.04-1.93 (1H, m), 1.75-1.66 (1H, m); Chiral HPLC (Diacel Chiralpak IA, 5 μm, 4.6×250 mm, 30 min method, 1.0 ml/min, isocratic 30% EtOH in isohexane (0.2% TFA): RT=5.37 min (7.89 minor), ~90% ee @ 254 nm.

112: (S)-1-(3-fluoro-4-methoxyphenyl)-5-(1-(4,4-difluorocyclohexyl)-5-(3,5-dimethylisoxazol-4-yl)-1H-benzo[d]imidazol-2-yl)pyrrolidin-2-one (S)-1-(3-chloro-4-methoxyphenyl)-5-(1-(4,4-difluorocyclohexyl)-5-(3,5-dimethylisoxazol-4-yl)-1H-benzo[d]imidazol-2-yl)pyrrolidin-2-one

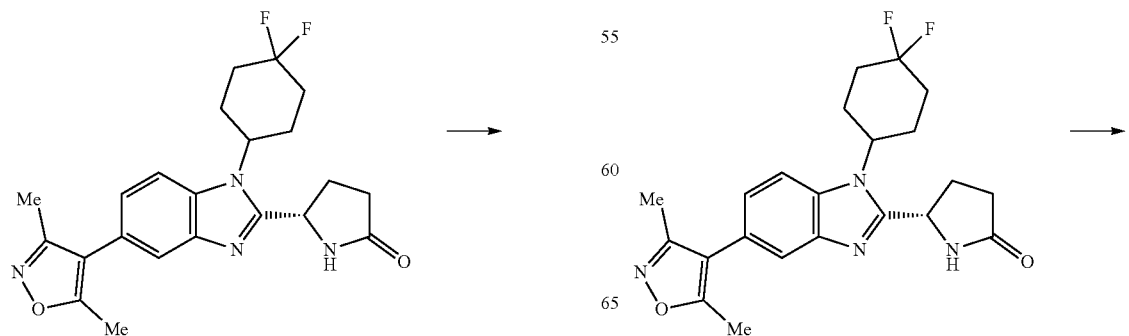

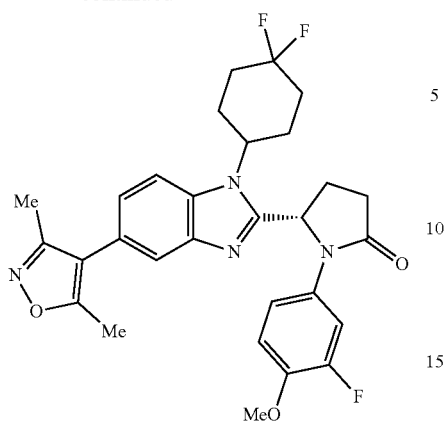

DBU (0.027 ml, 0.181 mmol) was added to a solution of Intermediate E12 (50 mg, 0.121 mmol) in MeCN (2 ml, 38.3 mmol), and stirred for 10 min. CuTMEDA (11.21 mg, 0.024 mmol) was added, sonicated and stirred for a 10 min, (3-fluoro-4-methoxyphenyl)boronic acid (30.8 mg, 0.181 mmol) added and the reaction stirred at RT for 18 hr. The mixture was concentrated under reduced pressure then the crude product was purified by chromatography on silica gel (12 g column, 0-10% MeOH/DCM) to afford (S)-5-(1-(4,4-difluorocyclohexyl)-5-(3,5-dimethylisoxazol-4-yl)-1H-benzo[d]imidazol-2-yl)-1-(3-fluoro-4-methoxyphenyl)pyrrolidin-2-one (44 mg, 67%) as a pink solid; Rt 2.20 min; m/z 539 (M+H)+ (ES+); 1H NMR (d6-DMSO) δ: 7.65-7.54 (3H, m), 7.22 (1H, dd, J=8.5, 1.7 Hz), 7.14-7.05 (2H, m), 6.00 (1H, dd, J=8.6, 1.7 Hz), 4.81 (1H, s), 3.75 (3H, s), 2.82-2.69 (1H, m), 2.70-2.57 (1H, m), 2.46-2.38 (2H, m), 2.37 (3H, s), 2.30-2.21 (4H, m), 2.20 (3H, s), 2.18-2.10 (2H, m), 2.05-1.92 (1H, m), 1.82-1.70 (1H, m). Chiral HPLC (Diacel Chiralpak IA, 5 µm, 4.6×250 mm, 30 min method, 1.0 mL/min, isocratic 30% EtOH in isohexane (0.2% TFA): RT=5.54 min (7.90 min minor), ~90% ee @ 254 nm.

Example 113: (5S)-1-(3,4-difluorophenyl)-5-(5-(3,5-dimethylisoxazol-4-yl)-1-(2-methyltetrahydro-2H-pyran-4-yl)-1H-benzo[d]imidazol-2-yl)pyrrolidin-2-one (2S)—N-(5-(3,5-dimethylisoxazol-4-yl)-2-((2-methyltetrahydro-2H-pyran-4-yl)amino)phenyl)-5-oxopyrrolidine-2-carboxamide (Intermediate D13)

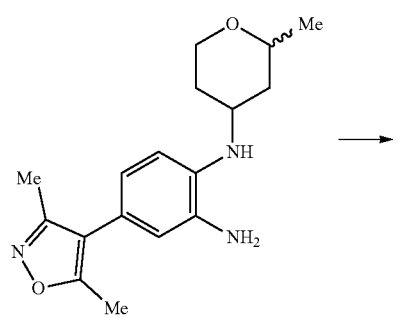

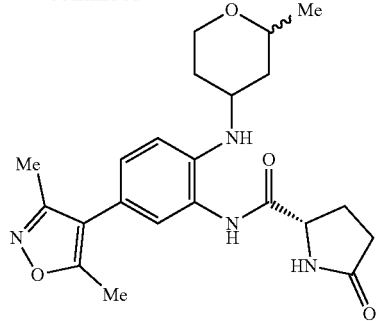

HATU (1.791 g, 4.71 mmol) was added to a solution of 4 Intermediate C13 (1.45 g, 4.28 mmol), (S)-5-oxopyrrolidine-2-carboxylic acid (0.608 g, 4.71 mmol) and N,N-diisopropylethylamine (0.897 mL, 5.14 mmol) in DMF (8 mL, 103 mmol) then stirred at room temperature overnight. The mixture was diluted with water (20 mL) then extracted with ethyl acetate (3×40 mL). The combined organic phases were washed with 1M aqueous HCl (10 mL), saturated aqueous NaHCO₃ (10 mL) and saturated brine (3×10 mL), then dried (MgSO₄), filtered and concentrated to give a brown oil, which was purified by flash chromatography (40 g column, 0-10% MeOH/DCM) to afford Intermediate D13 (1.63 g, 3.91 mmol, 91%) as a white foam; Rt 1.61 min; m/z 413 (M+H)+ (ES+); 1H NMR (d6-DMSO) consistent with product structure as a mixture of diastereomers (ratio ~9:1) at >95% purity (5S)-5-(5-(3,5-dimethylisoxazol-4-yl)-1-(2-methyltetrahydro-2H-pyran-4-yl)-1H-benzo[d]imidazol-2-yl)pyrrolidin-2-one (Intermediate E13

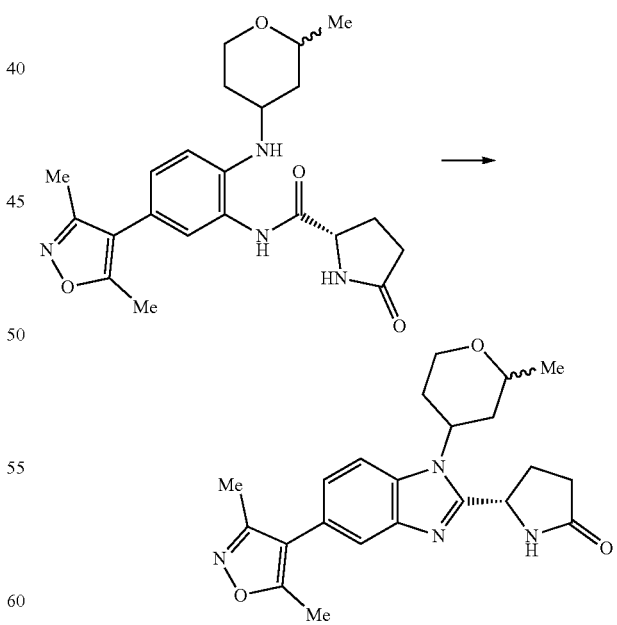

Intermediate D13 (1.60 g, 3.88 mmol) was heated to 80° C. in ACETIC ACID (8.88 ml, 155 mmol) for 20 h. After cooling to RT, the mixture was concentrated under reduced pressure. The reaction mixture was diluted with MeOH (30 mL) and solid potassium carbonate (1 g) was added. The

305 mixture was stirred for 1 h before concentrating onto loose silica gel. The crude product was purified by flash chromatography on silica gel (40 g column, 0-10% (0.7 M Ammonia/MeOH)/DCM) to afford (5S)-5-(5-(3,5-dimethylisoxazol-4-yl)-1-(2-methyl tetrahydro-2H-pyran-4-yl)-1H-benzo[d]imidazol-2-yl)pyrrolidin-2-one Intermediate E13 (970 mg, 63%) as a tanned solid; Rt 1.36 min; m/z 395 (M+H)+ (ES+).

(5S)-1-(3,4-difluorophenyl)-5-(5-(3,5-dimethylisoxazol-4-yl)-1-(2-methyltetrahydro-2H-pyran-4-yl)-1H-benzo[d]imidazol-2-yl)pyrrolidin-2-one

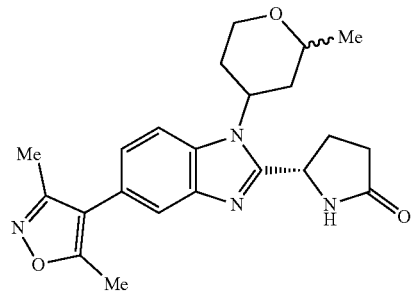

DBU (0.042 ml, 0.279 mmol) was added to a solution of Intermediate E13 (50 mg, 0.127 mmol) in MeCN (2 ml, 38.3 mmol), and stirred for 10 min. CuTMEDA (11.77 mg, 0.025 mmol) was added, sonicated and stirred for a 10 min, then (3,4-difluorophenyl)boronic acid (40.0 mg, 0.254 mmol) added and the reaction stirred at RT for 18 h. The mixture was concentrated under reduced pressure then the crude product was purified by chromatography on silica gel (12 g column, 0-10% MeOH/DCM) to afford (5S)-1-(3,4-difluorophenyl)-5-(5-(3,5-dimethylisoxazol-4-yl)-1-(2-methyltetrahydro-2H-pyran-4-yl)-1H-benzo[d]imidazol-2-yl)pyrrolidin-2-one (54 mg, 83%) as a light pink solid; Rt 2.03 min; m/z 507 (M+H)+ (ES+); 1H NMR (d6-DMSO) δ: NMR consistent as a mixture of 4 diastereoisomers.

306

Example 114: (5S)-1-(3-chloro-4-methoxyphenyl)-5-(5-(3,5-dimethylisoxazol-4-yl)-1-(2-methyltetrahydro-2H-pyran-4-yl)-1H-benzo[d]imidazol-2-yl)pyrrolidin-2-one (5S)-1-(3-chloro-4-methoxyphenyl)-5-(5-(3,5-dimethylisoxazol-4-yl)-1-(2-methyltetrahydro-2H-pyran-4-yl)-1H-benzo[d]imidazol-2-yl)pyrrolidin-2-one

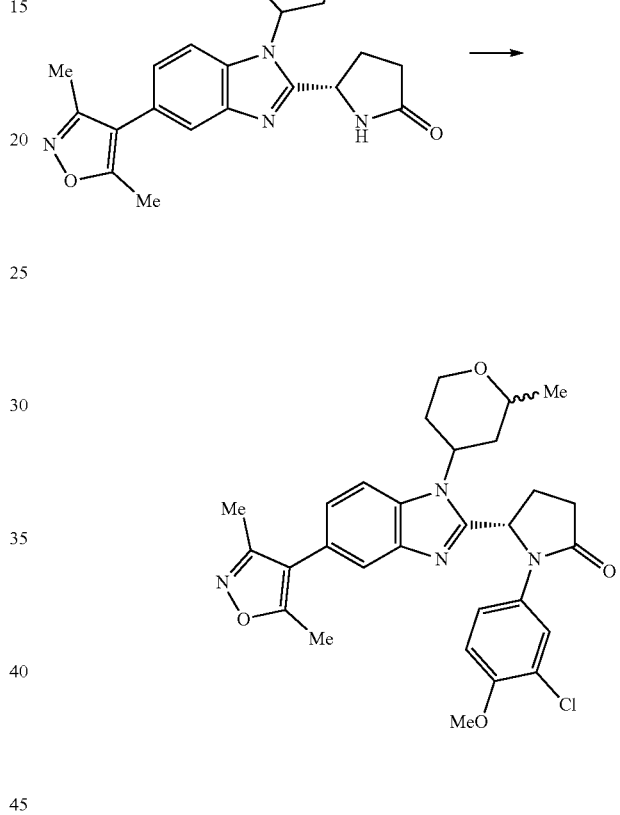

DBU (0.042 ml, 0.279 mmol) was added to a solution of Intermediate E13 (50 mg, 0.127 mmol) in MeCN (2 ml, 38.3 mmol), and stirred for 10 min. CuTMEDA (11.77 mg, 0.025 mmol) was added, sonicated and stirred for a 10 min, then boronic acid added and the reaction stirred at RT for 18 hr. The mixture was concentrated under reduced pressure then the crude product was purified by chromatography on silica gel (24 g column, 0-10% MeOH/DCM) to afford (5S)-1-(3-chloro-4-methoxyphenyl)-5-(5-(3,5-dimethylisoxazol-4-yl)-1-(2-methyltetrahydro-2H-pyran-4-yl)-1H-benzo[d]imidazol-2-yl)pyrrolidin-2-one (48 mg, 0.089 mmol, 70%) as a tan solid; Rt 1.98 min; m/z 535 (M+H)+ (ES+); 1H NMR (d6-DMSO) δ: NMR consistent as a mixture of 4 diastereoisomers.

Example 115: (5S)-5-(5-(3,5-dimethylisoxazol-4-yl)-1-(2-methyltetrahydro-2H-pyran-4-yl)-1H-benzo[d]imidazol-2-yl)-1-(3-fluoro-4-methoxyphenyl)pyrrolidin-2-one (5S)-5-(5-(3,5-dimethylisoxazol-4-yl)-1-(2-methyl-tetrahydro-2H-pyran-4-yl)-1H-benzo[d]imidazol-2-yl)-1-(3-fluoro-4-methoxyphenyl)pyrrolidin-2-one

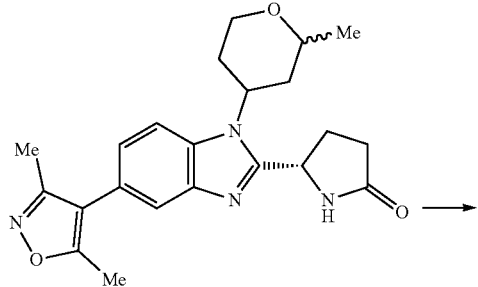

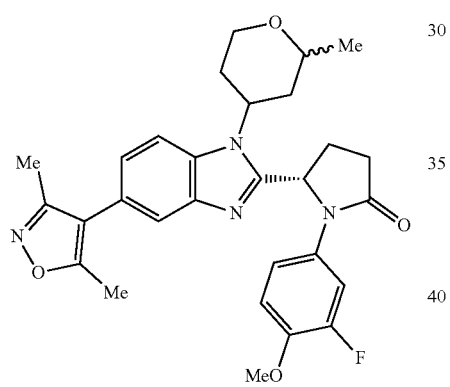

DBU (0.042 ml, 0.279 mmol) was added to a solution of Intermediate E13 (50 mg, 0.127 mmol) in MeCN (2 ml, 38.3 mmol), and stirred for 10 min. CuTMEDA (11.77 mg, 0.025 mmol) was added, sonicated and stirred for a 10 min, then (3-fluoro-4-methoxyphenyl) boronic acid (43.1 mg, 0.254 mmol) added and the reaction stirred at RT for 18 hr. The mixture was concentrated under reduced pressure then the crude product was purified by chromatography on silica gel (24 g column, 0-10% MeOH/DCM) to afford (5S)-5-(5-(3,5-dimethylisoxazol-4-yl)-1-(2-methyltetrahydro-2H-pyran-4-yl)-1H-benzo[d]imidazol-2-yl)-1-(3-fluoro-4-methoxyphenyl)pyrrolidin-2-one (39 mg, 59%) as a pink solid; Rt 1.91 min; m/z 519 (M+H)+ (ES+); 1H NMR (d6-DMSO) δ: NMR consistent as a mixture of 4 diastereoisomers.

Example 118: (S)-1-(3,4-difluorophenyl)-5-(5-(3,5-dimethylisoxazol-4-yl)-1-((1s,4R)-4-hydroxy-4-methylcyclohexyl)-1H-benzo[d]imidazol-2-yl)pyrrolidin-2-one (S)—N-(5-(3,5-dimethylisoxazol-4-yl)-2-(((1s,4R)-4-hydroxy-4-methylcyclohexyl) amino)phenyl)-5-oxopyrrolidine-2-carboxamide (Intermediate D15)

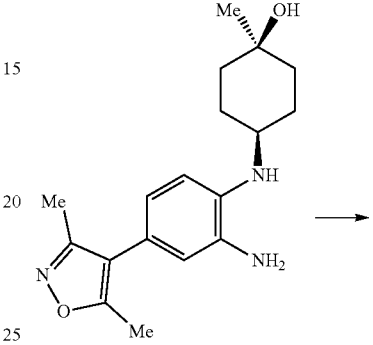

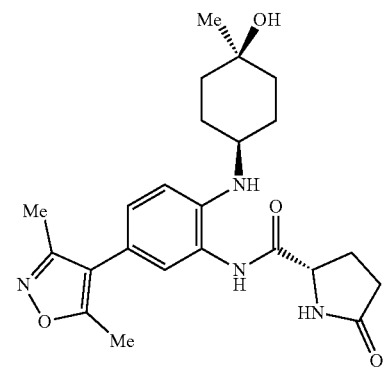

HATU (750 mg, 1.972 mmol) was added to a stirred solution of TEA (0.3 mL, 2.152 mmol), (S)-5-oxopyrrolidine-2-carboxylic acid (0.25 g, 1.936 mmol) and Intermediate C15 (574 mg, 1.820 mmol) in N,N-dimethylformamide (10 mL) then the mixture was stirred at room temperature for 2 h. The mixture was diluted with brine (100 mL) then extracted with ethyl acetate (3×100 mL). The combined organic phases were concentrated under reduced pressure. The crude product was purified by chromatography on the Companion (40 g column, 50-100% THF/DCM) then triturated in diethyl ether to afford (S)—N-(5-(3,5-dimethylisoxazol-4-yl)-2-(((1s,4R)-4-hydroxy-4-methylcyclohexyl)amino)phenyl)-5-oxo pyrrolidine-2-carboxamide (773 mg, 95% yield) as a pale pink solid; Rt 1.58 min; m/z 427 (M+H)+ (ES+).

309

(S)-5-(5-(3,5-dimethylisoxazol-4-yl)-1-((1s,4R)-4-hydroxy-4-methylcyclohexyl)-1H-benzo[d]imidazol-2-yl)pyrrolidin-2-one (Intermediate E15)

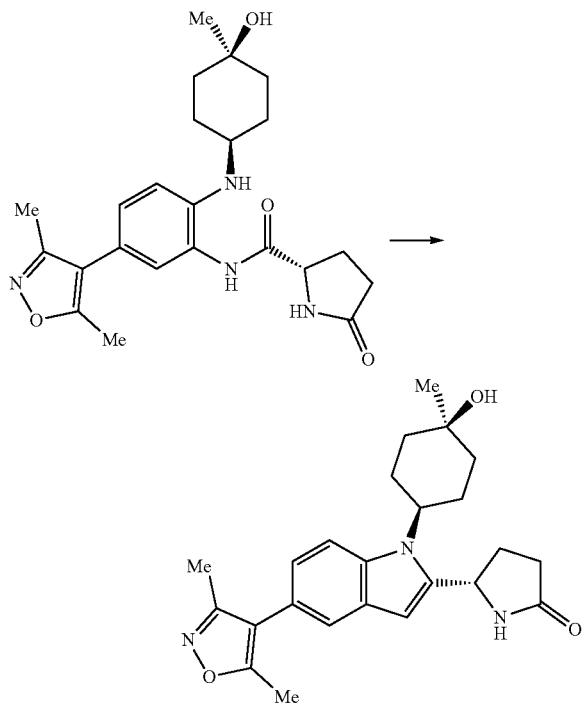

Intermediate D15 (750 mg, 1.758 mmol) was heated to 80° C. in acetic acid (15 mL) for 1.5 h. The solvents were removed under reduced pressure then the mixture was dissolved in dichloromethane (50 mL) and diethylamine (6 mL) and concentrated onto loose silica gel. The silicate was purified by chromatography on the Companion (40 g column, 50-75% THF/DCM) then triturated in diethyl ether (15 mL) to afford (S)-5-(5-(3,5-dimethylisoxazol-4-yl)-1-((1s,4R)-4-hydroxy-4-methylcyclohexyl)-1H-benzo[d]imidazol-2-yl)pyrrolidin-2-one Intermediate E15 (550 mg, 76%) as a white solid; Rt 1.19 min; m/z 409 (M+H)+ (ES+).

(S)-1-(3,4-difluorophenyl)-5-(5-(3,5-dimethylisoxazol-4-yl)-1-((1s,4R)-4-hydroxy-4-methylcyclohexyl)-1H-benzo[d]imidazol-2-yl)pyrrolidin-2-one

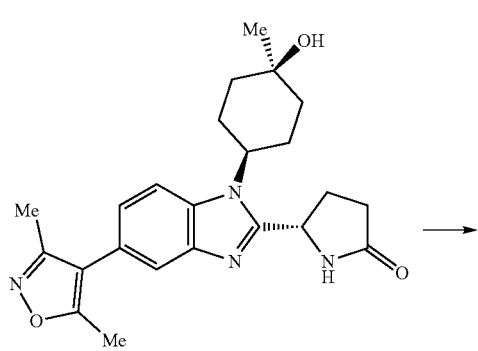

310

-continued

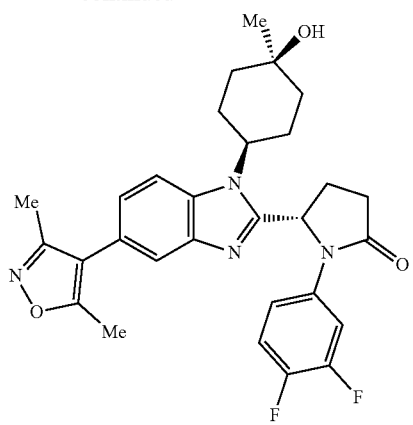

CuTMEDA (10 mg, 0.022 mmol) was added to a stirred suspension Intermediate E15 (70 mg, 0.171 mmol) and DBU (28 µL, 0.186 mmol) in acetonitrile (6 mL). (3,4-Difluorophenyl)boronic acid (30 mg, 0.190 mmol) was added and the mixture was heated to 70° C. for 3 h. The volatiles were removed under reduced pressure then the residue was dissolved in THF, filtered and adsorbed onto loose silica gel. Purification by chromatography on the Companion (12 g column, 0-50% THF/DCM) then triturated in diethyl ether to give (S)-1-(3,4-difluorophenyl)-5-(5-(3,5-dimethylisoxazol-4-yl)-1-((1s,4R)-4-hydroxy-4-methyl cyclohexyl)-1H-benzo[d]imidazol-2-yl)pyrrolidin-2-one (47 mg, 52.2% yield) as a beige solid; Rt 1.92 min; m/z 521 (M+H)+ (ES+); 1H NMR (d6-DMSO) δ: 7.83 (ddd, J=13.2, 7.4, 2.6 Hz, 1H), 7.76 (d, J=8.5 Hz, 1H), 7.61 (d, J=1.6 Hz, 1H), 7.39 (dd, J=10.7, 9.2 Hz, 1H), 7.23 (dd, J=8.4, 1.7 Hz, 1H), 7.19-7.13 (m, 1H), 6.08 (dd, J=8.1, 2.0 Hz, 1H), 4.52 (tt, 1H), 4.47 (s, 1H), 2.82-2.52 (m, 5H), 2.38 (s, 3H), 2.21 (s, 3H), 2.13-2.03 (m, 1H), 1.79-1.50 (m, 6H), 1.23 (s, 3H).

Example 119: (S)-5-(5-(3,5-dimethylisoxazol-4-yl)-1-((1s,4R)-4-hydroxy-4-methylcyclohexyl)-1H-benzo[d]imidazol-2-yl)-1-(3-fluoro-4-methoxyphenyl)pyrrolidin-2-one

(S)-5-(5-(3,5-dimethylisoxazol-4-yl)-1-((1s,4R)-4-hydroxy-4-methylcyclohexyl)-1H-benzo[d]imidazol-2-yl)-1-(3-fluoro-4-methoxyphenyl)pyrrolidin-2-one

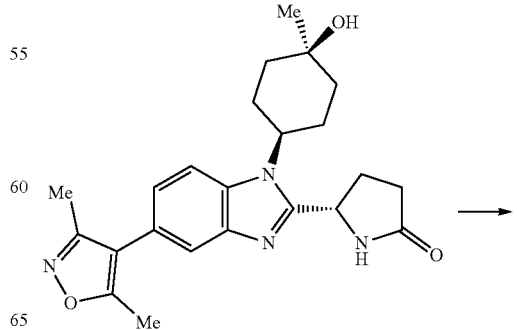

311
-continued

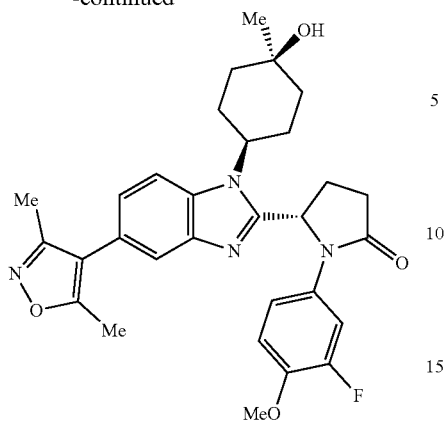

312
-continued

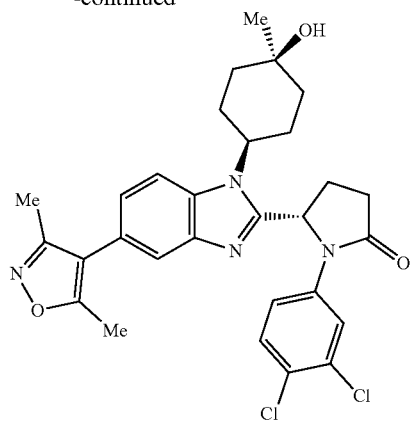

Intermediate E15 (70 mg, 0.170 mmol), (3-fluoro-4-methoxyphenyl)boronic acid (30 mg, 0.177 mmol), CuTMEDA (10 mg, 0.022 mmol) and DBU (26 μL, 0.172 mmol) in acetonitrile (3 mL) was heated to 70° C. for 2 h. The mixture was concentrated onto loose silica gel. The silicate was purified by chromatography on the Companion (4 g column, 5-50% THF/DCM) then triturated in diethyl ether to yield (S)-5-(5-(3,5-dimethylisoxazol-4-yl)-1-((1s,4R)-4-hydroxy-4-methylcyclohexyl)-1H-benzo[d]imidazol-2-yl)-1-(3-fluoro-4-methoxyphenyl) pyrrolidin-2-one (43 mg, 47%) as a white solid; Rt 1.78 min; m/z 533 (M+H)+ (ES+); 1H NMR (d6-DMSO) δ: 7.74 (d, J=8.5 Hz, 1H), 7.66-7.54 (m, 2H), 7.22 (dd, J=8.5, 1.3 Hz, 1H), 7.14-7.01 (m, 2H), 6.01 (d, J=7.9 Hz, 1H), 4.62-4.32 (m, 2H), 3.75 (s, 3H), 2.84-2.70 (m, 1H), 2.70-2.52 (m, 4H), 2.38 (s, 3H), 2.21 (s, 3H), 2.15-2.06 (m, 1H), 1.80-1.66 (m, 2H), 1.66-1.51 (m, 3H), 1.48-1.37 (m, 1H), 1.22 (s, 3H).

A mixture of Intermediate E15 (70 mg, 0.170 mmol), (3,4-dichlorophenyl)boronic acid (35 mg, 0.183 mmol), CuTMEDA (10 mg, 0.022 mmol) and DBU (26 μl, 0.172 mmol) in acetonitrile (3 mL) was heated to 70° C. for 2 h. The mixture was concentrated onto loose silica gel. The silicate was purified by chromatography on the Companion (4 g column, 5-50% THF/DCM) then triturated in ethyl ether to yield (S)-1-(3,4-dichlorophenyl)-5-(5-(3,5-dimethylisoxazol-4-yl)-1-((1s,4R)-4-hydroxy-4-methylcyclohexyl)-1H-benzo[d]imidazol-2-yl) pyrrolidin-2-one (49 mg, 50%) as a white solid; Rt 2.14 min; m/z 553 (M+H)+ (ES+); 1H NMR (d6-DMSO) δ: 7.99 (d, J=2.5 Hz, 1H), 7.76 (d, J=8.5 Hz, 1H), 7.60 (d, J=1.6 Hz, 1H), 7.58 (d, J=8.9 Hz, 1H), 7.41 (dd, J=8.9, 2.6 Hz, 1H), 7.23 (dd, J=8.4, 1.7 Hz, 1H), 6.14 (d, J=8.3 Hz, 1H), 4.63-4.51 (m, 1H), 4.48 (s, 1H), 2.84-2.53 (m, 5H), 2.38 (s, 3H), 2.21 (s, 3H), 2.13-2.02 (m, 1H), 1.81-1.51 (m, 6H), 1.24 (s, 3H).

Example 120: (S)-1-(3,4-dichlorophenyl)-5-(5-(3,5-dimethylisoxazol-4-yl)-1-((1s,4R)-4-hydroxy-4-methylcyclohexyl)-1H-benzo[d]imidazol-2-yl)pyrrolidin-2-one (S)-1-(3,4-dichlorophenyl)-5-(5-(3,5-dimethylisoxazol-4-yl)-1-((1s,4R)-4-hydroxy-4-methylcyclohexyl)-1H-benzo[d]imidazol-2-yl)pyrrolidin-2-one Example 121: (S)-1-(4-chloro-3-fluorophenyl)-5-(5-(3,5-dimethylisoxazol-4-yl)-1-((1s,4R)-4-hydroxy-4-methylcyclohexyl)-1H-benzo[d]imidazol-2-yl)pyrrolidin-2-one (S)-1-(4-chloro-3-fluorophenyl)-5-(5-(3,5-dimethylisoxazol-4-yl)-1-((1s,4R)-4-hydroxy-4-methylcyclohexyl)-1H-benzo[d]imidazol-2-yl)pyrrolidin-2-one

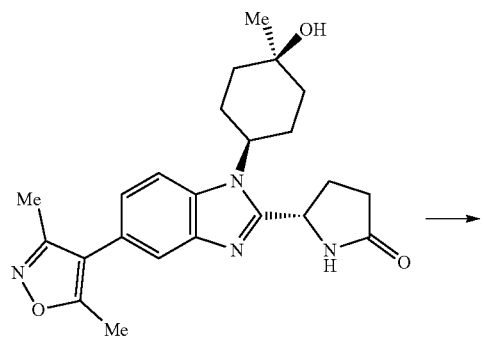

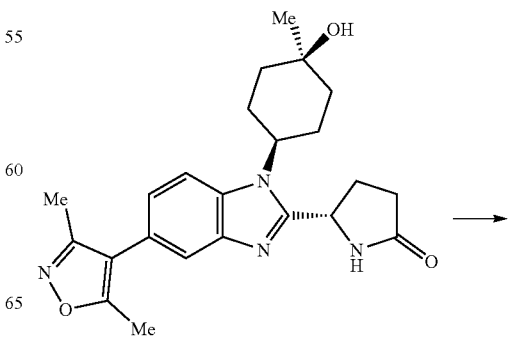

313
-continued

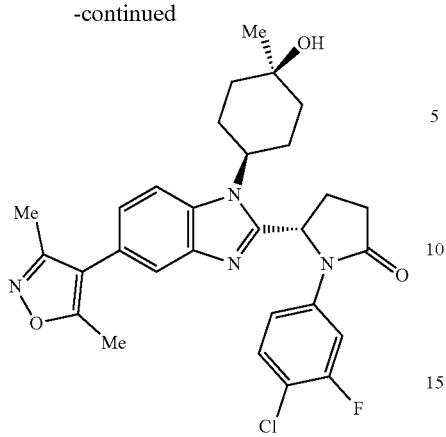

A mixture of Intermediate E15 (70 mg, 0.170 mmol), (4-chloro-3-fluorophenyl)boronic acid (32 mg, 0.184 mmol), CuTMEDA (10 mg, 0.022 mmol) and DBU (26 μl, 0.172 mmol) in acetonitrile (3 mL) was heated to 70° C. for 2 h. The mixture was concentrated onto loose silica gel. The silicate was purified by chromatography on the Companion (4 g column, 5-50% THF/DCM) then triturated in diethyl ether to yield ((S)-1-(4-chloro-3-fluorophenyl)-5-(5-(3,5-dimethylisoxazol-4-yl)-1-((1s,4R)-4-hydroxy-4-methylcyclohexyl)-1H-benzo[d]imidazol-2-yl)pyrrolidin-2-one (38 mg, 40%) as a white solid; Rt 2.06 min; m/z 537 (M+H)+ (ES+); 1H NMR (d6-DMSO) δ: 7.84 (dd, J=12.1, 2.4 Hz, 1H), 7.77 (d, J=8.5 Hz, 1H), 7.60 (d, J=1.6 Hz, 1H), 7.52 (t, J=8.8 Hz, 1H), 7.28-7.19 (m, 2H), 6.13 (d, J=7.8 Hz, 1H), 4.61-4.48 (m, 1H), 4.44 (br s, 1H), 2.82-2.52 (m, 5H), 2.37 (s, 3H), 2.21 (s, 3H), 2.12-2.03 (m, 1H), 1.81-1.52 (m, 6H), 1.24 (s, 3H).

Example 122: (S)-1-(3-chloro-4-methoxyphenyl)-5-(5-(3,5-dimethylisoxazol-4-yl)-1-(2-oxaspiro[3.3]heptan-6-yl)-1H-benzo[d]imidazol-2-yl)pyrrolidin-2-one (S)—N-(2-(2-oxaspiro[3.3]heptan-6-ylamino)-5-(3,5-dimethylisoxazol-4-yl)phenyl)-5-oxopyrrolidine-2-carboxamide (Intermediate D16)

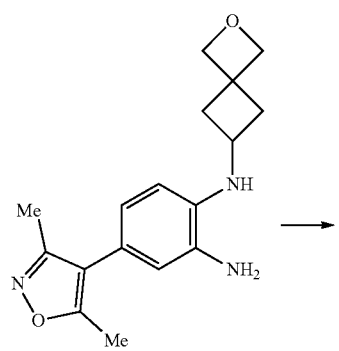

314
-continued

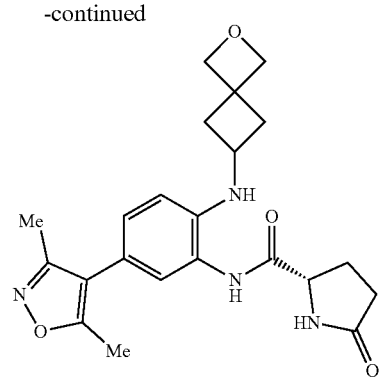

A solution of Intermediate C16 (1.47 g, 4.91 mmol), 2-(3H-[1,2,3]triazolo[4,5-b]pyridin-3-yl)-1,1,3,3-tetramethyl isouronium hexafluorophosphate(V) (2.054 g, 5.40 mmol), (S)-5-oxopyrrolidine-2-carboxylic acid (0.697 g, 5.40 mmol) and TEA (2.053 mL, 14.73 mmol) in DMF (20 mL) was stirred at room temperature for 2 h. The mixture was partitioned between ethyl acetate (200 mL) and water (100 mL), then the layers separated. The organic phase was washed with brine (100 ml), dried (MgSO4) and concentrated in vacuo to give a purple oil. Intermediate D16 (1.6 g, 3.04 mmol) was used in the subsequent step without further purification; Rt 1.53 min; m/z 411 (M+H)+ (ES+).

(S)-5-(5-(3,5-dimethylisoxazol-4-yl)-1-(2-oxaspiro[3.3]heptan-6-yl)-1H-benzo[d]imidazol-2-yl)pyrrolidin-2-one (Intermediate E16)

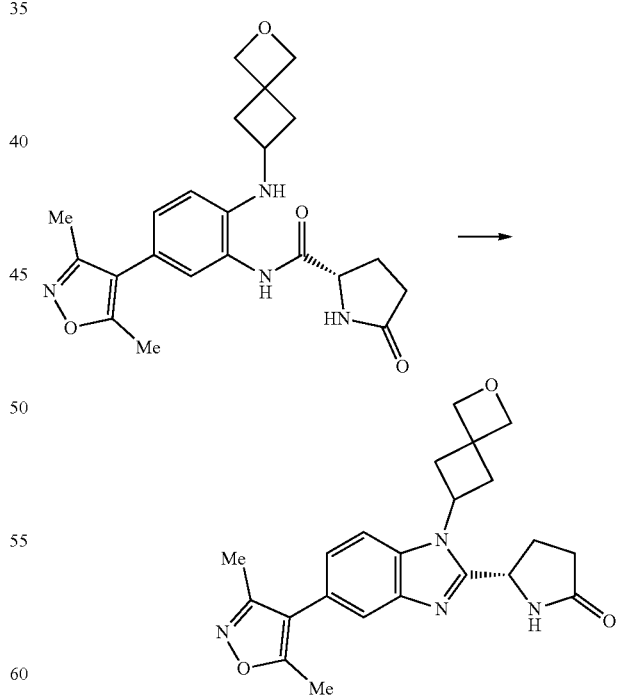

Intermediate D16 was dissolved in acetic acid (6 mL) and stirred at 80° C. for 18 hrs. The reaction mixture was cooled to RT and the solvent was removed in vacuo. The residue was purified by chromatography (24 g silica, 0-10% methanol in DCM, gradient elution). Fractions containing the product were combined and concentrated in vacuo. to give the crude (S)-5-(5-(3,5-dimethylisoxazol-4-yl)-1-(2-oxaspiro[3.3]heptan-6-yl)-1H-benzo[d]imidazol-2-yl)pyrrolidin-2-one Intermediate E16 (ca 206 mg, 13%); Rt 1.53 min; m/z 411 (M+H)+ (ES+).

(S)-1-(3-chloro-4-methoxyphenyl)-5-(5-(3,5-dimethylisoxazol-4-yl)-1-(2-oxaspiro[3.3]heptan-6-yl)-1H-benzo[d]imidazol-2-yl)pyrrolidin-2-one

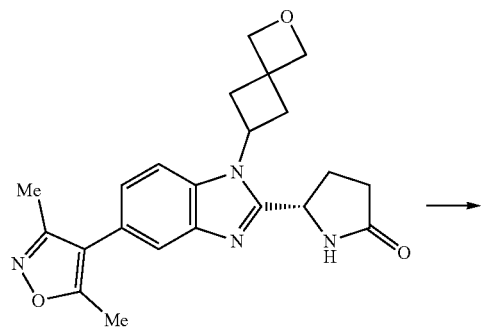

CuTMEDA (17.75 mg, 0.038 mmol) was added to a solution of DBU (40.3 μl, 0.268 mmol), Intermediate E16 (100 mg, 0.255 mmol) and (3-chloro-4-methoxyphenyl)boronic acid (52.2 mg, 0.280 mmol) in acetonitrile (4 ml) with stirring for 18 h at 40° C. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (S)-1-(4-chloro-3-fluorophenyl)-5-(5-(3,5-dimethylisoxazol-4-yl)-1-((1s,4R)-4-hydroxy-4-methylcyclohexyl)-1H-benzo[d]imidazol-2-yl)pyrrolidin-2-one (53 mg, 38%) as an off white solid; Rt 1.91 min; m/z 533 (M+H)+ (ES+); 1H NMR (d6-DMSO) δ: 7.78-7.67 (m, 2H), 7.62 (dd, J=1.7, 0.6 Hz, 1H), 7.28-7.15 (m, 2H), 7.07 (d, J=9.1 Hz, 1H), 5.91 (dd, J=8.2, 2.3 Hz, 1H), 5.76 (s, 1H), 5.09 (p, J=8.9 Hz, 1H), 4.83-4.73 (m, 2H), 4.70 (s, 2H), 3.78 (s, 3H), 3.03 (t, J=10.1 Hz, 2H), 2.91-2.51 (m, 3H), 2.51-2.45 (m, 1H), 2.37 (s, 3H), 2.20 (s, 3H), 2.15-2.05 (m, 1H).

Example 123: (S)-5-(5-(3,5-dimethylisoxazol-4-yl)-1-(2-oxaspiro[3.3]heptan-6-yl)-1H-benzo[d]imidazol-2-yl)-1-(3-fluoro-4-methoxyphenyl)pyrrolidin-2-one (S)-5-(5-(3,5-dimethylisoxazol-4-yl)-1-(2-oxaspiro[3.3]heptan-6-yl)-1H-benzo[d]imidazol-2-yl)-1-(3-fluoro-4-methoxyphenyl)pyrrolidin-2-one

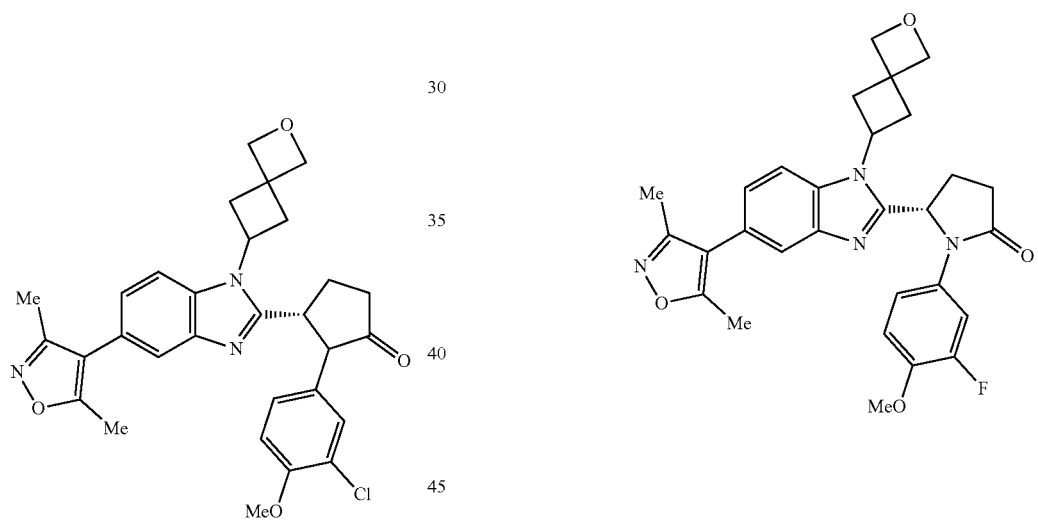

CuTMEDA (17.75 mg, 0.038 mmol) was added to a solution of DBU (40.3 μl, 0.268 mmol), Intermediate E16 (100 mg, 0.255 mmol) and (3-fluoro-4-methoxyphenyl)boronic acid (47.6 mg, 0.280 mmol) in acetonitrile (4 mL) with stirring for 18 h at 40° C. The mixture was concentrated under reduced pressure. The residue was taken up in the minimum of DCM, passed through a syringe filter and the solution then purified by chromatography on the Companion (12 g column, 0-10% MeOH in DCM, gradient elution) to afford (S)-5-(5-(3,5-dimethylisoxazol-4-yl)-1-(2-oxaspiro[3.3]heptan-6-yl)-1H-benzo[d]imidazol-2-yl)-1-(3-fluoro-4-methoxyphenyl)pyrrolidin-2-one (43 mg, 32%) as an off white solid; Rt 1.84 min; m/z 517 (M+H)+ (ES+); 1H NMR (d6-DMSO) δ: 7.70 (dd, J=8.5, 0.7 Hz, 1H), 7.63-7.52 (m, 2H), 7.18 (dd, J=8.4, 1.7 Hz, 1H), 7.07 (dd, J=4.6, 2.0 Hz, 2H), 5.87 (dd, J=8.2, 2.2 Hz, 1H), 5.08 (p, J=8.9 Hz, 1H), 4.82-4.73 (m, 2H), 4.69 (s, 2H), 3.75 (s, 3H), 3.03 (q, J=9.8 Hz, 2H), 2.92-2.51 (m, 4H), 2.36 (s, 3H), 2.19 (s, 3H), 2.12-2.00 (m, 1H), 1.70-1.58 (m, 1H).

Example 141: (S)-5-(1-((R)-3,3-difluorocyclopentyl)-5-(3,5-dimethylisoxazol-4-yl)-1H-benzo[d]imidazol-2-yl)-1-(3,4-difluorophenyl)pyrrolidin-2-one (R)-3-((4-(3,5-dimethylisoxazol-4-yl)-2-nitrophenyl)amino)cyclopentanone

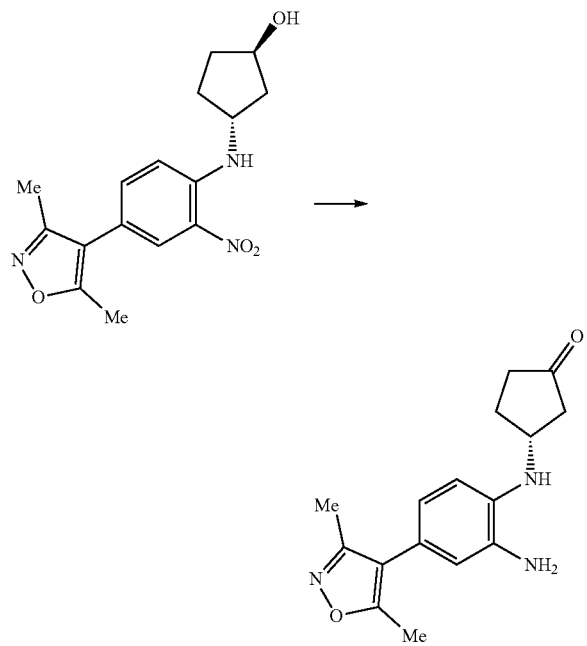

A stirred solution of DMSO (101 µL, 1.418 mmol) in DCM (1703 µL, 26.5 mmol) at −78° C. was treated with oxalyl chloride dropwise (124 µL, 1.418 mmol). After 15 min at −78° C., a solution of (1R,3R)-3-((4-(3,5-dimethylisoxazol-4-yl)-2-nitrophenyl)amino)cyclopentanol (300 mg, 0.945 mmol) in DCM (1 mL) was slowly added. After 45 min at −78° C., DIPEA (826 µl, 4.73 mmol) was slowly added. The reaction mixture was stirred at −70° C. for 20 h, then quenched with NaHCO$_3$ (20 mL) and diluted in DCM (10 mL) then split by passing through a PhaseSep©, washing with further DCM. The solution was concentrated in vacuo to give an orange red crude solid (0.378 g), which was purified by flash chromatography on the Companion (12 g, DCM/AcOEt: 100/0 to 90/10) to afford (R)-3-((4-(3,5-dimethylisoxazol-4-yl)-2-nitrophenyl)amino)cyclopentanone (0.264 g, 86%) as a sticky orange oil; Rt 2.00 min; m/z 316 (M+H)+ (ES+).

(R)—N-(3,3-difluorocyclopentyl)-4-(3,5-dimethylisoxazol-4-yl)-2-nitroaniline

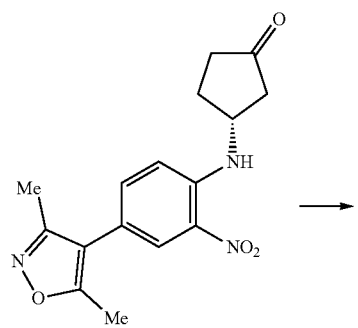

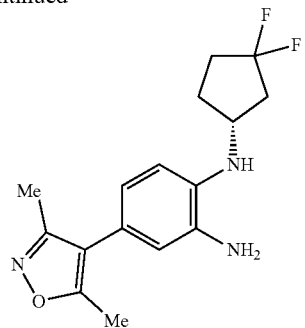

DAST (3.51 ml, 9.51 mmol) was added dropwise to stirred, cooled (0° C.) solution of (R)-3-((4-(3,5-dimethylisoxazol-4-yl)-2-nitrophenyl)amino)cyclopentanone (1.0 g, 3.17 mmol) in DCE (9.99 ml, 127 mmol). The reaction was stirred at RT over the week end then for another 20 h. The reaction was quenched into saturated aqueous NaHCO$_3$ solution (100 mL) (gas evolution), the phases separated, the aqueous extracted with DCM (3×150 mL), the combined organics were dried on MgSO$_4$ and filtered through a PhaseSep© and concentrated in vacuo to give a dark brown crude oil which was purified by chromatography column (24 g, DCM 100%) to give (R)—N-(3,3-difluorocyclopentyl)-4-(3,5-dimethylisoxazol-4-yl)-2-nitroaniline (0.87 g, 80%) was isolated as a red oil; Rt 2.44 min; m/z 338 (M+H)+ (ES+).

(R)—N$^1$-(3,3-difluorocyclopentyl)-4-(3,5-dimethylisoxazol-4-yl)benzene-1,2-diamine

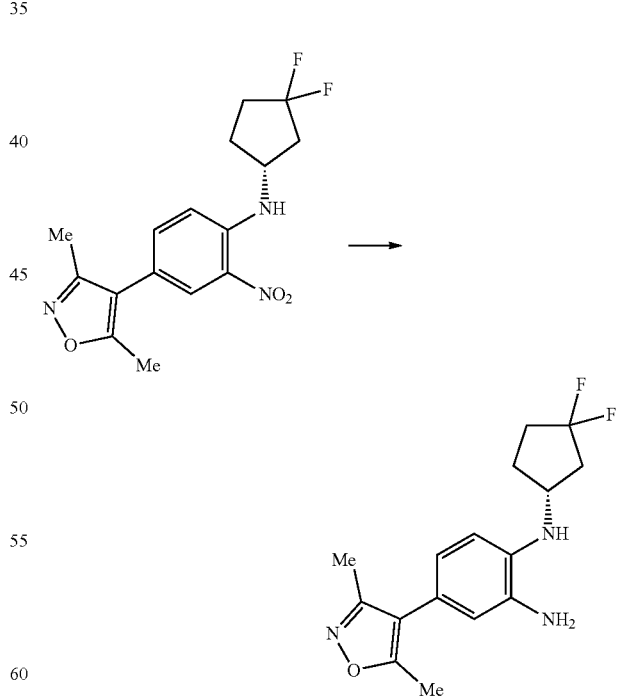

Sodium dithionite (5.52 g, 26.8 mmol) was added to a mixture (R)—N-(3,3-difluorocyclopentyl)-4-(3,5-dimethylisoxazol-4-yl)-2-nitroaniline (0.903 g, 2.68 mmol), concentrated ammonia (2.085 ml, 53.5 mmol), water (8.10 ml, 450 mmol) and THF (10.09 ml, 123 mmol) then stirred at room temperature overnight. After 15 h of stirring, the reaction mixture was filtered to remove the white solid. The solid was washed with AcOEt (100 mL). The layers were separated then the aqueous extracted with EtOAc (2×100 mL), the combined organics washed with water (50 mL) and brine (50 mL), dried (MgSO$_4$), filtered and evaporated in vacuo to give a crude material as a brown solid, which was dissolved in AcOEt (50 mL), washed with aqueous NaOH (1M; 10 mL) and brine (20 mL). The organic layer was dried (MgSO$_4$), filtered and concentrated to give a beige foam, which The foam was dissolved in DCM and loaded on SCX. Capture (washing using MeOH) and release using 1% NH3 in MeOH afforded (R)—N$^1$-(3,3-difluorocyclopentyl)-4-(3,5-dimethylisoxazol-4-yl)benzene-1,2-diamine (0.685 g, 79%) was isolated as a brown glass; Rt 1.88 min; m/z 308 (M+H)+ (ES+).

(S)—N-(2-(((R)-3,3-difluorocyclopentyl)amino)-5-(3,5-dimethylisoxazol-4-yl)phenyl)-5-oxo pyrrolidine-2-carboxamide

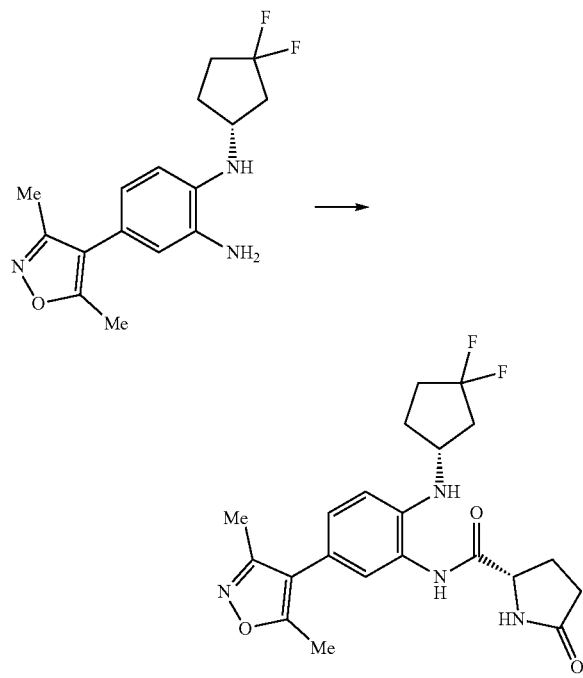

DIPEA (0.973 ml, 5.57 mmol) was added to a solution of (R)—N$^1$-(3,3-difluorocyclopentyl)-4-(3,5-dimethylisoxazol-4-yl)benzene-1,2-diamine (0.685 g, 2.229 mmol), (S)-5-oxopyrrolidine-2-carboxylic acid (0.317 g, 2.452 mmol) and HATU (1.102 g, 2.90 mmol) in DMF (7.42 mL, 96 mmol). The brown solution was stirred at RT for 15 h, then diluted with DCM (100 mL) and washed with sodium bicarbonate saturated aqueous solution (100 mL). The aqueous extracts were extracted with DCM (2×100 mL) and the organics were combined and washed with brine (100 ml), dried (MgSO$_4$), filtered and concentrated in vacuo to give a crude mixture. The crude was dried on silica and purified by chromatography column (24 g, DCM/AcOEt: 100/0 to 100/100) to give (S)—N-(2-(((R)-3,3-difluorocyclopentyl)amino)-5-(3,5-dimethylisoxazol-4-yl)phenyl)-5-oxopyrrolidine-2-carboxamide (0.7 g, 72%) was isolated as an off white solid; Rt 1.78 min; m/z 419 (M+H)+ (ES+).

(S)-5-(1-((R)-3,3-difluorocyclopentyl)-5-(3,5-dimethylisoxazol-4-yl)-1H-benzo[d]imidazol-2-yl)pyrrolidin-2-one

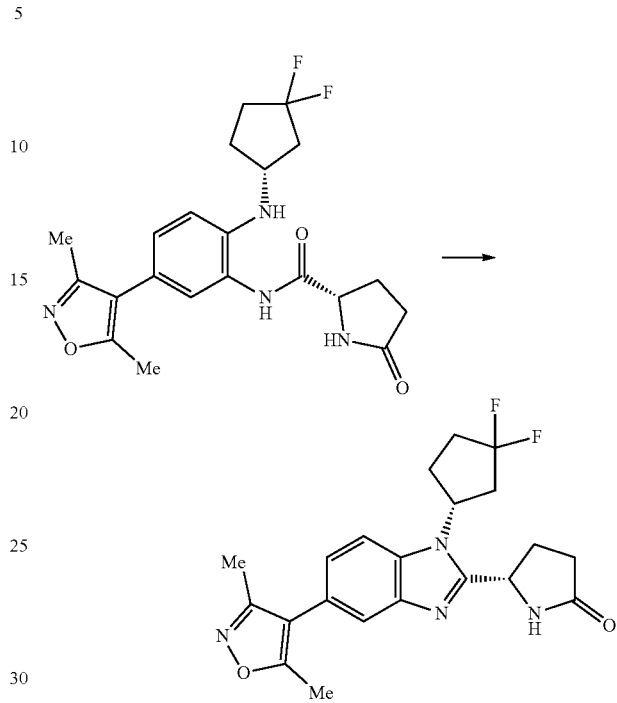

(S)—N-(2-(((R)-3,3-difluorocyclopentyl)amino)-5-(3,5-dimethylisoxazol-4-yl)phenyl)-5-oxo pyrrolidine-2-carboxamide (0.7 g, 1.673 mmol) was dissolved in acetic acid (6.70 mL, 117 mmol) and stirred at 70° C. for 15 h. The reaction was cooled down to r.t. and stored in the cold room over the week-end and the reaction was concentrated in vacuo. The crude brown oil was purified by flash chromatography (12 g, DCM/MeOH: 100/0 to 90/10) then by capture and release on SCX resin to afford a brown oil (530 mg), which was purified by chromatography column (12 g, AcOEt/MeOH: 100/0 to 95/5) to afford (S)-5-(1-((R)-3,3-difluorocyclopentyl)-5-(3,5-dimethylisoxazol-4-yl)-1H-benzo[d]imidazol-2-yl)pyrrolidin-2-one (0.267 g, 38%) was isolated as a white solid; Rt 1.65 min; m/z 401 (M+H)+ (ES+).

(S)-5-(1-((R)-3,3-difluorocyclopentyl)-5-(3,5-dimethylisoxazol-4-yl)-1H-benzo[d]imidazol-2-yl)-1-(3,4-difluorophenyl)pyrrolidin-2-one

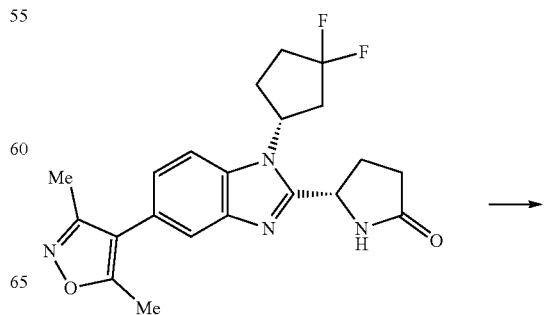

321
-continued

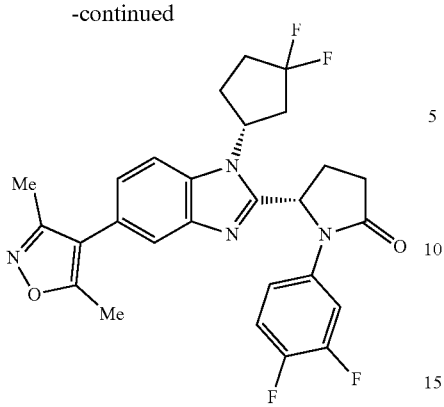

322
-continued

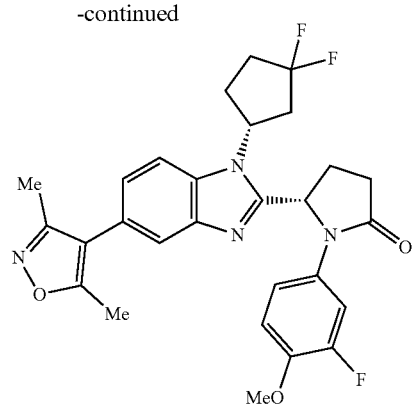

CuTMEDA (29.0 mg, 0.062 mmol) was added to a stirred solution of (S)-5-(1-((R)-3,3-difluorocyclopentyl)-5-(3,5-dimethylisoxazol-4-yl)-1H-benzo[d]imidazol-2-yl)pyrrolidin-2-one (50 mg, 0.125 mmol) in pyridine (1.50 mL, 18.61 mmol) then the mixture was stirred for 15 min at 40° C. (3,4-difluorophenyl)boronic acid (52.3 mg, 0.331 mmol) was added then the mixture was heated to 40° C. for 2 h. The reaction was cooled down to RT and stirred overnight at the same temperature. The mixture was diluted with ethyl acetate (20 mL) then washed with water (3×10 mL). The organic phase was then filtered through a phase sep cartridge and concentrated under reduced pressure. The residue was taken up in DCM purified by chromatography on the Companion (4 g column, 0-10% (10% MeOH in DCM) in DCM, gradient elution). After concentration of the combined fractions, diethyl ether (10 mL) was added and the suspension was concentrated in vacuo to afford ((S)-5-(1-((R)-3,3-difluorocyclopentyl)-5-(3,5-dimethylisoxazol-4-yl)-1H-benzo[d]imidazol-2-yl)-1-(3,4-difluoro phenyl)pyrrolidin-2-one (51 mg, 78%) as a white foam; Rt 2.33 min; m/z 513 (M+H)+ (ES+); 1H NMR (d6-DMSO) δ: 7.89-7.79 (m, 1H), 7.67-7.59 (m, 2H), 7.42-7.32 (m, 1H), 7.28-7.17 (m, 2H), 6.09 (td, J=8.2 Hz, 1H), 5.39 (p, J=9.1 Hz, 1H), 2.88-2.44 (m, 7H), 2.36 (s, 3H), 2.34-2.22 (m, 2H), 2.20 (s, 3H), 2.16-2.01 (m, 1H).

CuTMEDA (29.0 mg, 0.062 mmol) was added to a stirred solution of (S)-5-(1-((R)-3,3-difluorocyclopentyl)-5-(3,5-dimethylisoxazol-4-yl)-1H-benzo[d]imidazol-2-yl)pyrrolidin-2-one (50 mg, 0.125 mmol) in pyridine (1.505 mL, 18.61 mmol) then the mixture was stirred for 15 min at 40° C. (3-fluoro-4-methoxyphenyl)boronic acid (56.2 mg, 0.331 mmol) was added then the mixture was heated to 40° C. for 2 h. The mixture was diluted with ethyl acetate (20 mL) then washed with water (3×10 mL). The organic phase was then filtered through a phase sep cartridge and concentrated under reduced pressure. The residue was taken up in DCM purified by chromatography on the Companion (4 g column, 0-10% (10% MeOH in DCM) in DCM, gradient elution). After concentration of the combined fractions, diethyl ether (10 mL) was added and the suspension was concentrated in vacuo to afford (S)-5-(1-((R)-3,3-difluoro cyclopentyl)-5-(3, 5-dimethylisoxazol-4-yl)-1H-benzo[d]imidazol-2-yl)-1-(3-fluoro-4-methoxy phenyl)pyrrolidin-2-one (53 mg, 79%) as a yellowish foam; Rt 2.21 min; m/z 525 (M+H)+ (ES+); 1H NMR (d6-DMSO) δ: 7.66-7.64 (m, 1H), 7.64-7.58 (m, 2H), 7.24 (dt, J=8.5, 1.9 Hz, 1H), 7.14-7.02 (m, 2H), 6.03 (td, J=7.6 Hz, 1H), 5.46-5.32 (m, 1H), 3.75 (s, 3H), 2.82-2.42 (m, 7H), 2.37 (s, 3H), 2.34-2.22 (m, 2H), 2.20 (s, 3H), 2.15-2.07 (m, 1H).

Example 142: (S)-5-(1-((R)-3,3-difluorocyclopentyl)-5-(3,5-dimethylisoxazol-4-yl)-1H-benzo[d]imidazol-2-yl)-1-(3-fluoro-4-methoxyphenyl)pyrrolidin-2-one (S)-5-(1-((R)-3,3-difluorocyclopentyl)-5-(3,5-dimethylisoxazol-4-yl)-1H-benzo[d]imidazol-2-yl)-1-(3-fluoro-4-methoxyphenyl)pyrrolidin-2-one Example 143: (S)-5-(1-((R)-3,3-difluorocyclopentyl)-5-(3,5-dimethylisoxazol-4-yl)-1H-benzo[d]imidazol-2-yl)-1-(3-fluoro-4-methoxyphenyl)pyrrolidin-2-one (S)-5-(1-((R)-3,3-difluorocyclopentyl)-5-(3,5-dimethylisoxazol-4-yl)-1H-benzo[d]imidazol-2-yl)-1-(3-fluoro-4-methoxyphenyl)pyrrolidin-2-one

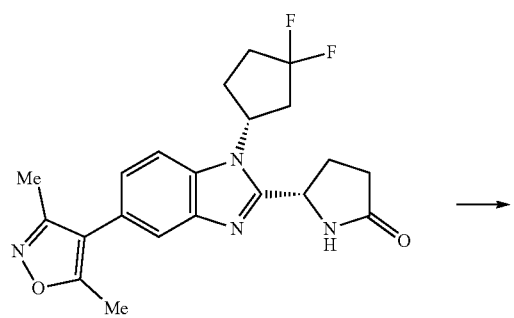

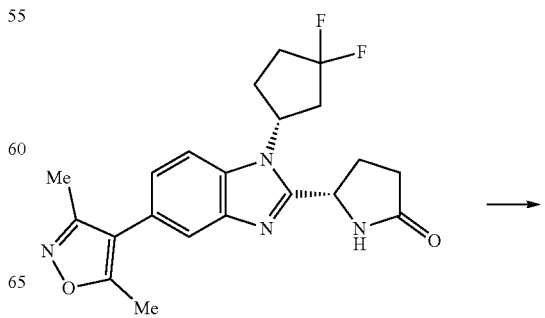

323
-continued

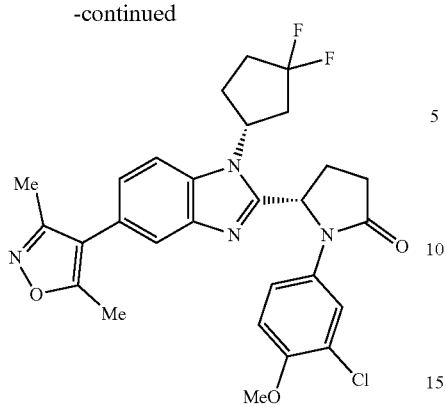

CuTMEDA (29.0 mg, 0.062 mmol) was added to a stirred solution of (S)-5-(1-((R)-3,3-difluorocyclopentyl)-5-(3,5-dimethylisoxazol-4-yl)-1H-benzo[d]imidazol-2-yl)pyrrolidin-2-one (50 mg, 0.125 mmol) in pyridine (1.50 mL, 18.61 mmol) then the mixture was stirred for 15 min at 40° C. (3-Chloro-4-methoxyphenyl)boronic acid (61.7 mg, 0.331 mmol) was added then the mixture was heated to 40° C. for 2 h. The reaction was cooled down to RT and the mixture was diluted with ethyl acetate (20 mL) then washed with water (3×10 mL). The organic phase was then filtered through a PhaseSep cartridge and concentrated under reduced pressure. The residue was taken up in DCM purified by chromatography on the Companion (4 g column, 0-10% (10% MeOH in DCM) in DCM, gradient elution). After concentration of the combined fractions, diethyl ether (10 mL) was added and the suspension was concentrated in vacuo to afford (S)-1-(3-chloro-4-methoxyphenyl)-5-(1-((R)-3,3-difluorocyclopentyl)-5-(3,5-dimethylisoxazol-4-yl)-1H-benzo[d]imidazol-2-yl)pyrrolidin-2-one (52 mg, 75%) as a white foam; Rt 2.28 min; m/z 541 (M+H)+ (ES+); 1H NMR (d6-DMSO) δ: 7.79 (dd, J=3.9, 2.6 Hz, 1H), 7.65 (d, 1H), 7.61 (t, J=8.4 Hz, 1H), 7.33-7.21 (m, 2H), 7.07 (dd, J=9.1, 2.9 Hz, 1H), 6.06 (td, J=8.6 Hz, 1H), 5.42 (q, J=9.2 Hz, 1H), 3.77 (s, 3H), 2.82-2.40 (m, 7H), 2.37 (s, 3H), 2.34-2.22 (m, 2H), 2.20 (s, 3H), 2.18-2.07 (m, 1H).

Example 144: (5S)-1-(3,4-difluorophenyl)-5-(5-(3,5-dimethylisoxazol-4-yl)-1-(2-hydroxypropyl)-1H-benzo[d]imidazol-2-yl)pyrrolidin-2-one and
Example 145: (5S)-1-(3,4-difluorophenyl)-5-(5-(3,5-dimethylisoxazol-4-yl)-1-(2-hydroxypropyl)-1H-benzo[d]imidazol-2-yl)pyrrolidin-2-one (2S)—N-(5-(3,5-dimethylisoxazol-4-yl)-2-((2-hydroxypropyl)amino)phenyl)-5-oxopyrrolidine-2-carboxamide

324
-continued

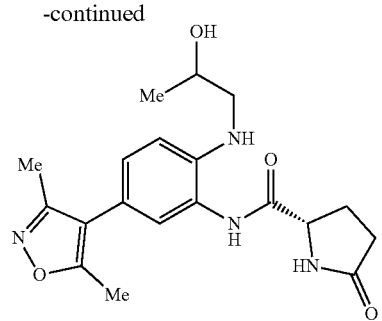

TEA (2.88 mL, 20.66 mmol) was added to a solution of Intermediate C19 (1.8 g, 6.89 mmol), (S)-5-oxopyrrolidine-2-carboxylic acid (0.978 g, 7.58 mmol) and HATU (2.88 g, 7.58 mmol) in DMF (15 ml, 194 mmol) then stirred at RT for 6 hrs. The bulk of the DMF was removed under vacuum. The loose residue was diluted with water (10 mL) then extracted with DCM (50 mL). The organic phase was washed with water (10 ml) then passed through a phase sep cartridge and concentrated in vacuo. The residue was purified by chromatography (24 g silica, 0-10% methanol in DCM, gradient elution) to afford (2S)—N-(5-(3,5-dimethylisoxazol-4-yl)-2-((2-hydroxypropyl)amino)phenyl)-5-oxopyrrolidine-2-carboxamide (1.94 g, 68%) as a tan solid; Rt 0.79 min; m/z 373 (M+H)+ (ES+).

(5S)-5-(5-(3,5-dimethylisoxazol-4-yl)-1-(2-hydroxypropyl)-1H-benzo[d]imidazol-2-yl)pyrrolidin-2-one
(2 Single Diastereoisomers, Alcohol Stereochemistry Unknown)

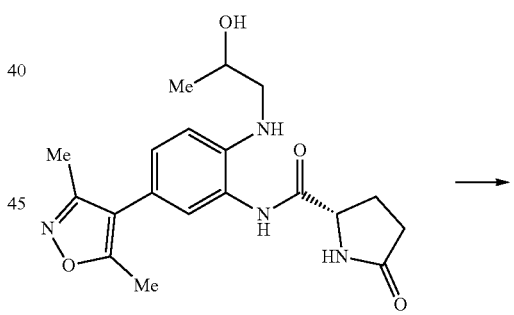

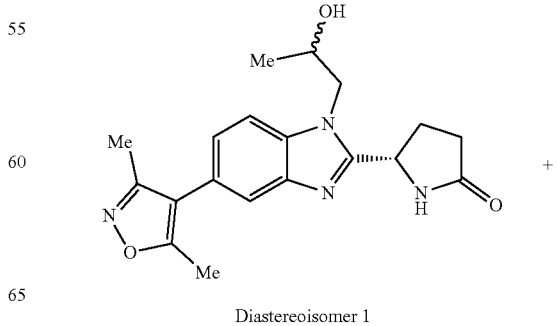

Diastereoisomer 1

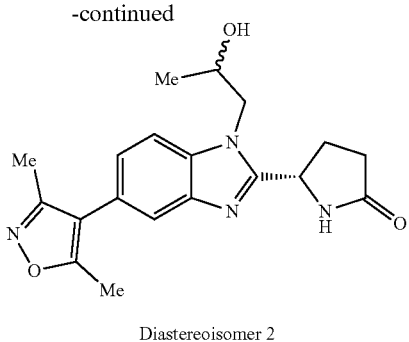

Diastereoisomer 2

(2S)—N-(5-(3,5-dimethylisoxazol-4-yl)-2-((2-hydroxypropyl)amino)phenyl)-5-oxopyrrolidine-2-carboxamide (1.94 g, 5.21 mmol) was heated to 80° C. in acetic acid (11.93 mL, 208 mmol) for 3 h. The reaction mixture was concentrated. The crude product was purified by flash chromatography (40 g column, 0-10% (0.7 M Ammonia/MeOH)/DCM) to afford (5S)-5-(5-(3,5-dimethylisoxazol-4-yl)-1-(2-hydroxypropyl)-1H-benzo[d]imidazol-2-yl)pyrrolidin-2-one Diastereoisomer 1 (666 mg, 36%) and (5S)-5-(5-(3,5-dimethylisoxazol-4-yl)-1-(2-hydroxy propyl)-1H-benzo[d]imidazol-2-yl)pyrrolidin-2-one Diastereoisomer 2 (671 mg, 34% yield) as tan solids (absolute stereochemistry of alcohol unknown).

Diastereoisomer 1: Rt 0.74 min; m/z 355 (M+H)+ (ES+); Diastereoisomer 2 Rt 0.68 min; m/z 355 (M+H)+ (ES+).

(5S)-1-(3,4-difluorophenyl)-5-(5-(3,5-dimethylisoxazol-4-yl)-1-(2-hydroxypropyl)-1H-benzo[d]imidazol-2-yl)pyrrolidin-2-one (Diastereoisomer 1)

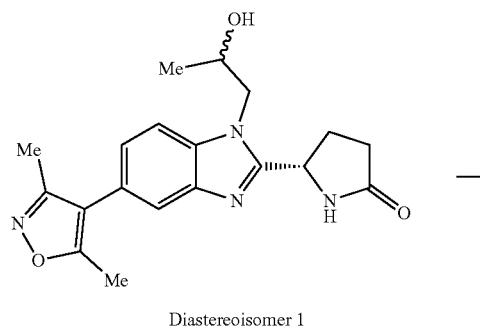

Diastereoisomer 1

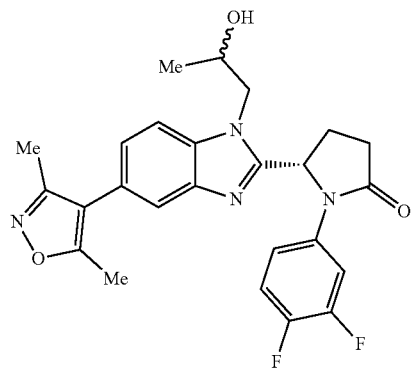

Diastereoisomer 1

DBU (0.085 ml, 0.564 mmol) was added to a solution of (5S)-5-(5-(3,5-dimethylisoxazol-4-yl)-1-(2-hydroxypropyl)-1H-benzo[d]imidazol-2-yl)pyrrolidin-2-one Diastereoisomer 1 (100 mg, 0.282 mmol) in MeCN (2.5 ml, 47.9 mmol), DCM (0.25 ml, 3.89 mmol) and the mixture was stirred for 10 min. CuTMEDA (13.10 mg, 0.028 mmol) was added, stirred for a 10 min, (3,4-difluorophenyl)boronic acid (49.0 mg, 0.310 mmol) added and the reaction stirred at 35° C. for 20 h. Additional (3,4-difluorophenyl)boronic acid (49.0 mg, 0.310 mmol) and (3,4-difluorophenyl)boronic acid (49.0 mg, 0.310 mmol) were added and the mixture was stirred for a further 5 h. The mixture was concentrated onto loose silica gel. The silicate was purified by chromatography on the Companion (12 g column, 0-4% MeOH/DCM) to afford (5S)-1-(3,4-difluorophenyl)-5-(5-(3,5-dimethylisoxazol-4-yl)-1-(2-hydroxypropyl)-1H-benzo[d]imidazol-2-yl)pyrrolidin-2-one (Diastereoisomer 1) (40 mg, 30%) as an off white solid; Rt 1.82 min; m/z 467 (M+H)+ (ES+); 1H NMR (d6-DMSO) δ: 7.86 (1H, ddd, J=13.6, 7.4, 2.7 Hz), 7.68 (1H, d, J=8.3 Hz), 7.57 (1H, d, J=1.5 Hz), 7.49 (1H, d, J=8.9 Hz), 7.37-7.23 (1H, m), 7.20 (1H, dd, J=8.4, 1.6 Hz), 5.95 (1H, d, J=7.0 Hz), 5.28 (1H, d, J=4.1 Hz), 4.46-4.27 (1H, m), 4.17-3.98 (2H, m), 2.75-2.56 (3H, m), 2.57-2.53 (1H, m), 2.36 (3H, s), 2.19 (3H, s), 1.29 (3H, d, J=5.5 Hz). Chiral HPLC (Diacel Chiralpak IA, 5 um, 4.6×250 mm, 30 min method, 1.0 mL/min, isocratic 30% EtOH in isohexane (0.2% TFA): RT=6.95 min, >99% de @ 254 nm.

(5S)-1-(3,4-difluorophenyl)-5-(5-(3,5-dimethylisoxazol-4-yl)-1-(2-hydroxypropyl)-1H-benzo[d]imidazol-2-yl)pyrrolidin-2-one (Diastereoisomer 2)

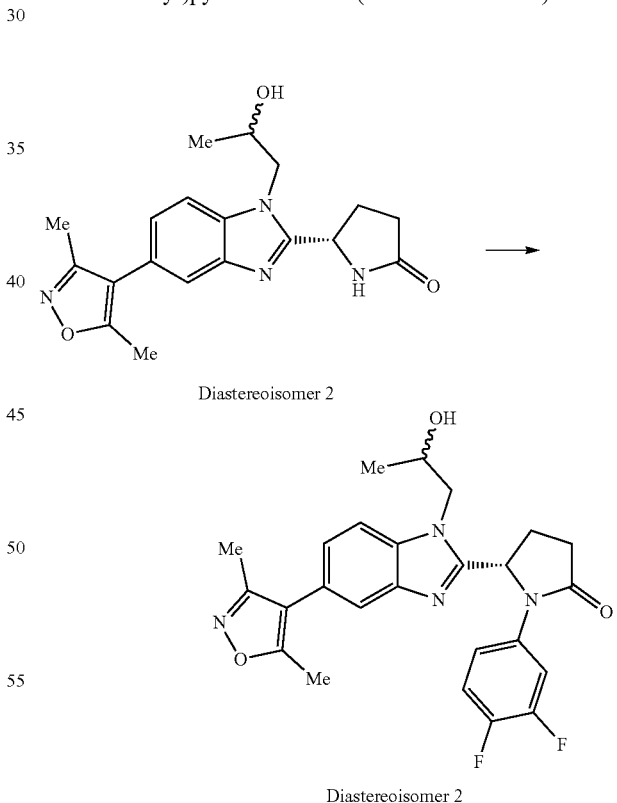

Diastereoisomer 2

Diastereoisomer 2

DBU (0.085 mL, 0.564 mmol) was added to a solution of (5S)-5-(5-(3,5-dimethylisoxazol-4-yl)-1-(2-hydroxypropyl)-1H-benzo[d]imidazol-2-yl)pyrrolidin-2-one Diastereoisomer 2 (100 mg, 0.282 mmol) in MeCN (2.5 ml, 47.9 mmol), DCM (0.25 mL, 3.89 mmol) and the mixture was stirred for 10 min. CuTMEDA (13.10 mg, 0.028 mmol) was added, the mixture was stirred for a 10 min, (3,4-difluorophenyl)boronic acid (49.0 mg, 0.310 mmol) added and the reaction stirred at 35° C. for 20 h. Additional CuTMEDA (13.10 mg, 0.028 mmol) and (3,4-difluorophenyl)boronic acid (49.0 mg, 0.310 mmol) were added and the mixture was stirred for a further 5 h. The mixture was concentrated onto loose silica gel. The silicate was purified by flash chromatography on the Companion (12 g column, 0-4% MeOH/DCM then 4 g column, 100% EtOAc) to afford (5S)-1-(3,4-difluorophenyl)-5-(5-(3,5-dimethylisoxazol-4-yl)-1-(2-hydroxypropyl)-1H-benzo[d]imidazol-2-yl)pyrrolidin-2-one (Diastereoisomer 2) (22 mg, 16%) as a colourless solid; Rt 1.81 min; m/z 467 (M+H)+ (ES+); 1H NMR (d6-DMSO) δ: 7.78 (1H, ddd, J=13.2, 7.4, 2.5 Hz), 7.66 (1H, dd, J=8.4, 0.7 Hz), 7.59 (1H, dd, J=1.6, 0.6 Hz), 7.41-7.22 (2H, m), 7.19 (1H, dd, J=8.3, 1.6 Hz), 5.96 (1H, dd, J=8.2, 2.2 Hz), 5.20 (1H, d, J=4.5 Hz), 4.35-4.21 (2H, m), 4.13-3.97 (1H, m), 2.83-2.72 (1H, m), 2.63-2.51 (2H, m), 2.36 (3H, s), 2.28-2.20 (1H, m), 2.19 (3H, s), 1.22 (3H, d, J=6.3 Hz); Chiral HPLC (Lab 1 Bay 4, Diacel Chiralpak IA, 5 um, 4.6×250 mm, 30 min method, 1.0 ml/min, isocratic 30% EtOH in isohexane (0.2% TFA): RT=6.39 min, >99% de @ 254 nm.

General Route B: Convergent Approach to γ-Lactam Analogues from N-Arylpyroglutamic Acid Ex 109 (S)-1-(3,4-difluorophenyl)-5-(5-(3,5-dimethylisoxazol-4-yl)-1-(trans-(1r,3r)-3-ethoxycyclopentyl)-1H-benzo[d]imidazol-2-yl)pyrrolidin-2-one 4-(3,5-Dimethylisoxazol-4-yl)-N-(trans-(1r,3r)-3-ethoxycyclopentyl)-2-nitroaniline

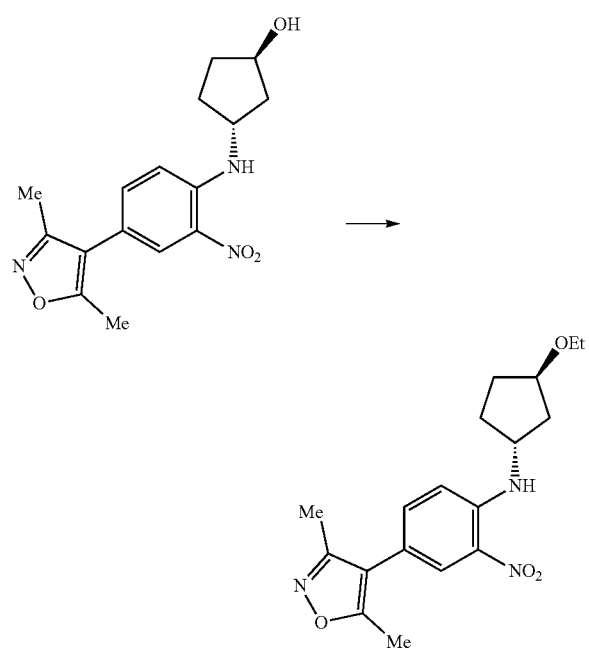

4-(3,5-dimethylisoxazol-4-yl)-N-trans-((1r,3r)-3-ethoxycyclopentyl)-2-nitroaniline (0.417 g, 1.159 mmol, 73.6% yield) is dissolved in dry THF (9.94 ml, 121 mmol). This solution is cooled to 0° C., then 18-CROWN-6 (0.458 g, 1.733 mmol) in dry THF (9.94 ml, 121 mmol) was added followed with NaH (0.069 g, 1.733 mmol). After 15 mn of stirring, ETHYL IODIDE (0.140 ml, 1.733 mmol) is added. The reaction was stirred overnight at RT then saturated ammonium chloride (10 mL) was added, followed by DCM (2×5 mL) the mixture is shaken in a separating funnel. The organic layer was then filtered through a PhaseSep© cartridge then concentrated to give an orange oil, which was purified by flash chromatography (24 g, DCM/MeOH: 100/0 to 95/5) to afford 4-(3,5-dimethylisoxazol-4-yl)-N-trans-((1r,3r)-3-ethoxycyclopentyl)-2-nitroaniline (0.417 g, 74% yield) was isolated as an orange oil; Rt 2.58 min (method 1), m/z 346 (M+H)+ (ES+).

4-(3,5-dimethylisoxazol-4-yl)-N$^1$-(trans-(1r,3r)-3-ethoxycyclopentyl)benzene-1,2-diamine

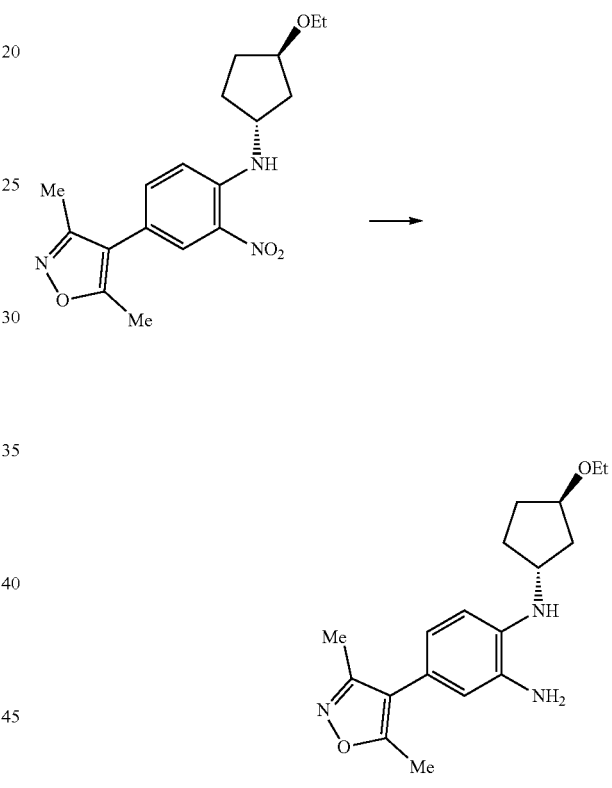

4-(3,5-Dimethylisoxazol-4-yl)-N-(trans-(1r,3r)-3-ethoxycyclopentyl)-2-nitroaniline (0.417 g, 1.207 mmol) and concentrated ammonia (0.752 ml, 19.32 mmol) were dissolved in THF/water (1:1, 23 mL) then sodium dithionite (2.488 g, 12.07 mmol) was added and the reaction mixture stirred at RT for 18 hours. The layers were separated, the aqueous further extracted with EtOAc (2×100 mL). The combined organics were washed with water (50 mL) and brine (50 mL), dried (MgSO$_4$), filtered and evaporated in vacuo to give 4-(3,5-dimethylisoxazol-4-yl)-N$^1$-(trans-(1r,3r)-3-ethoxycyclopentyl)benzene-1,2-diamine (0.31 g, 80%) as a pink solid; Rt 1.64 min (method 1), m/z 316 (M+H)+ (ES+).

(S)-1-(3,4-difluorophenyl)-5-oxopyrrolidine-2-carboxylic acid

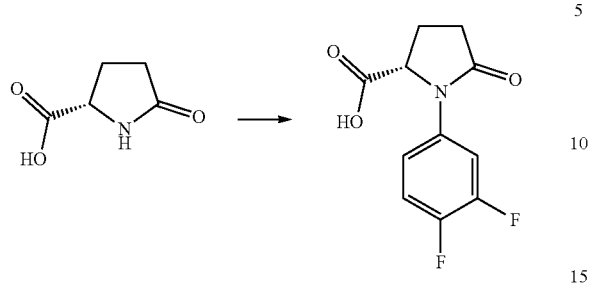

DBU (2.4 ml, 15.92 mmol) was added to a suspension of (S)-5-oxopyrrolidine-2-carboxylic acid (1.0 g, 7.75 mmol) in acetonitrile (15 mL) then stirred for 10 minutes at room temperature. CuTMEDA (100 mg, 0.215 mmol) was added then the mixture was stirred for a further 10 minutes. (3,4-difluorophenyl)boronic acid (1.25 g, 7.92 mmol) was added then the mixture was heated to 50° C. for 18 h. CuTMEDA (100 mg, 0.215 mmol) was added then the mixture was stirred for a further 18 h (Reaction A). Subsequently, DBU (20 ml, 133 mmol) was added to a suspension of (S)-5-oxopyrrolidine-2-carboxylic acid (8.0 g, 62.0 mmol) in acetonitrile (15 mL) then stirred for 10 minutes at room temperature. CuTMEDA (1.5 g, 3.23 mmol) was added then the mixture was stirred for a further 10 minutes. (3,4-difluorophenyl)boronic acid (10.0 g, 63.3 mmol) was added then the mixture was heated to 50° C. for 18 h (Reaction B). The mixture of Reaction A was combined with that of Reaction B then concentrated under reduced pressure. The residue was diluted with water (200 mL) then extracted with diethyl ether (2×200 mL). The aqueous layer was treated with 1 M aqueous hydrogen chloride (200 mL, 200 mmol) then extracted with ethyl acetate (3×200 mL). The combined organic phases were concentrated onto loose silica gel. The silicate was purified on a silica gel filter plug, eluting with EtOAc/dichloromethane (0-100%) to give after prolonged rotary evaporation (S)-1-(3,4-difluorophenyl)-5-oxopyrrolidine-2-carboxylic acid (2.8 g, 16%) as a pale yellow glass; Rt 1.41 min (method 1), m/z 242 (M+H)+ (ES+).

(S)-1-(3,4-difluorophenyl)-N-(5-(3,5-dimethylisoxazol-4-yl)-2-((trans-(1r,3r)-3-ethoxy cyclopentyl)amino)phenyl)-5-oxopyrrolidine-2-carboxamide

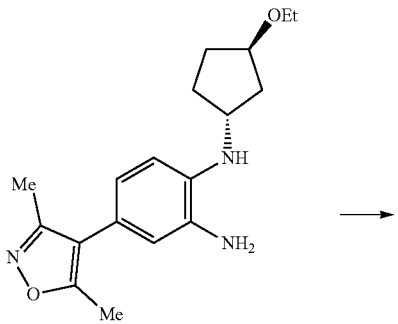

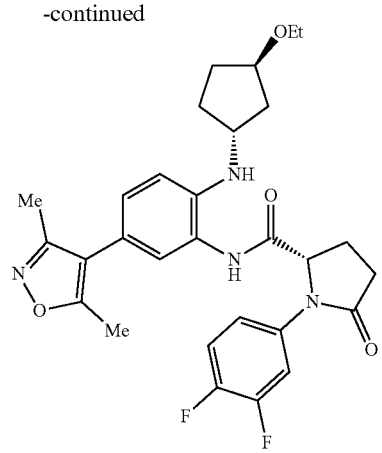

DIPEA (0.208 ml, 1.189 mmol) was added to a solution of 4-(3,5-dimethylisoxazol-4-yl)-N1-(trans-(1r,3r)-3-ethoxycyclopentyl)benzene-1,2-diamine (0.15 g, 0.476 mmol), (S)-1-(3,4-difluorophenyl)-5-oxopyrrolidine-2-carboxylic acid (0.126 g, 0.523 mmol) and HATU (0.235 g, 0.618 mmol) in DMF (1.583 ml, 20.45 mmol). The brown solution was stirred at RT for 3 h then the mixture was partitioned between ethyl acetate (100 mL) and water (100 mL), then the layers separated. The organic phase was washed with water (3×100 mL) and with brine (100 mL), then concentrated in vacuo to give a crude brown oil (340 mg), which was purified by flash chromatography on the Companion (4 g, 0-10% MeOH/DCM) to give (S)-1-(3,4-difluorophenyl)-N-(5-(3,5-dimethylisoxazol-4-yl)-2-(((1R,3R)-3-ethoxycyclopentyl)amino) phenyl)-5-oxopyrrolidine-2-carboxamide (0.238 g, 91%) was obtained as a colourless foam; Rt 2.24 min (method 1), m/z 539 (M+H)+ (ES+).

(S)-1-(3,4-difluorophenyl)-5-(5-(3,5-dimethylisoxazol-4-yl)-1-(trans-(1r,3r)-3-ethoxycyclopentyl)-1H-benzo[d]imidazol-2-yl)pyrrolidin-2-one

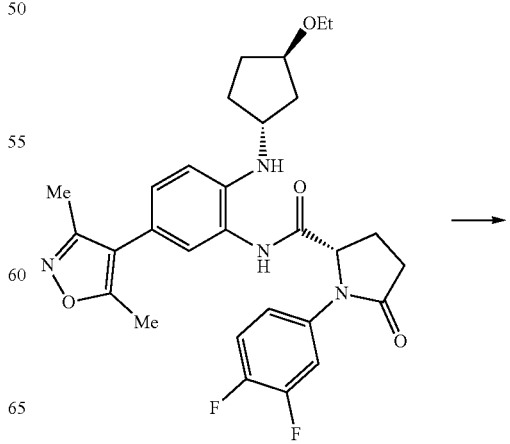

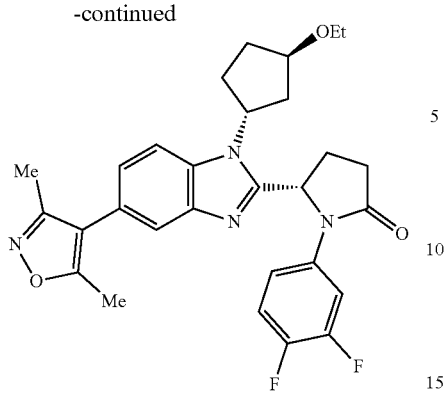

(S)-1-(3,4-difluorophenyl)-N-(5-(3,5-dimethylisoxazol-4-yl)-2-((trans-(1r,3r)-3-ethoxycyclopentyl)amino)phenyl)-5-oxopyrrolidine-2-carboxamide (0.238 g, 0.442 mmol) was dissolved in acetic acid (1.771 ml, 30.9 mmol) and stirred at 70° C. for 15 h. After 15 h, the reaction was cooled down to RT and concentrated in vacuo to give a brown oil, which was purified by flash chromatography on the Companion (4 g, DCM/MeOH: 100/0 to 90/10). The impure fractions containing the desired product were combined (150 mg) and purified again on a 12 g column using the same conditions then using a different solvent system (12 g, DCM/AcOEt: 100/0 to 0/100) to give a brown solid (69 mg). Final purification by flash chromatography on the Companion (4 g, DCM/AcOEt: 100/0 to 0/100) gave (S)-1-(3,4-difluorophenyl)-5-(5-(3,5-dimethylisoxazol-4-yl)-1-(trans-(1r,3r)-3-ethoxycyclopentyl)-1H-benzo[d]imidazol-2-yl)pyrrolidin-2-one (14 mg, 6%) as a beige solid; Rt 2.25 min (method 1), m/z 521 (M+H)+ (ES+); 1H NMR (d6-DMSO) δ: 7.80 (tdd, J=13.7, 7.4, 2.6 Hz, 1H), 7.66-7.57 (m, 2H), 7.42-7.33 (m, 1H), 7.28-7.19 (m, 1H), 7.19-7.15 (m, 1H), 6.20-6.04 (dd, 1H), 5.25-5.10 (m, 1H), 4.33-4.19 (m, 1H), 3.54-3.44 (m, 2H), 2.79-2.52 (m, 3H), 2.43-2.27 (m, 5H), 2.26-2.02 (m, 7H), 1.89-1.75 (m, 1H), 1.17 (t, J=7.0 Hz, 3H).

Example 116: 5-(2-((S)-1-(3,4-difluorophenyl)-5-oxopyrrolidin-2-yl)-5-(3,5-dimethylisoxazol-4-yl)-1H-benzo[d]imidazol-1-yl)piperidin-2-one (2S)-1-(3,4-difluorophenyl)-N-(5-(3,5-dimethylisoxazol-4-yl)-2-((2-oxopiperidin-4-yl)amino)phenyl)-5-oxopyrrolidine-2-carboxamide (Intermediate D14)

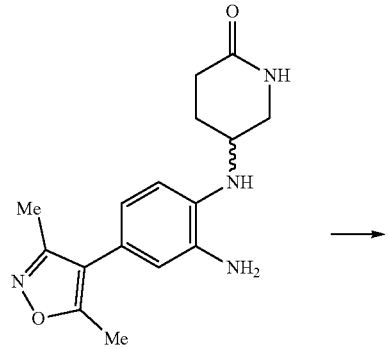

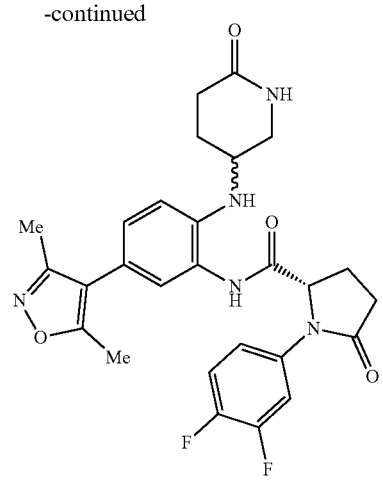

DIPEA (288 μL, 1.649 mmol) was added to a solution of 4-((2-amino-4-(3,5-dimethylisoxazol-4-yl)phenyl)amino)piperidin-2-one (198 mg, 0.660 mmol), (S)-1-(3,4-difluorophenyl)-5-oxopyrrolidine-2-carboxylic acid (175 mg, 0.726 mmol) and HATU (326 mg, 0.857 mmol) in DMF (2196 μL, 28.4 mmol). The green solution was stirred at RT for 15 h then partitioned between ethyl acetate (100 mL) and water (100 mL), then the layers separated. The organic phase was further washed with brine (100 mL) and concentrated in vacuo to give a crude oil. Purification by flash chromatography on the Companion (12 g, 0-10% MeOH/DCM) to afford (2S)-1-(3,4-difluorophenyl)-N-(5-(3,5-dimethylisoxazol-4-yl)-2-((2-oxopiperidin-4-yl)amino)phenyl)-5-oxopyrrolidine-2-carboxamide Intermediate D14 (0.356 g, 93%) as a colorless oil; Rt 1.68 min (method 1), m/z 524 (M+H)+ (ES+).

5-(2-((S)-1-(3,4-difluorophenyl)-5-oxopyrrolidin-2-yl)-5-(3,5-dimethylisoxazol-4-yl)-1H-benzo[d]imidazol-1-yl)piperidin-2-one

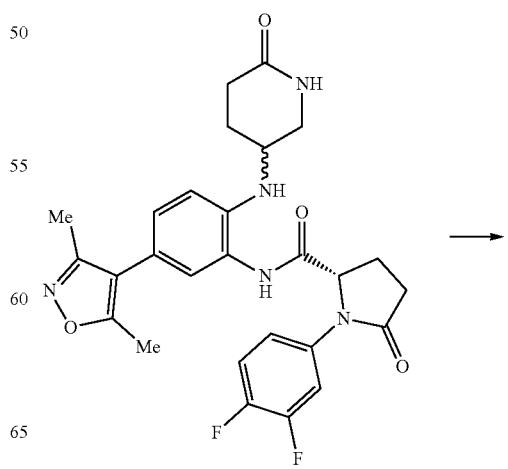

333
-continued

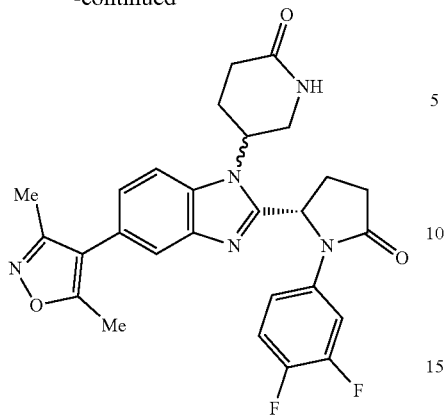

Intermediate D14 (0.191 g, 0.317 mmol) was dissolved in acetic acid (1.27 mL, 22.22 mmol) and heated at 90° C. The reaction was concentrated in vacuo and TFA (1.71 mL, 22.22 mmol) was added. The mixture was heated at 70° C. for 15 h, the mixture was cooled down to RT and concentrated in vacuo/pre-adsorbed on silica gel. Flash chromatography on the Companion (4 g, DCM/MeOH: 100/0 to 90/10) gave 5-(2-((S)-1-(3,4-difluorophenyl)-5-oxopyrrolidin-2-yl)-5-(3,5-dimethylisoxazol-4-yl)-1H-benzo[d]imidazol-1-yl)piperidin-2-one (31 mg, 19%) as a pink solid; Rt 1.64 min (method 1), m/z 506 (M+H)+ (ES+); 1H NMR (d6-DMSO) δ: 7.92 (d, J=8.5 Hz, 1H), 7.83 (ddd, 1H), 7.80-7.75 (m, 1H), 7.64-7.58 (m, 1H), 7.36 (dt, J=10.5, 9.1 Hz, 1H), 7.26-7.20 (m, 1H), 7.17 (dd, J=8.5, 1.7 Hz, 1H), 6.15 (d, J=7.4 Hz, 1H), 5.06-4.95 (m, 1H), 3.91 (t, J=11.1 Hz, 1H), 3.44-3.35 (m, 1H), 2.90-2.73 (m, 1H), 2.73-2.62 (m, 1H), 2.62-2.49 (m, 1H), 2.48-2.38 (m, 1H), 2.36 (s, 3H), 2.19 (s, 3H), 2.13-1.98 (m, 2H).

Example 117: (S)-1-(3,4-difluorophenyl)-5-(5-(3,5-dimethylisoxazol-4-yl)-1H-benzo[d]imidazol-2-yl)pyrrolidin-2-one (S)-1-(3,4-difluorophenyl)-5-(5-(3,5-dimethylisoxazol-4-yl)-1H-benzo[d]imidazol-2-yl)pyrrolidin-2-one 334
-continued Intermediate D14 (356 mg, 0.612 mmol) was dissolved in acetic acid (2.725 mL, 47.6 mmol) and heated at 90° C. for 4 h. The reaction was concentrated in vacuo and TFA (3.67 mL, 47.6 mmol) was added. The mixture was heated at 70° C. for 15 h, then cooled down to RT and concentrated in vacuo. The resulting black oil was purified by flash chromatogprahy on the Companion (4 g, DCM/MeOH: 100/0 to 90/10) to afford (S)-1-(3,4-difluorophenyl)-5-(5-(3,5-dimethylisoxazol-4-yl)-1H-benzo[d]imidazol-2-yl)pyrrolidin-2-one (112 mg, 39%) was isolated as a beige solid; Rt 1.70 min (method 1), m/z 409 (M+H)+ (ES+); 1H NMR (d6-DMSO) δ: 7.79 (ddd, J=13.1, 7.4, 2.6 Hz, 1H), 7.62 (dd, J=8.3, 0.7 Hz, 1H), 7.53 (d, J=1.7 Hz, 1H), 7.44-7.32 (m, 1H), 7.29-7.25 (m, 1H), 7.19 (dd, J=8.3, 1.6 Hz, 1H), 5.74 (d, 1H), 2.85-2.75 (m, 1H), 2.73-2.62 (m, 1H), 2.61-2.48 (m, 1H), 2.37 (s, 3H), 2.23-2.14 (m+s, 4H).

Example 124: (S)-1-(3,4-difluorophenyl)-5-(5-(3,5-dimethylisoxazol-4-yl)-1-((1r,3S)-3-hydroxycyclobutyl)-1H-benzo[d]imidazol-2-yl)pyrrolidin-2-one and Example 125: (1S,3r)-3-(2-((S)-1-(3,4-difluorophenyl)-5-oxopyrrolidin-2-yl)-5-(3,5-dimethylisoxazol-4-yl)-1H-benzo[d]imidazol-1-yl)cyclobutyl acetate (S)-1-(3,4-difluorophenyl)-N-(5-(3,5-dimethylisoxazol-4-yl)-2-(((1r,3S)-3-hydroxycyclobutyl)amino)phenyl)-5-oxopyrrolidine-2-carboxamide

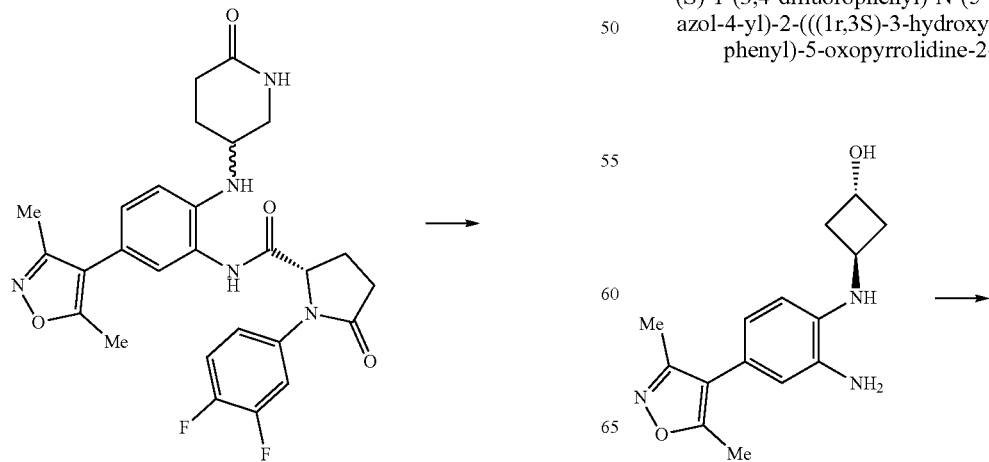

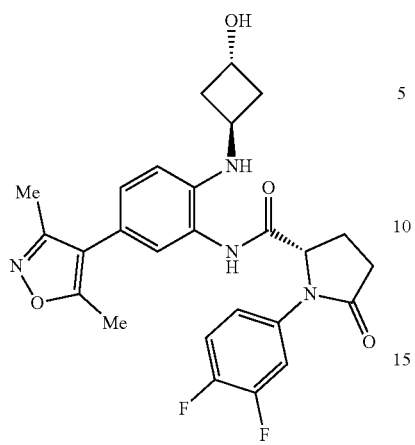

TEA (765 μL, 5.49 mmol) was added to a solution of Intermediate C17 (500 mg, 1.829 mmol), (S)-1-(3,4-difluorophenyl)-5-oxopyrrolidine-2-carboxylic acid (485 mg, 2.012 mmol) and HATU (765 mg, 2.012 mmol) in DMF (5 mL) then stirred at RT for 48 h. The bulk of the DMF was removed under vacuum. The loose residue was diluted with water (10 mL) then extracted with DCM (30 mL). The organic phase was washed with water (10 ml) then passed through a phase sep cartridge and concentrated in vacuo. The residue was purified by chromatography (24 g silica, 0-10% methanol in DCM, gradient elution) to afford (S)-1-(3,4-difluorophenyl)-N-(5-(3,5-dimethylisoxazol-4-yl)-2-(((1r,3S)-3-hydroxycyclobutyl)amino) phenyl)-5-oxopyrrolidine-2-carboxamide (500 mg, 55%) as a pale brown solid; Rt 1.79 min; m/z 497 (M+H)+ (ES+).

(S)-1-(3,4-difluorophenyl)-5-(5-(3,5-dimethylisoxazol-4-yl)-1-((1r,3S)-3-hydroxycyclo butyl)-1H-benzo[d]imidazol-2-yl)pyrrolidin-2-one

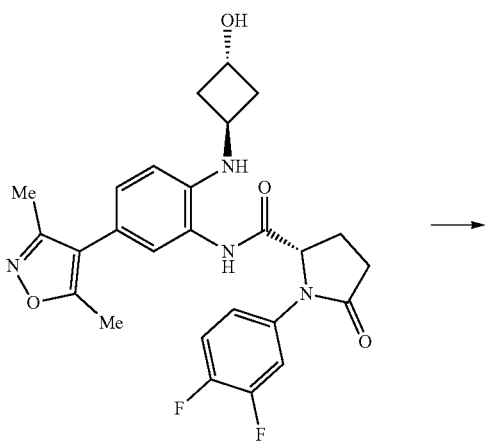

⟶

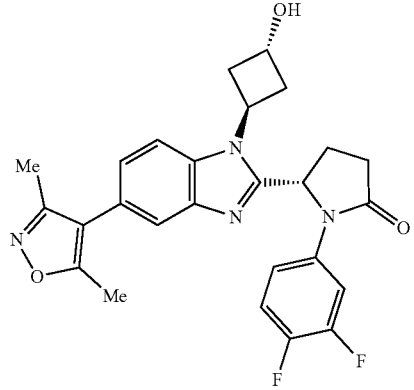

+

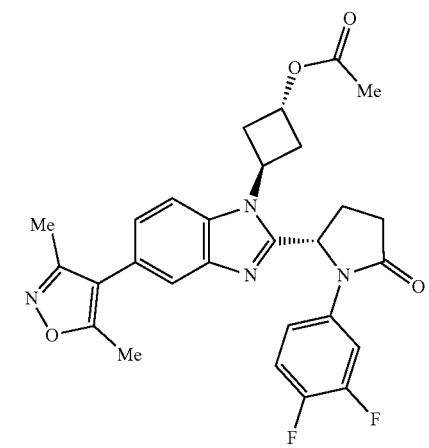

(S)-1-(3,4-difluorophenyl)-N-(5-(3,5-dimethylisoxazol-4-yl)-2-(((1r,3S)-3-hydroxycyclobutyl) amino)phenyl)-5-oxopyrrolidine-2-carboxamide (100 mg, 0.201 mmol) was dissolved in acetic acid (1 mL) and stirred at 80° C. for 18 h. The reaction mixture was cooled to RT and the solvent was removed in vacuo. The residue was purified by chromatography (12 g silica, 0-10% methanol in DCM, gradient elution). Product fractions were combined and concentrated in vacuo to afford ((S)-1-(3,4-difluorophenyl)-5-(5-(3,5-dimethylisoxazol-4-yl)-1-((1r,3S)-3-hydroxycyclobutyl)-1H-benzo[d]imidazol-2-yl)pyrrolidin-2-one (41 mg, 41%) as a light beige solid; Rt 1.79 min (method 1), m/z 479 (M+H)+ (ES+); 1H NMR (d6-DMSO) δ: 7.86-7.74 (m, 2H), 7.60 (d, J=1.6 Hz, 1H), 7.43-7.30 (m, 1H), 7.20 (dt, J=9.1, 2.0 Hz, 2H), 6.04-5.96 (m, 1H), 5.49 (p, J=8.6 Hz, 1H), 5.37 (d, J=3.9 Hz, 1H), 4.61 (s, 1H), 3.08 (dtd, J=36.6, 15.0, 14.1, 6.5 Hz, 2H), 2.74-2.52 (m, 3H), 2.46 (m, 1H), 2.36 (s, 3H), 2.19 (s, 3H), 2.11-1.96 (m, 2H).

Fractions containing the acetate were combined and concentrated in vacuo to afford (1S,3r)-3-(2-((S)-1-(3,4-difluorophenyl)-5-oxopyrrolidin-2-yl)-5-(3,5-dimethylisoxazol-4-yl)-1H-benzo[d]imidazol-1-yl)cyclobutyl acetate (27 mg, 24%) as a; Rt 2.11 min (method 1), m/z 521 (M+H)+ (ES+); 1H NMR (d6-DMSO) δ: 7.92 (d, J=8.4 Hz, 1H), 7.83 (ddd, J=13.2, 7.5, 2.7 Hz, 1H), 7.63 (d, J=1.6 Hz, 1H), 7.37 (dt, J=10.6, 9.1 Hz, 1H), 7.22 (dd, J=8.5, 1.7 Hz, 1H), 6.03 (d, J=7.1 Hz, 1H), 5.51 (p, J=8.7 Hz, 1H), 5.34 (t, J=7.3 Hz, 1H), 3.44-3.14 (m, 3H), 2.76-2.51 (m, 4H), 2.37 (s, 3H), 2.20 (s, 3H), 2.13 (s, 3H), 2.07 (m, 1H).

General Route C: Reductive Amination Approach to γ-Lactam Analogues

Example 126: (S)-5-(1-benzyl-5-(3,5-dimethylisoxazol-4-yl)-1H-benzo[d]imidazol-2-yl)-1-(3,4-difluorophenyl)pyrrolidin-2-one 5-(3,5-dimethylisoxazol-4-yl)-2-nitroaniline

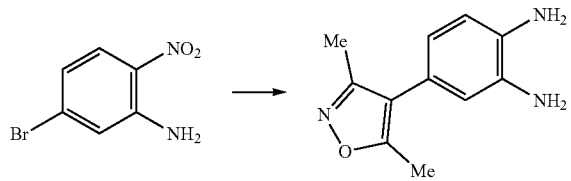 [SMILES: Nc1cc(Br)ccc1[N+](=O)[O-] ; Cc1noc(C)c1-c1ccc(N)c(N)c1]

A mixture of potassium carbonate (14.33 g, 104 mmol), (3,5-dimethylisoxazol-4-yl)boronic acid (7.31 g, 51.8 mmol) and 5-bromo-2-nitroaniline (7.5 g, 34.6 mmol) in 1,4-dioxane:water (4:1, 150 mL) was evacuated then backfilled with nitrogen three times. PdCl$_2$(dppf) (1.770 g, 2.419 mmol) was added then the mixture was heated to 90° C. under nitrogen for 16 hrs. The reaction mixture was cooled to rt then diluted with water (50 mL) and extracted with ethyl acetate (2×45 mL). Combined organics were dried (MgSO$_4$), filtered and evaporated under reduced pressure. The crude product was dissolved in DCM and passed through a plug of silica (~2 cm thick) to afford a yellow solid, which was triturated with Et$_2$O (2×100 mL). The resultant solid was filtered, 5 rinsing with Et$_2$O (50 mL), and dried in vacuo to afford 5-(3,5-dimethylisoxazol-4-yl)-2-nitroaniline (6.64 g, 79%) as a yellow solid; Rt 1.88 min (method 1), m/z 234 (M+H)+ (ES+).

(S)-1-(3,4-difluorophenyl)-5-oxopyrrolidine-2-carbonyl chloride

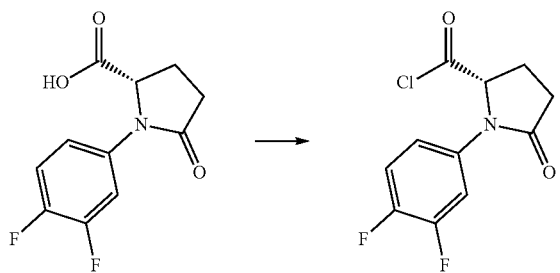 [SMILES: O=C(O)[C@@H]1CCC(=O)N1c1ccc(F)c(F)c1 ; O=C(Cl)[C@@H]1CCC(=O)N1c1ccc(F)c(F)c1]

To a suspension of (S)-1-(3,4-difluorophenyl)-5-oxopyrrolidine-2-carboxylic acid (1.45 g, 6 mmol) in anhydrous THF (5 mL, 61.0 mmol) cooled to 0° C., thionyl chloride (0.482 mL, 6.60 mmol) was added dropwise. The resulting solution was stirred for 6 h at room temperature and the solvent was evaporated under vacuum to give the crude (S)-1-(3,4-difluorophenyl)-5-oxopyrrolidine-2-carbonyl chloride (1.6 g, 51%) which was used without further purification.

(S)-1-(3,4-difluorophenyl)-N-(5-(3,5-dimethylisoxazol-4-yl)-2-nitrophenyl)-5-oxopyrrolidine-2-carboxamide

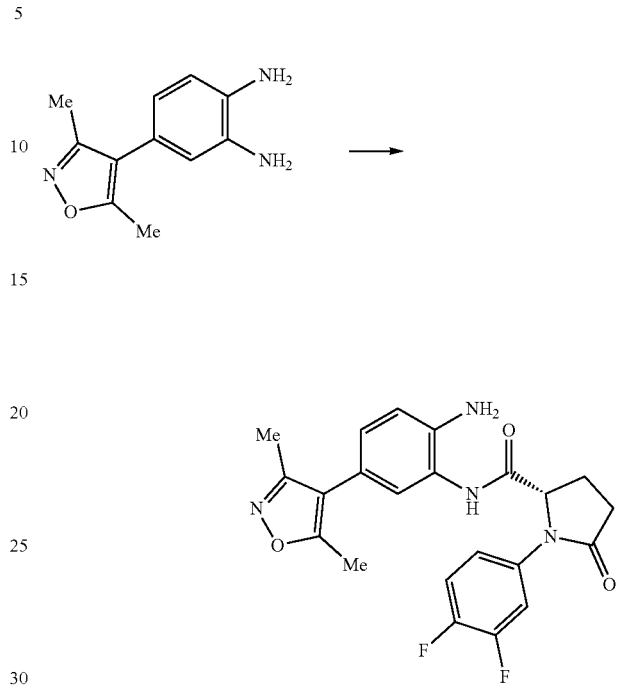

(S)-1-(3,4-difluorophenyl)-5-oxopyrrolidine-2-carbonyl chloride (779 mg, 3 mmol) in DCM (7 mL, 109 mmol) was added to a solution of 5-(3,5-dimethylisoxazol-4-yl)-2-nitroaniline (636 mg, 2.73 mmol) in DCM (7 mL, 109 mmol) at 0° C. then stirred at room temperature for 18 hours. The mixture was diluted with water (20 mL) then extracted with ethyl acetate (3×30 mL). The combined organic phases were washed with 1M HCl (10 mL), saturated aqueous NaHCO$_3$ (10 mL) and saturated brine (10 mL), then dried (MgSO$_4$), filtered and concentrated to give a brown oil. The crude product was purified by flash chromatography (40 g column, 0-100% EtOAc/isohexane) to afford (S)-1-(3,4-difluorophenyl)-N-(5-(3,5-dimethylisoxazol-4-yl)-2-nitrophenyl)-5-oxopyrrolidine-2-carboxamide (425 mg, 32%) as a yellow solid; Rt 1.13 min (method 1), m/z 427 (M+H)+ (ES+).

(S)—N-(2-amino-5-(3,5-dimethylisoxazol-4-yl)phenyl)-1-(3,4-difluorophenyl)-5-oxopyrrolidine-2-carboxamide

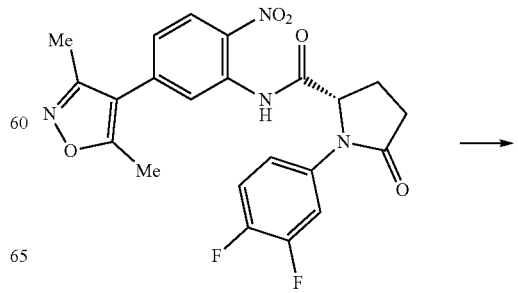

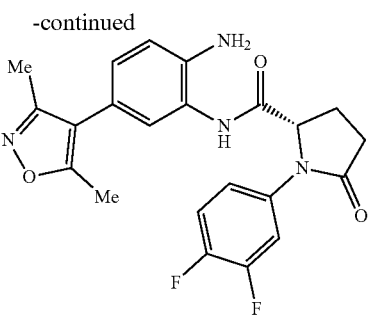

A suspension of (S)-1-(3,4-difluorophenyl)-N-(5-(3,5-dimethylisoxazol-4-yl)-2-nitrophenyl)-5-oxopyrrolidine-2-carboxamide (420 mg, 0.920 mmol) and 5% Pt/Al2O3-5R94 (42 mg, 10.76 μmol) in ethanol (25 ml, 428 mmol) was stirred under 2 bar of hydrogen at room temperature for 24 h. The white suspension was diluted with THF (10 mL) and then filtered through Celite©, washing with ethanol (50 mL) and THF (20 mL) and the solvent was removed under reduced pressure. The resulting yellow solid was dissolved in ethanol (25 mL, 428 mmol) and THF (5 mL) and 5% Pt/Al2O3-5R94 (42 mg, 10.76 μmol) was added and the reaction mixture was stirred under 2 bar of hydrogen at room temperature for a further 3 h. The reaction mixture was filtered through Celite©, washing with Ethanol (50 mL) and THF (20 mL) and the solvent was removed under reduced pressure to give (S)—N-(2-amino-5-(3,5-dimethylisoxazol-4-yl)phenyl)-1-(3,4-difluorophenyl)-5-oxopyrrolidine-2-carboxamide (386 mg, 89%) a yellow solid; Rt 1.13 min (method 1), m/z 427 (M+H)+ (ES+).

(S)-5-(1-benzyl-5-(3,5-dimethylisoxazol-4-yl)-1H-benzo[d]imidazol-2-yl)-1-(3,4-difluorophenyl)pyrrolidin-2-one

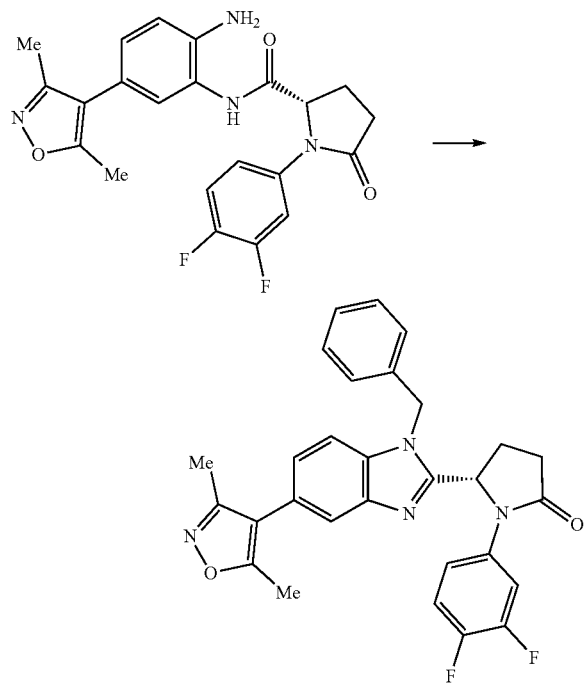

To a mixture of (S)—N-(2-amino-5-(3,5-dimethylisoxazol-4-yl)phenyl)-1-(3,4-difluorophenyl)-5-oxopyrrolidine-2-carboxamide (30 mg, 0.070 mmol) and DCM (1 mL, 15.54 mmol) were added benzaldehyde (9.30 μL, 0.091 mmol) and acetic acid (0.5 mL, 8.73 mmol). The mixture was stirred at room temperature for 20 minutes then pyridine borane (0.015 mL, 0.141 mmol) was added. The mixture was stirred at room temperature for 1 hour, then a few drops of concentrated HCl were added and the mixture was stirred at 80° C. for 1 hour. Additional acetic acid (0.5 mL, 8.73 mmol) was added and stirred at RT overnight. The mixture was concentrated under reduced pressure. The crude product was purified by chromatography on silica gel (12 g column, 0-5% MeOH/DCM) to afford ((S)-5-(1-benzyl-5-(3,5-dimethylisoxazol-4-yl)-1H-benzo[d]imidazol-2-yl)-1-(3,4-difluorophenyl)pyrrolidin-2-one (15 mg, 41%) as a tanned solid; Rt 2.26 min (method 1), m/z 499 (M+H)+ (ES+); 1H NMR (d6-DMSO) δ: 7.69-7.57 (m, 3H), 7.41-7.30 (m, 3H), 7.31-7.16 (m, 4H), 7.10-6.97 (m, 1H), 5.95-5.83 (m, 1H), 5.73 (d, J=16.6 Hz, 1H), 5.63 (d, J=16.6 Hz, 1H), 2.80-2.66 (m, 2H), 2.49-2.42 (m, 1H), 2.38 (s, 3H), 2.21 (s, 3H), 1.90-1.79 (m, 1H); Chiral HPLC (Diacel Chiralpak IA, 5 μm, 4.6×250 mm, 30 min method, 1.0 mL/min, isocratic 30% EtOH in isohexane (0.2% TFA): 156281, RT=5.65 min, >99% ee @ 254 nm.

Example 127: (S)-1-(3,4-difluorophenyl)-5-(5-(3,5-dimethylisoxazol-4-yl)-1-propyl-1H-benzo[d]imidazol-2-yl)pyrrolidin-2-one (5)-1-(3,4-difluorophenyl)-5-(5-(3,5-dimethylisoxazol-4-yl)-1-propyl-1H-benzo[d]imidazol-2-yl)pyrrolidin-2-one

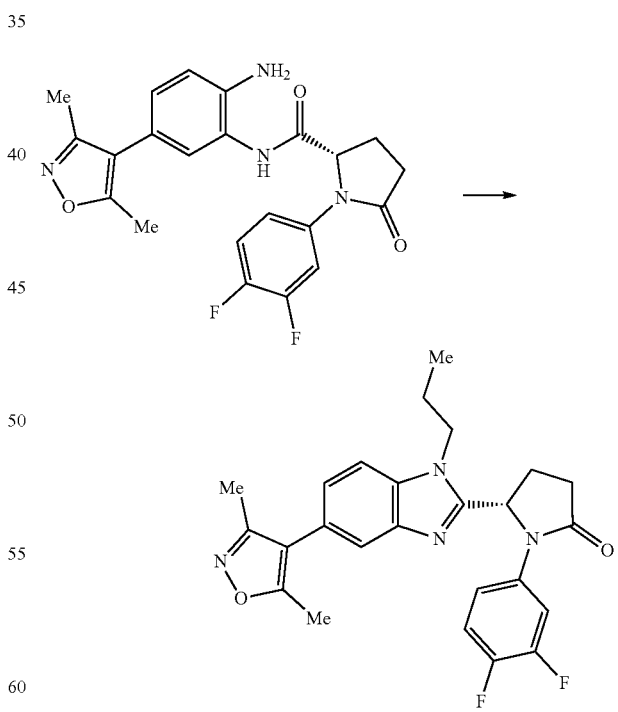

To a solution of (S)—N-(2-amino-5-(3,5-dimethylisoxazol-4-yl)phenyl)-1-(3,4-difluorophenyl)-5-oxopyrrolidine-2-carboxamide (50 mg, 0.117 mmol) in THF (2 mL, 24.41 mmol) was added propionaldehyde (11.00 μL, 0.152 mmol) and stirred at RT for 1 h. Then sodium triacetoxyborohydride (39.8 mg, 0.188 mmol) was added and stirred at RT for 4 h. Additional propionaldehyde (3 µL) was added and the mixture was stirred for a further 3 h. The reaction mixture was diluted with MeOH and loaded onto a column of SCX (2 g) in MeOH. The column was washed with MeOH and then the product was eluted with 0.7 M ammonia in MeOH. The resultant mixture was concentrated in vacuo to afford Product IV as a yellow residue (82 mg). The yellow residue was heated to 80° C. in acetic acid (2 mL, 34.9 mmol) for 18 h. The reaction mixture was concentrated and the crude product was purified by preparative HPLC (Acquity, Acidic (0.1% Formic acid), Waters X-Select Prep-C18, 5 µm, 19×50 mm column, 35-65% MeCN in Water) to afford (S)-1-(3,4-difluorophenyl)-5-(5-(3,5-dimethylisoxazol-4-yl)-1-propyl-1H-benzo[d]imidazol-2-yl)pyrrolidin-2-one (10 mg, 18%) as a tan solid; Rt 2.10 min (method 1), m/z 451 (M+H)+ (ES+); 1H NMR (d6-DMSO) δ: 7.76 (1H, ddd, J=13.0, 7.4, 2.6 Hz), 7.71-7.64 (1H, m), 7.59 (1H, dd, J=1.6, 0.6 Hz), 7.37 (1H, dt, J=10.6, 9.1 Hz), 7.24-7.14 (2H, m), 6.03-5.95 (1H, m), 4.35 (1H, dt, J=14.8, 7.4 Hz), 4.25 (1H, dt, J=14.8, 7.6 Hz), 2.88-2.73 (1H, m), 2.70-2.52 (2H, m), 2.36 (3H, s), 2.19 (3H, s), 2.08 (1H, t, J=10.6 Hz), 1.78 (2H, q, J=7.4 Hz), 0.95 (3H, t, J=7.4 Hz).

Example 128: (S)-1-(3,4-difluorophenyl)-5-(5-(3,5-dimethylisoxazol-4-yl)-1-isobutyl-1H-benzo[d]imidazol-2-yl)pyrrolidin-2-one (S)-1-(3,4-difluorophenyl)-5-(5-(3,5-dimethylisoxazol-4-yl)-1-isobutyl-1H-benzo[d]imidazol-2-yl)pyrrolidin-2-one mixture was diluted with MeOH and loaded onto a column of SCX (2 g) in MeOH. The column was washed with MeOH and then the product was eluted with 0.7 M ammonia in MeOH. The resultant mixture was concentrated in vacuo to afford a yellow residue, which was heated to 80° C. in acetic acid (2 mL, 34.9 mmol) for 18 h. The reaction mixture was concentrated and the crude product was purified by preparative HPLC (Acquity, Acidic (0.1% Formic acid), Waters X-Select Prep-C18, 5 µm, 19×50 mm column, 35-65% MeCN in Water) to afford (S)-1-(3,4-difluorophenyl)-5-(5-(3,5-dimethylisoxazol-4-yl)-1-isobutyl-1H-benzo[d]imidazol-2-yl)pyrrolidin-2-one (10 mg, 9%) as a tan solid; Rt 2.21 min (method 1), m/z 465 (M+H)+ (ES+); 1H NMR (d6-DMSO) δ: 7.76-7.65 (m, 2H), 7.61 (d, J=1.6 Hz, 1H), 7.44-7.30 (m, 1H), 7.24-7.14 (m, 2H), 5.99-5.92 (m, 1H), 4.24 (dd, J=14.6, 7.2 Hz, 1H), 4.08 (dd, J=14.5, 8.2 Hz, 1H), 2.80 (dd, J=16.5, 9.0 Hz, 1H), 2.70-2.53 (m, 2H), 2.38 (s, 3H), 2.33 (p, J=1.9 Hz, 1H), 2.21 (s, 3H), 2.13-2.05 (m, 1H), 0.96 (d, J=6.6 Hz, 3H), 0.90 (d, J=6.6 Hz, 3H); Chiral HPLC (Diacel Chiralpak IA, 5 µm, 4.6×250 mm, 30 min method, 1.0 mL/min, isocratic 30% EtOH in isohexane (0.2% TFA): RT=13.2 min, >99% ee @ 254 nm.

Example 129: (S)-1-(3,4-difluorophenyl)-5-(5-(3,5-dimethylisoxazol-4-yl)-1-(3-methoxypropyl)-1H-benzo[d]imidazol-2-yl)pyrrolidin-2-one (S)-1-(3,4-difluorophenyl)-5-(5-(3,5-dimethylisoxazol-4-yl)-1-(3-methoxypropyl)-1H-benzo[d]imidazol-2-yl)pyrrolidin-2-one

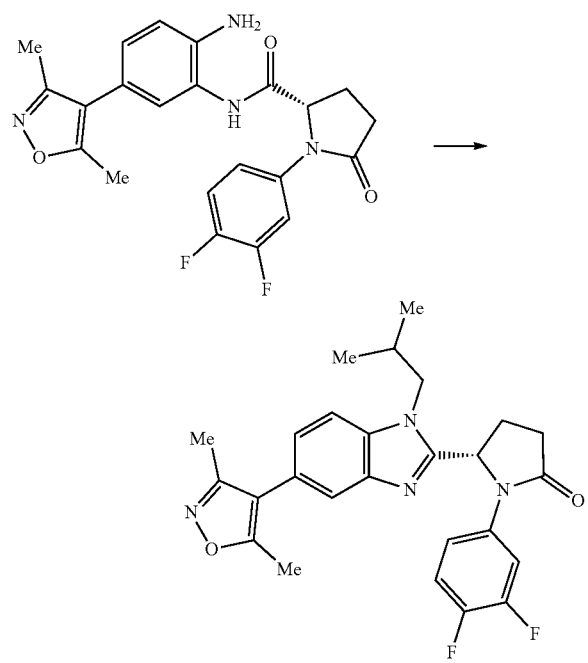

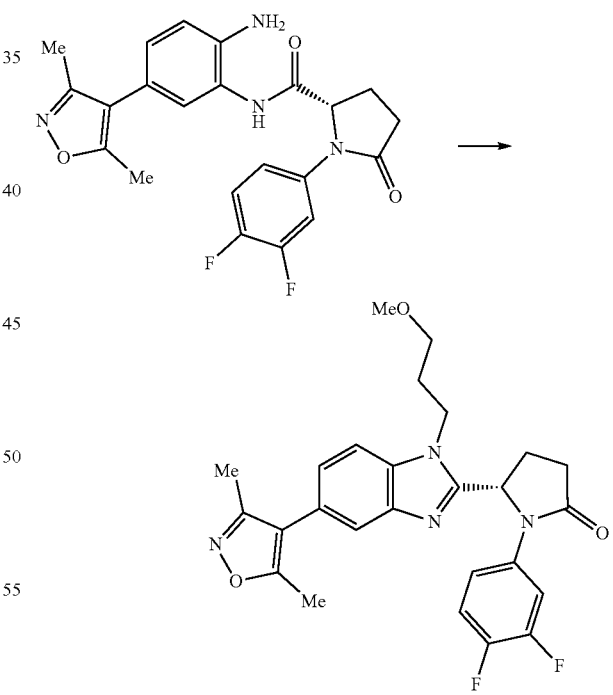

(S)—N-(2-amino-5-(3,5-dimethylisoxazol-4-yl)phenyl)-1-(3,4-difluorophenyl)-5-oxopyrrolidine-2-carboxamide (100 mg, 0.235 mmol) and isobutyraldehyde (0.025 mL, 0.469 mmol) in THF (2 mL, 24.41 mmol) at rt was added acetic acid (0.013 mL, 0.235 mmol) and was stirred at RT for 1 h. Then sodium triacetoxyborohydride (80 mg, 0.375 mmol) was added and stirred at RT for 4 h. The reaction To a solution of (S)—N-(2-amino-5-(3,5-dimethylisoxazol-4-yl)phenyl)-1-(3,4-difluorophenyl)-5-oxopyrrolidine-2-carboxamide (100 mg, 0.235 mmol) in THF (2 mL, 24.41 mmol) was added 3-methoxypropanal (31.0 mg, 0.352 mmol) and stirred at RT for 1 h. Then sodium triacetoxyborohydride (80 mg, 0.375 mmol) was added and stirred at RT for 4 h. The reaction mixture was diluted with MeOH and loaded onto a column of SCX (2 g) in MeOH. The column was washed with MeOH and then the product was eluted with 0.7 M ammonia in MeOH. The resultant mixture was concentrated in vacuo to afford a yellow residue (82 mg), which was heated to 80° C. in acetic acid (2 mL, 34.9 mmol) for 18 h. The reaction mixture was concentrated and the crude product was purified by preparative HPLC (Acquity, Acidic (0.1% Formic acid), Waters X-Select Prep-C18, 5 μm, 19×50 mm column, 35-65% MeCN in Water) to afford (S)-1-(3,4-difluorophenyl)-5-(5-(3,5-dimethylisoxazol-4-yl)-1-(3-methoxy propyl)-1H-benzo[d]imidazol-2-yl)pyrrolidin-2-one (8 mg, 7%) as a tan solid; Rt 2.00 min (method 1), m/z 481 (M+H)+ (ES+); 1H NMR (d6-DMSO) δ: 7.76 (ddd, J=13.2, 7.4, 2.6 Hz, 1H), 7.66-7.58 (m, 2H), 7.42-7.31 (m, 1H), 7.27-7.14 (m, 1H), 5.93 (dd, J=8.4, 2.0 Hz, 1H), 4.44 (dt, J=14.5, 7.2 Hz, 1H), 4.33 (dt, J=14.9, 7.4 Hz, 1H), 3.39 (t, J=6.0 Hz, 2H), 3.26 (s, 3H), 2.82-2.53 (m, 3H), 2.37 (s, 3H), 2.35-2.31 (m, 1H), 2.20 (s, 3H), 2.16-2.08 (m, 1H), 2.02 (t, J=6.6 Hz, 2H); Chiral HPLC (Diacel Chiralpak IA, 5 μm, 4.6×250 mm, 30 min method, 1.0 ml/min, isocratic 30% EtOH in isohexane (0.2% TFA): RT=7.65 min, >99% ee @ 254 nm.

Example 130: (S)-5-(1-((4,4-difluorocyclohexyl)methyl)-5-(3,5-dimethylisoxazol-4-yl)-1H-benzo[d]imidazol-2-yl)-1-(3,4-difluorophenyl)pyrrolidin-2-one (S)—N-(5-(3,5-dimethylisoxazol-4-yl)-2-nitrophenyl)-5-oxopyrrolidine-2-carboxamide

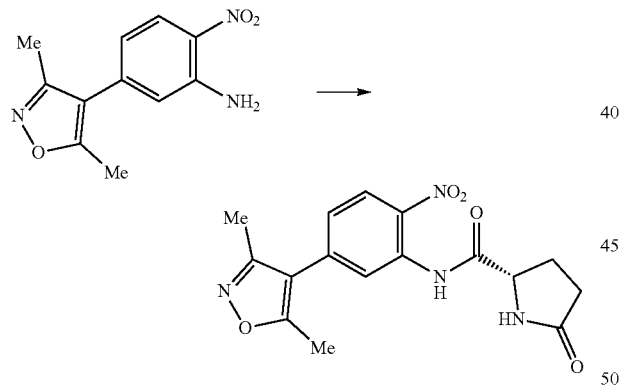

(S)-5-oxopyrrolidine-2-carbonyl chloride (0.940 g, 6.37 mmol) in DCM (7 mL, 109 mmol) was added to a solution of 5-(3,5-dimethylisoxazol-4-yl)-2-nitroaniline (1.35 g, 5.79 mmol) in DCM (7 mL, 109 mmol) at 0° C. then stirred at room temperature overnight. The mixture was diluted with water (20 mL) then extracted with ethyl acetate (3×30 mL). The combined organic phases were washed with aqueous 1M HCl (10 mL), saturated aqueous NaHCO3 (10 mL) and saturated brine (10 mL), then dried (MgSO4), filtered and concentrated to give a brown oil, which was purified by chromatography on silica gel (40 g column, 0-100% EtOAc/isohexane) to afford (S)—N-(5-(3,5-dimethylisoxazol-4-yl)-2-nitrophenyl)-5-oxopyrrolidine-2-carboxamide (1.25 g, 62%) as a yellow solid; Rt 1.53 min (method 1), m/z 345 (M+H)+ (ES+).

(S)—N-(2-amino-5-(3,5-dimethylisoxazol-4-yl)phenyl)-5-oxopyrrolidine-2-carboxamide

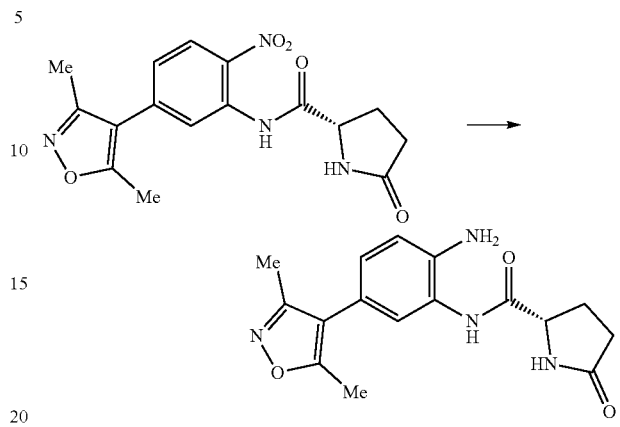

A suspension of (S)—N-(5-(3,5-dimethylisoxazol-4-yl)-2-nitrophenyl)-5-oxopyrrolidine-2-carboxamide (550 mg, 1.597 mmol) and 5% Pt/Al2O3-5R94 (55 mg, 0.014 mmol) in ethanol (30 mL, 514 mmol) was stirred under 2 bar of hydrogen at room temperature for 20 h. The reaction mixture was filtered through Celite©, washing with ethanol (50 mL) and the solvent was removed under reduced pressure to give (S)—N-(2-amino-5-(3,5-dimethylisoxazol-4-yl)phenyl)-5-oxopyrrolidine-2-carboxamide (540 mg, 100% yield) as a yellow solid; Rt 1.14 min (method 1), m/z 315 (M+H)+ (ES+).

(S)-5-(1-((4,4-difluorocyclohexyl)methyl)-5-(3,5-dimethylisoxazol-4-yl)-1H-benzo[d]imidazol-2-yl)pyrrolidin-2-one

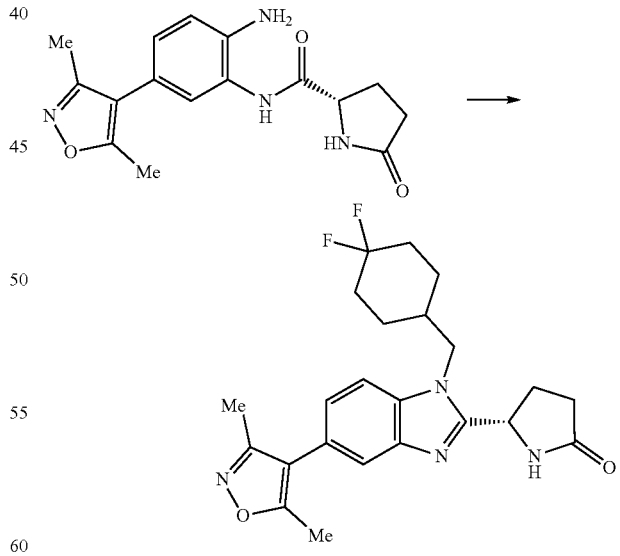

4,4-difluorocyclohexanecarbaldehyde (70.5 mg, 0.476 mmol) was added to a solution of (S)—N-(2-amino-5-(3,5-dimethylisoxazol-4-yl)phenyl)-5-oxopyrrolidine-2-carboxamide (125 mg, 0.366 mmol) in DCM (4 mL, 62.2 mmol) at RT and stirred for 20 mins. Then acetic acid (2 mL, 34.9 mmol) was added and stirred at RT for a further 20 mins then pyridine borane (0.078 mL, 0.732 mmol) was added. The reaction mixture was stirred at room temperature for 1 h then a few drops of concentrated HCl were added and the mixture was stirred at 80° C. for 2 h. The mixture was concentrated under reduced pressure. The crude product was purified by chromatography on silica gel (12 g column, 0-5% (0.7 M Ammonia/MeOH)/DCM) to afford (S)-5-(1-((4,4-difluorocyclohexyl)methyl)-5-(3,5-dimethylisoxazol-4-yl)-1H-benzo[d]imidazol-2-yl)pyrrolidin-2-one (45 mg, 27%) as a yellow solid; Rt 1.70 min (method 1), m/z 429 (M+H)+ (ES+).

(S)-5-(1-((4,4-difluorocyclohexyl)methyl)-5-(3,5-dimethylisoxazol-4-yl)-1H-benzo[d]imidazol-2-yl)-1-(3,4-difluorophenyl)pyrrolidin-2-one

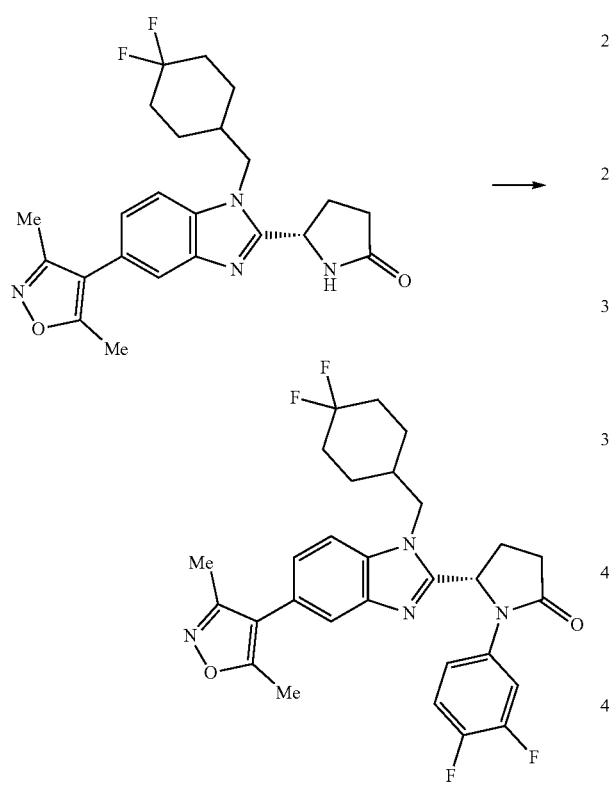

DBU (0.024 ml, 0.158 mmol) was added to a solution of (S)-5-(1-((4,4-difluorocyclohexyl)methyl)-5-(3,5-dimethylisoxazol-4-yl)-1H-benzo[d]imidazol-2-yl)pyrrolidin-2-one (45 mg, 0.105 mmol) in MeCN (1.5 mL, 28.7 mmol), and stirred at RT for 10 min. CuTMEDA (9.76 mg, 0.021 mmol) was added, sonicated and stirred for a further 10 min. Then (3,4-difluorophenyl)boronic acid (24.88 mg, 0.158 mmol) was added and the reaction stirred at 35° C. for 24 hr. The mixture was concentrated under reduced pressure then the crude product was purified by chromatography on silica gel (12 g column, 0-10% MeOH/DCM) to afford (S)-5-(1-((4,4-difluorocyclohexyl)methyl)-5-(3,5-dimethylisoxazol-4-yl)-1H-benzo[d]imidazol-2-yl)-1-(3,4-difluorophenyl)pyrrolidin-2-one (28 mg, 49%) as a tan solid; Rt 2.30 min (method 1), m/z 541 (M+H)+ (ES+); 1H NMR (d6-DMSO) δ: 7.76-7.64 (2H, m), 7.61 (1H, d, J=1.5 Hz), 7.38 (1H, dt, J=10.7, 9.1 Hz), 7.28-7.08 (2H, m), 5.96 (1H, dd, J=8.3, 2.0 Hz), 4.33 (1H, dd, J=14.6, 7.2 Hz), 4.19 (1H, dd, J=14.7, 8.0 Hz), 2.88-2.75 (1H, m), 2.71-2.51 (2H, m), 2.37 (3H, s), 2.20 (3H, s), 2.06-1.91 (4H, m), 1.85-1.61 (3H, m), 1.56-1.33 (3H, m); Chiral HPLC (Diacel Chiralpak IA, 5 μm, 4.6×250 mm, 30 min method, 1.0 mL/min, isocratic 30% EtOH in isohexane (0.2% TFA): 156287, RT=6.65 min, >99% ee @ 254 nm.

Example 131: (S)-5-(1-benzyl-5-(3,5-dimethylisoxazol-4-yl)-1H-benzo[d]imidazol-2-yl)-1-(3-fluoro-4-methoxyphenyl)pyrrolidin-2-one (S)-5-(1-benzyl-5-(3,5-dimethylisoxazol-4-yl)-1H-benzo[d]imidazol-2-yl)pyrrolidin-2-one

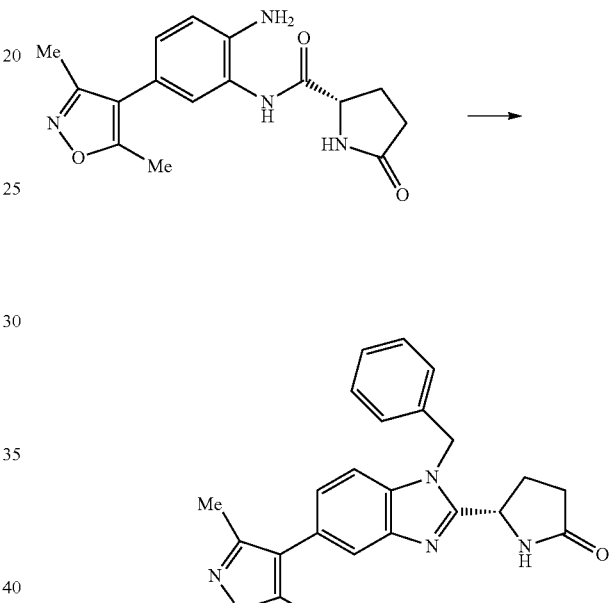

To a mixture of (S)—N-(2-amino-5-(3,5-dimethylisoxazol-4-yl)phenyl)-5-oxopyrrolidine-2-carboxamide (50 mg, 0.146 mmol) in DCM (2 mL, 31.1 mmol) were added benzaldehyde (0.019 ml, 0.190 mmol) and acetic acid (1 mL, 17.47 mmol). The mixture was stirred at room temperature for 20 minutes then pyridine borane (0.031 mL, 0.293 mmol) was added. The mixture was stirred at room temperature for 1 hour. The reaction mixture was diluted with MeOH (2 mL) and loaded onto a column of SCX (1.5 g). The column was washed with MeOH and then the product was eluted with 7 M ammonia in MeOH. The resultant mixture was concentrated in vacuo a yellow oil, which was dissolved in acetic acid (1 mL, 17.47 mmol) and was heated to 80° C. for 1 h. The crude product was loaded onto a column of SCX (1 g) in MeOH. The column was washed with MeOH and then the product was eluted with 7 M ammonia in MeOH. The resultant mixture was concentrated in vacuo to afford crude product as a pink solid. The crude product was purified by flash chromatography on silica gel (4 g column, 0-8% (0.7 M Ammonia/MeOH)/DCM) to afford (S)-5-(1-benzyl-5-(3,5-dimethylisoxazol-4-yl)-1H-benzo[d]imidazol-2-yl)pyrrolidin-2-one (22 mg, 35%) as a colourless solid at 90% purity.

347

(S)-5-(1-benzyl-5-(3,5-dimethylisoxazol-4-yl)-1H-benzo[d]imidazol-2-yl)-1-(3-fluoro-4-methoxyphenyl)pyrrolidin-2-one

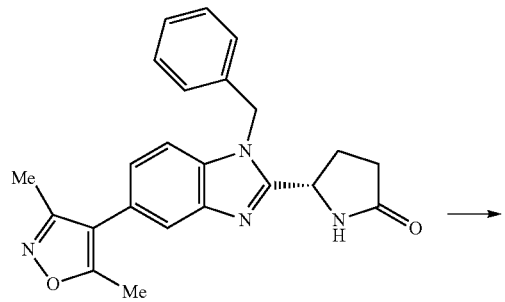

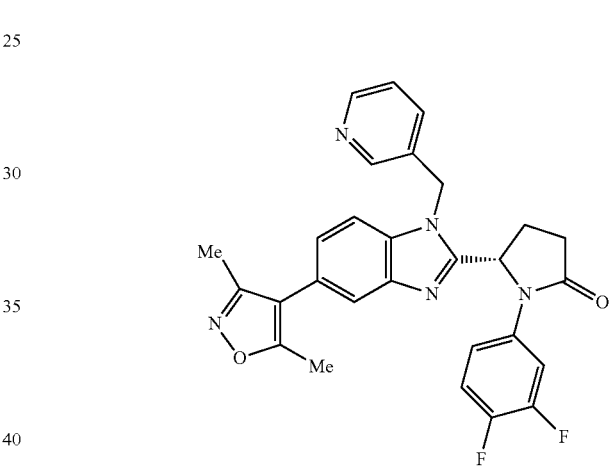

DBU (0.012 ml, 0.077 mmol) was added to a solution of (S)-5-(1-benzyl-5-(3,5-dimethylisoxazol-4-yl)-1H-benzo[d]imidazol-2-yl)pyrrolidin-2-one (22 mg, 0.051 mmol) in MeCN (1.5 ml, 28.7 mmol), and stirred for 10 min at rt. CuTMEDA (4.76 mg, 10.25 μmol) was added, sonicated and stirred for a further 10 min. Then (3-fluoro-4-methoxyphenyl)boronic acid (13.06 mg, 0.077 mmol) was added and the reaction stirred at 35° C. for 24 hr. The mixture was concentrated under reduced pressure then the crude product was purified by chromatography on silica gel (12 g column, 0-10% MeOH/DCM) to afford (S)-5-(1-benzyl-5-(3,5-dimethylisoxazol-4-yl)-1H-benzo[d]imidazol-2-yl)-1-(3-fluoro-4-methoxyphenyl)pyrrolidin-2-one (10 mg, 37%) as a colourless solid; Rt 2.14 min (method 1), m/z 511 (M+H)+ (ES+); 1H NMR (d6-DMSO) δ: 7.64 (1H, dd, J=1.7, 0.7 Hz), 7.62 (1H, dd, J=8.4, 0.7 Hz), 7.46-7.39 (1H, m), 7.38-7.28 (3H, m), 7.20 (1H, dd, J=8.3, 1.6 Hz), 7.18-7.13 (2H, m), 6.99-6.89 (2H, m), 5.88-5.81 (1H, m), 5.68 (1H, d, J=16.5 Hz), 5.61 (1H, d, J=16.5 Hz), 3.74 (3H, s), 2.77-2.65 (1H, m), 2.45 (2H, dd, J=12.3, 8.1 Hz), 2.37 (3H, s), 2.20 (3H, s), 1.90-1.81 (1H, m); Chiral HPLC (Diacel Chiralpak IA, 5 μm, 4.6×250 mm, 30 min method, 1.0 mL/min, isocratic 30% EtOH in isohexane (0.2% TFA): RT=14.1 min, 97% ee @ 254 nm.

348

Example 132: (S)-1-(3,4-difluorophenyl)-5-(5-(3,5-dimethylisoxazol-4-yl)-1-(pyridin-3-ylmethyl)-1H-benzo[d]imidazol-2-yl)pyrrolidin-2-one (S)-1-(3,4-difluorophenyl)-5-(5-(3,5-dimethylisoxazol-4-yl)-1-(pyridin-3-ylmethyl)-1H-benzo[d]imidazol-2-yl)pyrrolidin-2-one

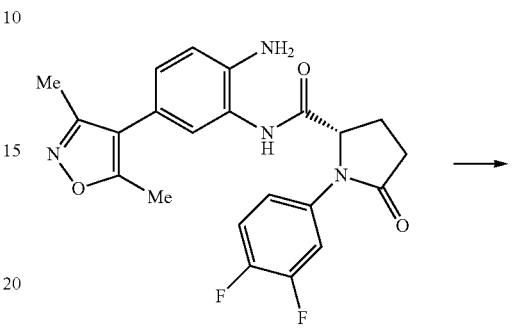

To a mixture of (S)—N-(2-amino-5-(3,5-dimethylisoxazol-4-yl)phenyl)-1-(3,4-difluorophenyl)-5-oxopyrrolidine-2-carboxamide (40 mg, 0.094 mmol) and DCM (1 mL, 15.54 mmol) were added nicotinaldehyde (0.011 mL, 0.122 mmol) and acetic acid (0.5 mL, 8.73 mmol). The mixture was stirred at room temperature for 20 mins then pyridine borane (0.020 mL, 0.188 mmol) was added. The mixture was stirred at room temperature for 1 h then a few drops of concentrated HCl were added and stirring continued at RT for 5 min. Then acetic acid (1 mL, 17.47 mmol) was added and the mixture was stirred at 80° C. for 18 h. The mixture was concentrated under reduced pressure. The crude product was purified by chromatography on silica gel (12 g column, 0-5% (0.7 M Ammonia/MeOH)/DCM) to afford (S)-1-(3,4-difluorophenyl)-5-(5-(3,5-dimethylisoxazol-4-yl)-1-(pyridin-3-ylmethyl)-1H-benzo[d]imidazol-2-yl)pyrrolidin-2-one (21 mg, 43%) as a colourless solid; Rt 1.66 min (method 1), m/z 500 (M+H)+ (ES+); 1H NMR (d6-DMSO) δ: 8.58-8.47 (2H, m), 7.69-7.64 (2H, m), 7.59 (1H, ddd, J=13.0, 7.4, 2.6 Hz), 7.48 (1H, dt, J=8.0, 1.9 Hz), 7.36 (1H, ddd, J=7.9, 4.8, 0.9 Hz), 7.31-7.20 (2H, m), 7.12-7.03 (1H, m), 5.99-5.93 (1H, m), 5.81-5.65 (2H, m), 2.80-2.68 (1H, m), 2.55-2.52 (1H, m), 2.48-2.43 (1H, m), 2.37 (3H, s), 2.20 (3H, s), 1.91-1.81 (1H, m).

349

Example 133: (S)-1-(3,4-difluorophenyl)-5-(5-(3,5-dimethylisoxazol-4-yl)-1-((1s,3R)-3-(hydroxymethyl)cyclobutyl)-1H-benzo[d]imidazol-2-yl)pyrrolidin-2-one and Example 134: (S)-1-(3,4-difluorophenyl)-5-(5-(3,5-dimethylisoxazol-4-yl)-1-((1r,3S)-3-(hydroxymethyl)cyclobutyl)-1H-benzo[d]imidazol-2-yl)pyrrolidin-2-one (S)-5-(5-(3,5-dimethylisoxazol-4-yl)-1-(3-(hydroxymethyl)cyclobutyl)-1H-benzo[d]imidazol-2-yl)pyrrolidin-2-one

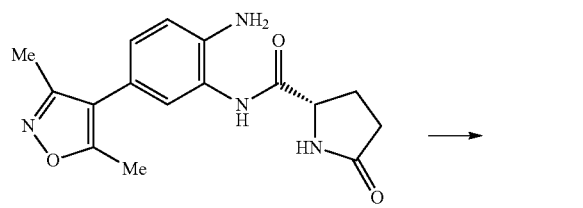

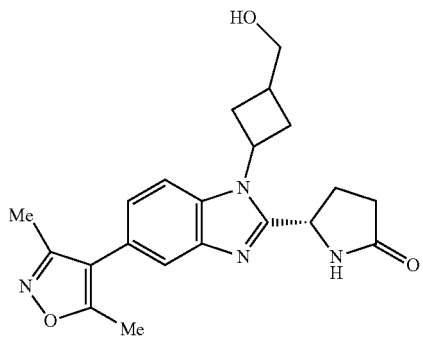

To a mixture of (S)—N-(2-amino-5-(3,5-dimethylisoxazol-4-yl)phenyl)-5-oxopyrrolidine-2-carboxamide (125 mg, 0.366 mmol) in DCM (4 ml, 62.2 mmol) was added 3-(hydroxymethyl)cyclobutanone (47.6 mg, 0.476 mmol) and ACETIC ACID (2 ml, 34.9 mmol). The mixture was stirred at rt for 20 mins then PYRIDINE BORANE (0.078 ml, 0.732 mmol) was added and stirred at rt for 1 hr. A few drops of concentrated HCl were added and the mixture was stirred at 80° C. for 16 hour. The mixture was concentrated under reduced pressure. The yellow residue was dissolved in MeOH (3 ml) and $K_2CO_3$ (76 mg, 0.549 mmol) was added and stirred at RT for 48 hrs then the mixture was concentrated in vacuo then partitioned between water (10 mL) and EtOAc (3×20 mL). The combined organics were washed with brine (15 mL), dried (MgSO4), and concentrated in vacuo to afford (S)-5-(5-(3,5-dimethylisoxazol-4-yl)-1-(3-(hydroxymethyl)cyclobutyl)-1H-benzo[d]imidazol-2-yl)pyrrolidin-2-one (150 mg, 81%) as a 1:1 mixture of diastereoisomers; Rt 1.08 min (method 1), m/z 381 (M+H)+ (ES+).

350

(S)-1-(3,4-difluorophenyl)-5-(5-(3,5-dimethylisoxazol-4-yl)-1-((1s,3R)-3-(hydroxyl methyl)cyclobutyl)-1H-benzo[d]imidazol-2-yl)pyrrolidin-2-one and (S)-1-(3,4-difluorophenyl)-5-(5-(3,5-dimethylisoxazol-4-yl)-1-((1r,3S)-3-(hydroxymethyl) cyclobutyl)-1H-benzo[d]imidazol-2-yl)pyrrolidin-2-one

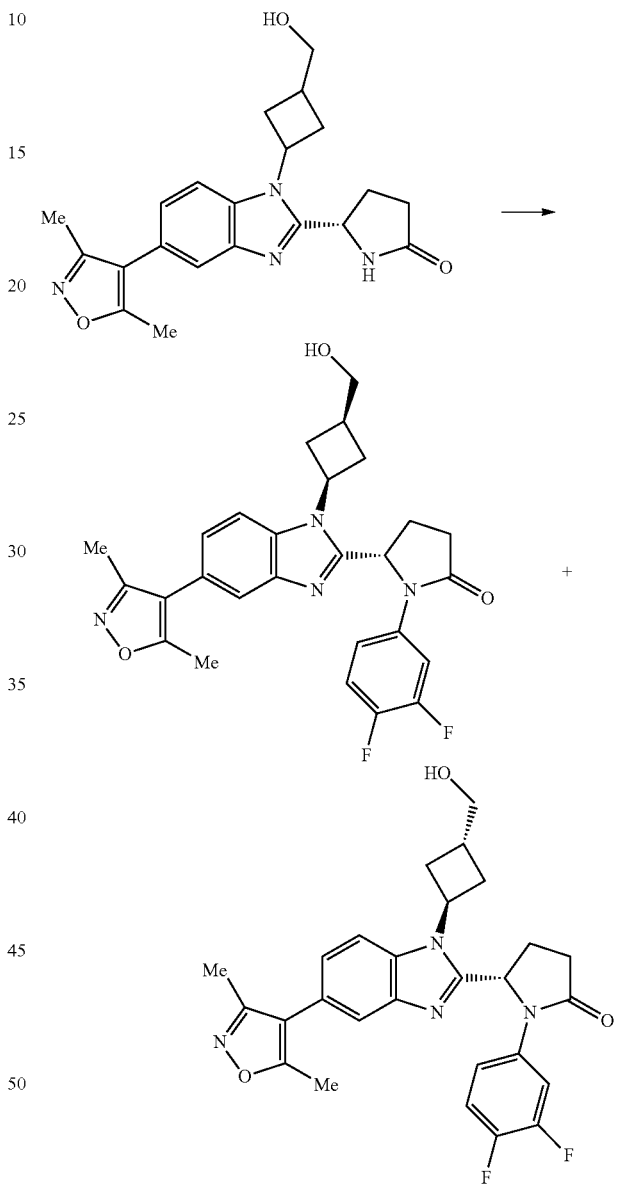

DBU (0.083 mL, 0.549 mmol) was added to a solution of (S)-5-(5-(3,5-dimethylisoxazol-4-yl)-1-(3-(hydroxymethyl) cyclobutyl)-1H-benzo[d]imidazol-2-yl)pyrrolidin-2-one (139 mg, 0.366 mmol) in MeCN (8 mL, 153 mmol), and stirred for 10 min. CuTMEDA (34.0 mg, 0.073 mmol) was added, sonicated and stirred for a 10 min, (3,4-difluorophenyl)boronic acid (87 mg, 0.549 mmol) added and the reaction stirred at 35° C. for 24 h. Additional DBU (0.083 mL, 0.549 mmol), CuTMEDA (34.0 mg, 0.073 mmol) and (3,4-difluorophenyl)boronic acid (87 mg, 0.549 mmol) were added and the reaction mixture was stirred for a further 18 h at 35° C. The mixture was concentrated under reduced pressure then the crude product was purified by chromatography on silica gel (24 g column, 0-5% (0.7 M Ammonia/MeOH)/DCM) to afford (S)-1-(3,4-difluorophenyl)-5-(5-(3,5-dimethylisoxazol-4-yl)-1-((1s,3R)-3-(hydroxymethyl)cyclobutyl)-1H-benzo[d]imidazol-2-yl)pyrrolidin-2-one (20 mg, 11%) as a yellow solid; Rt 1.78 min (method 1), m/z 493 (M+H)+ (ES+); 1H NMR (d6-DMSO) δ: 8.09 (1H, d, J=8.4 Hz), 7.79 (1H, ddd, J=13.2, 7.4, 2.6 Hz), 7.59 (1H, d, J=1.6 Hz), 7.37 (1H, dt, J=10.5, 9.1 Hz), 7.23-7.15 (2H, m), 6.01 (1H, dd, J=8.2, 2.1 Hz), 5.17-5.03 (1H, m), 4.97 (1H, t, J=5.1 Hz), 3.55 (2H, t, J=4.5 Hz), 2.88-2.57 (5H, m), 2.58-2.52 (1H, m), 2.49-2.39 (2H, m), 2.37 (3H, s), 2.20 (3H, s), 2.14-2.01 (1H, m); Chiral HPLC (Diacel Chiralpak IA, 5 μm, 4.6×250 mm, 30 min method, 1.0 mL/min, isocratic 30% EtOH in isohexane (0.2% TFA): RT=4.56 min, >99% de @254 nm.

A second fraction then gave (S)-1-(3,4-difluorophenyl)-5-(5-(3,5-dimethylisoxazol-4-yl)-1-((1r,3S)-3-(hydroxymethyl)cyclobutyl)-1H-benzo[d]imidazol-2-yl)pyrrolidin-2-one (15 mg, 8%) as a yellow solid; Rt 1.79 min (method 1), m/z 493 (M+H)+ (ES+); 1H NMR (d6-DMSO) δ: 7.92 (1H, d, J=8.4 Hz), 7.77 (1H, ddd, J=13.2, 7.4, 2.6 Hz), 7.61 (1H, d, J=1.7 Hz), 7.36 (1H, dt, J=10.6, 9.2 Hz), 7.26-7.15 (2H, m), 6.03-5.95 (1H, m), 5.37-5.24 (1H, m), 4.79 (1H, t, J=5.2 Hz), 3.65 (2H, dd, J=6.8, 5.1 Hz), 3.02-2.83 (2H, m), 2.77-2.51 (1H, m), 2.65-2.60 (3H, m), 2.37 (2H, s), 2.36-2.30 (3H, m), 2.20 (3H, s), 2.08-1.96 (1H, m). Chiral HPLC (Diacel Chiralpak IA, 5 μm, 4.6×250 mm, 30 min method, 1.0 mL/min, isocratic 30% EtOH in isohexane (0.2% TFA): RT=4.72 min, >99% de @ 254 nm.

Example 135: (S)-5-(1-(cyclopropylmethyl)-5-(3,5-dimethylisoxazol-4-yl)-1H-benzo[d]imidazol-2-yl)-1-(3,4-difluorophenyl)pyrrolidin-2-one (S)-5-(1-(cyclopropylmethyl)-5-(3,5-dimethylisoxazol-4-yl)-1H-benzo[d]imidazol-2-yl)-1-(3,4-difluorophenyl)pyrrolidin-2-one

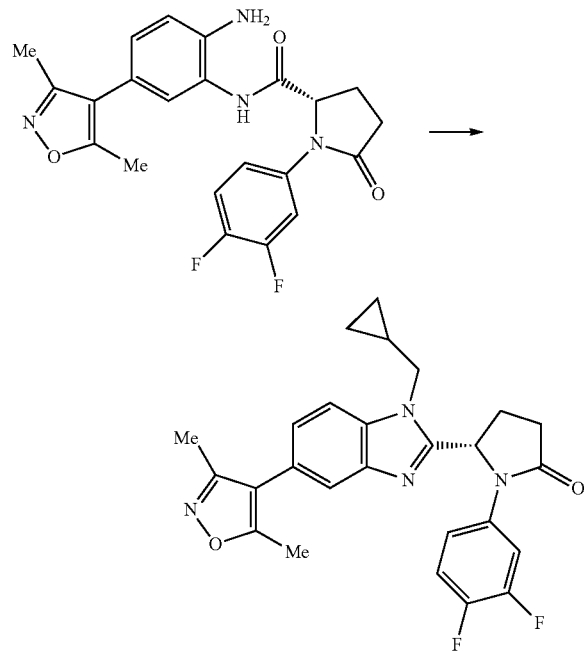

To a mixture of (S)—N-(2-amino-5-(3,5-dimethylisoxazol-4-yl)phenyl)-1-(3,4-difluorophenyl)-5-oxopyrrolidine-2-carboxamide (50 mg, 0.117 mmol) and DCM (1 mL, 15.54 mmol) were added cyclopropanecarbaldehyde (0.011 mL, 0.152 mmol) and acetic acid (0.5 mL, 8.73 mmol). The mixture was stirred at room temperature for 20 min then pyridine borane (0.025 ml, 0.235 mmol) was added. The mixture was stirred at room temperature for 1 h, then a few drops of concentrated HCl were added and stirring continued at RT for 5 min. Acetic acid (0.5 mL, 8.73 mmol) was added and the mixture was stirred at 80° C. for 18 h. The mixture was concentrated under reduced pressure. The crude product was purified by flash chromatography on the Companion (12 g column, 0-5% MeOH/DCM) to afford ((S)-5-(1-(cyclopropylmethyl)-5-(3,5-dimethylisoxazol-4-yl)-1H-benzo[d]imidazol-2-yl)-1-(3,4-difluorophenyl)pyrrolidin-2-one (16 mg, 29%) as a tan solid; Rt 2.11 min (method 1), m/z 463 (M+H)+ (ES+); 1H NMR (d6-DMSO) δ: 7.76 (1H, ddd, J=13.1, 7.4, 2.6 Hz), 7.72 (1H, dd, J=8.4, 0.6 Hz), 7.60 (1H, dd, J=1.6, 0.6 Hz), 7.36 (1H, dt, J=10.7, 9.1 Hz), 7.24-7.15 (2H, m), 5.97 (1H, dd, J=8.3, 1.9 Hz), 4.33 (1H, dd, J=15.2, 7.0 Hz), 4.23 (1H, dd, J=15.1, 7.0 Hz), 2.80 (1H, dt, J=16.0, 9.3 Hz), 2.72-2.52 (2H, m), 2.37 (3H, s), 2.20 (3H, s), 2.09 (1H, dd, J=12.9, 8.4 Hz), 1.34-1.19 (1H, m), 0.65-0.47 (4H, m).

Example 136: (S)-3-(2-(1-(3,4-difluorophenyl)-5-oxopyrrolidin-2-yl)-5-(3,5-dimethylisoxazol-4-yl)-1H-benzo[d]imidazol-1-yl)propyl acetate (S)-3-(2-(1-(3,4-difluorophenyl)-5-oxopyrrolidin-2-yl)-5-(3,5-dimethylisoxazol-4-yl)-1H-benzo[d]imidazol-1-yl)propyl acetate

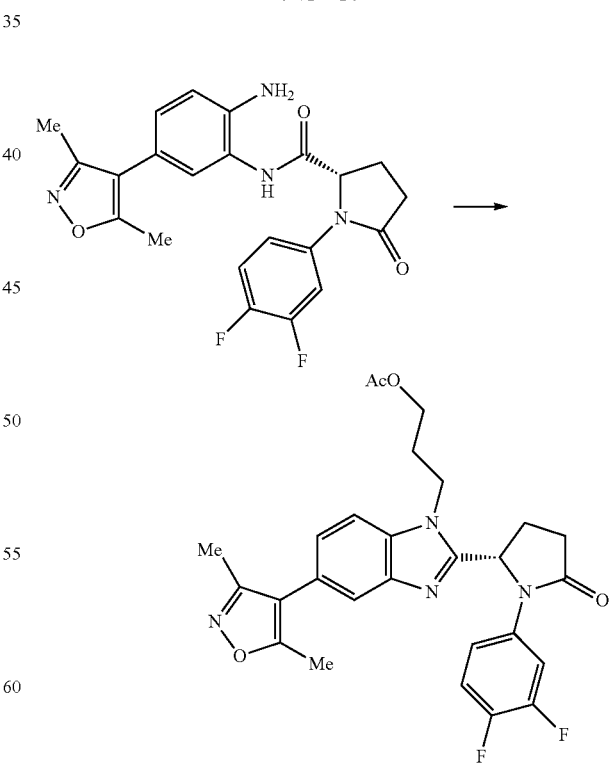

To a mixture of (S)—N-(2-amino-5-(3,5-dimethylisoxazol-4-yl)phenyl)-3-(2-(1-(3,4-difluorophenyl)-5-oxopyrrolidine-2-carboxyl)-5-(3,5-di (40 mg, 0.094 mmol) and DCM (1 mL, 15.54 mmol) were added 3-((tert-butyldimethylsilyl)oxy)propanal (0.026 ml, 0.122 mmol) and acetic acid (0.5 mL, 8.73 mmol). The mixture was stirred at room temperature for 20 minutes then pyridine borane (0.020 ml, 0.188 mmol) was added. The mixture was stirred at room temperature for 1 hour then a few drops of concentrated HCl were added and stirring continued at RT for 5 min. Then acetic acid (1 mL, 17.47 mmol) was added and the mixture was stirred at 80° C. for 18 h. The mixture was concentrated under reduced pressure. The crude product was purified by preparative HPLC (Waters, Acidic (0.1% Formic acid), Waters X-Select Prep-C18, 5 μm, 19×50 mm column, 35-65% MeCN in Water) to afford ((S)-3-(2-(1-(3,4-difluorophenyl)-5-oxopyrrolidin-2-yl)-5-(3,5-dimethylisoxazol-4-yl)-1H-benzo[d]imidazol-1-yl)propyl acetate (4 mg, 8%) as a colourless solid; Rt 1.96 min (method 1), m/z 509 (M+H)+ (ES+); 1H NNR (d6-DMSO) δ: 7.69-7.58 (2H, m), 7.57 (1H, dd, J=1.6, 0.7 Hz), 7.28 (1H, dd, J=8.4, 1.6 Hz), 7.21 (1H, dt, J=10.2, 8.8 Hz), 7.12 (1H, dddd, J=9.0, 3.9, 2.6, 1.5 Hz), 5.91 (1H, dd, J=8.4, 3.7 Hz), 4.57-4.42 (2H, m), 4.20-4.06 (2H, m), 2.98 (1H, ddd, J=16.8, 9.5, 7.6 Hz), 2.89-2.78 (1H, m), 2.78-2.67 (1H, m), 2.41 (3H, s), 2.37-2.27 (1H, m), 2.25 (3H, s), 2.22-2.12 (2H, m), 1.90 (3H, s).

Example 137: (S)-5-(1-(3-aminocyclobutyl)-5-(3,5-dimethylisoxazol-4-yl)-1H-benzo[d]imidazol-2-yl)-1-(3,4-difluorophenyl)pyrrolidin-2-one (S)-5-(1-(3-aminocyclobutyl)-5-(3,5-dimethylisoxazol-4-yl)-1H-benzo[d]imidazol-2-yl)-1-(3,4-difluorophenyl)pyrrolidin-2-one

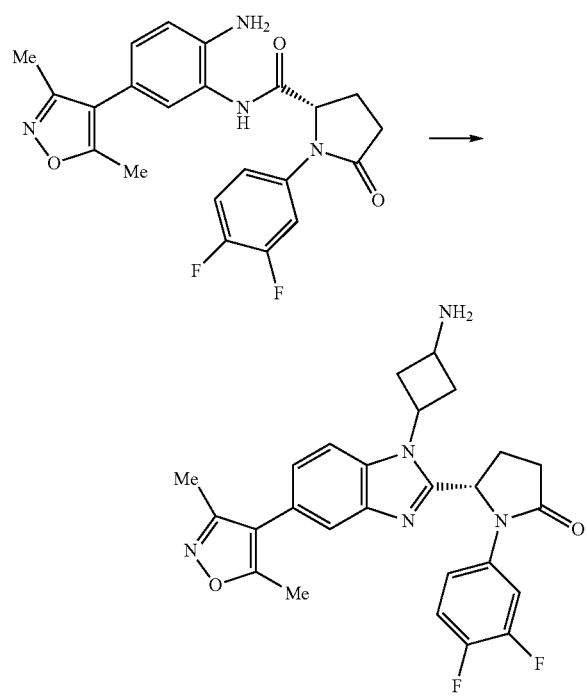

To a mixture of (S)—N-(2-amino-5-(3,5-dimethylisoxazol-4-yl)phenyl)-1-(3,4-difluorophenyl)-5-oxopyrrolidine-2-carboxamide (50 mg, 0.117 mmol) and DCM (1 mL, 15.54 mmol) were added tert-butyl (3-oxocyclobutyl)carbamate (21.72 mg, 0.117 mmol) and acetic acid (0.5 mL, 8.73 mmol). The mixture was stirred at room temperature for 20 min then pyridine borane (0.025 mL, 0.235 mmol) was added. The mixture was stirred at room temperature for 1 h. A few drops of concentrated HCl were added and stirred at RT for 5 min. Then acetic acid (1 mL, 17.47 mmol) was added and the mixture was stirred at 80° C. for 18 h. The mixture was concentrated under reduced pressure and the crude product was purified by chromatography on silica gel (12 g column, 0-5% MeOH/DCM) to afford (S)-5-(1-(3-aminocyclobutyl)-5-(3,5-dimethylisoxazol-4-yl)-1H-benzo[d]imidazol-2-yl)-1-(3,4-difluoro phenyl)pyrrolidin-2-one (29 mg, 50%) as a tan solid; Rt 1.22 min (method 1), m/z 478 (M+H)+ (ES+); 1H NMR (d6-DMSO) δ: two diastereoisomers in a 3:1 ratio, 8.04 (d, J=8.5 Hz, 1H, major), 7.89-7.76 (m, 2H, mixture), 7.59-7.63 (m, 2H, mixture), 7.42-7.34 (m, 2H, mixture), 7.26-7.12 (m, 3H, mixture), 5.99-5.91 (m, 2H, mixture), 4.82-4.69 (m, 1H, major), 4.55-4.43 (m, 1H, minor), 3.31-3.19 (m, 1H, mixture), 2.89-2.76 (m, 2H, mixture), 2.77-2.60 (m, 3H, mixture), 2.59-2.52 (m, 1H, mixture), 2.37 (s, 3H, mixture), 2.33-2.24 (m, 1H, mixture), 2.20 (s, 3H, mixture), 2.11-2.01 (m, 1H, mixture).

Example 138: (S)-1-(3,4-difluorophenyl)-5-(5-(3,5-dimethylisoxazol-4-yl)-1-(thiazol-4-ylmethyl)-1H-benzo[d]imidazol-2-yl)pyrrolidin-2-one

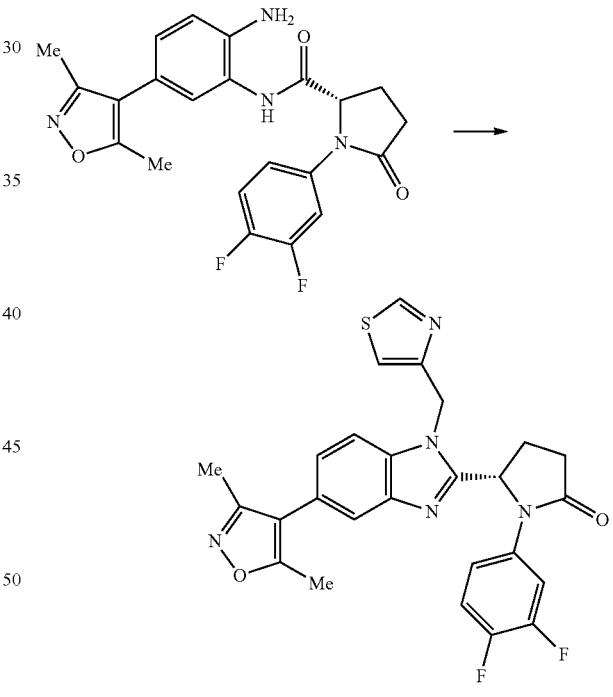

To a solution of (S)—N-(2-amino-5-(3,5-dimethylisoxazol-4-yl)phenyl)-1-(3,4-difluorophenyl)-5-oxopyrrolidine-2-carboxamide (75 mg, 0.176 mmol) in DCM (1.5 mL, 23.31 mmol) were added thiazole-4-carbaldehyde (0.032 mL, 0.229 mmol) and acetic acid (0.75 mL, 13.10 mmol). The mixture was stirred at room temperature for 20 minutes then pyridine borane (0.037 mL, 0.352 mmol) was added. The mixture was stirred at room temperature for 1 hour.

A few drops of concentrated HCl were added and stirring continued at RT for 5 min. Then acetic acid (0.75 mL, 13.10 mmol) was added and the mixture was stirred at 80° C. for 18 h. The mixture was concentrated under reduced pressure.

The crude product was purified by chromatography on silica gel (12 g column, 0-5% MeOH/DCM) to afford (S)-1-(3,4-difluorophenyl)-5-(5-(3,5-dimethylisoxazol-4-yl)-1-(thiazol-4-ylmethyl)-1H-benzo[d]imidazol-2-yl)pyrrolidin-2-one (65 mg, 72%) as a tanned solid; Rt 2.01 min (method 1), m/z 506 (M+H)+ (ES+); 1H NMR (d6-DMSO) δ: 9.14 (d, J=1.9 Hz, 1H), 7.99 (d, J=2.0 Hz, 1H), 7.88 (ddd, J=13.6, 7.4, 2.6 Hz, 1H), 7.79-7.70 (m, 1H), 7.62-7.53 (m, 1H), 7.49-7.39 (m, 1H), 7.34 (dt, J=10.5, 9.2 Hz, 1H), 7.20 (dd, J=8.4, 1.6 Hz, 1H), 6.18-6.10 (m, 1H), 5.80 (d, J=16.1 Hz, 1H), 5.71 (d, J=16.1 Hz, 1H), 2.80-2.57 (m, 3H), 2.35 (s, 3H), 2.18 (s, 3H), 2.15-2.09 (m, 1H).

Example 139: (S)-5-(1-(3-aminocyclobutyl)-5-(3,5-dimethylisoxazol-4-yl)-1H-benzo[d]imidazol-2-yl)-1-(3,4-difluorophenyl)pyrrolidin-2-one (S)-5-(1-(3-aminocyclobutyl)-5-(3,5-dimethylisoxazol-4-yl)-1H-benzo[d]imidazol-2-yl)-1-(3,4-difluorophenyl)pyrrolidin-2-one

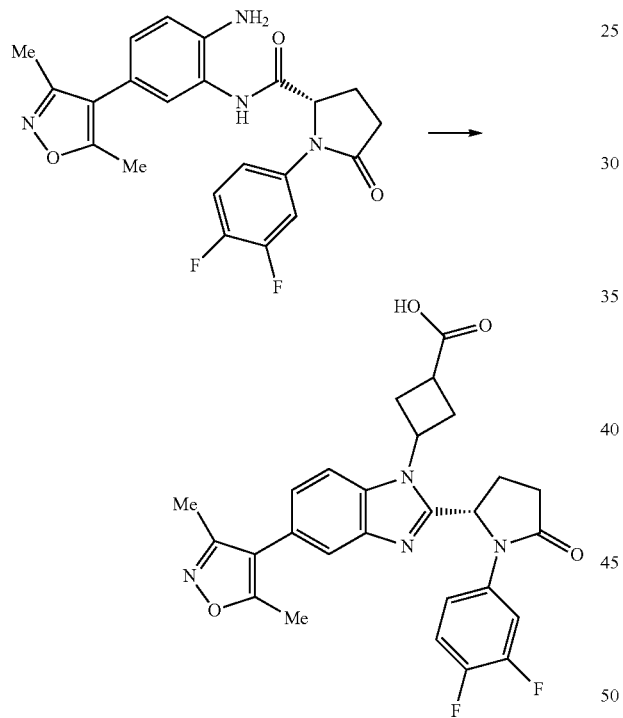

To a mixture of (S)—N-(2-amino-5-(3,5-dimethylisoxazol-4-yl)phenyl)-1-(3,4-difluorophenyl)-5-oxopyrrolidine-2-carboxamide (0.094 ml, 0.176 mmol) and DCM (1.5 mL, 23.31 mmol) were added 3-oxocyclobutanecarboxylic acid (26.1 mg, 0.229 mmol) and acetic acid (0.75 mL, 13.10 mmol). The mixture was stirred at room temperature for 20 minutes then pyridine borane (0.037 mL, 0.352 mmol) was added. The mixture was stirred at room temperature for 1 hour. A few drops of concentrated HCl were added and stirring continued at RT for 5 min. Then acetic acid (0.75 mL, 13.10 mmol) was added and the mixture was stirred at 80° C. for 18 hr. The mixture was concentrated under reduced pressure. The crude product was purified by chromatography on silica gel (12 g column, 0-5% MeOH/DCM) to afford (S)-3-(2-(1-(3,4-difluorophenyl)-5-oxopyrrolidin-2-yl)-5-(3,5-dimethylisoxazol-4-yl)-1H-benzo[d]imidazol-1-yl)cyclobutanecarboxylic acid (40 mg, 43%) as a tanned solid; Rt 1.91 min (method 1), m/z 507 (M+H)+ (ES+); 1H NMR (d6-DMSO) δ: 8.45 (d, J=8.5 Hz, 0.5H), 8.12 (t, J=5.7 Hz, 0.5H), 7.96 (t, J=5.7 Hz, 0.5H), 7.91 (d, J=8.4 Hz, 0.5H), 7.87-7.74 (m, 1H), 7.64-7.60 (m, 1H), 7.47-7.31 (m, 1H), 7.30-7.11 (m, 1H), 6.05 (d, J=7.8 Hz, 0.5H), 5.97 (d, J=7.0 Hz, 0.5H), 5.44-5.32 (m, 0.5H), 5.30-5.20 (m, 0.5H), 3.16-3.07 (m, 5H), 3.06-2.91 (m, 1H), 2.77-2.58 (m, 4H), 2.38 (2×s, 3H), 2.22 (2×s, 3H), 2.12-2.00 (m, 2H), 1.53-1.39 (m, 2H), 0.93-0.84 (m, 3H).

Example 140: (S)-3-(2-(1-(3,4-difluorophenyl)-5-oxopyrrolidin-2-yl)-5-(3,5-dimethylisoxazol-4-yl)-1H-benzo[d]imidazol-1-yl)-N-propylcyclobutanecarboxamide (S)-5-(1-(3-aminocyclobutyl)-5-(3,5-dimethylisoxazol-4-yl)-1H-benzo[d]imidazol-2-yl)-1-(3,4-difluorophenyl)pyrrolidin-2-one

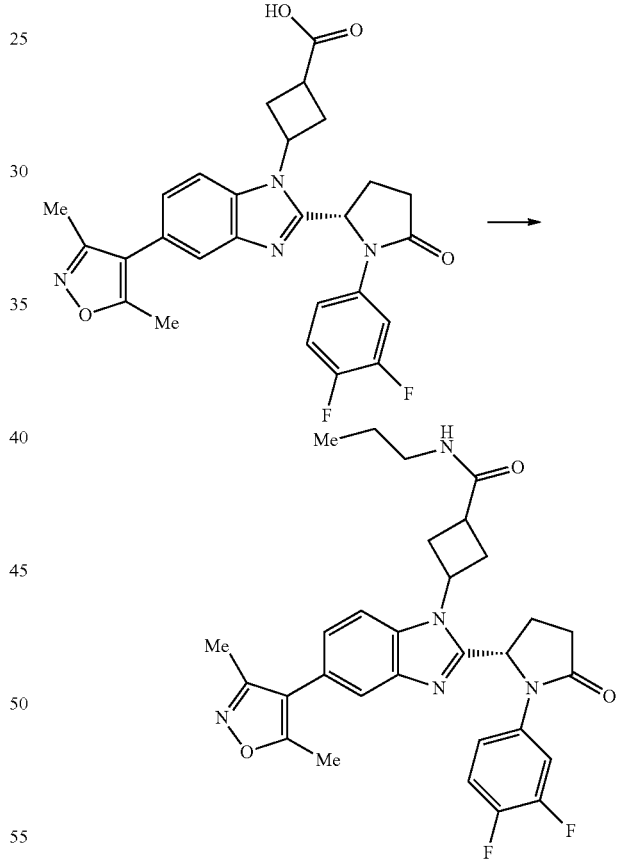

TEA (24.77 µL, 0.178 mmol) was added to a solution of N-propylamine (5.42 µL, 0.065 mmol), (S)-3-(2-(1-(3,4-difluorophenyl)-5-oxopyrrolidin-2-yl)-5-(3,5-dimethylisoxazol-4-yl)-1H-benzo[d]imidazol-1-yl)cyclobutanecarboxylic acid (30 mg, 0.059 mmol) and HATU (24.77 mg, 0.065 mmol) in DCM (3.81 µL, 0.059 mmol) then stirred at rt for 24 h. The residue was diluted with water (10 mL) then extracted with DCM (50 mL). The organic phase was washed with water (10 ml) then passed through a phase sep cartridge and concentrated in vacuo. The residue was purified by chromatography (24 g silica, 0-10% methanol in DCM, gradient elution) to afford a 40:60 mixture of (S)-3-(2-(1-(3,4-difluorophenyl)-5-oxopyrrolidin-2-yl)-5-(3,5-dimethylisoxazol-4-yl)-1H-benzo[d]imidazol-1-yl)-N-propyl-cyclobutanecarboxamide (15 mg, 46%) as a colourless solid; Rt 2.00 min (method 1), m/z 548 (M+H)+ (ES+); 1H NMR (d6-DMSO) δ: 8.45 (d, J=8.5 Hz, 0.5H), 8.12 (t, J=5.7 Hz, 0.5H), 7.96 (t, J=5.7 Hz, 0.5H), 7.91 (d, J=8.4 Hz, 0.5H), 7.87-7.74 (m, 1H), 7.64-7.60 (m, 1H), 7.47-7.31 (m, 1H), 7.30-7.11 (m, 1H), 6.05 (d, J=7.8 Hz, 0.5H), 5.97 (d, J=7.0 Hz, 0.5H), 5.44-5.32 (m, 0.5H), 5.30-5.20 (m, 0.5H), 3.16-3.07 (m, 5H), 3.06-2.91 (m, 1H), 2.77-2.58 (m, 4H), 2.38 (2×s, 3H), 2.22 (2×s, 3H), 2.12-2.00 (m, 2H), 1.53-1.39 (m, 2H), 0.93-0.84 (m, 3H).

General Route D: Non-Convergent Approach Towards Valerolactam Analogues

Example 146: (R)-1-(3,4-dichlorophenyl)-6-(5-(3,5-dimethylisoxazol-4-yl)-1-((R)-1-(methylsulfonyl) pyrrolidin-3-yl)-1H-benzo[d]imidazol-2-yl)piperidin-2-one (R)—N-(5-(3,5-dimethylisoxazol-4-yl)-2-(((R)-1-(methylsulfonyl)pyrrolidin-3-yl)amino)phenyl)-6-oxopiperidine-2-carboxamide

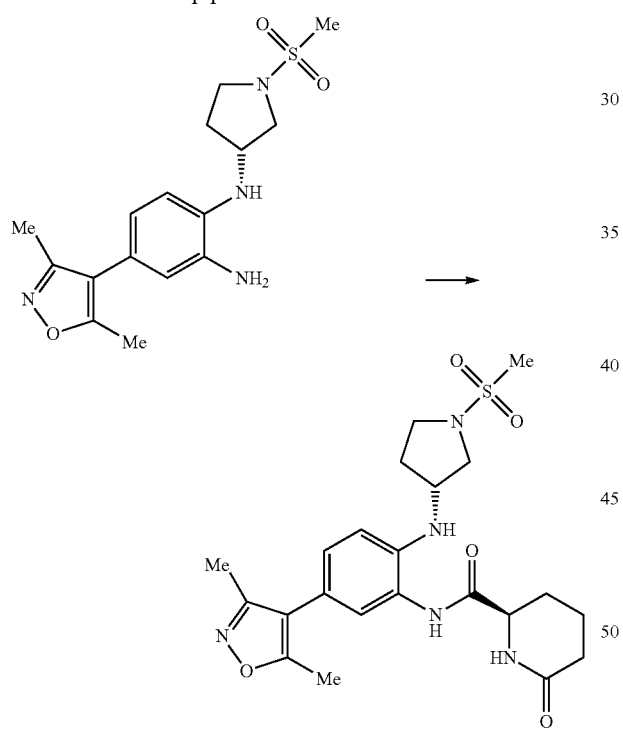

DIPEA (0.623 mL, 3.57 mmol) was added to a solution of (R)-4-(3,5-dimethylisoxazol-4-yl)-N¹-(1-(methylsulfonyl) pyrrolidin-3-yl)benzene-1,2-diamine (0.5 g, 1.427 mmol), HATU (0.705 g, 1.855 mmol) and (R)-6-oxopiperidine-2-carboxylic acid (0.225 g, 1.569 mmol) in DMF (5 mL, 1.427 mmol) and stirred for 20 h. The mixture was evaporated in vacuo and the residue dissolved in EtOAc (20 mL), washed with saturated aqueous NaHCO₃ solution (20 mL), water (20 mL) and brine (10 mL), dried (MgSO4), filtered and evaporated in vacuo. The residual brown gum was purified by chromatography on silica gel (40 g column, 0-10% MeOH in (50% DCM/EtOAc)) to give (R)—N-(5-(3,5-dimethyl-isoxazol-4-yl)-2-(((R)-1-(methylsulfonyl)pyrrolidin-3-yl) amino)phenyl)-6-oxopiperidine-2-carboxamide (0.63 g, 93%) as a white solid; Rt 1.52 min (method 1), m/z 476 (M+H)+ (ES+).

(R)-6-(5-(3,5-dimethylisoxazol-4-yl)-1-((R)-1-(methylsulfonyl)pyrrolidin-3-yl)-1H-benzo[d]imidazol-2-yl)piperidin-2-one

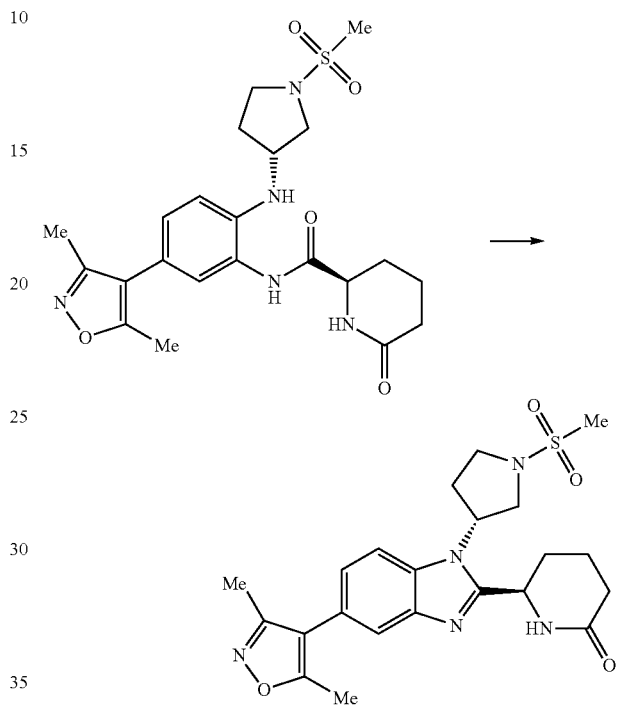

(R)—N-(5-(3,5-dimethylisoxazol-4-yl)-2-(((R)-1-(methylsulfonyl)pyrrolidin-3-yl)amino)phenyl)-6-oxopiperidine-2-carboxamide (0.61 g, 1.283 mmol) was dissolved in TFA (20 mL, 1.283 mmol) and stirred at 70° C. for 3 days. The mixture was evaporated in vacuo and the residual brown gum purified by flash chromatography (40 g column, 0-20% MeOH in (50% DCM/EtOAc)) to give (R)-6-(5-(3,5-dimethylisoxazol-4-yl)-1-((R)-1-(methylsulfonyl)pyrrolidin-3-yl)-1H-benzo[d]imidazol-2-yl)piperidin-2-one (0.53 g, 90%) as a colourless foam; Rt 2.00 min (method 1), m/z 602 (M+H)+ (ES+).

(R)-1-(3,4-dichlorophenyl)-6-(5-(3,5-dimethylisoxazol-4-yl)-1-((R)-1-(methylsulfonyl) pyrrolidin-3-yl)-1H-benzo[d]imidazol-2-yl)piperidin-2-one

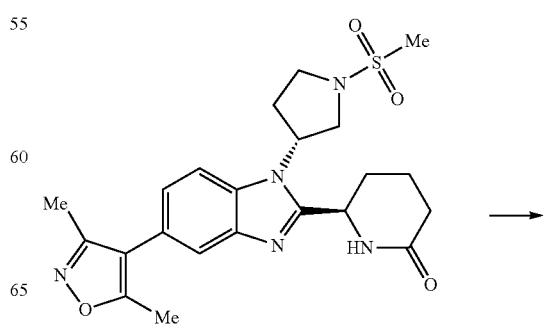

359
-continued

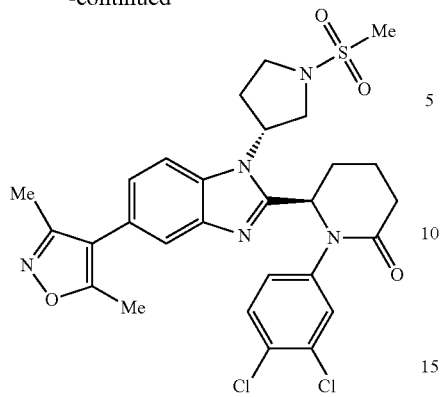

DBU (0.036 mL, 0.240 mmol) was added to a solution of (R)-6-(5-(3,5-dimethylisoxazol-4-yl)-1-((R)-1-(methylsulfonyl)pyrrolidin-3-yl)-1H-benzo[d]imidazol-2-yl)piperidin-2-one (50 mg, 0.109 mmol) in dichloroethane (1 mL, 0.109 mmol) and stirred for 10 min. CuTMEDA (18.78 mg, 0.040 mmol) was added, stirred for a 10 min, (3,4-dichlorophenyl)boronic acid (20.85 mg, 0.109 mmol) added and the reaction stirred for 20 h. The reaction was diluted with EtOAc (20 mL), washed with saturated aqueous NaHCO$_3$ solution (10 mL), water (10 mL) and brine (5 mL), dried (MgSO$_4$), filtered and evaporated in vacuum. The residual gum was purified by flash chromatography (24 g column, 0-20% MeOH in (50% EtOAc/DCM)) to give (R)-1-(3,4-dichlorophenyl)-6-(5-(3,5-dimethylisoxazol-4-yl)-1-((R)-1-(methylsulfonyl) pyrrolidin-3-yl)-1H-benzo[d]imidazol-2-yl)piperidin-2-one (6 mg, 8%) as an off white solid; Rt 2.00 min (method 1), m/z 602 (M+H)+ (ES+); 1H NMR (d6-DMSO) δ: 7.76 (d, J=1.6 Hz, 1H), 7.70 (d, J=8.4 Hz, 1H), 7.60 (d, J=2.4 Hz, 1H), 7.55 (d, J=8.7 Hz, 1H), 7.26 (dd, J=8.4, 1.7 Hz, 1H), 7.21 (dd, J=8.7, 2.4 Hz, 1H), 5.82 (t, J=4.5 Hz, 1H), 5.38 (p, J=8.6 Hz, 1H), 3.70 (ddd, J=9.7, 6.9, 4.4 Hz, 1H), 3.56-3.30 (m, 4H), 3.06 (s, 3H), 2.65-2.52 (m, 2H), 2.46 (d, J=8.2 Hz, 1H), 2.42 (s, 3H), 2.25 (s, 3H), 2.15-2.06 (m, 2H), 1.89 (s, 1H), 1.80 (s, 1H).

(S)-1-(3,4-dichlorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one (S)—N-(5-(3,5-dimethylisoxazol-4-yl)-2-(((R)-1-(methylsulfonyl)pyrrolidin-3-yl)amino)phenyl)-6-oxopiperidine-2-carboxamide

360
-continued

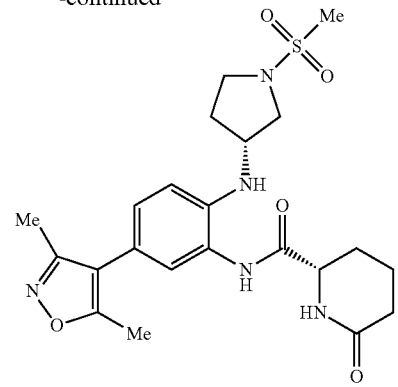

DIPEA (0.623 mL, 3.57 mmol) was added to a solution of (R)-4-(3,5-dimethylisoxazol-4-yl)-N$^1$-(1-(methylsulfonyl)pyrrolidin-3-yl)benzene-1,2-diamine (0.5 g, 1.427 mmol), HATU (0.705 g, 1.855 mmol) and (S)-6-oxopiperidine-2-carboxylic acid (0.225 g, 1.569 mmol) in DMF (5 ml, 1.427 mmol) and stirred for 20 h. The DMF was evaporated in vacuo and the residue dissolved in EtOAc (20 mL), washed with aqNaHCO3 (20 mL), water (20 mL) and brine (10 mL), dried (MgSO4), filtered and evaporated in vacuo. The residual brown gum was purified by flash chromatography (40 g column, 0-10% MeOH in (50% DCM/EtOAc)) to give (S)—N-(5-(3,5-dimethylisoxazol-4-yl)-2-(((R)-1-(methylsulfonyl)pyrrolidin-3-yl)amino)phenyl)-6-oxopiperidine-2-carboxamide (0.62 g, 90%) as a white foam; Rt 1.54 min (method 1), m/z 476 (M+H)+ (ES+).

(S)-6-(5-(3,5-dimethylisoxazol-4-yl)-1-((R)-1-(methylsulfonyl)pyrrolidin-3-yl)-1H-benzo[d]imidazol-2-yl)piperidin-2-one

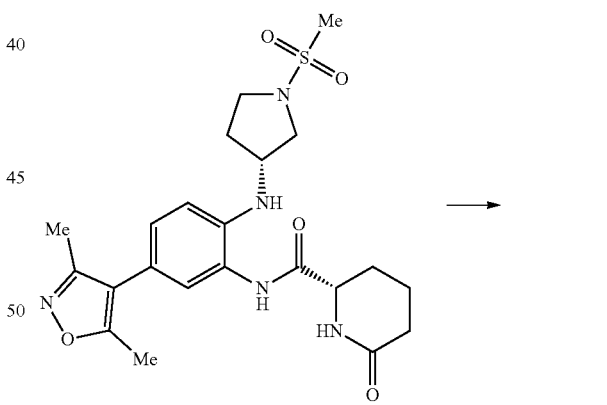

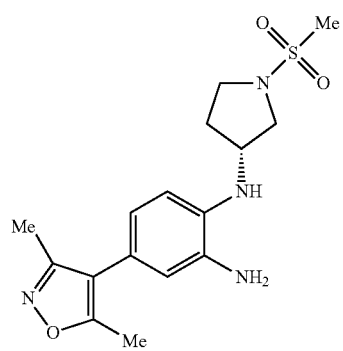

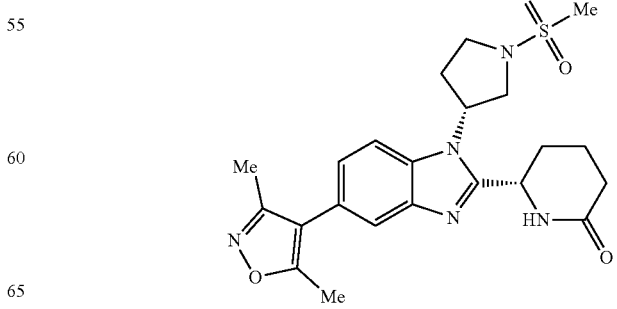

(S)—N-(5-(3,5-dimethylisoxazol-4-yl)-2-(((R)-1-(methylsulfonyl)pyrrolidin-3-yl)amino)phenyl)-6-oxopiperidine-2-carboxamide (0.6 g, 1.262 mmol) was dissolved in TFA (20 mL, 1.262 mmol) and stirred at 70° C. for 3 days. The mixture was concentrated in vacuo and the residual brown gum purified by flash chromatography (40 g column, 0-20% MeOH in (50% DCM/EtOAc)) to give (S)-6-(5-(3,5-dimethylisoxazol-4-yl)-1-((R)-1-(methylsulfonyl)pyrrolidin-3-yl)-1H-benzo[d]imidazol-2-yl)piperidin-2-one (0.53 g, 92%) as a white solid; Rt 1.52 min (method 2), m/z 458 (M+H)+ (ES+).

(S)-1-(3,4-dichlorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one

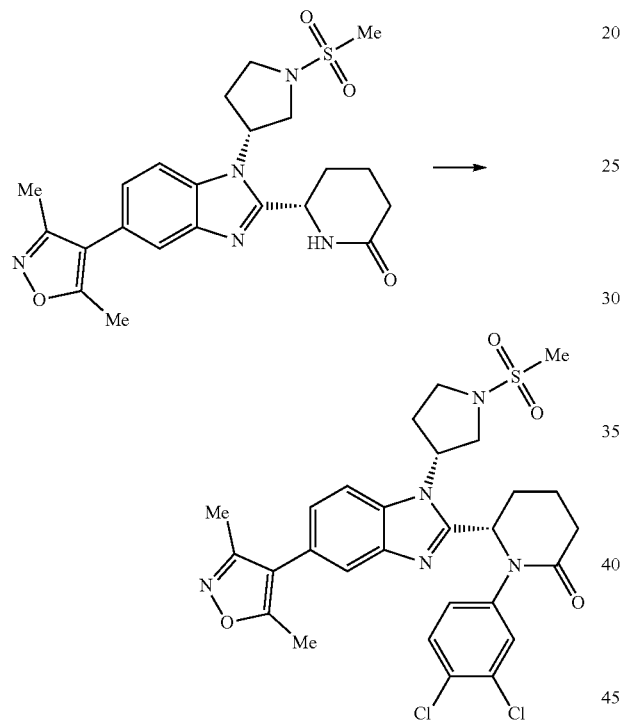

DBU (0.036 mL, 0.240 mmol) was added to a solution of (S)-6-(5-(3,5-dimethylisoxazol-4-yl)-1-((R)-1-(methylsulfonyl)pyrrolidin-3-yl)-1H-benzo[d]imidazol-2-yl)piperidin-2-one (50 mg, 0.109 mmol) in DCM (2 ml, 0.109 mmol), and stirred for 10 min. CuTMEDA (10.15 mg, 0.022 mmol) was added, sonicated and stirred for a 10 min, (3,4-dichlorophenyl)boronic acid (41.7 mg, 0.219 mmol) added and the reaction stirred for 48 h. The reaction was diluted with EtOAc (20 ml), washed with aqNaHCO3 (10 ml), water (10 ml) and brine (5 ml), dried (MgSO4), filtered and evaporated in vacuum. The residual gum was purified by chromatography on silica gel (24 g column, 0-20% MeOH in (50% EtOAc/DCM)) to give (S)-1-(3,4-dichlorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one (18 mg, 27% yield as an off white solid; Rt 2.00 min (method 1), m/z 602 (M+H)+ (ES+); 1H NMR (d6-DMSO) δ: 7.75 (d, J=1.6 Hz, 1H), 7.71 (d, J=8.5 Hz, 1H), 7.61 (d, J=2.4 Hz, 1H), 7.55 (d, J=8.7 Hz, 1H), 7.29-7.19 (m, 2H), 5.83 (t, J=4.7 Hz, 1H), 5.45-5.32 (m, 1H), 3.79 (dd, J=10.6, 8.9 Hz, 1H), 3.70-3.57 (m, 2H), 3.33 (m, 2H), 3.08 (s, 3H), 2.67-2.52 (m, 2H), 2.41 (s, 3H), 2.46-2.27 (m, 1H), 2.25 (s, 3H), 2.20-2.03 (m, 2H), 1.91 (d, J=7.6 Hz, 1H), 1.79 (d, J=9.5 Hz, 1H).

Example 148: (S)-1-(4-chloro-3-fluorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one (S)-1-(4-chloro-3-fluorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one

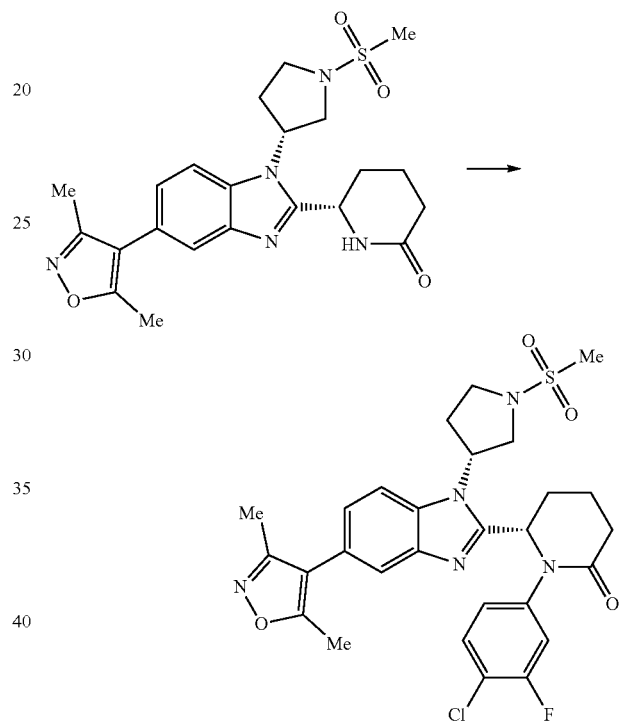

DBU (0.054 mL, 0.361 mmol) was added to a solution of (S)-6-(5-(3,5-dimethylisoxazol-4-yl)-1-((R)-1-(methylsulfonyl)pyrrolidin-3-yl)-1H-benzo[d]imidazol-2-yl)piperidin-2-one (75 mg, 0.164 mmol) in DCM (2 mL, 0.164 mmol), and stirred for 10 min. CuTMEDA (15.23 mg, 0.033 mmol) was added, sonicated and stirred for a 10 min. (4-Chloro-3-fluorophenyl)boronic acid (57.2 mg, 0.328 mmol) was added and the reaction stirred at RT for 18 h. DBU (20 μl), CuTMEDA (10 mg) and boronic acid (20 mg) were added and the reaction stirred at rt for a further 7 hr. The mixture was concentrated under reduced pressure then the crude product was purified by chromatography on silica gel (24 g column, 0-10% MeOH/DCM) to afford (S)-1-(4-chloro-3-fluorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one (40 mg, 41%) as a light pink solid; Rt 1.95 min (method 1), m/z 586 (M+H)+ (ES+); 1H NMR (d6-DMSO) δ: 7.75-7.72 (1H, m), 7.70 (1H, d, J=8.5 Hz), 7.50 (1H, t, J=8.6 Hz), 7.37 (1H, dd, J=10.9, 2.3 Hz), 7.25 (1H, dd, J=8.5, 1.7 Hz), 7.11 (1H, ddd, J=8.6, 2.3, 1.0 Hz), 5.81 (1H, t, J=4.6 Hz), 5.45-5.30 (1H, m), 3.79 (1H, dd, J=10.6, 8.9 Hz), 3.68-3.57 (2H, m), 3.32-3.25 (1H, m), 3.07

(3H, s), 2.65-2.51 (2H, m), 2.40 (3H, s), 2.39-2.26 (2H, m), 2.24 (3H, s), 2.19-2.09 (2H, m), 1.98-1.85 (1H, m), 1.83-1.72 (1H, m); Chiral HPLC (Diacel Chiralpak IA, 5 μm, 4.6×250 mm, 30 min method, 1.0 mL/min, isocratic 30% EtOH in isohexane (0.2% TFA): RT=8.96 min, >99% de @254 nm.

Example 149: (S)-1-(3,4-difluorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one (S)-1-(3,4-difluorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one

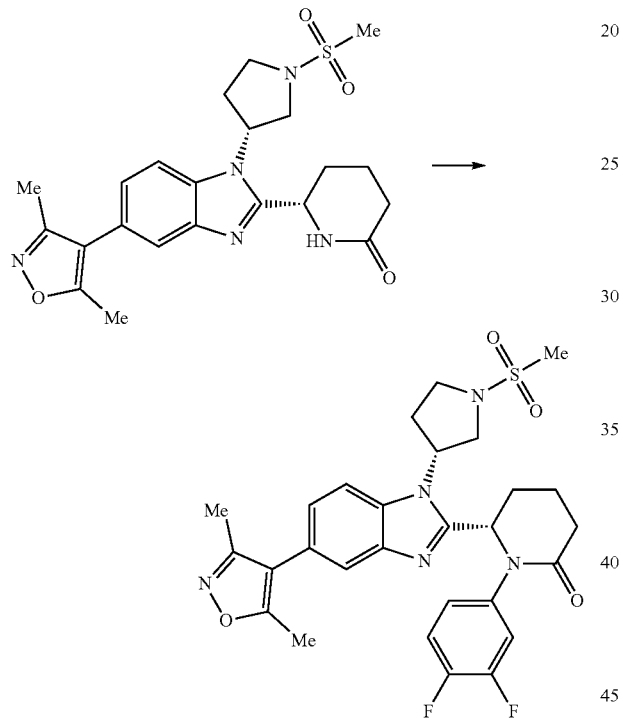

DBU (0.054 mL, 0.361 mmol) was added to a solution of (S)-6-(5-(3,5-dimethylisoxazol-4-yl)-1-((R)-1-(methylsulfonyl)pyrrolidin-3-yl)-1H-benzo[d]imidazol-2-yl)piperidin-2-one (75 mg, 0.164 mmol) in DCM (2 mL, 0.164 mmol), and stirred for 10 min. CuTMEDA (15.23 mg, 0.033 mmol) was added, sonicated and stirred for a 10 min. (3,4-Difluorophenyl)boronic acid (51.8 mg, 0.328 mmol) was added and the reaction stirred at RT for 18 hr. The mixture was concentrated under reduced pressure then the crude product was purified by chromatography on silica gel (24 g column, 0-10% MeOH/DCM) to afford (S)-1-(3,4-difluorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one (39 mg, 40%) as a tan solid; Rt 1.86 min (method 1), m/z 570 (M+H)+ (ES+); 1H NMR (d6-DMSO) δ: 7.75 (1H, d, J=1.6 Hz), 7.69 (1H, d, J=8.4 Hz), 7.42-7.29 (2H, m), 7.25 (1H, dd, J=8.5, 1.7 Hz), 7.11-7.02 (1H, m), 5.76 (1H, t, J=4.7 Hz), 5.40-5.29 (1H, m), 3.81-3.73 (1H, m), 3.65-3.57 (2H, m), 3.31-3.25 (1H, m), 3.06 (3H, s), 2.63-2.52 (2H, m), 2.41 (3H, s), 2.38-2.35 (1H, m), 2.35-2.26 (1H, m), 2.24 (3H, s), 2.16-2.08 (2H, m), 2.02-1.87 (1H, m), 1.84-1.72 (1H, m); Chiral HPLC (Diacel Chiralpak IA, 5 μm, 4.6×250 mm, 30 min method, 1.0 mL/min, isocratic 30% EtOH in isohexane (0.2% TFA): RT=7.86 min, >99% de @ 254 nm.

Example 150: (S)-1-(3-chloro-4-methoxyphenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one (S)-1-(3-chloro-4-methoxyphenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one

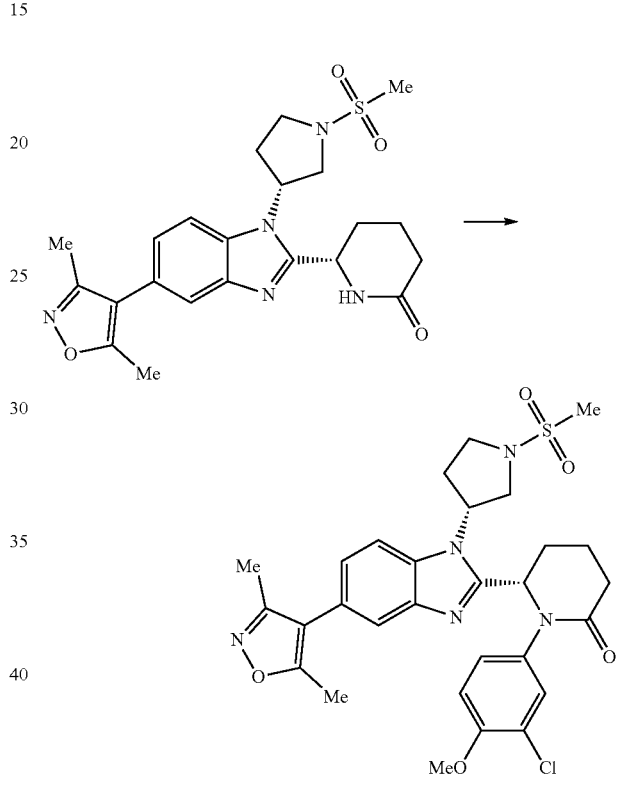

DBU (0.054 mL, 0.361 mmol) was added to a solution of (S)-6-(5-(3,5-dimethylisoxazol-4-yl)-1-((R)-1-(methylsulfonyl)pyrrolidin-3-yl)-1H-benzo[d]imidazol-2-yl)piperidin-2-one (75 mg, 0.164 mmol) in DCM (2 mL, 0.164 mmol), and stirred for 10 min. CuTMEDA (15.23 mg, 0.033 mmol) was added, sonicated and stirred for a 10 min. (3-Chloro-4-methoxyphenyl)boronic acid (61.1 mg, 0.328 mmol) was added and the reaction stirred at RT for 18 h. The mixture was concentrated under reduced pressure then the crude product was purified by chromatography on silica gel (24 g column, 0-10% MeOH/DCM) to afford (S)-1-(3-chloro-4-methoxyphenyl)-6-(5-(3,5-dimethylisoxazol-4-yl)-1-((R)-1-(methylsulfonyl) pyrrolidin-3-yl)-1H-benzo[d]imidazol-2-yl)piperidin-2-one (23 mg, 22%) as a pink solid; Rt 1.83 min (method 1), m/z 598 (M+H)+ (ES+); 1H NMR (d6-DMSO) δ: 7.75 (1H, d, J=1.6 Hz), 7.68 (1H, d, J=8.4 Hz), 7.36 (1H, d, J=2.4 Hz), 7.24 (1H, dd, J=8.5, 1.7 Hz), 7.12 (1H, dd, J=8.8, 2.5 Hz), 7.01 (1H, d, J=8.9 Hz), 5.73 (1H, t, J=4.8 Hz), 5.42-5.31 (1H, m), 3.81-3.72 (4H, m), 3.66-3.54 (2H, m), 3.31-3.22 (1H, m), 3.06 (3H, s), 2.61-2.52 (1H, m), 2.41 (3H, s), 2.39-2.29 (1H, m), 2.24 (3H, s), 2.17-2.08 (2H, m), 2.06-1.89 (3H, m), 1.84-1.72 (1H, m); Chiral HPLC (Diacel Chiralpak IA, 5 µm, 4.6×250 mm, 30 min method, 1.0 mL/min, isocratic 30% EtOH in isohexane (0.2% TFA): RT=11.53 min, >99% de @ 254 nm.

Example 151: (S)-1-(3-fluoro-4-methoxyphenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one (S)-1-(3-fluoro-4-methoxyphenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one

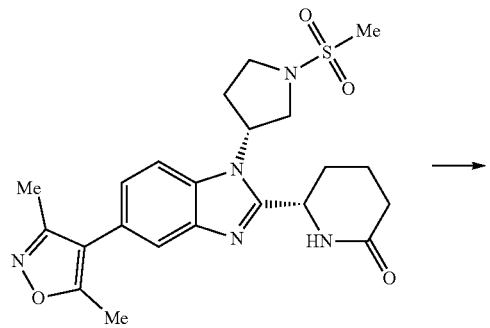

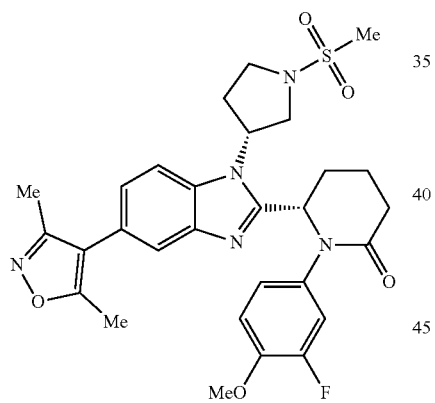

DBU (0.054 mL, 0.361 mmol) was added to a solution of (S)-6-(5-(3,5-dimethylisoxazol-4-yl)-1-((R)-1-(methylsulfonyl)pyrrolidin-3-yl)-1H-benzo[d]imidazol-2-yl)piperidin-2-one (75 mg, 0.164 mmol) in DCM (2 mL, 0.164 mmol), and stirred for 10 min. CuTMEDA (15.23 mg, 0.033 mmol) was added, sonicated and stirred for a 10 min. (3-Fluoro-4-methoxyphenyl)boronic acid (55.7 mg, 0.328 mmol) was added and the reaction stirred at RT for 18 h. The mixture was concentrated under reduced pressure then the crude product was purified by chromatography on silica gel (24 g column, 0-10% MeOH/DCM) to afford (S)-1-(3-fluoro-4-methoxyphenyl)-6-(5-(3,5-dimethylisoxazol-4-yl)-1-((R)-1-(methylsulfonyl) pyrrolidin-3-yl)-1H-benzo[d]imidazol-2-yl)piperidin-2-one (26 mg, 27%) as a tan solid; Rt 1.77 min (method 1), m/z 582 (M+H)+ (ES+); 1H NMR (d6-DMSO) δ: 7.75 (1H, d, J=1.7 Hz), 7.68 (1H, d, J=8.6 Hz), 7.24 (1H, dd, J=8.5, 1.7 Hz), 7.12 (1H, dd, J=12.7, 2.4 Hz), 7.08-7.00 (1H, m), 6.99-6.91 (1H, m), 5.70 (1H, d, J=5.0 Hz), 5.42-5.30 (1H, m), 3.80-3.70 (4H, m), 3.66-3.53 (2H, m), 3.30-3.24 (1H, m), 3.06 (3H, s), 2.63-2.53 (1H, m), 2.41 (3H, s), 2.39-2.32 (2H, m), 2.24 (3H, s), 2.16-2.08 (1H, m), 2.01 (3H, s), 1.84-1.70 (1H, m); Chiral HPLC (Diacel Chiralpak IA, 5 µm, 4.6×250 mm, 30 min method, 1.0 mL/min, isocratic 30% EtOH in isohexane (0.2% TFA): 156251D, RT=11.82 min, >99% de @ 254 nm.

Example 152: (S)-6-(5-(3,5-dimethylisoxazol-4-yl)-1-((1r,4S)-4-methoxycyclohexyl)-1H-benzo[d]imidazol-2-yl)-1-(3,4-difluorophenyl)piperidin-2-one (S)—N-(5-(3,5-dimethylisoxazol-4-yl)-2-(((1r,4S)-4-methoxycyclohexyl)amino)phenyl)-6-oxo piperidine-2-carboxamide

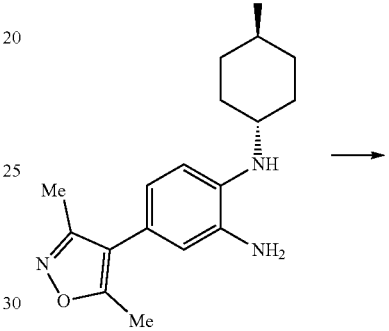

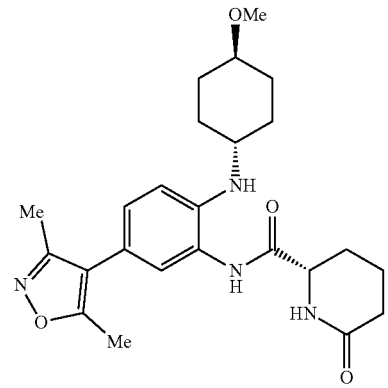

HATU (1061 mg, 2.79 mmol) was added to a solution of (S)-6-oxopiperidine-2-carboxylic acid (399 mg, 2.79 mmol), Intermediate C8 (800 mg, 2.54 mmol) and N,N-diisopropylethylamine (0.532 ml, 3.04 mmol) in DMF (6 ml, 77 mmol) then stirred at room temperature overnight. The mixture was diluted with water (20 mL) then extracted with ethyl acetate (3×50 mL). The combined organic phases were washed with 1M HCl (10 mL), Sat. NaHCO3 (10 mL) and saturated brine (3×10 mL), then dried (MgSO4), filtered and concentrated to give a brown oil. The crude product was purified by chromatography on silica gel (40 g column, 0-10% MeOH/DCM) to afford (S)—N-(5-(3,5-dimethylisoxazol-4-yl)-2-(((1r,4S)-4-methoxycyclohexyl) amino)phenyl)-6-oxopiperidine-2-carboxamide (693 mg, 53%) as a pink solid; Rt 1.64 min (method 1), m/z 441 (M+H)+ (ES+).

367

(S)-6-(5-(3,5-dimethylisoxazol-4-yl)-1-((1r,4S)-4-methoxycyclohexyl)-1H-benzo[d]imidazol-2-yl)piperidin-2-one

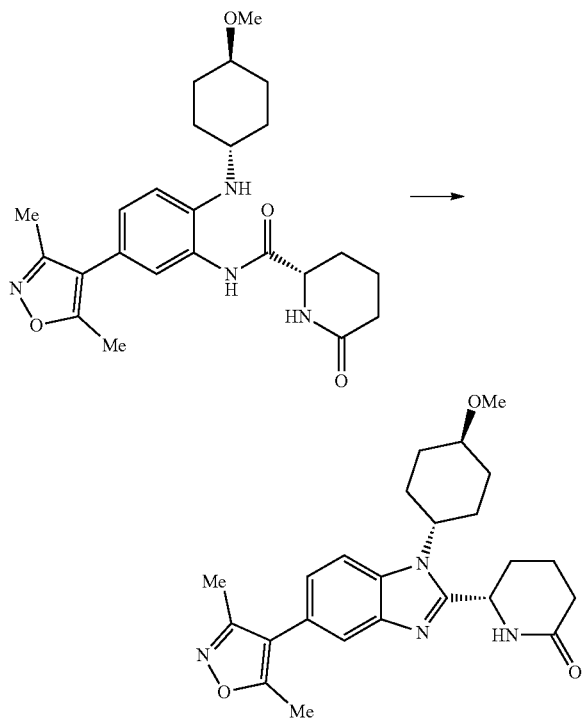

(S)—N-(5-(3,5-dimethylisoxazol-4-yl)-2-(((1r,4S)-4-methoxycyclohexyl)amino)phenyl)-6-oxo piperidine-2-carboxamide (200 mg, 0.454 mmol) was heated to 80° C. in acetic acid (1040 μL, 18.16 mmol) for 24 h. The crude product was loaded onto a column of SCX (2 g) in MeOH. The column was washed with MeOH and then the product was eluted with 7 M ammonia in MeOH. The resultant mixture was concentrated in vacuo to afford (S)-6-(5-(3,5-dimethyl isoxazol-4-yl)-1-((1r,4S)-4-methoxycyclohexyl)-1H-benzo[d]imidazol-2-yl)piperidin-2-one (120 mg, 62%) as a pink solid; Rt 1.71 min (method 1), m/z 423 (M+H)+ (ES+).

(S)-6-(5-(3,5-dimethylisoxazol-4-yl)-1-((1r,4S)-4-methoxycyclohexyl)-1H-benzo[d]imidazol-2-yl)-1-(3,4-difluorophenyl)piperidin-2-one

368

-continued

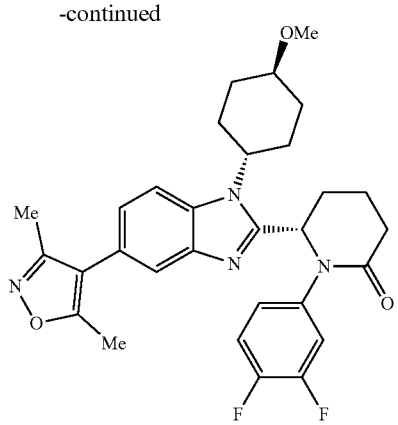

DBU (0.080 mL, 0.531 mmol) was added to a solution of (S)-6-(5-(3,5-dimethylisoxazol-4-yl)-1-((1r,4S)-4-methoxycyclohexyl)-1H-benzo[d]imidazol-2-yl)piperidin-2-one (120 mg, 0.241 mmol) in DCM (2 mL, 0.241 mmol), and stirred at RT for 10 min. CuTMEDA (22.42 mg, 0.048 mmol) was added, sonicated and stirred at RT for a further 10 min. Then (3,4-difluorophenyl)boronic acid (76 mg, 0.483 mmol) was added and the reaction stirred at RT for 18 hr. The mixture was concentrated under reduced pressure then the crude product was purified by chromatography on silica gel (24 g column, 0-10% MeOH/DCM) to afford (S)-6-(5-(3,5-dimethylisoxazol-4-yl)-1-((1r,4S)-4-methoxycyclohexyl)-1H-benzo[d]imidazol-2-yl)-1-(3,4-di-fluorophenyl)piperidin-2-one (37 mg, 28%) as a light pink solid; the enantiomers were separated by chiral preparative HPLC (General method E); Rt 2.07 min; m/z 535 (M+H)+ (ES+); 1H NMR (d6-DMSO) δ: 7.78 (1H, d, J=8.5 Hz), 7.69 (1H, d, J=1.6 Hz), 7.42-7.28 (2H, m), 7.14 (1H, dd, J=8.5, 1.7 Hz), 7.08-7.01 (1H, m), 5.77 (1H, t, J=4.6 Hz), 4.45-4.29 (1H, m), 3.45-3.34 (1H, m), 3.28 (3H, s), 2.63-2.52 (2H, m), 2.40 (3H, s), 2.37-2.28 (2H, m), 2.23 (3H, s), 2.21-2.11 (2H, m), 2.07 (3H, s), 1.87-1.71 (2H, m), 1.46-1.29 (2H, m), 1.29-1.17 (1H, m).

Example 153: (S)-1-(4-chloro-3-fluorophenyl)-6-(5-(3,5-dimethylisoxazol-4-yl)-1-((1r,4S)-4-methoxycyclohexyl)-1H-benzo[d]imidazol-2-yl)piperidin-2-one (S)-1-(4-chloro-3-fluorophenyl)-6-(5-(3,5-dimethylisoxazol-4-yl)-1-((1r,4S)-4-methoxy cyclohexyl)-1H-benzo[d]imidazol-2-yl)piperidin-2-one

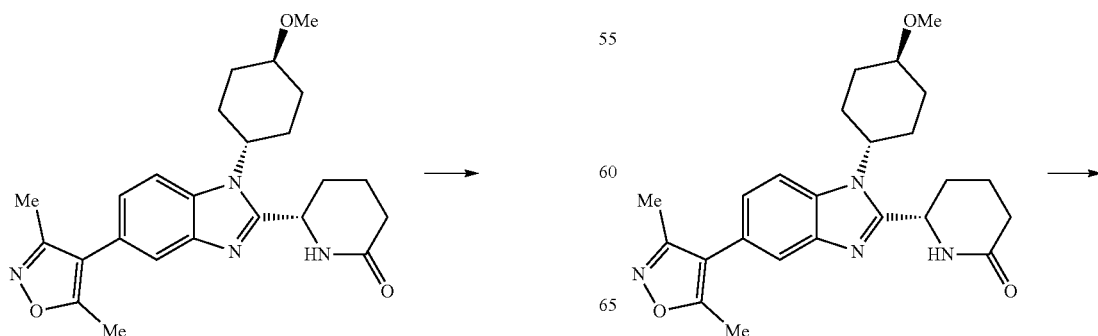

369 | 370
-continued | -continued

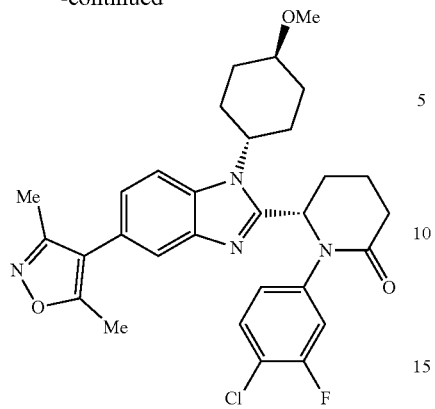 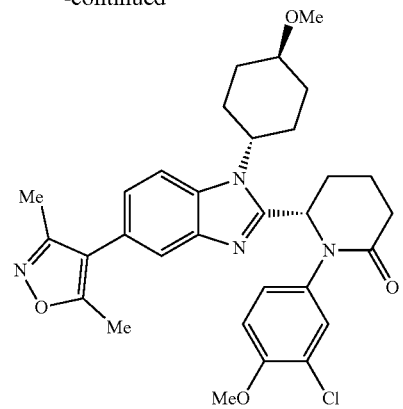

DBU (0.039 ml, 0.260 mmol) was added to a solution of (S)-6-(5-(3,5-dimethylisoxazol-4-yl)-1-((1r,4S)-4-methoxycyclohexyl)-1H-benzo[d]imidazol-2-yl)piperidin-2-one (50 mg, 0.118 mmol) in DCM (0.2 mL, 0.118 mmol) and MeCN (2 mL, 38.3 mmol), and stirred for 10 min. CuTMEDA (10.99 mg, 0.024 mmol) was added, sonicated and stirred for a 10 min, (4-chloro-3-fluorophenyl)boronic acid (41.3 mg, 0.237 mmol) added and the reaction stirred at 35° C. for 24 h. The mixture was concentrated under reduced pressure then the crude product was purified by chromatography on silica gel (24 g column, 0-10% MeOH/DCM) to afford (S)-1-(4-chloro-3-fluorophenyl)-6-(5-(3,5-dimethylisoxazol-4-yl)-1-((1r,4S)-4-methoxycyclohexyl)-1H-benzo[d]imidazol-2-yl)piperidin-2-one (23 mg, 34%) as a light pink solid; Rt 2.17 min; m/z 551 (M+H)+ (ES+); 1H NMR (d6-DMSO) δ: 7.79 (d, J=8.5 Hz, 1H), 7.69 (d, J=1.7 Hz, 1H), 7.50 (t, J=8.6 Hz, 1H), 7.38 (dd, J=10.9, 2.3 Hz, 1H), 7.15 (dd, J=8.5, 1.7 Hz, 1H), 7.09 (ddd, J=8.7, 2.3, 1.0 Hz, 1H), 5.85-5.79 (m, 1H), 4.45-4.33 (m, 1H), 3.46-3.36 (m, 1H), 3.29 (s, 3H), 2.65-2.54 (m, 2H), 2.41 (s, 3H), 2.39-2.27 (m, 2H), 2.24 (s, 3H), 2.20-2.10 (m, 2H), 2.10-1.91 (m, 3H), 1.88-1.73 (m, 2H), 1.46-1.32 (m, 2H), 1.32-1.22 (m, 1H). Chiral HPLC (Diacel Chiralpak IA, 5 μm, 4.6×250 mm, 30 min method, 1.0 mL/min, isocratic 30% EtOH in isohexane (0.2% TFA): RT=5.69 min, >99% de @ 254 nm.

DBU (0.039 mL, 0.260 mmol) was added to a solution of (S)-6-(5-(3,5-dimethylisoxazol-4-yl)-1-((1r,4S)-4-methoxycyclohexyl)-1H-benzo[d]imidazol-2-yl)piperidin-2-one (50 mg, 0.118 mmol) in DCM (0.2 mL, 0.118 mmol) and MeCN (2 mL, 38.3 mmol), and stirred for 10 min. CuTMEDA (10.99 mg, 0.024 mmol) was added, sonicated and stirred for a 10 min, (3-chloro-4-methoxyphenyl)boronic acid (44.1 mg, 0.237 mmol) added and the reaction stirred at 35° C. for 24 hr. The mixture was concentrated under reduced pressure then the crude product was purified by chromatography on silica gel (24 g column, 0-10% MeOH/DCM) to afford (S)-1-(3-chloro-4-methoxyphenyl)-6-(5-(3,5-dimethylisoxazol-4-yl)-1-((1r,4S)-4-methoxycyclohexyl)-1H-benzo[d]imidazol-2-yl)piperidin-2-one (20 mg, 29%) as a pink solid; Rt 2.02 min; m/z 563 (M+H)+ (ES+); 1H NMR (d6-DMSO) δ: 7.76 (d, J=8.5 Hz, 1H), 7.70 (d, J=1.6 Hz, 1H), 7.38 (d, J=2.4 Hz, 1H), 7.13 (dd, J=8.5, 1.7 Hz, 1H), 7.09 (dd, J=8.8, 2.5 Hz, 1H), 7.00 (d, J=9.0 Hz, 1H), 5.79-5.70 (m, 1H), 4.45-4.31 (m, 1H), 3.76 (s, 3H), 3.45-3.35 (m, 1H), 3.28 (s, 3H), 2.64-2.53 (m, 1H), 2.41 (s, 3H), 2.38-2.27 (m, 2H), 2.24 (s, 3H), 2.18-1.97 (m, 6H), 1.87-1.74 (m, 2H), 1.49-1.28 (m, 2H), 1.18-1.09 (m, 1H); Chiral HPLC (Diacel Chiralpak IA, 5 μm, 4.6×250 mm, 30 min method, 1.0 mL/min, isocratic 30% EtOH in isohexane (0.2% TFA): RT=7.00 min, >99% de @ 254 nm.

Example 154: (S)-1-(3-chloro-4-methoxyphenyl)-6-(5-(3,5-dimethylisoxazol-4-yl)-1-((1r,4S)-4-methoxycyclohexyl)-1H-benzo[d]imidazol-2-yl)piperidin-2-one (S)-1-(3-chloro-4-methoxyphenyl)-6-(5-(3,5-dimethylisoxazol-4-yl)-1-((1r,4S)-4-methoxycyclohexyl)-1H-benzo[d]imidazol-2-yl)piperidin-2-one Example 155: (S)-6-(5-(3,5-dimethylisoxazol-4-yl)-1-((1r,4S)-4-methoxycyclohexyl)-1H-benzo[d]imidazol-2-yl)-1-(3-fluoro-4-methoxyphenyl)piperidin-2-one (S)-6-(5-(3,5-dimethylisoxazol-4-yl)-1-((1r,4S)-4-methoxycyclohexyl)-1H-benzo[d]imidazol-2-yl)-1-(3-fluoro-4-methoxyphenyl)piperidin-2-one

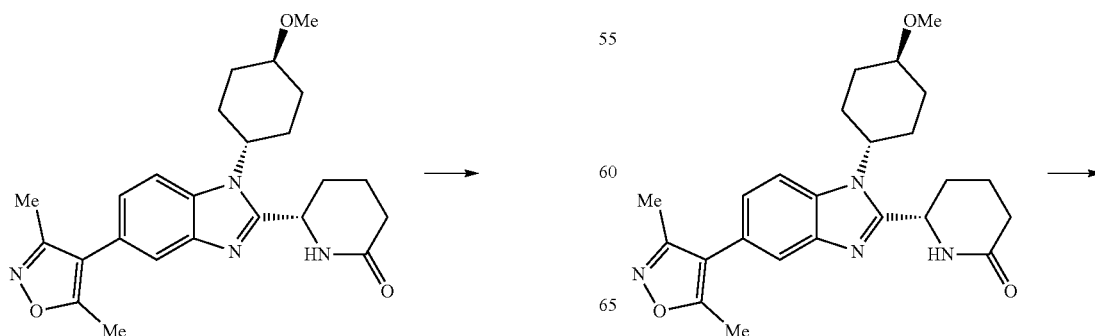

-continued

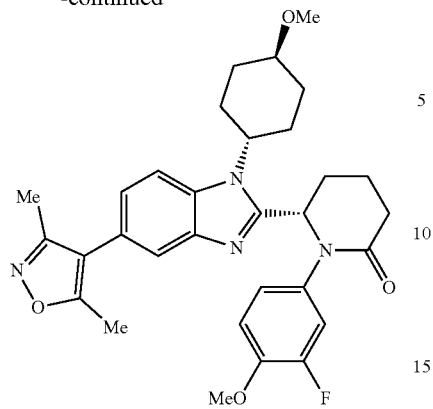

DBU (0.039 mL, 0.260 mmol) was added to a solution of (S)-6-(5-(3,5-dimethylisoxazol-4-yl)-1-((1r,4S)-4-methoxycyclohexyl)-1H-benzo[d]imidazol-2-yl)piperidin-2-one (50 mg, 0.118 mmol) in DCM (0.2 mL, 0.118 mmol) and MeCN (2 mL, 38.3 mmol), and stirred for 10 min. CuTMEDA (10.99 mg, 0.024 mmol) was added, sonicated and stirred for a 10 min, (3-fluoro-4-methoxyphenyl)boronic acid (40.2 mg, 0.237 mmol) added and the reaction stirred at 35° C. for 24 hr. The mixture was concentrated under reduced pressure then the crude product was purified by chromatography on silica gel (24 g column, 0-10% MeOH/DCM) to afford (S)-6-(5-(3,5-dimethylisoxazol-4-yl)-1-((1r,4S)-4-methoxycyclohexyl)-1H-benzo[d]imidazol-2-yl)-1-(3-fluoro-4-methoxyphenyl)piperidin-2-one (25 mg, 37%) as a tan solid; Rt 1.94 min; m/z 547 (M+H)+ (ES+); 1H NMR (d6-DMSO) δ: 7.76 (1H, d, J=8.5 Hz), 7.69 (1H, d, J=1.6 Hz), 7.16-7.07 (2H, m), 7.07-6.98 (1H, m), 6.98-6.92 (1H, m), 5.75-5.68 (1H, m), 4.42-4.28 (1H, m), 3.74 (3H, s), 3.46-3.36 (1H, m), 3.28 (3H, s), 2.64-2.52 (2H, m), 2.40 (3H, s), 2.37-2.27 (2H, m), 2.24 (3H, s), 2.20-1.95 (5H, m), 1.77 (2H, d, J=11.6 Hz), 1.49-1.26 (2H, m), 1.20-1.07 (1H, m); Chiral HPLC (Diacel Chiralpak IA, 5 μm, 4.6×250 mm, 30 min method, 1.0 mL/min, isocratic 30% EtOH in isohexane (0.2% TFA): RT=7.58 min, >99% de @ 254 nm.

Example 156: (S)-1-(3,4-difluorophenyl)-6-(5-(3,5-dimethylisoxazol-4-yl)-1-((1s,4R)-4-hydroxy-4-methylcyclohexyl)-1H-benzo[d]imidazol-2-yl)piperidin-2-one (S)—N-(5-(3,5-dimethylisoxazol-4-yl)-2-(((1s,4R)-4-hydroxy-4-methylcyclohexyl) amino)phenyl)-6-oxopiperidine-2-carboxamide -continued

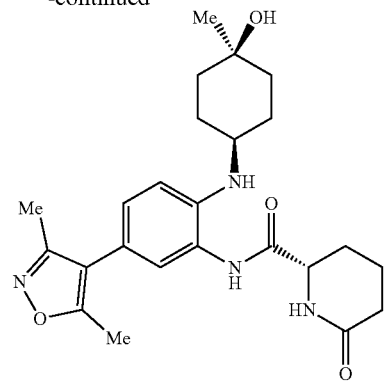

HATU (900 mg, 2.367 mmol) was added to a stirred solution of TEA (0.35 mL, 2.51 mmol), (S)-6-oxopiperidine-2-carboxylic acid (350 mg, 2.445 mmol) and Intermediate C24 (710 mg, 2.206 mmol) in N,N-dimethylformamide (10 mL) then the mixture was stirred at room temperature for 2 h. The mixture was diluted with brine (100 mL) then extracted with ethyl acetate (3×100 mL). The combined organic phases were concentrated under reduced pressure. The crude product was purified by chromatography on the Companion (40 g column, 50-100% THF/DCM) then triturated in diethyl ether to afford (S)—N-(5-(3,5-dimethylisoxazol-4-yl)-2-(((1s,4R)-4-hydroxy-4-methylcyclohexyl) amino)phenyl)-6-oxopiperidine-2-carboxamide (822 mg, 80%) as a white solid; Rt 1.62 min; m/z 441 (M+H)+ (ES+).

(S)-6-(5-(3,5-dimethylisoxazol-4-yl)-1-((1s,4R)-4-hydroxy-4-methylcyclohexyl)-1H-benzo[d]imidazol-2-yl)piperidin-2-one

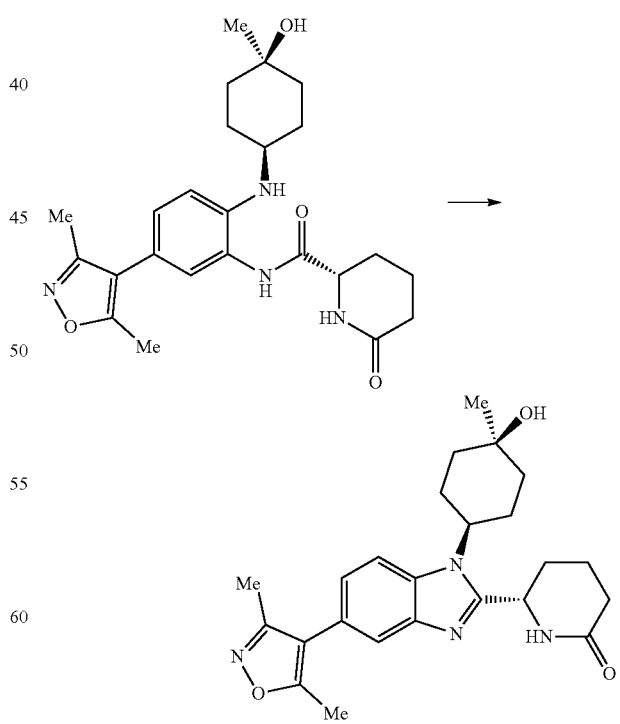

(S)—N-(5-(3,5-dimethylisoxazol-4-yl)-2-(((1s,4R)-4-hydroxy-4-methylcyclohexyl)amino)phenyl)-6-oxopiperidine- 2-carboxamide (800 mg, 1.780 mmol) was heated to 80° C. in acetic acid (20 mL) for 4 h. The acetic acid was removed under reduced pressure then the residue was dissolved in DCM:MeOH:diethylamine (25 mL, 8:1:1) and concentrated onto loose silica gel. The silicate was purified by chromatography on the Companion (40 g column, 15-75% DCM/THF) then triturated in diethyl ether to afford (S)-6-(5-(3,5-dimethylisoxazol-4-yl)-1-((1s,4R)-4-hydroxy-4-methylcyclohexyl)-1H-benzo[d]imidazol-2-yl)piperidin-2-one (480 mg, 61%) as a white solid; Rt 1.26 min; m/z 423 (M+H)+ (ES+); 1H NMR (d6-DMSO) δ: 7.75 (d, J=8.5 Hz, 1H), 7.73 (d, J=2.2 Hz, 1H), 7.65 (d, J=1.5 Hz, 1H), 7.23 (dd, J=8.4, 1.7 Hz, 1H), 5.12-5.00 (m, 1H), 4.50-4.36 (m, 1H), 4.43 (s, 1H), 2.71-2.54 (m, 2H), 2.41 (s, 3H), 2.31-2.24 (m, 2H), 2.24 (s, 3H), 2.17-2.03 (m, 1H), 1.92-1.49 (m, 9H), 1.21 (s, 3H).

(S)-1-(3,4-difluorophenyl)-6-(5-(3,5-dimethylisoxazol-4-yl)-1-((1s,4R)-4-hydroxy-4-methylcyclohexyl)-1H-benzo[d]imidazol-2-yl)piperidin-2-one

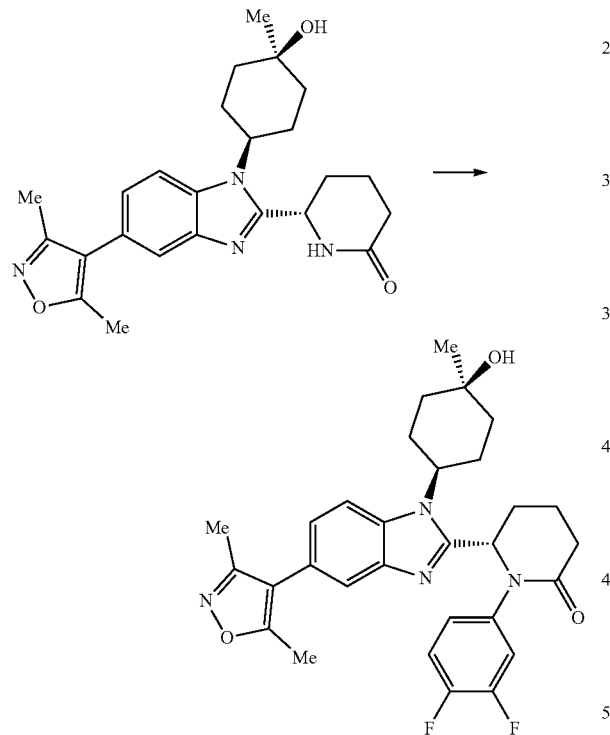

CuTMEDA (10 mg, 0.022 mmol), (S)-6-(5-(3,5-dimethylisoxazol-4-yl)-1-((1s,4R)-4-hydroxy-4-methylcyclohexyl)-1H-benzo[d]imidazol-2-yl)piperidin-2-one (70 mg, 0.166 mmol), (3,4-difluorophenyl)boronic acid (30 mg, 0.190 mmol) and DBU (27 μL, 0.179 mmol) were heated to 70° C. in acetonitrile (2 mL) for 18 h. The mixture was concentrated onto loose silica gel. The silicate was purified by chromatography on the Companion (12 g column, 0-50% THF/DCM) then purified further on the Companion (4 g column, 1-4% MeOH/DCM) to afford (S)-1-(3,4-difluorophenyl)-6-(5-(3,5-dimethylisoxazol-4-yl)-1-((1s,4R)-4-hydroxy-4-methylcyclohexyl)-1H-benzo[d]imidazol-2-yl)piperidin-2-one (35 mg, 37%) as an off-white solid; the enantiomers were separated by chiral preparative HPLC (General method A); Rt 1.82 min; m/z 535 (M+H)+ (ES+); 1H NMR (d6-DMSO) δ: 7.71 (d, J=1.6 Hz, 1H), 7.68 (d, J=8.6 Hz, 1H), 7.41-7.29 (m, 2H), 7.22 (dd, J=8.4, 1.7 Hz, 1H), 7.08-6.99 (m, 1H), 5.75-5.70 (m, 1H), 4.42 (s, 1H), 4.41-4.28 (m, 1H), 2.64-2.52 (m, 2H), 2.48-2.31 (m, 3H), 2.41 (s, 3H), 2.24 (s, 3H), 2.10-1.90 (m, 2H), 1.84-1.43 (m, 6H), 1.18 (s, 3H), 1.07-0.91 (m, 1H).

Example 157: (S)-1-(3-chloro-4-methoxyphenyl)-6-(5-(3,5-dimethylisoxazol-4-yl)-1-((1s,4R)-4-hydroxy-4-methylcyclohexyl)-1H-benzo[d]imidazol-2-yl)piperidin-2-one (S)-1-(3-chloro-4-methoxyphenyl)-6-(5-(3,5-dimethylisoxazol-4-yl)-1-((1s,4R)-4-hydroxy-4-methylcyclohexyl)-1H-benzo[d]imidazol-2-yl)piperidin-2-one

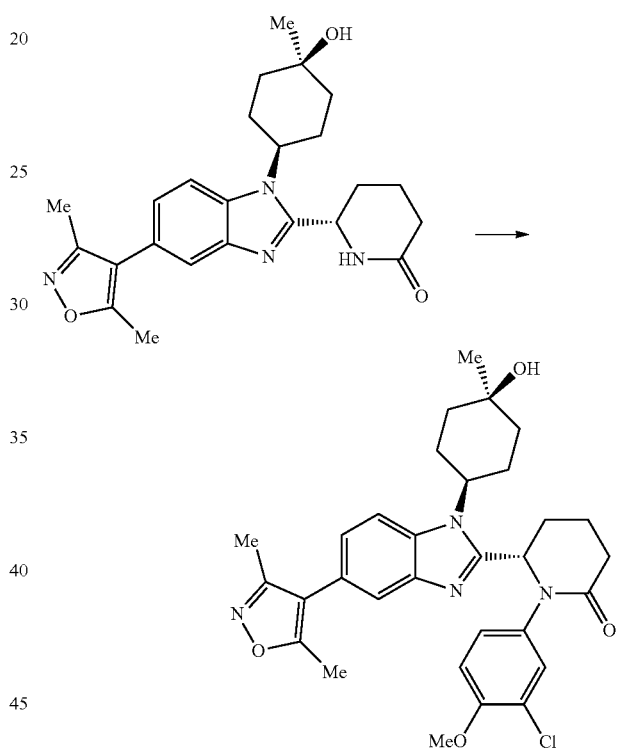

CuTMEDA (10 mg, 0.022 mmol), (S)-6-(5-(3,5-dimethylisoxazol-4-yl)-1-((1s,4R)-4-hydroxy-4-methylcyclohexyl)-1H-benzo[d]imidazol-2-yl)piperidin-2-one (70 mg, 0.166 mmol), (3-chloro-4-methoxyphenyl)boronic acid (35 mg, 0.188 mmol) and DBU (27 μl, 0.179 mmol) were heated to 70° C. in acetonitrile (2 mL) for 18 h. The mixture was concentrated onto loose silica gel. The silicate was purified by chromatography on the Companion (12 g column, 0-50% THF/DCM) then purified further on the Companion (4 g column, 1-4% MeOH/DCM) to afford (S)-1-(3-chloro-4-methoxyphenyl)-6-(5-(3,5-dimethylisoxazol-4-yl)-1-((1s,4R)-4-hydroxy-4-methylcyclohexyl)-1H-benzo[d]imidazol-2-yl)piperidin-2-one (25 mg, 0.042 mmol, 25.5% yield) as an off white solid; Rt 1.79 min; m/z 563 (M+H)+ (ES+); 1H NMR (d6-DMSO) δ: 7.71 (d, J=1.6 Hz, 1H), 7.67 (d, J=8.5 Hz, 1H), 7.37 (d, J=2.4 Hz, 1H), 7.20 (dd, J=8.5, 1.7 Hz, 1H), 7.09 (dd, J=8.8, 2.5 Hz, 1H), 7.00 (d, J=8.9 Hz, 1H), 5.74-5.65 (m, 1H), 4.41 (s, 1H), 4.40-4.27 (m, 1H), 3.75 (s, 3H), 2.62-2.52 (m, 2H), 2.48-2.29 (m, 3H), 2.41 (s, 3H), 2.24 (s, 3H), 2.11-1.93 (m, 2H), 1.84-1.72 (m, 1H), 1.72-1.64 (m, 1H), 1.63-1.44 (m, 4H), 1.18 (s, 3H), 0.97-0.84 (m, 1H).

Example 158: (S)-1-(3,4-dichlorophenyl)-6-(5-(3,5-dimethylisoxazol-4-yl)-1-((1s,4R)-4-hydroxy-4-methylcyclohexyl)-1H-benzo[d]imidazol-2-yl)piperidin-2-one (S)-1-(3,4-dichlorophenyl)-6-(5-(3,5-dimethylisoxazol-4-yl)-1-((1s,4R)-4-hydroxy-4-methylcyclohexyl)-1H-benzo[d]imidazol-2-yl)piperidin-2-one

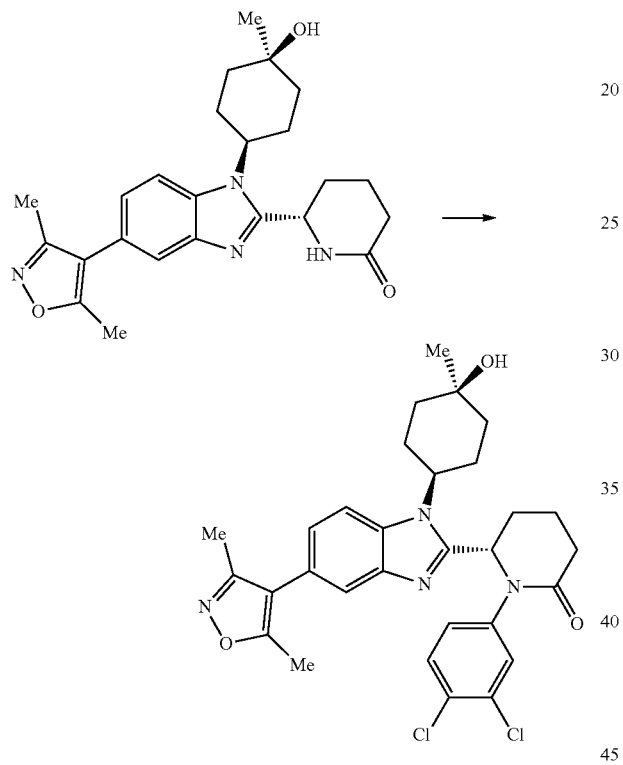

Example 159: (S)-6-(5-(3,5-dimethylisoxazol-4-yl)-1-((1s,4R)-4-hydroxy-4-methylcyclohexyl)-1H-benzo[d]imidazol-2-yl)-1-(3-fluoro-4-methoxyphenyl)piperidin-2-one (S)-6-(5-(3,5-dimethylisoxazol-4-yl)-1-((1s,4R)-4-hydroxy-4-methylcyclohexyl)-1H-benzo[d]imidazol-2-yl)-1-(3-fluoro-4-methoxyphenyl)piperidin-2-one

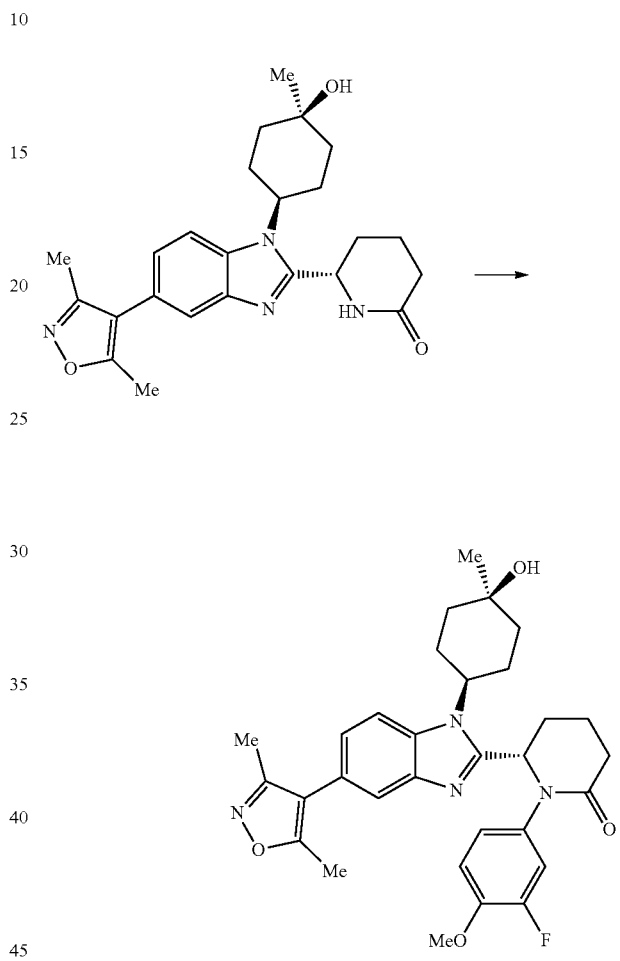

CuTMEDA (10 mg, 0.022 mmol), (S)-6-(5-(3,5-dimethylisoxazol-4-yl)-1-((1s,4R)-4-hydroxy-4-methylcyclohexyl)-1H-benzo[d]imidazol-2-yl)piperidin-2-one (70 mg, 0.166 mmol), (3,4-dichlorophenyl)boronic acid (35 mg, 0.183 mmol) and DBU (27 µL, 0.179 mmol) were heated to 70° C. in acetonitrile (2 mL) for 18 h. The mixture was concentrated onto loose silica gel. The silicate was purified by chromatography on the Companion (12 g column, 0-50% THF/DCM) then purified further on the Companion (4 g column, 1.5-4% MeOH/DCM) to afford (S)-1-(3,4-dichlorophenyl)-6-(5-(3,5-dimethylisoxazol-4-yl)-1-((1s,4R)-4-hydroxy-4-methylcyclohexyl)-1H-benzo[d]imidazol-2-yl)piperidin-2-one (19 mg, 19%) as a white solid; Rt 2.01 min; m/z 567 (M+H)+ (ES+); 1H NMR (d6-DMSO) δ: 7.72-7.66 (m, 2H), 7.62 (d, J=2.4 Hz, 1H), 7.53 (d, J=8.7 Hz, 1H), 7.22 (dd, J=8.4, 1.7 Hz, 1H), 7.18 (dd, J=8.7, 2.4 Hz, 1H), 5.81 (t, J=4.7 Hz, 1H), 4.44 (s, 1H), 4.42-4.31 (m, 1H), 2.66-2.53 (m, 3H), 2.49-2.42 (m, 1H), 2.41 (s, 3H), 2.39-2.32 (m, 1H), 2.25 (s, 3H), 2.10-1.89 (m, 2H), 1.84-1.74 (m, 1H), 1.74-1.66 (m, 1H), 1.66-1.46 (m, 4H), 1.19 (s, 3H), 1.07-0.95 (m, 1H).

CuTMEDA (10 mg, 0.022 mmol), (S)-6-(5-(3,5-dimethylisoxazol-4-yl)-1-((1s,4R)-4-hydroxy-4-methylcyclohexyl)-1H-benzo[d]imidazol-2-yl)piperidin-2-one (70 mg, 0.166 mmol), (3-fluoro-4-methoxyphenyl)boronic acid (32 mg, 0.188 mmol) and DBU (27 µL, 0.179 mmol) were heated to 70° C. in acetonitrile (2 mL) for 18 h. The mixture was concentrated onto loose silica gel. The silicate was purified by chromatography on the Companion (12 g column, 0-50% THF/DCM) then purified further on the Companion (4 g column, 1.5-4% MeOH/DCM) to afford (S)-6-(5-(3,5-dimethylisoxazol-4-yl)-1-((1s,4R)-4-hydroxy-4-methylcyclohexyl)-1H-benzo[d]imidazol-2-yl)-1-(3-fluoro-4-methoxyphenyl)piperidin-2-one (18 mg, 19%) as a white solid; Rt 1.72 min; m/z 547 (M+H)+ (ES+); 1H NMR (d6-DMSO) δ: 7.71 (d, J=1.6 Hz, 1H), 7.68 (d, J=8.5 Hz, 1H), 7.21 (dd, J=8.4, 1.7 Hz, 1H), 7.13 (dd, J=12.8, 2.4 Hz, 1H), 7.03 (dd, J=9.2 Hz, 1H), 6.95 (ddd, J=8.8, 2.4, 1.2 Hz, 1H), 5.69 (t, J=4.5 Hz, 1H), 4.42 (s, 1H), 4.40-4.27 (m, 1H), 3.74 (s, 3H), 2.62-2.53 (m, 2H), 2.49-2.43 (m, 1H), 2.42 (s, 3H), 2.41-2.28 (m, 2H), 2.25 (s, 3H), 2.10-1.96 (m, 2H), 1.84-1.42 (m, 6H), 1.18 (s, 3H), 1.00-0.79 (m, 1H).

Example 160: (S)-1-(4-chloro-3-fluorophenyl)-6-(5-(3,5-dimethylisoxazol-4-yl)-1-((1s,4R)-4-hydroxy-4-methylcyclohexyl)-1H-benzo[d]imidazol-2-yl)piperidin-2-one (S)-1-(4-chloro-3-fluorophenyl)-6-(5-(3,5-dimethylisoxazol-4-yl)-1-((1s,4R)-4-hydroxy-4-methylcyclohexyl)-1H-benzo[d]imidazol-2-yl)piperidin-2-one Example 161: (S)-1-(3,4-difluorophenyl)-6-(5-(3,5-dimethylisoxazol-4-yl)-1-((1r,3S)-3-hydroxycyclobutyl)-1H-benzo[d]imidazol-2-yl)piperidin-2-one (S)—N-(5-(3,5-dimethylisoxazol-4-yl)-2-(((1r,3S)-3-hydroxycyclobutyl)amino)phenyl)-6-oxo piperidine-2-carboxamide

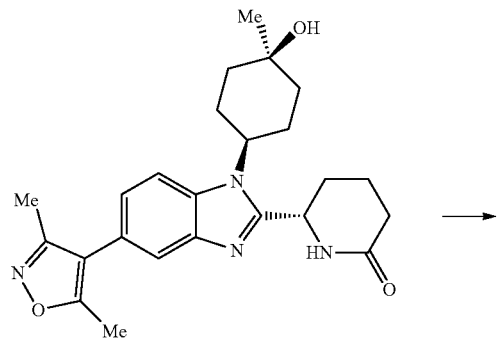

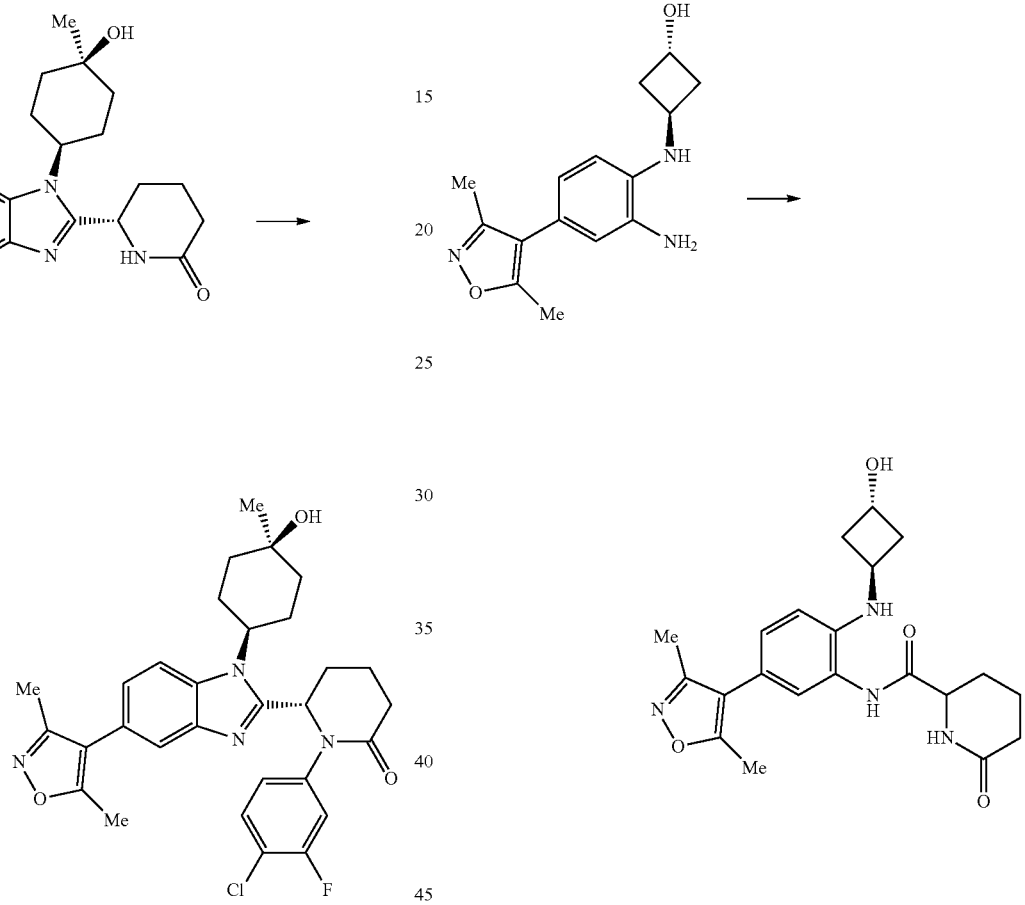

CuTMEDA (10 mg, 0.022 mmol), (S)-6-(5-(3,5-dimethylisoxazol-4-yl)-1-((1s,4R)-4-hydroxy-4-methylcyclohexyl)-1H-benzo[d]imidazol-2-yl)piperidin-2-one (70 mg, 0.166 mmol), (4-chloro-3-fluorophenyl)boronic acid (32 mg, 0.184 mmol) and DBU (27 μl, 0.179 mmol) were heated to 70° C. in acetonitrile (2 mL) for 18 h. The mixture was concentrated onto loose silica gel. The silicate was purified by chromatography on the Companion (12 g column, 0-50% THF/DCM) then purified further on the Companion (4 g column, 1.5-4% MeOH/DCM) to afford ((S)-1-(4-chloro-3-fluorophenyl)-6-(5-(3,5-dimethylisoxazol-4-yl)-1-((1s,4R)-4-hydroxy-4-methylcyclohexyl)-1H-benzo[d]imidazol-2-yl)piperidin-2-one (20 mg, 21%) as a white solid; Rt 1.93 min; m/z 551 (M+H)+ (ES+); 1H NMR (d6-DMSO) δ: 7.74-7.66 (m, 2H), 7.50 (dd, J=8.6 Hz, 1H), 7.38 (dd, J=10.9, 2.3 Hz, 1H), 7.23 (dd, J=8.5, 1.6 Hz, 1H), 7.08 (ddd, J=8.7, 2.3, 1.0 Hz, 1H), 5.79 (t, J=4.6 Hz, 1H), 4.44 (s, 1H), 4.37 (t, J=12.3 Hz, 1H), 2.65-2.52 (m, 3H), 2.49-2.43 (m, 1H), 2.41 (s, 3H), 2.40-2.32 (m, 1H), 2.25 (s, 3H), 2.10-1.89 (m, 2H), 1.84-1.44 (m, 6H), 1.19 (s, 3H), 1.08-0.98 (m, 1H).

TEA (3.06 mL, 21.95 mmol) was added to a solution of (1r,3r)-3-((2-amino-4-(3,5-dimethylisoxazol-4-yl)phenyl)amino)cyclobutanol (2 g, 7.32 mmol), (S)-6-oxopiperidine-2-carboxylic acid (1.152 g, 8.05 mmol) and HATU (3.06 g, 8.05 mmol) in DMF (20 mL) then stirred at room temperature for 18 hrs. The mixture was concentrated on the rotovap to remove the bulk of the DMF. The loose residue was diluted with DCM (200 ml) and washed with water (2×50 mL). The organic phase was collected via phase sep cartridge and concentrated in vacuo to afford a viscous orange oil. The crude material was purified by chromatography (80 g silica, 0-10% MeOH in DCM, gradient elution). Product fractions were concentrated in vacuo to afford (S)—N-(5-(3,5-dimethylisoxazol-4-yl)-2-(((1r,3 S)-3-hydroxycyclobutyl)amino)phenyl)-6-oxopiperidine-2-carboxamide (587 mg, 20%) as a brown/yellow sticky solid/foam; Rt 1.38 min; m/z 399 (M+H)+ (ES+).

(S)-6-(5-(3,5-dimethylisoxazol-4-yl)-1-((1r,3S)-3-hydroxycyclobutyl)-1H-benzo[d]imidazol-2-yl)piperidin-2-one

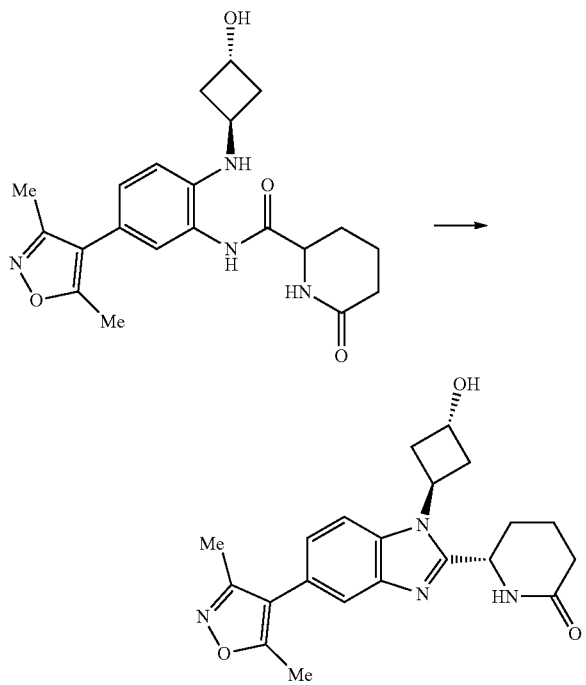

(S)—N-(5-(3,5-dimethylisoxazol-4-yl)-2-(((1r,3 S)-3-hydroxycyclobutyl)amino)phenyl)-6-oxo piperidine-2-carboxamide (585 mg, 1.468 mmol) was dissolved in acetic acid (2 mL) and stirred at 80° C. for 18 hrs. The reaction mixture was cooled to RT and the solvent was removed in vacuo. The residue was purified by chromatography (12 g silica, 0-10% methanol in DCM, gradient elution). Product fractions were combined and concentrated in vacuo to afford the crude (S)-6-(5-(3,5-dimethylisoxazol-4-yl)-1-((1r,3S)-3-hydroxycyclobutyl)-1H-benzo[d]imidazol-2-yl)piperidin-2-one (950 mg) as a light brown solid; Rt 1.18 min; m/z 381 (M+H)+ (ES+).

(S)-1-(3,4-difluorophenyl)-6-(5-(3,5-dimethylisoxazol-4-yl)-1-((1r,3S)-3-hydroxycyclo butyl)-1H-benzo[d]imidazol-2-yl)piperidin-2-one

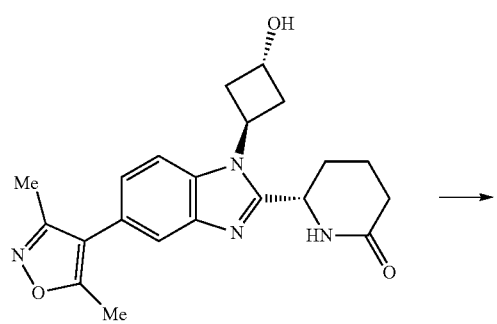

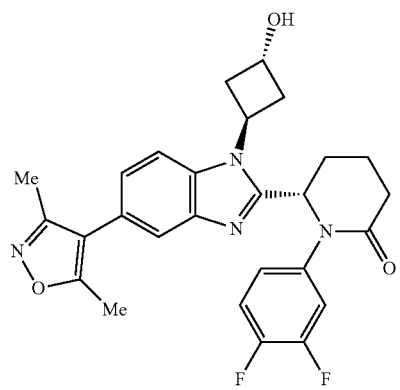

DBU (83 μL, 0.552 mmol) was added to a solution of (S)-6-(5-(3,5-dimethylisoxazol-4-yl)-1-((1r,3S)-3-hydroxycyclobutyl)-1H-benzo[d]imidazol-2-yl)piperidin-2-one (200 mg, 0.526 mmol), CuTMEDA (36.6 mg, 0.079 mmol) and (3,4-difluorophenyl)boronic acid (91 mg, 0.578 mmol) in acetonitrile (2 mL). The reaction mixture was stirred for 18 h at 40° C., then concentrated under reduced pressure. DCM and silica was added and the solvent removed in vacuo. The crude product (adsorbed to silica) was purified by chromatography (12 g silica, 0-10% MeOH in DCM, gradient elution) to afford (S)-1-(3,4-difluorophenyl)-6-(5-(3,5-dimethylisoxazol-4-yl)-1-((1r,3S)-3-hydroxycyclo butyl)-1H-benzo[d]imidazol-2-yl)piperidin-2-one (97 mg, 36%) as a light yellow glass which scratched to a crystalline solid; Rt 1.70 min; m/z 493 (M+H)+ (ES+); 1H NMR (d6-DMSO) δ: 7.81-7.69 (m, 2H), 7.40 (ddd, J=12.0, 7.4, 2.5 Hz, 1H), 7.33 (dt, J=10.7, 9.0 Hz, 1H), 7.19 (dd, J=8.5, 1.7 Hz, 1H), 7.14-7.05 (m, 1H), 6.55 (s, 1H), 5.68 (dd, J=5.4, 4.0 Hz, 1H), 5.37-5.24 (m, 2H), 4.54 (s, 1H), 2.98 (dt, J=12.8, 7.8 Hz, 1H), 2.86 (dt, J=15.0, 7.7 Hz, 1H), 2.60-2.46 (m, 2H), 2.40 (m, 4H), 2.23 (s, 3H), 2.19 (m, 1H), 2.03 (m, 1H), 1.91-1.71 (m, 2H).

Example 162: (S)-1-(3-chloro-4-methoxyphenyl)-6-(5-(3,5-dimethylisoxazol-4-yl)-1-((1r,3S)-3-hydroxycyclobutyl)-1H-benzo[d]imidazol-2-yl)piperidin-2-one

(S)-1-(3-chloro-4-methoxyphenyl)-6-(5-(3,5-dimethylisoxazol-4-yl)-1-((1r,3S)-3-hydroxycyclobutyl)-1H-benzo[d]imidazol-2-yl)piperidin-2-one

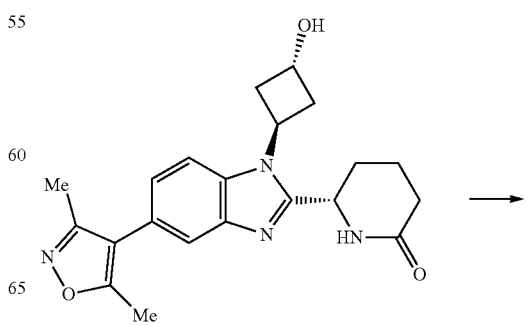

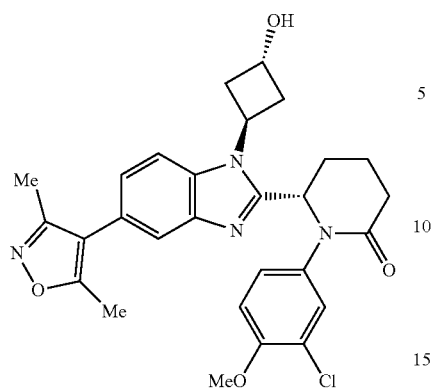

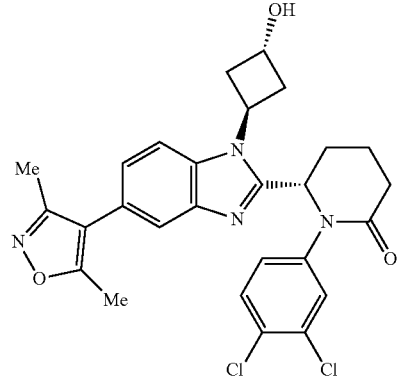

DBU (83 µL, 0.552 mmol) was added to a solution of (S)-6-(5-(3,5-dimethylisoxazol-4-yl)-1-((1r,3S)-3-hydroxycyclobutyl)-1H-benzo[d]imidazol-2-yl)piperidin-2-one (200 mg, 0.526 mmol), CuTMEDA (36.6 mg, 0.079 mmol) and (3-chloro-4-methoxyphenyl)boronic acid (108 mg, 0.578 mmol) in acetonitrile (2 mL). The reaction mixture was stirred for 18 h at 40° C., then concentrated under reduced pressure. DCM and silica was added and the solvent removed in vacuo. The crude product (adsorbed to silica) was purified by chromatography (12 g silica, 0-10% MeOH in DCM, gradient elution) and sonicated with ether (removing the solvent in vacuo) to afford (S)-1-(3-chloro-4-methoxyphenyl)-6-(5-(3,5-dimethylisoxazol-4-yl)-1-((1r,3S)-3-hydroxycyclobutyl)-1H-benzo[d]imidazol-2-yl)piperidin-2-one (52 mg, 17%) as a light yellow solid; Rt 1.69 min; m/z 521 (M+H)+ (ES+); 1H NMR (d6-DMSO) δ: 7.80-7.69 (m, 2H), 7.38 (d, J=2.5 Hz, 1H), 7.22-7.12 (m, 2H), 7.00 (d, J=8.9 Hz, 1H), 5.64 (t, J=4.8 Hz, 1H), 5.36-5.27 (m, 2H), 4.53 (s, 1H), 3.75 (s, 3H), 2.98 (dt, J=12.7, 7.7 Hz, 1H), 2.84 (dt, J=14.9, 7.7 Hz, 1H), 2.60-2.35 (m, 4H), 2.40 (s, 3H), 2.24 (s, 3H), 2.27-2.15 (m, 1H), 2.01 (s, 1H), 1.88 (s, 1H), 1.77 (s, 1H).

DBU (83 µL, 0.552 mmol) was added to a solution of (S)-6-(5-(3,5-dimethylisoxazol-4-yl)-1-((1r,3S)-3-hydroxycyclobutyl)-1H-benzo[d]imidazol-2-yl)piperidin-2-one (200 mg, 0.526 mmol), CuTMEDA (36.6 mg, 0.079 mmol) and (3,4-dichlorophenyl)boronic acid (110 mg, 0.578 mmol) in acetonitrile (2 mL). The reaction mixture was stirred for 18 h at 40° C., then concentrated under reduced pressure. DCM and silica was added and the solvent removed in vacuo. The crude product (adsorbed to silica) was purified by chromatography (12 g silica, 0-10% MeOH in DCM, gradient elution) and sonicated with ether (removing the solvent in vacuo) to afford (S)-1-(3,4-dichlorophenyl)-6-(5-(3,5-dimethylisoxazol-4-yl)-1-((1r,3S)-3-hydroxycyclobutyl)-1H-benzo[d]imidazol-2-yl)piperidin-2-one (71 mg, 25%) as a light yellow solid; Rt 1.90 min; m/z 525 (M+H)+ (ES+); 1H NMR (d6-DMSO) δ: 7.78 (d, J=8.5 Hz, 1H), 7.71 (d, J=1.6 Hz, 1H), 7.62 (d, J=2.4 Hz, 1H), 7.53 (d, J=8.7 Hz, 1H), 7.22 (ddd, J=21.6, 8.6, 2.0 Hz, 2H), 5.74 (t, J=4.7 Hz, 1H), 5.32 (q, J=8.7 Hz, 2H), 4.55 (t, J=7.1 Hz, 1H), 2.99 (dt, J=12.6, 7.7 Hz, 1H), 2.87 (dt, J=12.5, 7.6 Hz, 1H), 2.63-2.45 (m, 2H), 2.44-2.35 (m, 5H), 2.27-2.21 (m, 5H), 2.07-1.99 (m, 1H), 1.85-1.75 (m, 1H).

Example 163: (S)-1-(3,4-dichlorophenyl)-6-(5-(3,5-dimethylisoxazol-4-yl)-1-((1r,3S)-3-hydroxycyclo butyl)-1H-benzo[d]imidazol-2-yl)piperidin-2-one (S)-1-(3,4-dichlorophenyl)-6-(5-(3,5-dimethylisoxazol-4-yl)-1-((1r,3S)-3-hydroxycyclo butyl)-1H-benzo[d]imidazol-2-yl)piperidin-2-one Example 164: (S)-1-(3,4-difluorophenyl)-6-(5-(3,5-dimethylisoxazol-4-yl)-1-((1r,4S)-4-hydroxy-4-methylcyclohexyl)-1H-benzo[d]imidazol-2-yl)piperidin-2-one (S)-1-(3,4-difluorophenyl)-6-(5-(3,5-dimethylisoxazol-4-yl)-1-((1r,4S)-4-hydroxy-4-methylcyclohexyl)-1H-benzo[d]imidazol-2-yl)piperidin-2-one

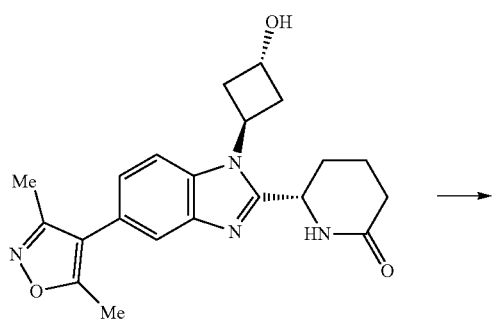

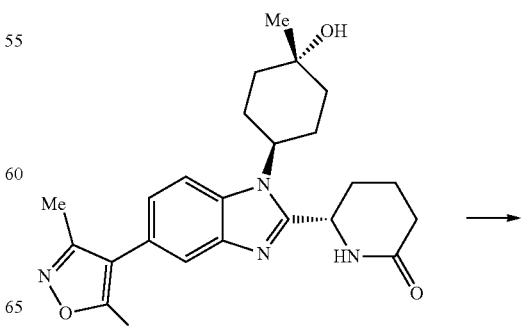

-continued

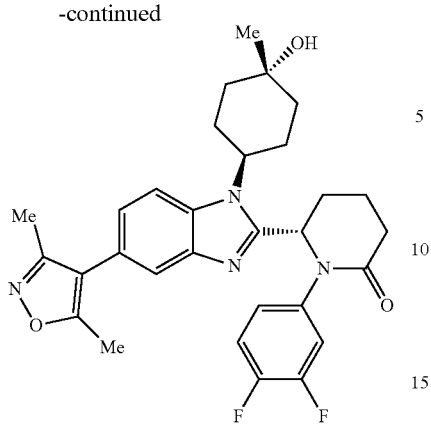

CuTMEDA (13.79 mg, 0.030 mmol) was added to a solution of (S)-6-(5-(3,5-dimethylisoxazol-4-yl)-1-(trans-(1r,4S)-4-hydroxy-4-methylcyclohexyl)-1H-benzo[d]imidazol-2-yl)piperidin-2-one (96.5 mg, 0.228 mmol), (3,4-difluorophenyl)boronic acid (54.1 mg, 0.343 mmol) and DBU (0.038 ml, 0.251 mmol) in acetonitrile (3.0 ml, 57.4 mmol) were heated to 70° C. for 6 h. (3,4-Difluorophenyl)boronic acid (20 mg) was added and stirring continued at the same temperature for a further 16 h. The mixture was concentrated onto loose silica gel. The silicate was purified by chromatography on the Companion (12 g column, 1-3%; isocratic 3% then 10% MeOH/DCM) to afford (S)-1-(3,4-difluorophenyl)-6-(5-(3,5-dimethylisoxazol-4-yl)-1-((1r,4S)-4-hydroxy-4-methylcyclohexyl)-1H-benzo[d]imidazol-2-yl)piperidin-2-one (56 mg, 44%) as a brown yellow solid; Rt 1.84 min; m/z 535 (M+H)+ (ES+); 1H NMR (d₆-DMSO) δ: 7.71 (d, J=1.6 Hz, 1H), 7.62 (d, J=8.5 Hz, 1H), 7.39 (ddd, 1H), 7.36-7.29 (m, 1H), 7.21-7.17 (m, 1H), 7.08-7.02 (m, 1H), 5.80-5.76 (m, 1H), 4.58 (s, 1H), 4.41-4.28 (m, 1H), 2.64-2.52 (m, 2H), 2.40 (s, 3H), 2.39-2.30 (m, 1H), 2.24 (s, 3H), 2.21-2.07 (m, 2H), 2.06-1.92 (m, 2H), 1.83-1.72 (m, 2H), 1.70-1.56 (m, 4H), 1.32 (s, 3H), 1.15 (dd, J=12.8, 8.8 Hz, 1H).

Example 165: (S)-1-(3-chloro-4-methoxyphenyl)-6-(5-(3,5-dimethylisoxazol-4-yl)-1-((1r,4S)-4-hydroxy-4-methylcyclohexyl)-1H-benzo[d]imidazol-2-yl)piperidin-2-one (S)-1-(3-chloro-4-methoxyphenyl)-6-(5-(3,5-dimethylisoxazol-4-yl)-1-((1r,4S)-4-hydroxy-4-methylcyclohexyl)-1H-benzo[d]imidazol-2-yl)piperidin-2-one

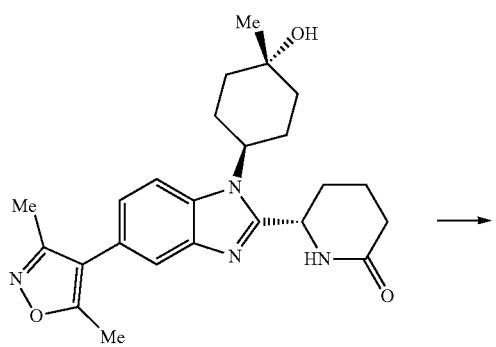

-continued

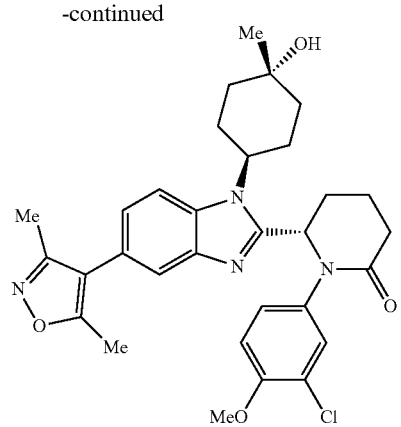

CuTMEDA (13.79 mg, 0.030 mmol) was added to a solution of (3-chloro-4-methoxyphenyl)boronic acid (63.9 mg, 0.343 mmol), (S)-6-(5-(3,5-dimethylisoxazol-4-yl)-1-(trans-(1r,4S)-4-hydroxy-4-methylcyclohexyl)-1H-benzo[d]imidazol-2-yl)piperidin-2-one (96.5 mg, 0.228 mmol) and DBU (0.038 ml, 0.251 mmol) in acetonitrile (3.0 mL, 57.4 mmol) were heated to 70° C. for 6 h then more (3-chloro-4-methoxyphenyl)boronic acid (20 mg) was added and stirring continued for 22 h. CuTMEDA (14 mg) was added and the reaction was heated for a further 3 h. The mixture was concentrated onto loose silica gel. The silicate was purified by chromatography on the Companion (12 g column, 1-3%; isocratic then 10% MeOH/DCM) to afford (S)-1-(3-chloro-4-methoxyphenyl)-6-(5-(3,5-dimethyl isoxazol-4-yl)-1-((1r,4S)-4-hydroxy-4-methylcyclohexyl)-1H-benzo[d]imidazol-2-yl)piperidin-2-one (52.7 mg, 39%) as a brown yellow solid; Rt 1.81 min; m/z 564 (M+H)+ (ES+); 1H NMR (d₆-DMSO) δ: 7.71 (d, J=1.7 Hz, 1H), 7.60 (d, J=8.5 Hz, 1H), 7.39 (d, J=2.4 Hz, 1H), 7.18 (dd, J=8.4, 1.7 Hz, 1H), 7.09 (dd, J=8.8, 2.5 Hz, 1H), 6.99 (d, J=8.9 Hz, 1H), 5.74 (t, 1H), 4.57 (s, 1H), 4.40-4.29 (m, 1H), 3.75 (s, 3H), 2.61-2.52 (m, 2H), 2.41 (s, 3H), 2.38-2.30 (m, 1H), 2.26-2.13 (m+s, 1H), 2.11-1.96 (m, 3H), 1.85-1.75 (m, 1H), 1.74-1.64 (m, 4H), 1.63-1.54 (m, 1H), 1.31 (s, 3H), 1.09-1.01 (m, 1H).

Example 166: (S)-6-(5-(3,5-dimethylisoxazol-4-yl)-1-((1r,4S)-4-hydroxy-4-methylcyclohexyl)-1H-benzo[d]imidazol-2-yl)-1-(3-fluoro-4-methoxyphenyl)piperidin-2-one (S)-6-(5-(3,5-dimethylisoxazol-4-yl)-1-((1r,4S)-4-hydroxy-4-methylcyclohexyl)-1H-benzo[d]imidazol-2-yl)-1-(3-fluoro-4-methoxyphenyl)piperidin-2-one

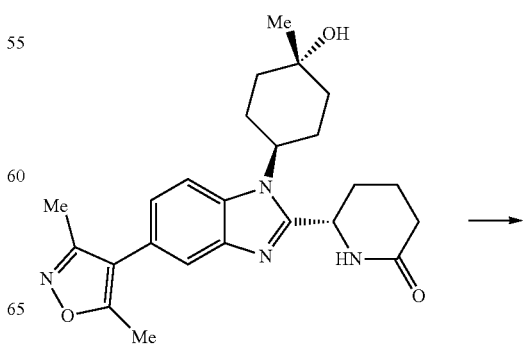

-continued

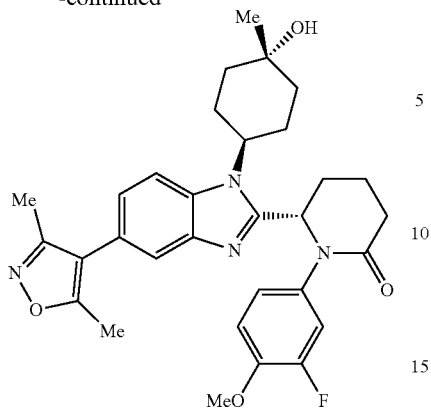

CuTMEDA (13.79 mg, 0.030 mmol) was added to a solution of (3-fluoro-4-methoxyphenyl)boronic acid (58.2 mg, 0.343 mmol), (3-fluoro-4-methoxyphenyl)boronic acid (58.2 mg, 0.343 mmol) and DCM (0.30 ml, 4.66 mmol) in acetonitrile (3.0 ml, 57.4 mmol) were heated to 70° C. for 6 h. 3-Fluoro-4-methoxyphenyl)boronic acid (20 mg) was added after 6 h of heating then the mixture stirred for 22 h at the same temperature before more CuTMEDA (14 mg) was added and the reaction was heated for a further 3 h. The mixture was concentrated onto loose silica gel. The silicate was purified by chromatography on the Companion (12 g column, 1-3% MeOH/DCM then isocratic and up to 10% MeOH) to afford (S)-6-(5-(3,5-dimethylisoxazol-4-yl)-1-((1r,4S)-4-hydroxy-4-methylcyclohexyl)-1H-benzo[d]imidazol-2-yl)-1-(3-fluoro-4-methoxyphenyl)piperidin-2-one (52 mg, 40%) as a beige solid; the enantiomers were separated by chiral preparative HPLC (General method C); Rt 1.71 min; m/z 507 (M+H)+ (ES+); 1H NMR (d6-DMSO) δ: 7.71 (d, J=1.6 Hz, 1H), 7.61 (d, J=8.4 Hz, 1H), 7.18 (dd, J=8.5, 1.7 Hz, 1H), 7.13 (dd, J=12.7, 2.4 Hz, 1H), 7.02 (t, J=9.1 Hz, 1H), 6.96 (ddd, J=2.4, 1.1 Hz, 1H), 5.72 (t, 1H), 4.57 (s, 1H), 4.39-4.27 (m, 1H), 3.73 (s, 3H), 2.57-2.52 (m, 1H), 2.47-2.29 (m+s, 5H), 2.28-2.16 (m+s, 4H), 2.14-1.96 (m, 3H), 1.84-1.67 (m, 4H), 1.62-1.56 (m, 2H), 1.34-1.29 (s, 3H), 1.02 (m, 1H).

Example 167: (S)-1-(3,4-dichlorophenyl)-6-(5-(3,5-dimethylisoxazol-4-yl)-1-isobutyl-1H-benzo[d]imidazol-2-yl)piperidin-2-one (S)-1-(3,4-dichlorophenyl)-6-(5-(3,5-dimethylisoxazol-4-yl)-1-isobutyl-1H-benzo[d]imidazol-2-yl)piperidin-2-one

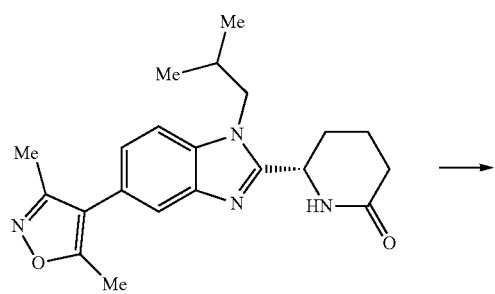

-continued

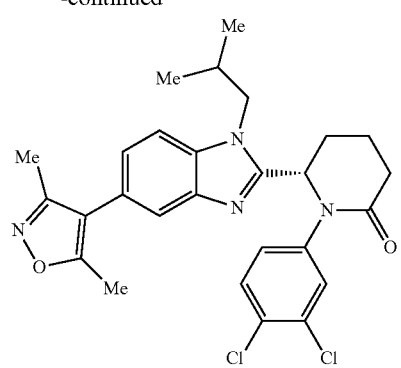

DBU (86 μL, 0.573 mmol) was added to a solution of (S)-6-(5-(3,5-dimethylisoxazol-4-yl)-1-isobutyl-1H-benzo[d]imidazol-2-yl)piperidin-2-one (200 mg, 0.546 mmol), CuTMEDA (38.0 mg, 0.082 mmol) and (3,4-dichlorophenyl)boronic acid (115 mg, 0.600 mmol) in acetonitrile (3 mL). The reaction mixture was stirred for 18 h at 40° C., and then concentrated under reduced pressure. DCM and silica was added and the solvent removed in vacuo. The crude product (adsorbed to silica) was purified by chromatography (12 g silica, 0-10% MeOH in DCM, gradient elution). Product fractions were combined and concentrated in vacuo. The residue was sonicated with ether and the solid collected by filtration to (S)-1-(3,4-dichloro phenyl)-6-(5-(3,5-dimethylisoxazol-4-yl)-1-isobutyl-1H-benzo[d]imidazol-2-yl)piperidin-2-one (49 mg, 17%) as a light beige solid; Rt 2.37 min; m/z 511 (M+H)+ (ES+); 1H NMR (d6-DMSO) δ: 7.71 (d, J=1.6 Hz, 1H), 7.61 (d, J=8.4 Hz, 1H), 7.18 (dd, J=8.5, 1.7 Hz, 1H), 7.13 (dd, J=12.7, 2.4 Hz, 1H), 7.02 (t, J=9.1 Hz, 1H), 6.96 (ddd, J=2.4, 1.1 Hz, 1H), 5.72 (t, 1H), 4.57 (s, 1H), 4.39-4.27 (m, 1H), 3.73 (s, 3H), 2.57-2.52 (m, 1H), 2.47-2.29 (m+s, 5H), 2.28-2.16 (m+s, 4H), 2.14-1.96 (m, 3H), 1.84-1.67 (m, 4H), 1.62-1.56 (m, 2H), 1.34-1.29 (s, 3H), 1.02 (m, 1H).

Example 168: (S)-1-(3-chloro-4-methoxyphenyl)-6-(5-(3,5-dimethylisoxazol-4-yl)-1-isobutyl-1H-benzo[d]imidazol-2-yl)piperidin-2-one (S)-1-(3-chloro-4-methoxyphenyl)-6-(5-(3,5-dimethylisoxazol-4-yl)-1-isobutyl-1H-benzo[d]imidazol-2-yl)piperidin-2-one

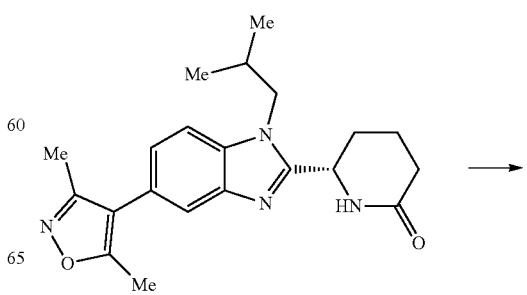

387

-continued

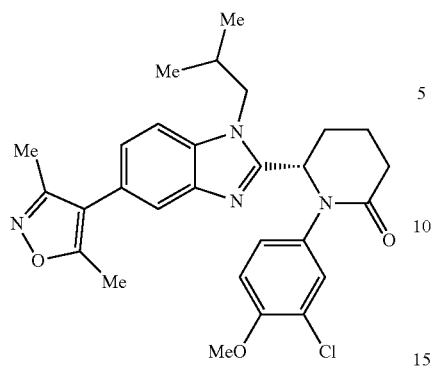

DBU (86 µL, 0.573 mmol) was added to a solution of (S)-6-(5-(3,5-dimethylisoxazol-4-yl)-1-isobutyl-1H-benzo[d]imidazol-2-yl)piperidin-2-one (200 mg, 0.546 mmol), CuTMEDA (38.0 mg, 0.082 mmol) and (3-chloro-4-methoxyphenyl)boronic acid (112 mg, 0.600 mmol) in acetonitrile (3 mL). The reaction mixture was stirred for 18 h at 40° C., and then concentrated under reduced pressure. DCM and silica was added and the solvent removed in vacuo. The crude product was pre-adsorbed to silica and purified by chromatography (12 g silica, 0-10% MeOH in DCM, gradient elution) and finally sonicated with diethyl ether (removing the solvent in vacuo) to afford (S)-1-(3-chloro-4-methoxyphenyl)-6-(5-(3,5-dimethylisoxazol-4-yl)-1-isobutyl-1H-benzo[d]imidazol-2-yl)piperidin-2-one (55 mg, 19%) as a light pink/purple solid; Rt 2.14 min; m/z 507 (M+H)+ (ES+); 1H NMR (d6-DMSO) δ: Rt 2.14 min; m/z 547 (M+H)+ (ES+); 1H NMR (d6-DMSO) δ: 7.73 (dd, J=1.6, 0.6 Hz, 1H), 7.57 (dd, J=8.4, 0.7 Hz, 1H), 7.31 (d, J=2.5 Hz, 1H), 7.18 (dd, J=8.4, 1.6 Hz, 1H), 7.11 (dd, J=8.8, 2.5 Hz, 1H), 6.99 (d, J=8.9 Hz, 1H), 5.51 (dd, J=5.6, 3.1 Hz, 1H), 3.95 (dd, J=14.6, 6.8 Hz, 1H), 3.89-3.73 (m, 1H), 3.74 (s, 3H), 3.17 (d, J=4.0 Hz, 1H), 2.62-2.52 (m, 1H), 2.41 (s, 3H), 2.24 (s, 3H), 2.10 (d, J=9.9 Hz, 1H), 2.06-1.97 (m, 1H), 1.95-1.79 (m, 1H), 1.77-1.70 (m, 1H), 1.62 (s, 1H), 0.75 (d, J=6.6 Hz, 3H), 0.48 (d, J=6.6 Hz, 3H).

Example 169: (S)-6-(5-(3,5-dimethylisoxazol-4-yl)-1-isobutyl-1H-benzo[d]imidazol-2-yl)-1-(3-fluoro-4-methoxyphenyl)piperidin-2-one (S)-6-(5-(3,5-dimethylisoxazol-4-yl)-1-isobutyl-1H-benzo[d]imidazol-2-yl)-1-(3-fluoro-4-methoxyphenyl)piperidin-2-one

388

-continued

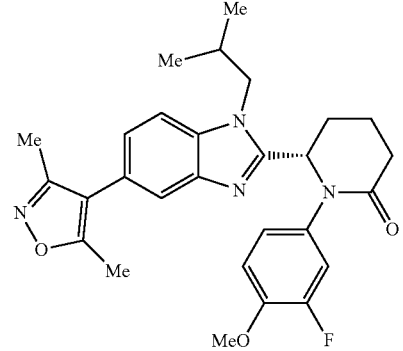

DBU (86 µL, 0.573 mmol) was added to a solution of (S)-6-(5-(3,5-dimethylisoxazol-4-yl)-1-isobutyl-1H-benzo[d]imidazol-2-yl)piperidin-2-one (200 mg, 0.546 mmol), CuTMEDA (38.0 mg, 0.082 mmol) and (3-fluoro-4-methoxyphenyl)boronic acid (102 mg, 0.600 mmol) in acetonitrile (3 mL). The reaction mixture was stirred for 18 h at 40° C., and then concentrated under reduced pressure. DCM and silica was added and the solvent removed in vacuo. The crude product (adsorbed to silica) was purified by chromatography (12 g silica, 0-10% MeOH in DCM, gradient elution) and sonicated with ether (removing the solvent in vacuo) to afford (S)-6-(5-(3,5-dimethylisoxazol-4-yl)-1-isobutyl-1H-benzo[d]imidazol-2-yl)-1-(3-fluoro-4-methoxyphenyl)piperidin-2-one (27 mg, 10%) as a light pink/purple solid; the enantiomers were separated by chiral preparative HPLC (General method F); Rt 2.06 min; m/z 491 (M+H)+ (ES+); 1H NMR (d6-DMSO) δ: 6 7.73 (dd, J=1.6, 0.6 Hz, 1H), 7.57 (dd, J=8.4, 0.6 Hz, 1H), 7.18 (dd, J=8.3, 1.6 Hz, 1H), 7.11-6.90 (m, 3H), 5.49 (dd, J=5.5, 3.1 Hz, 1H), 3.94 (dd, J=14.5, 6.7 Hz, 1H), 3.83 (dd, J=14.5, 8.7 Hz, 1H), 3.73 (s, 3H), 2.56 (dd, J=13.4, 5.2 Hz, 1H), 2.41 (s, 3H), 2.35 (m, 1H), 2.25 (s, 3H), 2.15-1.97 (m, 2H), 1.95-1.79 (m, 1H), 1.74 (m, 1H), 0.76 (d, J=6.6 Hz, 3H), 0.48 (d, J=6.6 Hz, 3H).

Example 170: (S)-6-(1-(4,4-difluorocyclohexyl)-5-(3,5-dimethylisoxazol-4-yl)-1H-benzo[d]imidazol-2-yl)-1-(3-fluoro-4-methoxyphenyl)piperidin-2-one (S)—N-(2-((4,4-difluorocyclohexyl)amino)-5-(3,5-dimethylisoxazol-4-yl)phenyl)-6-oxopiperidine-2-carboxamide

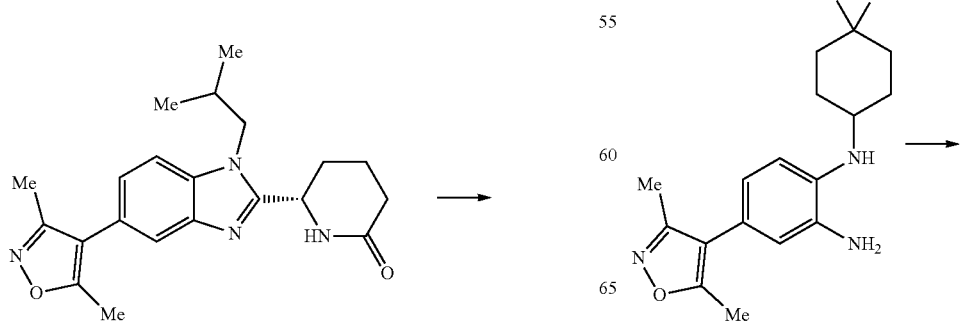

-continued

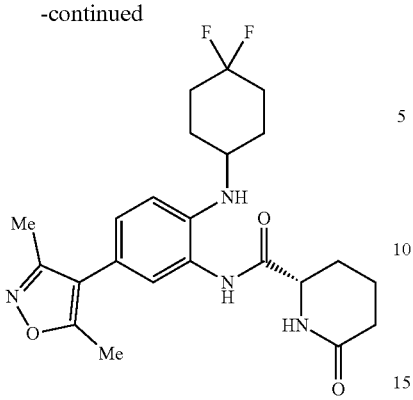

HATU (1.4 g, 3.68 mmol) was added to a stirred solution of TEA (0.6 ml, 4.30 mmol), (S)-6-oxopiperidine-2-carboxylic acid (500 mg, 3.49 mmol) and Intermediate C12 (1.0 g, 3.11 mmol) in N,N-dimethylformamide (10 mL) then the mixture was stirred at room temperature for 2 h. The mixture was concentrated under reduced pressure then purified by chromatography on the Companion (40 g column, 0-25% THF/DCM) and triturated in diethyl ether to afford (S)—N-(2-((4,4-difluorocyclohexyl)amino)-5-(3,5-dimethylisoxazol-4-yl)phenyl)-6-oxopiperidine-2-carboxamide (1.5 g, 97%) as a white solid; Rt 1.94 min; m/z 447 (M+H)+ (ES+).

(S)-6-(1-(4,4-difluorocyclohexyl)-5-(3,5-dimethylisoxazol-4-yl)-1H-benzo[d]imidazol-2-yl)piperidin-2-one

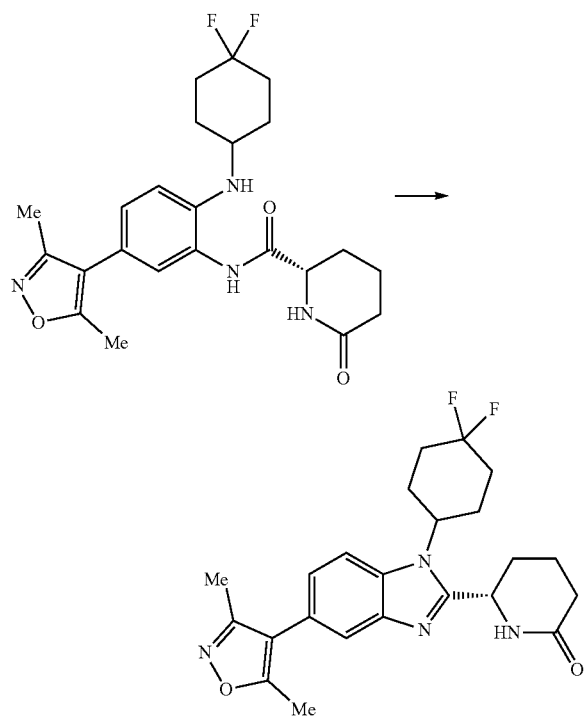

(S)—N-(2-((4,4-difluorocyclohexyl)amino)-5-(3,5-dimethylisoxazol-4-yl)phenyl)-6-oxopiperidine-2-carboxamide (1.5 g, 3.02 mmol) was heated to 80° C. in acetic acid (25 mL) for 18 h. The solvents were removed under reduced pressure then the residue was dissolved in DCM:MeOH:DEA (20:2.5:2.5, 25 mL) and concentrated onto loose silica gel. The silicate was purified by chromatography on the Companion (40 g column, 15-75% THF/DCM) then triturated in diethyl ether to afford (S)-6-(1-(4,4-difluorocyclohexyl)-5-(3,5-dimethylisoxazol-4-yl)-1H-benzo[d]imidazol-2-yl)piperidin-2-one (878 mg, 67%) as a white solid; Rt 1.78 min; m/z 429 (M+H)+ (ES+).

(S)-6-(1-(4,4-difluorocyclohexyl)-5-(3,5-dimethylisoxazol-4-yl)-1H-benzo[d]imidazol-2-yl)-1-(3-fluoro-4-methoxyphenyl)piperidin-2-one

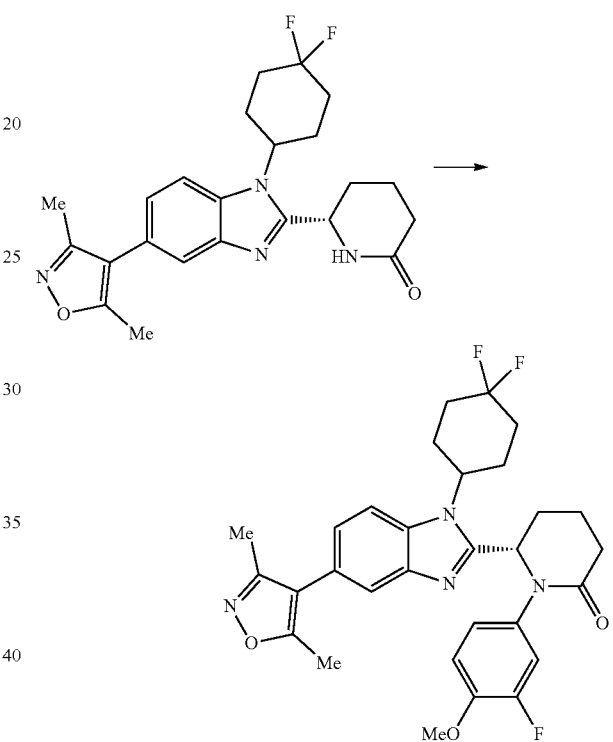

CuTMEDA (55 mg, 0.118 mmol) was added to a suspension of (S)-6-(1-(4,4-difluorocyclohexyl)-5-(3,5-dimethylisoxazol-4-yl)-1H-benzo[d]imidazol-2-yl)piperidin-2-one (100 mg, 0.233 mmol) in pyridine (5 mL) then stirred at 40° C. for 15 minutes. (3-fluoro-4-methoxyphenyl)boronic acid (100 mg, 0.588 mmol) was added then the mixture was stirred at 40° C. for 2 h. The mixture was diluted with ethyl acetate (25 mL) then washed with water (3×25 mL) and saturated brine (25 mL). The organic phase was dried (MgSO4), filtered and concentrated under reduced pressure. The crude product was purified by chromatography on the Companion (12 g column, 0-25% THF) then triturated in diethyl ether to afford (S)-6-(1-(4,4-difluorocyclohexyl)-5-(3,5-dimethylisoxazol-4-yl)-1H-benzo[d]imidazol-2-yl)-1-(3-fluoro-4-methoxyphenyl)piperidin-2-one (106 mg, 81%) as a white solid; the enantiomers were separated by chiral preparative HPLC (General method B); Rt 2.18 min; m/z 597 (M+H)+ (ES+); 1H NMR (d$_6$-DMSO) δ: 7.74 (d, J=1.6 Hz, 1H), 7.52 (d, J=8.5 Hz, 1H), 7.22 (dd, J=8.5, 1.7 Hz, 1H), 7.10 (dd, J=12.7, 2.4 Hz, 1H), 7.05 (dd, J=9.2 Hz, 1H), 6.95 (ddd, J=8.8, 2.4, 1.2 Hz, 1H), 5.76-5.60 (m, 1H), 4.74-4.56 (m, 1H), 3.75 (s, 3H), 2.63-2.52 (m, 2H), 2.41 (s, 3H), 2.39-2.26 (m, 2H), 2.25 (s, 3H), 2.24-1.85 (m, 8H), 1.83-1.73 (m, 1H), 1.30-1.18 (m, 1H).

Example 171: (S)-6-(1-(4,4-difluorocyclohexyl)-5-(3,5-dimethylisoxazol-4-yl)-1H-benzo[d]imidazol-2-yl)-1-(3,4-difluorophenyl)piperidin-2-one (S)-6-(1-(4,4-difluorocyclohexyl)-5-(3,5-dimethylisoxazol-4-yl)-1H-benzo[d]imidazol-2-yl)-1-(3,4-difluorophenyl)piperidin-2-one

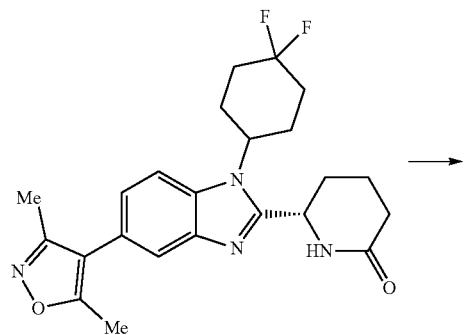

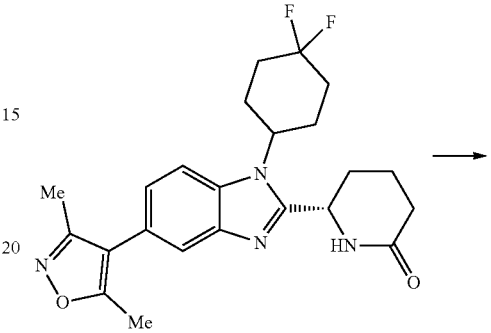

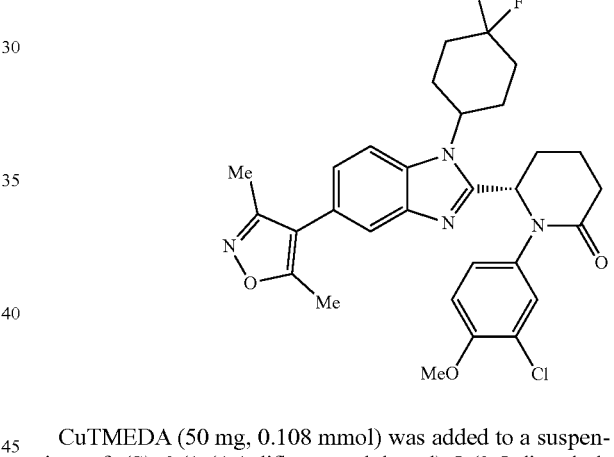

CuTMEDA (28 mg, 0.060 mmol) was added to a stirred solution of (S)-6-(1-(4,4-difluorocyclohexyl)-5-(3,5-dimethylisoxazol-4-yl)-1H-benzo[d]imidazol-2-yl)piperidin-2-one (50 mg, 0.116 mmol) and DBU (35 µL, 0.232 mmol) in acetonitrile (2 mL) then the mixture was stirred for 30 minutes. (3,4-difluorophenyl)boronic acid (35 mg, 0.222 mmol) was added then the mixture was heated to 50° C. overnight. The mixture was concentrated onto loose silica under reduced pressure. The crude product was purified by chromatography on the Companion (12 g column, 5-25% THF/DCM) to afford (S)-6-(1-(4,4-difluorocyclohexyl)-5-(3,5-dimethylisoxazol-4-yl)-1H-benzo[d]imidazol-2-yl)-1-(3,4-difluorophenyl)piperidin-2-one (35 mg, 53%) as a white solid; Rt 2.27 min; m/z 541 (M+H)+ (ES+); 1H NMR ($d_6$-DMSO) δ: 7.74 (d, J=1.6 Hz, 1H), 7.54 (d, J=8.5 Hz, 1H), 7.43-7.29 (m, 2H), 7.23 (dd, J=8.5, 1.7 Hz, 1H), 7.11-6.97 (m, OH), 5.79-5.67 (m, 1H), 4.75-4.56 (m, 1H), 2.67-2.52 (m, 2H), 2.48-2.42 (m, 1H), 2.41 (s, 3H), 2.40-2.26 (m, 3H), 2.24 (s, 3H), 2.23-2.03 (m, 5H), 2.03-1.90 (m, 2H), 1.85-1.73 (m, 1H), 1.44-1.30 (m, 1H).

Example 172: (S)-1-(3-chloro-4-methoxyphenyl)-6-(1-(4,4-difluorocyclohexyl)-5-(3,5-dimethylisoxazol-4-yl)-1H-benzo[d]imidazol-2-yl)piperidin-2-one (S)-1-(3-chloro-4-methoxyphenyl)-6-(1-(4,4-difluorocyclohexyl)-5-(3,5-dimethylisoxazol-4-yl)-1H-benzo[d]imidazol-2-yl)piperidin-2-one CuTMEDA (50 mg, 0.108 mmol) was added to a suspension of (S)-6-(1-(4,4-difluorocyclohexyl)-5-(3,5-dimethylisoxazol-4-yl)-1H-benzo[d]imidazol-2-yl)piperidin-2-one (75 mg, 0.175 mmol) in pyridine (5 mL) then stirred at 40° C. for 15 minutes. (3-Chloro-4-methoxyphenyl)boronic acid (100 mg, 0.536 mmol) was added then the mixture was stirred at 40° C. for 2 h. The mixture was diluted with ethyl acetate (25 mL) then washed with water (3×25 mL) and saturated brine (25 mL). The organic phase was dried ($MgSO_4$), filtered and concentrated under reduced pressure. The crude product was purified by flash chromatography on the Companion (12 g column, 0-25% THF) then triturated in diethyl ether to afford (S)-1-(3-chloro-4-methoxyphenyl)-6-(1-(4,4-difluorocyclohexyl)-5-(3,5-dimethyl isoxazol-4-yl)-1H-benzo[d]imidazol-2-yl)piperidin-2-one (35 mg, 0.060 mmol, 34.4% yield) as a white solid; Rt 2.26 min; m/z 569 (M+H)+ (ES+); 1H NMR ($d_6$-DMSO) δ: 7.74 (d, J=1.6 Hz, 1H), 7.52 (d, J=8.5 Hz, 1H), 7.37 (d, J=2.4 Hz, 1H), 7.21 (dd, J=8.4, 1.7 Hz, 1H), 7.08 (dd, J=8.8, 2.5 Hz, 1H), 7.01 (d, J=8.9 Hz, 1H), 5.74-5.67 (m, 1H), 4.74-4.58 (m, 1H), 3.76 (s, 3H), 2.65-2.53 (m, 2H), 2.45-2.25 (m, 6H), 2.24 (s, 3H), 2.23-1.98 (m, 6H), 1.98-1.88 (m, 1H), 1.85-1.74 (m, 1H), 1.30-1.13 (m, 1H).

Example 173: (S)-1-(3,4-dichlorophenyl)-6-(5-(3,5-dimethylisoxazol-4-yl)-1-((1r,4S)-4-hydroxycyclohexyl)-1H-benzo[d]imidazol-2-yl)piperidin-2-one (S)-1-(3,4-dichlorophenyl)-6-(5-(3,5-dimethylisoxazol-4-yl)-1-((1r,4S)-4-hydroxycyclohexyl)-1H-benzo[d]imidazol-2-yl)piperidin-2-one

Example 174: (S)-1-(3,4-difluorophenyl)-6-(5-(3,5-dimethylisoxazol-4-yl)-1-((1r,4S)-4-hydroxycyclohexyl)-1H-benzo[d]imidazol-2-yl)piperidin-2-one (S)-1-(3,4-difluorophenyl)-6-(5-(3,5-dimethylisoxazol-4-yl)-1-((1r,4S)-4-hydroxycyclohexyl)-1H-benzo[d]imidazol-2-yl)piperidin-2-one

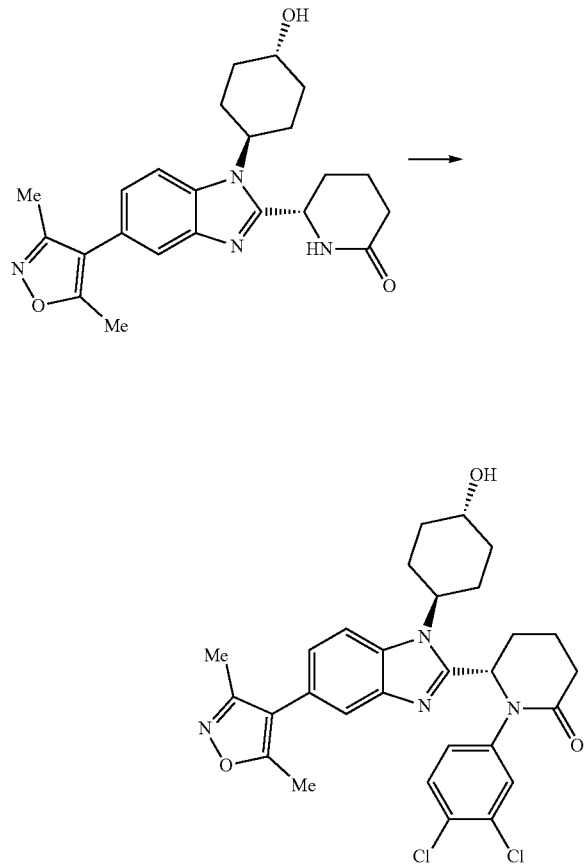

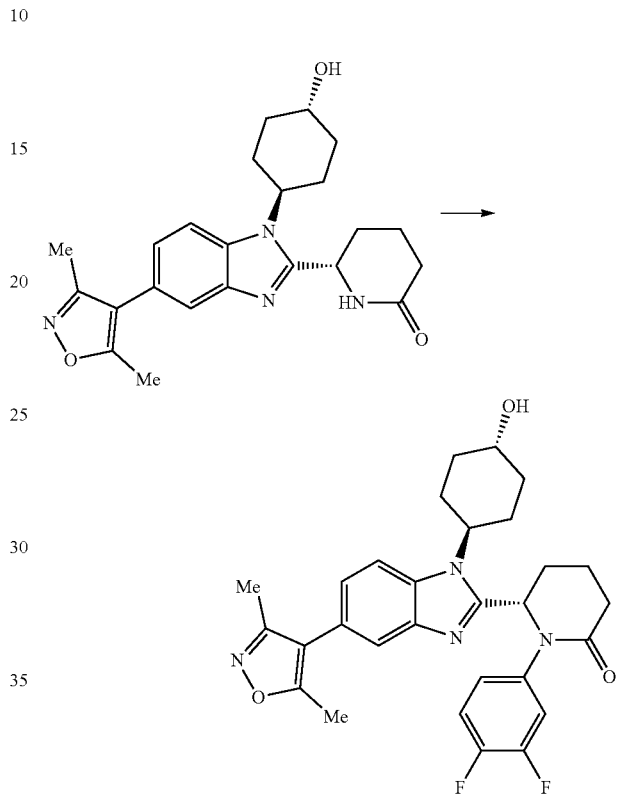

To a scintillation vial containing (S)-6-(5-(3,5-dimethylisoxazol-4-yl)-1-((1r,4S)-4-hydroxycyclohexyl)-1H-benzo[d]imidazol-2-yl)piperidin-2-one (157 mg, 0.384 mmol) in pyridine (3 mL) was added CuTMEDA (89 mg, 0.192 mmol). The reaction mixture was stirred at 40° C. for 15 minutes, then (3,4-dichlorophenyl)boronic acid (183 mg, 0.961 mmol) added and the reaction mixture was left to stir at 80° C. for 48 h. Rt 1.86 min; m/z 521 (M+H)+ (ES+); 1H NMR (d6-DMSO) δ: 7.76 (d, J=8.5 Hz, 1H), 7.69 (d, J=1.6 Hz, 1H), 7.43-7.27 (m, 2H), 7.13 (dd, J=8.5, 1.7 Hz, 1H), 7.04 (ddd, J=9.1, 4.0, 1.9 Hz, 1H), 5.80-5.73 (m, 1H), 4.71 (d, J=4.1 Hz, 1H), 4.31 (t, J=12.4 Hz, 1H), 3.74-3.53 (m, 1H), 2.63-2.50 (m, 2H), 2.40 (m, 5H), 2.23 (m, 6H), 2.03 (d, J=13.4 Hz, 2H), 2.01-1.91 (m, 2H), 1.86 (d, J=12.3 Hz, 1H), 1.81-1.65 (m, 1H), 1.35 (m, 4H).

To a scintillation vial containing (S)-6-(5-(3,5-dimethylisoxazol-4-yl)-1-((1r,4S)-4-hydroxy cyclohexyl)-1H-benzo[d]imidazol-2-yl)piperidin-2-one (157 mg, 0.384 mmol) in pyridine (3 mL) was added CuTMEDA (89 mg, 0.192 mmol). The reaction mixture was stirred at 40° C. for 15 minutes, then (3,4-difluorophenyl)boronic acid (152 mg, 0.961 mmol) added and the reaction mixture was left to stir at 80° C. for 48 h. The reaction mixture was cooled to RT and partitioned between ethyl acetate (20 mL) and water (10 mL). The organic phase was washed with further portions of water (2×10 mL), dried (MgSO4) and concentrated in vacuo. The crude residue was purified by chromatography (4 g silica, 0-10% MeOH in DCM, gradient elution) to afford (S)-1-(3,4-difluorophenyl)-6-(5-(3,5-dimethylisoxazol-4-yl)-1-((1r,4S)-4-hydroxycyclohexyl)-1H-benzo[d]imidazol-2-yl)piperidin-2-one (54 mg, 27%) as an off white solid; the enantiomers were separated by chiral preparative HPLC (General method D); Rt 1.86 min; m/z 521 (M+H)+ (ES+); 1H NMR (d6-DMSO) δ: 7.76 (d, J=8.5 Hz, 1H), 7.69 (d, J=1.6 Hz, 1H), 7.43-7.27 (m, 2H), 7.13 (dd, J=8.5, 1.7 Hz, 1H), 7.04 (ddd, J=9.1, 4.0, 1.9 Hz, 1H), 5.80-5.73 (m, 1H), 4.71 (d, J=4.1 Hz, 1H), 4.31 (t, J=12.4 Hz, 1H), 3.74-3.53 (m, 1H), 2.63-2.50 (m, 2H), 2.40 (m, 5H), 2.23 (m, 6H), 2.03 (d, J=13.4 Hz, 2H), 2.01-1.91 (m, 2H), 1.86 (d, J=12.3 Hz, 1H), 1.81-1.65 (m, 1H), 1.35 (m, 4H).

Example 175: (S)-1-(3-chloro-4-methoxyphenyl)-6-(5-(3,5-dimethylisoxazol-4-yl)-1-((1r,4S)-4-hydroxycyclohexyl)-1H-benzo[d]imidazol-2-yl)piperidin-2-one (S)-1-(3-chloro-4-methoxyphenyl)-6-(5-(3,5-dimethylisoxazol-4-yl)-1-((1r,4S)-4-hydroxycyclohexyl)-1H-benzo[d]imidazol-2-yl)piperidin-2-one

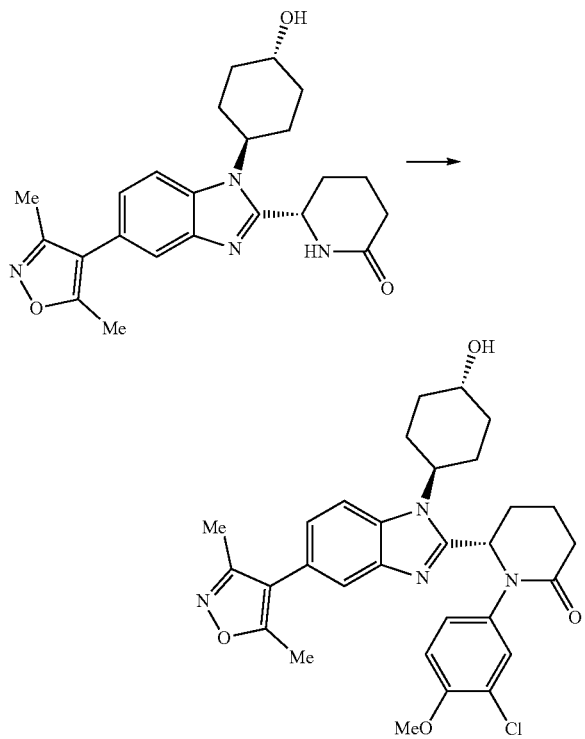

To a scintillation vial containing (S)-6-(5-(3,5-dimethylisoxazol-4-yl)-1-((1r,4S)-4-hydroxycyclohexyl)-1H-benzo[d]imidazol-2-yl)piperidin-2-one (157 mg, 0.384 mmol) in pyridine (3 mL) was added CuTMEDA (89 mg, 0.192 mmol). The reaction mixture was stirred at 40° C. for 15 minutes, then (3,4-dichlorophenyl)boronic acid (183 mg, 0.961 mmol) added and the reaction mixture was left to stir at 80° C. for 48 h.

Example 176: (S)-1-(3,4-difluorophenyl)-5-(1-((1r,4S)-4-hydroxycyclohexyl)-5-(5-(hydroxymethyl)-3-methylisoxazol-4-yl)-1H-benzo[d]imidazol-2-yl)pyrrolidin-2-one Trans-(1r,4r)-4-((4-bromo-2-nitrophenyl)amino)cyclohexanol

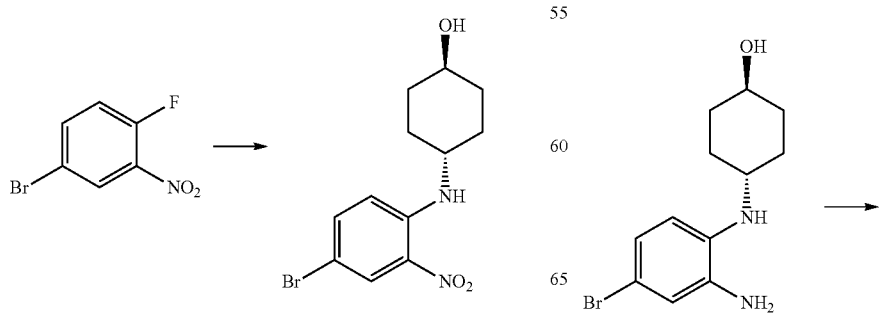

4-Bromo-1-fluoro-2-nitrobenzene (2.85 mL, 23.14 mmol), trans-(1r,4r)-4-aminocyclohexanol (4.00 g, 34.7 mmol) and TEA (6.45 mL, 46.3 mmol) were heated to reflux in THF (83 mL, 1018 mmol) for 48 h. The reaction was cooled down to RT, then the solvents were evaporated in vacuo and the orange residue was partitioned between EtOAc (100 mL) and DCM (100 mL) and saturated aqueous NaHCO$_3$ (100 mL) and the layers separated. The aqueous phase was extracted with further DCM (2×100 mL) and the combined organic extracts washed with water (100 mL) and brine (100 mL). The solution was concentrated onto loose silica gel. The silicate was purified by chromatography on the Companion (80 g column, 0-100% EtOAc/isohexane to afford trans-(1r,4r)-4-((4-bromo-2-nitrophenyl)amino)cyclohexanol (5.79, 78%) was isolated as an orange solid; Rt 2.22 min; m/z 316 (M+H)+ (ES+).

Trans-(1r,4r)-4-((2-amino-4-bromophenyl)amino)cyclohexanol

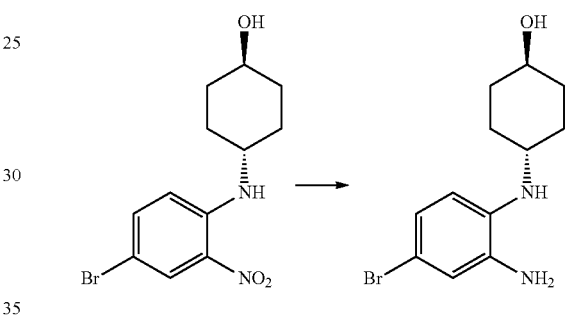

Trans-(1r,4r)-4-((4-bromo-2-nitrophenyl)amino)cyclohexanol (5.79 g, 18.37 mmol) and ammonium hydroxide (11.45 ml, 294 mmol) were dissolved in THF (175 ml, 2131 mmol) and WATER (174 ml, 9682 mmol), SODIUM DITHIONATE (37.9 g, 184 mmol) was added and the reaction mixture stirred at RT overnight. The layers were separated, the aqueous extracted with EtOAc (100 mL), the combined organics washed with brine (50 mL), dried (MgSO$_4$), filtered and evaporated in vacuo to give trans-(1r,4r)-4-((2-amino-4-bromophenyl)amino)cyclohexanol (3.87 g, 72%) as a pink solid; Rt 1.16 min; m/z 285 (M+H)+ (ES+).

(S)—N-(5-bromo-2-((trans-(1r,4r)-4-hydroxycyclohexyl)amino)phenyl)-1-(3,4-difluorophenyl)-5-oxopyrrolidine-2-carboxamide

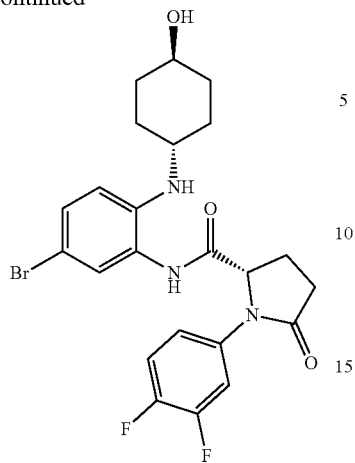

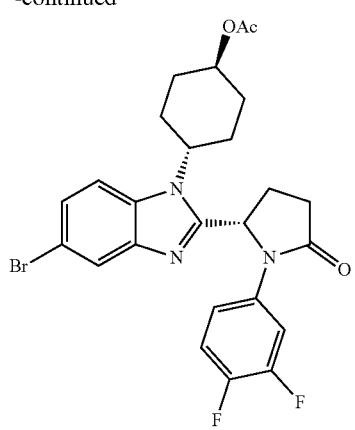

DIPEA (1.646 mL, 9.42 mmol) was added to a solution of trans-(1r,4r)-4-((2-amino-4-bromophenyl)amino)cyclohexanol (1.8 g, 6.31 mmol), (S)-1-(3,4-difluorophenyl)-5-oxopyrrolidine-2-carboxylic acid (1.0 g, 4.15 mmol) and HATU (1.863 g, 4.90 mmol) in DMF (12.55 ml, 162 mmol). The brown solution was stirred at RT for 15 h. The mixture was partitioned between ethyl acetate (100 mL) and water (100 mL), then the layers separated. The organic phase was washed with water (3×100 mL) and with brine (100 mL), concentrated in vacuo to give a crude dark oil (3.3 g), which was purified by flash chromatography on the Companion (40 g column, 0-10% MeOH/DCM) to afford (S)—N-(5-bromo-2-((trans-(1 r,4r)-4-hydroxycyclohexyl)amino)phenyl)-1-(3, 4-difluorophenyl)-5-oxopyrrolidine-2-carboxamide (1.36 g, 68%) as a grey purple foam; Rt 1.98 min; m/z 508 (M+H)+ (ES+).

(S)—N-(5-bromo-2-((trans-(1 r,4r)-4-hydroxycyclohexyl)amino)phenyl)-1-(3,4-difluorophenyl)-5-oxopyrrolidine-2-carboxamide (1.36 g, 2.68 mmol) was dissolved in acetic acid (10.72 mL, 187 mmol) and stirred at 70° C. for 72 h. The reaction was cooled down to RT and concentrated in vacuo. The crude brown oil was purified by flash chromatography on the Companion (4 g, DCM/MeOH: 100/0 to 90/10). The relevant fractions were concentrated and the residue dissolved in DCM (50 mL) and washed with a saturated solution of NaHCO₃ (2*50 mL). The organic was dried on a phase layer separator and concentrated in vacuo to give (S)-5-(5-bromo-1-((1r,4S)-4-hydroxycyclohexyl)-1H-benzo[d]imidazol-2-yl)-1-(3,4-difluorophenyl)pyrrolidin-2-one (365 mg, 26%) was isolated as a beige solid; Rt 2.36 min; m/z 534 (M+H)+ (ES+).

trans-(1r,4r)-4-(5-bromo-2-((S)-1-(3,4-difluorophenyl)-5-oxopyrrolidin-2-yl)-1H-benzo[d]imidazol-1-yl)cyclohexyl acetate trans-(1r,4r)-4-(2-((S)-1-(3,4-difluorophenyl)-5-oxopyrrolidin-2-yl)-5-(4,4,5,5-tetramethyl-1,3,2-dioxaborolan-2-yl)-1H-benzo[d]imidazol-1-yl)cyclohexyl acetate 1555-88

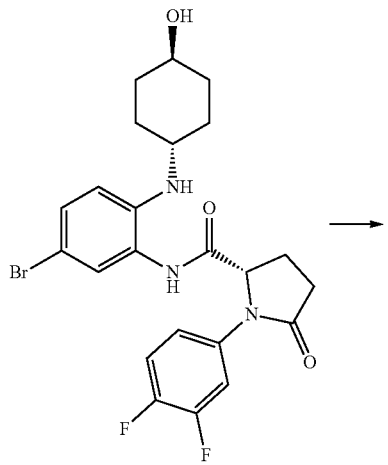

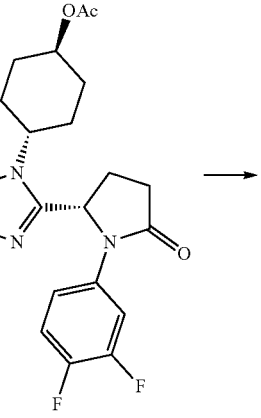

-continued

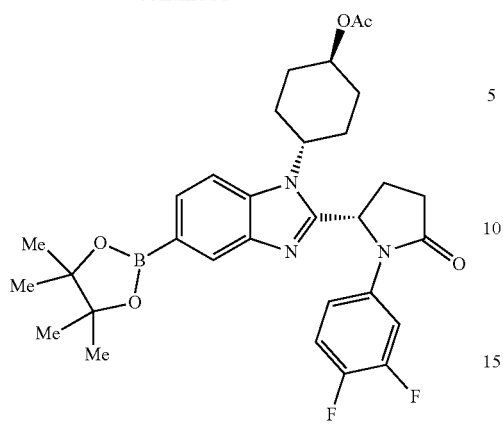

To a solution of trans-(1r,4r)-4-(5-bromo-2-((S)-1-(3,4-difluorophenyl)-5-oxopyrrolidin-2-yl)-1H-benzo[d]imidazol-1-yl)cyclohexyl acetate (0.345 g, 0.648 mmol) and Bis-(pinacolato) diboron (0.247 g, 0.972 mmol) in 1,4-dioxane (5.40 ml, 0.648 mmol) was added potassium dicarbonate (0.204 g, 2.074 mmol) and PdCl$_2$(dppf) (0.045 g, 0.062 mmol). The mixture was degassed with nitrogen and heated at 85° C. for 2 h and then cooled to RT and concentrated in vacuo. The crude product was purified by chromatography on the Companion (12 g column, 0-100% AcOEt/DCM) to afford trans-(1r,4r)-4-(2-((S)-1-(3,4-difluorophenyl)-5-oxopyrrolidin-2-yl)-5-(4,4,5,5-tetramethyl-1,3,2-dioxaborolan-2-yl)-1H-benzo[d]imidazol-1-yl) cyclohexyl acetate (0.244 g, 60%) as a brown solid; Rt 2.45 min; m/z 580 (M+H)+ (ES+).

(4-(1-(trans-(1r,4s)-4-acetoxycyclohexyl)-2-((S)-1-(3,4-difluorophenyl)-5-oxopyrrolidin-2-yl)-1H-benzo[d]imidazol-5-yl)-3-methylisoxazol-5-yl)methyl acetate

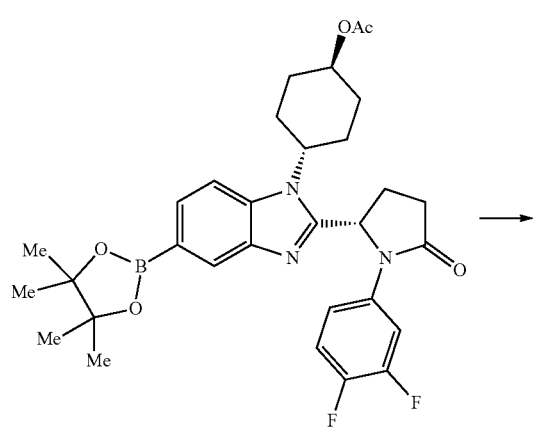

-continued

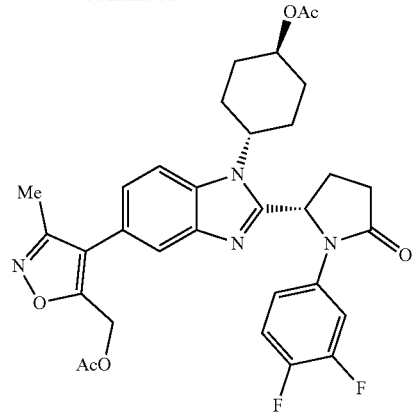

A mixture of water (0.293 ml, 16.26 mmol) and trans-(1r,4r)-4-(2-((S)-1-(3,4-difluorophenyl)-5-oxopyrrolidin-2-yl)-5-(4,4,5,5-tetramethyl-1,3,2-dioxaborolan-2-yl)-1H-benzo[d]imidazol-1-yl)cyclohexyl acetate (0.244 g, 0.421 mmol) and (4-bromo-3-methylisoxazol-5-yl)methyl acetate (0.068 g, 0.292 mmol) in PdCl2 (dppf) (0.021 g, 0.029 mmol) and POTASSIUM CARBONATE (0.121 g, 0.877 mmol) was purged with N2 for 10 mn. 1,4-DIOXANE (1.626 ml, 19.01 mmol) was then added. The reaction mixture was heated at 90° C. for 4.5 h. The reaction was cooled down to RT and concentrated in vacuo. The organic layer was concentrated in vacuo then was purified by flash chromatography (12 g, DCM/MeOH: 100/0 to 90/10) then by flash chromatography column (12 g, DCM/MeOH: 100/0 to 90/10) to afford (4-(1-(trans-(1r,4r)-4-acetoxycyclohexyl)-2-((S)-1-(3,4-difluorophenyl)-5-oxopyrrolidin-2-yl)-1H-benzo[d]imidazol-5-yl)-3-methylisoxazol-5-yl)methyl acetate (100 mg, 39%) was isolated as a brown solid; Rt 2.17 min; m/z 607 (M+H)+ (ES+).

(S)-1-(3,4-difluorophenyl)-5-(1-(((1r,4S)-4-hydroxycyclohexyl)-5-(5-(hydroxymethyl)-3-methylisoxazol-4-yl)-1H-benzo[d]imidazol-2-yl)pyrrolidin-2-one

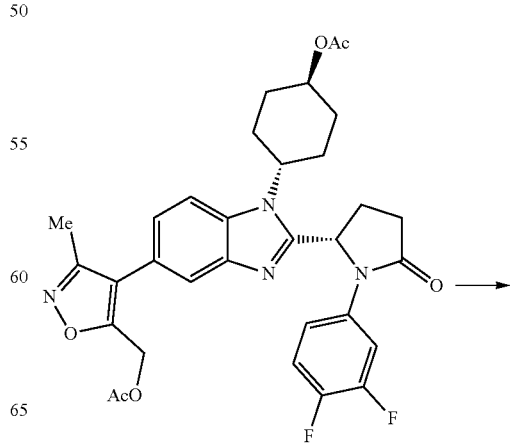

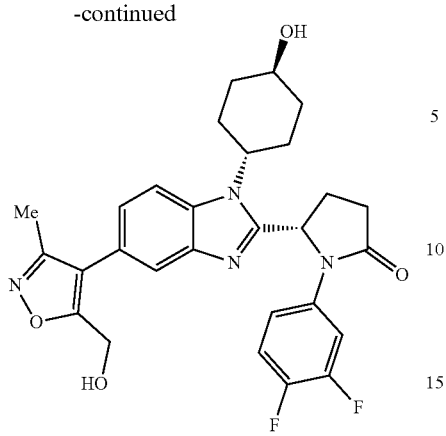

(4-(1-(trans-(1r,4s)-4-acetoxycyclohexyl)-2-((S)-1-(3,4-difluorophenyl)-5-oxopyrrolidin-2-yl)-1H-benzo[d]imidazol-5-yl)-3-methylisoxazol-5-yl)methyl acetate (107 mg, 0.123 mmol) was diluted in MeOH (4.995 mL, 123 mmol). Potassium carbonate (171 mg, 1.235 mmol) was added and the suspension was stirred at RT for 24 h. The reaction mixture was concentrated in vacuo, then the solid was dissolved in DCM (5 mL), sonicated and dry loaded on silica gel. The compound was purified by flash chromatography (DCM/MeOH: 100/0 to 90/10) to give (S)-1-(3,4-difluorophenyl)-5-(1-((1r,4S)-4-hydroxycyclohexyl)-5-(5-(hydroxymethyl)-3-methylisoxazol-4-yl)-1H-benzo[d]imidazol-2-yl)pyrrolidin-2-one (30 mg, 46%) was isolated as a white solid; Rt 1.55 min; m/z 523 (M+H)+ (ES+); 1H NMR (d6-DMSO) δ: 7.88-7.78 (m, 2H), 7.69 (d, J=1.6 Hz, 1H), 7.38 (dt, J=10.7, 9.2 Hz, 1H), 7.28 (dd, J=8.5, 1.7 Hz, 1H), 7.20-7.10 (m, 1H), 6.11 (dd, J=8.2, 2.0 Hz, 1H), 5.42 (t, J=5.5 Hz, 1H), 4.75 (d, J=4.2 Hz, 1H), 4.56-4.39 (m+d, 3H), 3.78-3.66 (m, 1H), 2.82-2.53 (m, 3H), 2.41 (s, 3H), 2.39-2.22 (m, 2H), 2.14-2.04 (m, 1H), 2.04-1.92 (m, 2H), 1.88-1.76 (m, 1H), 1.76-1.68 (m, 1H), 1.59-1.36 (m, 2H).

Example 177: (S)-1-(3,4-difluorophenyl)-5-(1-((1r,4S)-4-hydroxycyclohexyl)-5-(3-(hydroxymethyl)-5-methylisoxazol-4-yl)-1H-benzo[d]imidazol-2-yl)pyrrolidin-2-one (4-(1-((1r,4S)-4-Acetoxycyclohexyl)-2-((S)-1-(3,4-difluorophenyl)-5-oxopyrrolidin-2-yl)-1H-benzo[d]imidazol-5-yl)-5-methylisoxazol-3-yl)methyl acetate

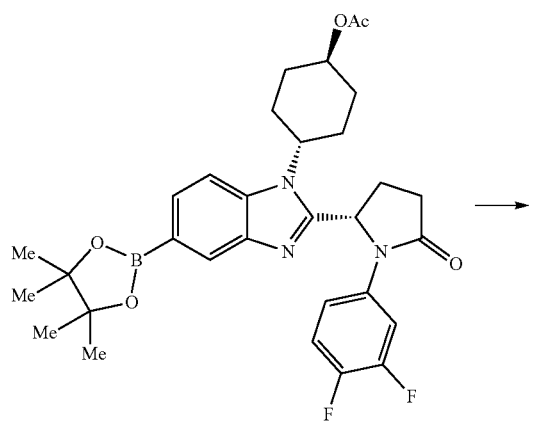

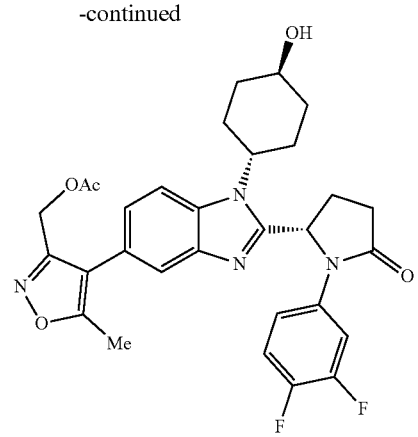

(S)-1-(3,4-difluorophenyl)-5-(1-((1r,4S)-4-hydroxycyclohexyl)-5-(3-(hydroxymethyl)-5-methylisoxazol-4-yl)-1H-benzo[d]imidazol-2-yl)pyrrolidin-2-one

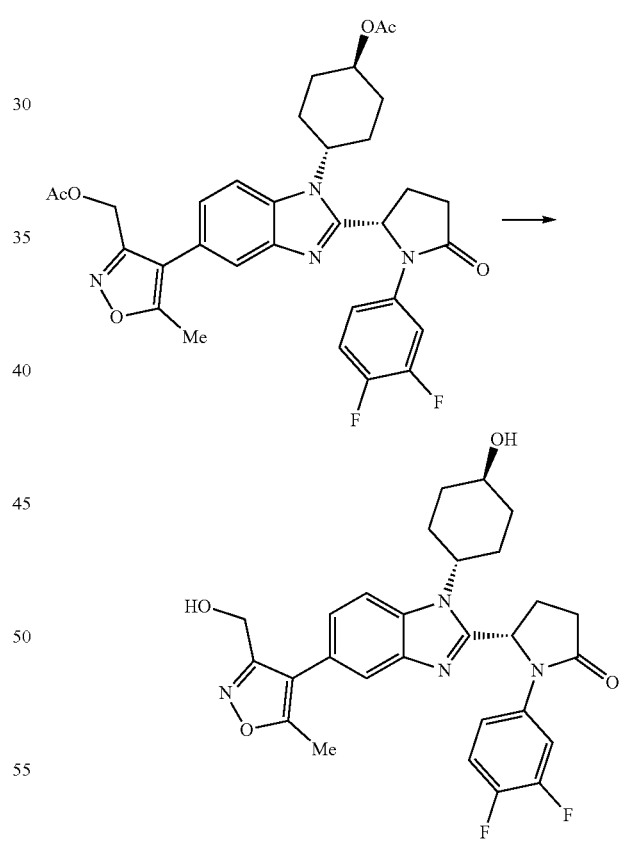

(4-(1-((1r,4S)-4-Acetoxycyclohexyl)-2-((S)-1-(3,4-difluorophenyl)-5-oxopyrrolidin-2-yl)-1H-benzo[d]imidazol-5-yl)-5-methylisoxazol-3-yl)methyl acetate (36.9 mg, 0.054 mmol) was diluted in MeOH (2166 μL, 53.5 mmol). Potassium carbonate (22.19 mg, 0.161 mmol) was added and the suspension was stirred at RT for 2 h. The reaction mixture was concentrated in vacuo and then the solid was dissolved in DCM (5 mL), sonicated and dry loaded on silica gel. The compound was purified by chromatography column (DCM/MeOH: 100/0 to 90/10) to afford (S)-1-(3,4-Difluorophenyl)-5-(1-((1r,4S)-4-hydroxycyclohexyl)-5-(3-(hydroxymethyl)-5-methylisoxazol-4-yl)-1H-benzo[d]imidazol-2-yl)pyrrolidin-2-one (8 mg, 28%) as a white solid; Rt 1.61 min; m/z 523 (M+H)+ (ES+); 1H NMR (d6-DMSO) δ: 7.88-7.77 (m, 2H), 7.69 (d, J=1.6 Hz, 1H), 7.38 (q, J=10.6, 9.2 Hz, 1H), 7.28 (dd, J=8.5, 1.7 Hz, 1H), 7.20-7.10 (m, 1H), 6.11 (dd, J=8.2, 2.0 Hz, 1H), 5.42 (t, J=5.5 Hz, 1H), 4.75 (d, J=4.2 Hz, 1H), 4.54-4.40 (m+d, 3H), 3.77-3.67 (m, 1H), 2.81-2.67 (m, 1H), 2.67-2.53 (m, 1H), 2.41 (s, 3H), 2.38-2.26 (m, 2H), 2.11-2.03 (m, 1H), 2.03-1.91 (m, 3H), 1.85-1.77 (m, 1H), 1.76-1.68 (m, 1H), 1.59-1.39 (m, 2H).

Example 178: (S)-6-(1-(4,4-difluorocyclohexyl)-5-(3,5-dimethylisoxazol-4-yl)-1H-benzo[d]imidazol-2-yl)-1-phenylpiperidin-2-one (S)-6-(1-(4,4-difluorocyclohexyl)-5-(3,5-dimethylisoxazol-4-yl)-1H-benzo[d]imidazol-2-yl)-1-phenylpiperidin-2-one

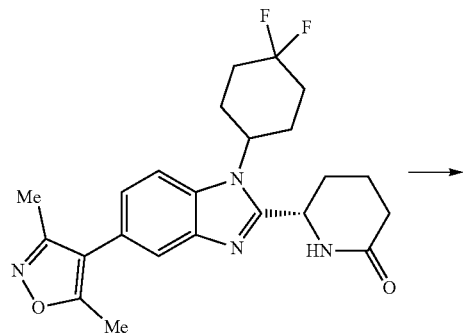

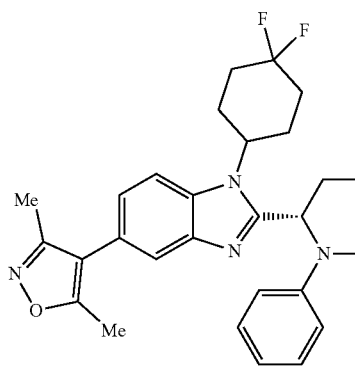

CuTMEDA (60 mg, 0.129 mmol) was added to a stirred suspension of (S)-6-(1-(4,4-difluorocyclohexyl)-5-(3,5-dimethylisoxazol-4-yl)-1H-benzo[d]imidazol-2-yl)piperidin-2-one (70 mg, 0.163 mmol) in pyridine (3 mL) at 40° C. then stirred for 15 minutes. Phenylboronic acid (100 mg, 0.820 mmol) was added then the mixture was stirred at 40° C. overnight. The mixture was diluted with dichloromethane (10 mL) then washed with water (2×15 mL) followed by saturated brine (15 mL). The organic phase was concentrated under reduced pressure then purified by flash chromatography on the Companion (4 g column, 0-50% THF/DCM). The product was triturated in diethyl ether to afford ((S)-6-(1-(4,4-difluorocyclohexyl)-5-(3,5-dimethylisoxazol-4-yl)-1H-benzo[d]imidazol-2-yl)-1-phenylpiperidin-2-one (64 mg, 74%) as a white solid; Rt 2.12 min; m/z 505 (M+H)+ (ES+); 1H NMR (d6-DMSO) δ: 7.73 (dd, J=1.7, 0.6 Hz, 1H), 7.50 (d, J=8.5 Hz, 1H), 7.31-7.09 (m, 6H), 5.76-5.64 (m, 1H), 4.62 (t, J=12.4 Hz, 1H), 2.67-2.52 (m, 2H), 2.45-2.31 (m, 2H), 2.41 (s, 3H), 2.25 (s, 3H), 2.23-1.79 (m, 9H), 1.10-1.01 (m, 1H).

Example 179: (S)-1-(3-chloro-4-methoxyphenyl)-6-(1-(3,3-difluorocyclobutyl)-5-(3,5-dimethylisoxazol-4-yl)-1H-benzo[d]imidazol-2-yl)piperidin-2-one (S)—N-(2-((3,3-difluorocyclobutyl)amino)-5-(3,5-dimethylisoxazol-4-yl)phenyl)-6-oxopiperidine-2-carboxamide

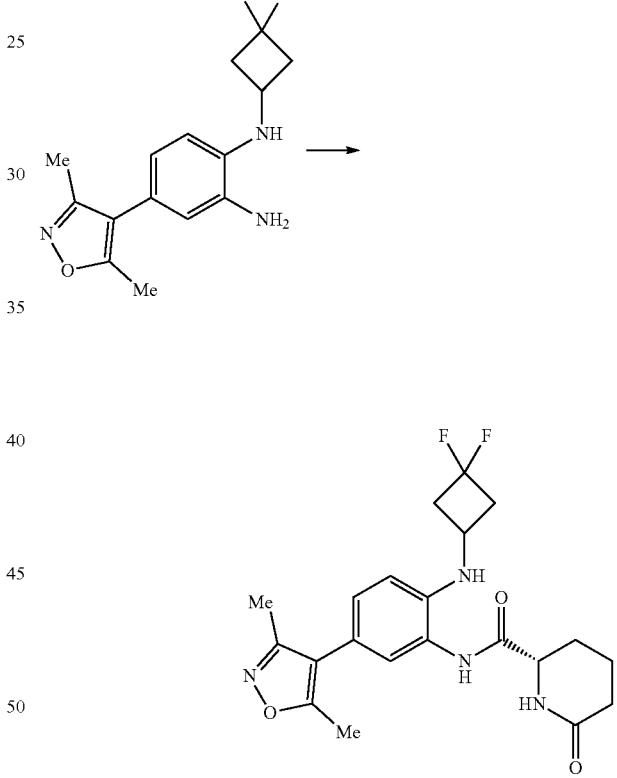

TEA (1.58 mL, 11.35 mmol) was added to a solution of N$^1$-(3,3-difluorocyclobutyl)-4-(3,5-dimethylisoxazol-4-yl)benzene-1,2-diamine (1.11 g, 3.78 mmol), (S)-6-oxopiperidine-2-carboxylic acid (0.596 g, 4.16 mmol) and HATU (1.583 g, 4.16 mmol) in DMF (10 mL) then stirred at RT for 18 h. The mixture was diluted with water (30 mL) then extracted with DCM (100 mL). The organic phase was washed with water (30 mL) then passed through a PhaseSep cartridge and concentrated in vacuo. The residue was purified by flash chromatography to afford (S)—N-(2-((3,3-difluorocyclobutyl)amino)-5-(3,5-dimethylisoxazol-4-yl)phenyl)-6-oxopiperidine-2-carboxamide (751 mg, 46%) as a viscous red brown oil; Rt 1.78 min; m/z 419 (M+H)+ (ES+).

405
(S)-6-(1-(3,3-difluorocyclobutyl)-5-(3,5-dimethyl-isoxazol-4-yl)-1H-benzo[d]imidazol-2-yl)piperidin-2-one

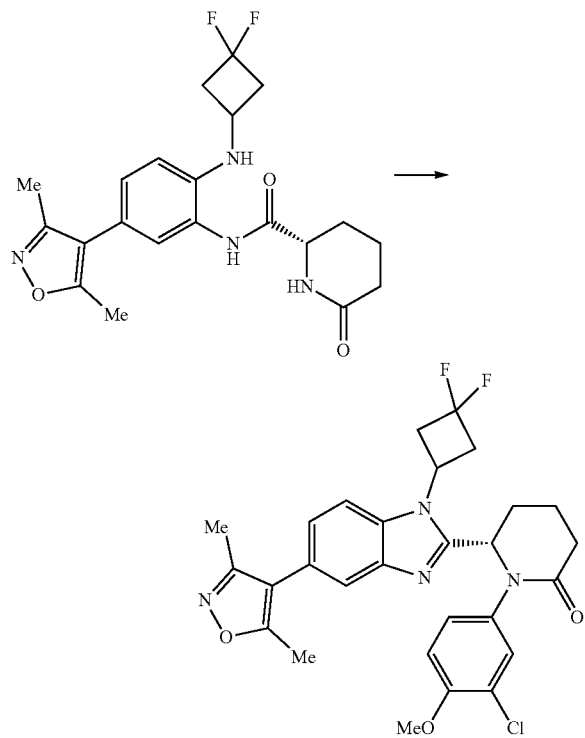

A solution of (S)—N-(2-((3,3-difluorocyclobutyl)amino)-5-(3,5-dimethylisoxazol-4-yl)phenyl)-6-oxopiperidine-2-carboxamide (1.58 g, 3.78 mmol) in acetic acid (5 mL) was heated at 80° C. for 18 h. The solvent was removed in vacuo, the crude product taken up in the minimum of DCM, and purified by chromatography (40 g silica, 0-10% MeOH in DCM, gradient elution). Product fractions were combined and concentrated in vacuo to afford (S)-6-(1-(3,3-difluoro-cyclobutyl)-5-(3,5-dimethylisoxazol-4-yl)-1H-benzo[d]imi-dazol-2-yl)piperidin-2-one (497 mg, 32%) as a beige solid; Rt 1.70 min; m/z 401 (M+H)+ (ES+).

(S)-6-(1-(4,4-difluorocyclohexyl)-5-(3,5-dimethyl-isoxazol-4-yl)-1H-benzo[d]imidazol-2-yl)-1-phenylpiperidin-2-one

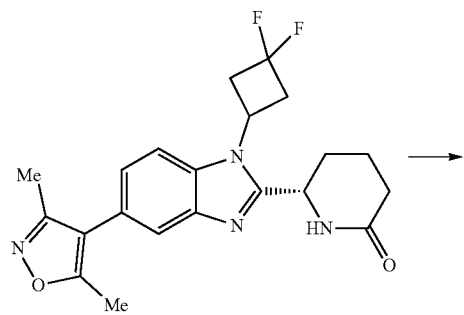

406
-continued

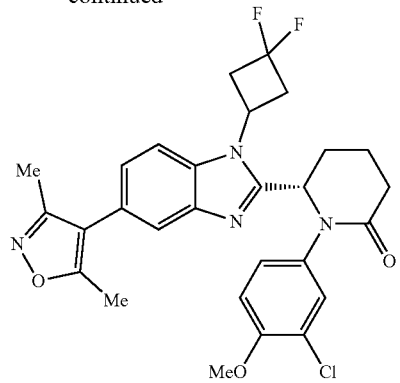

To a scintillation vial containing (S)-6-(1-(3,3-difluoro-cyclobutyl)-5-(3,5-dimethylisoxazol-4-yl)-1H-benzo[d]imi-dazol-2-yl)piperidin-2-one (100 mg, 0.250 mmol) in pyridine (3 mL) was added CuTMEDA (58.0 mg, 0.125 mmol). The reaction mixture was stirred at 40° C. for 15 minutes, then (3-chloro-4-methoxyphenyl)boronic acid (116 mg, 0.624 mmol) added and the reaction mixture was left to stir at 40° C. for 18 hrs. The reaction mixture was cooled to RT and partitioned between ethyl acetate (20 mL) and water (10 mL). The organic phase was washed with further portion of water (2×10 mL), dried (MgSO$_4$) and concentrated in vacuo. The crude residue was purified by chromatography (4 g silica, 0-4% MeOH in DCM, gradient elution) to afford (S)-1-(3-chloro-4-methoxyphenyl)-6-(1-(3,3-difluorocy-clobutyl)-5-(3,5-dimethylisoxazol-4-yl)-1H-benzo[d]imida-zol-2-yl)piperidin-2-one (74 mg, 55%) as a beige solid; Rt 2.17 min; m/z 541 (M+H)+ (ES+); 1H NMR (d6-DMSO) δ: 7.77 (dd, J=1.7, 0.6 Hz, 1H), 7.59 (dd, J=8.5, 0.6 Hz, 1H), 7.36 (d, J=2.5 Hz, 1H), 7.28 (dd, J=8.5, 1.7 Hz, 1H), 7.14 (dd, J=8.8, 2.5 Hz, 1H), 7.01 (d, J=8.9 Hz, 1H), 5.69 (t, J=4.8 Hz, 1H), 5.14 (dq, J=8.8, 3.7 Hz, 1H), 3.76 (s, 3H), 3.57-3.33 (m, 2H), 3.03 (m, 1H), 2.60-2.53 (m, 2H), 2.50-2.31 (m, 2H), 2.41 (s, 3H), 2.24 (s, 3H), 2.08 (d, J=5.6 Hz, 1H), 1.87 (s, 1H), 1.77 (s, 1H).

Example 180: (S)-6-(1-(3,3-difluorocyclobutyl)-5-(3,5-dimethylisoxazol-4-yl)-1H-benzo[d]imidazol-2-yl)-1-(3,4-difluorophenyl)piperidin-2-one (S)-6-(1-(4,4-difluorocyclohexyl)-5-(3,5-dimethyl-isoxazol-4-yl)-1H-benzo[d]imidazol-2-yl)-1-phenylpiperidin-2-one

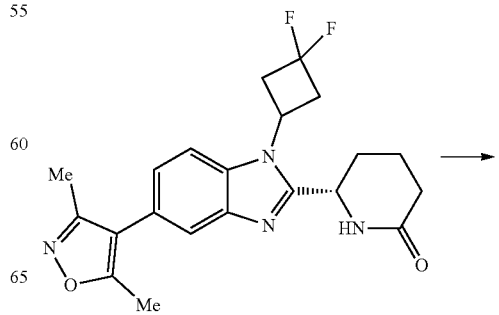

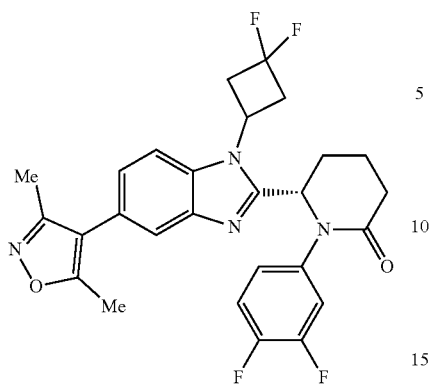

To a scintillation vial containing (S)-6-(1-(3,3-difluorocyclobutyl)-5-(3,5-dimethylisoxazol-4-yl)-1H-benzo[d]imidazol-2-yl)piperidin-2-one (100 mg, 0.250 mmol) in pyridine (3 ml) was added CuTMEDA (58.0 mg, 0.125 mmol). The reaction mixture was stirred at 40° C. for 15 minutes, then (3,4-difluorophenyl)boronic acid (99 mg, 0.624 mmol) added and the reaction mixture was left to stir at 40° C. for 18 h. The reaction mixture was cooled to RT and partitioned between ethyl acetate (20 mL) and water (10 mL). The organic phase was washed with further portion of water (2×10 mL), dried (MgSO₄) and concentrated in vacuo. The crude residue was purified by flash chromatography (4 g silica, 0-4% MeOH in DCM, gradient elution) to afford (S)-6-(1-(3,3-difluorocyclobutyl)-5-(3,5-dimethylisoxazol-4-yl)-1H-benzo[d]imidazol-2-yl)-1-(3,4-difluorophenyl)piperidin-2-one (78 mg, 60%) as an off white solid; Rt 2.18 min; m/z 513 (M+H)+ (ES+); 1H NMR (d6-DMSO) δ: 7.77 (d, J=1.6 Hz, 1H), 7.60 (d, J=8.4 Hz, 1H), 7.43-7.24 (m, 3H), 7.14-7.05 (m, 1H), 5.78-5.69 (m, 1H), 5.14 (td, J=8.5, 3.7 Hz, 1H), 3.58-3.33 (m, 2H), 3.10 (m, 1H), 2.61-2.46 (m, 2H), 2.40 (m, 5H), 2.24 (s, 3H), 2.07 (d, J=4.8 Hz, 1H), 1.83 (m, 1H), 1.77 (m, 1H).

To a scintillation vial containing (S)-6-(1-(3,3-difluorocyclobutyl)-5-(3,5-dimethylisoxazol-4-yl)-1H-benzo[d]imidazol-2-yl)piperidin-2-one (100 mg, 0.250 mmol) in pyridine (3 mL) was added CuTMEDA (58.0 mg, 0.125 mmol). The reaction mixture was stirred at 40° C. for 15 minutes, then (3-fluoro-4-methoxyphenyl)boronic acid (106 mg, 0.624 mmol) added and the reaction mixture was left to stir at 40° C. for 18 h. The reaction mixture was cooled to RT and partitioned between ethyl acetate (20 mL) and water (10 mL). The organic phase was washed with further portion of water (2×10 mL), dried (MgSO₄) and concentrated in vacuo. The crude residue was purified by chromatography (4 g silica, 0-4% MeOH in DCM, gradient elution) to afford (S)-6-(1-(3,3-difluorocyclobutyl)-5-(3,5-dimethylisoxazol-4-yl)-1H-benzo[d]imidazol-2-yl)-1-(3-fluoro-4-methoxyphenyl)piperidin-2-one (85 mg, 64%) as a beige solid; Rt 2.09 min; m/z 525 (M+H)+ (ES+); 1H NMR (d6-DMSO) δ: 7.77 (dd, J=1.7, 0.6 Hz, 1H), 7.60 (d, J=8.5 Hz, 1H), 7.28 (dd, J=8.4, 1.7 Hz, 1H), 7.13 (dd, J=12.7, 2.3 Hz, 1H), 7.08-6.95 (m, 2H), 5.68 (t, J=4.7 Hz, 1H), 5.14 (td, J=8.4, 3.7 Hz, 1H), 3.75 (s, 3H), 3.47 (dt, J=16.8, 8.5 Hz, 1H), 3.36-3.26 (m, 2H), 3.09-2.97 (m, 1H), 2.59-2.41 (m, 2H), 2.41 (s, 3H), 2.36 (m, 1H), 2.24 (s, 3H), 2.07 (d, J=13.0 Hz, 1H), 1.87 (m, 1H), 1.76 (m, 1H).

Example 181: (S)-6-(1-(3,3-difluorocyclobutyl)-5-(3,5-dimethylisoxazol-4-yl)-1H-benzo[d]imidazol-2-yl)-1-(3-fluoro-4-methoxyphenyl)piperidin-2-one (S)-6-(1-(3,3-difluorocyclobutyl)-5-(3,5-dimethylisoxazol-4-yl)-1H-benzo[d]imidazol-2-yl)-1-(3-fluoro-4-methoxyphenyl)piperidin-2-one Example 182: (1S,4r)-methyl 4-(2-((S)-1-(3,4-difluorophenyl)-6-oxopiperidin-2-yl)-5-(3,5-dimethylisoxazol-4-yl)-1H-benzo[d]imidazol-1-yl)cyclohexanecarboxylate (1S,4r)-methyl 4-(2-((S)-1-(3,4-difluorophenyl)-6-oxopiperidin-2-yl)-5-(3,5-dimethylisoxazol-4-yl)-1H-benzo[d]imidazol-1-yl)cyclohexanecarboxylate

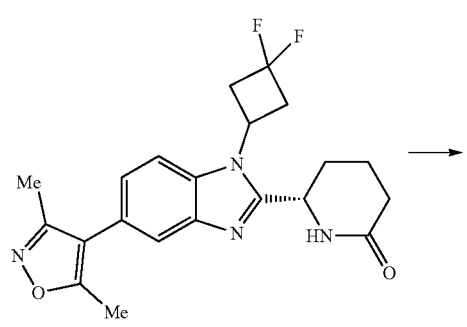

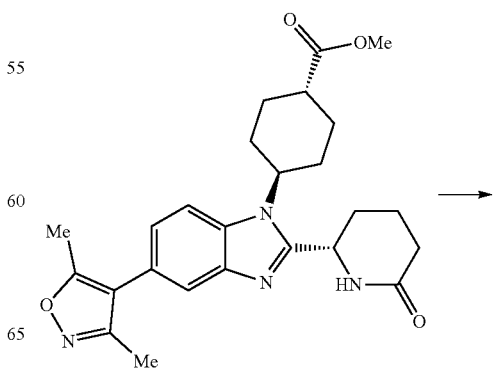

-continued

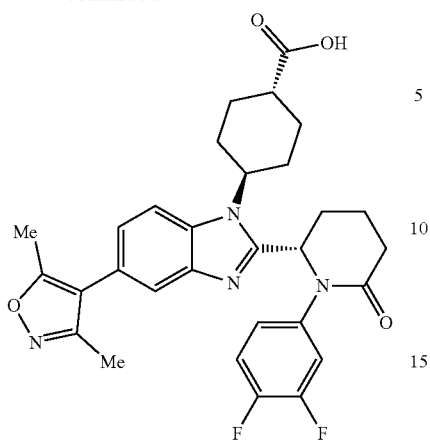

CuTMEDA (0.722 g, 1.554 mmol) was added to a stirred solution of (1S,4r)-methyl 4-(5-(3,5-dimethylisoxazol-4-yl)-2-((S)-6-oxopiperidin-2-yl)-1H-benzo[d]imidazol-1-yl)cyclohexanecarboxylate (1.4 g, 3.11 mmol) in pyridine (37.4 mL, 463 mmol) then the mixture was stirred for 15 min at 40° C. (3,4-Difluorophenyl)boronic acid (1.300 g, 8.23 mmol) was added then the mixture was heated to 40° C. for 2.5 h then stirred at RT overnight. The mixture was concentrated in vacuo to give a green residue which was diluted with ethyl acetate (100 mL) and filtered through a pad of Celite to remove the copper salts. The organic phase was washed with water (3×100 mL) and saturated brine (100 mL), dried (MgSO4), filtered and concentrated under reduced pressure and the crude product was purified by flash chromatography on the Companion (24 g column, DCM/MeOH: 100/0 to 90/10) then repurified by flash chromatography (12 g, DCM/AcOEt: 100/0 to 0/100) to afford (1S,4r)-methyl 4-(2-((S)-1-(3,4-difluorophenyl)-6-oxopiperidin-2-yl)-5-(3,5-dimethylisoxazol-4-yl)-1H-benzo[d]imidazol-1-yl)cyclohexanecarboxylate (1.0 g, 55%) was isolated as a pinkish foam; Rt 2.15 min; m/z 563 (M+H)+ (ES+); 1H NMR (d6-DMSO) δ: 7.85 (d, J=8.4 Hz, 1H), 7.69 (d, J=1.6 Hz, 1H), 7.42-7.28 (m, 2H), 7.14 (dd, J=8.4, 1.7 Hz, 1H), 7.09-7.00 (m, 1H), 5.78 (t, J=4.6 Hz, 1H), 4.44-4.32 (m, 1H), 3.63 (s, 3H), 2.71-2.59 (m, 1H), 2.59-2.43 (m, 2H), 2.40 (s, 3H), 2.39-2.25 (m, 2H), 2.23 (s, 3H), 2.22-2.13 (m, 1H), 2.08-1.99 (m, 2H), 1.99-1.91 (m, 2H), 1.87-1.72 (m, 2H), 1.71-1.56 (m, 2H), 1.28-1.18 (m, 1H).

Example 183: (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)cyclohexane carboxylic acid (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)cyclohexane carboxylic acid

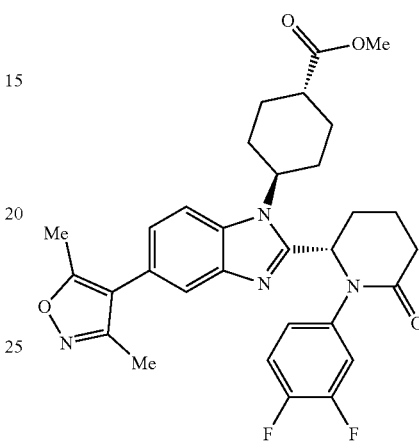

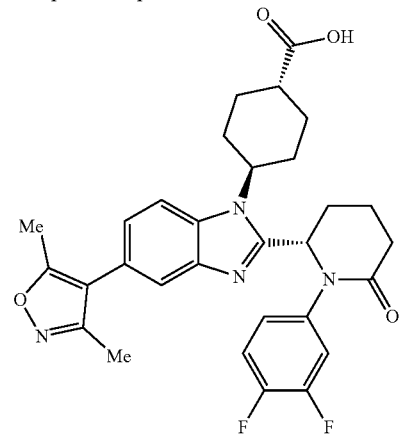

A solution of LiOH (0.054 g, 2.240 mmol) in water (15.85 mL, 880 mmol) was added to a solution of (1S,4r)-methyl 4-(2-((S)-1-(3,4-difluorophenyl)-6-oxopiperidin-2-yl)-5-(3,5-dimethylisoxazol-4-yl)-1H-benzo[d]imidazol-1-yl)cyclohexanecarboxylate (0.900 g, 1.600 mmol) in THF (15.86 mL, 194 mmol). The solution was stirred at 50° C. for 2 hours. At RT, aqueous 1M HCl (3 ml) was added (pH=2). The resulting white solid was filtered, washed with water (3×10 mL), washed with diethyl ether (3×5 mL). The solid was dried under vacuum at 40° C. for 15 hours to afford (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)cyclohexane carboxylic acid (698 mg, 77%) as a white solid; Rt 1.86 min; m/z 549 (M+H)+ (ES+); 1H NMR (d6-DMSO) δ: 12.17 (s, 1H), 7.86 (d, J=8.6 Hz, 1H), 7.70 (d, J=1.6 Hz, 1H), 7.43-7.28 (m, 2H), 7.15 (d, J=8.0 Hz, 1H), 7.09-7.00 (m, 0H), 5.80 (t, 1H), 4.44-4.30 (m, 1H), 2.64-2.45 (m, 2H), 2.41 (s, 3H), 2.39-2.25 (m, 2H), 2.24 (s, 3H), 2.21-2.10 (m, 1H), 2.08-2.00 (m, 2H), 2.00-1.92 (m, 2H), 1.87-1.73 (m, 2H), 1.68-1.53 (m, 2H), 1.28-1.18 (m, 1H).

Example 184: (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)-N-propylcyclohexane carboxamide (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)-N-propylcyclohexane carboxamide

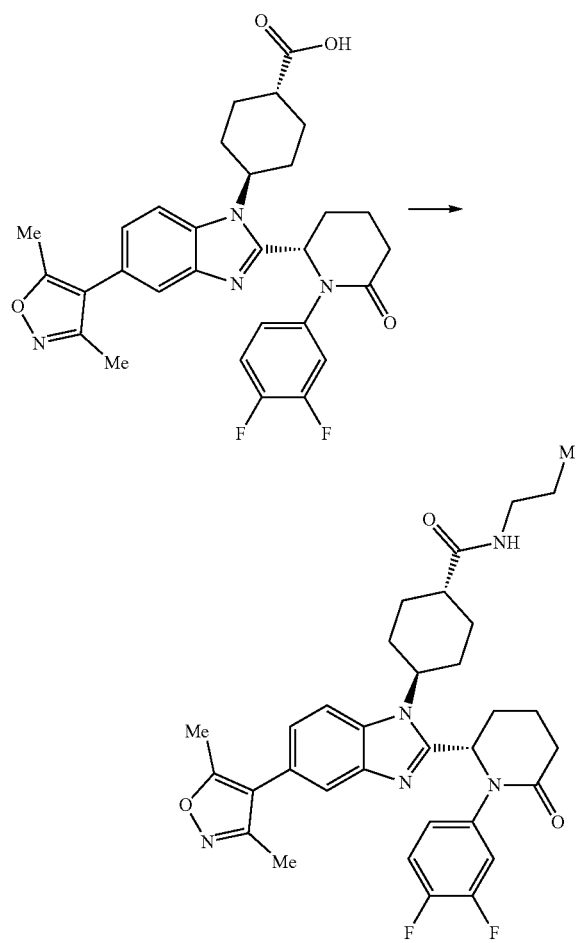

DIPEA (0.040 mL, 0.228 mmol) was added to a solution of propan-1-amine (8.23 µl, 0.100 mmol), (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)cyclohexane carboxylic acid (50 mg, 0.091 mmol) and HATU (45.0 mg, 0.118 mmol) in DMF (0.303 mL, 3.91 mmol). The brown solution was stirred at RT for 15 h, then the reaction mixture was diluted in AcOEt (30 mL) and washed with water (3×20 mL) and with brine (20 mL). The organic was dried on MgSO$_4$, filtered and concentrated in vacuo to give a beige foam as crude material. The crude was purified by flash chromatography on the Companion (4 g, DCM/AcOEt: 100/0 to 0/100) to give (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)-N-propylcyclohexane carboxamide (36 mg, 66% yield) was isolated as a white solid; Rt 1.99 min; m/z 590 (M+H)+ (ES+); 1H NMR (d6-DMSO) δ: 7.77-7.69 (m, 3H), 7.43-7.28 (m, 2H), 7.16 (dd, J=8.5, 1.6 Hz, 1H), 7.09-7.01 (m, 1H), 5.79 (t, J=4.9 Hz, 1H), 4.46-4.31 (m, 1H), 3.02 (q, J=6.5 Hz, 2H), 2.63-2.52 (m, 2H), 2.43-2.39 (m, 3H), 2.39-2.26 (m, 2H), 2.24 (s, 3H), 2.22-1.94 (m, 4H), 1.93-1.74 (m, 4H), 1.74-1.59 (m, 2H), 1.41 (h, J=7.3 Hz, 2H), 1.29-1.20 (m, 1H), 0.84 (t, J=7.4 Hz, 3H).

Example 185: (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)-N-methyl-N-propyl-cyclohexanecarboxamide (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)-N-methyl-N-propylcyclohexanecarboxamide

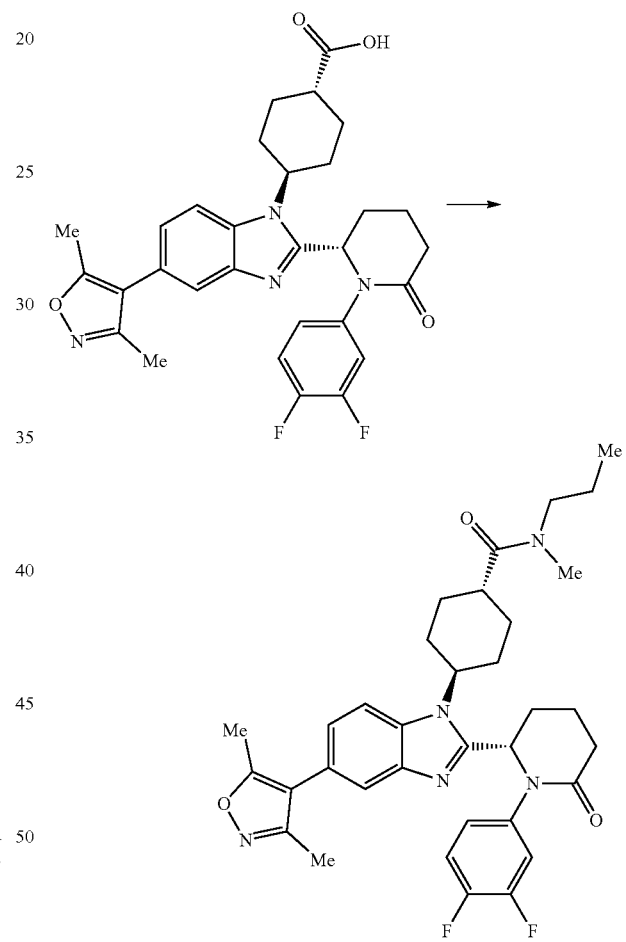

DIPEA (0.040 mL, 0.228 mmol) was added to a solution of N-methylpropan-1-amine (10.27 µl, 0.100 mmol), (1S,4r)-4-(2-((S)-1-(3,4-difluorophenyl)-6-oxopiperidin-2-yl)-5-(3,5-dimethyl isoxazol-4-yl)-1H-benzo[d]imidazol-1-yl)cyclohexanecarboxylic acid (50 mg, 0.091 mmol) and HATU (45.0 mg, 0.118 mmol) in DMF (0.303 mL, 3.91 mmol). The yellow solution was stirred at RT for 2 h. The reaction mixture was diluted in AcOEt (30 mL) and washed with water (3×20 mL) and with brine (20 mL). The organic was dried on MgSO4, filtered and concentrated in vacuo to give a beige foam as crude material, which was purified by flash chromatography on the Companion (4 g, DCM/AcOEt:

100/0 to 0/100) to give ((1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)-N-methyl-N-propylcyclohexanecarboxamide (35.1 mg, 62%) as a yellow glass; Rt 2.12 min; m/z 604 (M+H)+ (ES+); 1H NMR (d6-DMSO) δ: 7.97-7.86 (m, 1H), 7.70 (d, J=1.6 Hz, 1H), 7.44-7.27 (m, 2H), 7.15 (ddd, J=8.5, 4.9, 1.7 Hz, 1H), 7.10-7.00 (m, 1H), 5.88-5.78 (m, 1H), 4.47-4.31 (m, 1H), 3.37 (t, J=7.3 Hz, 1H), 3.30-3.21 (m, 1H), 3.06 (s, 1.6H), 2.96-2.89 (m, 1H), 2.80 (s, 11.4H), 2.60-2.52 (m, 1H), 2.44-2.29 (m+d, 6H), 2.29-2.13 (m+d, 4H), 2.09-1.91 (m, 2H), 1.86-1.61 (m, 6H), 1.61-1.52 (m, 1H), 1.46 (h, J=7.3 Hz, 1H), 1.22-1.13 (m, 1H), 0.91 (t, J=7.3 Hz, 1.4H), 0.81 (t, J=7.4 Hz, 1.6H).

Example 186: (S)-6-(1-(4,4-difluorocyclohexyl)-5-(3,5-dimethylisoxazol-4-yl)-1H-benzo[d]imidazol-2-yl)-1-(6-fluoropyridin-3-yl)piperidin-2-one (S)-6-(1-(4,4-difluorocyclohexyl)-5-(3,5-dimethylisoxazol-4-yl)-1H-benzo[d]imidazol-2-yl)-1-(6-fluoropyridin-3-yl)piperidin-2-one

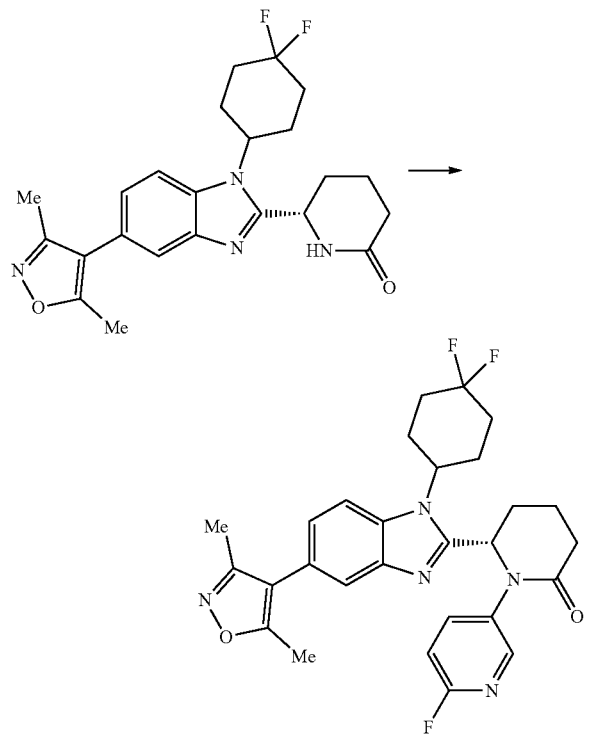

CuTMEDA (60 mg, 0.129 mmol) was added to a stirred suspension of (S)-6-(1-(4,4-difluorocyclohexyl)-5-(3,5-dimethylisoxazol-4-yl)-1H-benzo[d]imidazol-2-yl)piperidin-2-one (70 mg, 0.163 mmol) in pyridine (3 mL) at 40° C. then stirred for 15 minutes. (6-fluoropyridin-3-yl)boronic acid (100 mg, 0.710 mmol) was added then the mixture was stirred at 40° C. overnight. The mixture was diluted with dichloromethane (10 mL) then washed with water (2×15 mL) followed by saturated brine (15 mL). The organic phase was concentrated under reduced pressure then purified by chromatography on the Companion (4 g column, 0-50% THF/DCM). The product was triturated in diethyl ether to afford (S)-6-(1-(4,4-difluorocyclohexyl)-5-(3,5-dimethylisoxazol-4-yl)-1H-benzo[d]imidazol-2-yl)-1-(6-fluoropyridin-3-yl)piperidin-2-one (11 mg, 12%) as a white solid; Rt 2.10 min; m/z 524 (M+H)+ (ES+); 1H NMR (d6-DMSO) δ: 8.16-8.04 (m, 1H), 7.85 (ddd, J=8.7, 7.3, 2.7 Hz, 1H), 7.74 (d, J=1.6 Hz, 1H), 7.54 (d, J=8.5 Hz, 1H), 7.23 (dd, J=8.4, 1.7 Hz, 1H), 7.14 (dd, J=8.7, 3.0 Hz, 1H), 5.77 (t, J=4.6 Hz, 1H), 4.63 (t, J=12.4 Hz, 1H), 2.60 (dt, J=9.2, 5.3 Hz, 2H), 2.50-2.42 (m, 1H), 2.41 (s, 3H), 2.40-2.25 (m, 2H), 2.24 (s, 3H), 2.15 (dd, J=34.4, 15.8 Hz, 5H), 1.96 (d, J=12.1 Hz, 2H), 1.87-1.77 (m, 1H), 1.44-1.36 (m, 1H).

Example 187: (S)-6-(1-(4,4-difluorocyclohexyl)-5-(3,5-dimethylisoxazol-4-yl)-1H-benzo[d]imidazol-2-yl)-1-(5-fluoropyridin-3-yl)piperidin-2-one (S)-6-(1-(4,4-difluorocyclohexyl)-5-(3,5-dimethylisoxazol-4-yl)-1H-benzo[d]imidazol-2-yl)-1-(5-fluoropyridin-3-yl)piperidin-2-one

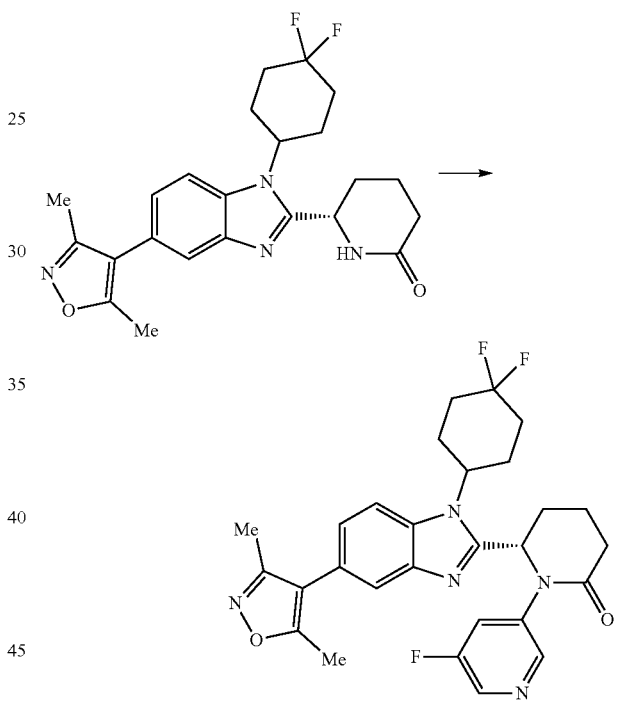

CuTMEDA (60 mg, 0.129 mmol) was added to a stirred suspension of (S)-6-(1-(4,4-difluorocyclohexyl)-5-(3,5-dimethylisoxazol-4-yl)-1H-benzo[d]imidazol-2-yl)piperidin-2-one (70 mg, 0.163 mmol) in pyridine (3 mL) at 40° C. then stirred for 15 minutes. (5-fluoropyridin-3-yl)boronic acid (100 mg, 0.710 mmol) was added then the mixture was stirred at 40° C. overnight. The mixture was diluted with dichloromethane (10 mL) then washed with water (2×15 mL) followed by saturated brine (15 mL). The organic phase was concentrated under reduced pressure then purified by chromatography on the Companion (4 g column, 0-50% THF/DCM). The product was triturated in diethyl ether to afford (S)-6-(1-(4,4-difluorocyclohexyl)-5-(3,5-dimethylisoxazol-4-yl)-1H-benzo[d]imidazol-2-yl)-1-(5-fluoro pyridin-3-yl)piperidin-2-one (5 mg, 6%) as a white solid; Rt 2.06 min; m/z 524 (M+H)+ (ES+); 1H NMR (d6-DMSO) δ: 8.38 (d, J=2.6 Hz, 1H), 8.34 (t, J=1.7 Hz, 1H), 7.75-7.72 (m, 1H), 7.69 (ddd, J=10.3, 2.7, 1.9 Hz, 1H), 7.54 (d, J=8.5 Hz, 1H), 7.23 (dd, J=8.5, 1.7 Hz, 1H), 5.85 (t, J=4.6 Hz, 1H), 4.73-4.55 (m, 1H), 2.66-2.53 (m, 2H), 2.47-2.26 (m, 3H), 2.41 (s, 3H), 2.24 (s, 3H), 2.13 (t, J=23.0 Hz, 5H), 1.98 (d, J=12.8 Hz, 2H), 1.82 (s, 1H), 1.42 (d, J=12.5 Hz, 1H).

Example 188: (S)-6-(1-(4,4-difluorocyclohexyl)-5-(3,5-dimethylisoxazol-4-yl)-1H-benzo[d]imidazol-2-yl)-1-(pyridin-3-yl)piperidin-2-one (S)-6-(1-(4,4-difluorocyclohexyl)-5-(3,5-dimethylisoxazol-4-yl)-1H-benzo[d]imidazol-2-yl)-1-(pyridin-3-yl)piperidin-2-one

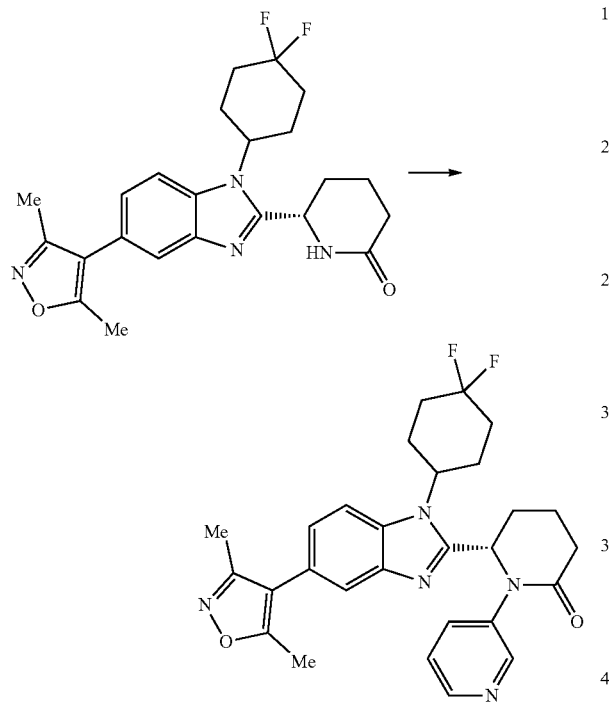

CuTMEDA (60 mg, 0.129 mmol) was added to a stirred suspension of (S)-6-(1-(4,4-difluorocyclohexyl)-5-(3,5-dimethylisoxazol-4-yl)-1H-benzo[d]imidazol-2-yl)piperidin-2-one (100 mg, 0.233 mmol) in pyridine (3 mL) at 40° C. then stirred for 15 minutes. pyridin-3-ylboronic acid (100 mg, 0.814 mmol) was added then the mixture was stirred at 40° C. overnight. The mixture was diluted with dichloromethane (10 mL) then washed with water (2×15 mL) followed by saturated brine (15 mL). The organic phase was concentrated under reduced pressure then purified by chromatography on the Companion (4 g column, 0-50% THF/DCM) then purified by preparative HPLC (Waters, Acidic (0.1% Formic acid), Acidic, Waters X-Select Prep-C18, 5 μm, 19×50 mm column, 25-70% MeCN in Water) to (S)-6-(1-(4,4-difluorocyclohexyl)-5-(3,5-dimethylisoxazol-4-yl)-1H-benzo[d]imidazol-2-yl)-1-(pyridin-3-yl)piperidin-2-one (26 mg, 21%) as a white solid; Rt 1.87 min; m/z 506 (M+H)+ (ES+); 1H NMR (d6-DMSO) δ: 8.43 (dd, J=2.5, 0.7 Hz, 1H), 8.32 (dd, J=4.7, 1.5 Hz, 1H), 7.74 (d, J=1.6 Hz, 1H), 7.65 (ddd, J=8.2, 2.5, 1.5 Hz, 1H), 7.52 (d, J=8.5 Hz, 1H), 7.33 (ddd, J=8.1, 4.7, 0.8 Hz, 1H), 7.22 (dd, J=8.5, 1.7 Hz, 1H), 5.79 (t, J=4.6 Hz, 1H), 4.72-4.56 (m, 1H), 2.66-2.52 (m, 2H), 2.49-2.42 (m, 1H), 2.41 (s, 3H), 2.40-2.25 (m, 2H), 2.24 (s, 3H), 2.22-1.90 (m, 7H), 1.83 (s, 1H), 1.33-1.17 (m, 1H).

Example 195: (S)-6-(1-(4,4-difluorocyclohexyl)-5-(3,5-dimethylisoxazol-4-yl)-1H-benzo[d]imidazol-2-yl)-1-(pyrimidin-5-yl)piperidin-2-one (S)-6-(1-(4,4-difluorocyclohexyl)-5-(3,5-dimethylisoxazol-4-yl)-1H-benzo[d]imidazol-2-yl)-1-(pyrimidin-5-yl)piperidin-2-one

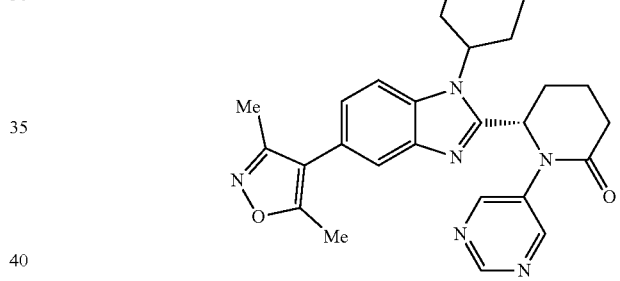

CuTMEDA (27.1 mg, 0.058 mmol) was added to a stirred solution of (S)-6-(1-(4,4-difluorocyclohexyl)-5-(3,5-dimethylisoxazol-4-yl)-1H-benzo[d]imidazol-2-yl)piperidin-2-one (50 mg, 0.117 mmol) in PYRIDINE (2 ml, 24.73 mmol) then the mixture was stirred for 15 min at 40° C. pyrimidin-5-ylboronic acid (38.3 mg, 0.309 mmol) was added then the mixture was heated to 40° C. for 2 h. The mixture was diluted with ethyl acetate (25 mL) then washed with water (3×25 mL) and saturated brine (25 mL). The mixture was concentrated under reduced pressure then the crude product was purified by chromatography on silica gel (24 g column, 0-10% MeOH/DCM) to afford ((S)-6-(1-(4,4-difluorocyclohexyl)-5-(3,5-dimethylisoxazol-4-yl)-1H-benzo[d]imidazol-2-yl)-1-(pyrimidin-5-yl)piperidin-2-one (8 mg, 13%) as a colourless solid; Rt 1.96 min; m/z 507 (M+H)+ (ES+); 1H NMR (d6-DMSO) δ: 8.94 (s, 1H), 8.74 (s, 2H), 7.77-7.67 (m, 1H), 7.54 (d, J=8.5 Hz, 1H), 7.23 (dd, J=8.5, 1.7 Hz, 1H), 5.89 (t, J=4.5 Hz, 1H), 4.77-4.54 (m, 1H), 2.66-2.58 (m, 2H), 2.48-2.44 (m, 2H), 2.40 (s, 3H), 2.37-2.26 (m, 2H), 2.24 (s, 3H), 2.21-2.05 (m, 4H), 2.05-1.80 (m, 3H), 1.56-1.43 (m, 1H).

General Route E: Non-Convergent Approach to Azabenzimidazole Analogues

Example 189 (S)-1-(3-chloro-4-methoxyphenyl)-6-(6-(3,5-dimethylisoxazol-4-yl)-3-((1r,4S)-4-hydroxycyclohexyl)-3H-imidazo[4,5-b]pyridin-2-yl)piperidin-2-one (S)-1-(3-chloro-4-methoxyphenyl)-6-(6-(3,5-dimethylisoxazol-4-yl)-3-((1r,4S)-4-hydroxycyclohexyl)-3H-imidazo[4,5-b]pyridin-2-yl)piperidin-2-one Example 190: (S)-1-(3,4-difluorophenyl)-6-(6-(3,5-dimethylisoxazol-4-yl)-3-((1r,4S)-4-hydroxycyclohexyl)-3H-imidazo[4,5-b]pyridin-2-yl)piperidin-2-one (S)-1-(3-chloro-4-methoxyphenyl)-6-(6-(3,5-dimethylisoxazol-4-yl)-3-((1r,4S)-4-hydroxycyclohexyl)-3H-imidazo[4,5-b]pyridin-2-yl)piperidin-2-one

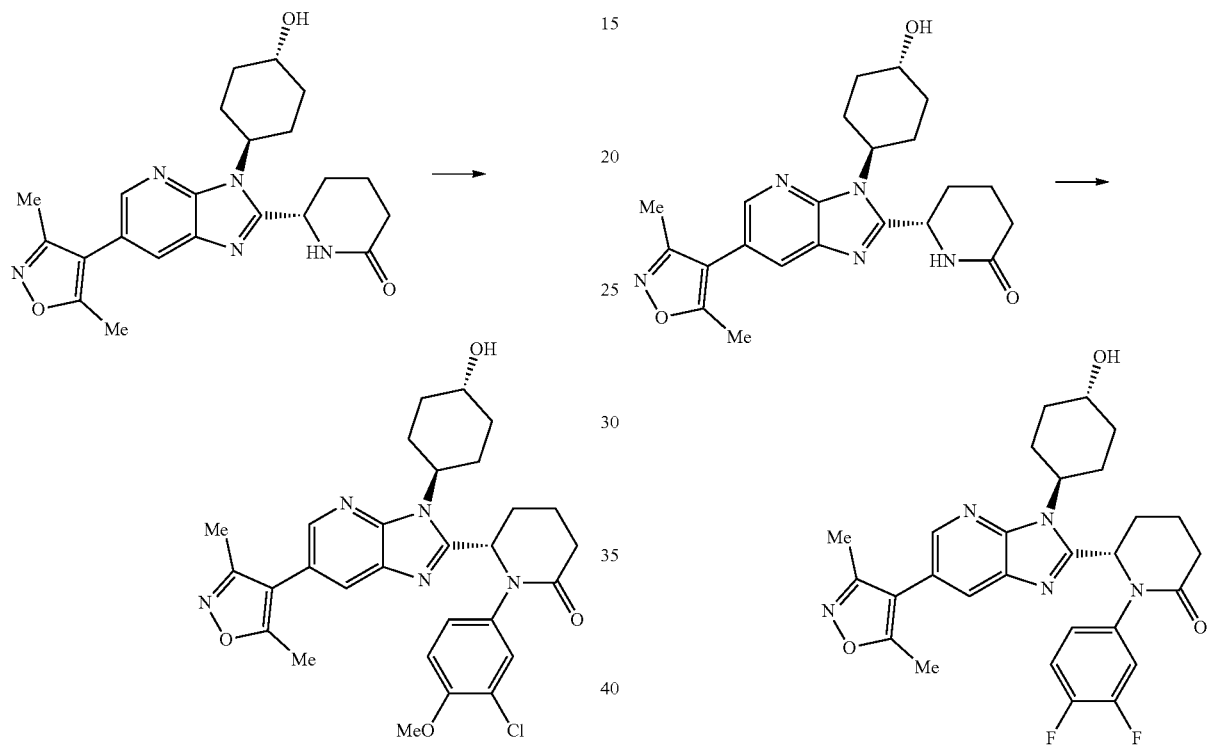

To a scintillation vial containing (S)-6-(6-(3,5-dimethylisoxazol-4-yl)-3-((1r,4S)-4-hydroxycyclohexyl)-3H-imidazo[4,5-b]pyridin-2-yl)piperidin-2-one (100 mg, 0.244 mmol) in pyridine (3 ml) was added CuTMEDA (56.7 mg, 0.122 mmol). The reaction mixture was stirred at 40° C. for 15 minutes, then (3-chloro-4-methoxyphenyl)boronic acid (114 mg, 0.611 mmol) added and the reaction mixture was left to stir at 40° C. for 18 hrs. The reaction mixture was cooled to rt and partitioned between ethyl acetate (20 mL) and water (10 mL). The organic phase was washed with further portion of water (2×10 mL), dried (MgSO4) and concentrated in vacuo. The crude residue was purified by chromatography (4 g silica, 0-10% MeOH in DCM, gradient elution). Product fractions were combined and concentrated in vacuo. The residue was triturated with ether to afford (S)-1-(3-chloro-4-methoxyphenyl)-6-(6-(3,5-dimethylisoxazol-4-yl)-3-((1r,4S)-4-hydroxycyclohexyl)-3H-imidazo[4,5-b]pyridin-2-yl)piperidin-2-one (66 mg, 49%) as a beige solid; Rt 1.76 min; m/z 550 (M+H)+ (ES+); 1H NMR (d6-DMSO) δ: 8.30 (d, J=2.0 Hz, 1H), 8.17 (d, J=2.0 Hz, 1H), 7.39 (d, J=2.4 Hz, 1H), 7.10 (dd, J=8.8, 2.5 Hz, 1H), 7.01 (d, J=8.9 Hz, 1H), 5.79 (t, J=4.8 Hz, 1H), 4.70 (d, J=4.1 Hz, 1H), 4.35 (m, 1H), 3.76 (s, 3H), 3.52 (m, 1H), 2.69-2.46 (m, 3H), 2.42 (s, 3H), 2.38 (m, 1H), 2.25 (s, 3H), 2.06 (m, 2H), 1.95 (d, J=12.5 Hz, 1H), 1.83 (m, 3H), 1.72 (d, J=12.5 Hz, 1H), 1.39 (m, 2H), 1.16-1.06 (m, 1H).

To a scintillation vial containing (S)-6-(6-(3,5-dimethylisoxazol-4-yl)-3-((1r,4S)-4-hydroxycyclohexyl)-3H-imidazo[4,5-b]pyridin-2-yl)piperidin-2-one (100 mg, 0.244 mmol) in pyridine (3 ml) was added CuTMEDA (56.7 mg, 0.122 mmol). The reaction mixture was stirred at 40° C. for 15 minutes, then (3,4-difluorophenyl)boronic acid (96 mg, 0.611 mmol) added and the reaction mixture was left to stir at 40° C. for 18 hrs. The reaction mixture was cooled to rt and partitioned between ethyl acetate (20 mL) and water (10 mL). The organic phase was washed with further portion of water (2×10 mL), dried (MgSO4) and concentrated in vacuo. The crude residue was purified by chromatography (4 g silica, 0-10% MeOH in DCM, gradient elution). Product fractions were combined and concentrated in vacuo. The residue was triturated with ether to afford (S)-1-(3,4-difluorophenyl)-6-(6-(3,5-dimethylisoxazol-4-yl)-3-((1r,4S)-4-hydroxycyclohexyl)-3H-imidazo[4,5-b]pyridin-2-yl)piperidin-2-one (61 mg, 47%) as a cream solid; Rt 1.77 min; m/z 522 (M+H)+ (ES+); 1H NMR (d6-DMSO) δ: 8.31 (d, J=2.0 Hz, 1H), 8.17 (d, J=2.0 Hz, 1H), 7.45-7.29 (m, 2H), 7.10-7.01 (m, 1H), 5.82 (t, J=4.5 Hz, 1H), 4.71 (d, J=4.2 Hz, 1H), 4.35 (m, 1H), 3.53 (m, 1H), 2.67-2.48 (m, 2H), 2.48-2.36 (m, 4H), 2.25 (s, 3H), 2.07 (m, 1H), 1.96 (d, J=12.2 Hz, 2H), 1.87 (d, J=12.0 Hz, 1H), 1.76 (t, J=15.8 Hz, 3H), 1.38 (m, 3H), 1.20 (d, J=12.5 Hz, 1H).

Example 191: (S)-6-(6-(3,5-dimethylisoxazol-4-yl)-3-((1r,4S)-4-hydroxycyclohexyl)-3H-imidazo[4,5-b]pyridin-2-yl)-1-(3-fluoro-4-methoxyphenyl)piperidin-2-one (S)-6-(6-(3,5-dimethylisoxazol-4-yl)-3-((1r,4S)-4-hydroxycyclohexyl)-3H-imidazo[4,5-b]pyridin-2-yl)-1-(3-fluoro-4-methoxyphenyl)piperidin-2-one

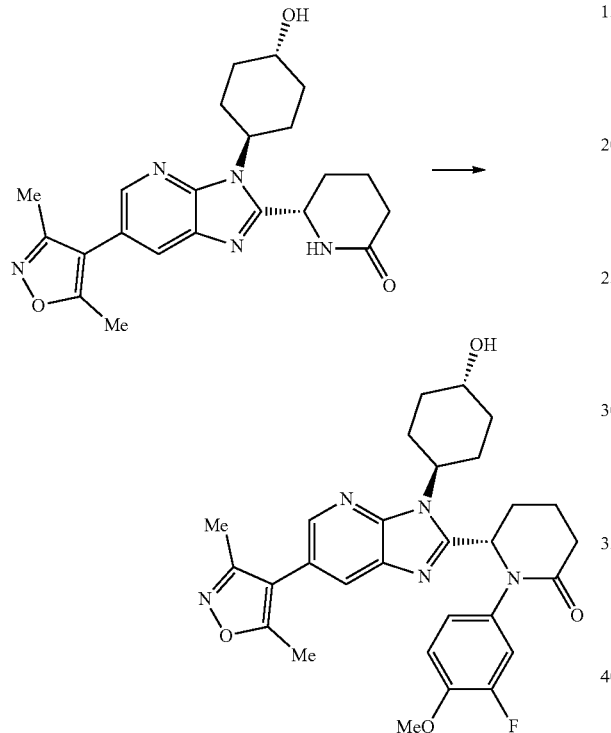

To a scintillation vial containing (S)-6-(6-(3,5-dimethylisoxazol-4-yl)-3-((1r,4S)-4-hydroxycyclohexyl)-3H-imidazo[4,5-b]pyridin-2-yl)piperidin-2-one (100 mg, 0.244 mmol) in pyridine (3 ml) was added CuTMEDA (56.7 mg, 0.122 mmol). The reaction mixture was stirred at 40° C. for 15 minutes, then (3-fluoro-4-methoxyphenyl)boronic acid (104 mg, 0.611 mmol) added and the reaction mixture was left to stir at 40° C. for 18 hrs. The reaction mixture was cooled to rt and partitioned between ethyl acetate (20 mL) and water (10 mL). The organic phase was washed with further portion of water (2×10 mL), dried (MgSO4) and concentrated in vacuo. The crude residue was purified by chromatography (4 g silica, 0-10% MeOH in DCM, gradient elution). Product fractions were combined and concentrated in vacuo. The residue was triturated with ether to afford (S)-6-(6-(3,5-dimethylisoxazol-4-yl)-3-((1r,4S)-4-hydroxycyclohexyl)-3H-imidazo[4,5-b]pyridin-2-yl)-1-(3-fluoro-4-methoxyphenyl) piperidin-2-one (59 mg, 45%) as a beige solid; Rt 1.70 min; m/z 534 (M+H)+ (ES+); 1H NMR (d6-DMSO) δ: 8.31 (d, J=2.0 Hz, 1H), 8.18 (d, J=2.0 Hz, 1H), 7.15 (dd, J=12.7, 2.4 Hz, 1H), 7.09-6.93 (m, 2H), 5.77 (t, J=4.6 Hz, 1H), 4.71 (d, J=4.1 Hz, 1H), 4.34 (s, 1H), 3.75 (s, 3H), 3.52 (m, 1H), 2.67-2.37 (m, 4H), 2.43 (s, 3H), 2.26 (s, 3H), 2.05 (m, 2H), 1.96 (d, J=12.9 Hz, 1H), 1.90-1.78 (m, 2H), 1.74 (d, J=13.2 Hz, 1H), 1.38 (t, J=13.6 Hz, 2H), 1.11 (m, 2H).

Example 192: (S)-1-(3-chloro-4-methoxyphenyl)-5-(3-(4,4-difluorocyclohexyl)-6-(3,5-dimethylisoxazol-4-yl)-3H-imidazo[4,5-b]pyridin-2-yl)pyrrolidin-2-one (S)-6-(6-(3,5-dimethylisoxazol-4-yl)-3-((1r,4S)-4-hydroxycyclohexyl)-3H-imidazo[4,5-b]pyridin-2-yl)-1-(3-fluoro-4-methoxyphenyl) pyrrolidin-2-one

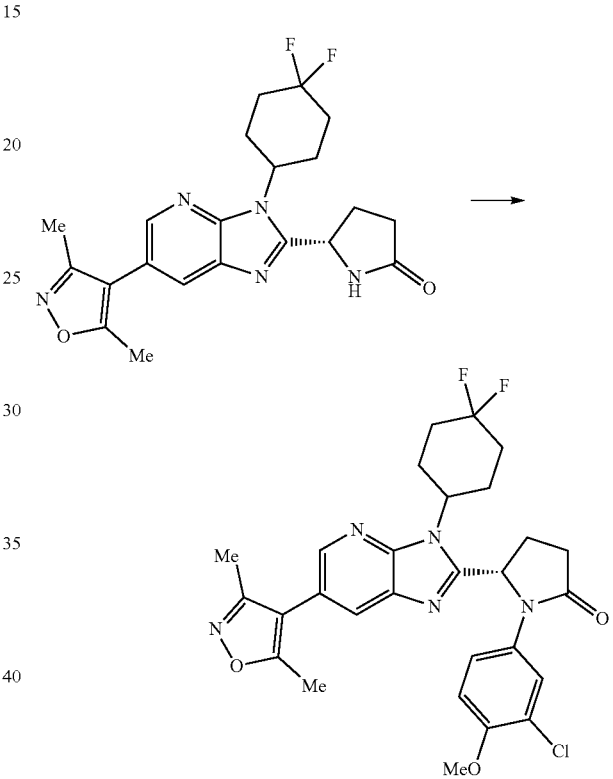

To a scintillation vial containing (S)-5-(3-(4,4-difluorocyclohexyl)-6-(3,5-dimethylisoxazol-4-yl)-3H-imidazo[4,5-b]pyridin-2-yl)pyrrolidin-2-one (100 mg, 0.241 mmol) in pyridine (3 ml) was added CuTMEDA (55.9 mg, 0.120 mmol). The reaction mixture was stirred at 40° C. for 15 minutes, then (3-chloro-4-methoxyphenyl)boronic acid (112 mg, 0.602 mmol) added and the reaction mixture was left to stir at 40° C. for 18 hrs. The reaction mixture was cooled to rt and partitioned between ethyl acetate (20 mL) and water (10 mL). The organic phase was washed with further portion of water (2×10 mL), dried (MgSO4) and concentrated in vacuo. The crude residue was purified by chromatography (4 g silica, 0-10% MeOH in DCM, gradient elution). Product fractions were combined and concentrated in vacuo. The residue was triturated with ether to afford (S)-1-(3-chloro-4-methoxyphenyl)-5-(3-(4,4-difluorocyclohexyl)-6-(3,5-dimethylisoxazol-4-yl)-3H-imidazo[4,5-b]pyridin-2-yl)pyrrolidin-2-one (33 mg, 24%) as a brown solid; Rt 2.35 min; m/z 556 (M+H)+ (ES+); 1H NMR (d6-DMSO) δ: 1H NMR (400 MHz, DMSO-d6) δ 8.34 (d, J=2.0 Hz, 1H), 8.10 (d, J=2.0 Hz, 1H), 7.81 (d, J=2.6 Hz, 1H), 7.28 (dd, J=9.0, 2.6 Hz, 1H), 7.08 (d, J=9.1 Hz, 1H), 6.09 (dd, J=8.3, 2.2 Hz, 1H), 4.78 (s, 1H), 3.77 (s, 3H), 2.93 (dt, J=23.5, 11.8 Hz, 2H), 2.83-2.50 (m, 3H), 2.39 (s, 3H), 2.23-2.08 (m, 8H), 1.95 (d, J=12.7 Hz, 1H), 1.68 (d, J=12.4 Hz, 1H).

Example 193: (S)-5-(3-(4,4-difluorocyclohexyl)-6-(3,5-dimethylisoxazol-4-yl)-3H-imidazo[4,5-b]pyridin-2-yl)-1-(3,4-difluorophenyl)pyrrolidin-2-one (S)-6-(6-(3,5-dimethylisoxazol-4-yl)-3-((1r,4S)-4-hydroxycyclohexyl)-3H-imidazo[4,5-b]pyridin-2-yl)-1-(3-fluoro-4-methoxyphenyl) pyrrolidin-2-one

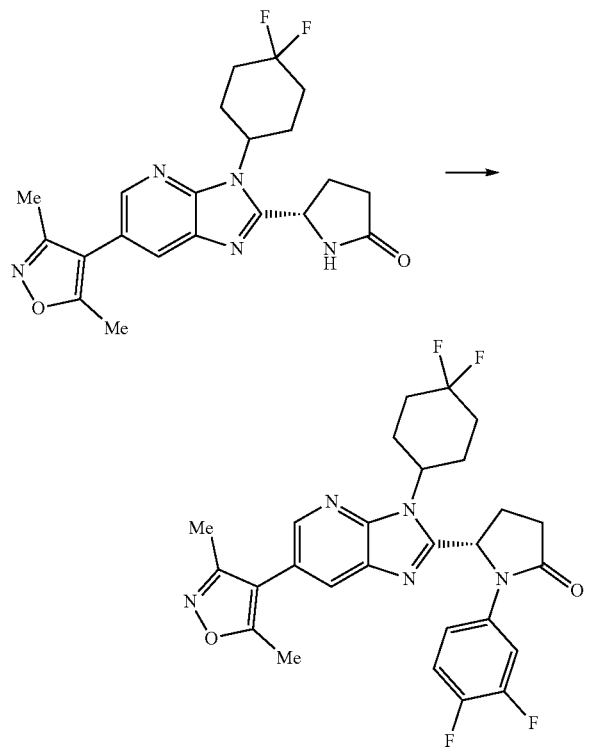

To a scintillation vial containing (S)-5-(3-(4,4-difluorocyclohexyl)-6-(3,5-dimethylisoxazol-4-yl)-3H-imidazo[4,5-b]pyridin-2-yl)pyrrolidin-2-one (100 mg, 0.241 mmol) in pyridine (3 ml) was added CuTMEDA (55.9 mg, 0.120 mmol). The reaction mixture was stirred at 40° C. for 15 minutes, then (3,4-difluorophenyl)boronic acid (95 mg, 0.602 mmol) added and the reaction mixture was left to stir at 40° C. for 18 hrs. The reaction mixture was cooled to rt and partitioned between ethyl acetate (20 mL) and water (10 mL). The organic phase was washed with further portion of water (2×10 mL), dried (MgSO4) and concentrated in vacuo. The crude residue was purified by chromatography (4 g silica, 0-10% MeOH in DCM, gradient elution). Product fractions were combined and concentrated in vacuo. The residue was triturated with ether to afford (S)-5-(3-(4,4-difluorocyclohexyl)-6-(3,5-dimethylisoxazol-4-yl)-3H-imidazo[4,5-b]pyridin-2-yl)-1-(3,4-difluorophenyl)pyrrolidin-2-one (70 mg, 55%) as a light pink solid; Rt 2.39 min; m/z 528 (M+H)+ (ES+); 1H NMR (d6-DMSO) δ: 1H NMR (400 MHz, DMSO-d6) δ 8.35 (d, J=2.0 Hz, 1H), 8.09 (d, J=2.0 Hz, 1H), 7.87 (ddd, J=13.2, 7.4, 2.7 Hz, 1H), 7.39 (dt, J=10.6, 9.2 Hz, 1H), 7.19 (dddd, J=9.0, 3.9, 2.6, 1.5 Hz, 1H), 6.16-6.08 (m, 1H), 4.76 (s, 1H), 3.04-2.88 (m, 2H), 2.78-2.63 (m, 2H), 2.61-2.50 (m, 1H), 2.39 (s, 3H), 2.21 (s, 3H), 2.21-2.03 (m, 5H), 1.98 (d, J=12.9 Hz, 1H), 1.89 (d, J=12.4 Hz, 1H).

Example 194: (S)-5-(3-(4,4-difluorocyclohexyl)-6-(3,5-dimethylisoxazol-4-yl)-3H-imidazo[4,5-b]pyridin-2-yl)-1-(3-fluoro-4-methoxyphenyl)pyrrolidin-2-one (S)-6-(6-(3,5-dimethylisoxazol-4-yl)-3-((1r,4S)-4-hydroxycyclohexyl)-3H-imidazo[4,5-b]pyridin-2-yl)-1-(3-fluoro-4-methoxyphenyl) pyrrolidin-2-one

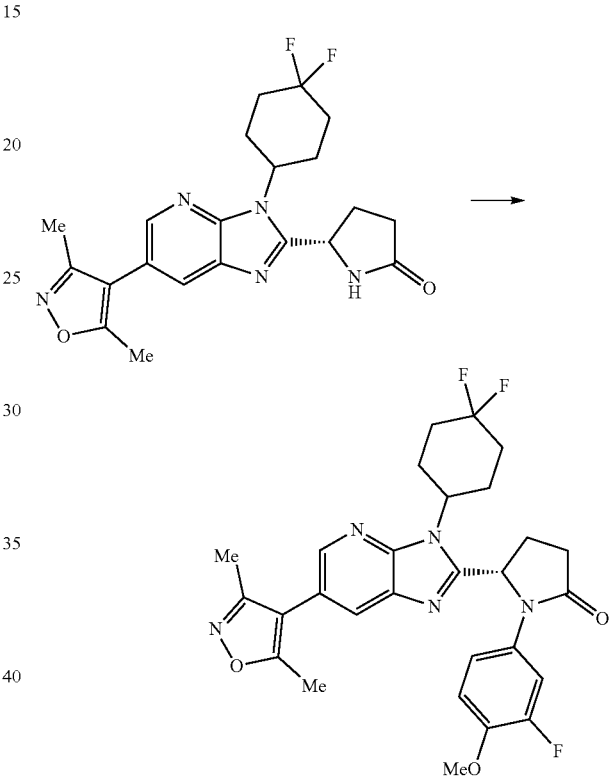

To a scintillation vial containing (S)-5-(3-(4,4-difluorocyclohexyl)-6-(3,5-dimethylisoxazol-4-yl)-3H-imidazo[4,5-b]pyridin-2-yl)pyrrolidin-2-one (100 mg, 0.241 mmol) in pyridine (3 ml) was added CuTMEDA (55.9 mg, 0.120 mmol). The reaction mixture was stirred at 40° C. for 15 minutes, then (3-fluoro-4-methoxyphenyl)boronic acid (102 mg, 0.602 mmol) added and the reaction mixture was left to stir at 40° C. for 18 hrs. The reaction mixture was cooled to rt and partitioned between ethyl acetate (20 mL) and water (10 mL). The organic phase was washed with further portion of water (2×10 mL), dried (MgSO4) and concentrated in vacuo. The crude residue was purified by chromatography (4 g silica, 0-10% MeOH in DCM, gradient elution). Product fractions were combined and concentrated in vacuo. The residue was triturated with ether to afford (S)-5-(3-(4,4-difluorocyclohexyl)-6-(3,5-dimethylisoxazol-4-yl)-3H-imidazo[4,5-b]pyridin-2-yl)-1-(3-fluoro-4-methoxyphenyl)pyrrolidin-2-one (38 mg, 29%) as a brown solid; Rt 2.28 min; m/z 540 (M+H)+ (ES+); 1H NMR (d6-DMSO) δ: 8.34 (d, J=2.0 Hz, 1H), 8.10 (d, J=2.0 Hz, 1H), 7.69-7.60 (m, 1H), 7.13-7.06 (m, 2H), 6.10-6.02 (m, 1H), 4.77 (s, 1H), 3.75 (s, 3H), 3.02-2.84 (m, 2H), 2.82-2.51 (m, 3H), 2.39 (s, 3H), 2.22 (s, 3H), 2.22-2.08 (m, 5H), 1.96 (d, J=12.7 Hz, 1H), 1.72 (d, J=12.5 Hz, 1H).

Example 196: (S)-1-(3,4-difluorophenyl)-6-(6-(3,5-dimethylisoxazol-4-yl)-3-isobutyl-3H-imidazo[4,5-b]pyridin-2-yl)piperidin-2-one (S)-1-(3,4-difluorophenyl)-6-(6-(3,5-dimethylisoxazol-4-yl)-3-isobutyl-3H-imidazo[4,5-b]pyridin-2-yl)piperidin-2-one

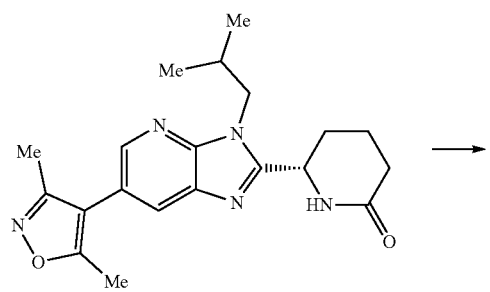

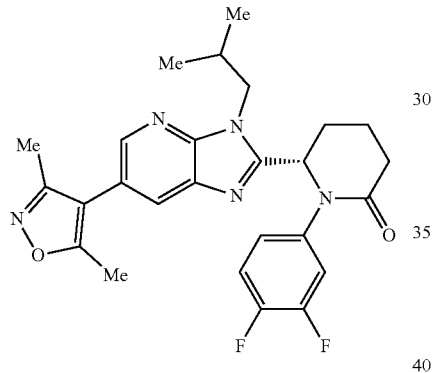

Example 197: (S)-6-(6-(3,5-dimethylisoxazol-4-yl)-3-isobutyl-3H-imidazo[4,5-b]pyridin-2-yl)-1-(3-fluoro-4-methoxyphenyl)piperidin-2-one (S)-6-(6-(3,5-dimethylisoxazol-4-yl)-3-isobutyl-3H-imidazo[4,5-b]pyridin-2-yl)-1-(3-fluoro-4-methoxyphenyl)piperidin-2-one

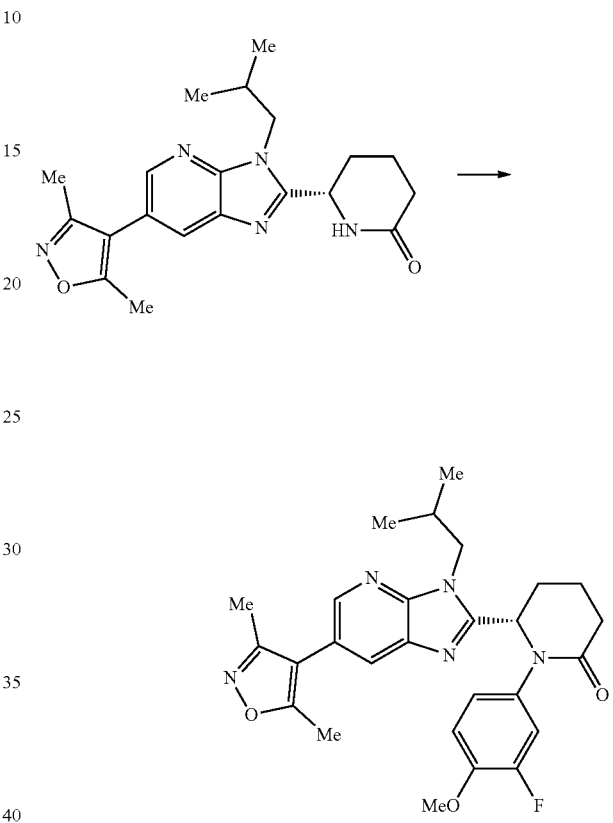

CuTMEDA (0.063 g, 0.136 mmol) was added to a stirred solution of (S)-6-(6-(3,5-dimethylisoxazol-4-yl)-3-isobutyl-3H-imidazo[4,5-b]pyridin-2-yl)piperidin-2-one (0.1 g, 0.272 mmol) in PYRIDINE (3.28 ml, 40.6 mmol) then the mixture was stirred for 15 min at 40° C. (3,4-difluorophenyl)boronic acid (0.107 g, 0.680 mmol) was added then the mixture was heated to 40° C. for 15 h. The reaction was cooled down to RT. The reaction was cooled down to r.t. The mixture was concentrated in vacuo to give a green residue which was diluted with DCM (10 mL). then washed with water (3×10 mL) and saturated brine (10 mL). The organic phase was filtered through a phase layer separator and concentrated under reduced pressure. The crude residue was purified by flash chromatography (4 g silica, 0-10% MeOH in DCM, gradient elution) to give (S)-1-(3,4-difluorophenyl)-6-(6-(3,5-dimethylisoxazol-4-yl)-3-isobutyl-3H-imidazo[4,5-b]pyridin-2-yl)piperidin-2-one (45 mg, 33%) was isolated as a brown pink solid; Rt 2.17 min; m/z 480 (M+H)+ (ES+); 1H NMR (d6-DMSO) δ: 8.31 (d, J=1.9 Hz, 1H), 8.23 (d, J=1.9 Hz, 1H), 7.41-7.28 (m, 2H), 7.13-7.04 (m, 1H), 5.64 (dd, J=5.7, 2.9 Hz, 1H), 4.08 (dd, J=14.1, 6.7 Hz, 1H), 3.85 (dd, J=14.1, 8.8 Hz, 1H), 2.64-2.51 (m, 2H), 2.46-2.35 (m+s, 4H), 2.25 (s, 3H), 2.12-2.00 (m, 3H), 1.80-1.70 (m, 1H), 0.75 (d, J=6.7 Hz, 3H), 0.50 (d, J=6.6 Hz, 3H).

CuTMEDA (0.063 g, 0.136 mmol) was added to a stirred solution of (S)-6-(6-(3,5-dimethylisoxazol-4-yl)-3-isobutyl-3H-imidazo[4,5-b]pyridin-2-yl)piperidin-2-one (0.1 g, 0.272 mmol) in PYRIDINE (3.28 ml, 40.6 mmol) then the mixture was stirred for 15 min at 40° C. (3-fluoro-4-methoxyphenyl)boronic acid (0.116 g, 0.680 mmol) was added then the mixture was heated to 40° C. for 15 h. The reaction was cooled to RT. The reaction was cooled down to r.t. The mixture was concentrated in vacuo to give a green residue which was diluted with DCM (10 mL) then washed with water (3×10 mL) and saturated brine (10 mL). The organic phase was filtered through a phase layer separator and concentrated under reduced pressure. The crude residue was purified by chromatography (4 g silica, 0-10% MeOH in DCM, gradient elution) to give (S)-6-(6-(3,5-dimethylisoxazol-4-yl)-3-isobutyl-3H-imidazo[4,5-b]pyridin-2-yl)-1-(3-fluoro-4-methoxyphenyl)piperidin-2-one (48 mg, 35%) was isolated as a brown glass; Rt 2.02 min; m/z 492 (M+H)+ (ES+); 1H NMR (d6-DMSO) δ: 8.31 (d, J=2.0 Hz, 1H), 8.23 (d, J=2.0 Hz, 1H), 7.09 (dd, J=12.6, 2.3 Hz, 1H), 7.05-6.95 (m, 2H), 5.58 (dd, J=5.6, 2.8 Hz, 1H), 4.05 (dd, J=14.1, 6.7 Hz, 1H), 3.85 (dd, J=14.1, 8.7 Hz, 1H), 3.73 (s, 3H), 2.56-2.51 (m, 2H), 2.46-2.34 (m, 4H), 2.26 (s, 3H), 2.10-2.00 (m, 3H), 1.79-1.70 (m, 1H), 0.73 (d, J=6.7 Hz, 3H), 0.50 (d, J=6.6 Hz, 3H).

425

General Route F: Convergent Approach to N-Alkyllactam Analogues

Example 198: (S)-1-benzyl-5-(5-(3,5-dimethylisoxazol-4-yl)-1-((1r,4S)-4-methoxycyclohexyl)-1H-benzo[d]imidazol-2-yl)pyrrolidin-2-one (S)-1-benzyl-5-(5-(3,5-dimethylisoxazol-4-yl)-1-((1r,4S)-4-methoxycyclohexyl)-1H-benzo[d]imidazol-2-yl)pyrrolidin-2-one

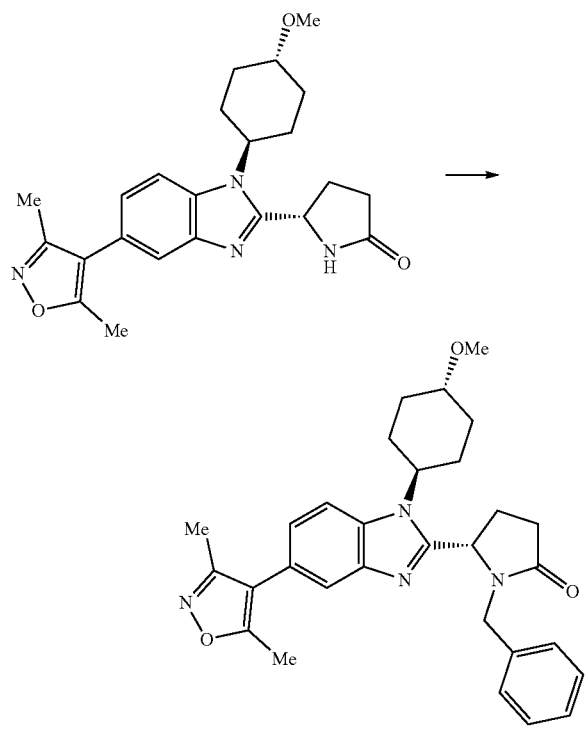

A solution of (S)-5-(5-(3,5-dimethylisoxazol-4-yl)-1-((1r,4S)-4-methoxycyclohexyl)-1H-benzo[d]imidazol-2-yl)pyrrolidin-2-one (50 mg, 0.121 mmol) in N,N-dimethylformamide (1 mL) were treated with 1.0 M NaHMDS in tetrahydrofuran (125 µl, 0.125 mmol) then stirred at room temperature for 5 minutes. A solution of benzyl bromide (21 mg, 0.123 mmol) in N,N-dimethylformamide (1 mL) were added then the mixtures were stirred at room temperature for 18 h. The mixture was diluted with water (6 mL) then extracted with dichloromethane (2×6 mL). The combined organic phases were washed with saturated brine (6 mL) then concentrated under reduced pressure. The crude products were purified by chromatography on the Companion (4 g column, 0-50% THF/DCM) then triturated in diethyl ether:isohexane (1:1, 8 mL) to afford (S)-1-benzyl-5-(5-(3,5-dimethylisoxazol-4-yl)-1-((1r,4S)-4-methoxycyclohexyl)-1H-benzo[d]imidazol-2-yl)pyrrolidin-2-one (42 mg, 66%) as a white solid. Rt 1.97 min; m/z 499 (M+H)+ (ES+); 1H NMR (d6-DMSO) δ: 7.84 (d, J=8.5 Hz, 1H), 7.69 (dd, J=1.7, 0.6 Hz, 1H), 7.38-7.24 (m, 3H), 7.21-7.13 (m, 3H), 5.10 (dd, J=7.9, 3.0 Hz, 1H), 4.99 (d, J=15.5 Hz, 1H), 4.26 (t, J=12.3 Hz, 1H), 3.79 (d, J=15.5 Hz, 1H), 3.37-3.30 (m, 1H), 3.26 (s, 3H), 2.60-2.53 (m, 1H), 2.50-2.42 (m, 2H), 2.42 (s, 3H), 2.31-2.12 (m, 2H), 2.25 (s, 3H), 2.10-2.01 (m, 2H), 2.01-1.91 (m, 1H), 1.84-1.75 (m, 1H), 1.74-1.64 (m, 1H), 1.39-1.13 (m, 2H).

426

Example 199: Biological Testing

Surface Plasmon Resonance (BIAcore) Analysis of Binding to EP300, CBP and BRD4 BD1

BIAcore data for compound binding to EP300 and BRD4 was acquired using a T200 BIAcore instrument at 4° C. His-tagged EP300 Bromodomain (1046-1163), His-tagged CBP Bromodomain (1081-1197) and BRD4 Bromodomain 1 (49-170) proteins were captured onto an NTA chip via a combined capture and amine coupling method. NTA groups were first chelated with 30 mM nickel chloride and then activated with 0.2 M N-ethyl-N'-(diethylaminopropyl)-carbodiimide (EDC) and 0.05 µM N-hydroxysuccimide (NHS).

Bromodomain proteins diluted to 9.6M in PBS 0.05% Tween-20 were injected at 10l/min and covalently bound. Ethanolamine injections were performed to cap unreacted moieties on the surface and remove uncoupled protein. A typical immobilisation resulted in ~2-4 kRU of protein immobilised on the surface.

Test compounds were serially diluted to generate 1, 10, 100, 1000 and 10000 nM solutions in running buffer (PBS with 0.005% Tween-20, 0.1% DMSO). Using a flow rate of 90 µL/min throughout, runs consisted of injections of compound with escalating concentration, interspersed with buffer blank runs consisting of 5 repeat injections of running buffer.

Sensorgrams were analyzed with BIAevaluation (GE Healthcare) using a 1:1 interaction model to generate $k_a$ and $k_d$ values to describe the kinetics of binding. $K_D$ values were derived from the quotient of $k_d$ and $k_a$. Compounds were tested twice against EP300, CBP and/or BRD4 bromodomain surfaces to obtain geometric means of the kinetic and affinity parameters. All compounds tested gave $K_D$ values in the range of 0.5-10,000 nM. For instance, against EP300 and CBP, compounds 70-140 gave $K_D$ values in the range of 1-200 nM.

Cell Viability Assay

The 22Rv1 cell line was obtained from ATCC (UK) and cultured according to the supplier's recommendations. Cell growth inhibitory activity of representative compounds was determined using the CellTiter-Glo® Luminescent Cell Viability Assay kit (Promega, USA).

22Rv1 cells were maintained in RPMI 1640 media containing 10% Foetal Bovine Serum, 2 mM Glutamine, 1 mM sodium pyruvate and 100 units of Penicillin-100 g of Streptomycin. Cells were incubated at 37° C. in a humidified atmosphere with 95% 02 and 5% $CO_2$. 2000 cells were seeded per well in Poly-D-Lysine (PDL) coated 96-well black clear bottom plates (VWR, UK) in 50 µL of growth medium. After 48 hours, medium was removed and replaced with growth medium containing diluted test compounds. Compound dilutions were performed by serially diluting in half log intervals DMSO stocks at a maximum concentration of 10 mM, for a total of 7 dilutions. A 1 µl aliquot of each dilution point was added to 99 µl of growth medium and 50 µL added to each well containing cells, providing 100 µM compound at the maximum concentration point (1% DMSO). 1% DMSO treated cells served as a high control.

Cells were incubated for a further 72 hours at 37° C. and cell viability determined using the CellTiter-Glo® Luminescent Cell Viability Assay according to the manufacturer's instructions. Briefly, a volume of CellTiter-Glo® reagent equal to the volume of growth media was added to each well. Plates were shaken for approximately 2 minutes and incubated at room temperature (22° C.) for 10 minutes. The luminescence signal was measured using an Envision plate reader with an integration time of 1 second per well.

All data was normalised to the mean of 6 high-controls. The half maximum inhibitor concentration (IC50) was calculated from a 4-parameter logistic curve fit of the data using the Dotmatics software (UK). All compounds tested gave IC50 values in the range of 100 nM-100 µM, typically from 100 nM-30 µM.

Cell based assays are likely to show some variability due to the complexity of the system and it is understood that the results of these assays may vary as assay conditions are varied. Some level of cell growth inhibition is indicative of the compound having some inhibitory activity in specified cells, whereas lack of the inhibition below the highest concentration tested does not necessarily indicate the compound has no inhibitory activity on the cells.

Example 200: Tablet Composition

Tablets, each weighing 0.15 g and containing 25 mg of a compound of the invention are manufactured as follows:
Composition for 10,000 tablets
Compound of the invention (250 g)
Lactose (800 g)
Corn starch (415 g)
Talc powder (30 g)
Magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium is added, carefully mixed and processed into tablets.

Example 201: Injectable Formulation

| Compound of the invention | 200 mg |
| Hydrochloric Acid Solution 0.1M or Sodium Hydroxide Solution 0.1M q.s. | to pH 4.0 to 7.0 |
| Sterile water q.s. to | 10 mL |

The compound of the invention is dissolved in most of the water (35°-40° C.) and the pH adjusted to between 4.0 and 7.0 with the hydrochloric acid or the sodium hydroxide as appropriate. The batch is then made up to volume with water and filtered through a sterile micropore filter into a sterile 10 mL amber glass vial (type 1) and sealed with sterile closures and overseals.

Example 202: Intramuscular Injection

| Compound of the invention | 200 mg |
| Benzyl Alcohol | 0.10 g |
| Glycofurol 75 | 1.45 g |
| Water for injection q.s to | 3.00 mL |

The compound of the invention is dissolved in the glycofurol. The benzyl alcohol is then added and dissolved, and water added to 3 ml. The mixture is then filtered through a sterile micropore filter and sealed in sterile 3 ml glass vials (type 1).

Example 203: Syrup Formulation

| Compound of invention | 250 mg |
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

The compound of the invention is dissolved in a mixture of the glycerol and most of the purified water. An aqueous solution of the sodium benzoate is then added to the solution, followed by addition of the sorbitol solution and finally the flavour. The volume is made up with purified water and mixed well.

The invention claimed is:

1. A compound which is an arylimidazolyl isoxazole of formula (I):

(I)

wherein:
$R^0$ and R, which are the same or different, are each H or $C_1$-$C_6$ alkyl which is unsubstituted or substituted by OH, —OC(O)R' or OR' wherein R' is unsubstituted $C_1$-$C_6$ alkyl;
W is N or CH;
$R^1$ is a group which is unsubstituted or substituted and is selected from C-linked 4- to 6-membered heterocyclyl; $C_3$-$C_6$ cycloalkyl; $C_1$-$C_6$ alkyl which is unsubstituted or substituted by $C_6$-$C_{10}$ aryl, 5- to 12-membered N-containing heteroaryl, $C_3$-$C_6$ cycloalkyl, OH, —OC(O)R' or OR' wherein R' is as defined above; and a spiro group of the following formula:

Y is —$CH_2$—, —$CH_2CH_2$— or —$CH_2CH_2CH_2$—;
n is 0 or 1;
$R^2$ is a group selected from $C_6$-$C_{10}$ aryl, 5- to 12-membered N-containing heteroaryl, $C_3$-$C_6$ cycloalkyl and $C_5$-$C_6$ cycloalkenyl, wherein the group is unsubstituted or substituted and wherein $C_6$-$C_{10}$ aryl is optionally fused to a 5- or 6-membered heterocyclic ring;
or a pharmaceutically acceptable salt thereof.

2. A compound according to claim 1, wherein the arylimidazolyl isoxazole has the following formula (Ia):

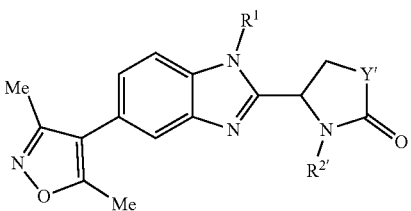

(Ia)

wherein
R¹ is as defined in claim 1;
Y' is —CH₂— or —CH₂CH₂—; and
R²' is a group selected from C₆-C₁₀ aryl optionally fused to a 5- or 6-membered heterocyclic ring and C₅-C₆ heteroaryl, the group being unsubstituted or mono-, di- or tri-substituted.

3. A compound according to claim 1 wherein R¹ is selected from the following structures:

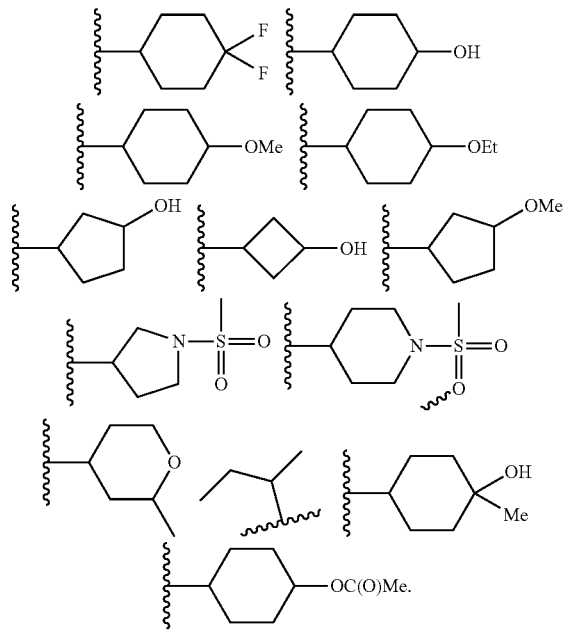

4. A compound according to claim 1 which is the S enantiomer (based on the chiral C atom of the pyrrolidin-2-one or piperidin-2-one ring).

5. A compound according to claim 1 which is selected from:
- 5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one;
- 5-(5-(3,5-dimethylisoxazol-4-yl)-1-(tetrahydro-2H-pyran-4-yl)-1H-benzo[d]imidazol-2-yl)-1-phenylpyrrolidin-2-one;
- 5-(5-(3,5-dimethylisoxazol-4-yl)-1-(1,1-dioxidotetrahydro-2H-thiopyran-4-yl)-1H-benzo[d]imidazol-2-yl)-1-phenylpyrrolidin-2-one;
- (S)-5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one;
- (R)-5-(5-(3,5-dimethylisoxazol-4-yl)-1-((R)-1-(methylsulfonyl)pyrrolidin-3-yl)-1H-benzo[d]imidazol-2-yl)-1-phenylpyrrolidin-2-one;
- (S)-5-(5-(3,5-dimethylisoxazol-4-yl)-1-((R)-1-(methylsulfonyl)pyrrolidin-3-yl)-1H-benzo[d]imidazol-2-yl)-1-(3-fluorophenyl)pyrrolidin-2-one;
- (S)-1-(3,4-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;
- (S)-1-(4-chloro-3-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;
- (S)-1-(3-chloro-4-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;
- (S)-1-(3,5-dichlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;
- (S)-1-(3-chloro-5-fluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;
- (S)-1-(3-chloro-5-methoxyphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;
- (S)-5-(5-(3,5-dimethylisoxazol-4-yl)-1-((R)-1-(methylsulfonyl)pyrrolidin-3-yl)-1H-benzo[d]imidazol-2-yl)-1-(3-fluoro-4-methoxyphenyl)pyrrolidin-2-one;
- (S)-1-(3-chloro-4-methoxyphenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;
- (S)-5-(5-(3,5-dimethylisoxazol-4-yl)-1-((R)-1-(methylsulfonyl)pyrrolidin-3-yl)-1H-benzo[d]imidazol-2-yl)-1-(4-methoxyphenyl)pyrrolidin-2-one;
- (S)-5-(5-(3,5-dimethylisoxazol-4-yl)-1-((R)-1-(methylsulfonyl)pyrrolidin-3-yl)-1H-benzo[d]imidazol-2-yl)-1-(4-propoxyphenyl)pyrrolidin-2-one;
- (S)-1-(4-chlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;
- (S)-5-(5-(3,5-dimethylisoxazol-4-yl)-1-((R)-1-(methylsulfonyl)pyrrolidin-3-yl)-1H-benzo[d]imidazol-2-yl)-1-(pyridin-3-yl)pyrrolidin-2-one;
- (S)-5-(5-(3,5-dimethylisoxazol-4-yl)-1-((R)-1-(methylsulfonyl)pyrrolidin-3-yl)-1H-benzo[d]imidazol-2-yl)-1-(6-fluoropyridin-3-yl)pyrrolidin-2-one;
- (S)-5-(5-(3,5-dimethylisoxazol-4-yl)-1-((R)-1-(methylsulfonyl)pyrrolidin-3-yl)-1H-benzo[d]imidazol-2-yl)-1-(naphthalen-1-yl)pyrrolidin-2-one;
- (S)-5-(5-(3,5-dimethylisoxazol-4-yl)-1-((R)-1-(methylsulfonyl)pyrrolidin-3-yl)-1H-benzo[d]imidazol-2-yl)-1-(5-fluoropyridin-3-yl)pyrrolidin-2-one;
- (S)-1-(3,5-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;
- (S)-1-(5-chloro-6-methoxypyridin-3-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;
- (S)-5-(5-(3,5-dimethylisoxazol-4-yl)-1-((R)-1-(methylsulfonyl)pyrrolidin-3-yl)-1H-benzo[d]imidazol-2-yl)-1-(3-fluoro-5-methoxyphenyl)pyrrolidin-2-one;
- (S)-5-(5-(3,5-dimethylisoxazol-4-yl)-1-((R)-1-(methylsulfonyl)pyrrolidin-3-yl)-1H-benzo[d]imidazol-2-yl)-1-(3-(trifluoromethoxy)phenyl)pyrrolidin-2-one;
- (S)-1-(2,3-dihydrobenzofuran-5-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;
- (S)-1-(3,4-dichlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;

(S)-5-(5-(3,5-dimethylisoxazol-4-yl)-1-((R)-1-(methyl-sulfonyl)pyrrolidin-3-yl)-1i-benzo[d]imidazol-2-yl)-1-(6-methoxypyridin-3-yl)pyrrolidin-2-one;

(S)-5-(5-(3,5-dimethylisoxazol-4-yl)-1-((R)-1-(methyl-sulfonyl)pyrrolidin-3-yl)-1H-benzo[d]imidazol-2-yl)-1-(3,4,5-trifluorophenyl)pyrrolidin-2-one;

(S)-5-(5-(3,5-dimethylisoxazol-4-yl)-1-((R)-1-(methyl-sulfonyl)pyrrolidin-3-yl)-1H-benzo[d]imidazol-2-yl)-1-(4-(trifluoromethyl)phenyl)pyrrolidin-2-one;

(S)-5-(5-(3,5-dimethylisoxazol-4-yl)-1-((R)-1-(methyl-sulfonyl)pyrrolidin-3-yl)-1H-benzo[d]imidazol-2-yl)-1-(4-(trifluoromethyl)phenyl)pyrrolidin-2-one;

(S)-5-(5-(3,5-dimethylisoxazol-4-yl)-1-((R)-1-(methyl-sulfonyl)pyrrolidin-3-yl)-1H-benzo[d]imidazol-2-yl)-1-(3-ethoxy-5-fluorophenyl)pyrrolidin-2-one;

(S)-5-(5-(3,5-dimethylisoxazol-4-yl)-1-((R)-1-(methyl-sulfonyl)pyrrolidin-3-yl)-1H-benzo[d]imidazol-2-yl)-1-(o-tolyl)pyrrolidin-2-one;

(S)-5-(5-(3,5-dimethylisoxazol-4-yl)-1-((R)-1-(methyl-sulfonyl)pyrrolidin-3-yl)-1H-benzo[d]imidazol-2-yl)-1-(5-fluoro-2-methylphenyl)pyrrolidin-2-one;

3-((S)-2-(5-(3,5-dimethylisoxazol-4-yl)-1-((R)-1-(meth-ylsulfonyl)pyrrolidin-3-yl)-1H-benzo[d]imidazol-2-yl)-5-oxopyrrolidin-1-yl)-5-fluorobenzonitrile;

(S)-1-(cyclohex-1-en-1-yl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;

(S)-1-(4,5-difluoro-2-methylphenyl)-5-(5-(3,5-dimethyl-isoxazol-4-yl)-1-((R)-1-(methylsulfonyl)pyrrolidin-3-yl)-1H-benzo[d]imidazol-2-yl)pyrrolidin-2-one;

(S)-1-(3,4-dichloro-2-methylphenyl)-5-(5-(3,5-dimethyl-isoxazol-4-yl)-1-((R)-1-(methylsulfonyl)pyrrolidin-3-yl)-1H-benzo[d]imidazol-2-yl)pyrrolidin-2-one;

(R)-5-(5-(3,5-dimethylisoxazol-4-yl)-1-((R)-1-(methyl-sulfonyl)pyrrolidin-3-yl)-1H-benzo[d]imidazol-2-yl)-1-(3-fluorophenyl)pyrrolidin-2-one;

(R)-1-(3,4-difluorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;

(R)-1-(4-chloro-3-fluorophenyl)-5-(5-(3,5-dimethylisox-azol-4-yl)-1-((R)-1-(methylsulfonyl)pyrrolidin-3-yl)-1H-benzo[d]imidazol-2-yl)pyrrolidin-2-one;

(R)-1-(3,5-dichlorophenyl)-5-(5-(3,5-dimethylisoxazol-4-yl)-1-((R)-1-(methylsulfonyl)pyrrolidin-3-yl)-1H-benzo[d]imidazol-2-yl)pyrrolidin-2-one;

(R)-1-(3-chloro-4-fluorophenyl)-5-(5-(3,5-dimethylisox-azol-4-yl)-1-((R)-1-(methylsulfonyl)pyrrolidin-3-yl)-1H-benzo[d]imidazol-2-yl)pyrrolidin-2-one;

(R)-1-(3-chloro-5-fluorophenyl)-5-(5-(3,5-dimethylisox-azol-4-yl)-1-((R)-1-(methylsulfonyl)pyrrolidin-3-yl)-1H-benzo[d]imidazol-2-yl)pyrrolidin-2-one;

(S)-1-(3,4-difluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one;

(S)-1-(3-chloro-4-fluorophenyl)-5-(5-(3,5-dimethylisox-azol-4-yl)-1-(1,1-dioxidotetrahydro-2H-thiopyran-4-yl)-1H-benzo[d]imidazol-2-yl)pyrrolidin-2-one;

(S)-5-(5-(3,5-dimethylisoxazol-4-yl)-1-(1,1-dioxidotetra-hydro-2H-thiopyran-4-yl)-1H-benzo[d]imidazol-2-yl)-1-(3-fluorophenyl)pyrrolidin-2-one;

(S)-1-(4-chloro-3-fluorophenyl)-5-(5-(3,5-dimethylisox-azol-4-yl)-1-(1,1-dioxidotetrahydro-2H-thiopyran-4-yl)-1H-benzo[d]imidazol-2-yl)pyrrolidin-2-one;

(S)-1-(3-chloro-5-methoxyphenyl)-5-(5-(3,5-dimethyl-isoxazol-4-yl)-1-(1,1-dioxidotetrahydro-2H-thiopyran-4-yl)-1H-benzo[d]imidazol-2-yl)pyrrolidin-2-one;

(S)-5-(5-(3,5-dimethylisoxazol-4-yl)-1-(1,1-dioxidotetra-hydro-2H-thiopyran-4-yl)-1H-benzo[d]imidazol-2-yl)-1-(3-fluoro-4-methoxyphenyl)pyrrolidin-2-one;

(S)-1-(3-chloro-4-methoxyphenyl)-5-(5-(3,5-dimethyl-isoxazol-4-yl)-1-(1,1-dioxidotetrahydro-2H-thiopyran-4-yl)-1H-benzo[d]imidazol-2-yl)pyrrolidin-2-one;

(S)-1-(3,5-dichlorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one;

(S)-1-(3-chloro-5-fluorophenyl)-5-(5-(3,5-dimethylisox-azol-4-yl)-1-(1,1-dioxidotetrahydro-2H-thiopyran-4-yl)-1H-benzo[d]imidazol-2-yl)pyrrolidin-2-one;

(S)-5-(5-(3,5-dimethylisoxazol-4-yl)-1-(1,1-dioxidotetra-hydro-2H-thiopyran-4-yl)-1H-benzo[d]imidazol-2-yl)-1-(3,4,5-trifluorophenyl)pyrrolidin-2-one;

(S)-1-(3,5-difluorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one;

(S)-5-(5-(3,5-dimethylisoxazol-4-yl)-1-(1,1-dioxidotetra-hydro-2H-thiopyran-4-yl)-1H-benzo[d]imidazol-2-yl)-1-(5-fluoro-6-methoxypyridin-3-yl)pyrrolidin-2-one;

(S)-1-(2,3-dihydrobenzofuran-5-yl)-5-(5-(3,5-dimethyl-isoxazol-4-yl)-1-(1,1-dioxidotetrahydro-2H-thiopyran-4-yl)-1H-benzo[d]imidazol-2-yl)pyrrolidin-2-one;

(S)-1-(3,4-dichlorophenyl)-5-(5-(3,5-dimethylisoxazol-4-yl)-1-(1,1-dioxidotetrahydro-2H-thiopyran-4-yl)-1H-benzo[d]imidazol-2-yl)pyrrolidin-2-one;

(S)-5-(5-(3,5-dimethylisoxazol-4-yl)-1-((1r,4 S)-4-hy-droxycyclohexyl)-1H-benzo[d]imidazol-2-yl)pyrroli-din-2-one;

(S)-1-(3,4-difluorophenyl)-5-(5-(3,5-dimethylisoxazol-4-yl)-1-((1r,4S)-4-hydroxycyclohexyl)-1H-benzo[d]imi-dazol-2-yl)pyrrolidin-2-one;

(S)-1-(4-chloro-3-fluorophenyl)-5-(5-(3,5-dimethylisox-azol-4-yl)-1-((1 r,4 S)-4-hydroxycyclohexyl)-1H-benzo[d]imidazol-2-yl)pyrrolidin-2-one;

(S)-5-(5-(3,5-dimethylisoxazol-4-yl)-1-((1r,4S)-4-hy-droxycyclohexyl)-1H-benzo[d]imidazol-2-yl)-1-(3-fluoro-4-methoxyphenyl)pyrrolidin-2-one;

(S)-1-(3-chloro-4-methoxyphenyl)-5-(5-(3,5-dimethyl-isoxazol-4-yl)-1-((1 r,4 S)-4-hydroxycyclohexyl)-1H-benzo[d]imidazol-2-yl)pyrrolidin-2-one;

(S)-1-(3-chloro-4-fluorophenyl)-5-(5-(3,5-dimethylisox-azol-4-yl)-1-((1 r,4 S)-4-hydroxycyclohexyl)-1H-benzo[d]imidazol-2-yl)pyrrolidin-2-one;

(S)-1-(2,3-dihydrobenzofuran-5-yl)-5-(5-(3,5-dimethyl-isoxazol-4-yl)-1-((1r,4 S)-4-hydroxycyclohexyl)-1H-benzo[d]imidazol-2-yl)pyrrolidin-2-one;

(S)-5-(5-(3,5-dimethylisoxazol-4-yl)-1-((1r,4S)-4-hy-droxycyclohexyl)-1H-benzo[d]imidazol-2-yl)-1-(naphthalen-1-yl)pyrrolidin-2-one;

(S)-1-(3,4-dichlorophenyl)-5-(5-(3,5-dimethylisoxazol-4-yl)-1-(4-hydroxycyclohexyl)-1H-benzo[d]imidazol-2-yl)pyrrolidin-2-one;

(S)-5-(5-(3,5-dimethylisoxazol-4-yl)-1-((S)-1,1-dioxido-tetrahydrothiophen-3-yl)-1H-benzo[d]imidazol-2-yl)pyrrolidin-2-one;

(S)-1-(3,4-difluorophenyl)-5-(5-(3,5-dimethylisoxazol-4-yl)-1-((S)-1,1-dioxidotetrahydrothiophen-3-yl)-1H-benzo[d]imidazol-2-yl)pyrrolidin-2-one;

Tert-butyl (S)-3-(2-((S)-1-(3,4-difluorophenyl)-5-oxopyr-rolidin-2-yl)-5-(3,5-dimethylisoxazol-4-yl)-1H-benzo[d]imidazol-1-yl)pyrrolidine-1-carboxylate;

Tert-butyl (R)-3-(2-((S)-1-(3,4-difluorophenyl)-5-oxopy-rrolidin-2-yl)-5-(3,5-dimethylisoxazol-4-yl)-1H-benzo[d]imidazol-1-yl)pyrrolidine-1-carboxylate;

(S)-1-(3,4-difluorophenyl)-5-(5-(3,5-dimethylisoxazol-4-yl)-1-((S)-1-(methylsulfonyl)pyrrolidin-3-yl)-1H-benzo[d]imidazol-2-yl)pyrrolidin-2-one;

(S)-5-(1-((R)-1-(cyclopropylsulfonyl)pyrrolidin-3-yl)-5-(3,5-dimethylisoxazol-4-yl)-1H-benzo[d]imidazol-2-yl)-1-(3,4-difluorophenyl) pyrrolidin-2-one;

(S)-5-(1-((R)-1-acetylpyrrolidin-3-yl)-5-(3,5-dimethylisoxazol-4-yl)-1H-benzo[d]imidazol-2-yl)-1-(3,4-difluorophenyl)pyrrolidin-2-one;

(S)-1-(3,4-difluorophenyl)-5-(5-(3,5-dimethylisoxazol-4-yl)-1-((R)-1-(3,3,3-trifluoropropanoyl)pyrrolidin-3-yl)-1H-benzo[d]imidazol-2-yl)pyrrolidin-2-one;

(5S)-1-(3,4-difluorophenyl)-5-(5-(3,5-dimethylisoxazol-4-yl)-1-(1-methylpyrrolidin-3-yl)-1H-benzo[d]imidazol-2-yl)pyrrolidin-2-one;

(5S)-1-(4-chloro-3-fluorophenyl)-5-(5-(3,5-dimethylisoxazol-4-yl)-1-(1-methylpyrrolidin-3-yl)-1H-benzo[d]imidazol-2-yl)pyrrolidin-2-one;

(5S)-1-(3,4-dichlorophenyl)-5-(5-(3,5-dimethylisoxazol-4-yl)-1-(1-methylpyrrolidin-3-yl)-1H-benzo[d]imidazol-2-yl)pyrrolidin-2-one;

(S)-1-(3,4-dichlorophenyl)-5-(5-(3,5-dimethylisoxazol-4-yl)-1-((1r,4 S)-4-methoxycyclohexyl)-1H-benzo[d]imidazol-2-yl)pyrrolidin-2-one;

(S)-1-(3,4-difluorophenyl)-5-(5-(3,5-dimethylisoxazol-4-yl)-1-((1r,4 S)-4-methoxycyclohexyl)-1H-benzo[d]imidazol-2-yl)pyrrolidin-2-one;

(S)-1-(3-chloro-4-methoxyphenyl)-5-(5-(3,5-dimethylisoxazol-4-yl)-1-((1r,4 S)-4-methoxycyclohexyl)-1H-benzo[d]imidazol-2-yl)pyrrolidin-2-one;

(S)-1-(2,3-dihydrobenzofuran-5-yl)-5-(5-(3,5-dimethylisoxazol-4-yl)-1-((1r,4 S)-4-methoxycyclohexyl)-1H-benzo[d]imidazol-2-yl)pyrrolidin-2-one;

(S)-1-(3-chloro-4-fluorophenyl)-5-(5-(3,5-dimethylisoxazol-4-yl)-1-((1r,4 S)-4-methoxycyclohexyl)-1H-benzo[d]imidazol-2-yl)pyrrolidin-2-one;

(S)-1-(4-chloro-3-fluorophenyl)-5-(5-(3,5-dimethylisoxazol-4-yl)-1-((1r,4S)-4-methoxycyclohexyl)-1H-benzo[d]imidazol-2-yl)pyrrolidin-2-one;

(S)-5-(5-(3,5-dimethylisoxazol-4-yl)-1-((1r,4 S)-4-methoxycyclohexyl)-1H-benzo[d]imidazol-2-yl)-1-(3-fluoro-4-methoxyphenyl)pyrrolidin-2-one;

(S)-1-(3,4-difluorophenyl)-5-(5-(3,5-dimethylisoxazol-4-yl)-1-((1 s,4R)-4-hydroxycyclohexyl)-1H-benzo[d]imidazol-2-yl)pyrrolidin-2-one;

(S)-1-(3,4-difluorophenyl)-5-(5-(3,5-dimethylisoxazol-4-yl)-1-((1 s,4R)-4-methoxycyclohexyl)-1H-benzo[d]imidazol-2-yl)pyrrolidin-2-one;

(S)-1-(3,4-difluorophenyl)-5-(5-(3,5-dimethylisoxazol-4-yl)-1-((1R,4s)-4-ethoxycyclohexyl)-1H-benzo[d]imidazol-2-yl)pyrrolidin-2-one;

(5S)-1-(3,4-dichlorophenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one;

(5S)-1-(4-chloro-3-fluorophenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one;

(5S)-1-(3-chloro-4-methoxyphenyl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one;

(5S)-1-(2,3-dihydrobenzofuran-5-yl)-5-(5-(3,5-dimethylisoxazol-4-yl)-1-(1,1-dioxidotetrahydro-2H-thiopyran-3-yl)-1H-benzo[d]imidazol-2-yl)pyrrolidin-2-one;

(S)-1-(3,4-dichlorophenyl)-5-(5-(3,5-dimethylisoxazol-4-yl)-1-(1-(methylsulfonyl)piperidin-4-yl)-1H-benzo[d]imidazol-2-yl)pyrrolidin-2-one;

(S)-1-(4-chloro-3-fluorophenyl)-5-(5-(3,5-dimethylisoxazol-4-yl)-1-(1-(methylsulfonyl)piperidin-4-yl)-1H-benzo[d]imidazol-2-yl)pyrrolidin-2-one;

(S)-1-(3-chloro-4-methoxyphenyl)-5-(5-(3,5-dimethylisoxazol-4-yl)-1-(1-(methylsulfonyl)piperidin-4-yl)-1H-benzo[d]imidazol-2-yl)pyrrolidin-2-one;

(S)-1-(2,3-dihydrobenzofuran-5-yl)-5-(5-(3,5-dimethylisoxazol-4-yl)-1-(1-(methylsulfonyl)piperidin-4-yl)-1H-benzo[d]imidazol-2-yl)pyrrolidin-2-one;

(S)-1-(3,4-difluorophenyl)-5-(5-(3,5-dimethylisoxazol-4-yl)-1-(1-(methylsulfonyl)piperidin-4-yl)-1H-benzo[d]imidazol-2-yl)pyrrolidin-2-one;

(S)-1-(3-chloro-4-fluorophenyl)-5-(5-(3,5-dimethylisoxazol-4-yl)-1-(1-(methylsulfonyl)piperidin-4-yl)-1H-benzo[d]imidazol-2-yl)pyrrolidin-2-one;

(S)-5-(5-(3,5-dimethylisoxazol-4-yl)-1-(1-(methylsulfonyl)piperidin-4-yl)-1H-benzo[d]imidazol-2-yl)-1-(3-fluoro-4-methoxyphenyl)pyrrolidin-2-one;

(S)-1-(4-chloro-3-fluorophenyl)-5-(5-(3,5-dimethylisoxazol-4-yl)-1-((1R,3R)-3-hydroxycyclopentyl)-1H-benzo[d]imidazol-2-yl)pyrrolidin-2-one;

(S)-1-(3-chloro-4-methoxyphenyl)-5-(5-(3,5-dimethylisoxazol-4-yl)-1-((1R,3R)-3-hydroxycyclopentyl)-1H-benzo[d]imidazol-2-yl)pyrrolidin-2-one;

(S)-1-(3,4-dichlorophenyl)-5-(5-(3,5-dimethylisoxazol-4-yl)-1-((1R,3R)-3-hydroxycyclopentyl)-1H-benzo[d]imidazol-2-yl)pyrrolidin-2-one;

(1R,3R)-3-(2-((S)-1-(3,4-difluorophenyl)-5-oxopyrrolidin-2-yl)-5-(3,5-dimethylisoxazol-4-yl)-1H-benzo[d]imidazol-1-yl)cyclopentyl acetate;

(1R,3R)-3-(2-((S)-1-(3-chloro-4-methoxyphenyl)-5-oxopyrrolidin-2-yl)-5-(3,5-dimethylisoxazol-4-yl)-1H-benzo[d]imidazol-1-yl)cyclopentyl acetate;

(S)-1-(3-chloro-4-methoxyphenyl)-5-(5-(3,5-dimethylisoxazol-4-yl)-1-(trans-(1r,3 r)-3-methoxycyclopentyl)-1H-benzo[d]imidazol-2-yl)pyrrolidin-2-one;

(S)-1-(3,4-dichlorophenyl)-5-(5-(3,5-dimethylisoxazol-4-yl)-1-(trans-(1r,3 r)-3-methoxycyclopentyl)-1H-benzo[d]imidazol-2-yl)pyrrolidin-2-one;

(S)-1-(4-chloro-3-fluorophenyl)-5-(5-(3,5-dimethylisoxazol-4-yl)-1-(trans-(1r,3 r)-3-methoxycyclopentyl)-1H-benzo[d]imidazol-2-yl)pyrrolidin-2-one;

(S)-1-(3,4-difluorophenyl)-5-(5-(3,5-dimethylisoxazol-4-yl)-1-(trans-(1r,3 r)-3-ethoxycyclopentyl)-1H-benzo[d]imidazol-2-yl)pyrrolidin-2-one;

(S)-5-(1-(4,4-difluorocyclohexyl)-5-(3,5-dimethylisoxazol-4-yl)-1H-benzo[d]imidazol-2-yl)-1-(3,4-difluorophenyl)pyrrolidin-2-one;

(S)-1-(3-chloro-4-methoxyphenyl)-5-(1-(4,4-difluorocyclohexyl)-5-(3,5-dimethylisoxazol-4-yl)-1H-benzo[d]imidazol-2-yl)pyrrolidin-2-one;

(S)-1-(3-fluoro-4-methoxyphenyl)-5-(1-(4,4-difluorocyclohexyl)-5-(3,5-dimethylisoxazol-4-yl)-1H-benzo[d]imidazol-2-yl)pyrrolidin-2-one;

(5S)-1-(3,4-difluorophenyl)-5-(5-(3,5-dimethylisoxazol-4-yl)-1-(2-methyltetrahydro-2H-pyran-4-yl)-1H-benzo[d]imidazol-2-yl)pyrrolidin-2-one;

(5S)-1-(3-chloro-4-methoxyphenyl)-5-(5-(3,5-dimethylisoxazol-4-yl)-1-(2-methyltetrahydro-2H-pyran-4-yl)-1H-benzo[d]imidazol-2-yl)pyrrolidin-2-one;

(5S)-5-(5-(3,5-dimethylisoxazol-4-yl)-1-(2-methyltetrahydro-2H-pyran-4-yl)-1H-benzo[d]imidazol-2-yl)-1-(3-fluoro-4-methoxyphenyl)pyrrolidin-2-one;

5-(2-((S)-1-(3,4-difluorophenyl)-5-oxopyrrolidin-2-yl)-5-(3,5-dimethylisoxazol-4-yl)-1H-benzo[d]imidazol-1-yl)piperidin-2-one;

(S)-1-(3,4-difluorophenyl)-5-(5-(3,5-dimethylisoxazol-4-yl)-1H-benzo[d]imidazol-2-yl)pyrrolidin-2-one;

(S)-1-(3,4-difluorophenyl)-5-(5-(3,5-dimethylisoxazol-4-yl)-1-((1 s,4R)-4-hydroxy-4-methylcyclohexyl)-1H-benzo[d]imidazol-2-yl)pyrrolidin-2-one;

(S)-5-(5-(3,5-dimethylisoxazol-4-yl)-1-((1 s,4R)-4-hydroxy-4-methylcyclohexyl)-1H-benzo[d]imidazol-2-yl)-1-(3-fluoro-4-methoxyphenyl)pyrrolidin-2-one;

(S)-1-(3,4-dichlorophenyl)-5-(5-(3,5-dimethylisoxazol-4-yl)-1-((1 s,4R)-4-hydroxy-4-methylcyclohexyl)-1H-benzo[d]imidazol-2-yl)pyrrolidin-2-one;

(S)-1-(4-chloro-3-fluorophenyl)-5-(5-(3,5-dimethylisoxazol-4-yl)-1-((1 s,4R)-4-hydroxy-4-methylcyclohexyl)-1H-benzo[d]imidazol-2-yl)pyrrolidin-2-one;

(S)-1-(3-chloro-4-methoxyphenyl)-5-(5-(3,5-dimethylisoxazol-4-yl)-1-(2-oxaspiro[3.3]heptan-6-yl)-1H-benzo[d]imidazol-2-yl)pyrrolidin-2-one;

(S)-5-(5-(3,5-dimethylisoxazol-4-yl)-1-(2-oxaspiro[3.3]heptan-6-yl)-1H-benzo[d]imidazol-2-yl)-1-(3-fluoro-4-methoxyphenyl)pyrrolidin-2-one;

(S)-1-(3,4-difluorophenyl)-5-(5-(3,5-dimethylisoxazol-4-yl)-1-((1r,3 S)-3-hydroxycyclobutyl)-1H-benzo[d]imidazol-2-yl)pyrrolidin-2-one;

(1S,3r)-3-(2-((S)-1-(3,4-difluorophenyl)-5-oxopyrrolidin-2-yl)-5-(3,5-dimethylisoxazol-4-yl)-1H-benzo[d]imidazol-1-yl)cyclobutyl acetate;

(S)-5-(1-benzyl-5-(3,5-dimethylisoxazol-4-yl)-1H-benzo[d]imidazol-2-yl)-1-(3,4-difluorophenyl)pyrrolidin-2-one;

(S)-1-(3,4-difluorophenyl)-5-(5-(3,5-dimethylisoxazol-4-yl)-1-propyl-1H-benzo[d]imidazol-2-yl)pyrrolidin-2-one;

(S)-1-(3,4-difluorophenyl)-5-(5-(3,5-dimethylisoxazol-4-yl)-1-isobutyl-1H-benzo[d]imidazol-2-yl)pyrrolidin-2-one;

(S)-1-(3,4-difluorophenyl)-5-(5-(3,5-dimethylisoxazol-4-yl)-1-(3-methoxypropyl)-1H-benzo[d]imidazol-2-yl)pyrrolidin-2-one;

(S)-5-(1-(4,4-difluorocyclohexyl)methyl)-5-(3,5-dimethylisoxazol-4-yl)-1H-benzo[d]imidazol-2-yl)-1-(3,4-difluorophenyl)pyrrolidin-2-one;

(S)-5-(1-benzyl-5-(3,5-dimethylisoxazol-4-yl)-1H-benzo[d]imidazol-2-yl)-1-(3-fluoro-4-methoxyphenyl)pyrrolidin-2-one;

(S)-1-(3,4-difluorophenyl)-5-(5-(3,5-dimethylisoxazol-4-yl)-1-(pyridin-3-ylmethyl)-1H-benzo[d]imidazol-2-yl)pyrrolidin-2-one;

(S)-1-(3,4-difluorophenyl)-5-(5-(3,5-dimethylisoxazol-4-yl)-1-((1 s,3R)-3-(hydroxymethyl)cyclobutyl)-1H-benzo[d]imidazol-2-yl)pyrrolidin-2-one;

(S)-1-(3,4-difluorophenyl)-5-(5-(3,5-dimethylisoxazol-4-yl)-1-((1r,3 S)-3-(hydroxymethyl)cyclobutyl)-1H-benzo[d]imidazol-2-yl)pyrrolidin-2-one;

(S)-5-(1-(cyclopropylmethyl)-5-(3,5-dimethylisoxazol-4-yl)-1H-benzo[d]imidazol-2-yl)-1-(3,4-difluorophenyl)pyrrolidin-2-one;

(S)-3-(2-(1-(3,4-difluorophenyl)-5-oxopyrrolidin-2-yl)-5-(3,5-dimethylisoxazol-4-yl)-1H-benzo[d]imidazol-1-yl)propyl acetate;

(S)-5-(1-(3-aminocyclobutyl)-5-(3,5-dimethylisoxazol-4-yl)-1H-benzo[d]imidazol-2-yl)-1-(3,4-difluorophenyl)pyrrolidin-2-one;

(S)-1-(3,4-difluorophenyl)-5-(5-(3,5-dimethylisoxazol-4-yl)-1-(thiazol-4-ylmethyl)-1H-benzo[d]imidazol-2-yl)pyrrolidin-2-one;

(S)-5-(1-(3-aminocyclobutyl)-5-(3,5-dimethylisoxazol-4-yl)-1H-benzo[d]imidazol-2-yl)-1-(3,4-difluorophenyl)pyrrolidin-2-one;

(S)-3-(2-(1-(3,4-difluorophenyl)-5-oxopyrrolidin-2-yl)-5-(3,5-dimethylisoxazol-4-yl)-1H-benzo[d]imidazol-1-yl)-N-propylcyclobutanecarboxamide;

(S)-5-(1-((R)-3,3-difluorocyclopentyl)-5-(3,5-dimethylisoxazol-4-yl)-1H-benzo[d]imidazol-2-yl)-1-(3,4-difluorophenyl)pyrrolidin-2-one;

(S)-5-(1-((R)-3,3-difluorocyclopentyl)-5-(3,5-dimethylisoxazol-4-yl)-1H-benzo[d]imidazol-2-yl)-1-(3-fluoro-4-methoxyphenyl)pyrrolidin-2-one;

(S)-5-(1-((R)-3,3-difluorocyclopentyl)-5-(3,5-dimethylisoxazol-4-yl)-1H-benzo[d]imidazol-2-yl)-1-(3-fluoro-4-methoxyphenyl)pyrrolidin-2-one;

(5S)-1-(3,4-difluorophenyl)-5-(5-(3,5-dimethylisoxazol-4-yl)-1-(2-hydroxypropyl)-1H-benzo[d]imidazol-2-yl)pyrrolidin-2-one; (diastereoisomer 1)

(5S)-1-(3,4-difluorophenyl)-5-(5-(3,5-dimethylisoxazol-4-yl)-1-(2-hydroxypropyl)-1H-benzo[d]imidazol-2-yl)pyrrolidin-2-one; (diastereoisomer 2)

(R)-1-(3,4-dichlorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one;

(S)-1-(3,4-dichlorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one;

(S)-1-(4-chloro-3-fluorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one;

(S)-1-(3,4-difluorophenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one;

(S)-1-(3-chloro-4-methoxyphenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one;

(S)-1-(3-fluoro-4-methoxyphenyl)-6-(5-(3,5-dimethylisoxazol-4-yl)-1-((R)-1-(methylsulfonyl)pyrrolidin-3-yl)-1H-benzo[d]imidazol-2-yl)piperidin-2-one;

(S)-6-(5-(3,5-dimethylisoxazol-4-yl)-1-((1r,4S)-4-methoxycyclohexyl)-1H-benzo[d]imidazol-2-yl)-1-(3,4-di-fluorophenyl)piperidin-2-one;

(S)-1-(4-chloro-3-fluorophenyl)-6-(5-(3,5-dimethylisoxazol-4-yl)-1-((1r,4 S)-4-methoxycyclohexyl)-1H-benzo[d]imidazol-2-yl)piperidin-2-one;

(S)-1-(3-chloro-4-methoxyphenyl)-6-(5-(3,5-dimethylisoxazol-4-yl)-1-((1r,4 S)-4-methoxycyclohexyl)-1H-benzo[d]imidazol-2-yl)piperidin-2-one;

(S)-6-(5-(3,5-dimethylisoxazol-4-yl)-1-((1r,4 S)-4-methoxycyclohexyl)-1H-benzo[d]imidazol-2-yl)-1-(3-fluoro-4-methoxyphenyl)piperidin-2-one;

(S)-1-(3,4-difluorophenyl)-6-(5-(3,5-dimethylisoxazol-4-yl)-1-((1 s,4R)-4-hydroxy-4-methylcyclohexyl)-1H-benzo[d]imidazol-2-yl)piperidin-2-one;

(S)-1-(3-chloro-4-methoxyphenyl)-6-(5-(3,5-dimethylisoxazol-4-yl)-1-((1 s,4R)-4-hydroxy-4-methylcyclohexyl)-1H-benzo[d]imidazol-2-yl)piperidin-2-one;

(S)-1-(3,4-dichlorophenyl)-6-(5-(3,5-dimethylisoxazol-4-yl)-1-((1 s,4R)-4-hydroxy-4-methylcyclohexyl)-1H-benzo[d]imidazol-2-yl)piperidin-2-one;

(S)-6-(5-(3,5-dimethylisoxazol-4-yl)-1-((1 s,4R)-4-hydroxy-4-methylcyclohexyl)-1H-benzo[d]imidazol-2-yl)-1-(3-fluoro-4-methoxyphenyl)piperidin-2-one;

(S)-1-(4-chloro-3-fluorophenyl)-6-(5-(3,5-dimethylisoxazol-4-yl)-1-((1 s,4R)-4-hydroxy-4-methylcyclohexyl)-1H-benzo[d]imidazol-2-yl)piperidin-2-one;

(S)-1-(3,4-difluorophenyl)-6-(5-(3,5-dimethylisoxazol-4-yl)-1-((1r,3 S)-3-hydroxycyclobutyl)-1H-benzo[d]imidazol-2-yl)piperidin-2-one;

(S)-1-(3-chloro-4-methoxyphenyl)-6-(5-(3,5-dimethylisoxazol-4-yl)-1-((1r,3 S)-3-hydroxycyclobutyl)-1H-benzo[d]imidazol-2-yl)piperidin-2-one;

(S)-1-(3,4-dichlorophenyl)-6-(5-(3,5-dimethylisoxazol-4-yl)-1-((1r,3 S)-3-hydroxycyclobutyl)-1H-benzo[d]imidazol-2-yl)piperidin-2-one;

(S)-1-(3,4-difluorophenyl)-6-(5-(3,5-dimethylisoxazol-4-yl)-1-((1r,4 S)-4-hydroxy-4-methylcyclohexyl)-1H-benzo[d]imidazol-2-yl)piperidin-2-one;

(S)-1-(3-chloro-4-methoxyphenyl)-6-(5-(3,5-dimethylisoxazol-4-yl)-1-((1r,4 S)-4-hydroxy-4-methylcyclohexyl)-1H-benzo[d]imidazol-2-yl)piperidin-2-one;

(S)-6-(5-(3,5-dimethylisoxazol-4-yl)-1-((1r,4 S)-4-hydroxy-4-methylcyclohexyl)-1H-benzo[d]imidazol-2-yl)-1-(3-fluoro-4-methoxyphenyl)piperidin-2-one;

(S)-1-(3,4-dichlorophenyl)-6-(5-(3,5-dimethylisoxazol-4-yl)-isobutyl-1H-benzo[d]imidazol-2-yl)piperidin-2-one;

(S)-1-(3-chloro-4-methoxyphenyl)-6-(5-(3,5-dimethylisoxazol-4-yl)-1-isobutyl-1H-benzo[d]imidazol-2-yl)piperidin-2-one;

(S)-6-(5-(3,5-dimethylisoxazol-4-yl)-isobutyl-1H-benzo[d]imidazol-2-yl)-1-(3-fluoro-4-methoxyphenyl)piperidin-2-one;

(S)-6-(1-(4,4-difluorocyclohexyl)-5-(3,5-dimethylisoxazol-4-yl)-1H-benzo[d]imidazol-2-yl)-1-(3-fluoro-4-methoxyphenyl)piperidin-2-one;

S)-6-(1-(4,4-difluorocyclohexyl)-5-(3,5-dimethylisoxazol-4-yl)-1H-benzo[d]imidazol-2-yl)-1-(3,4-difluorophenyl)piperidin-2-one;

(S)-1-(3-chloro-4-methoxyphenyl)-6-(1-(4,4-difluorocyclohexyl)-5-(3,5-dimethylisoxazol-4-yl)-1H-benzo[d]imidazol-2-yl)piperidin-2-one;

(S)-1-(3,4-dichlorophenyl)-6-(5-(3,5-dimethylisoxazol-4-yl)-1-((1r,4S)-4-hydroxycyclohexyl)-1H-benzo[d]imidazol-2-yl)piperidin-2-one;

(S)-1-(3,4-difluorophenyl)-6-(5-(3,5-dimethylisoxazol-4-yl)-1-((1r,4S)-4-hydroxycyclohexyl)-1H-benzo[d]imidazol-2-yl)piperidin-2-one;

(S)-1-(3-chloro-4-methoxyphenyl)-6-(5-(3,5-dimethylisoxazol-4-yl)-1-((1r,4S)-4-hydroxycyclohexyl)-1H-benzo[d]imidazol-2-yl)piperidin-2-one;

(S)-1-(3,4-difluorophenyl)-5-(1-((1r,4S)-4-hydroxycyclohexyl)-5-(5-(hydroxymethyl)-3-methylisoxazol-4-yl)-1H-benzo[d]imidazol-2-yl)pyrrolidin-2-one;

(S)-1-(3,4-difluorophenyl)-5-(1-((1r,4S)-4-hydroxycyclohexyl)-5-(3-(hydroxymethyl)-5-methylisoxazol-4-yl)-1H-benzo[d]imidazol-2-yl)pyrrolidin-2-one;

(S)-6-(1-(4,4-difluorocyclohexyl)-5-(3,5-dimethylisoxazol-4-yl)-1H-benzo[d]imidazol-2-yl)-1-phenylpiperidin-2-one;

(S)-1-(3-chloro-4-methoxyphenyl)-6-(1-(3,3-difluorocyclobutyl)-5-(3,5-dimethylisoxazol-4-yl)-1H-benzo[d]imidazol-2-yl)piperidin-2-one;

(S)-6-(1-(3,3-difluorocyclobutyl)-5-(3,5-dimethylisoxazol-4-yl)-1H-benzo[d]imidazol-2-yl)-1-(3,4-difluorophenyl)piperidin-2-one;

(S)-6-(1-(3,3-difluorocyclobutyl)-5-(3,5-dimethylisoxazol-4-yl)-1H-benzo[d]imidazol-2-yl)-1-(3-fluoro-4-methoxyphenyl)piperidin-2-one;

(1S,4r)-methyl 4-(2-((S)-1-(3,4-difluorophenyl)-6-oxopiperidin-2-yl)-5-(3,5-dimethylisoxazol-4-yl)-1H-benzo[d]imidazol-1-yl)cyclohexanecarboxylate;

(1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)cyclohexane carboxylic acid (1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)-N-propylcyclohexane carboxamide;

(1S,4r)-4-((2-(S)-1-(3,4-difluorophenyl)-6-oxopiperidin-2-yl)-5-(3,5-dimethylisoxazol-4-yl)-1H-benzo[d]imidazol-1-yl)-N-methyl-N-propylcyclohexanecarboxamide;

(S)-6-(1-(4,4-difluorocyclohexyl)-5-(3,5-dimethylisoxazol-4-yl)-1H-benzo[d]imidazol-2-yl)-1-(6-fluoropyridin-3-yl)piperidin-2-one;

(S)-6-(1-(4,4-difluorocyclohexyl)-5-(3,5-dimethylisoxazol-4-yl)-1H-benzo[d]imidazol-2-yl)-1-(5-fluoropyridin-3-yl)piperidin-2-one;

(S)-6-(1-(4,4-difluorocyclohexyl)-5-(3,5-dimethylisoxazol-4-yl)-1H-benzo[d]imidazol-2-yl)-1-(pyridin-3-yl)piperidin-2-one;

(S)-1-(3-chloro-4-methoxyphenyl)-6-(6-(3,5-dimethylisoxazol-4-yl)-3-((1r,4S)-4-hydroxycyclohexyl)-3H-imidazo[4,5-b]pyridin-2-yl)piperidin-2-one;

(S)-1-(3,4-difluorophenyl)-6-(6-(3,5-dimethylisoxazol-4-yl)-3-(1r,4S)-4-hydroxycyclohexyl)-3H-imidazo[4,5-b]pyridin-2-yl)piperidin-2-one;

(S)-6-(6-(3,5-dimethylisoxazol-4-yl)-3-((1r,4S)-4-hydroxycyclohexyl)-3H-imidazo[4,5-b]pyridin-2-yl)-1-(3-fluoro-4-methoxyphenyl)piperidin-2-one;

(S)-1-(3-chloro-4-methoxyphenyl)-5-(3-(4,4-difluorocyclohexyl)-6-(3,5-dimethylisoxazol-4-yl)-3H-imidazo[4,5-b]pyridin-2-yl)pyrrolidin-2-one;

(S)-5-(3-(4,4-difluorocyclohexyl)-6-(3,5-dimethylisoxazol-4-yl)-3H-imidazo[4,5-b]pyridin-2-yl)-1-(3,4-difluorophenyl)pyrrolidin-2-one;

(S)-5-(3-(4,4-difluorocyclohexyl)-6-(3,5-dimethylisoxazol-4-yl)-3H-imidazo[4,5-b]pyridin-2-yl)-1-(3-fluoro-4-methoxyphenyl)pyrrolidin-2-one;

(S)-6-(1-(4,4-difluorocyclohexyl)-5-(3,5-dimethylisoxazol-4-yl)-1H-benzo[d]imidazol-2-yl)-1-(pyrimidin-5-yl)piperidin-2-one;

(S)-1-(3,4-difluorophenyl)-6-(6-(3,5-dimethylisoxazol-4-yl)-3-isobutyl-3H-imidazo[4,5-b]pyridin-2-yl)piperidin-2-one; and (S)-6-(6-(3,5-dimethylisoxazol-4-yl)-3-isobutyl-3H-imidazo[4,5-b]pyridin-2-yl)-1-(3-fluoro-4-methoxyphenyl)piperidin-2-one;

(S)-1-benzyl-5-(5-(3,5-dimethylisoxazol-4-yl)-1-((1r,4S)-4-methoxycyclohexyl)-1H-benzo[d]imidazol-2-yl)pyrrolidin-2-one;

and the pharmaceutically acceptable salts thereof.

6. A process for producing a compound as defined in claim 1, which process comprises treating a compound of formula (II):

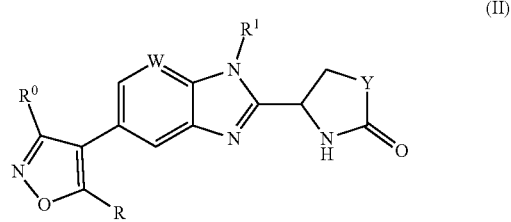

(II)

wherein each of R, R⁰, W and Y is as defined in claim 1, with a boronic acid of formula $R^2\text{—B(OH)}_2$ wherein $R^2$ is as defined in claim 1, in the presence of $Pd(PPh_3)_4$ and $Na_2CO_3$ in aqueous ethanol; or treating a compound of formula (III):

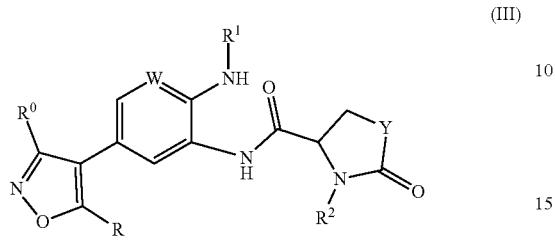

(III)

wherein each of R, R⁰, R¹, R², W and Y is as defined in claim 1, with acetic acid at 60-100° C. or HCl/1,4-dioxane 20-90%; or treating a compound of formula (II) as defined above with a compound of formula $R^2\text{—CH}_2Br$ in which $R^2$ is as defined in claim 1.

7. A process according to claim 6, which further comprises converting the resulting arylimidazolyl isoxazole of formula (I) into a pharmaceutically acceptable salt thereof.

8. A pharmaceutical composition which comprises a pharmaceutically acceptable carrier or diluent and, as an active ingredient, a compound as defined in claim 1.

* * * * *